(12) United States Patent
Mazed

(10) Patent No.: US 11,320,588 B1
(45) Date of Patent: May 3, 2022

(54) SUPER SYSTEM ON CHIP

(71) Applicant: Mohammad A. Mazed, Yorba Linda, CA (US)

(72) Inventor: Mohammad A. Mazed, Yorba Linda, CA (US)

( * ) Notice: Subject to any disclaimer, the term of this patent is extended or adjusted under 35 U.S.C. 154(b) by 16 days.

(21) Appl. No.: 16/602,404

(22) Filed: Sep. 28, 2019

Related U.S. Application Data

(63) Continuation-in-part of application No. 16/501,942, filed on Jul. 5, 2019, now abandoned, which is a continuation-in-part of application No. 16/350,829, filed on Jan. 18, 2019, now abandoned, which is a continuation-in-part of application No. 16/350,169, filed on Oct. 9, 2018, now abandoned, which is a continuation-in-part of application No. 15/932,598, filed on Mar. 19, 2018, now abandoned, which is a continuation-in-part of application No. 15/731,577, filed on Jul. 3, 2017, now Pat. No. 10,529,003, which is a continuation-in-part of application No. 14/999,601, filed on Jun. 1, 2016, now Pat. No. 9,923,124, which is a continuation-in-part of application No. 14/120,835, filed on Jul. 1, 2014, now Pat. No. 9,823,737, and a continuation-in-part of application No. 14/014,239, filed on Aug. 29, 2013, now Pat. No. 9,426,545, and a continuation-in-part of
(Continued)

(51) Int. Cl.
| | |
|---|---|
| *G02B 6/122* | (2006.01) |
| *G02B 6/12* | (2006.01) |
| *H01L 27/24* | (2006.01) |
| *G16H 30/40* | (2018.01) |
| *G06N 3/08* | (2006.01) |
| *G06N 10/00* | (2022.01) |
| *G01S 17/34* | (2020.01) |
| *A61F 2/14* | (2006.01) |

(52) U.S. Cl.
CPC .............. *G02B 6/122* (2013.01); *A61F 2/141* (2013.01); *G01S 17/34* (2020.01); *G02B 6/12002* (2013.01); *G06N 3/08* (2013.01); *G06N 10/00* (2019.01); *G16H 30/40* (2018.01); *H01L 27/2409* (2013.01); *G02B 2006/12102* (2013.01); *G02B 2006/12104* (2013.01); *G02B 2006/12121* (2013.01); *G02B 2006/12123* (2013.01); *G02B 2006/12138* (2013.01); *G02B 2006/12142* (2013.01); *G02B 2006/12145* (2013.01)

(58) Field of Classification Search
None
See application file for complete search history.

(56) References Cited

U.S. PATENT DOCUMENTS

| | | | | |
|---|---|---|---|---|
| 2010/0278479 A1* | 11/2010 | Bratkovski | ........ | G02B 6/12007 385/31 |
| 2011/0261608 A1* | 10/2011 | Borghetti | ............ | H01L 45/1641 365/148 |

(Continued)

*Primary Examiner* — Chris H Chu

(57) ABSTRACT

A Super System on Chip (SSoC) coupled with a photonic neural learning processor (PNLP), one or more quantum bits (qubits) and a machine learning algorithm for ultrafast data processing, image processing/recognition, deep learning/meta-learning and self-learning is disclosed. The Super System on Chip (SSoC) is interconnected/coupled electrically and/or optically in two-dimension (2-D) or in three-dimension (3-D).

45 Claims, 272 Drawing Sheets

Related U.S. Application Data application No. 13/663,376, filed on Oct. 29, 2012, now Pat. No. 9,557,271, and a continuation-in-part of application No. 13/448,378, filed on Apr. 16, 2012, now Pat. No. 9,697,556.

(60) Provisional application No. 62/230,249, filed on Jun. 1, 2015.

(56) References Cited

U.S. PATENT DOCUMENTS

| | | | |
|---|---|---|---|
| 2012/0011092 A1* | 1/2012 | Tang | G06N 3/063 706/33 |
| 2016/0019453 A1* | 1/2016 | Klefenz | H01L 45/1253 706/26 |
| 2017/0116514 A1* | 4/2017 | Abel | G06N 3/0675 |
| 2017/0236870 A1* | 8/2017 | Yang | H01L 45/165 438/404 |

* cited by examiner

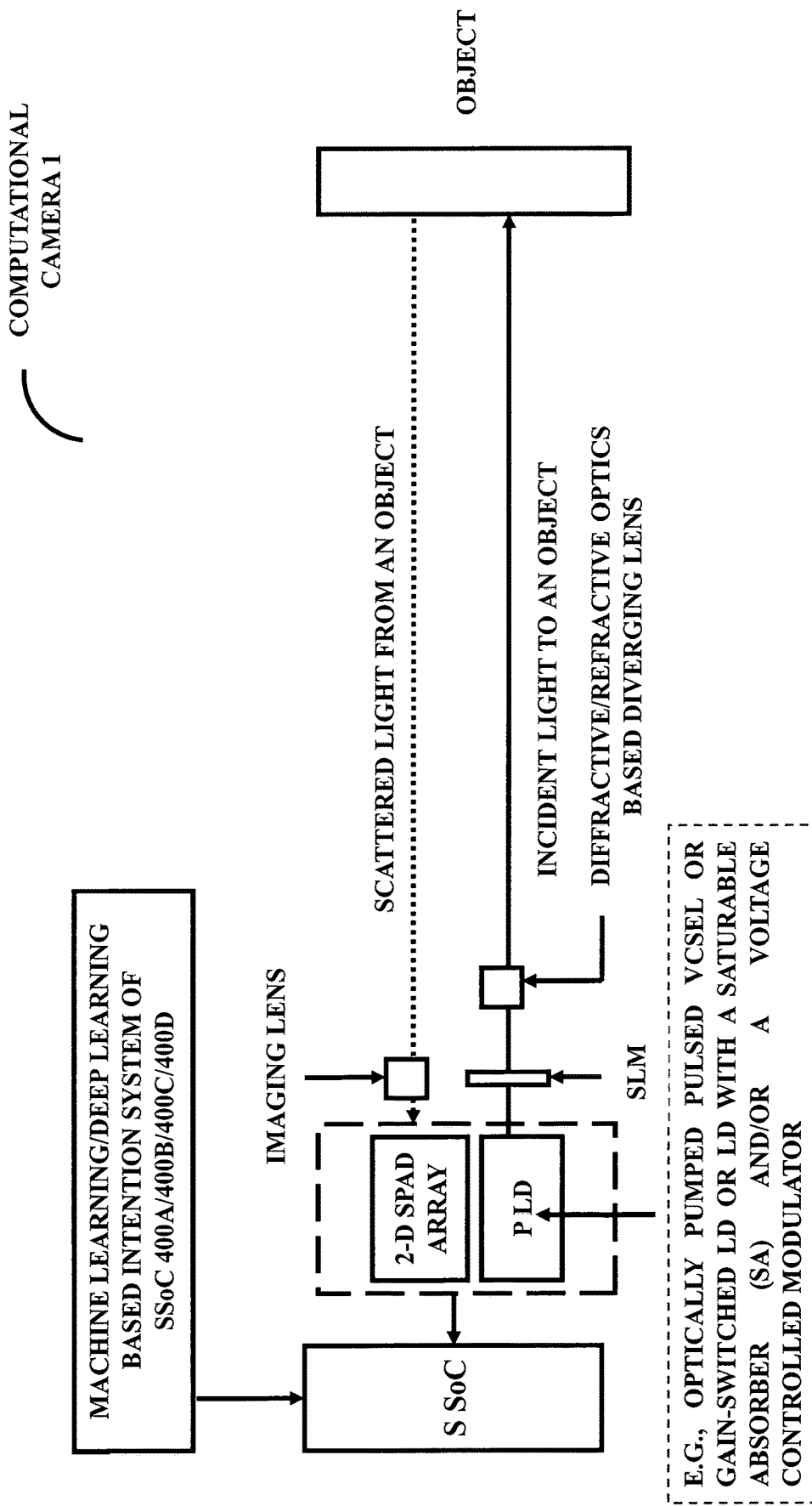
FIG. 3U1

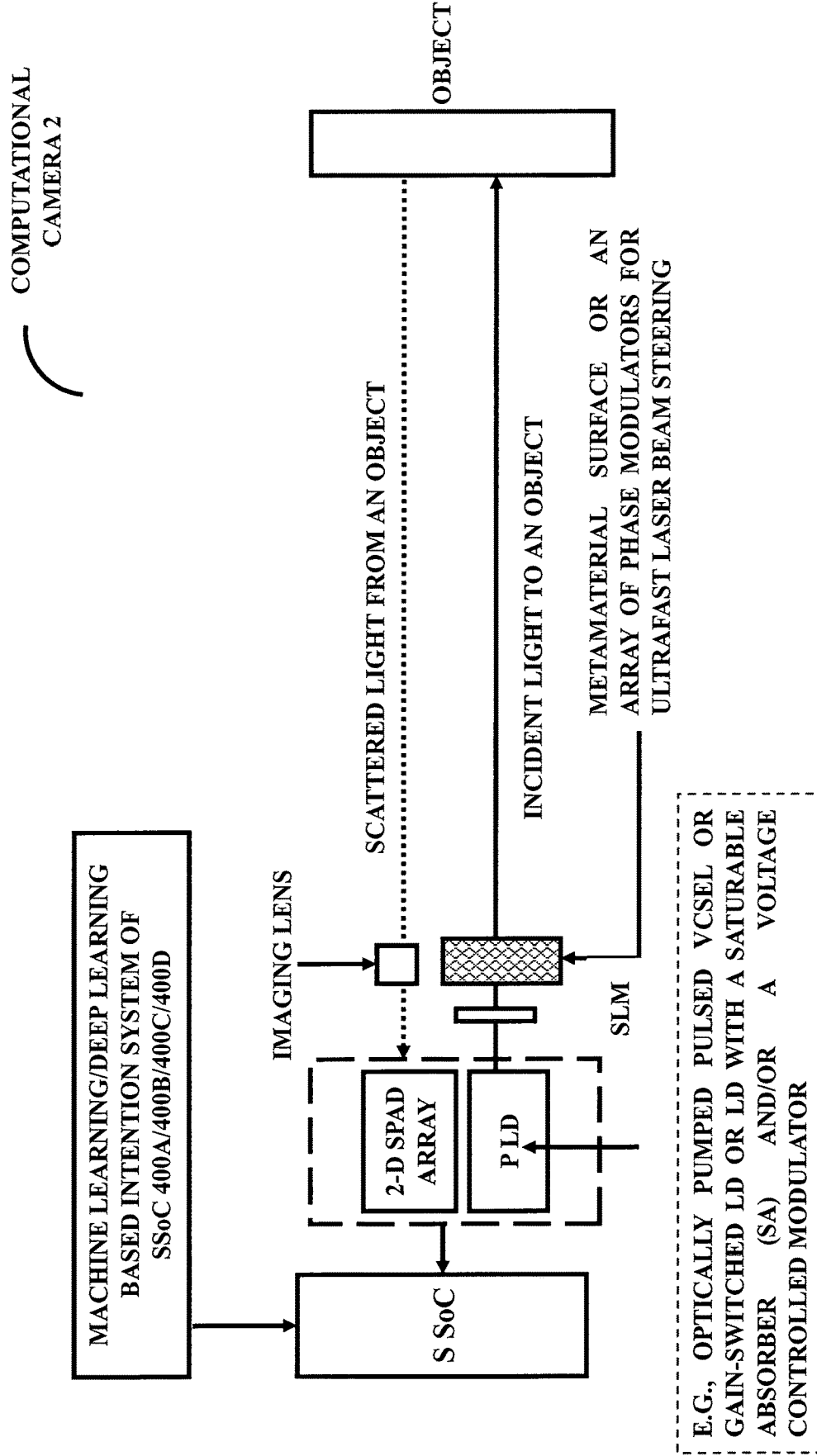
FIG. 3U2

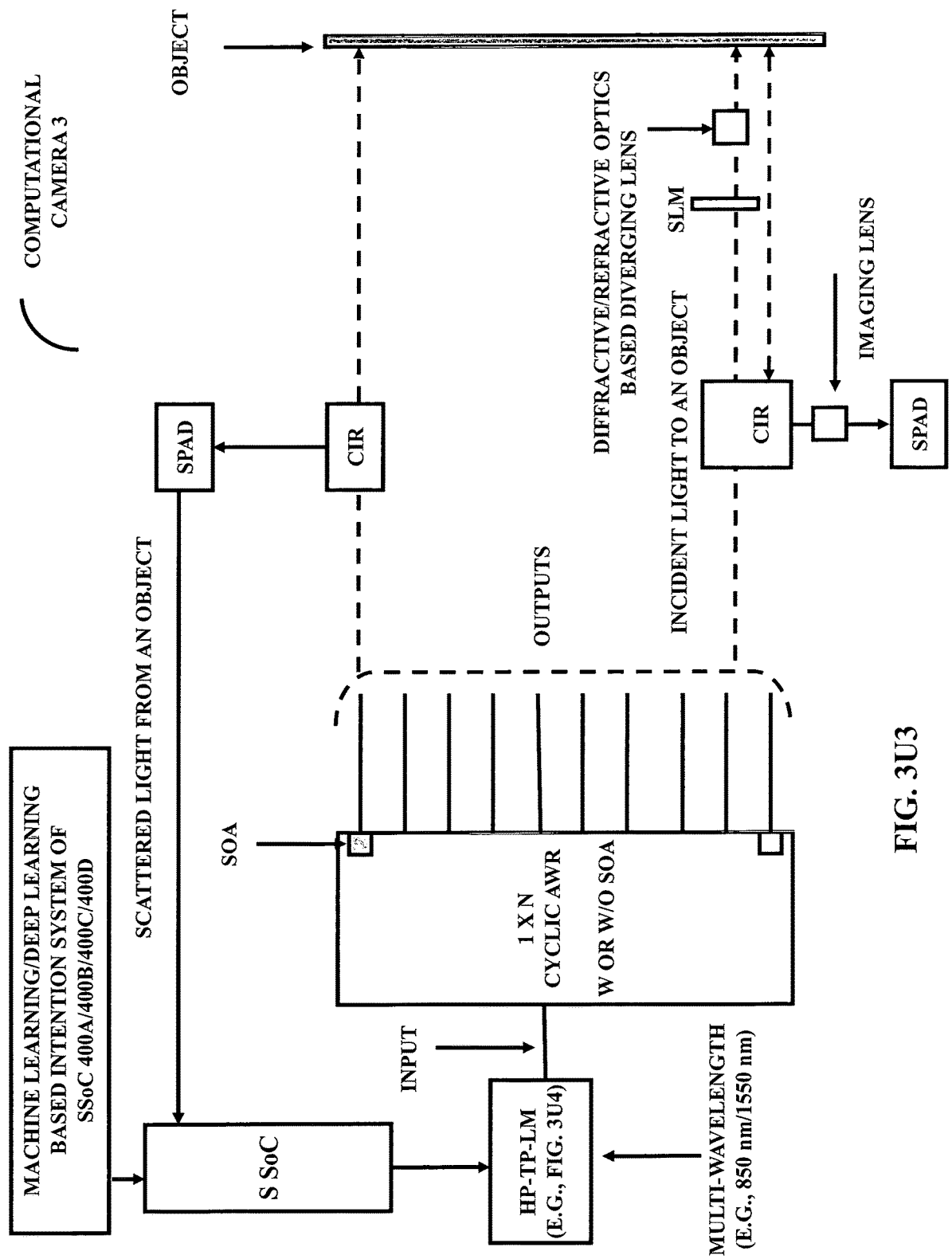
FIG. 3U3

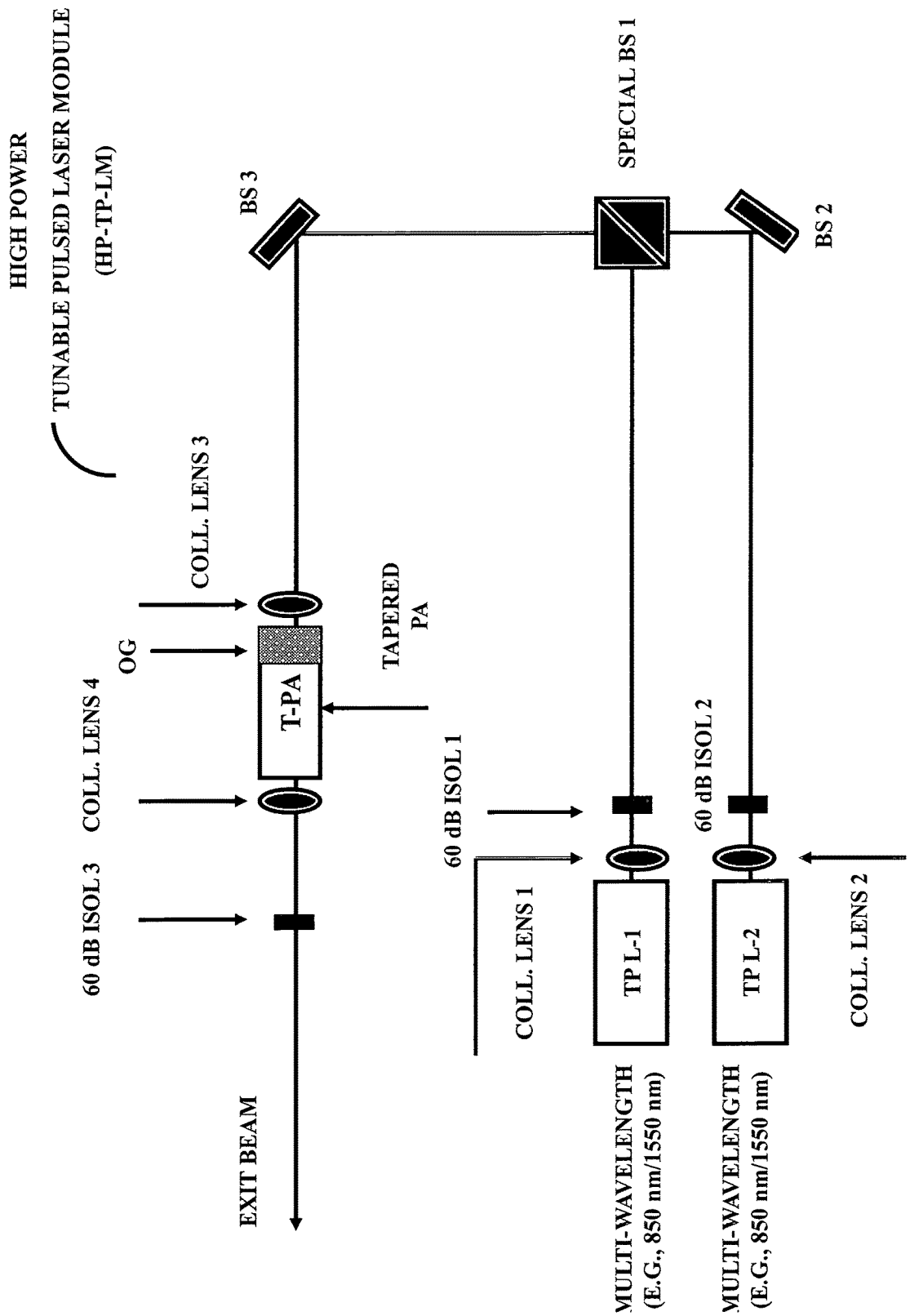
FIG. 3U4

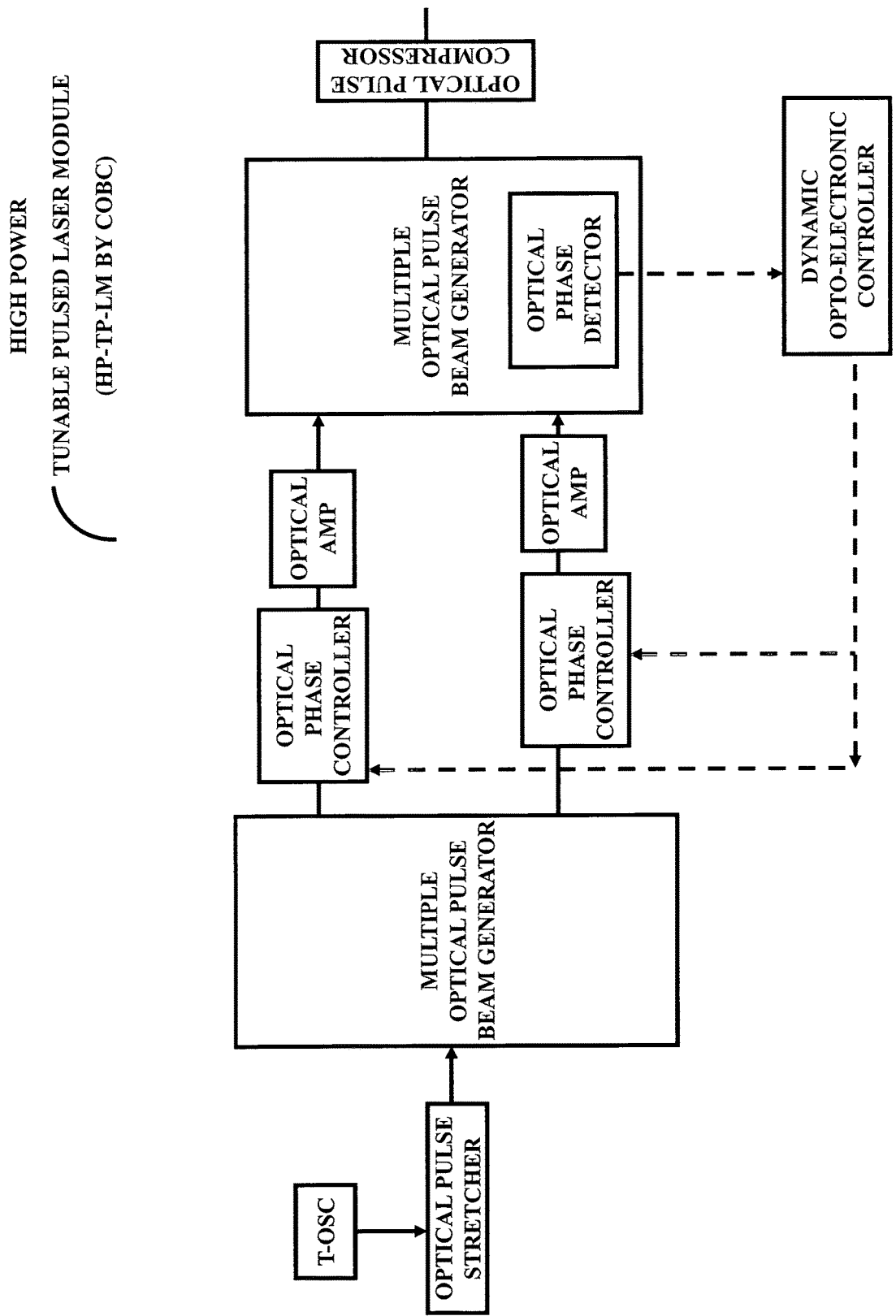
FIG. 3U5

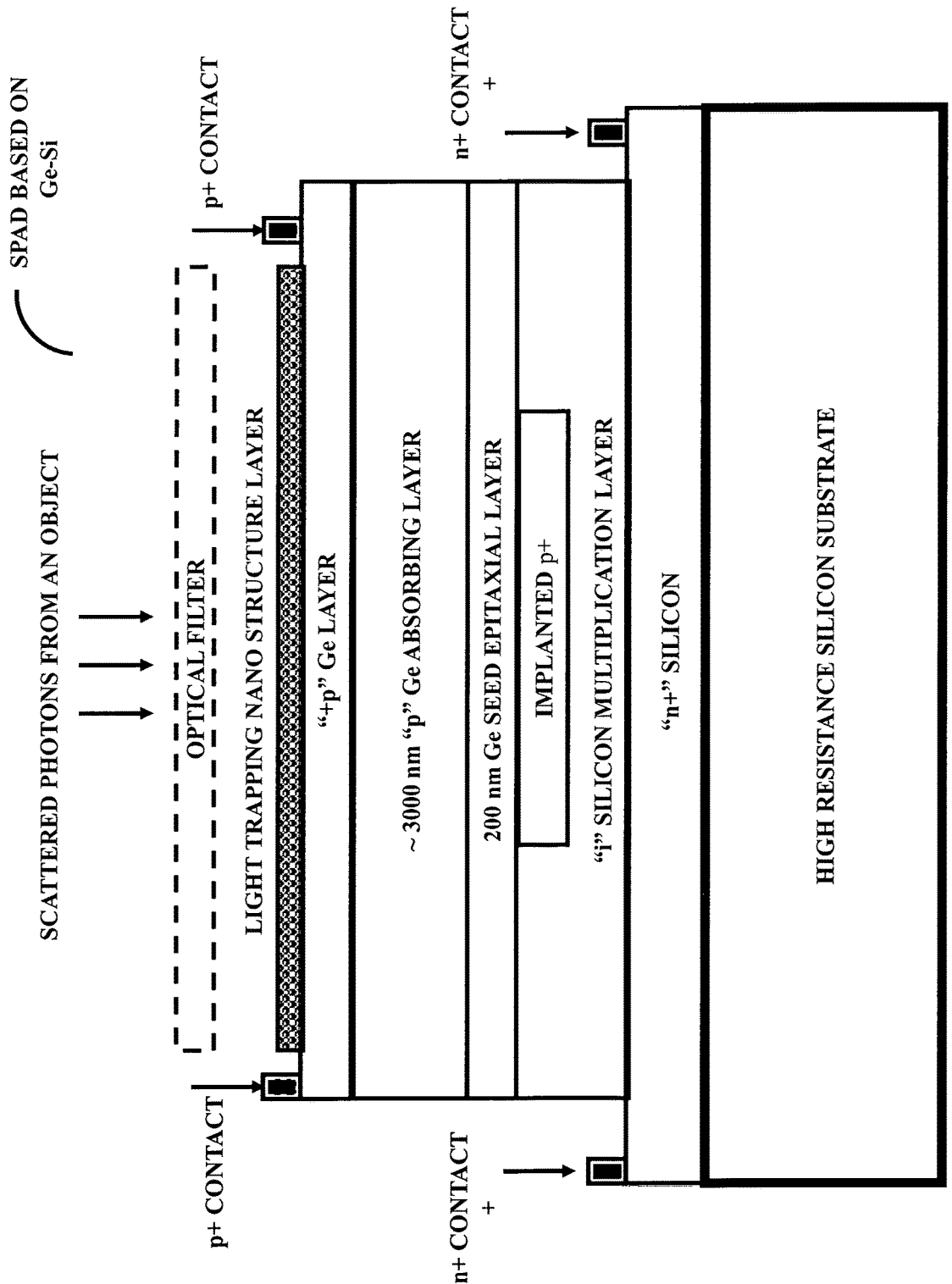
FIG. 3V1

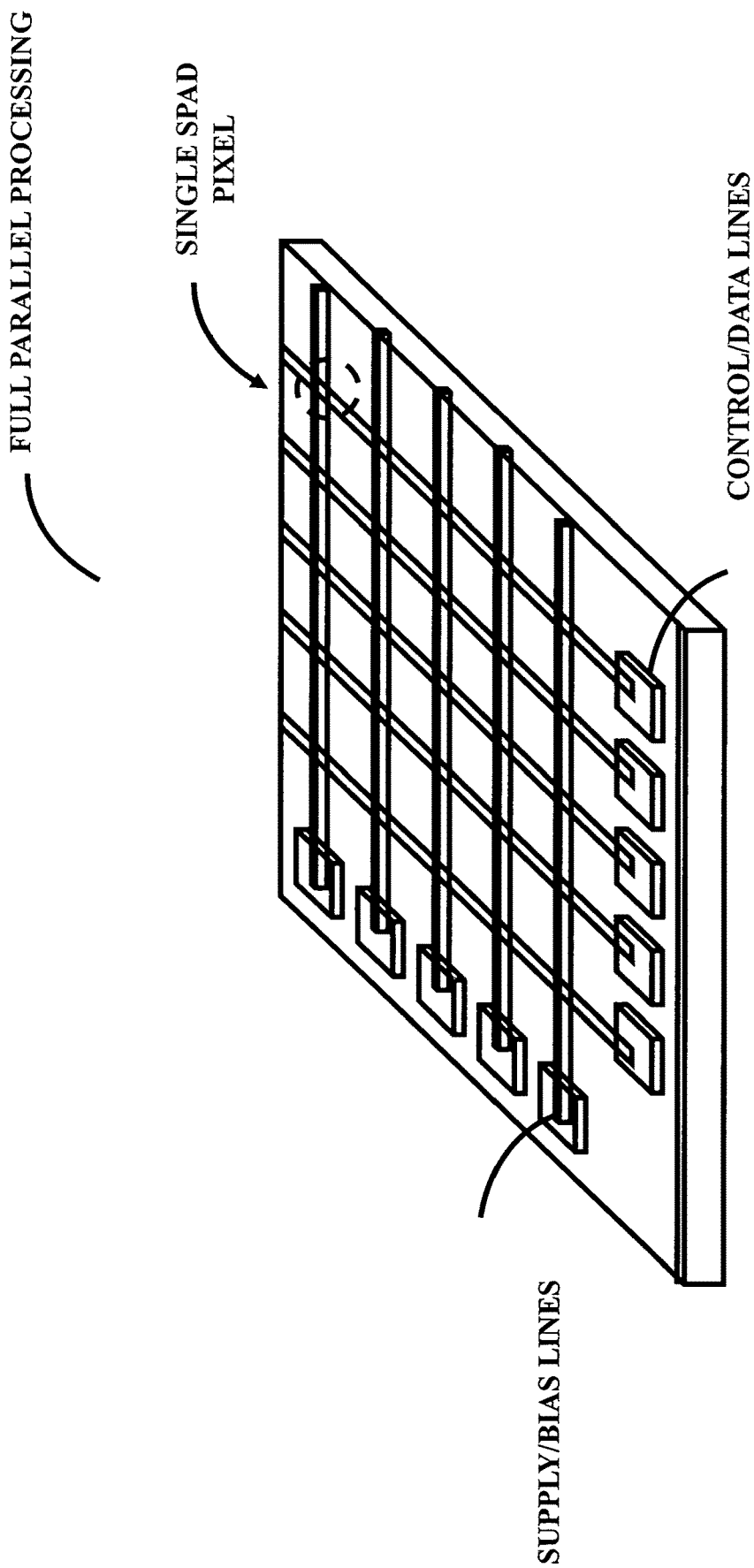
FIG. 3V2

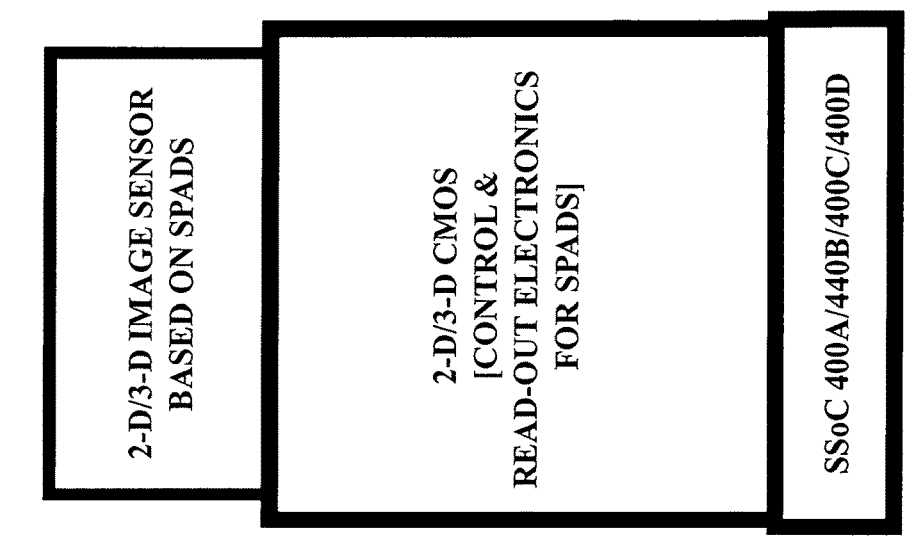
FIG. 3V3.3
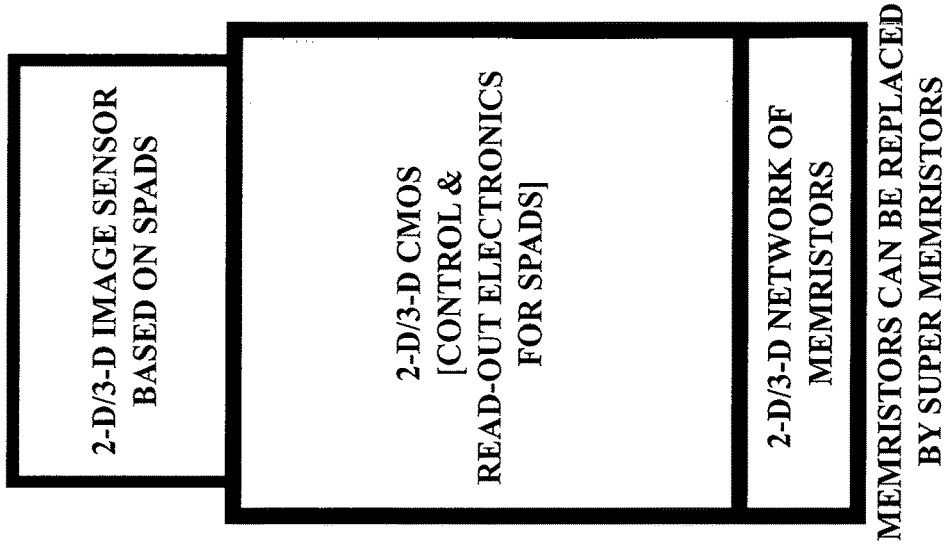
FIG. 3V3.2
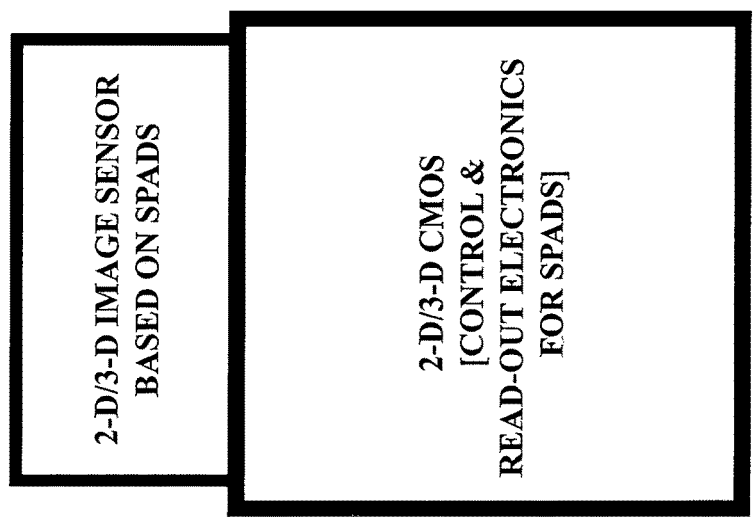
FIG. 3V3.1

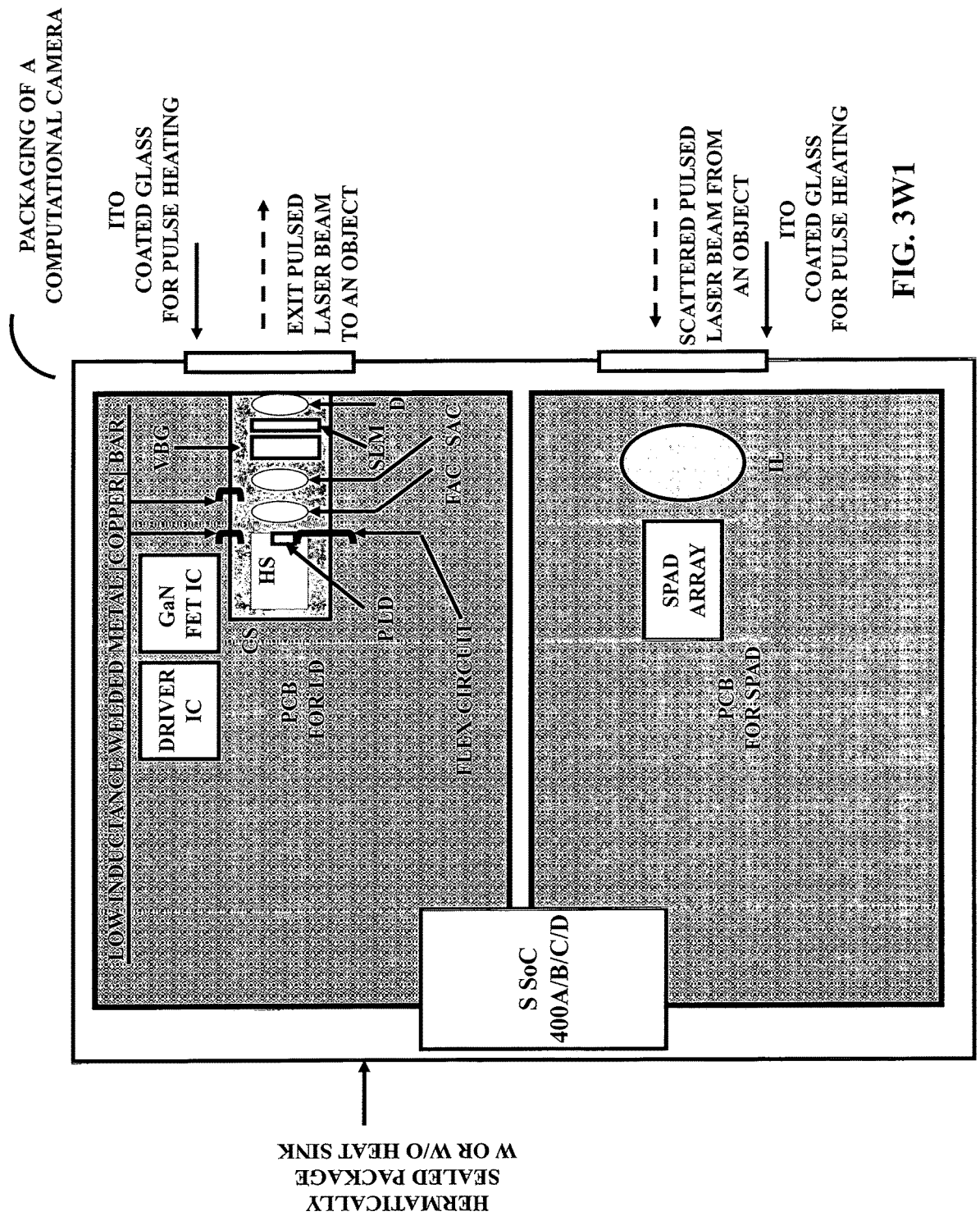
FIG. 3W1

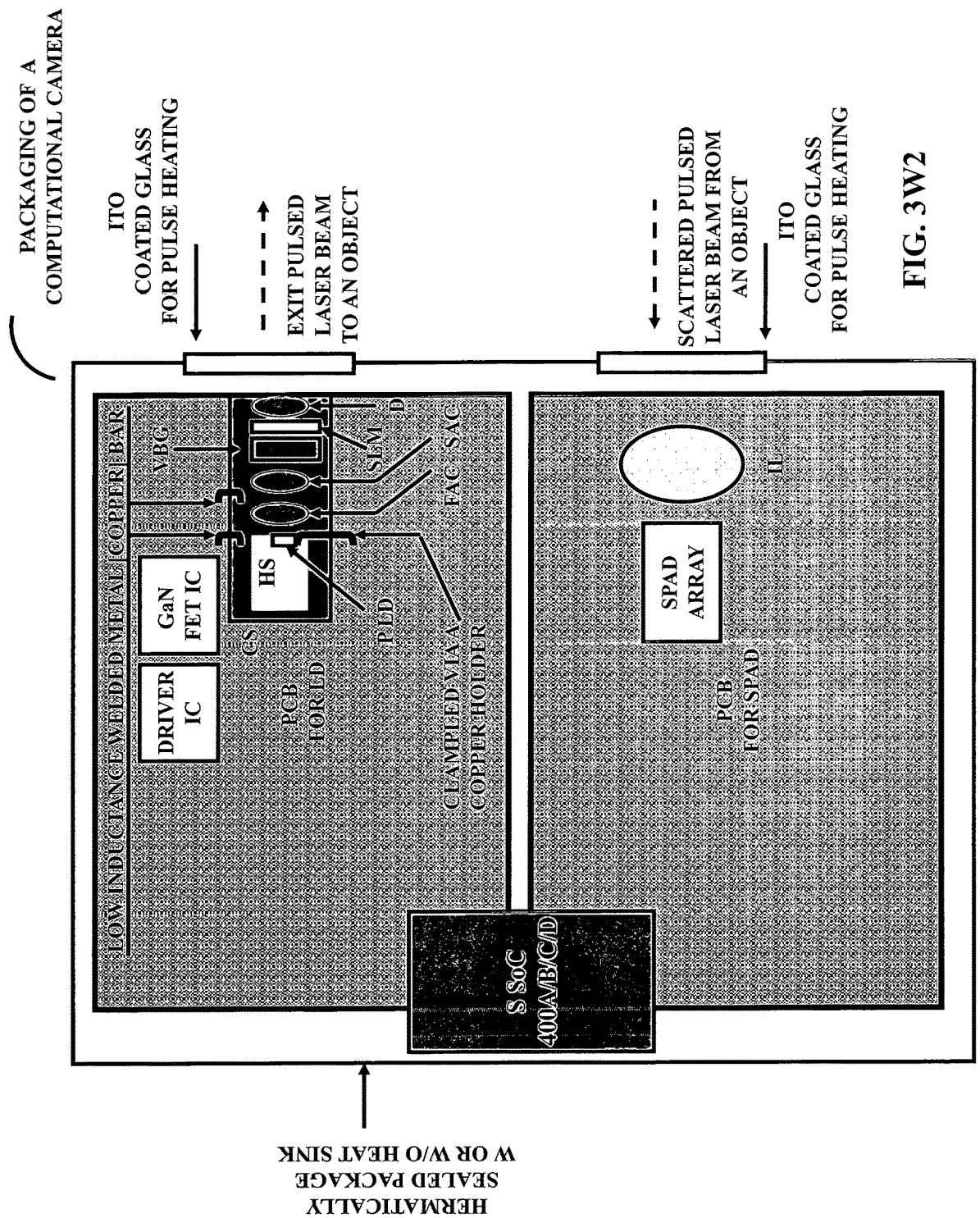
FIG. 3W2

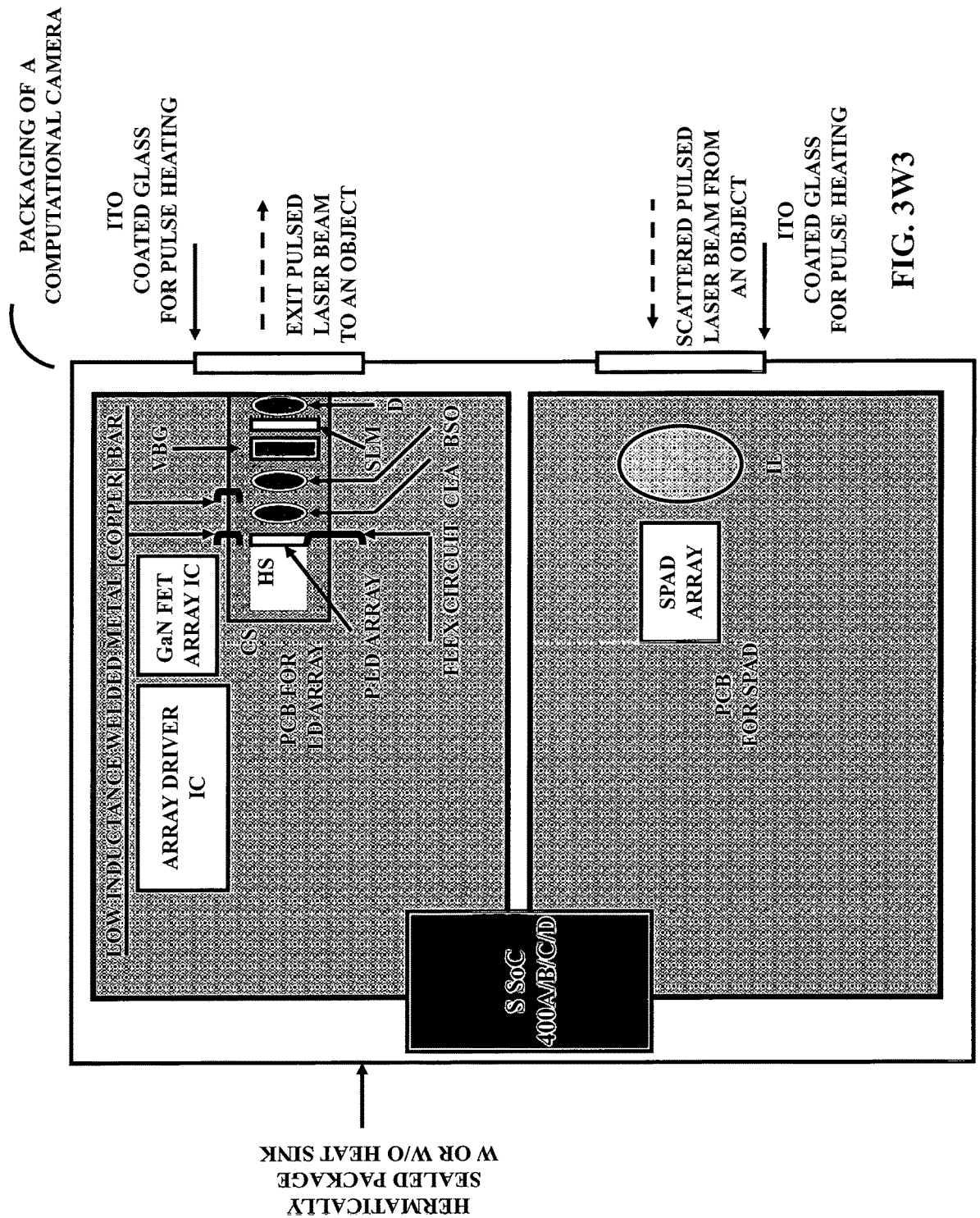
FIG. 3W3

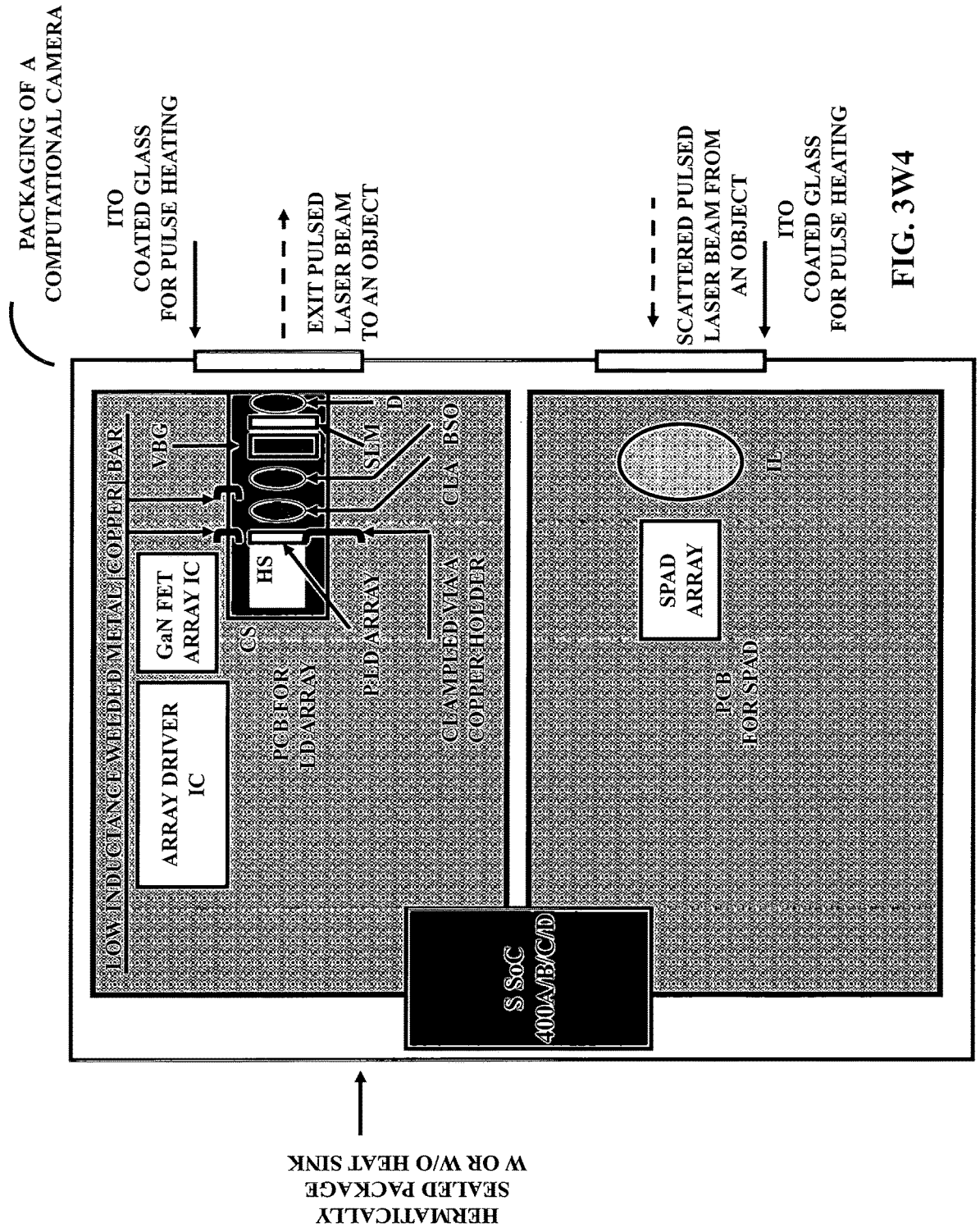
FIG. 3W4

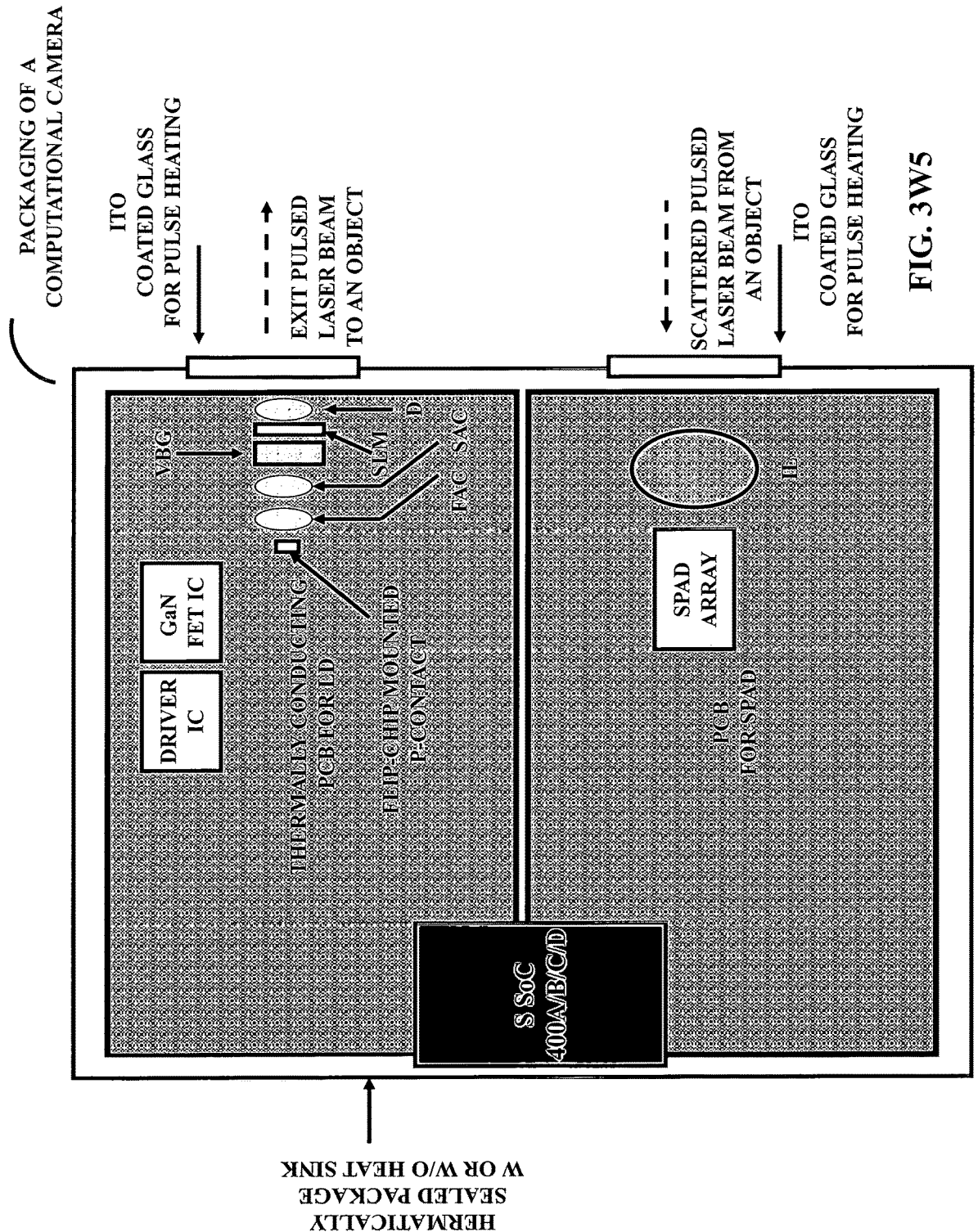
FIG. 3W5

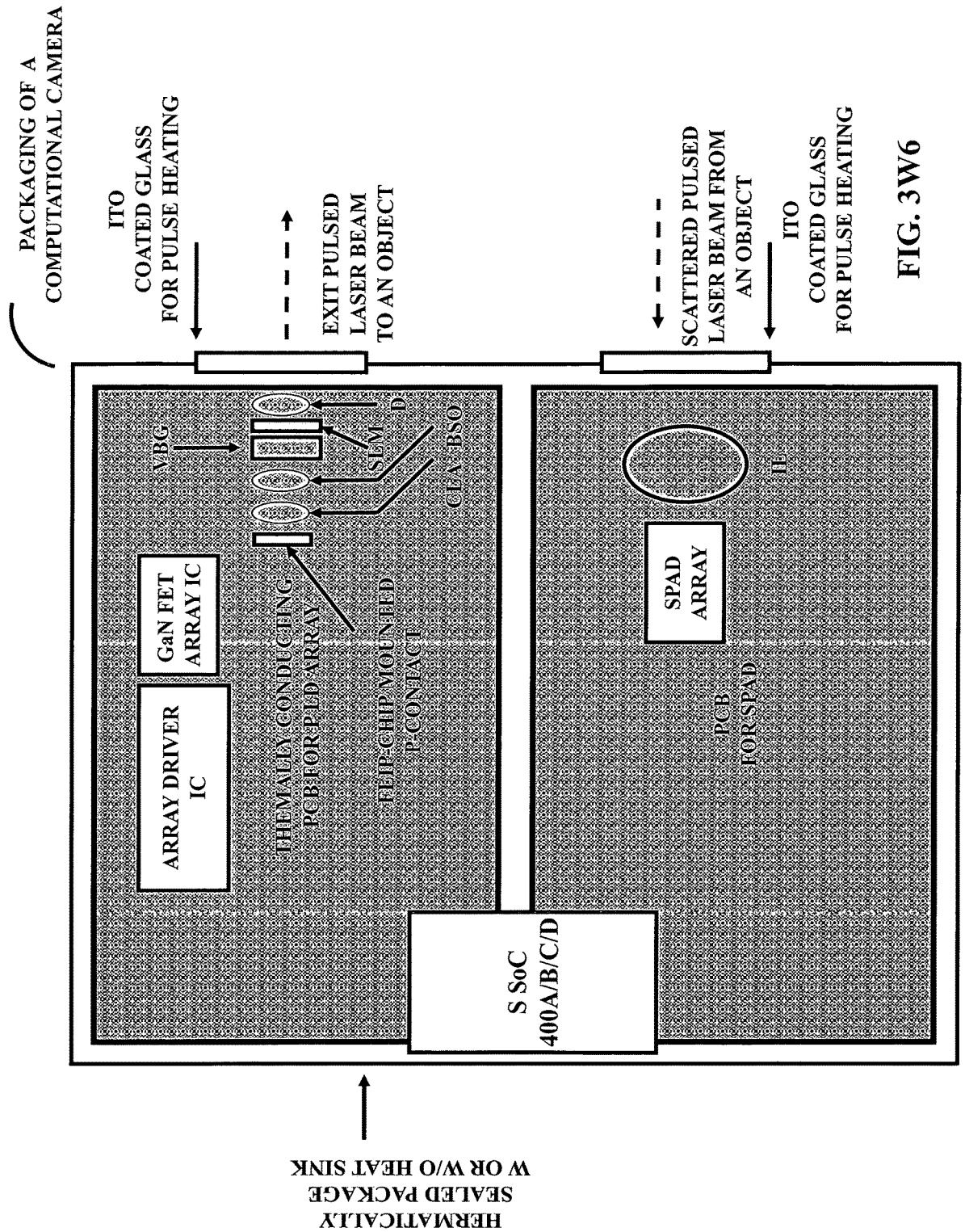
FIG. 3W6

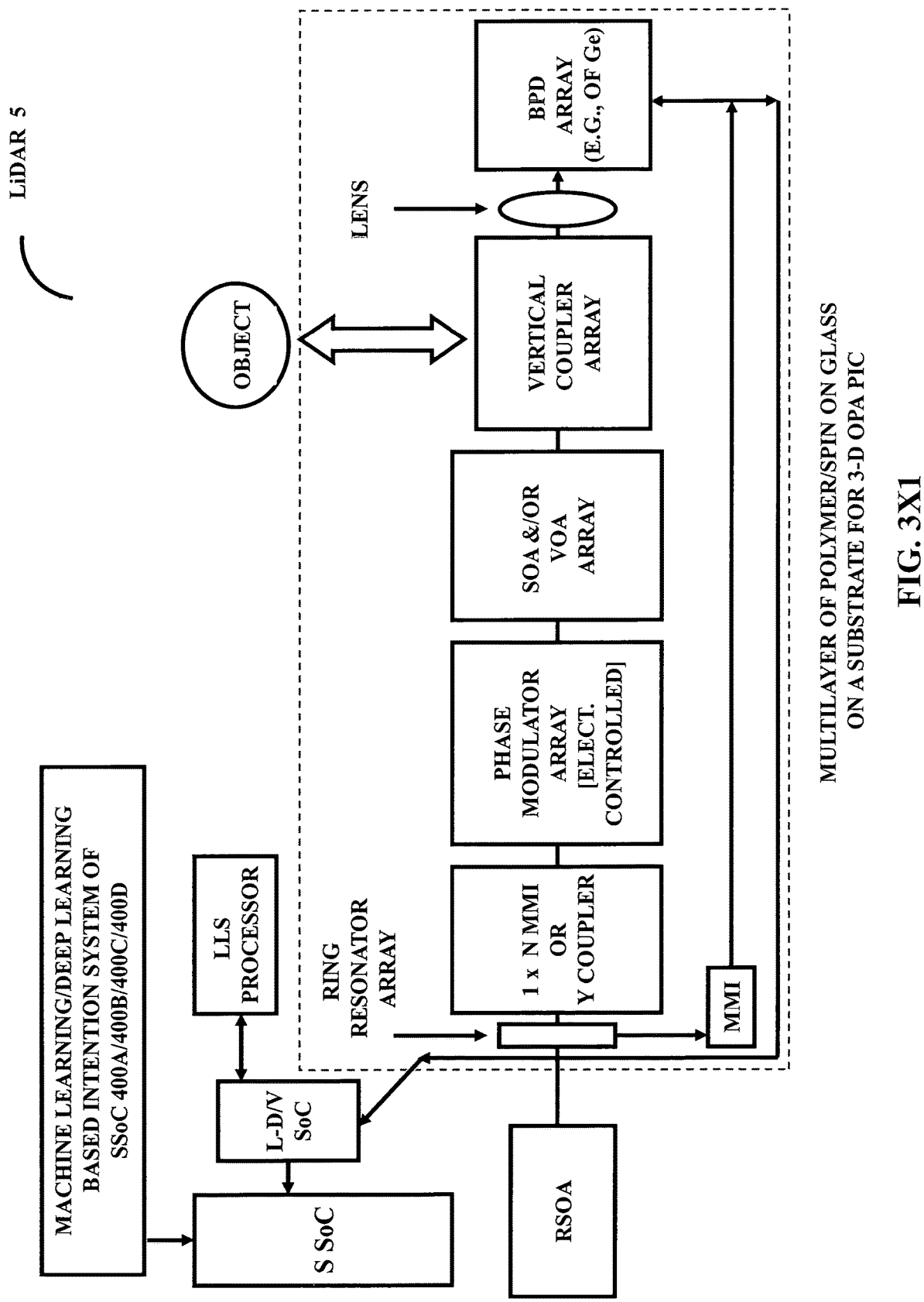
FIG. 3X1

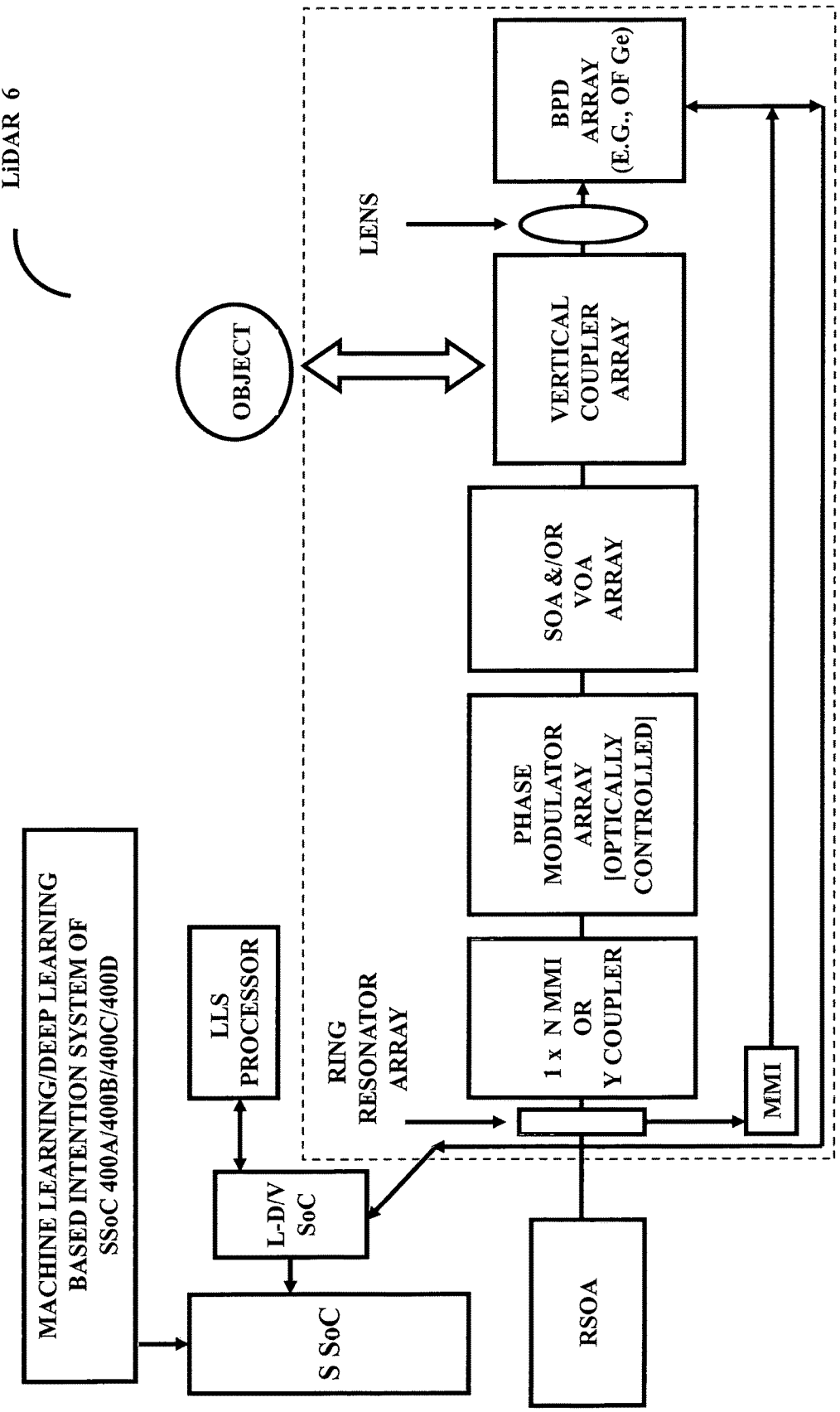
FIG. 3X2

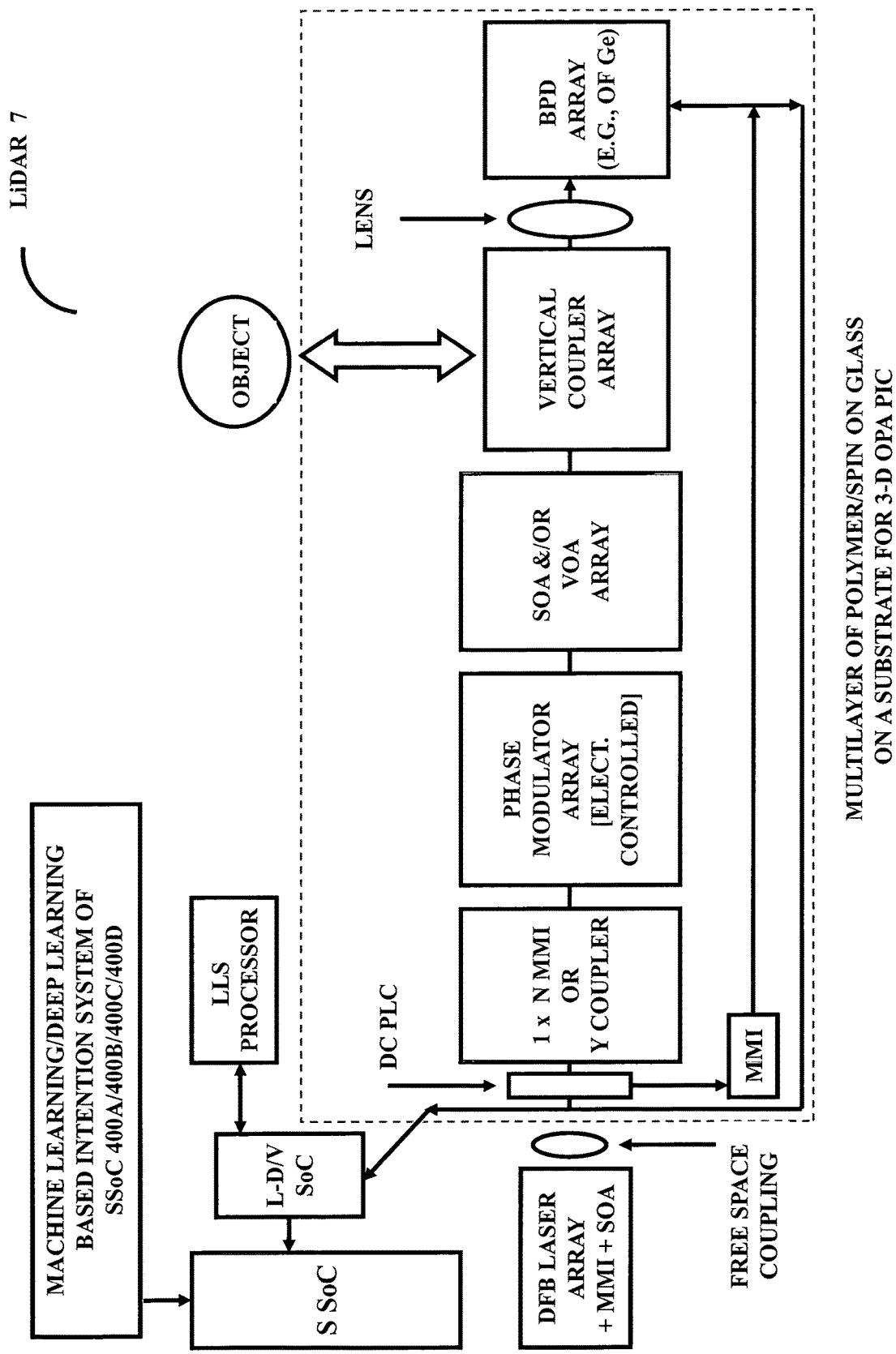
FIG. 3X3

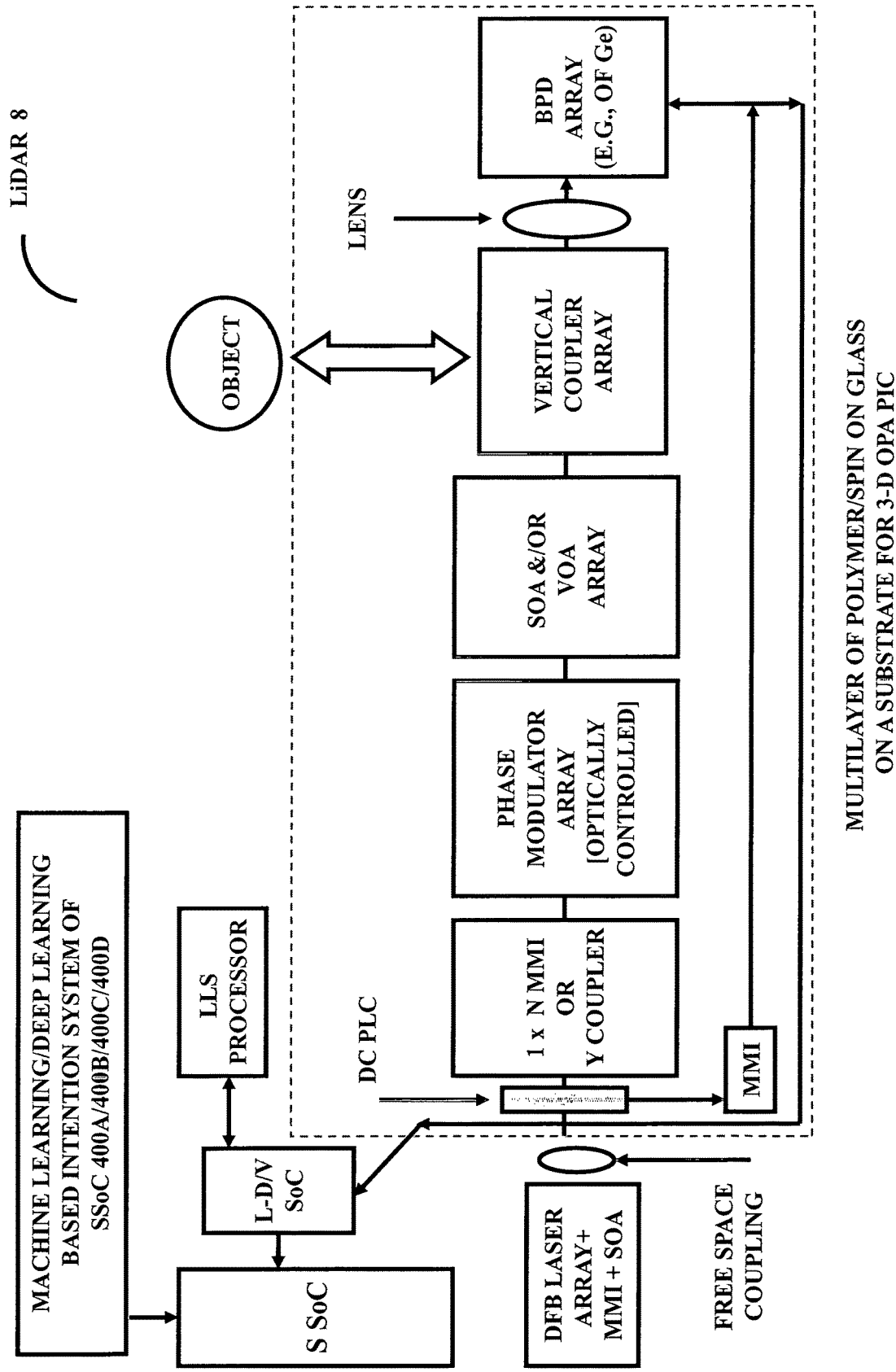
FIG. 3X4

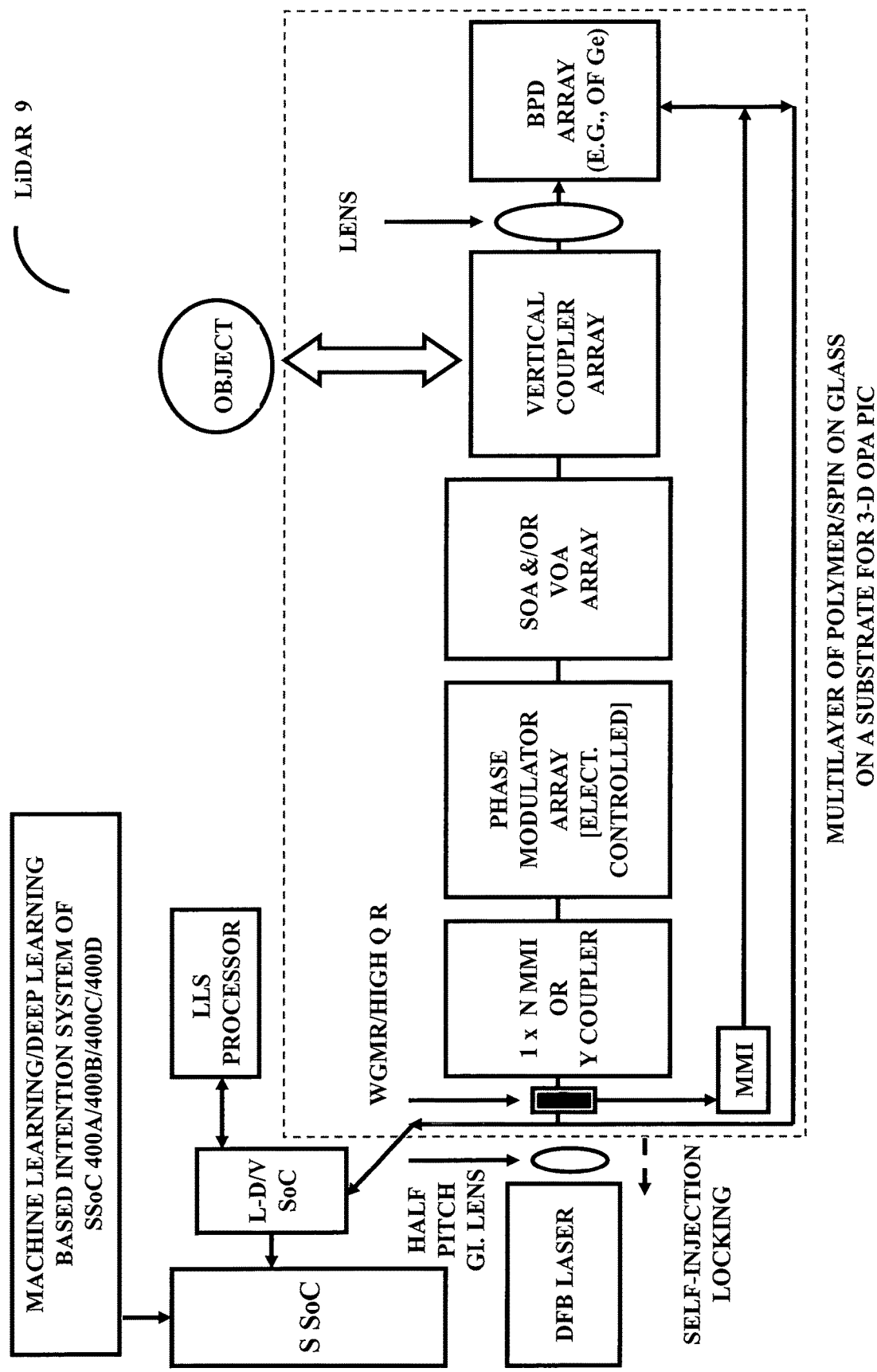
FIG. 3X5

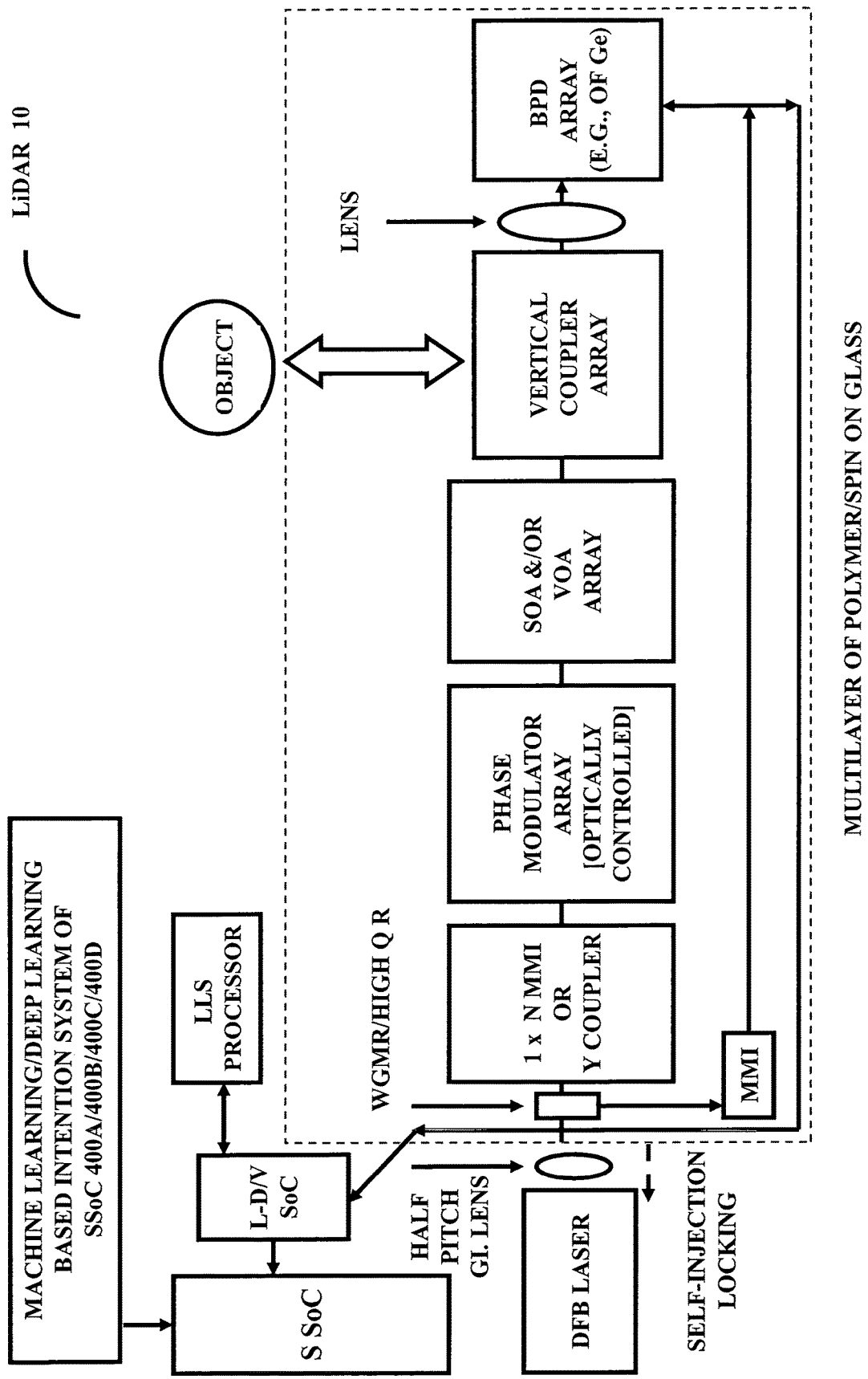
FIG. 3X6

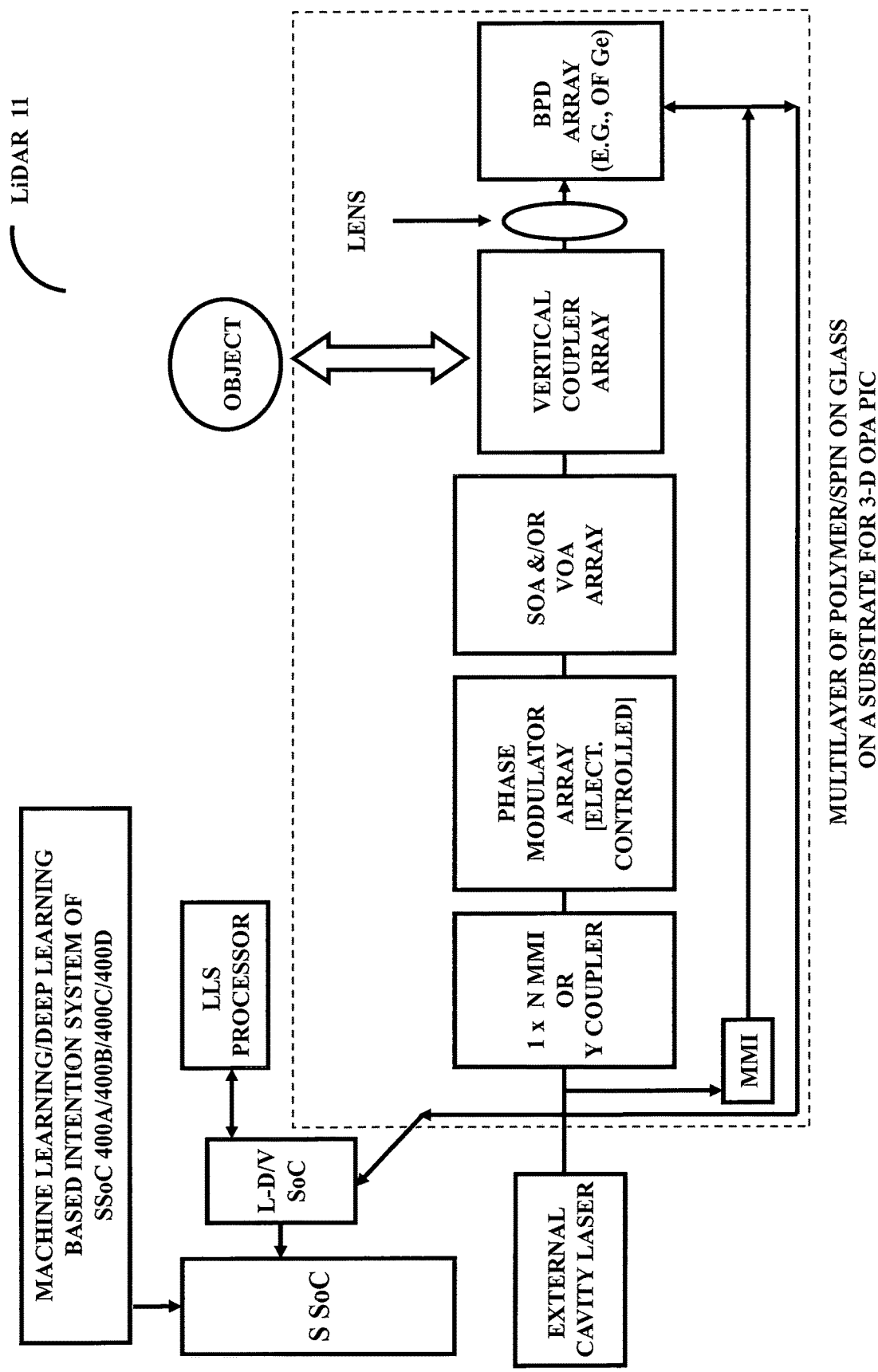
FIG. 3X7

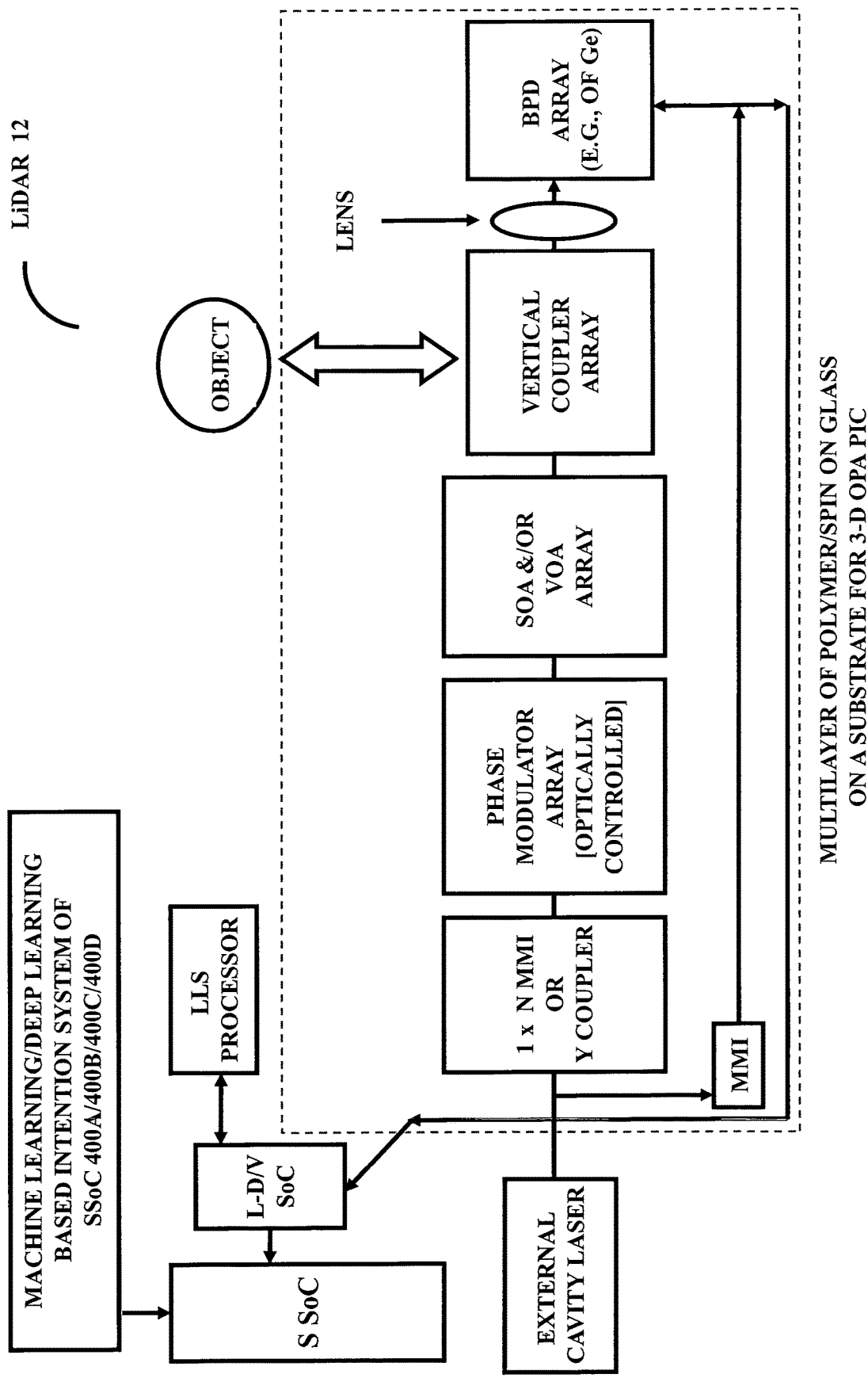
FIG. 3X8

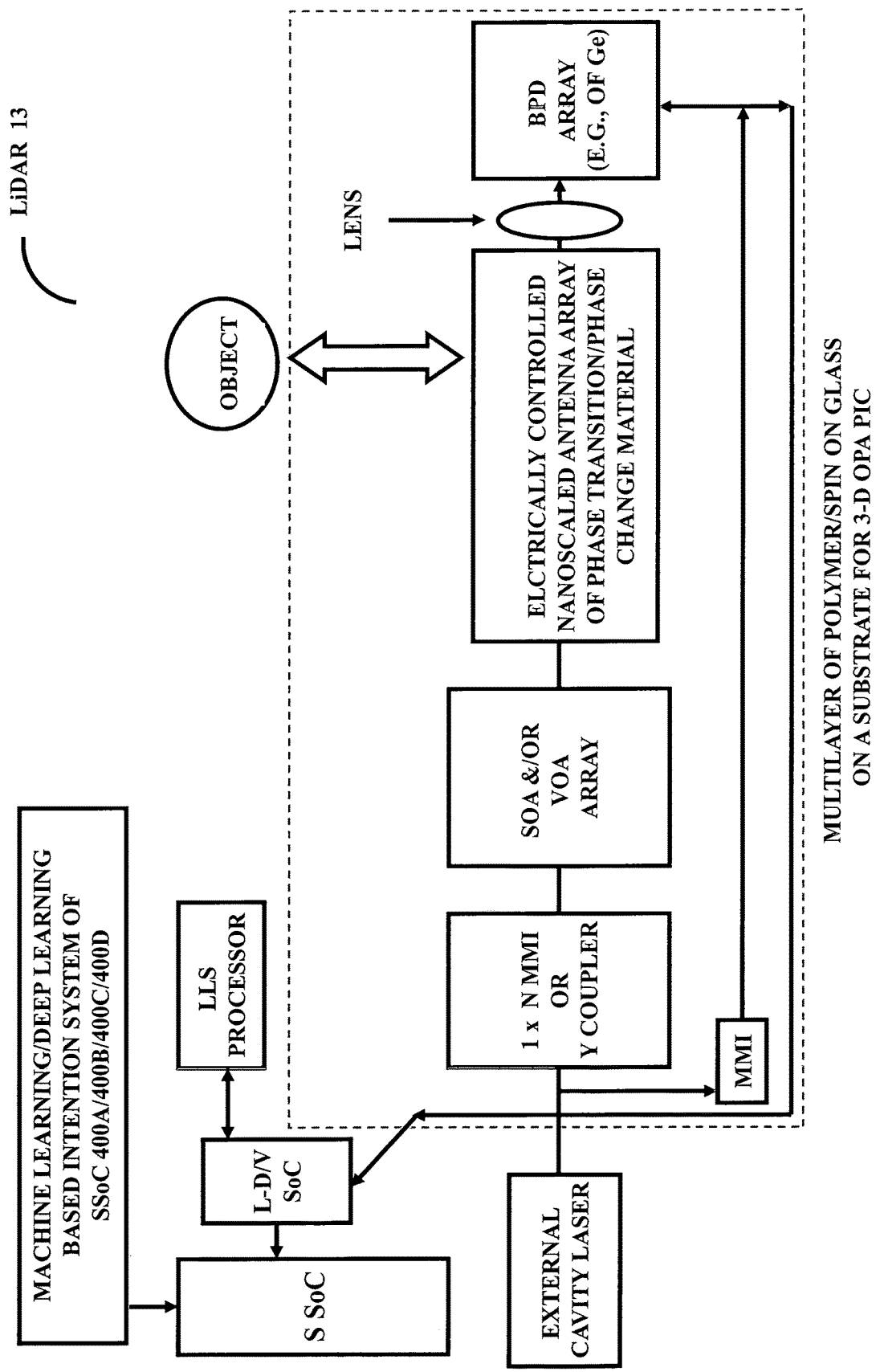
FIG. 3X9

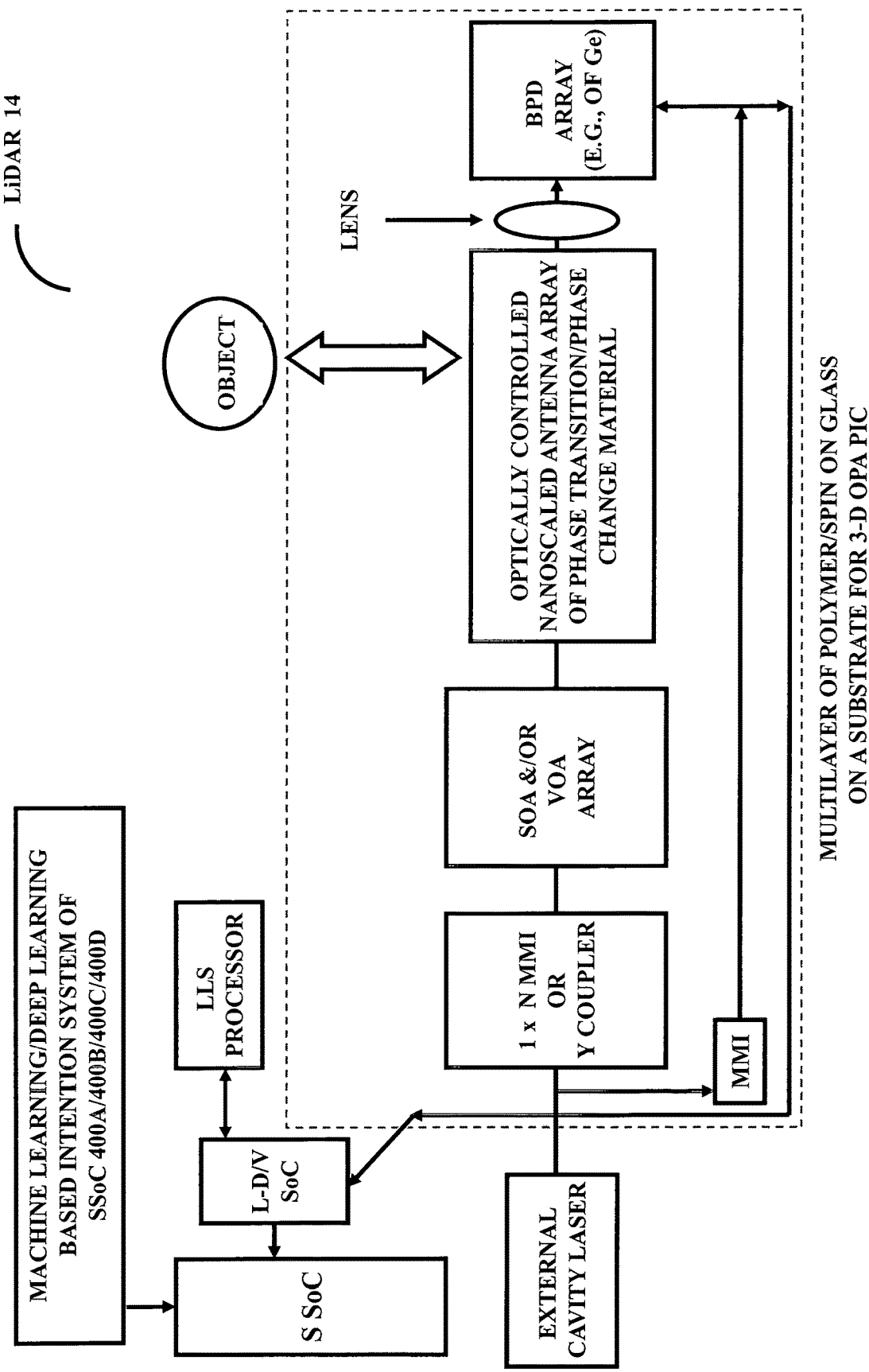
FIG. 3X10

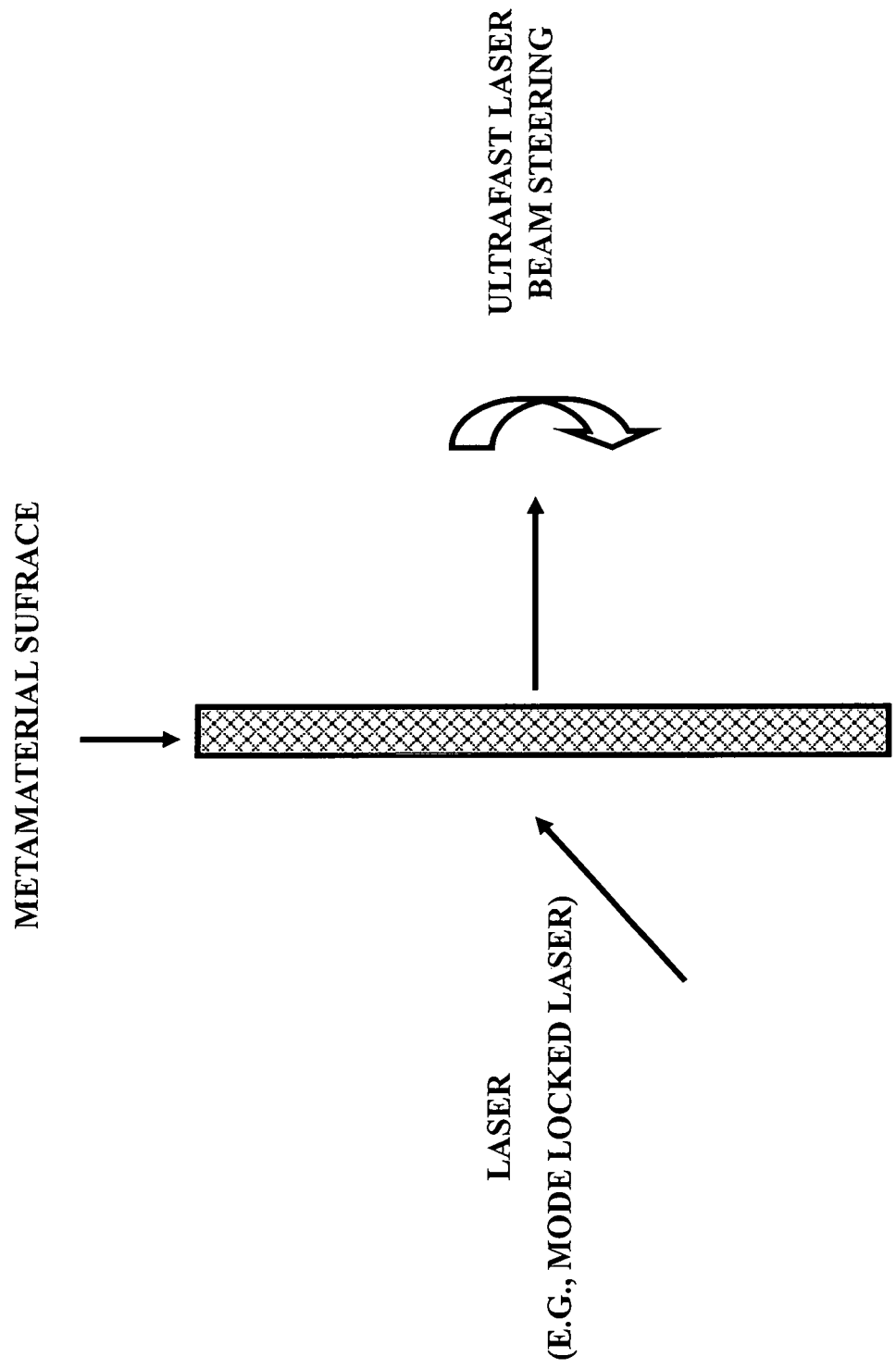
FIG. 3Y1

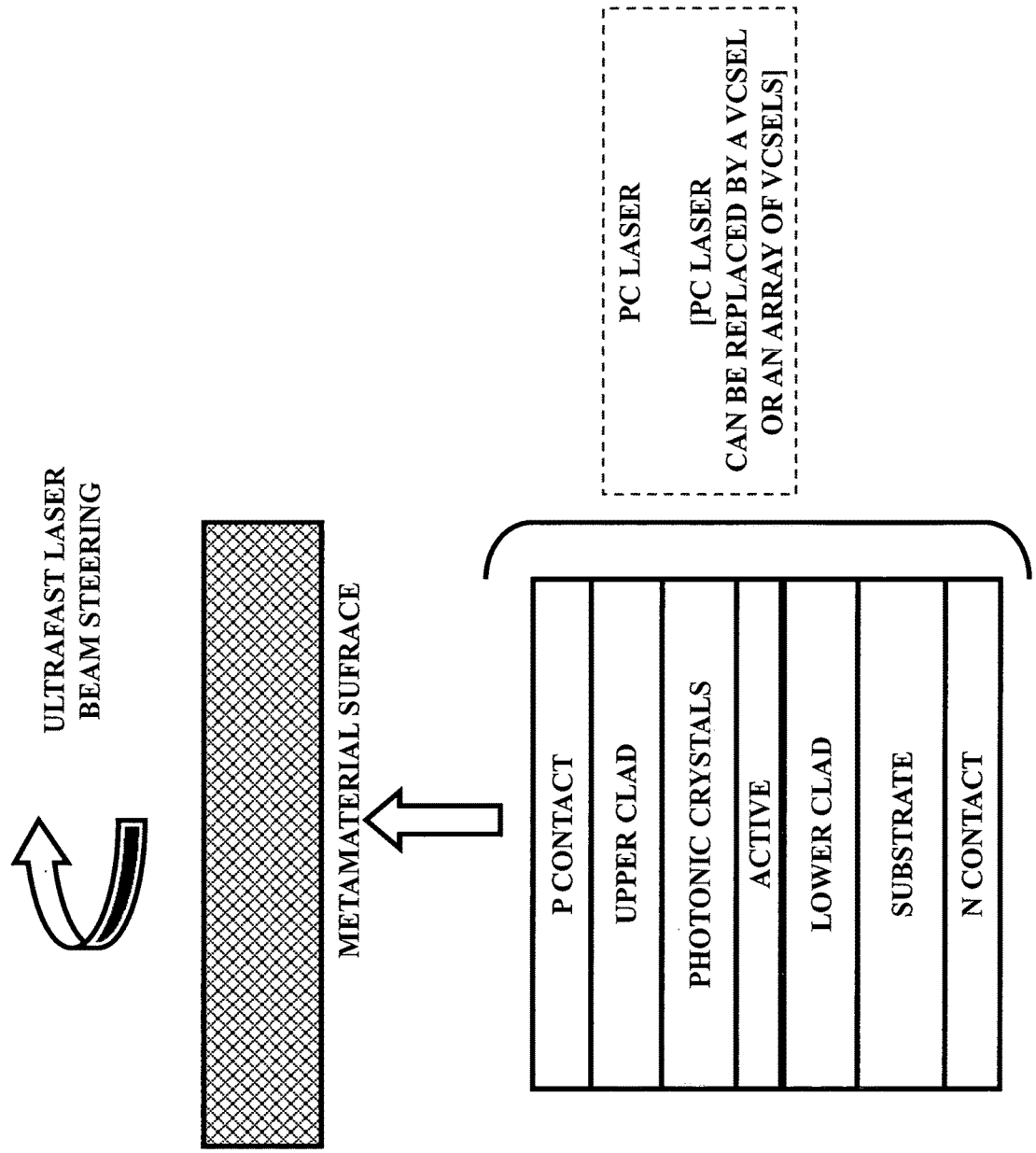
FIG. 3Y2

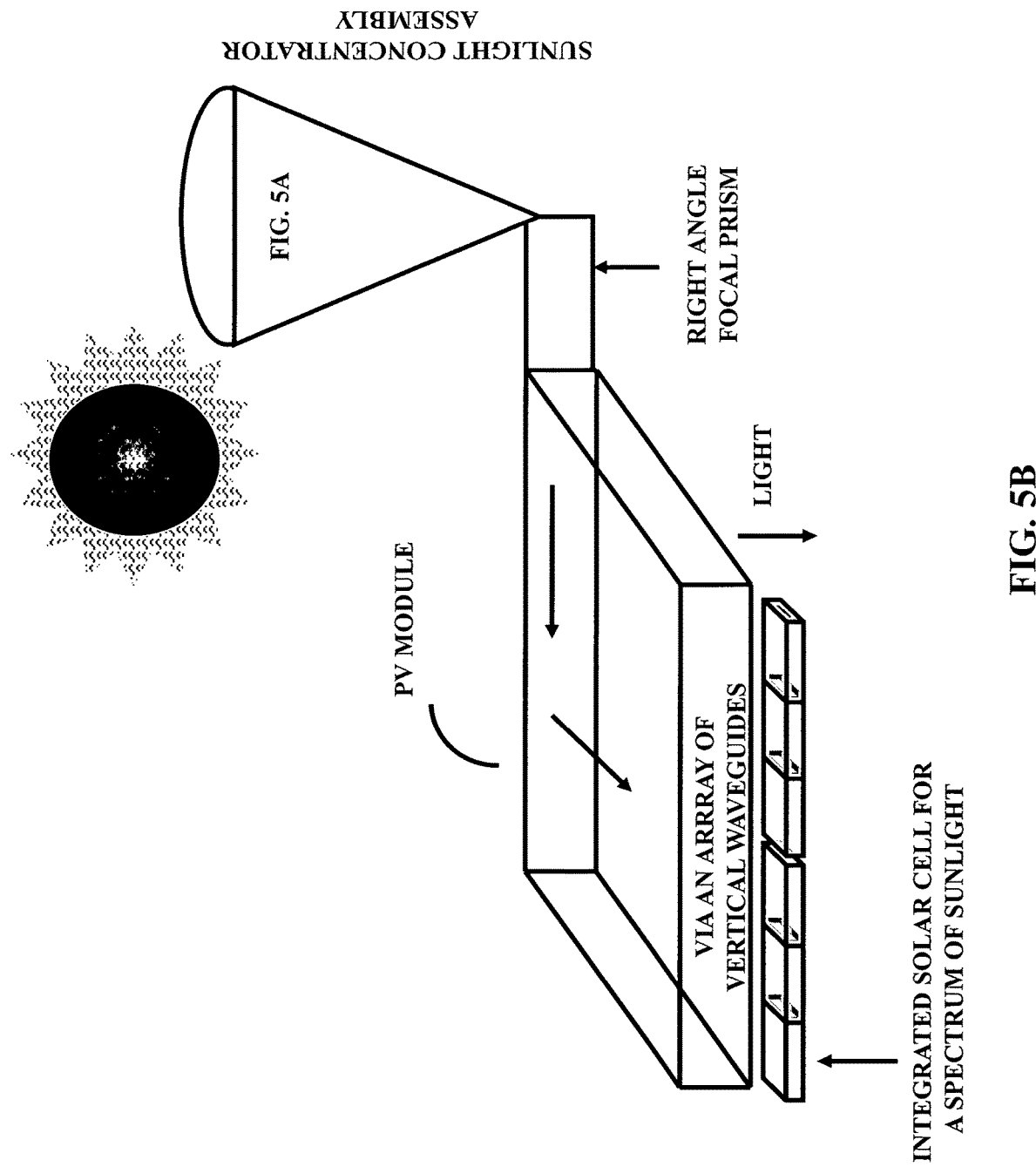

WIRED CHARGING CONFIGURATION OF CASH CARD

WIRELESS CHARGING CONFIGURATION OF CASH CARD

ELCTROMAGNETICALLY CHARGING THROUGH AIR

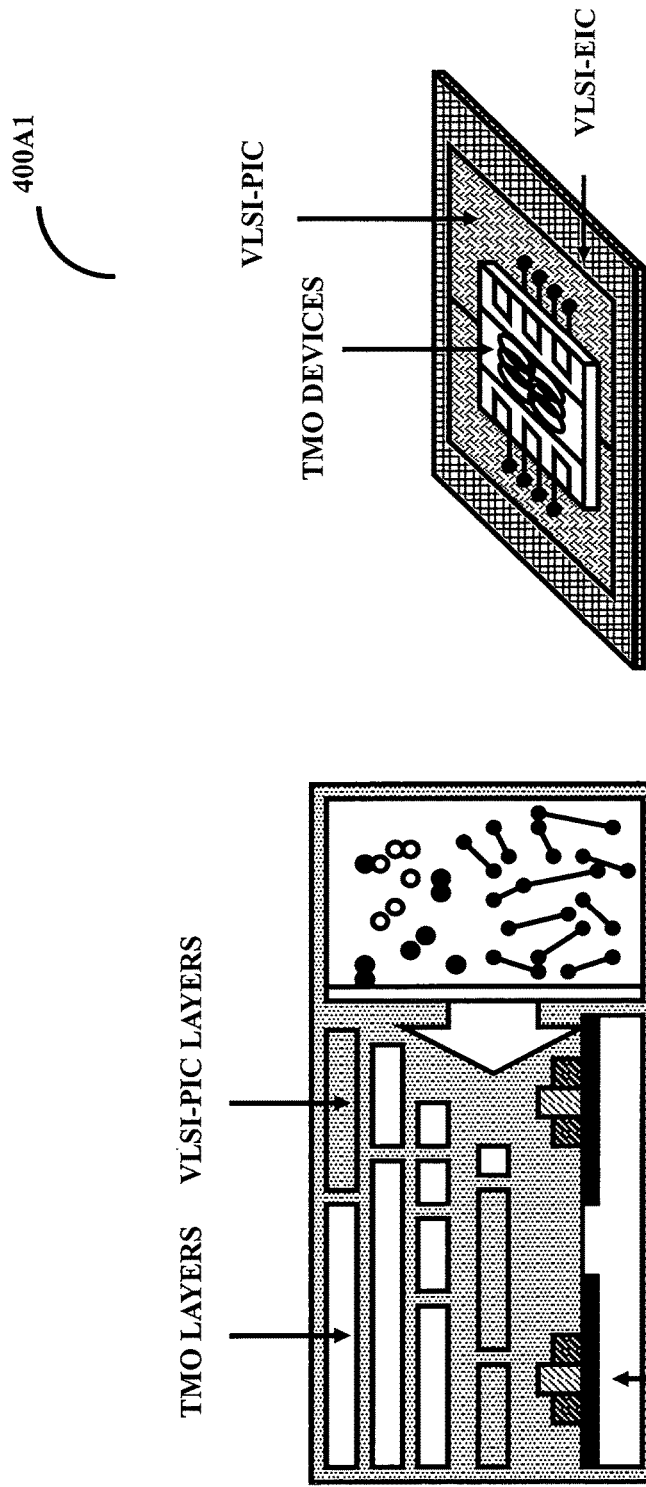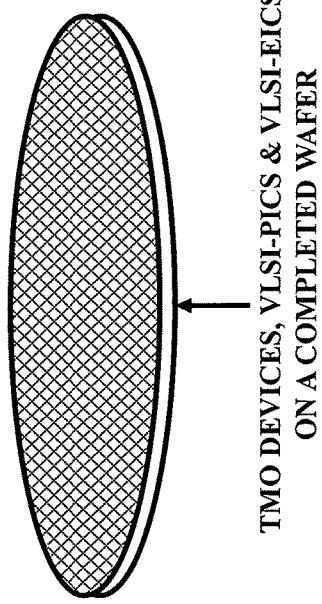
FIG. 15A
FIG. 15B
FIG. 15C

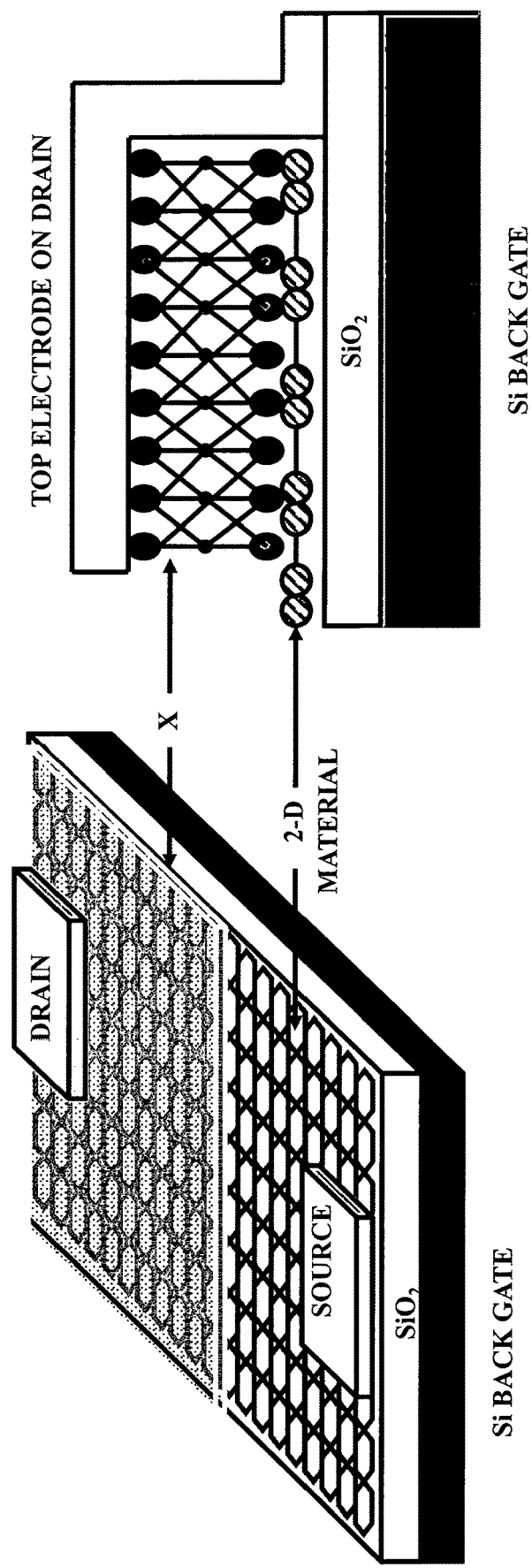

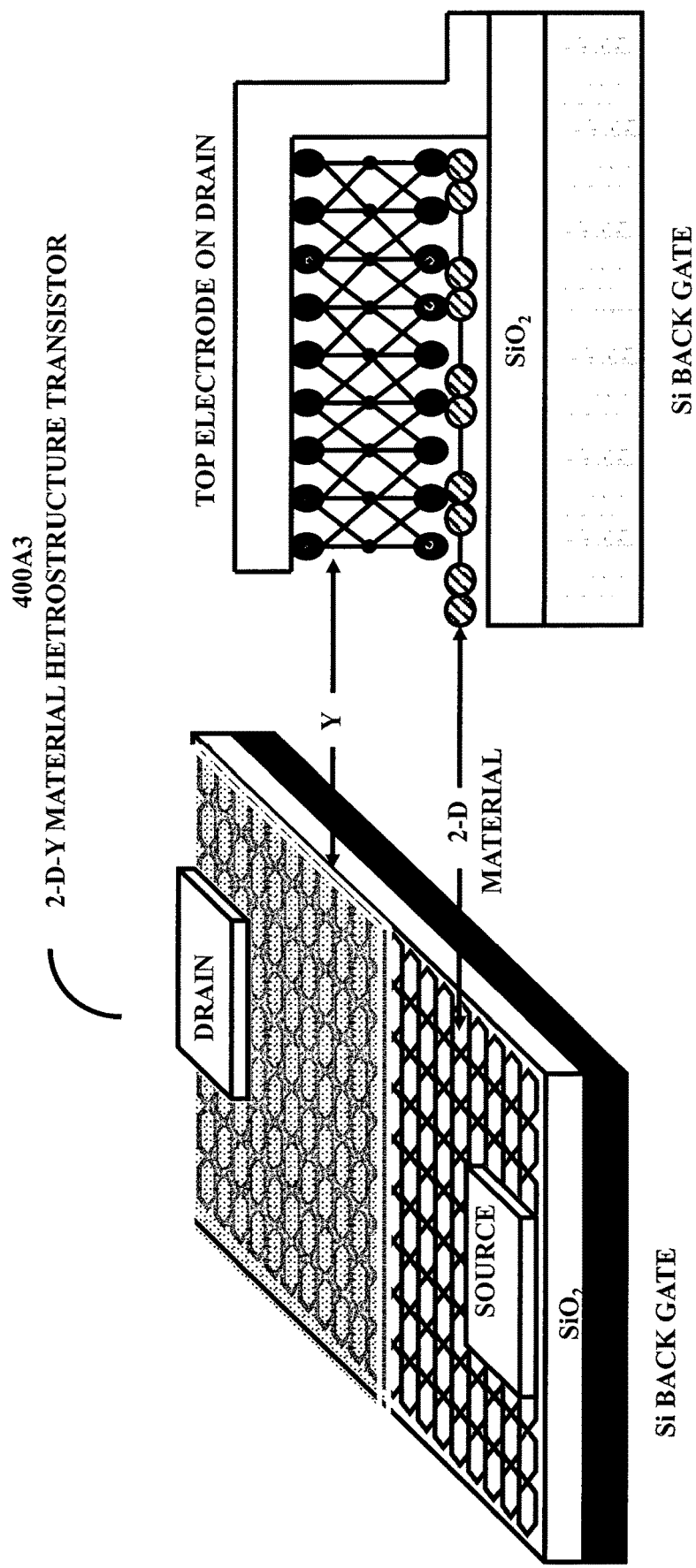

MEMRISTORS CAN BE REPLACED BY SUPER MEMRISTORS

MEMRISTORS CAN BE REPLACED BY SUPER MEMRISTORS

SSoC 400A

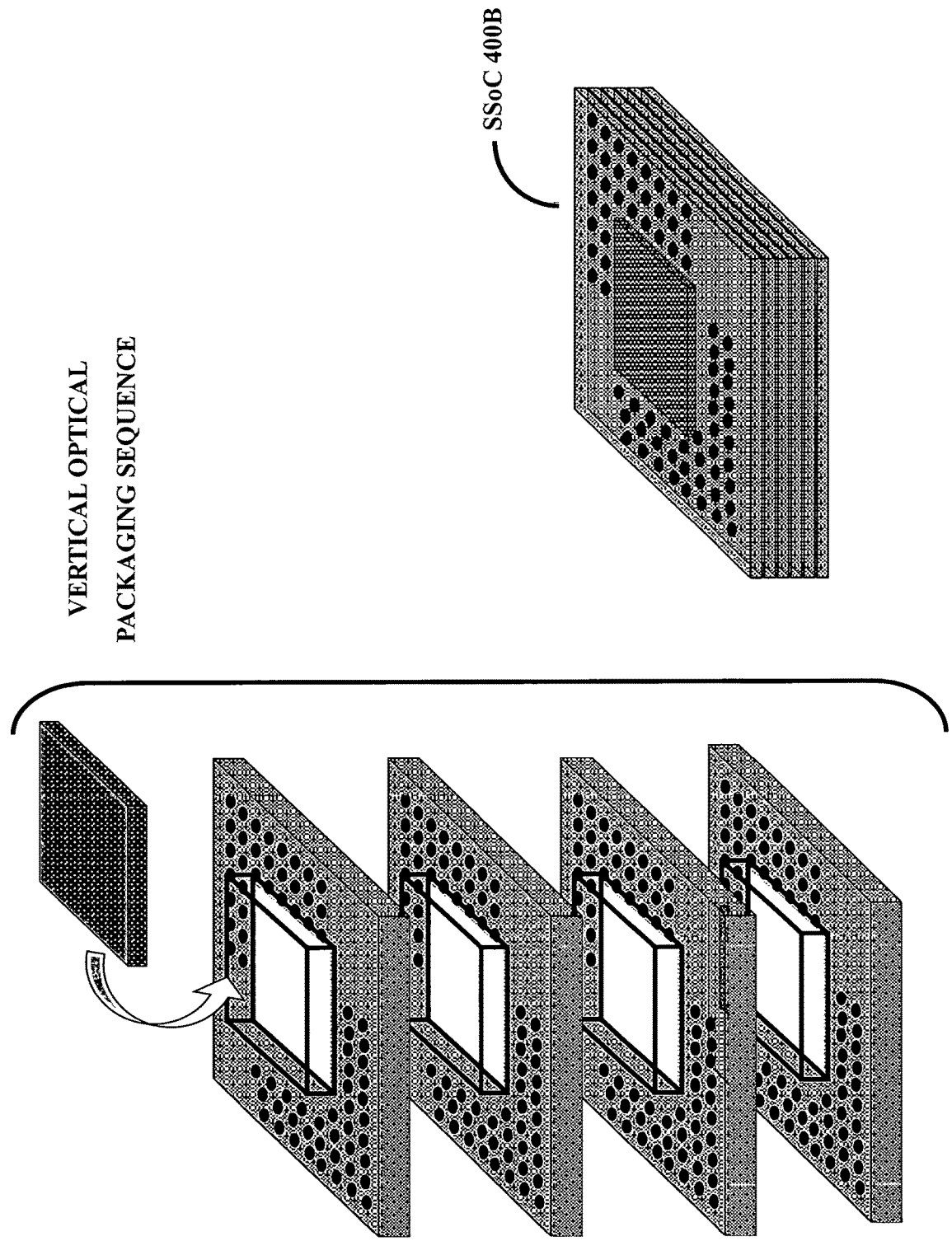

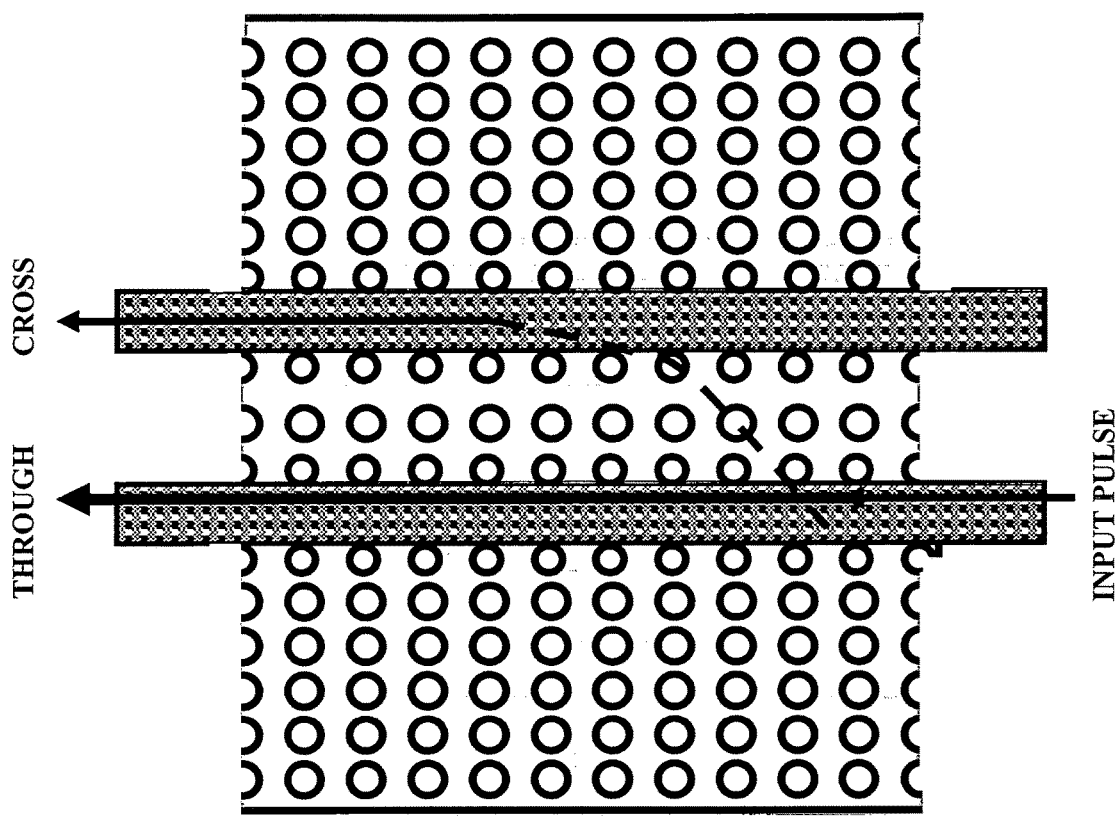

THREE-DIMENSIONAL NANO (SCALED) OPTICAL ELEMENT/ANTENNA (NOA)

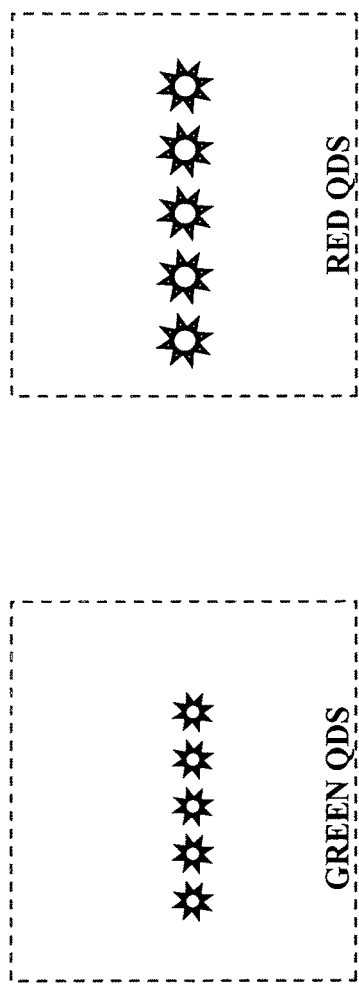
FIG. 31A  BLUE QDS
FIG. 31B  GREEN QDS
FIG. 31C  RED QDS
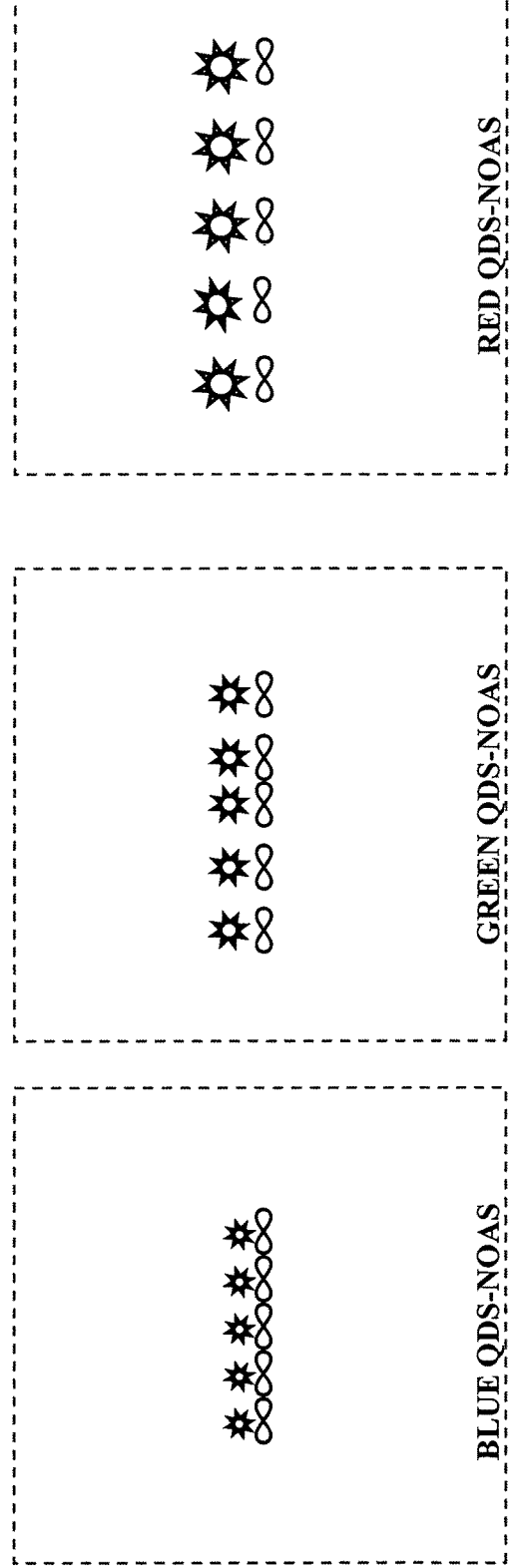
FIG. 31D  BLUE QDS-NOAS
FIG. 31E  GREEN QDS-NOAS
FIG. 31F  RED QDS-NOAS ELECTRICALLY SWITCHABLE LIGHT VALVE (LV)
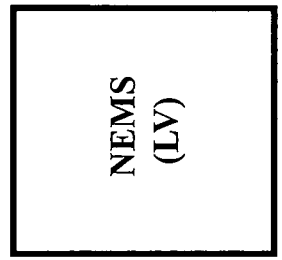
FIG. 32C NEMS (LV)
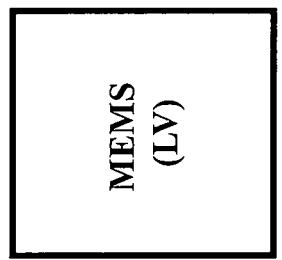
FIG. 32B MEMS (LV)
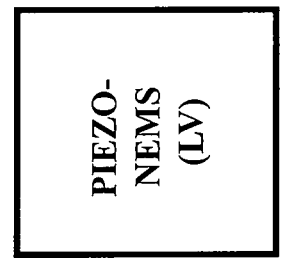
FIG. 32E PIEZO-NEMS (LV)
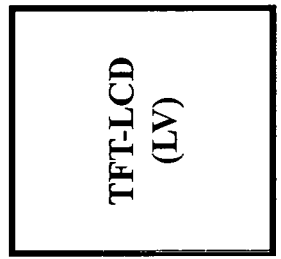
FIG. 32A TFT-LCD (LV)
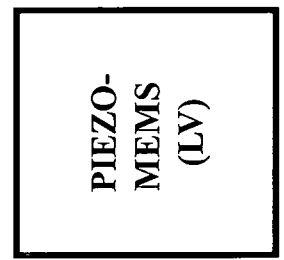
FIG. 32D PIEZO-MEMS (LV)

TYPICAL LAYER COMPOSITION OF UV/BLLUE μLED

| |
|---|
| p-InGaN (CONTACT) |
| p-GaN (LAYER) |
| p-AlGaN (ELECTRON BLOCKING) |
| Thin InGaN (SPACER) |
| MQW (ACTIVE) |
| Thick InGaN (SPACER) |
| n-GaN (CONTACT) |
| SUBSTRATE |

FIG. 36B

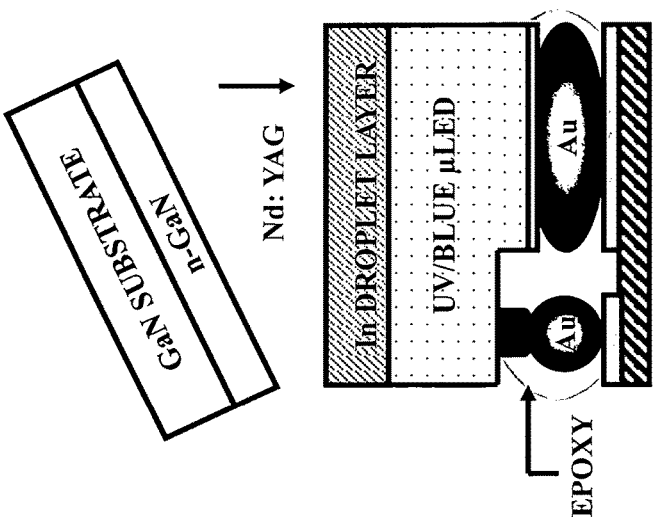
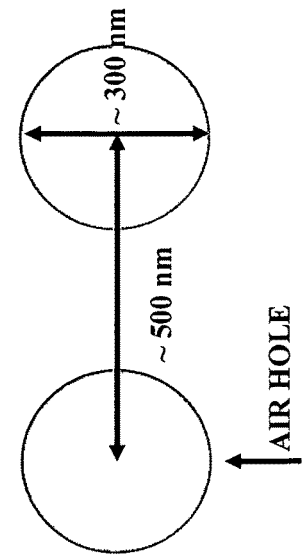
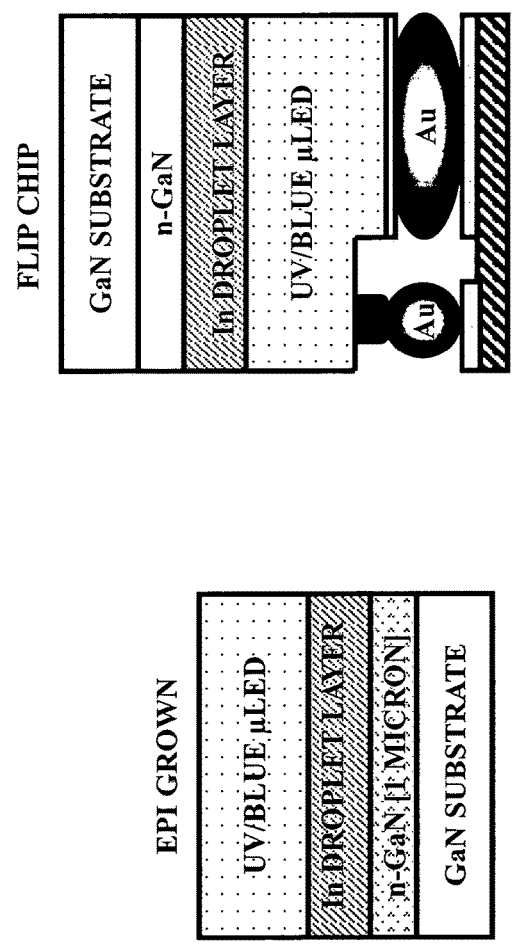
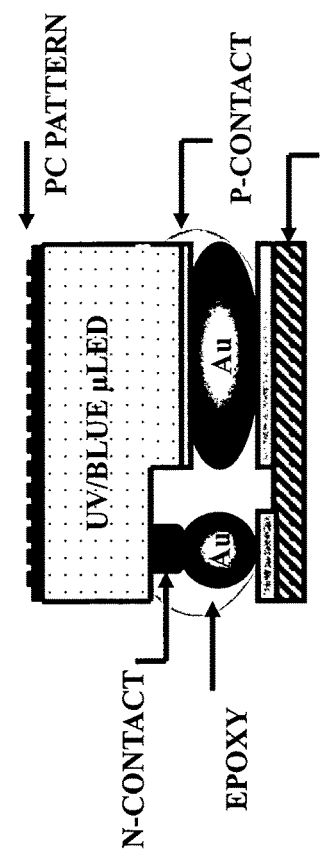
- EPOXY FILL
- SUBSTRATE LIFT-OFF PROCESS
FIG. 36C
FIG. 36D
FIG. 36E
FIG. 36F
FIG. 36G

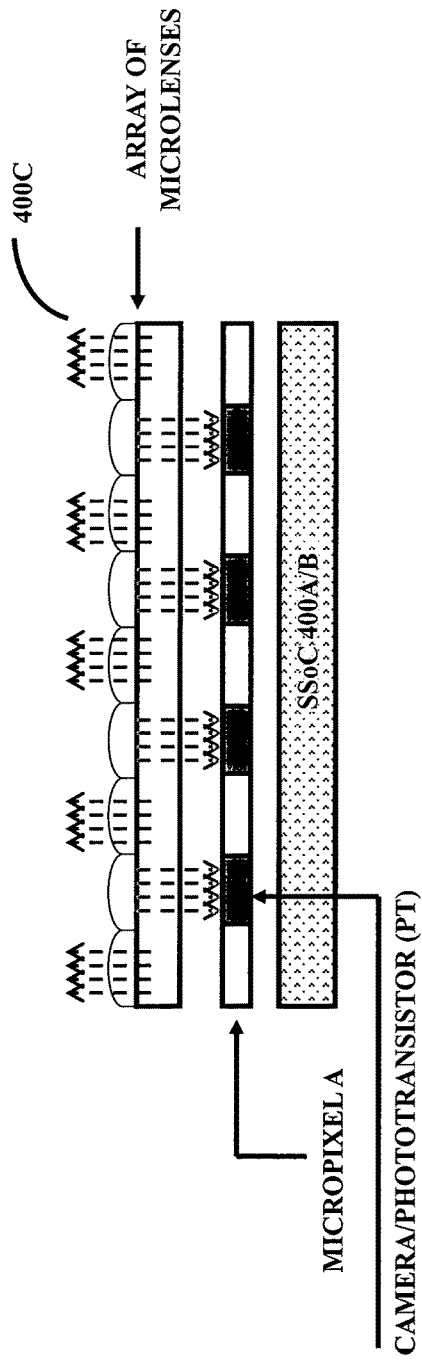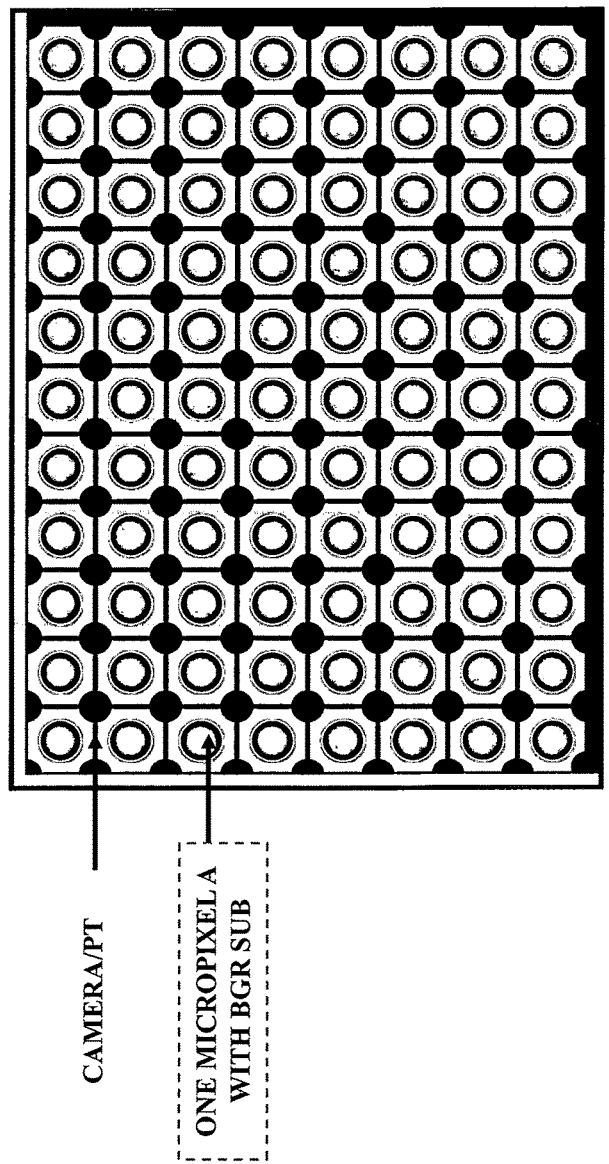
FIG. 42A
FIG. 42B

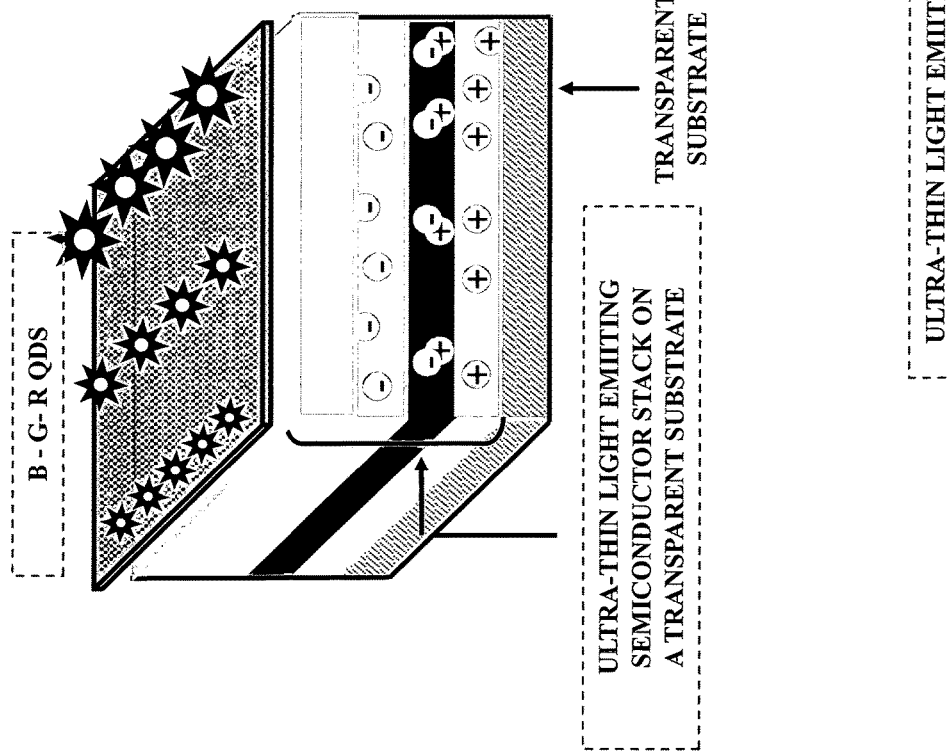
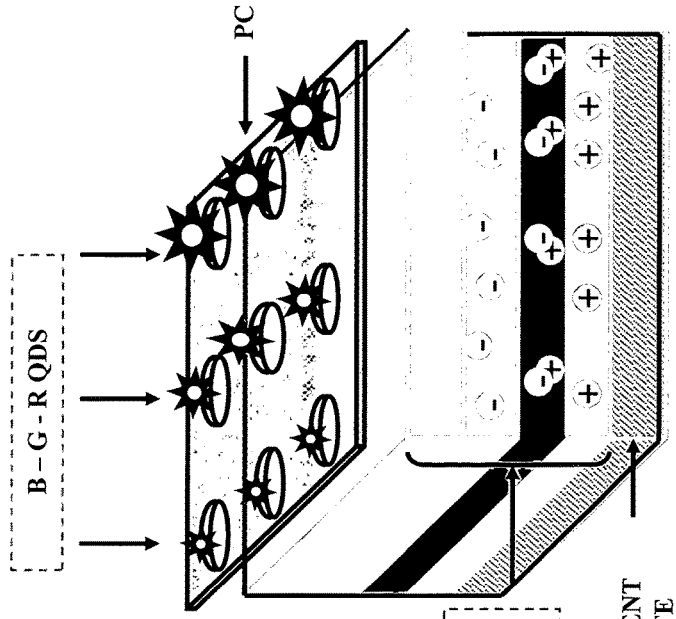
FIG. 46A
FIG. 46B

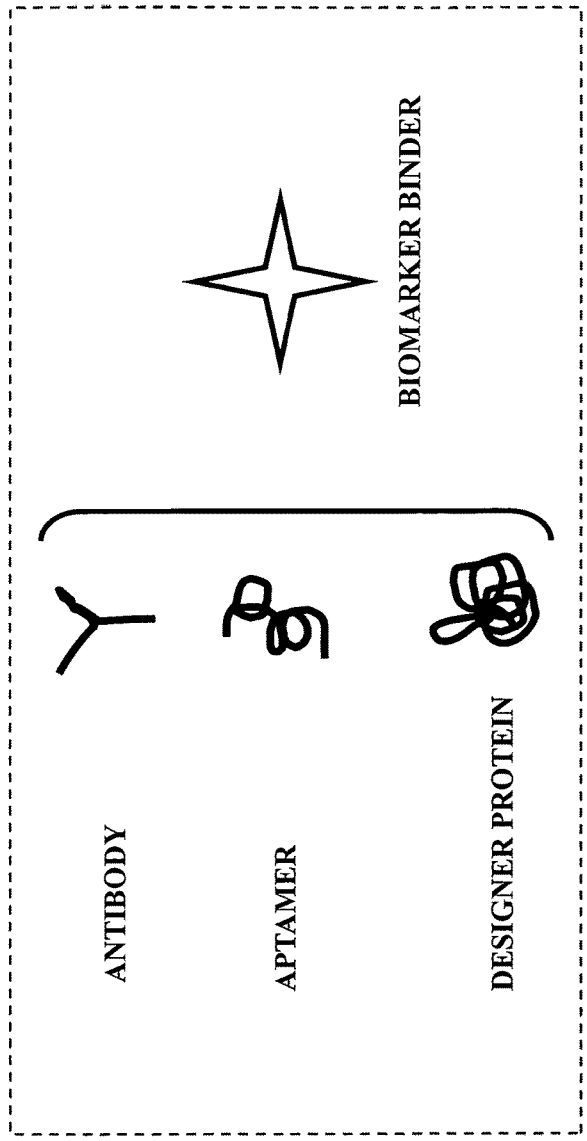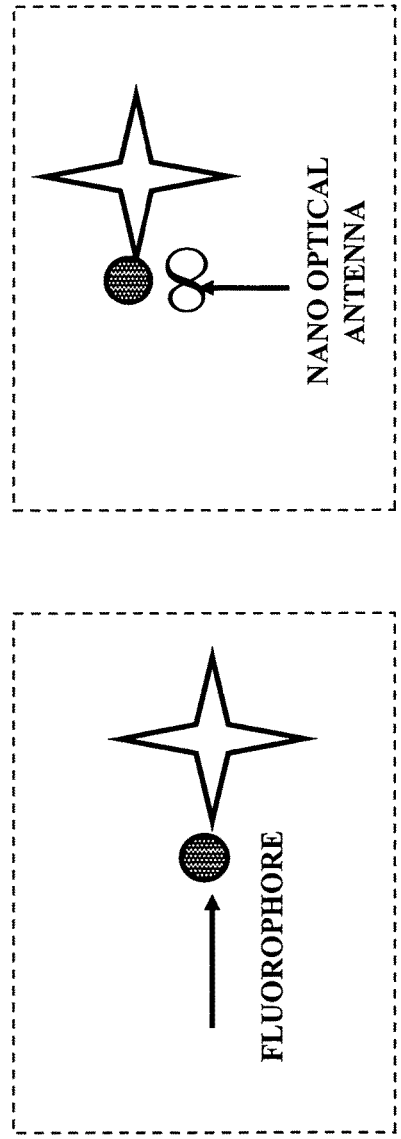
FIG. 54A  FIG. 54B  FIG. 54C

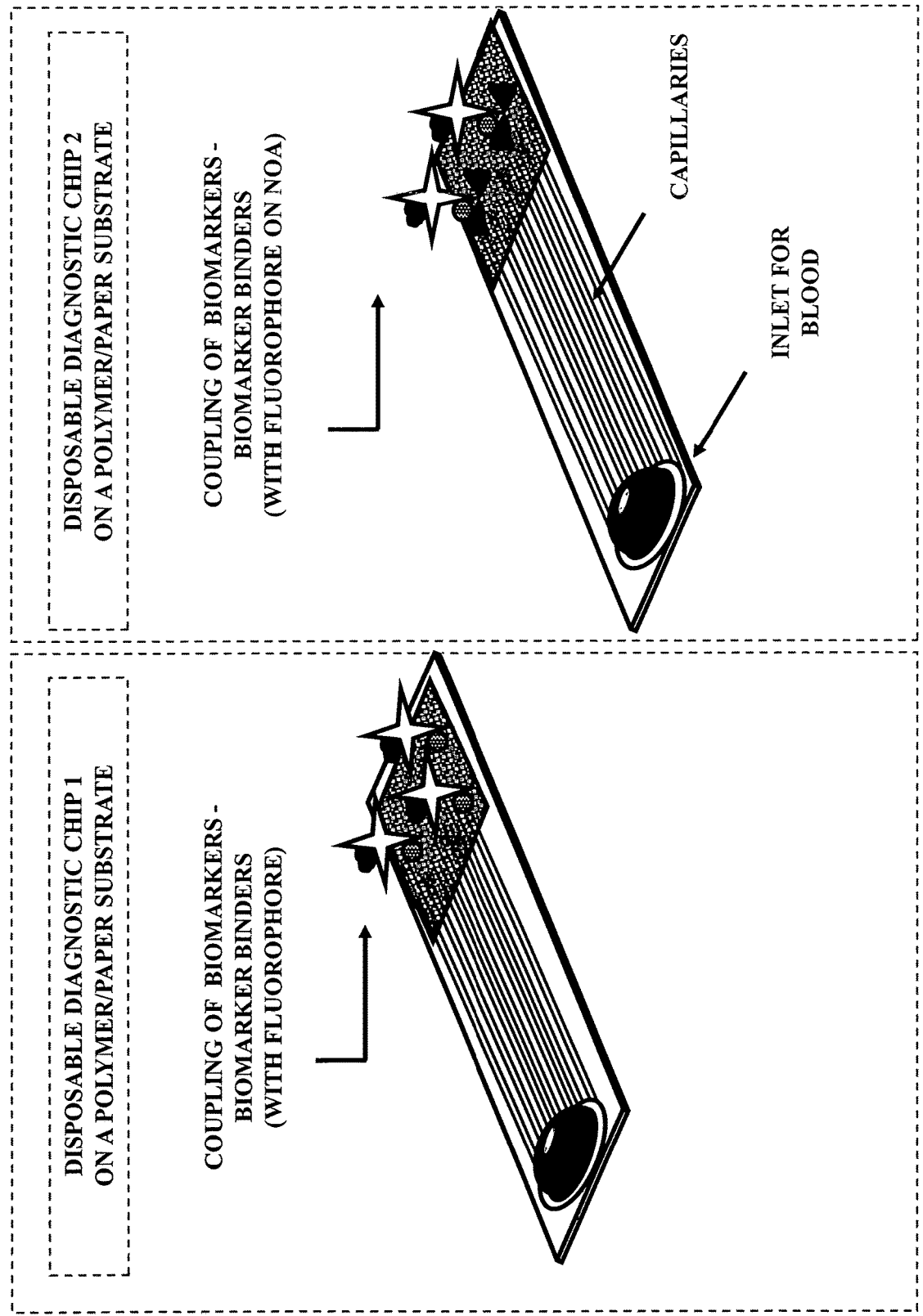

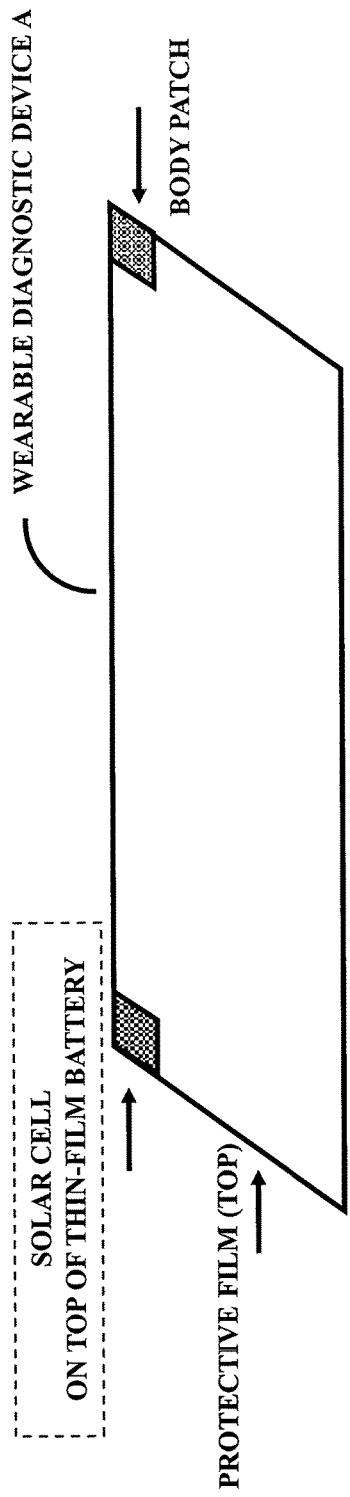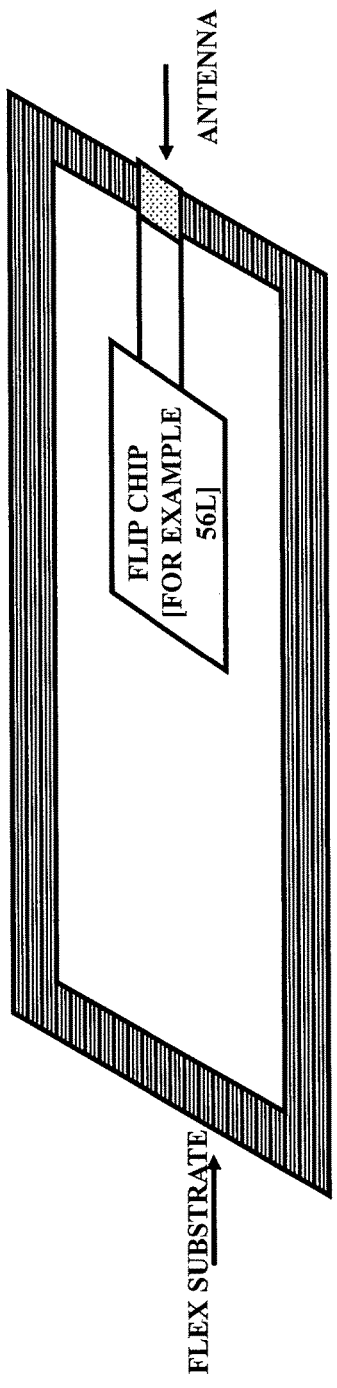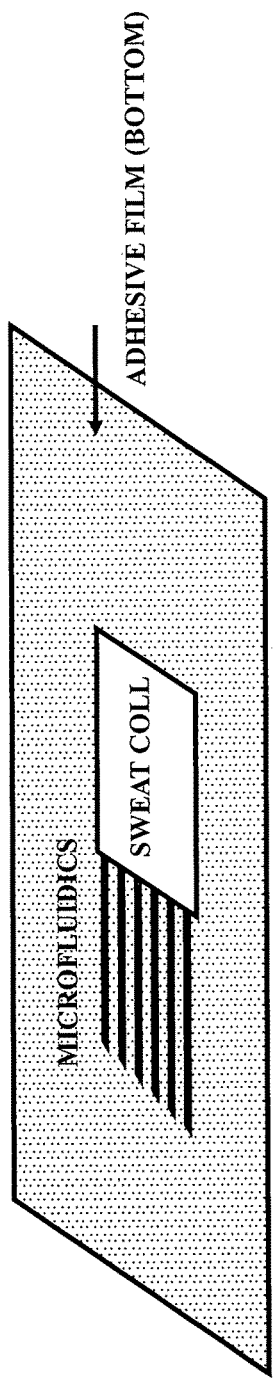
FIG. 56G
FIG. 56F
FIG. 56E

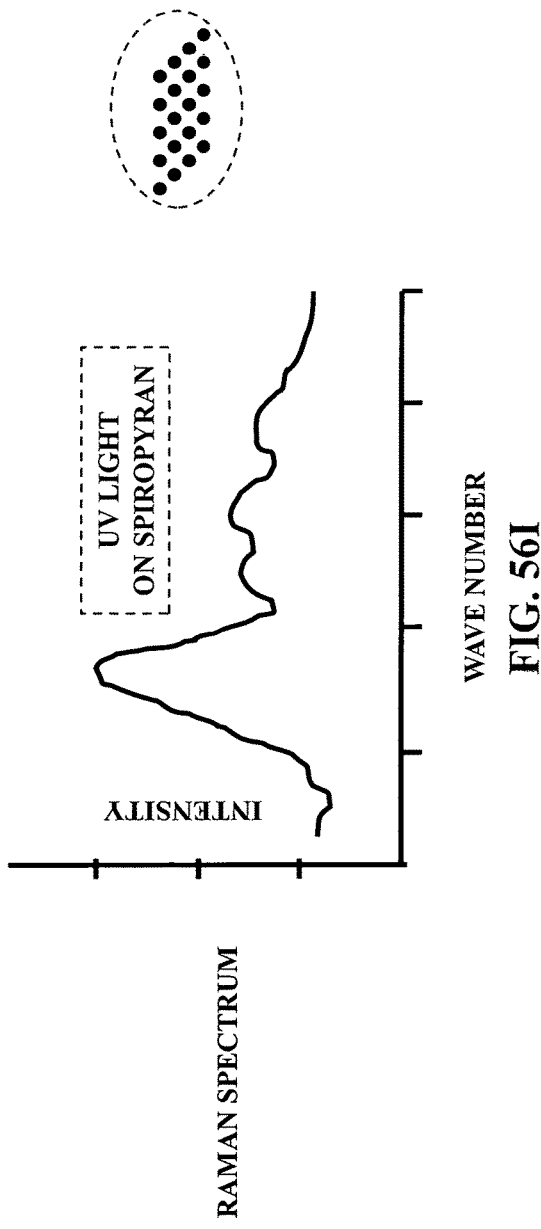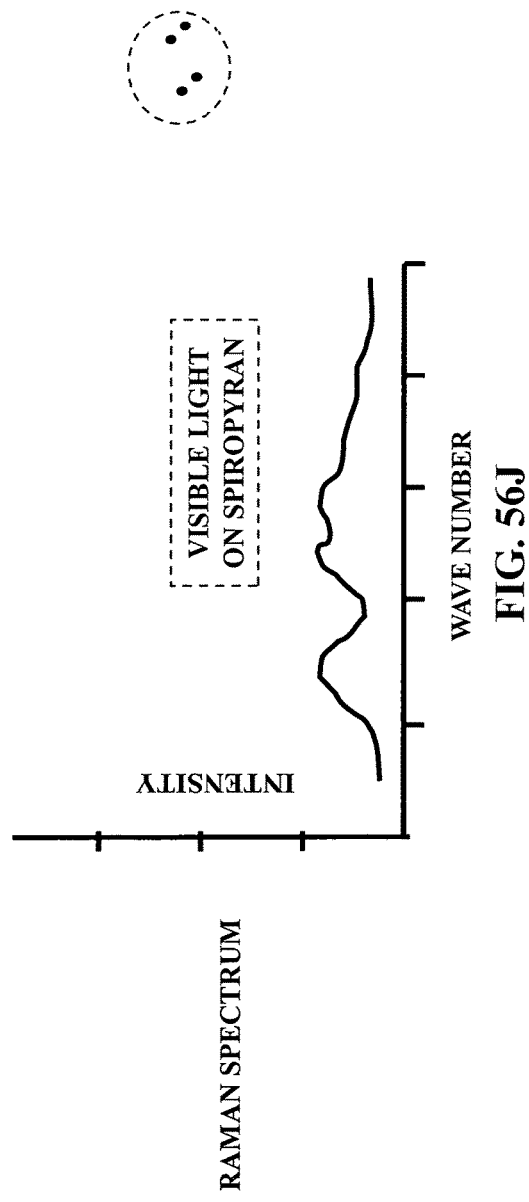

DELIVERING BIOACTIVE COMPOUND(S) IN SMART NANOSHELL

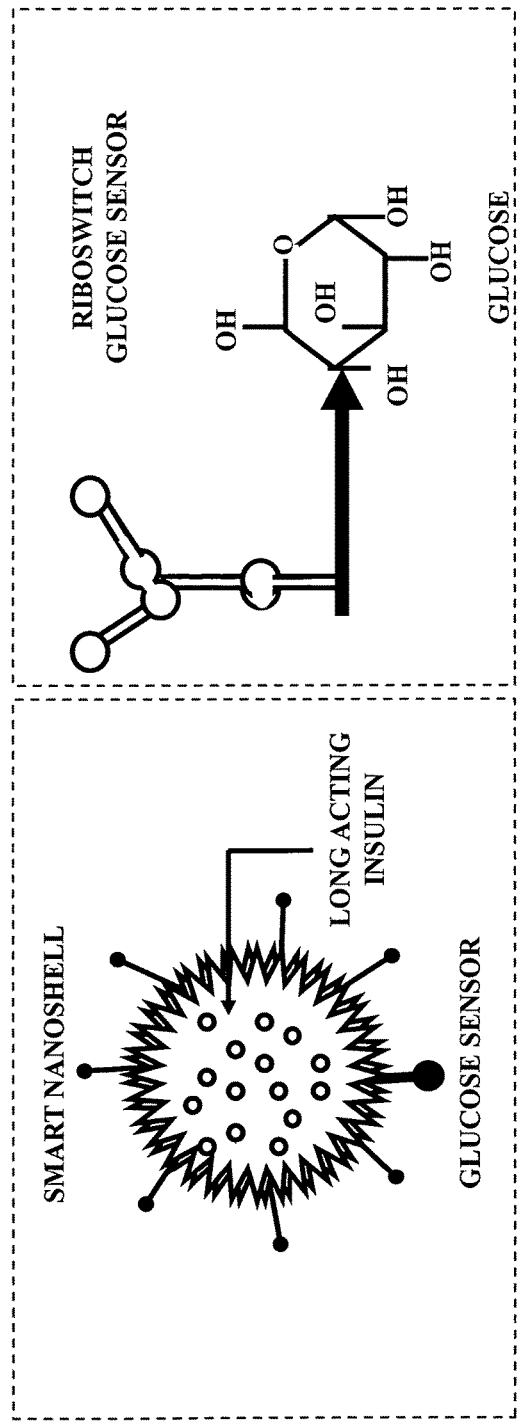
FIG. 57C
FIG. 57D
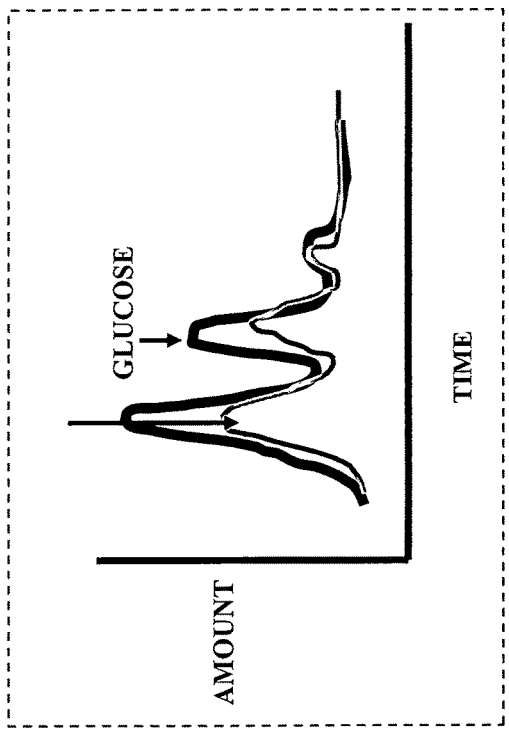
FIG. 57E

AN EXAMPLE OF A RIBOSWITCH

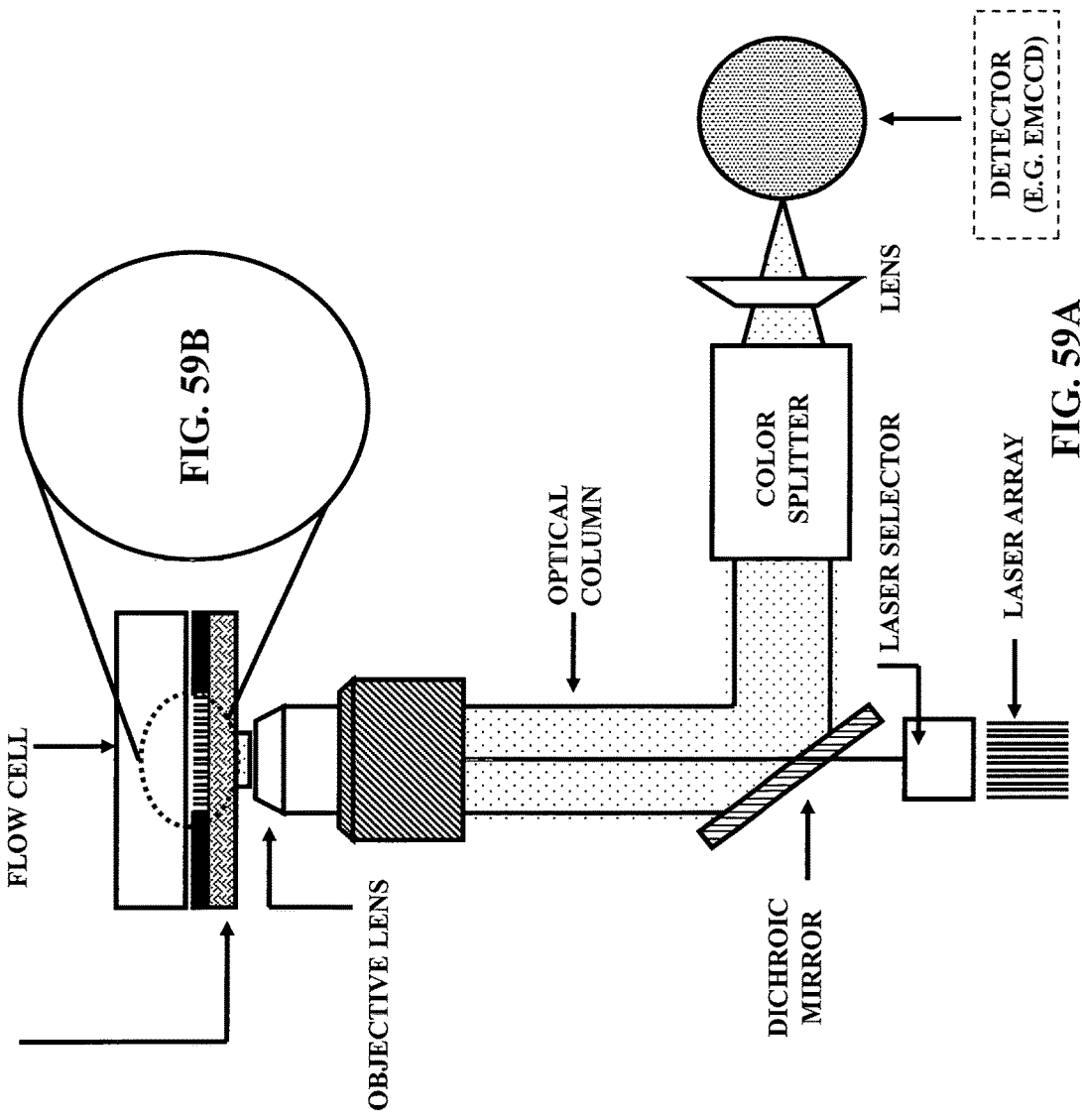

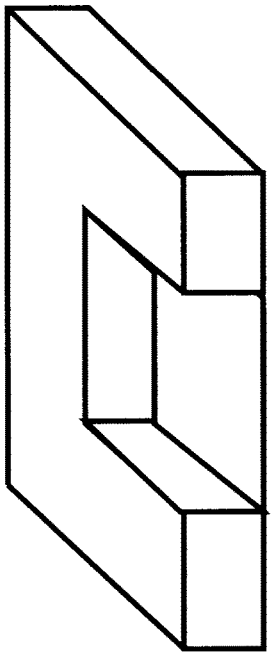
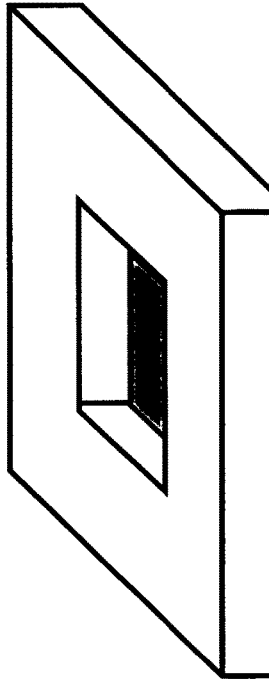
FIG. 59H
FIG. 59I
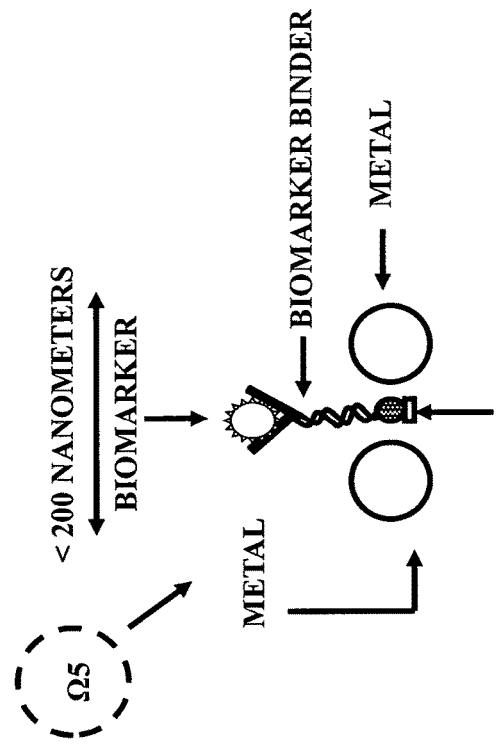
FIG. 59G

SUPER SYSTEM ON CHIP

CROSS REFERENCE OF RELATED APPLICATIONS

The present application is
a continuation-in-part (CIP) patent application of (a) U.S. Non-Provisional patent application Ser. No. 16/501,942 entitled "SYSTEM AND METHOD OF AMBIENT/PERVASIVE USER/HEALTHCARE EXPERIENCE", filed on Jul. 5, 2019,
wherein (a) is a continuation-in-part (CIP) patent application of (b) U.S. Non-Provisional patent application Ser. No. 16/350,829 entitled "SYSTEM AND METHOD OF AMBIENT/PERVASIVE USER/ HEALTHCARE EXPERIENCE", filed on Jan. 18, 2019,
wherein (b) is a continuation-in-part (CIP) patent application of (c) U.S. Non-Provisional patent application Ser. No. 16/350,169 entitled "SYSTEM AND METHOD OF AMBIENT/PERVASIVE USER/ HEALTHCARE EXPERIENCE", filed on Oct. 9, 2018,
wherein (c) is a continuation-in-part (CIP) patent application of (d) U.S. Non-Provisional patent application Ser. No. 15/932,598 entitled "SYSTEM AND METHOD OF AMBIENT/PERVASIVE USER/ HEALTHCARE EXPERIENCE", filed on Mar. 19, 2018,
wherein (d) is a continuation-in-part (CIP) patent application of (e) U.S. Non-Provisional patent application Ser. No. 15/731,577 entitled "OPTICAL BIOMODULE FOR DETECTION OF DISEASES AT AN EARLY ONSET, filed on Jul. 3, 2017,
wherein (d) a continuation-in-part (CIP) patent application of (f) U.S. Non-Provisional patent application Ser. No. 14/999,601 entitled "DISPLAY DEVICE", filed on Jun. 1, 2016, (resulted in a U.S. Pat. No. 9,923,124, issued on Mar. 20, 2018),
wherein (f) claims priority benefit to (g) U.S. Provisional Patent Application No. 62/230,249 entitled "SYSTEM AND METHOD OF AMBIENT/PERVASIVE USER/HEALTHCARE EXPERIENCE", filed on Jun. 1, 2015,
wherein (f) a continuation-in-part (CIP) patent application of (h) U.S. Non-Provisional patent application Ser. No. 14/120,835 entitled "AUGMENTED REALITY PERSONAL ASSISTANT APPARATUS", filed on Jul. 1, 2014 (resulted in a U.S. Pat. No. 9,823,737, issued on Nov. 21, 2017),
wherein (f) a continuation-in-part (CIP) patent application of (i) U.S. Non-Provisional patent application Ser. No. 14/014,239 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Aug. 29, 2013 (resulted in a U.S. Pat. No. 9,426,545, issued on Aug. 23, 2016),
wherein (f) a continuation-in-part (CIP) patent application of (j) U.S. Non-Provisional patent application Ser. No. 13/663,376 entitled "OPTICAL BIOMODULE FOR DETECTION OF DISEASES", filed on Oct. 29, 2012 (resulted in a U.S. Pat. No. 9,557,271, issued on Jan. 31, 2017) and
wherein (f) a continuation-in-part (CIP) patent application of (k) U.S. Non-Provisional patent application Ser. No. 13/448,378 entitled "SYSTEM AND METHOD FOR INTELLIGENT SOCIAL COMMERCE", filed on Apr. 16, 2012 (resulted in a U.S. Pat. No. 9,697,556, issued on Jul. 4, 2017).

The entire contents of all (i) U.S. Non-Provisional Patent Applications, (ii) U.S. Provisional Patent Applications, as listed in the previous paragraph and (iii) the filed (Patent) Application Data Sheet (ADS) are hereby incorporated by reference, as if they are reproduced herein in their entirety.

FIELD OF THE INVENTION

With the dawn of the Internet of Things (IoT), the present invention is multi-disciplined and highly diverse, as it relates to objects/object nodes, bioobjects/bioobject nodes which are connected with a Personal Human Operating System (Personal OS), intelligent portable internet appliances, intelligent wearable augmented reality personal assistant devices, wearable personal health assistant devices and intelligent (energy efficient) vehicles.

SUMMARY OF THE INVENTION

In view of the foregoing, one objective of the present invention is to design and construct a system and method for
    ambient/pervasive user experience in near real time/real time, and
    ambient/pervasive Personal Human Operating System

BRIEF DESCRIPTION OF THE DRAWINGS

Internet Connected Objects (Sensors), Devices & Systems

FIG. 3U consists of FIG. 3U1, FIG. 3U2, FIG. 3U3 and FIG. 3U4. FIG. 3U1 illustrates an embodiment of a standalone computational camera 1. FIGS. 3U2 illustrates another embodiment of a standalone computational camera 2. FIG. 3U3 illustrates another embodiment of a standalone computational camera 3. FIG. 3U4 illustrates an embodiment of a high power (wavelength) tunable pulsed laser module (HP-TP-LM).

FIG. 3V consists of FIG. 3V1, FIG. 3V2 and FIG. 3V3. Furthermore, FIG. 3V3. consists of FIG. 3V3.1, FIG. 3V3.2 and FIG. 3V3.3. FIG. 3V1 illustrates an embodiment to combine the low-noise silicon single photon avalanche multiplication with the infrared wavelength detection/absorption of a thick germanium (Ge) layer. FIG. 3V2 illustrates a two dimensional (2-D) array of single photon avalanche diodes in fully parallel processing.

Furthermore, FIG. 3V3 consists of FIG. 3V3.1, FIG. 3V3.2 and FIG. 3V3.2. FIG. 3V3.1 illustrates integration of an image sensor (based on single photon avalanche diodes-including single photon avalanche diodes fabricated/constructed on indium phosphide or germanium-on-silicon (Ge—Si) material) with a complementary metal-oxide-semiconductor integrated circuit (of control and read-out electronics). FIG. 3V3.2 illustrates integration of an image sensor (based on single photon avalanche diodes-including single photon avalanche diodes fabricated/constructed on indium phosphide or germanium-on-silicon material) with a complementary metal-oxide-semiconductor integrated circuit (of control and read-out electronics) plus a two-dimensional/three-dimensional array of memristors/a two-dimensional/three-dimensional network of memristors. FIG. 3V3.3 illustrates integration of an image sensor (based on single photon avalanche diodes-including single photon avalanche diodes fabricated/constructed on indium phosphide or germanium-on-silicon material) with a complementary metal-oxide-semiconductor integrated circuit (of control and read-out electronics) plus the Super System on Chip (SSoC).

FIGS. 3W1-3W4 illustrate four (4) embodiments of packaging of a computational camera.

FIG. 3W5 illustrates an embodiment of flip chip mounting a pulsed laser of a computational camera, wherein n-metal contact is fabricated/constructed by metallized via hole(s).

FIG. 3W6 illustrates an embodiment of flip chip mounting an array of pulsed lasers of a computational camera, wherein n-metal contact is fabricated/constructed by metallized via hole(s).

FIG. 3X consists of FIG. 3X1, FIG. 3X2, FIG. 3X3, FIG. 3X4, FIG. 3X5, FIG. 3X6, FIG. 3X7, FIG. 3X8, FIG. 3X9 and FIG. 3X10. FIGS. 3X1-3X10 illustrate ten (10) embodiments of an integrated detection and ranging subsystem on multilayer of polymer/spin-on-glass (SOG) on a substrate (e.g., silicon on insulator), utilizing a three-dimensional (3-D) photonic integrated circuit (PIC) based optical phase array (OPA).

FIG. 3Y consists of FIG. 3Y1 and FIG. 3Y2. FIGS. 3Y1-3Y2 illustrate two (2) embodiments for ultrafast laser beam steering (with two different pulsed lasers), utilizing a metamaterial surface.

Photovoltaic & Artificial Photosynthesis Module

Figure 5A:
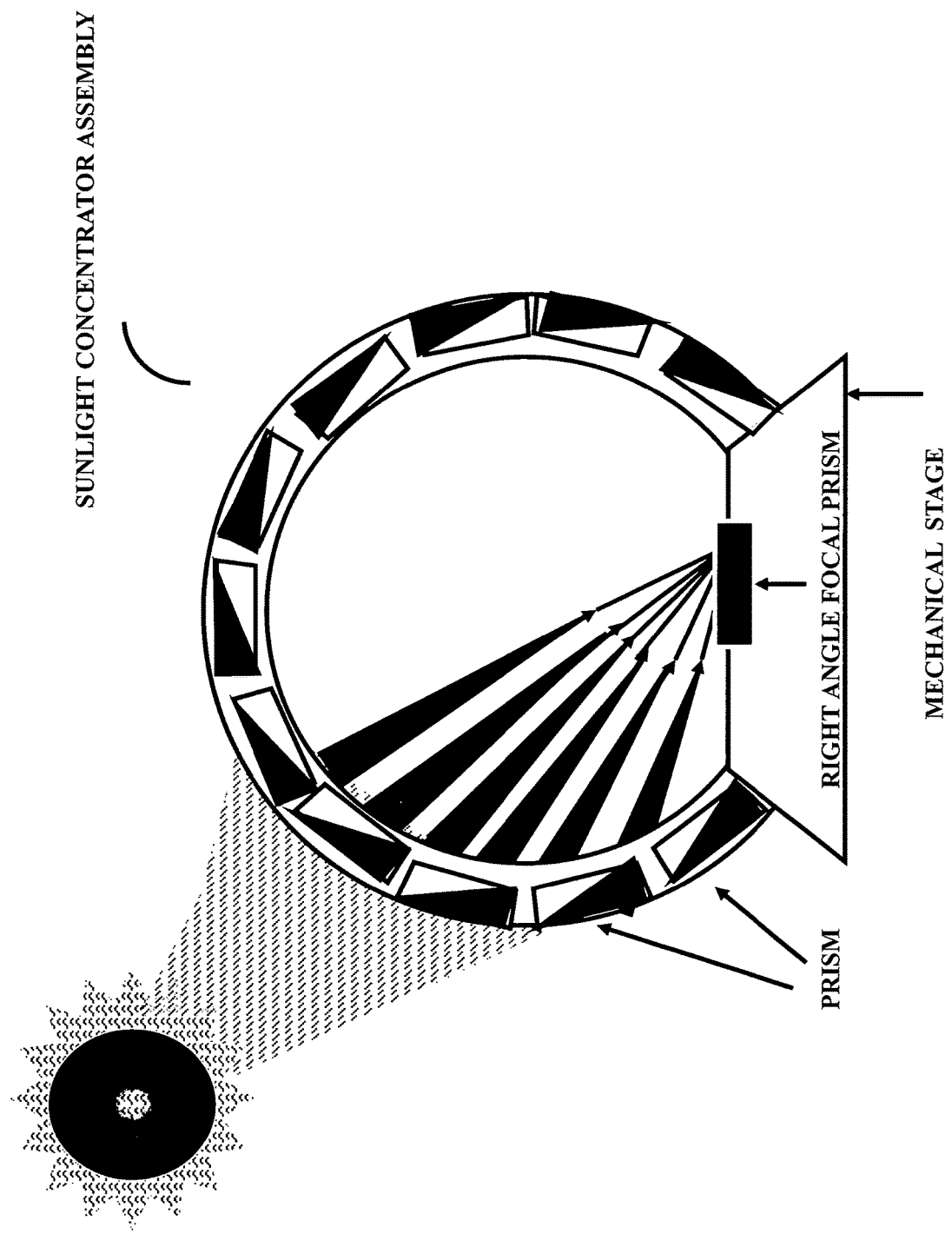

FIG. 5A illustrates an embodiment of an opto-mechanical assembly to collect sunlight.

Figure 5C:
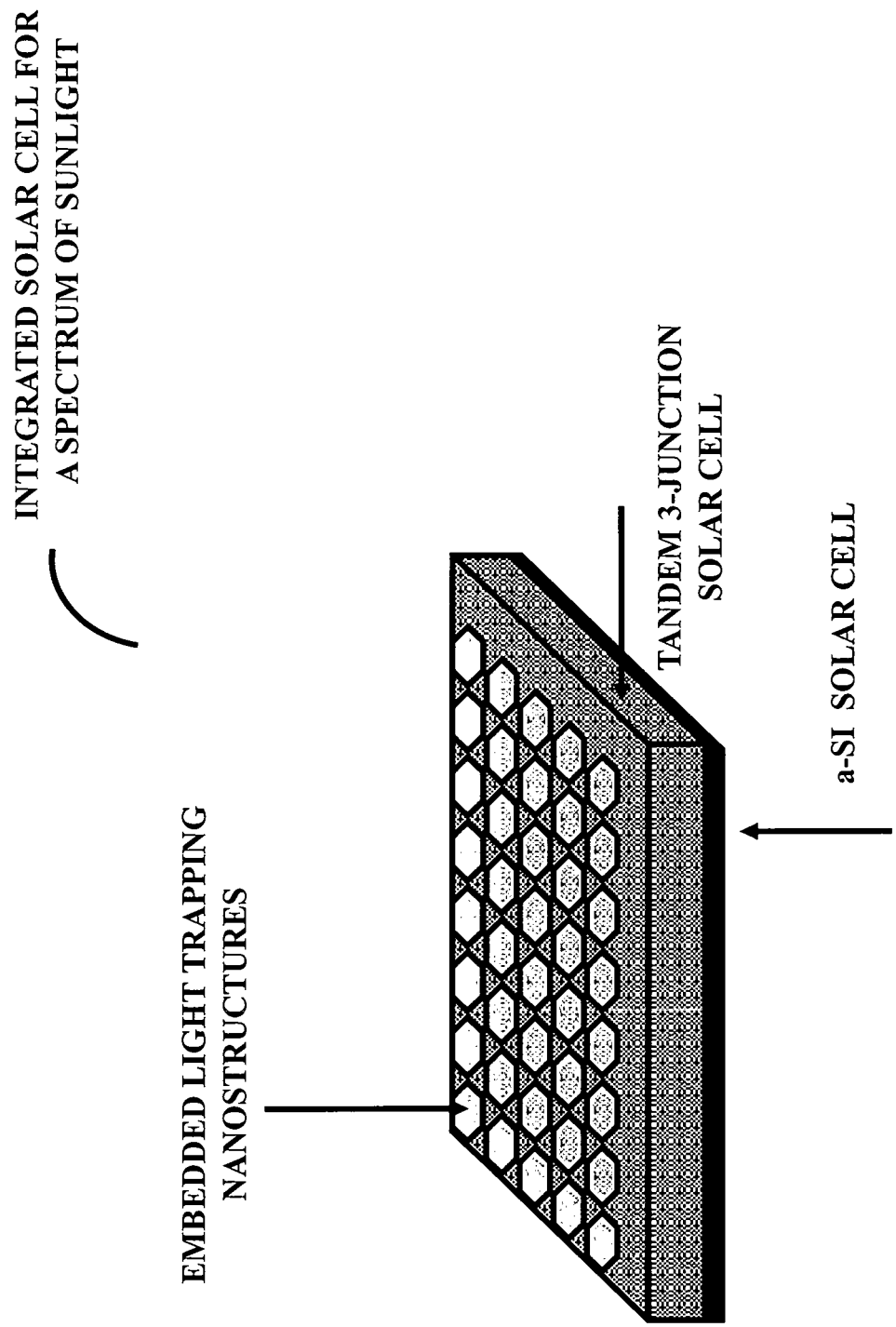

FIGS. 5B-5C illustrate an embodiment of a photovoltaic module.

Figure 5D:
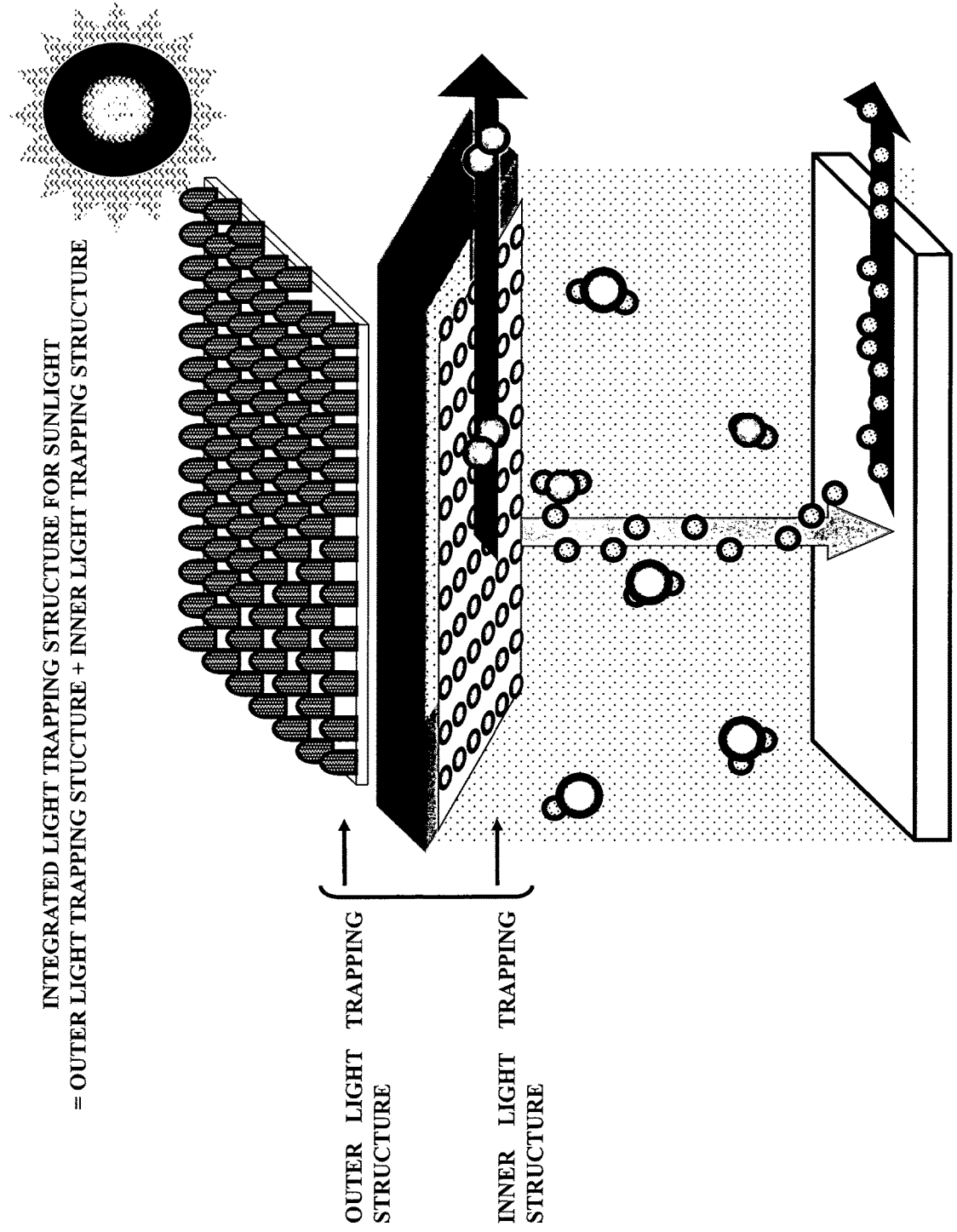
Figure 5E:
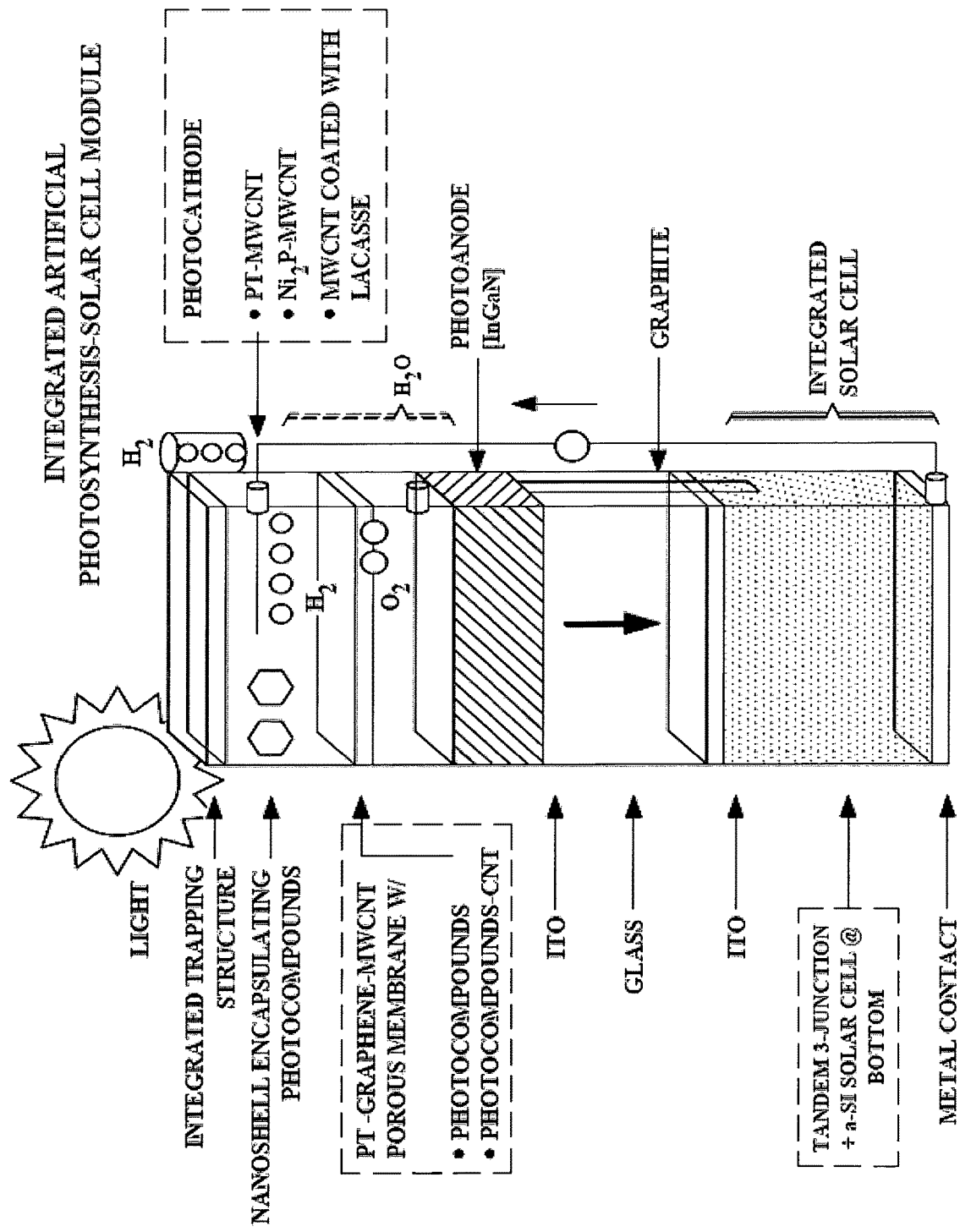

FIGS. 5D-5E illustrate an embodiment of an integrated artificial photosynthesis-solar cell module.

Figure 6:
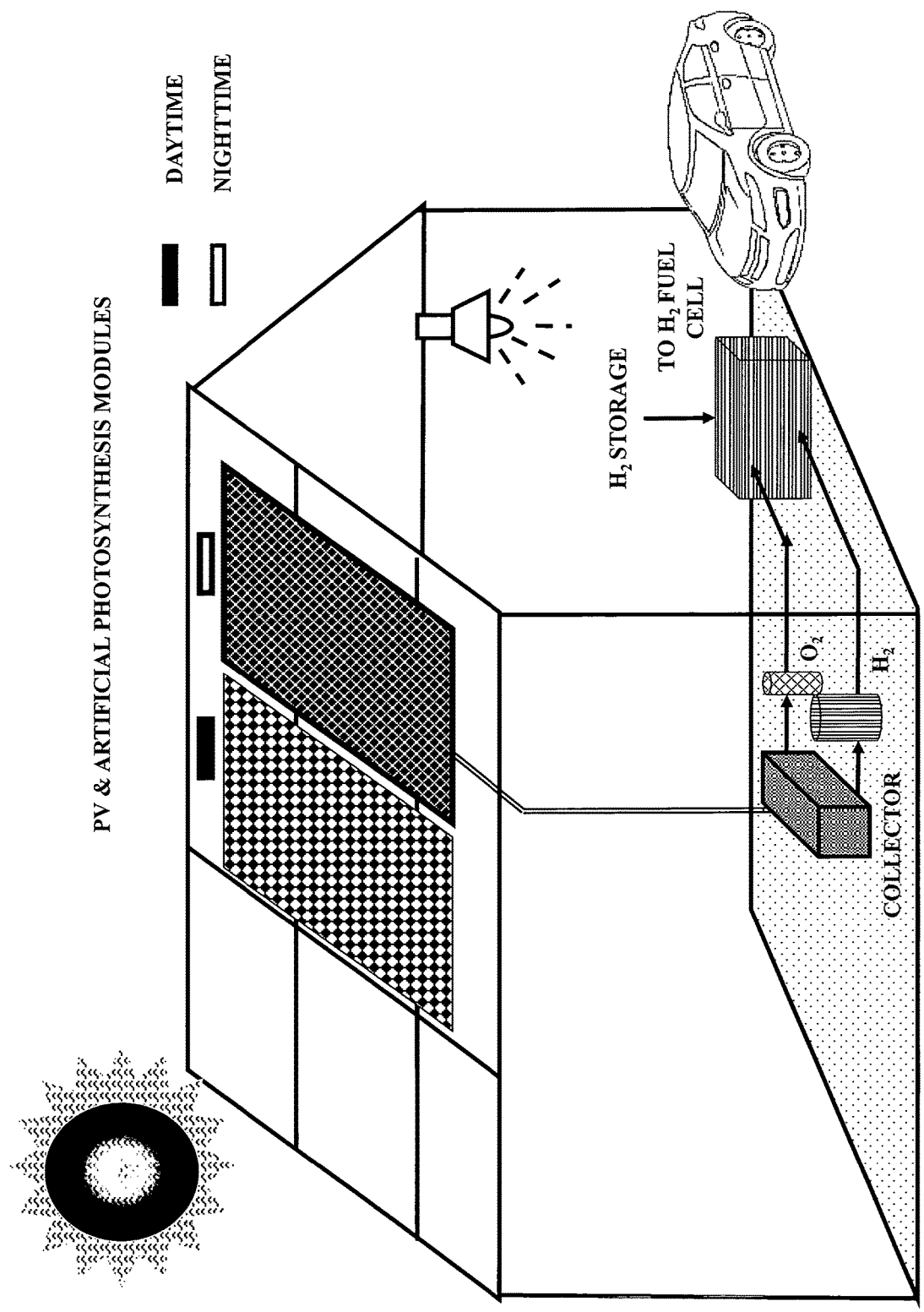

FIG. 6 illustrates an application of photovoltaic and artificial photosynthesis modules at a home.

Secure Payment System

FIGS. 7A-7E illustrate an embodiment of a near field communication (NFC) based secure payment system.

Figure 8A:
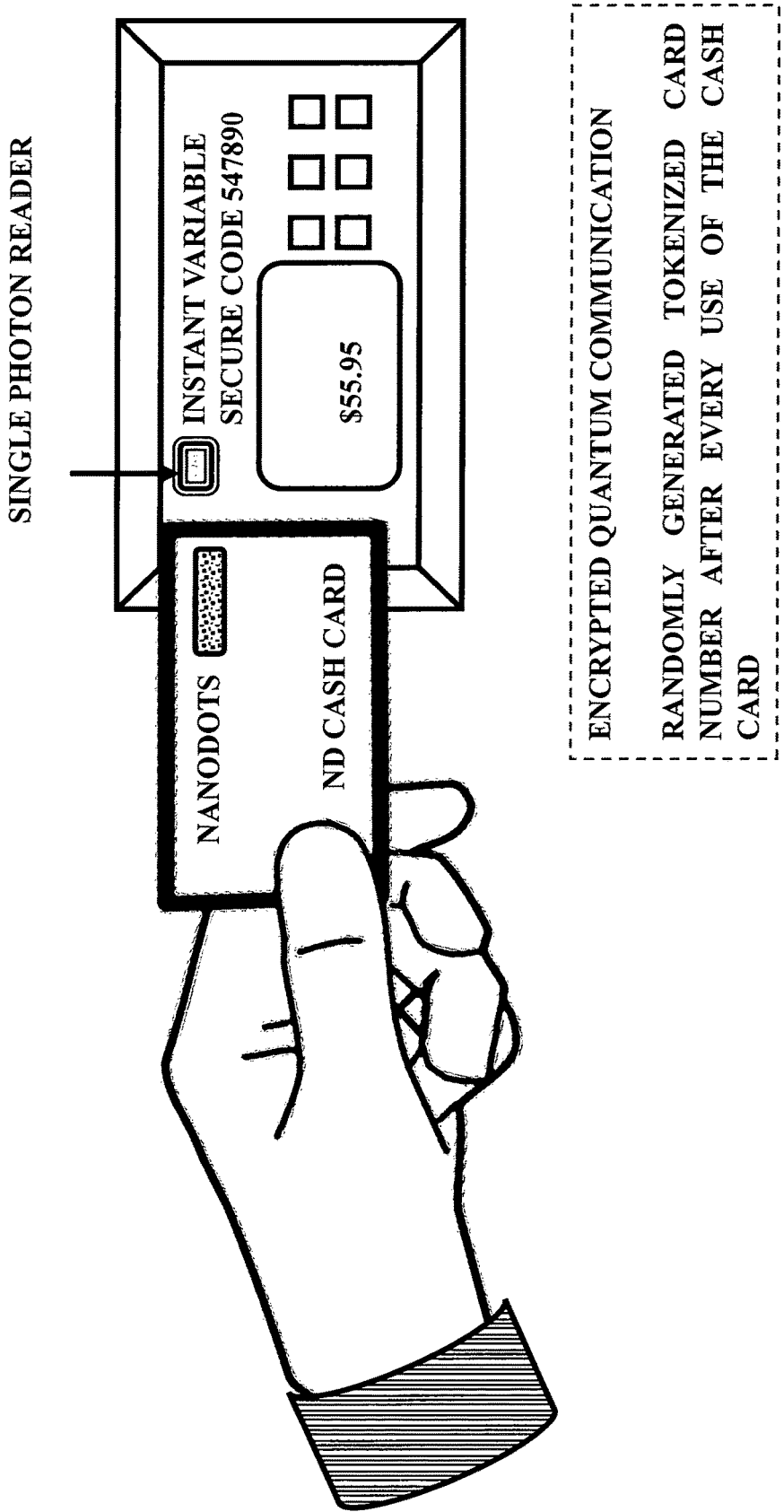
Figure 8B:
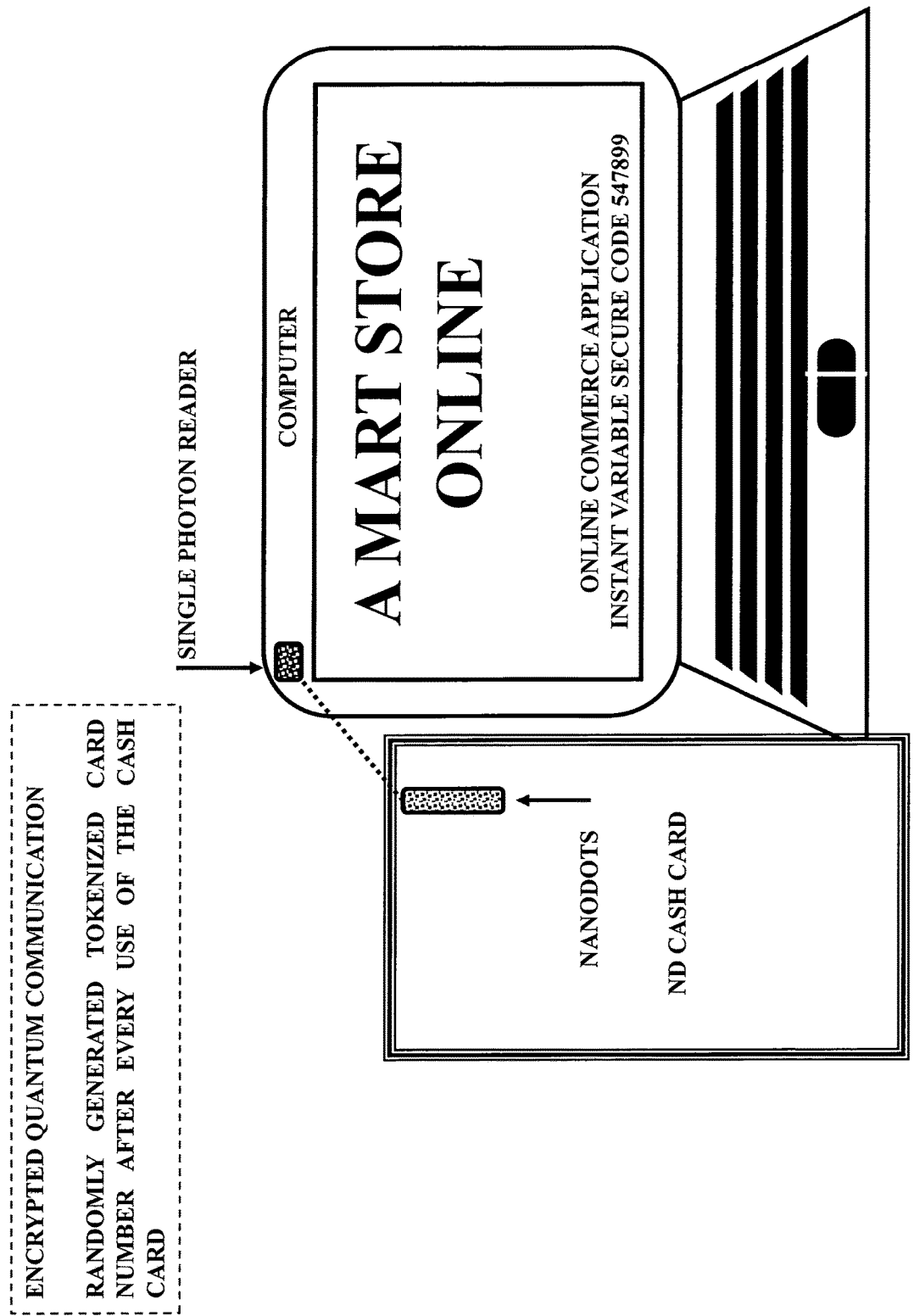
Figure 8C:
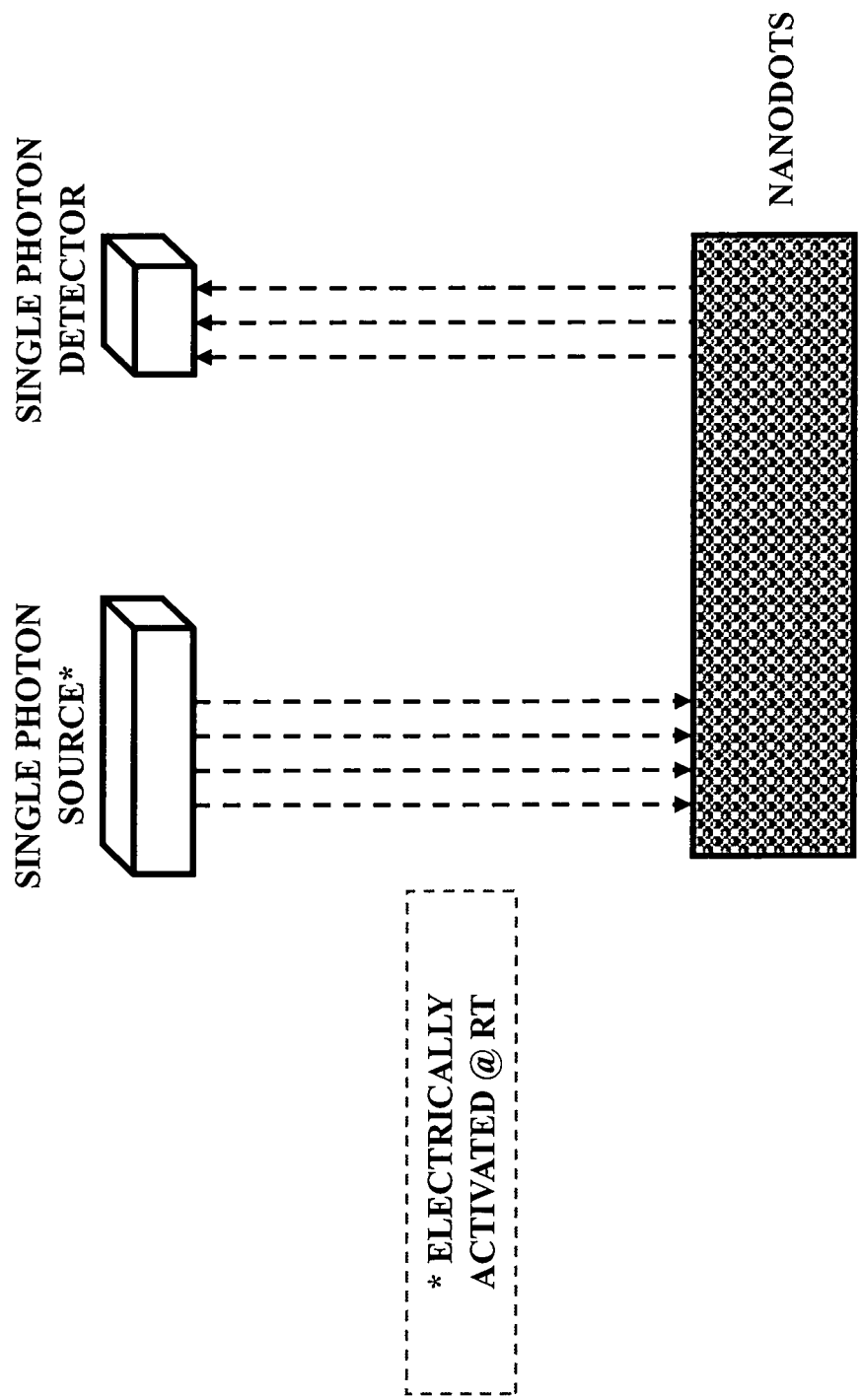

FIGS. 8A-8C illustrate an embodiment of a nanodots/quantum communication based secure payment system.

FIGS. 9A-9D illustrate four embodiments of a near field communication based physical cash card.

Figure 9A:
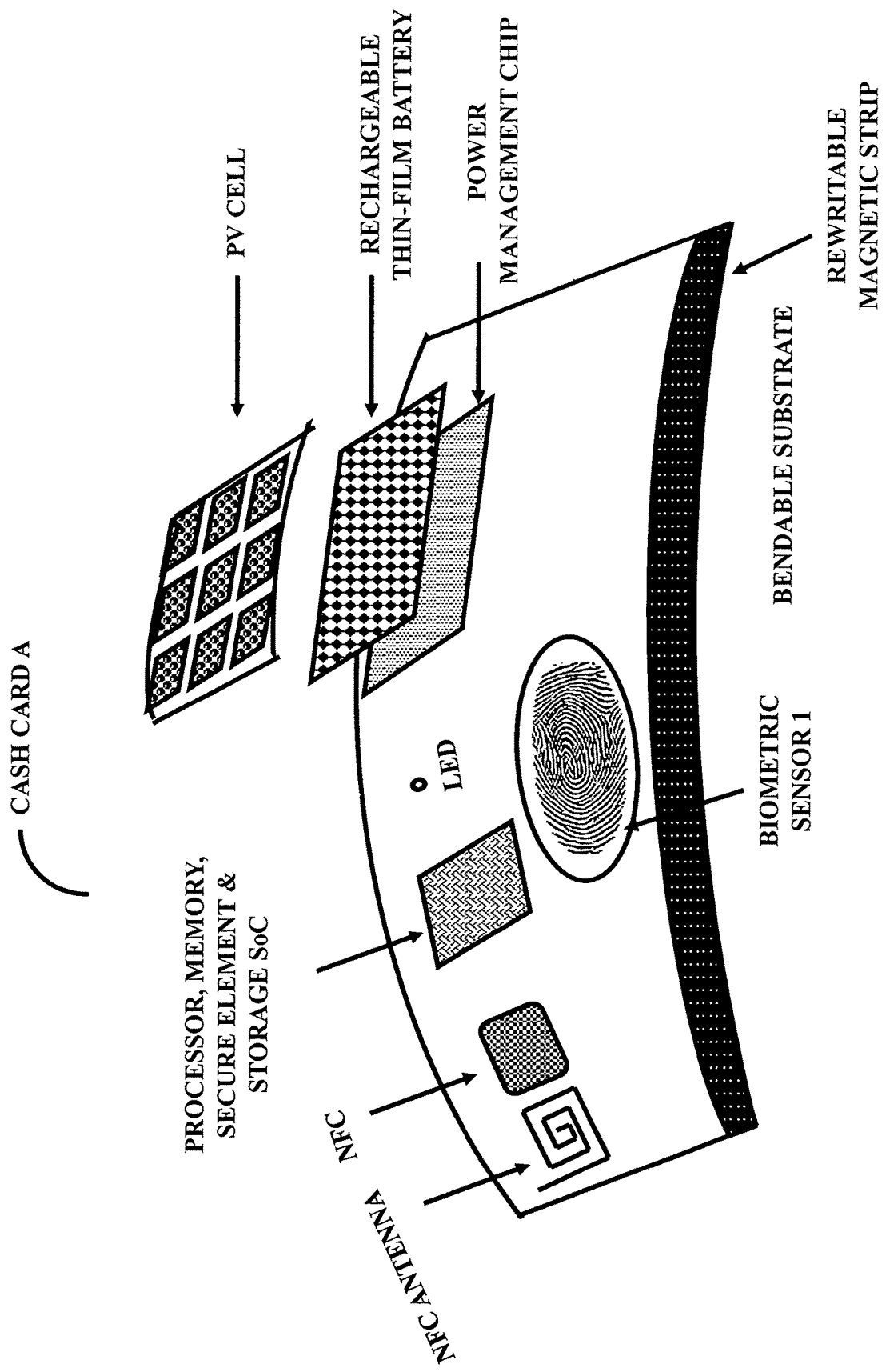
Figure 9B:
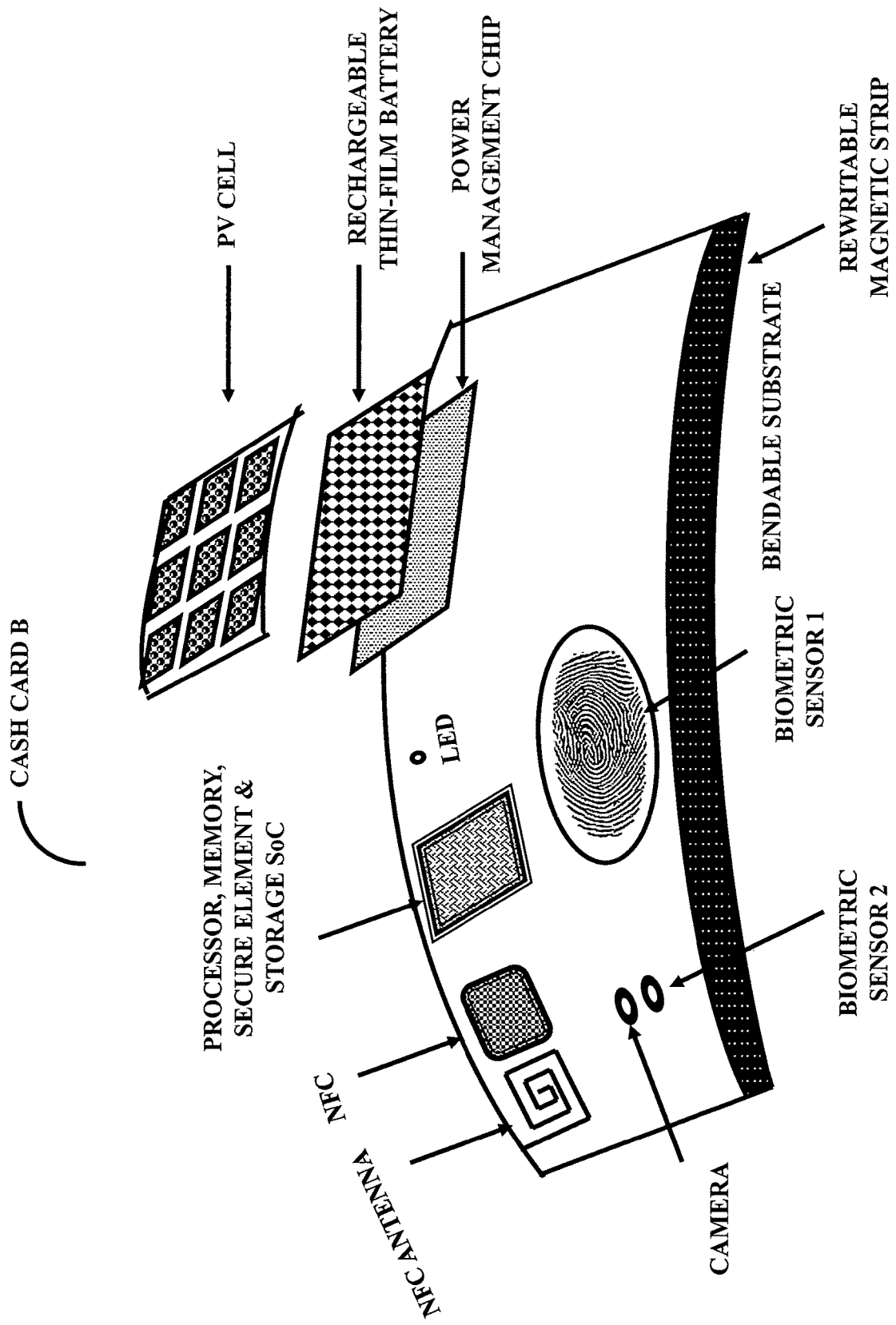
Figure 9C:
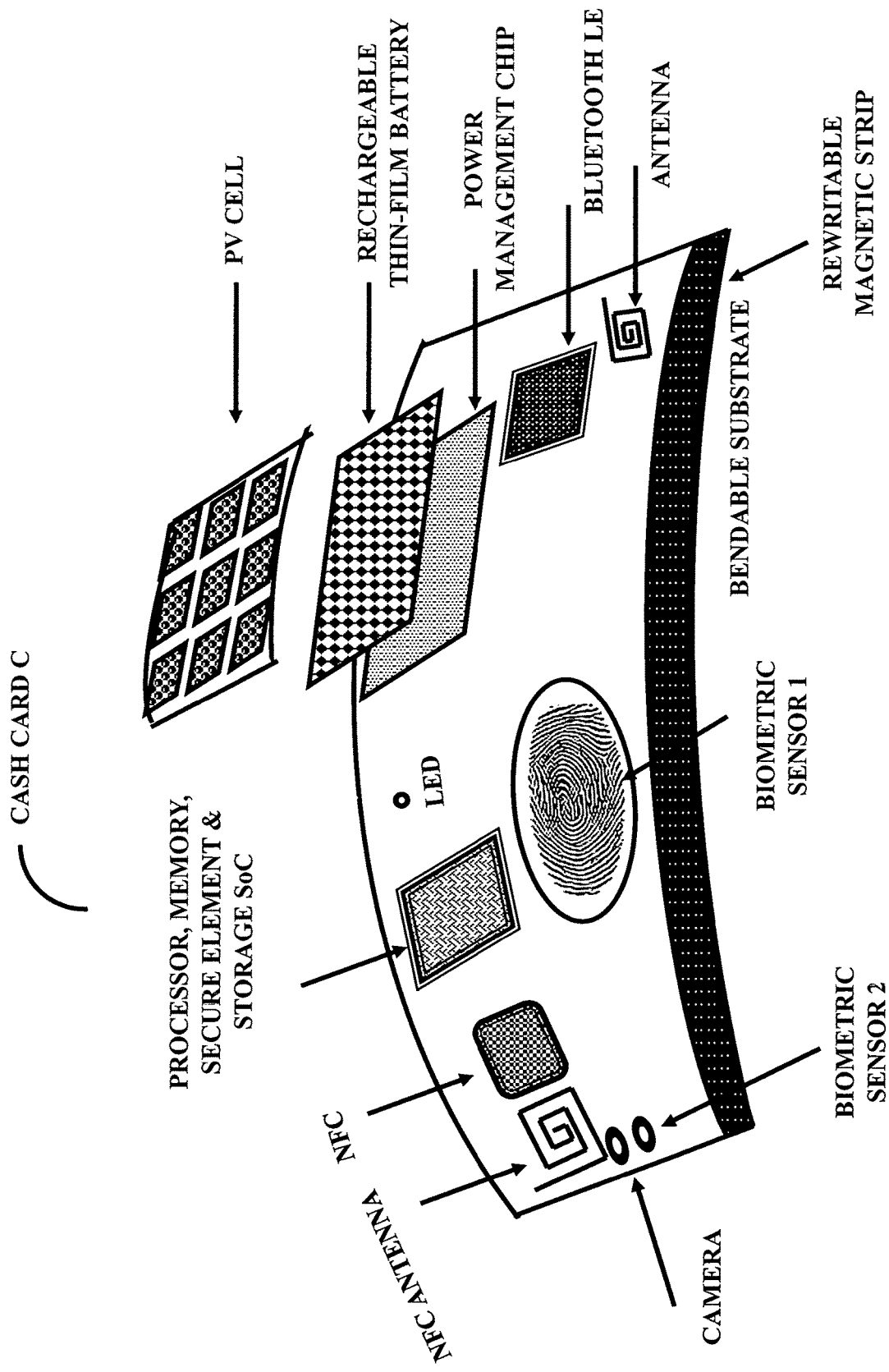
Figure 9D:
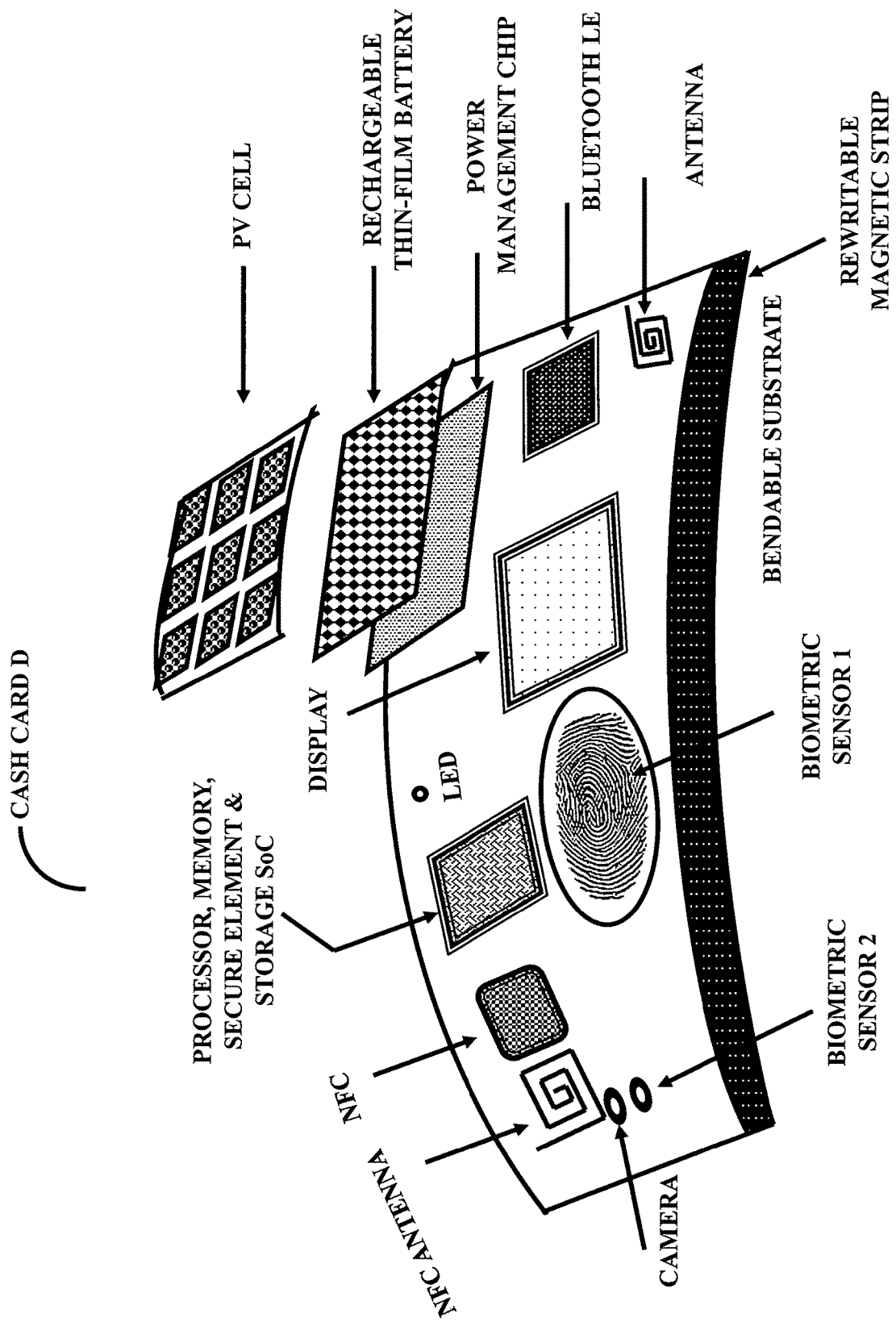
Figure 9E:
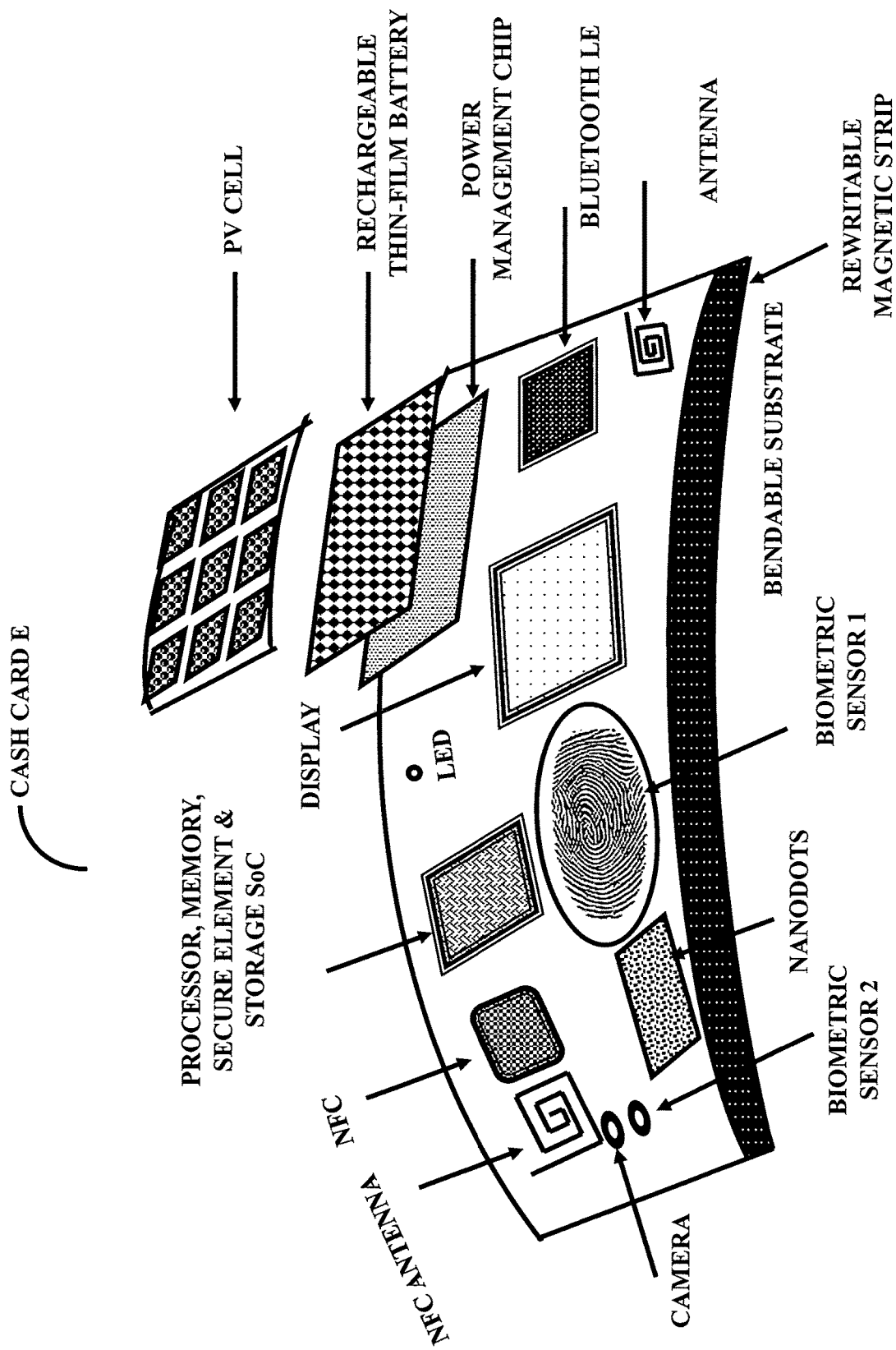

FIG. 9E illustrates an embodiment of a near field communication and nanodots based physical cash card.

Figure 10A:
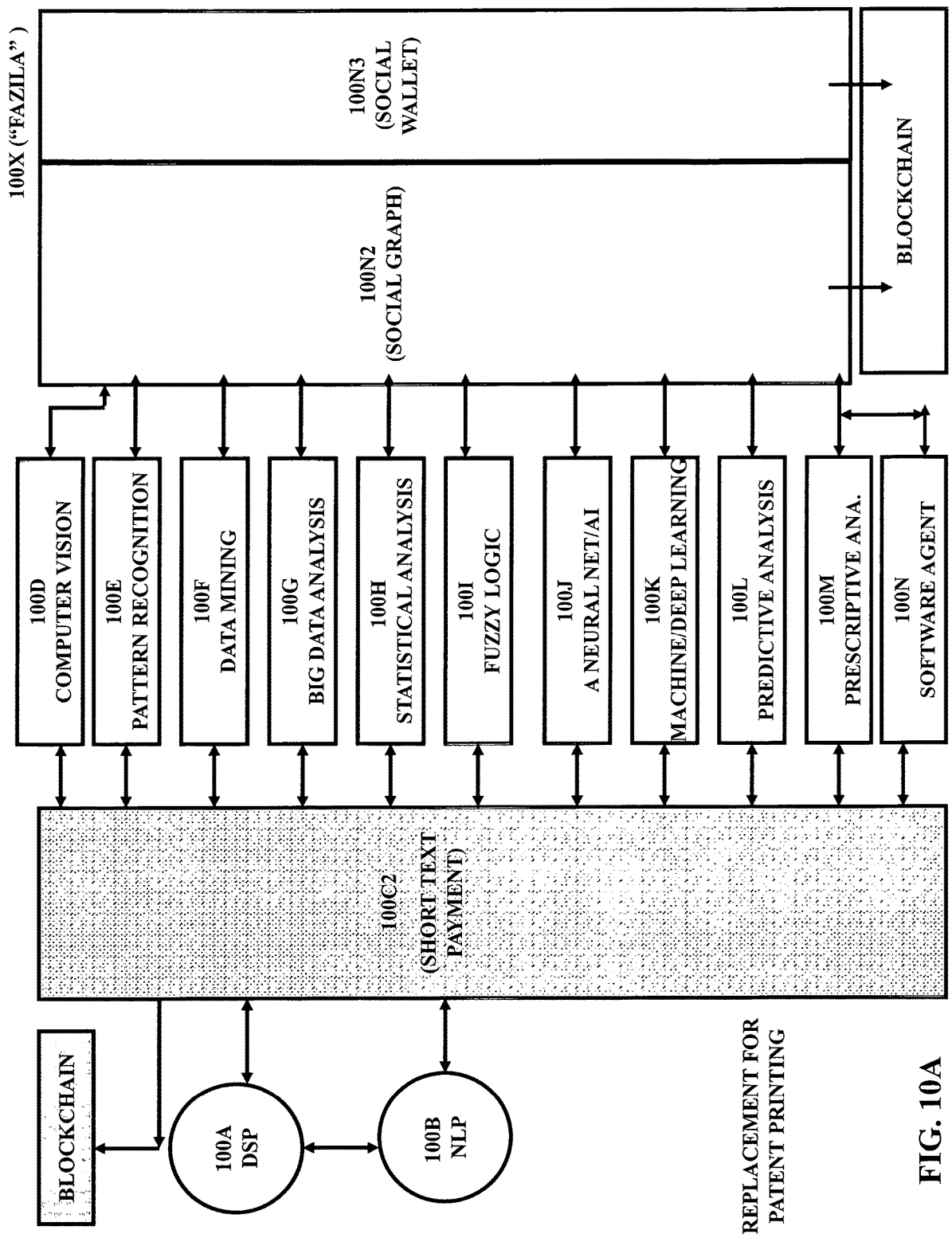
Figure 10B:
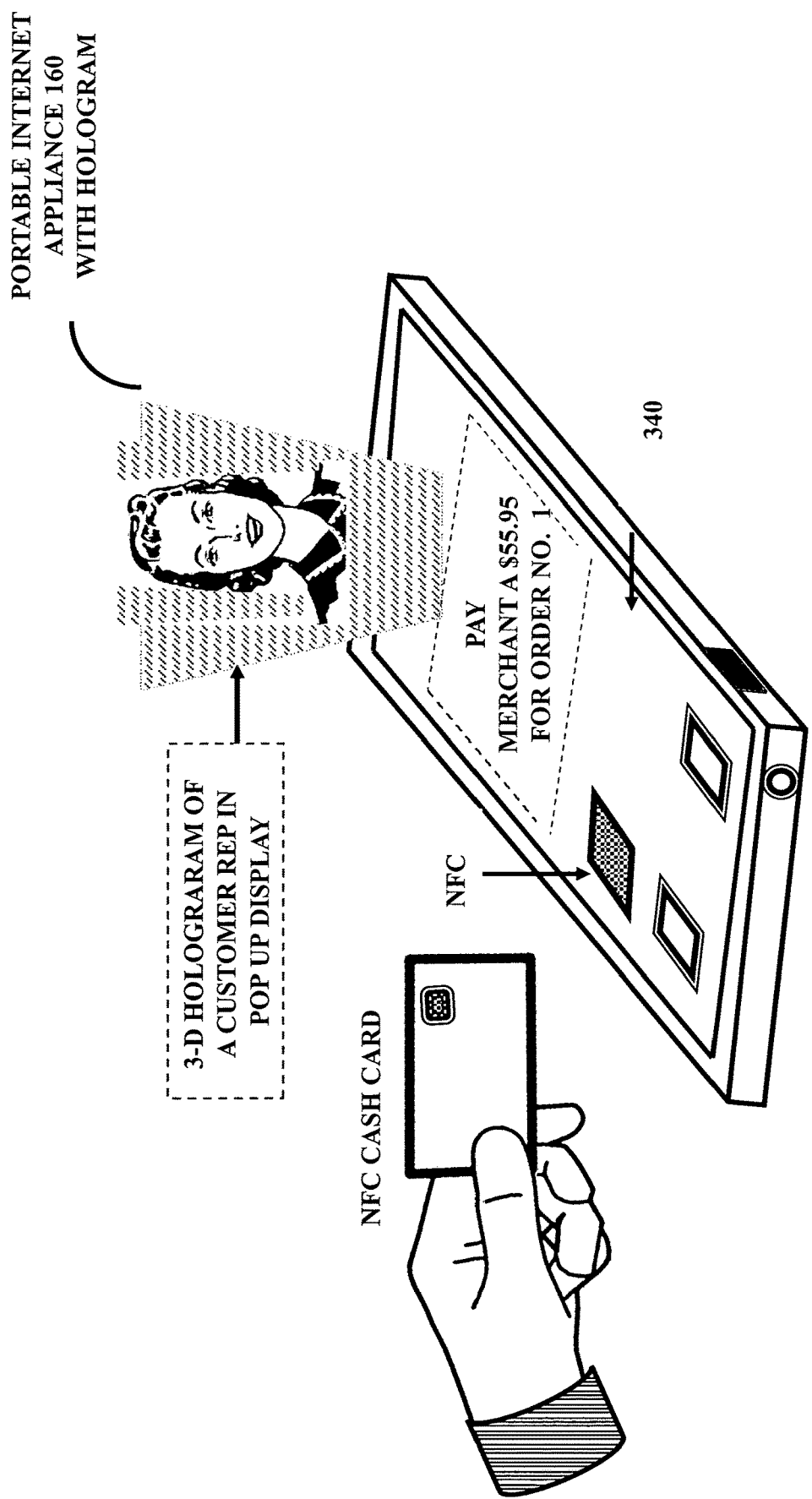
Figure 10C:
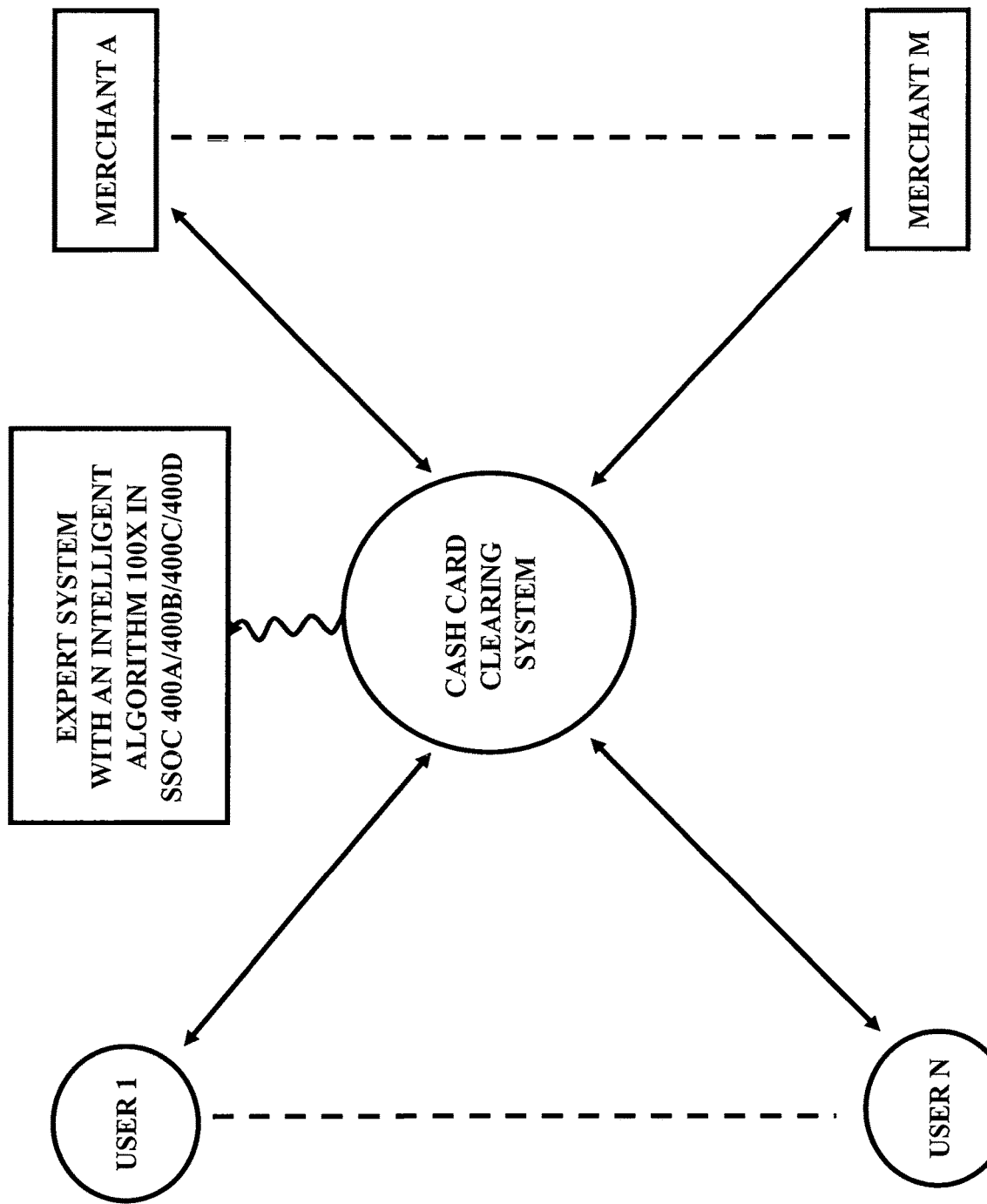

FIGS. 10A-10C illustrate a short text message payment application of the physical cash card.

Figure 10D:
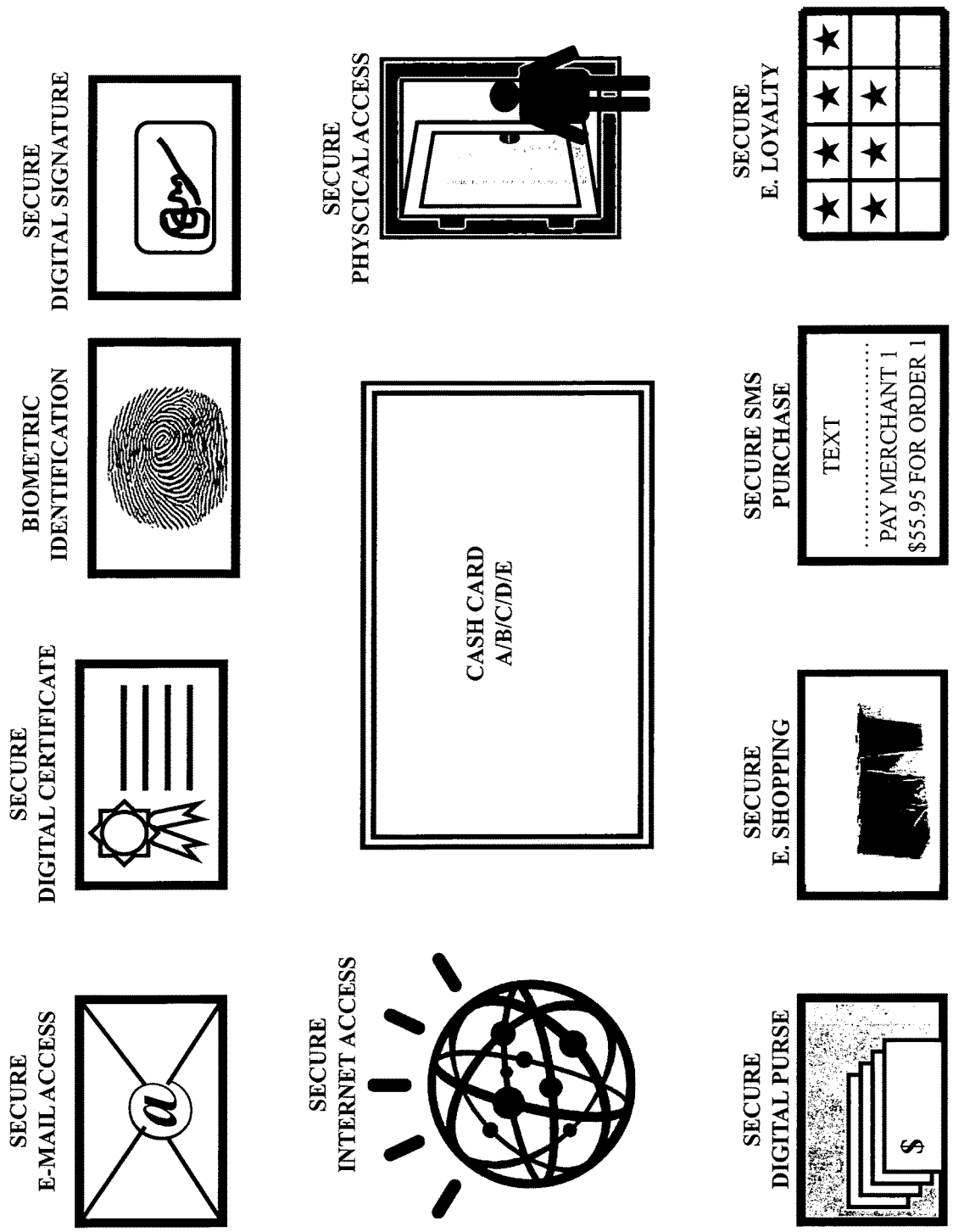

FIG. 10D illustrates a universal application of the physical cash card.

Object

Figure 11:
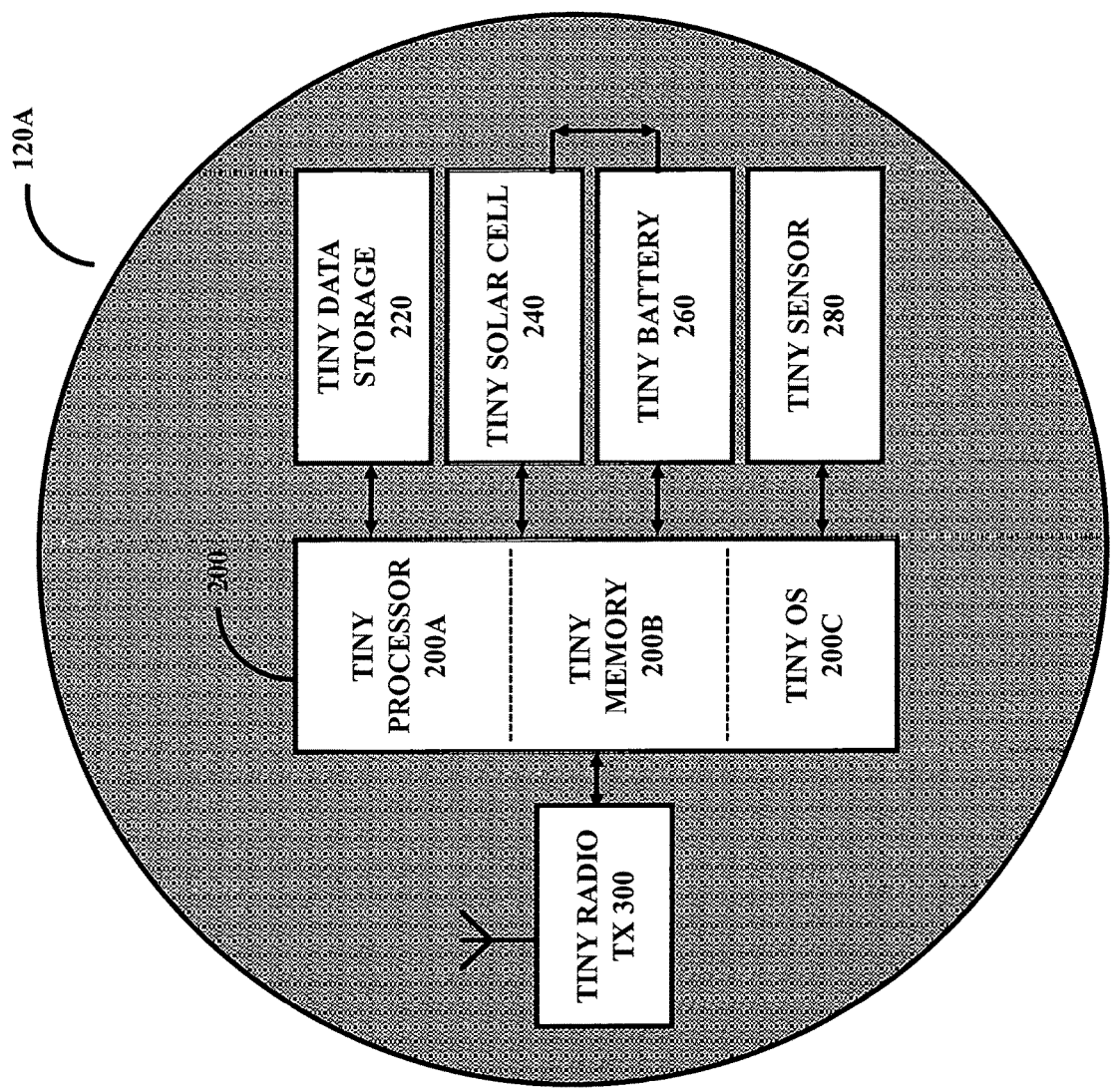

FIG. 11 illustrates an embodiment of an object.

Bioobject

Figure 12A:
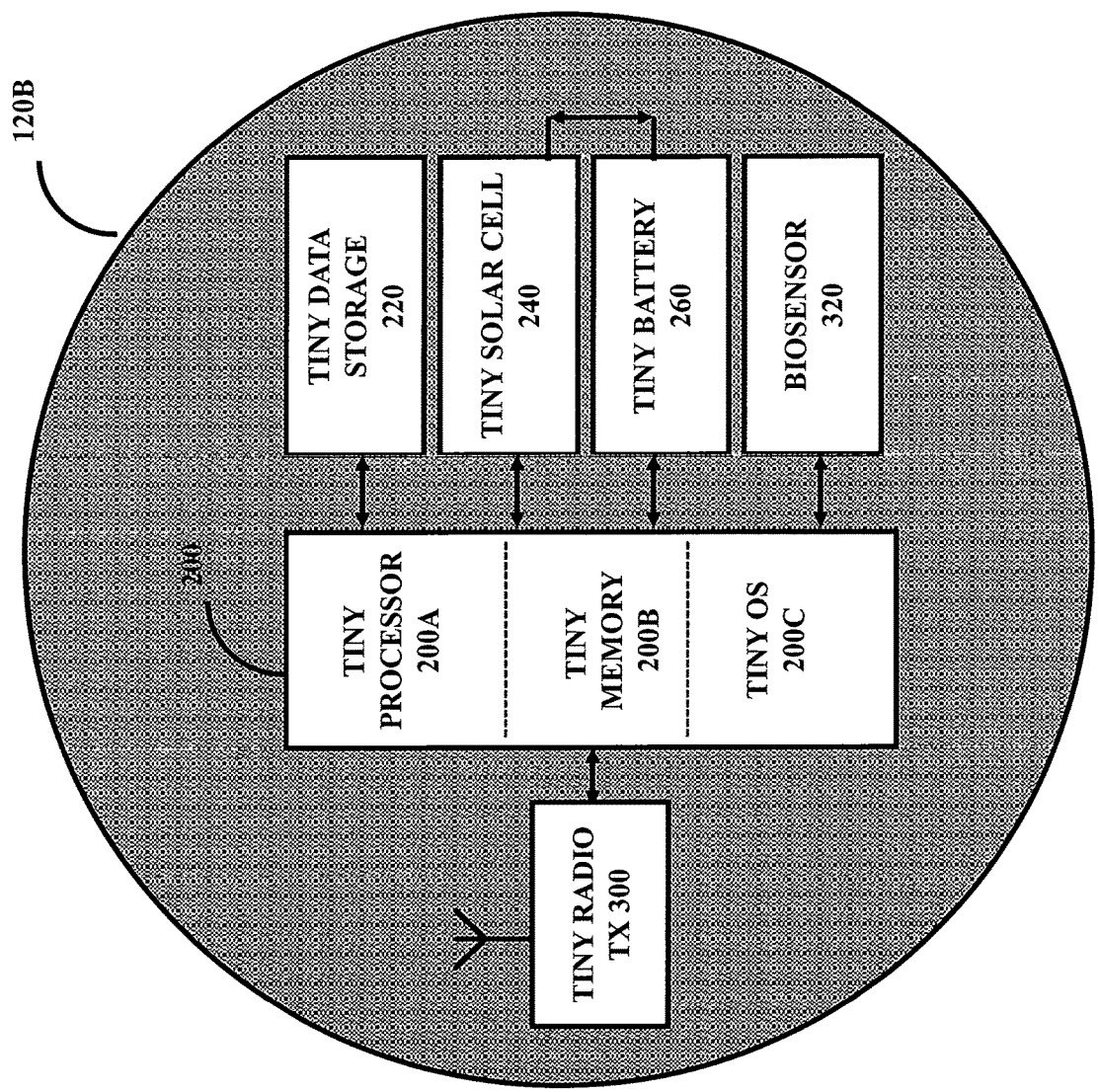
Figure 12B:
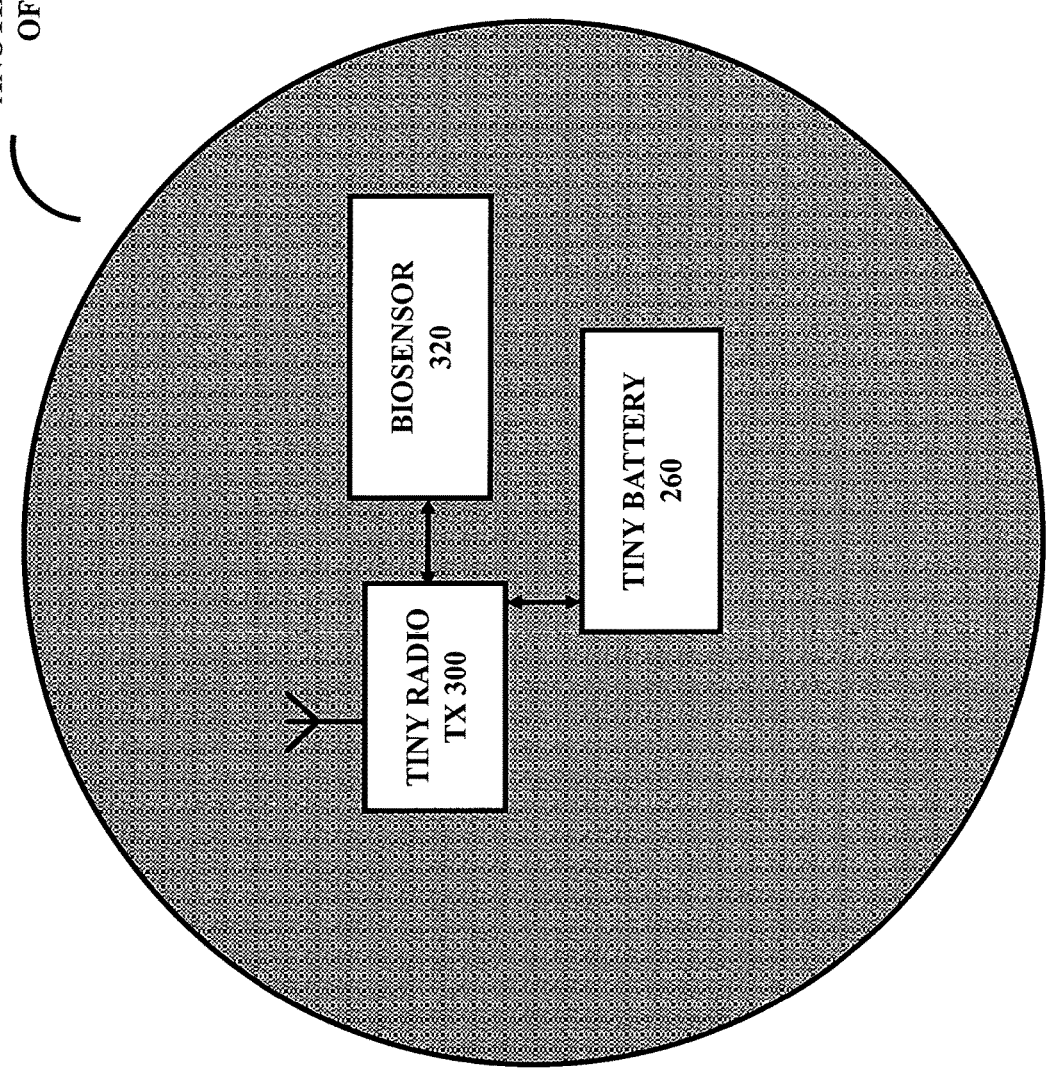
Figure 12C:
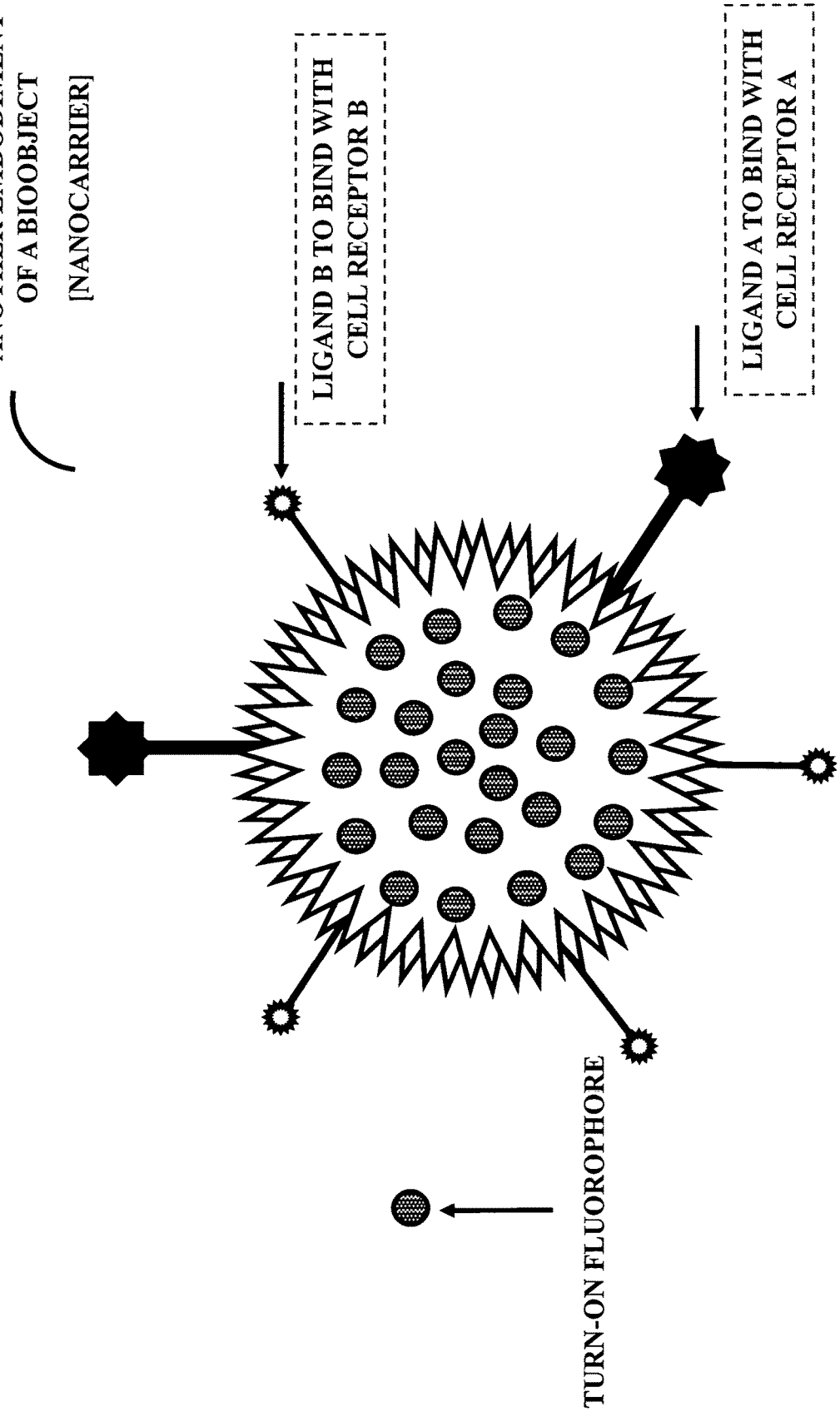

FIGS. 12A-12C illustrate three embodiments of a bioobject.

Figure 13:
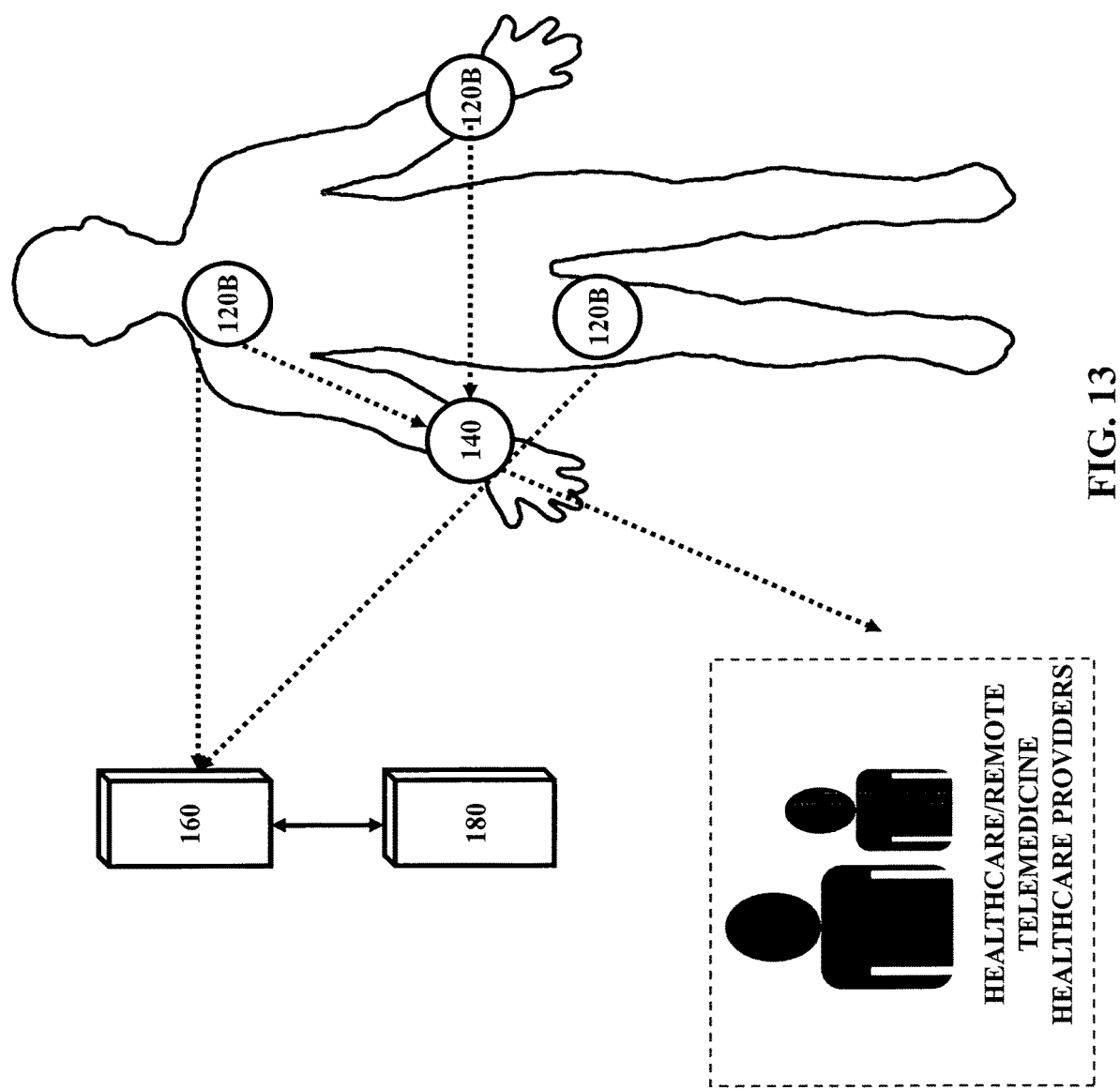

FIG. 13 illustrates an embodiment of interactions/communications among bioobject node(s), bioobject(s) with an intelligent portable internet appliance and an intelligent wearable augmented reality personal assistant device.

Intelligent Portable Internet Appliance

Figure 14A:
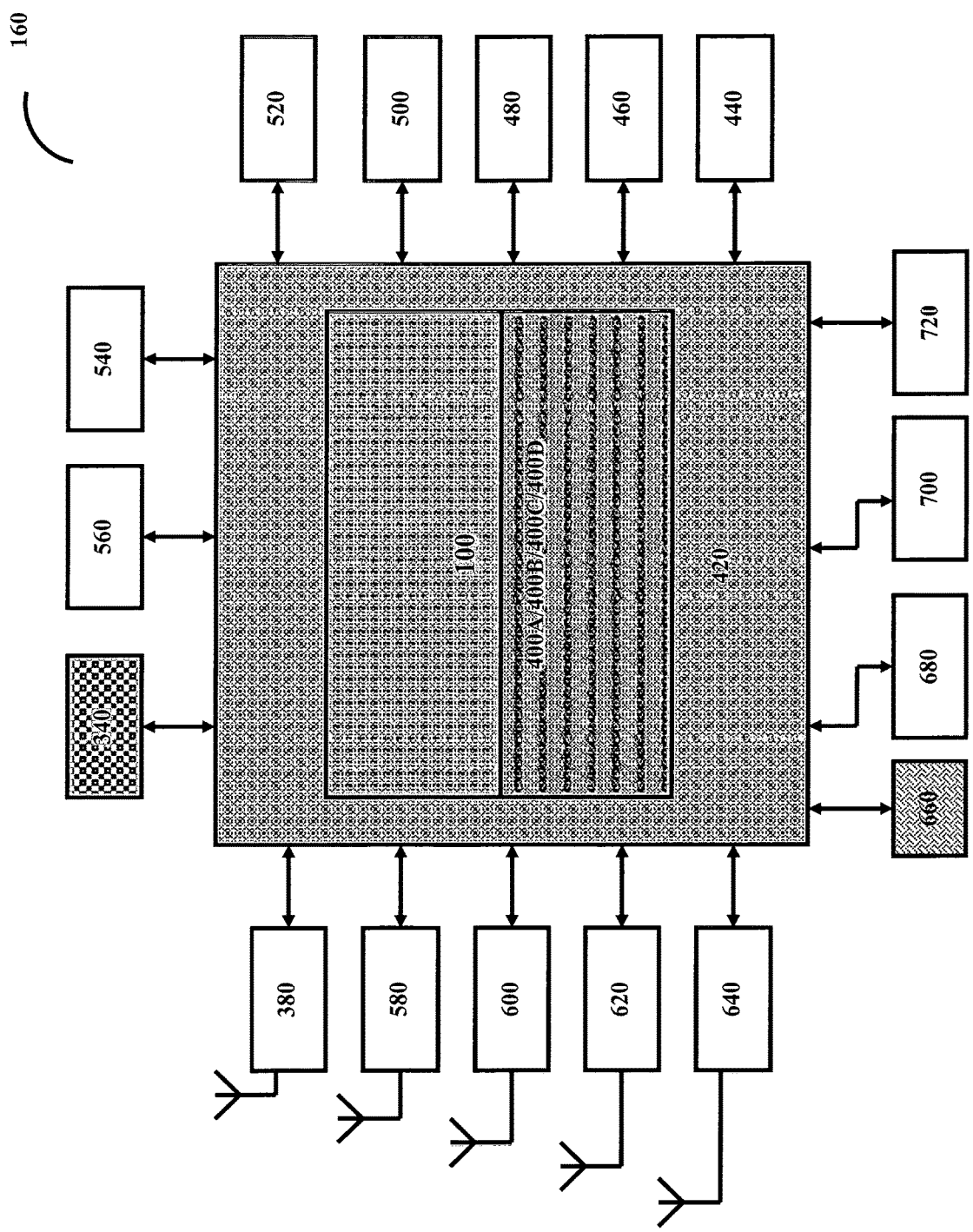
Figure 14B:
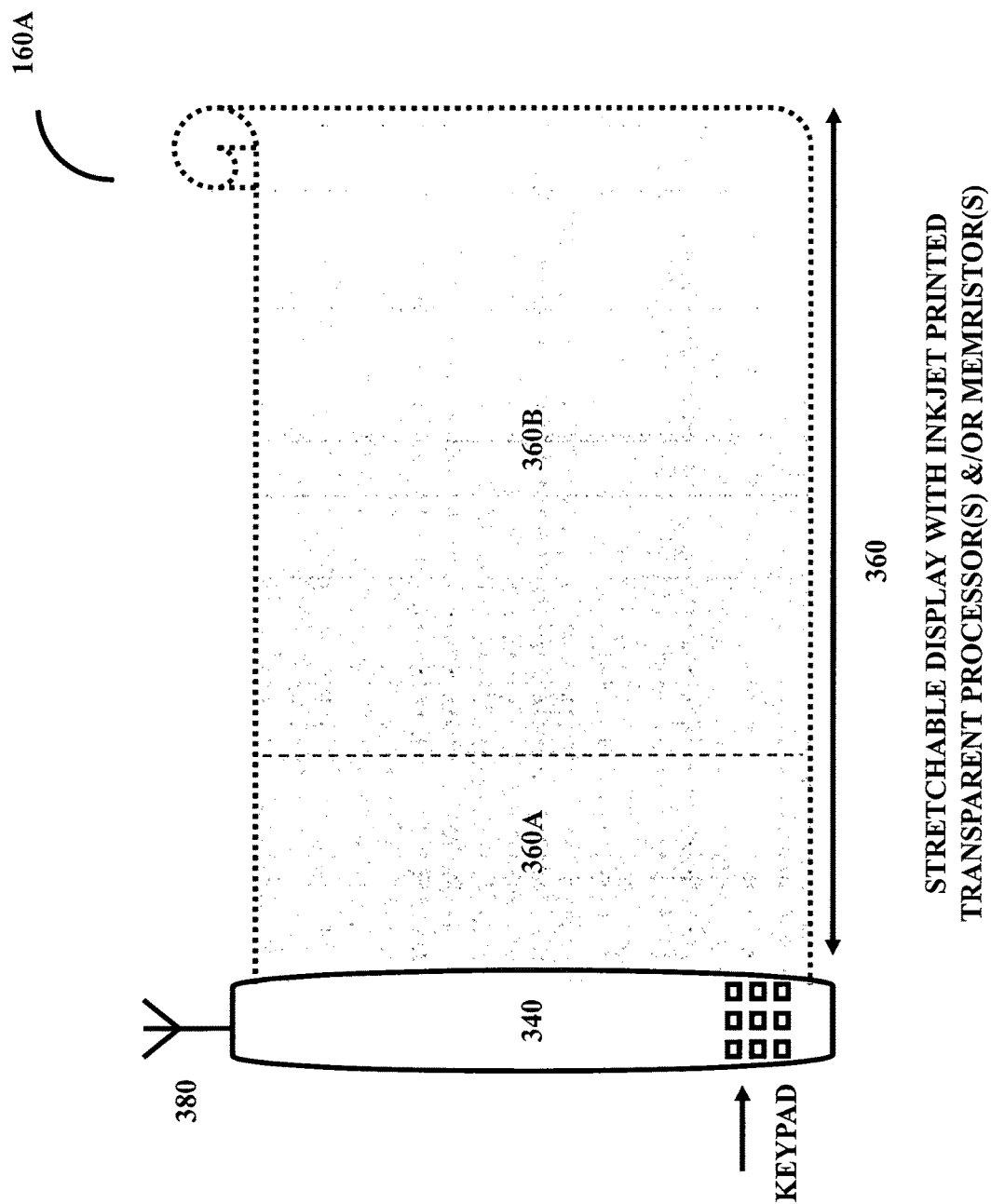

FIGS. 14A-14B illustrate two embodiments of the intelligent portable internet appliance.

Super System on Chip

FIGS. 15A-15G illustrate various embodiments of a digital processor.

Figure 16A:
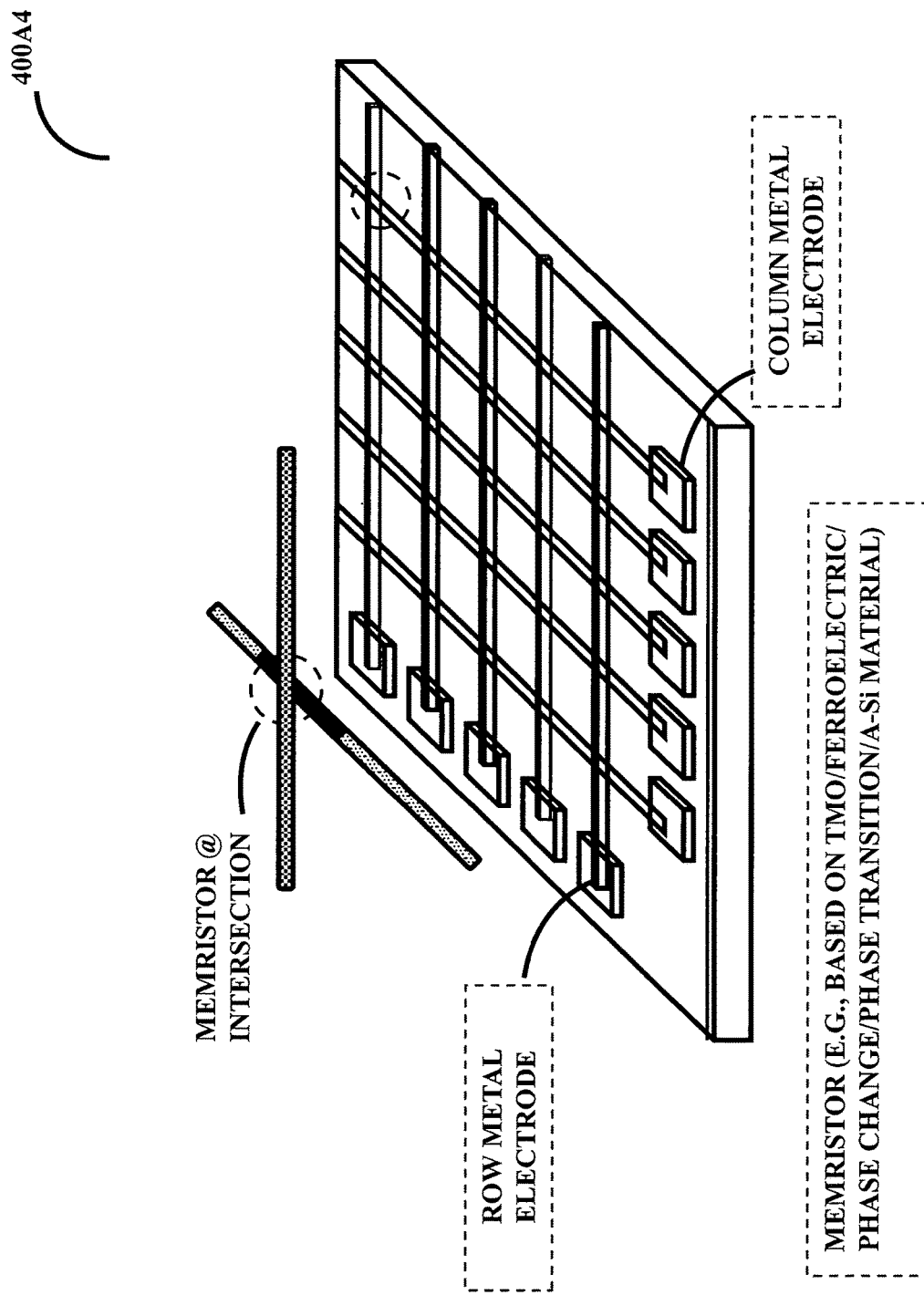

FIG. 16A illustrate an embodiment of a memristor.

Figure 16B:
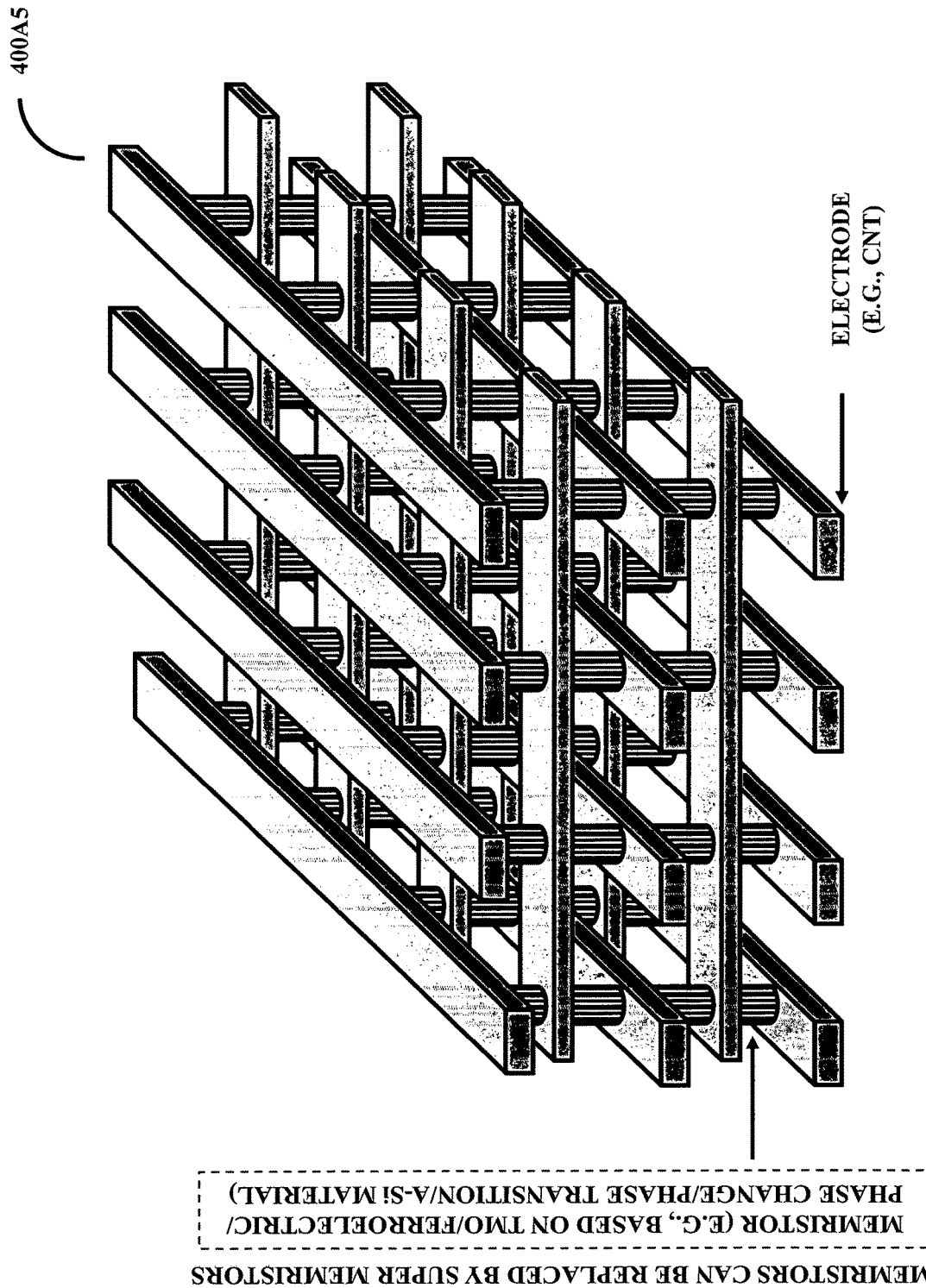

FIG. 16B illustrates an embodiment of a three-dimensional integration of a memristor.

Figure 16C:
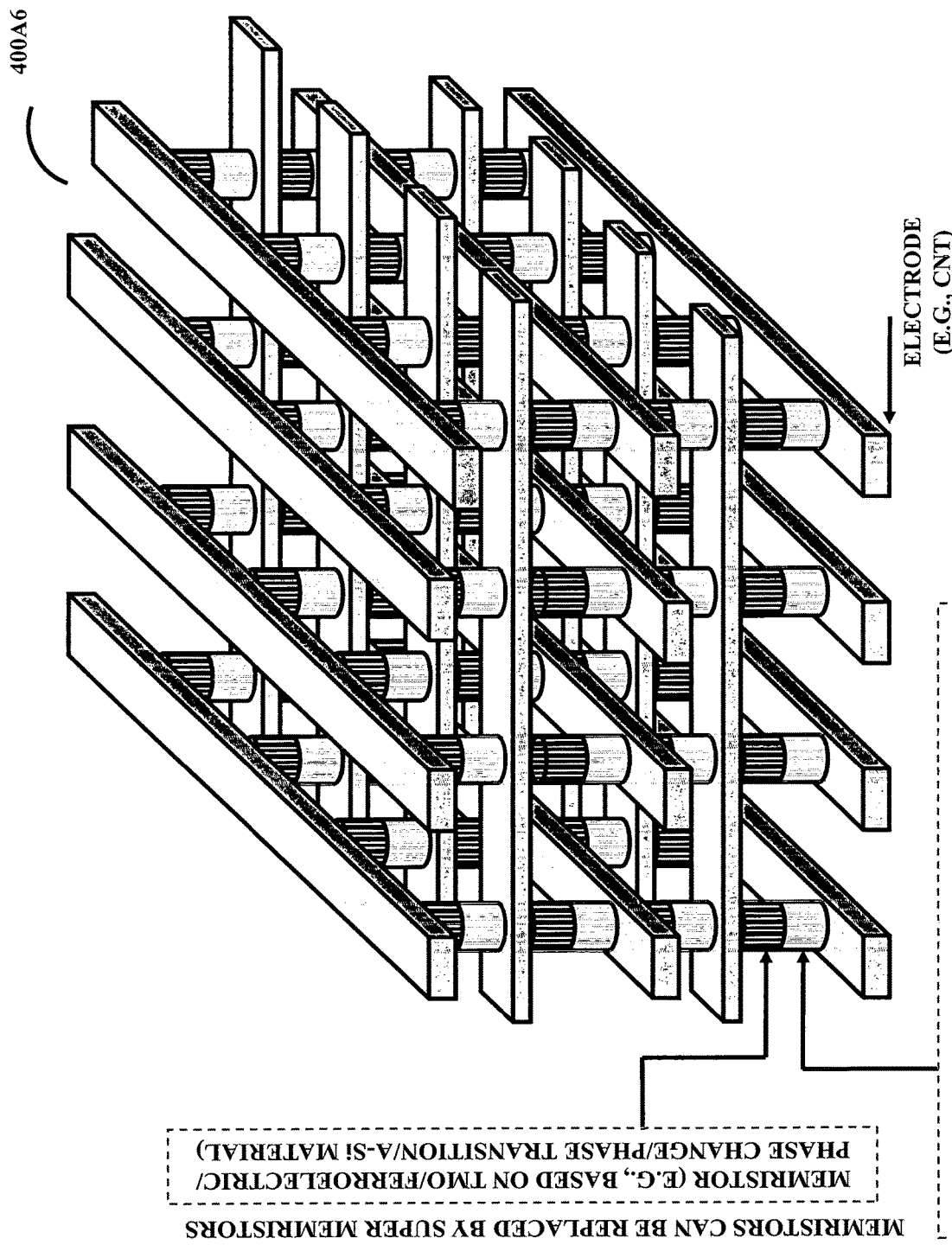

FIG. 16C illustrates an embodiment of a three-dimensional integration of a memristor with various versions of a digital processor.

Figure 16D:
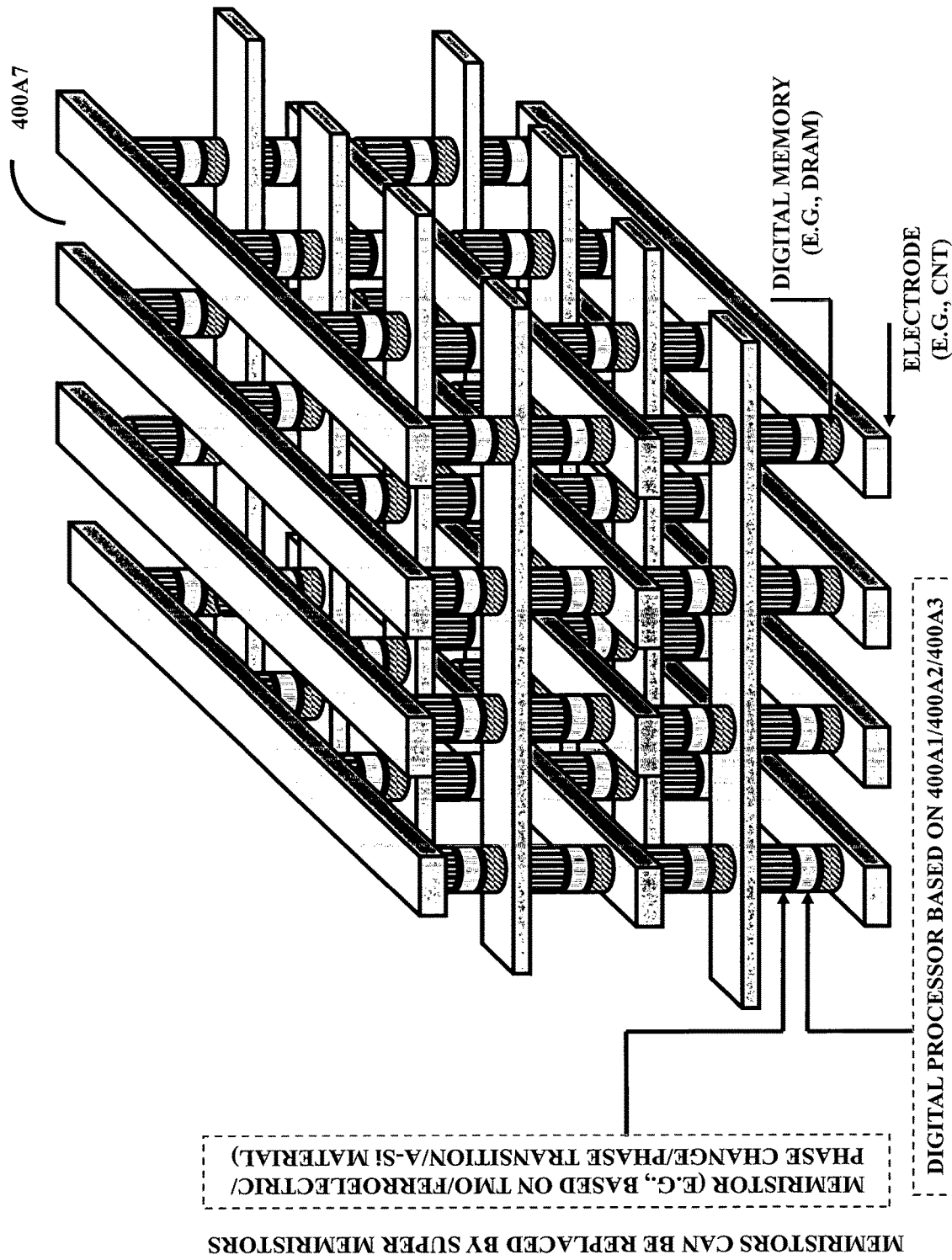

FIG. 16D illustrates an embodiment of a three-dimensional integration of a memristor and a digital memory with various versions of a digital processor.

Figure 17A:
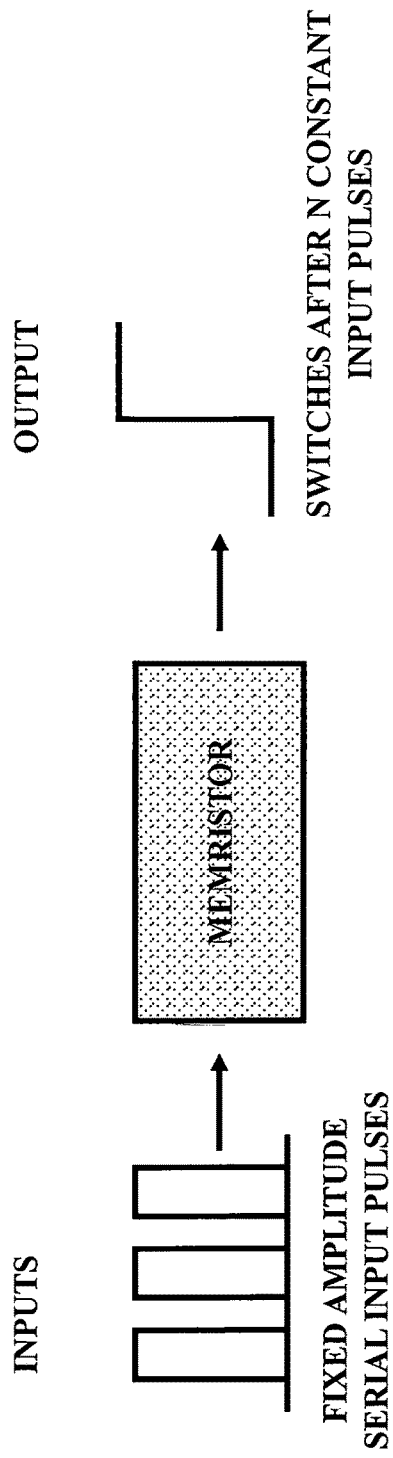
Figure 17B:
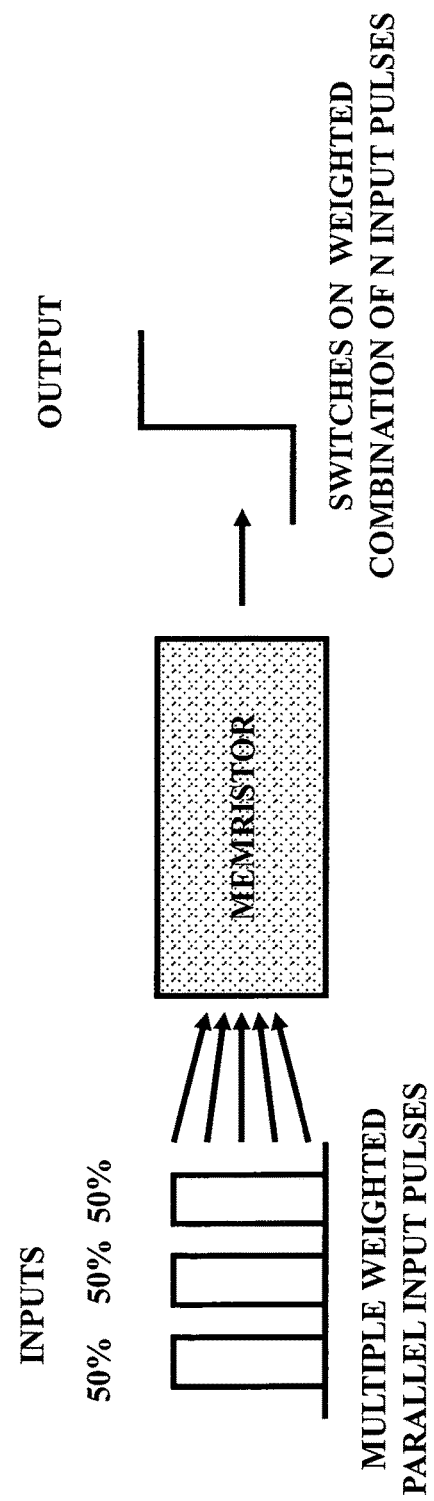

FIGS. 17A-17B illustrate an input-output relationship of a memristor.

Figure 17C:
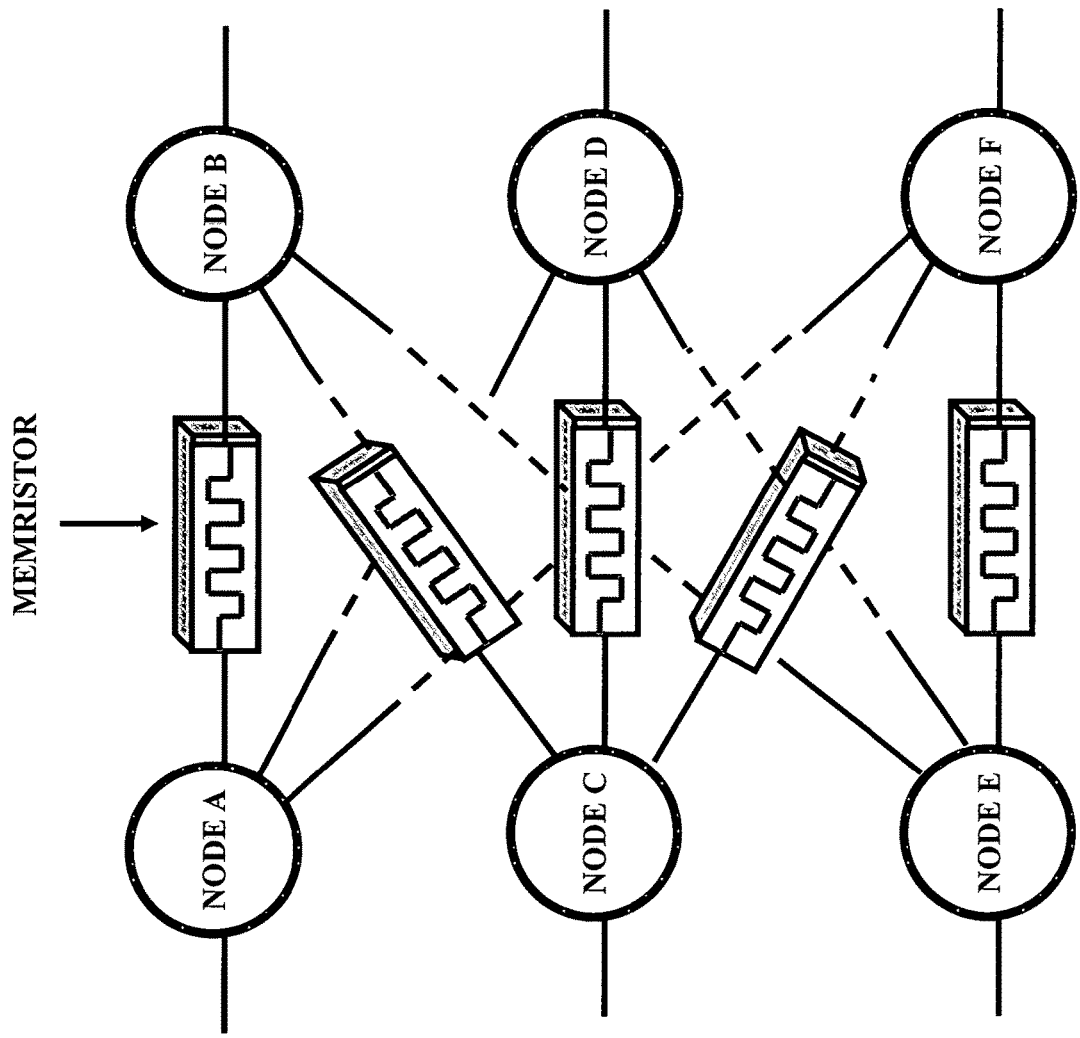

FIG. 17C illustrates interactions of memristors with nodes.

Figure 18A:
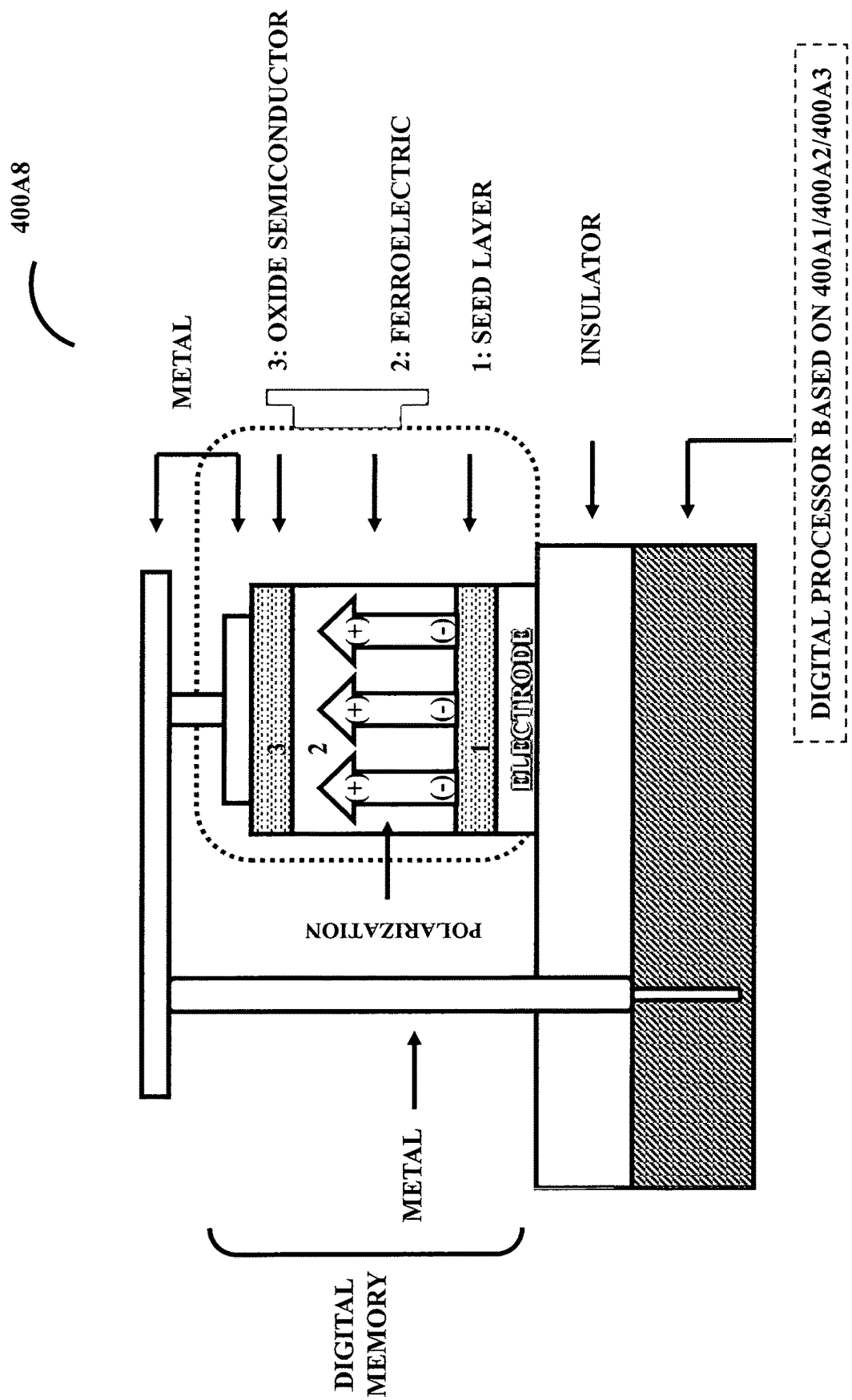
Figure 18B:
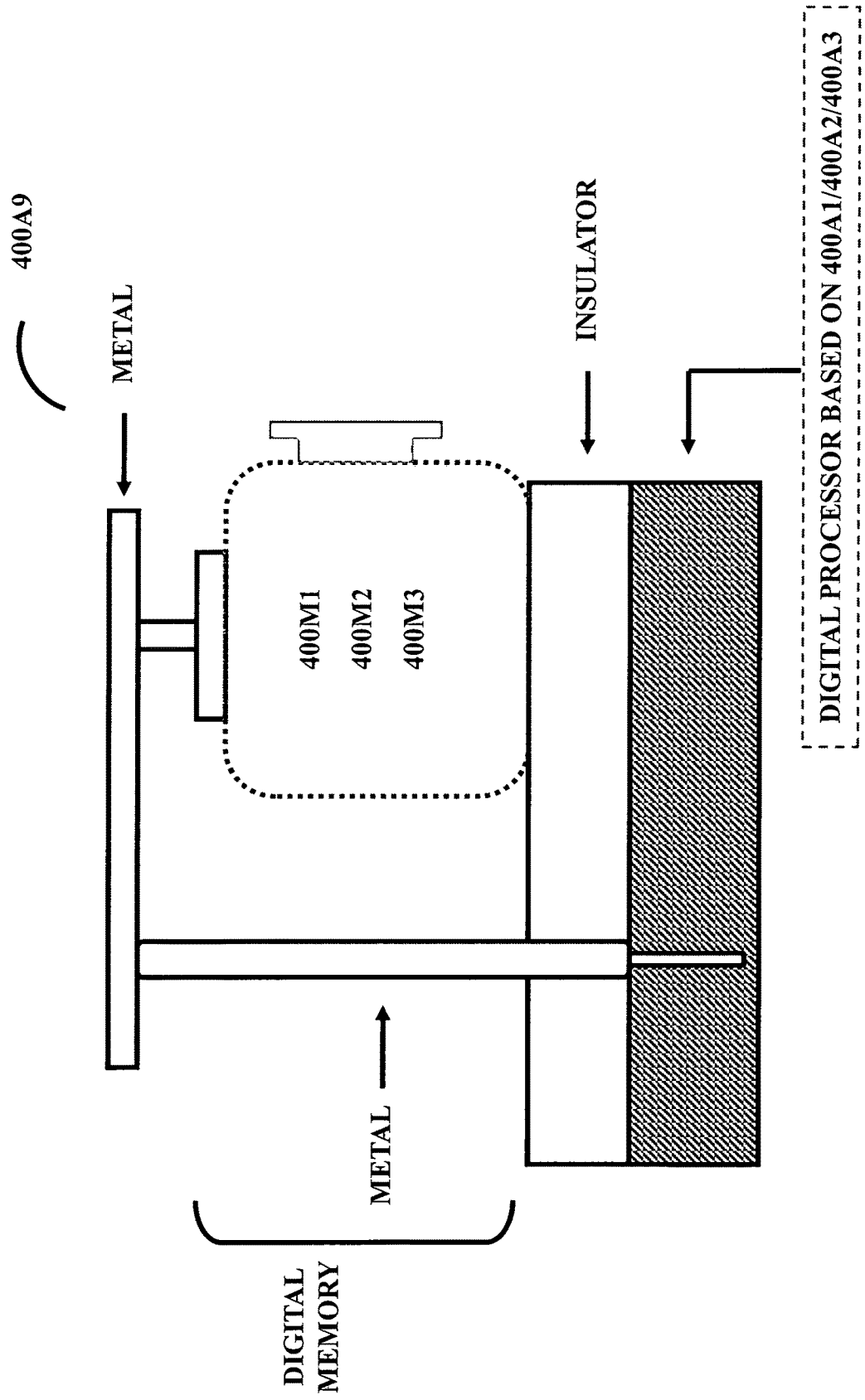

FIGS. 18A-18B illustrate various embodiments of three-dimensional integration of a digital memory with various versions of a System on Chip (SoC).

Figure 19A:
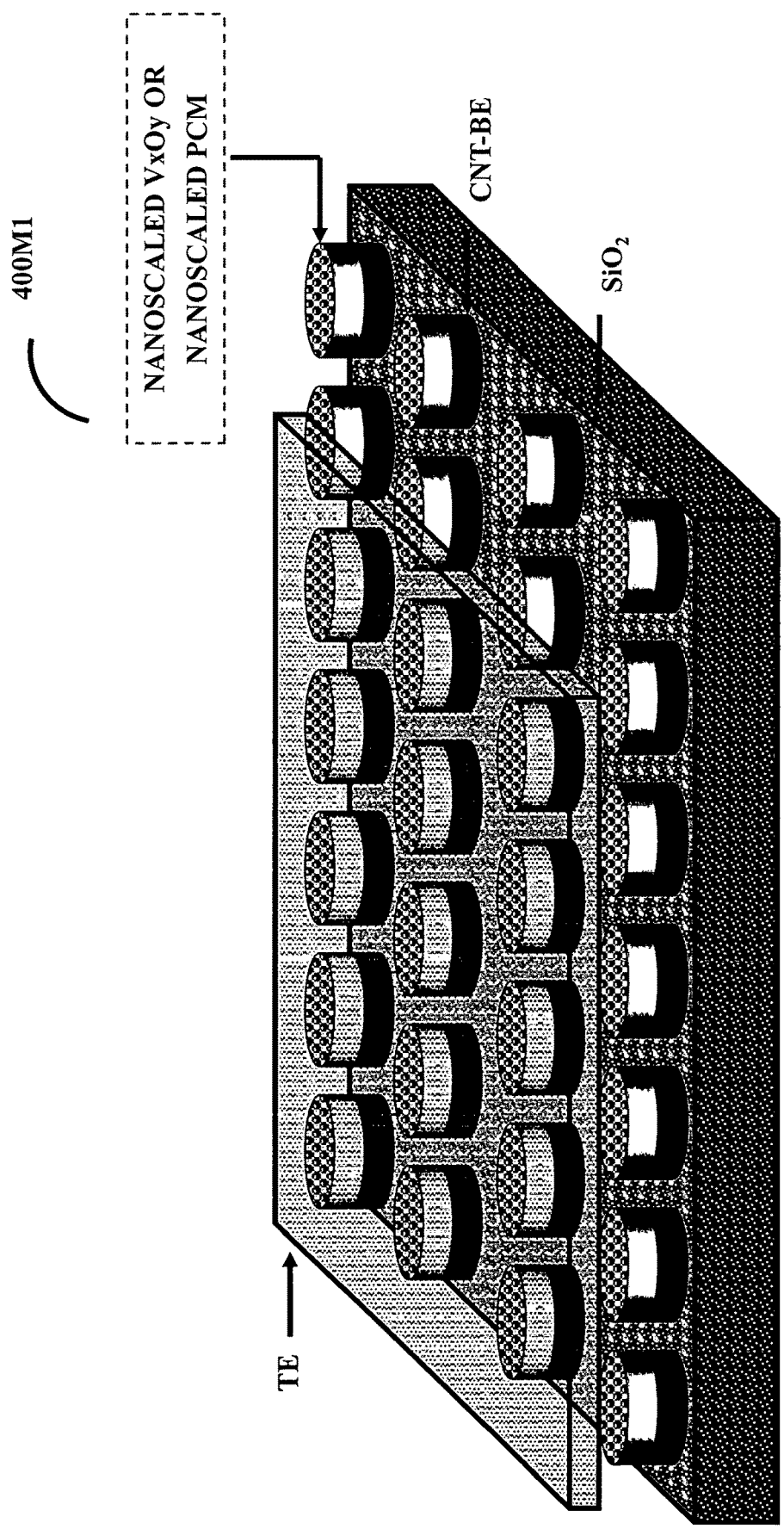
Figure 19B:
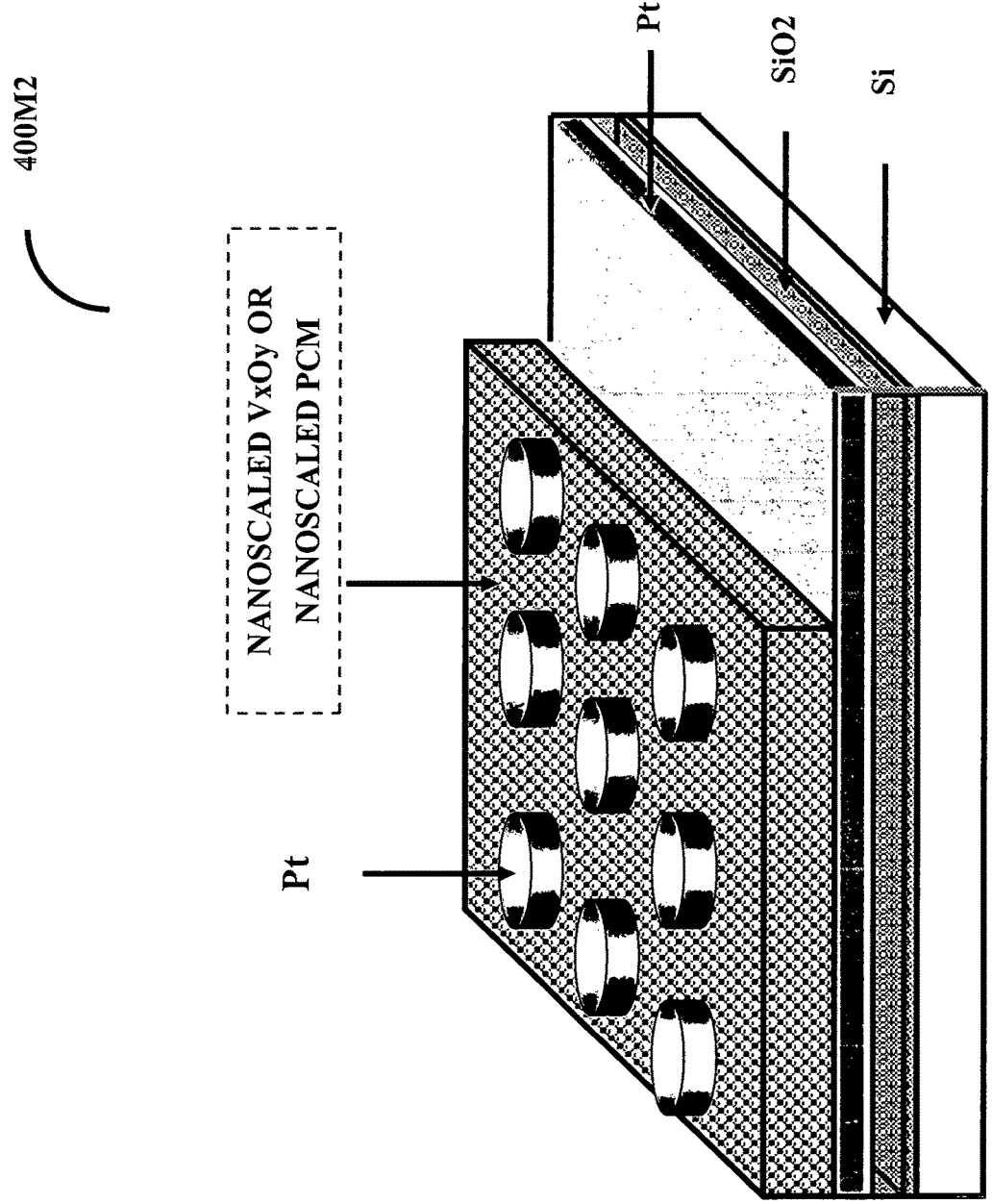
Figure 19C:
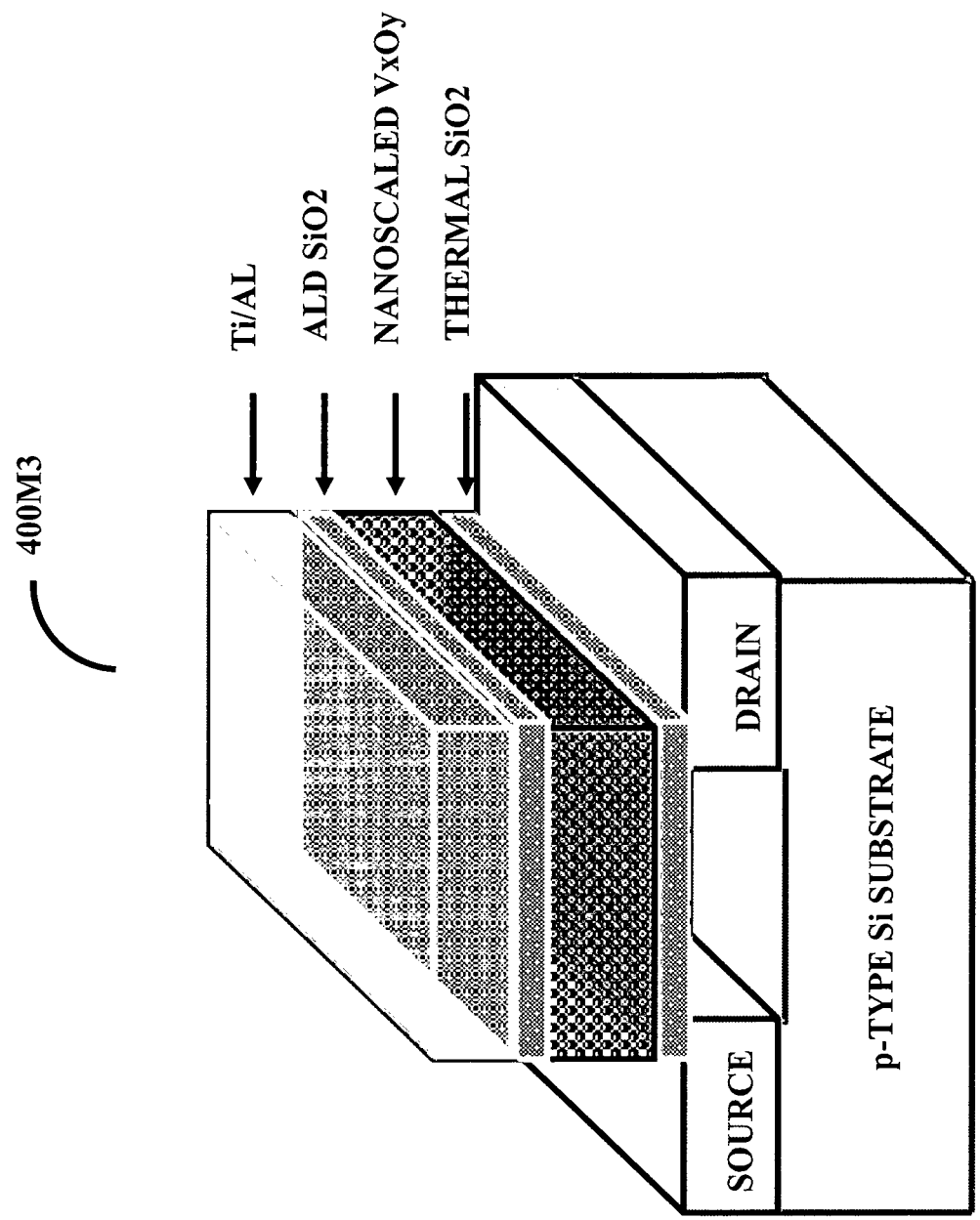

FIGS. 19A-19C illustrate three embodiments of a digital memory.

Packaging of Super System on Chip (SSoC)

FIGS. 20A-20G illustrate an embodiment of electrical interconnections to enable a Super System on Chip.

FIGS. 21A-21D illustrate an embodiment of optical interconnections to enable a Super System on Chip.

Figure 22A:
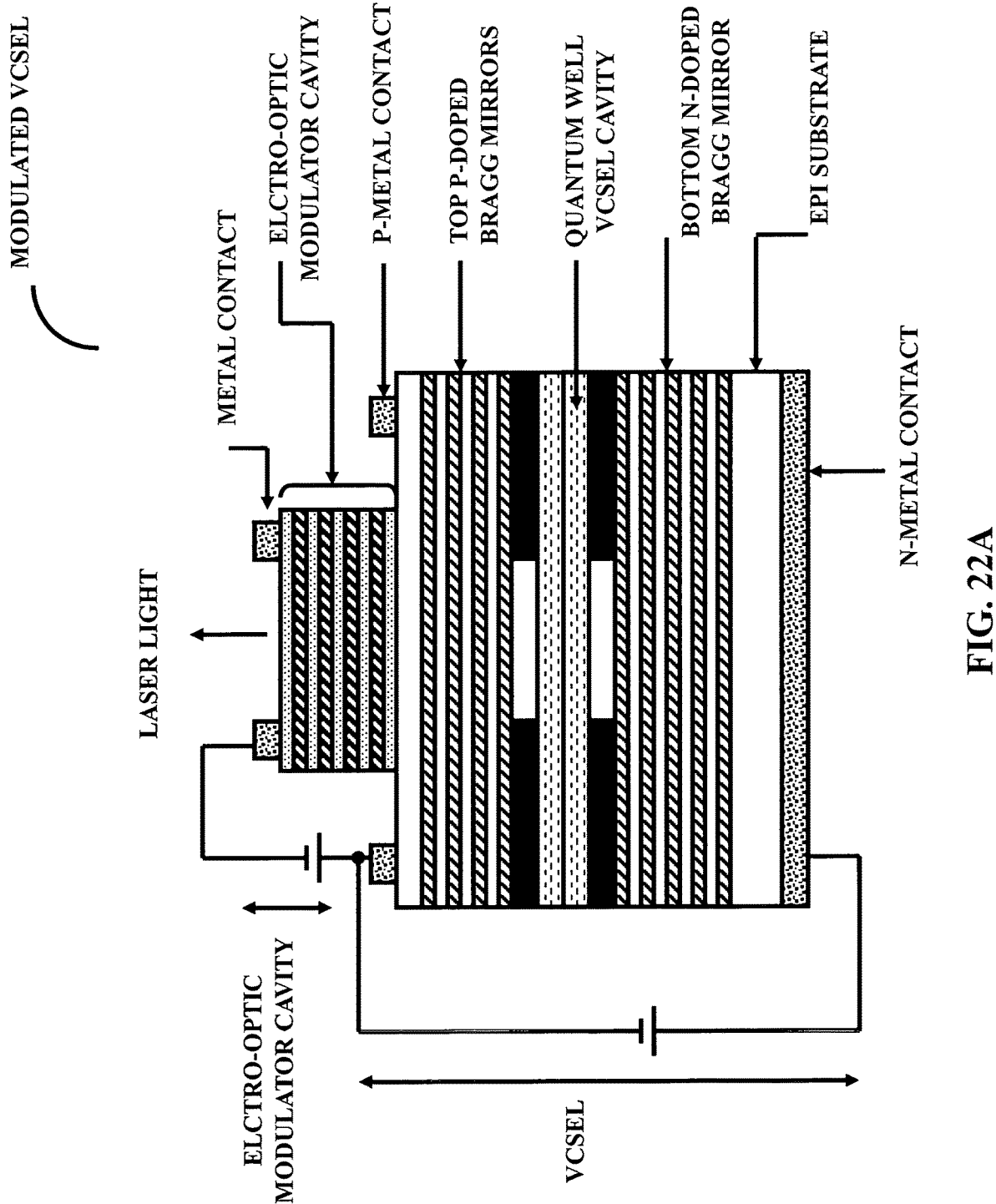
Figure 22B:
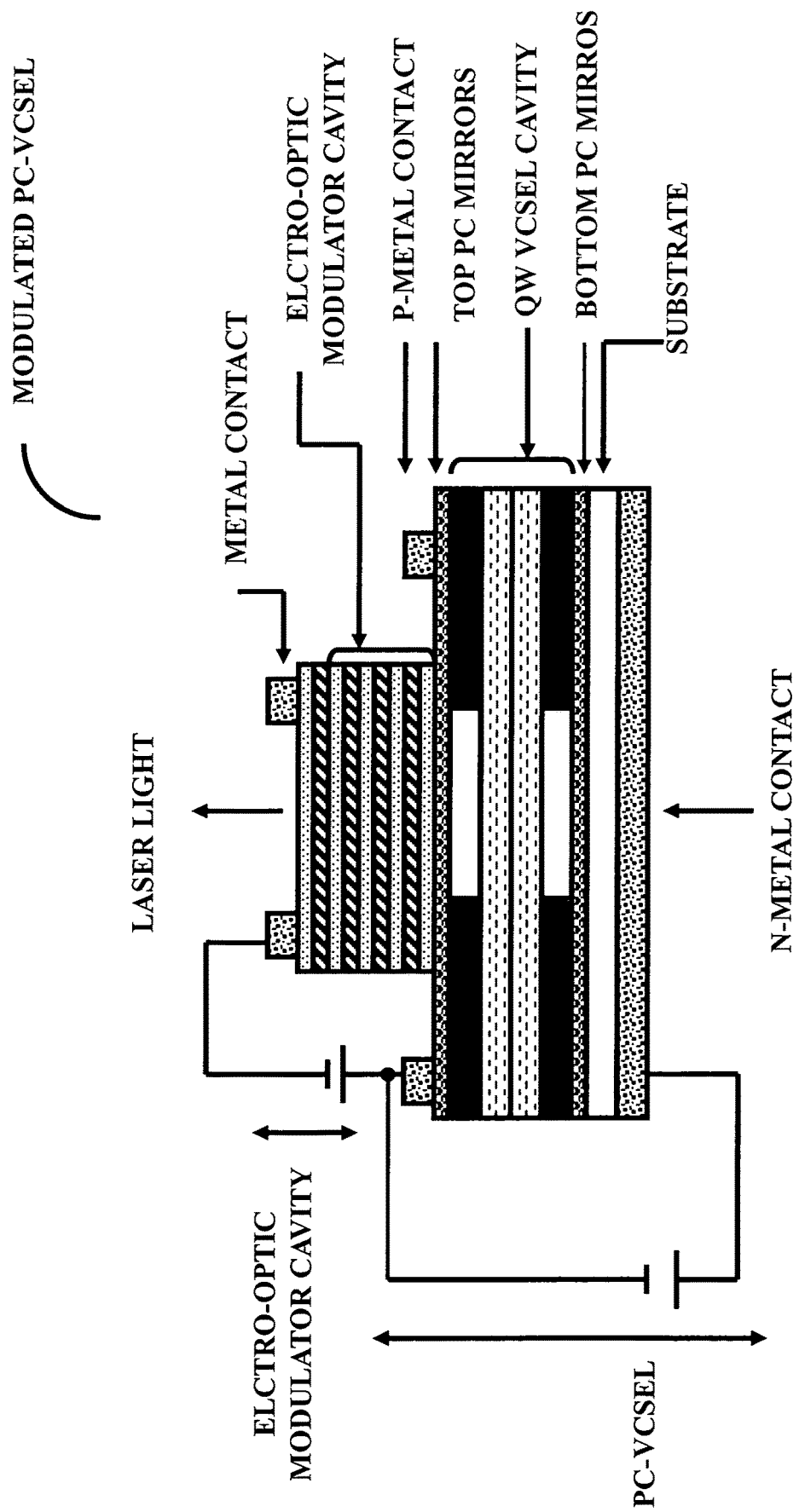

FIGS. 22A-22B illustrate two embodiments of a vertical cavity surface emitting laser for optical interconnections.

Figure 23:
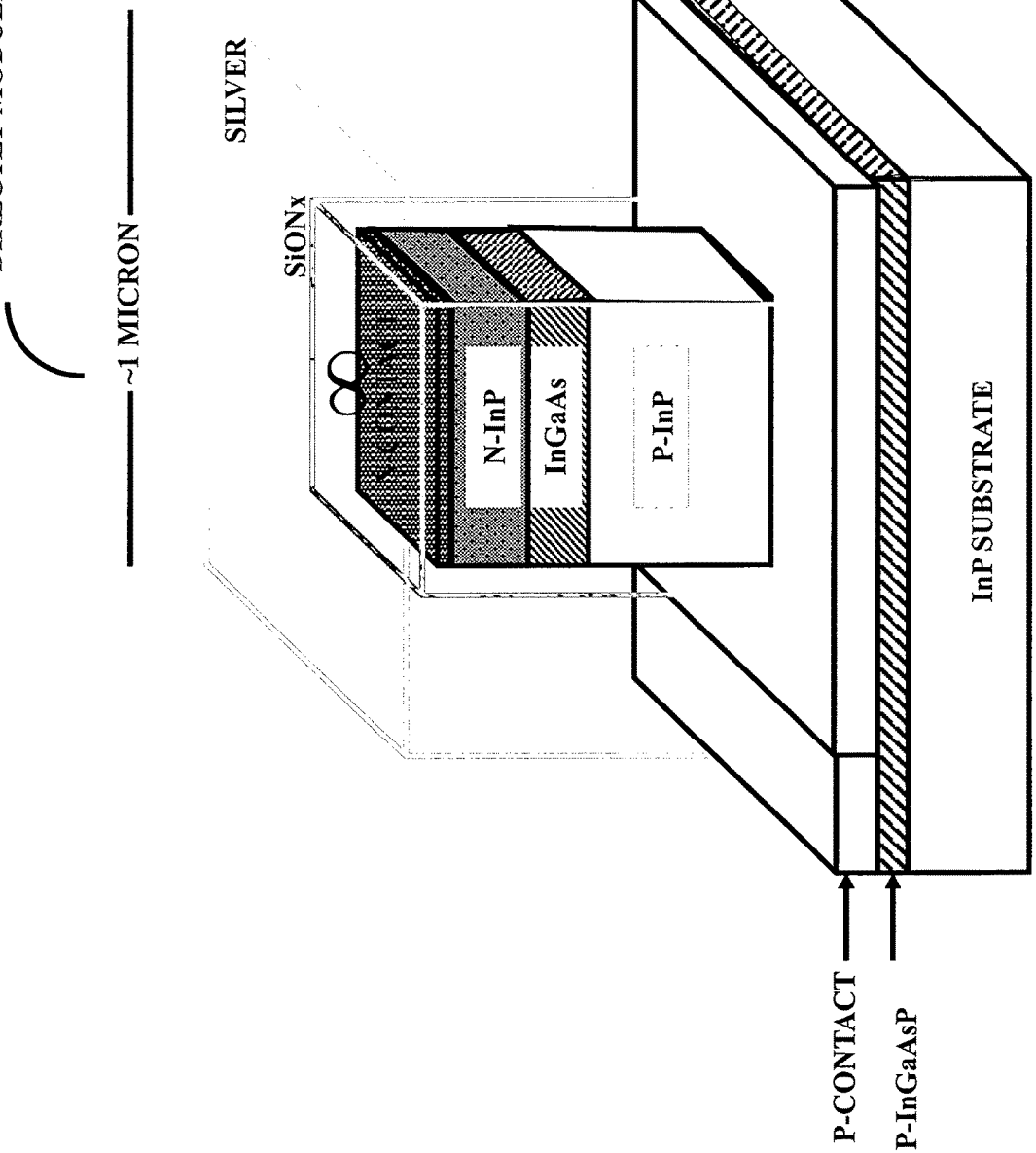

FIG. 23 illustrates an embodiment of a nanolaser for optical interconnections.

Figure 24:
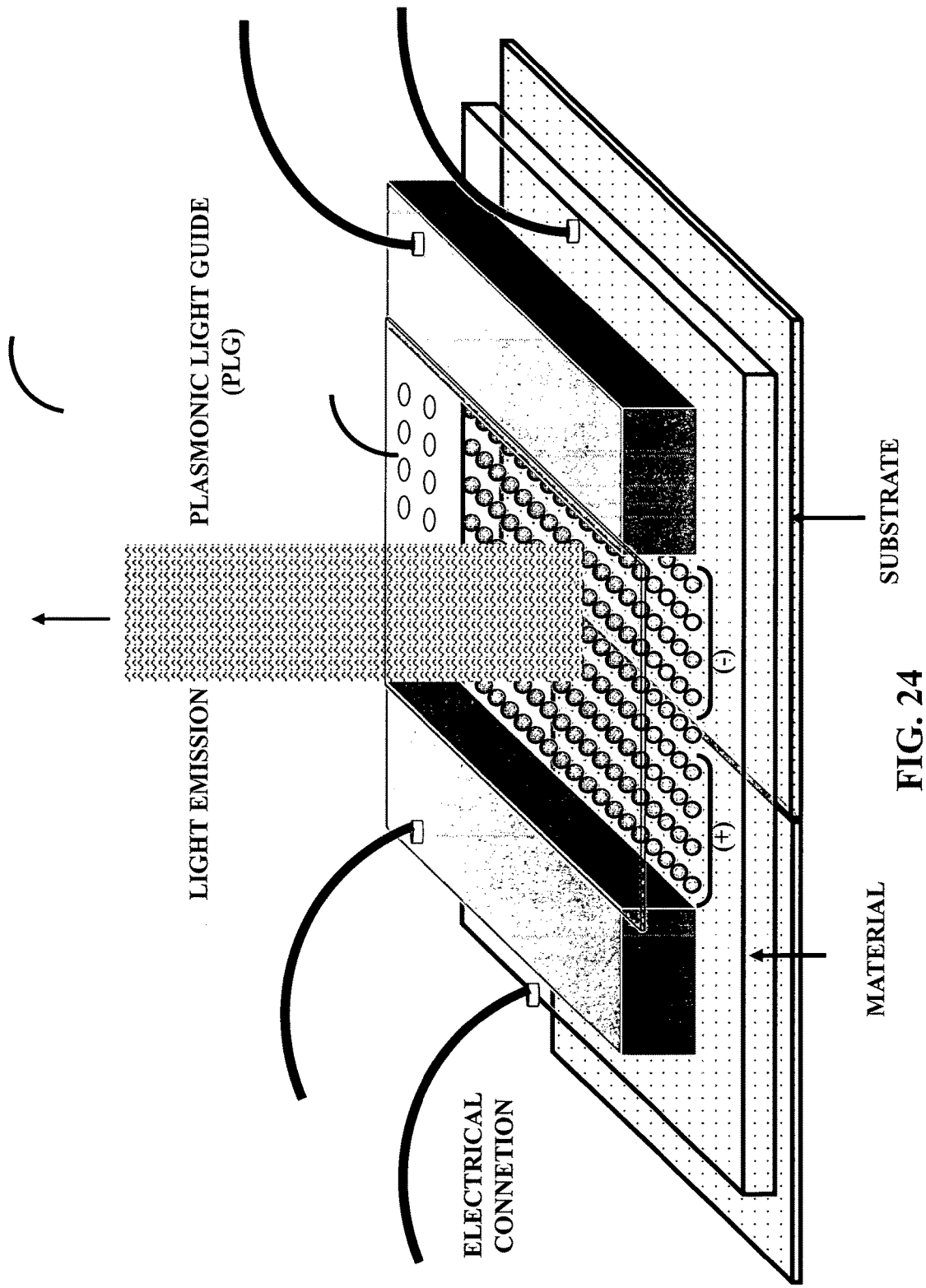

FIG. 24 illustrates an embodiment of a light emitting diode for optical interconnections.

Figure 25B:
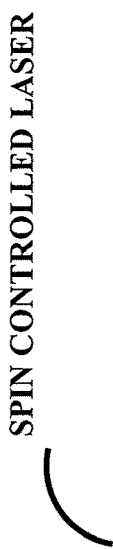
Figure 25B:
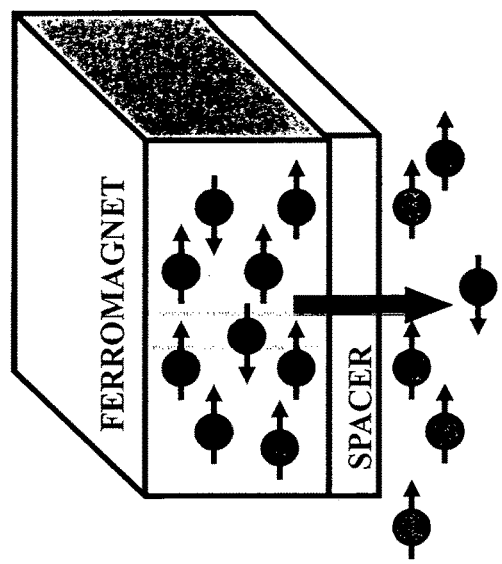
Figure 25A:
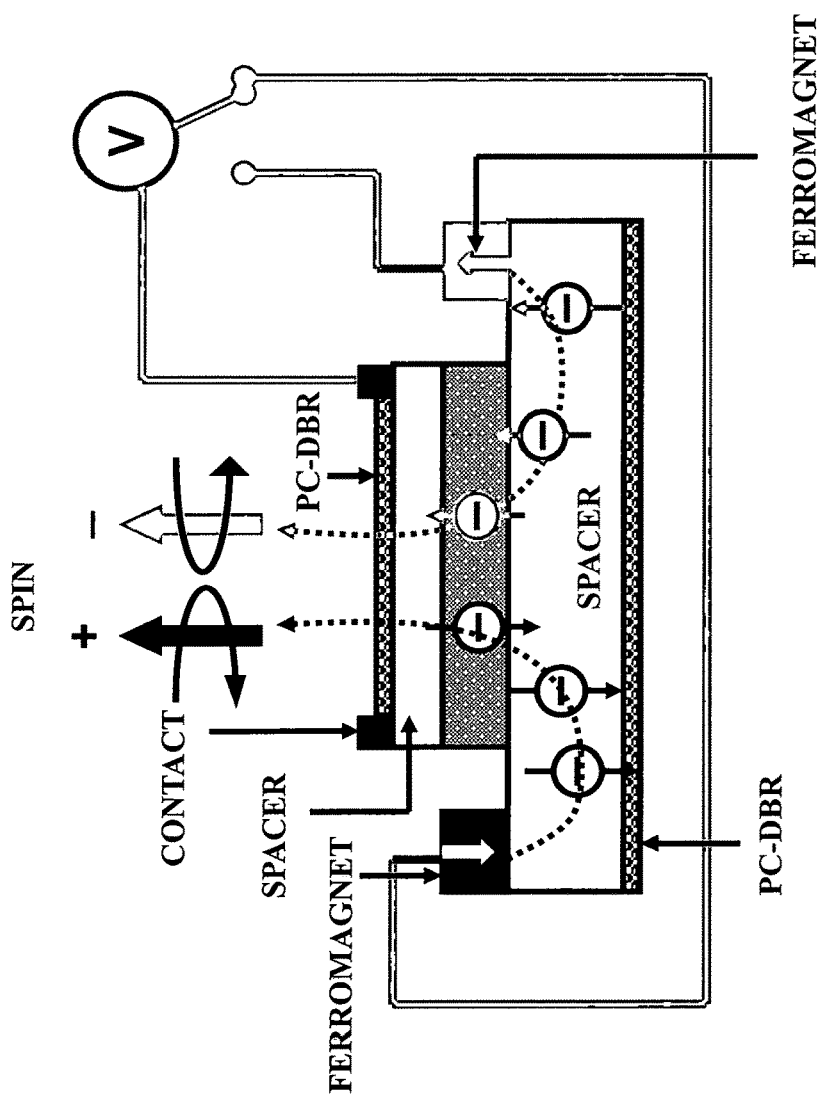

FIGS. 25A-25B illustrate an embodiment of a spin controlled laser for optical interconnections.

Optical Interconnections of Multiple Super System on Chips

FIGS. 26A-26D illustrate four embodiments of horizontally connecting a Super System on Chip on an opto-electronic printed circuit board (PCB).

Figure 27A:
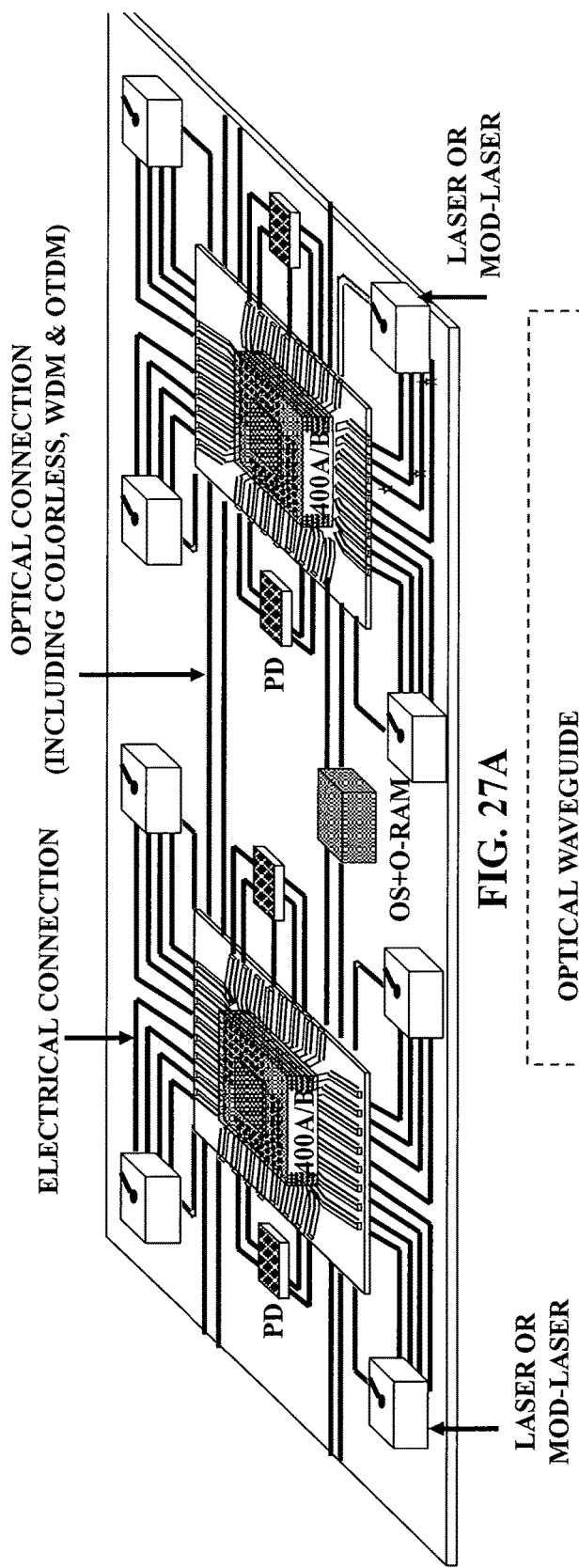
Figure 27B:
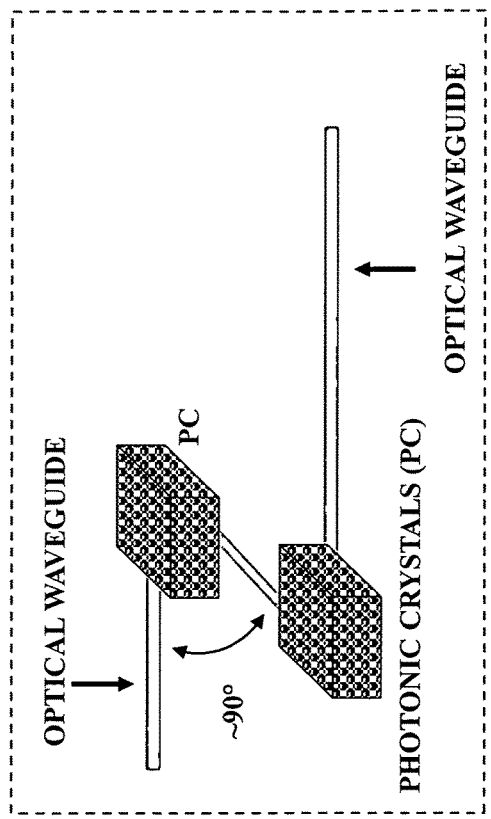

FIGS. 27A-27B illustrate an embodiment of horizontally connecting multiple Super System on Chips on an opto-electronic printed circuit board.

Figure 28A:
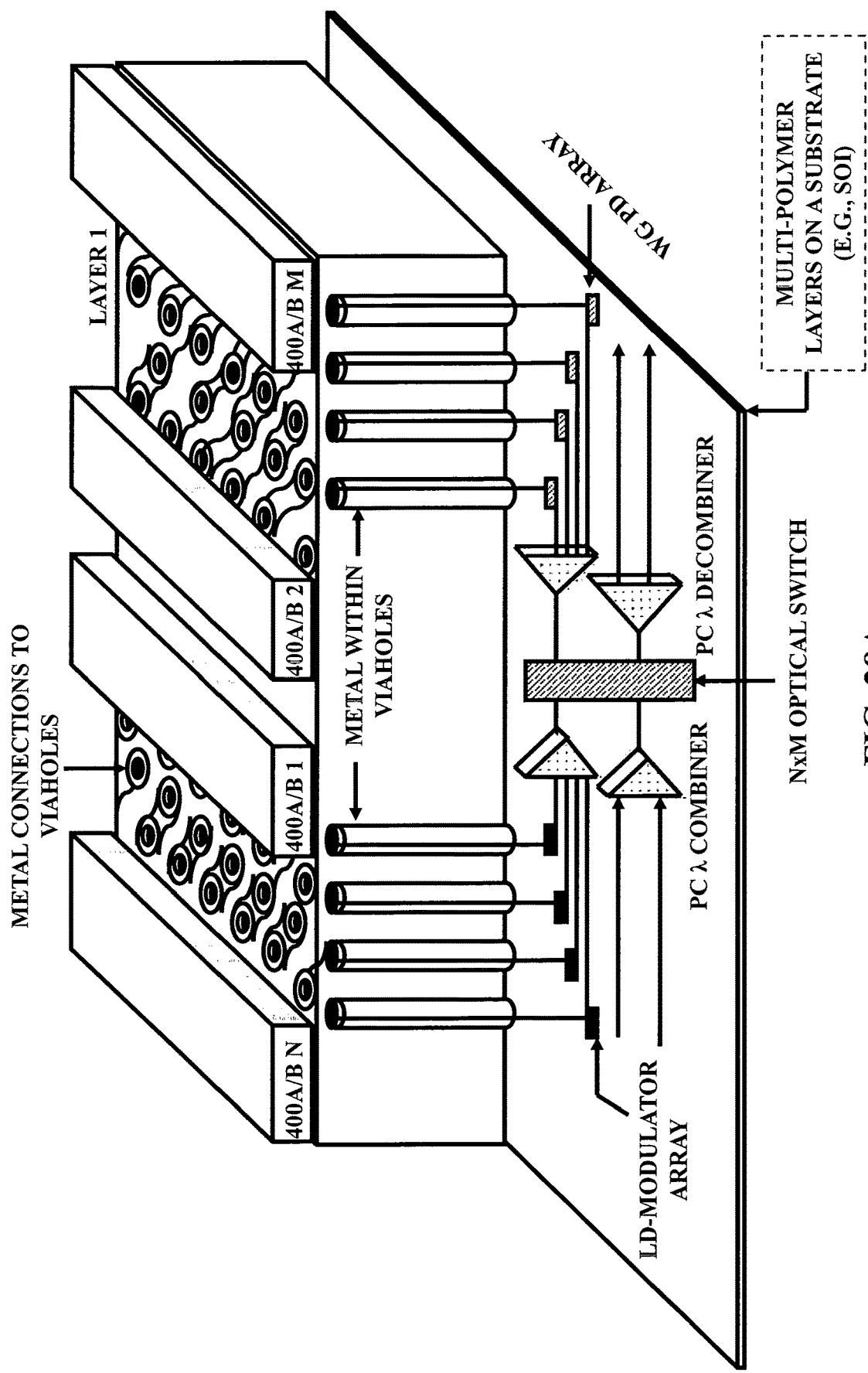
Figure 28B:
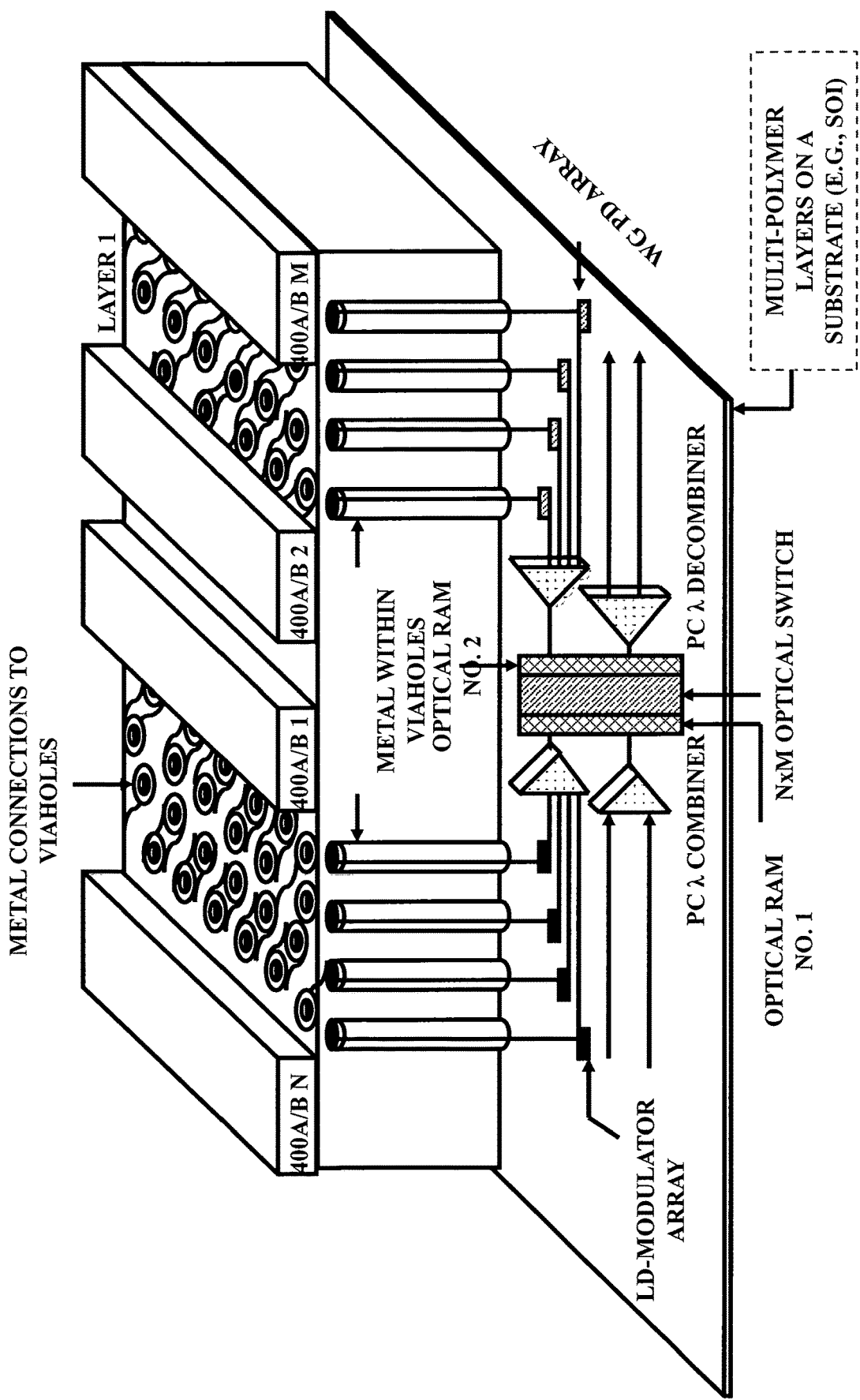

FIGS. 28A-28B illustrate two embodiments of vertically connecting multiple Super System on Chips on an opto-electronic printed circuit board.

Figures 28C, 28D:
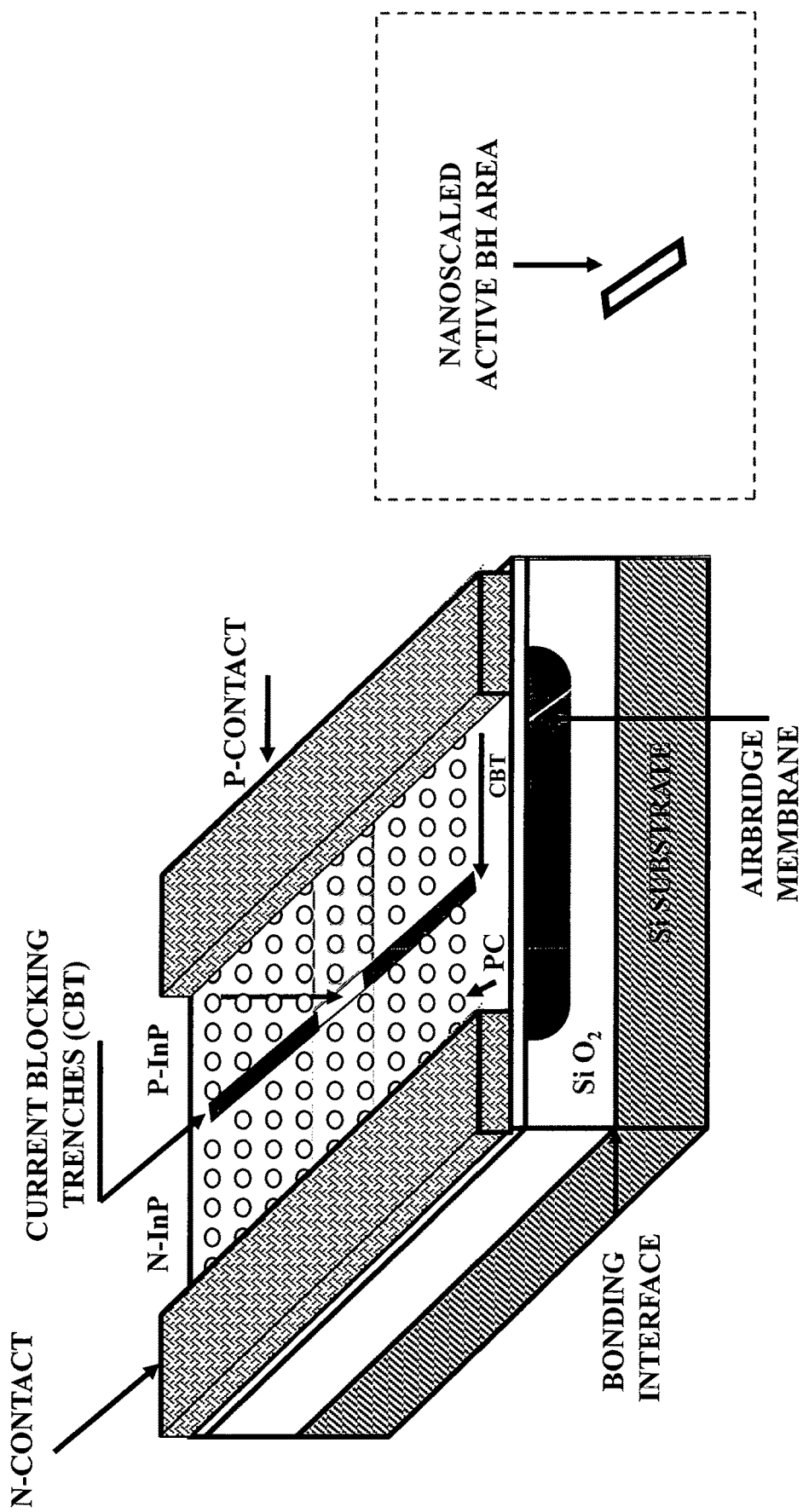

FIGS. 28C-28D illustrate an embodiment of a laser for vertically connecting multiple Super System on Chips on an opto-electronic printed circuit board.

Figure 28E:
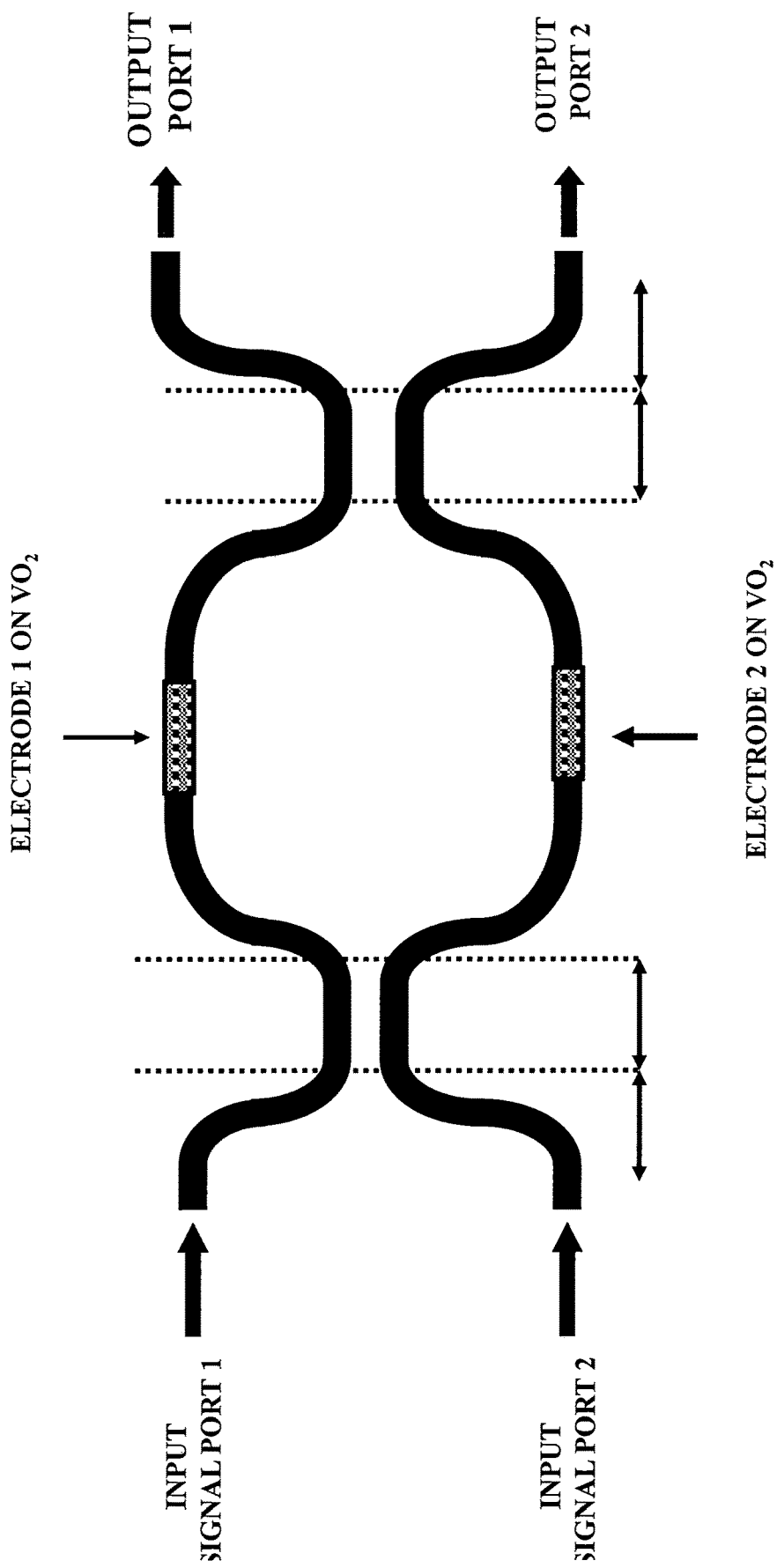
Figure 28G:
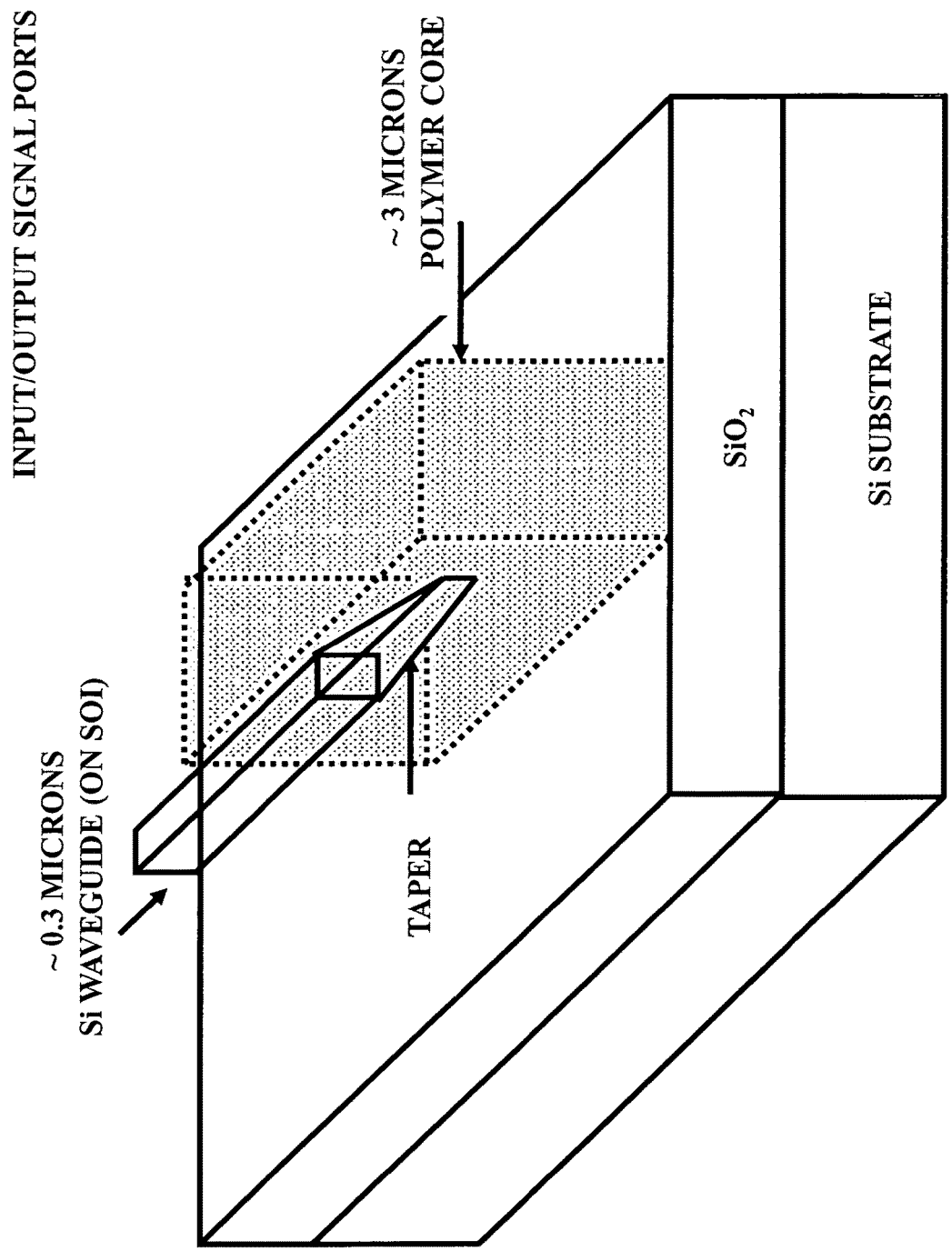

FIGS. 28E-28G illustrate an embodiment of an optical switch for vertically connecting multiple Super System on Chips on an opto-electronic printed circuit board.

Figure 28H:
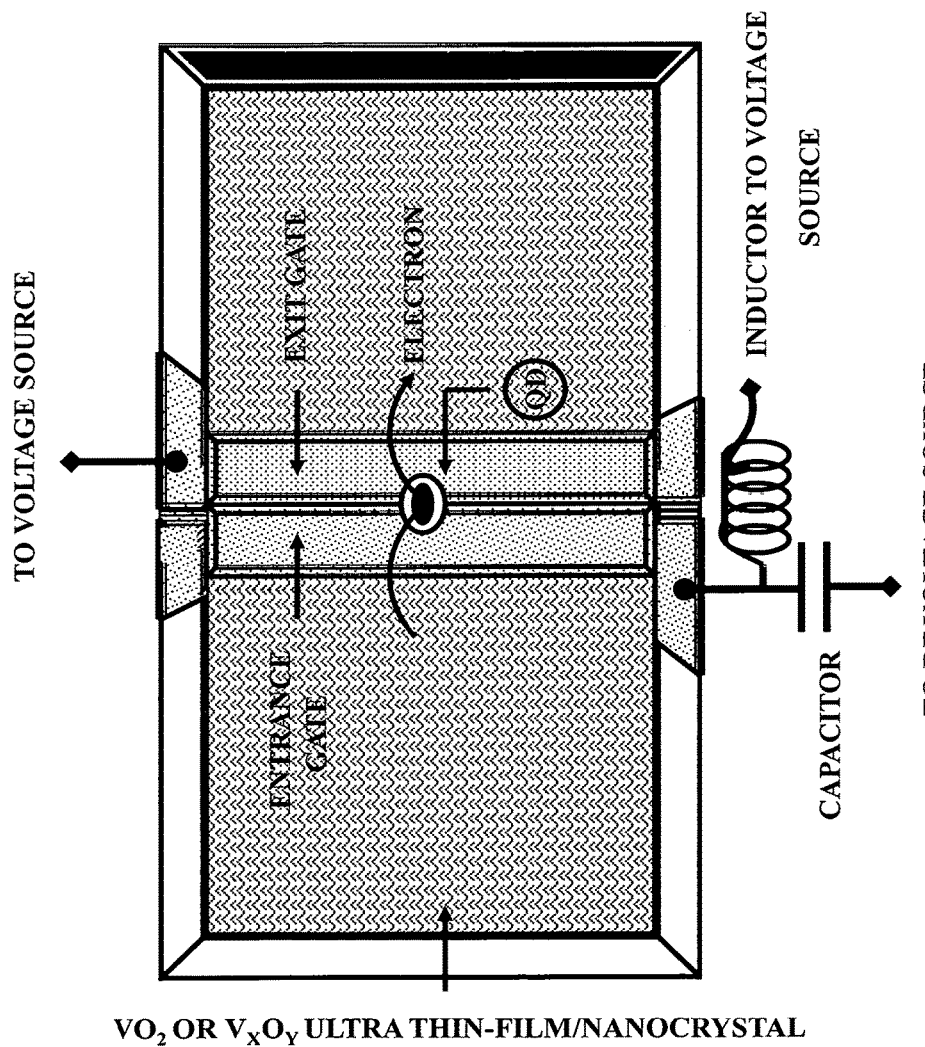
Figure 28I:
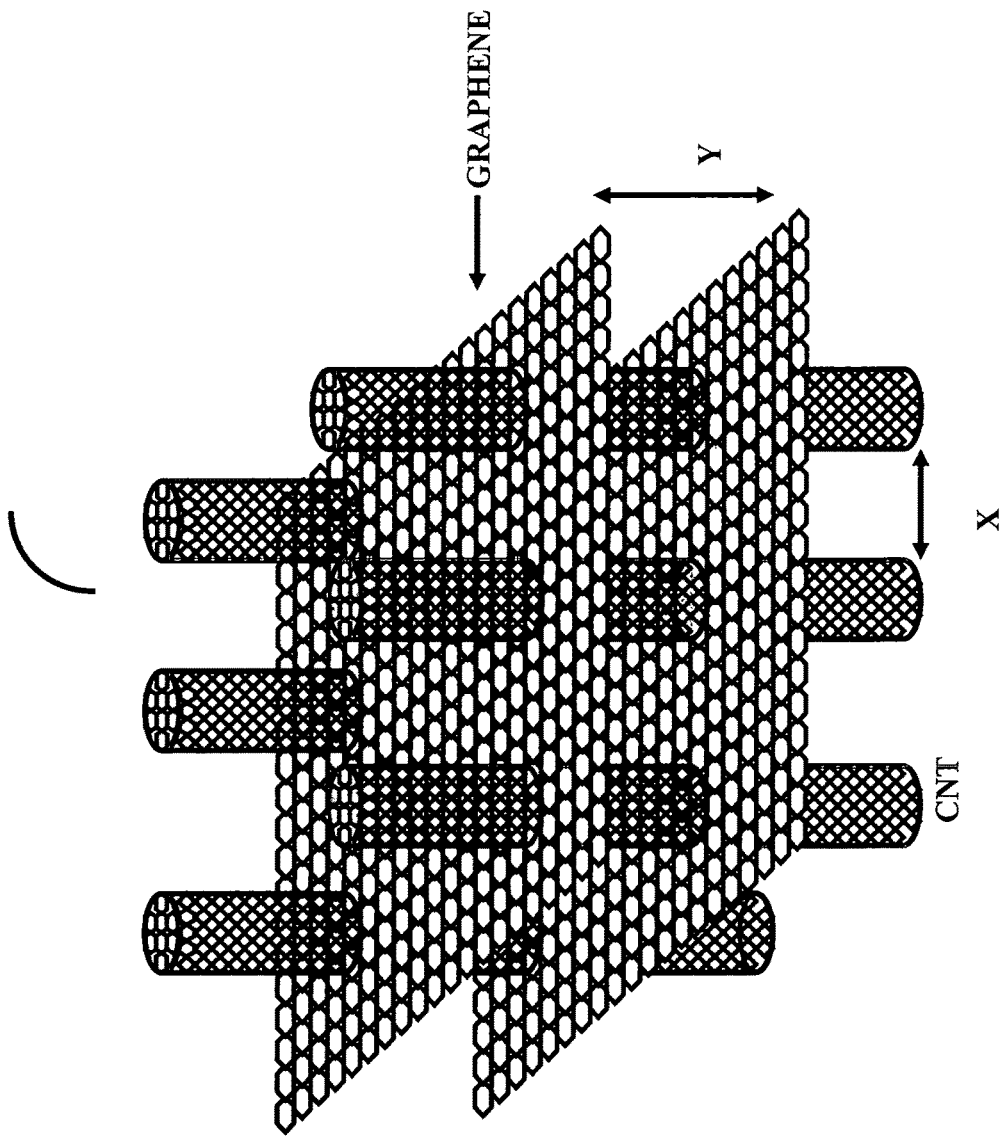

FIGS. 28H-28I illustrate two other components of the optical switch.

Figure 28J:
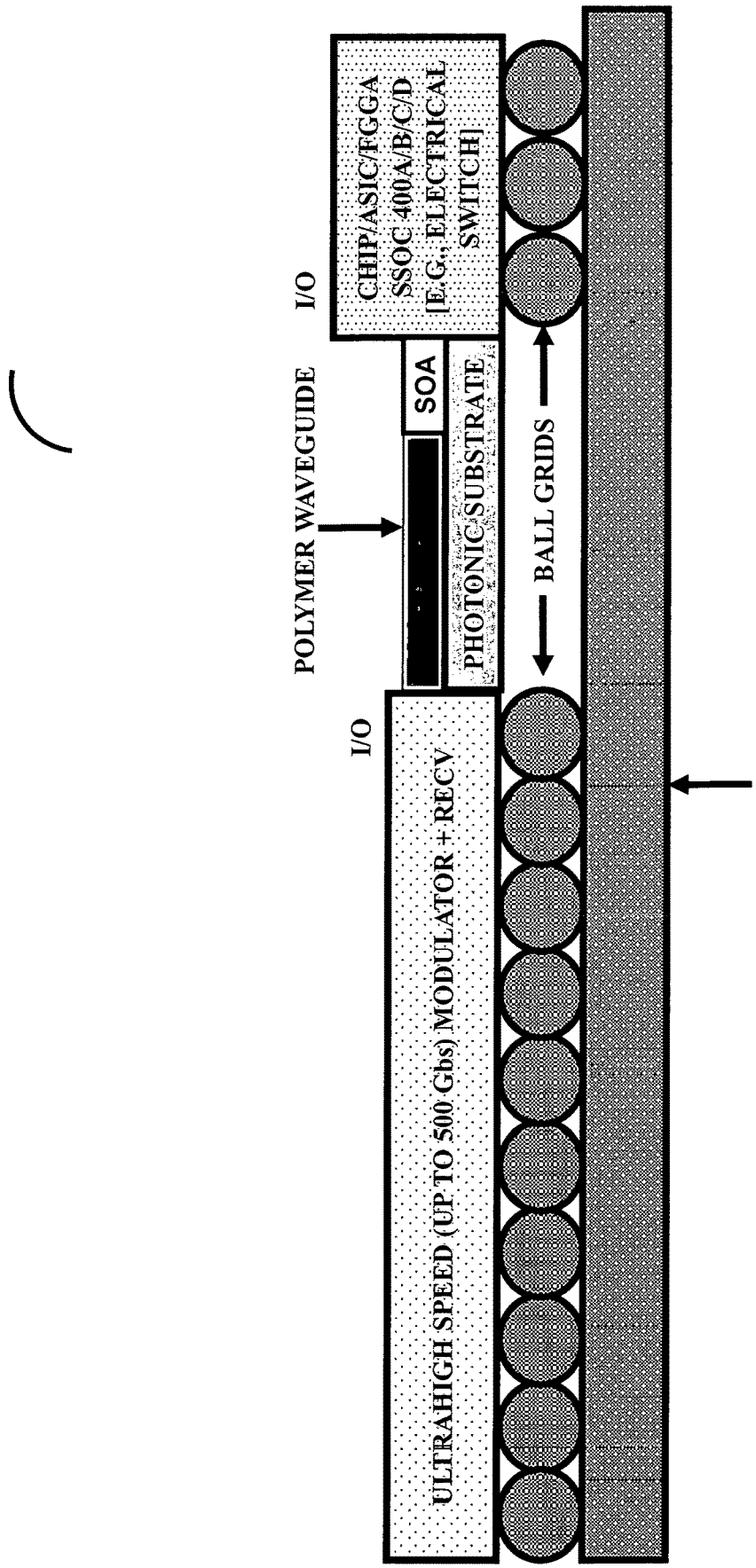

FIG. 28J illustrates an embodiment of optics to chip, utilizing ultrahigh speed modulator, semiconductor amplifier (SOA) and receiver.

Figure 28K:
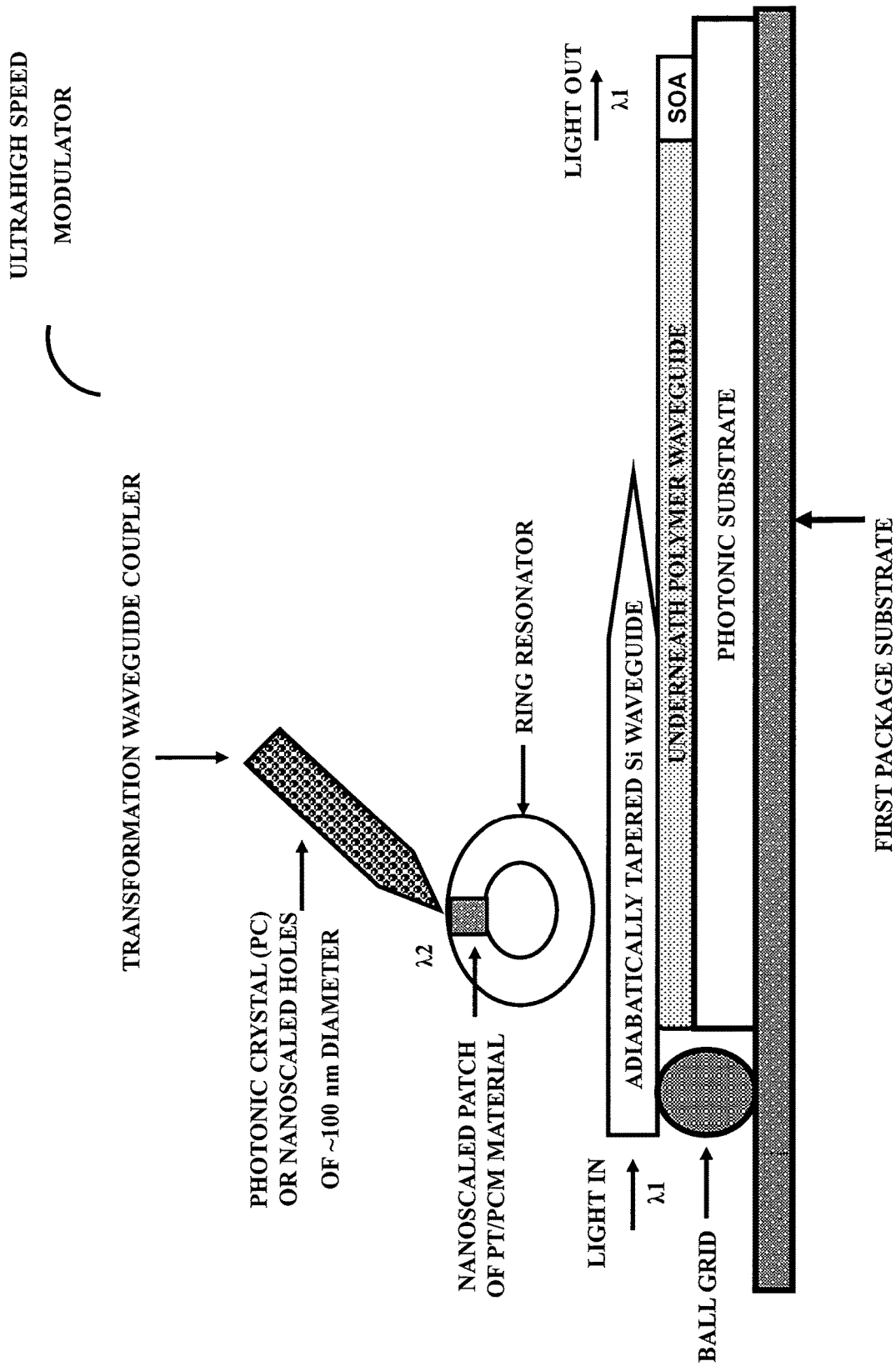

FIG. 28K illustrates an embodiment of ultrahigh speed modulator.

Ultrahigh Density Storage Device

Figure 29A:
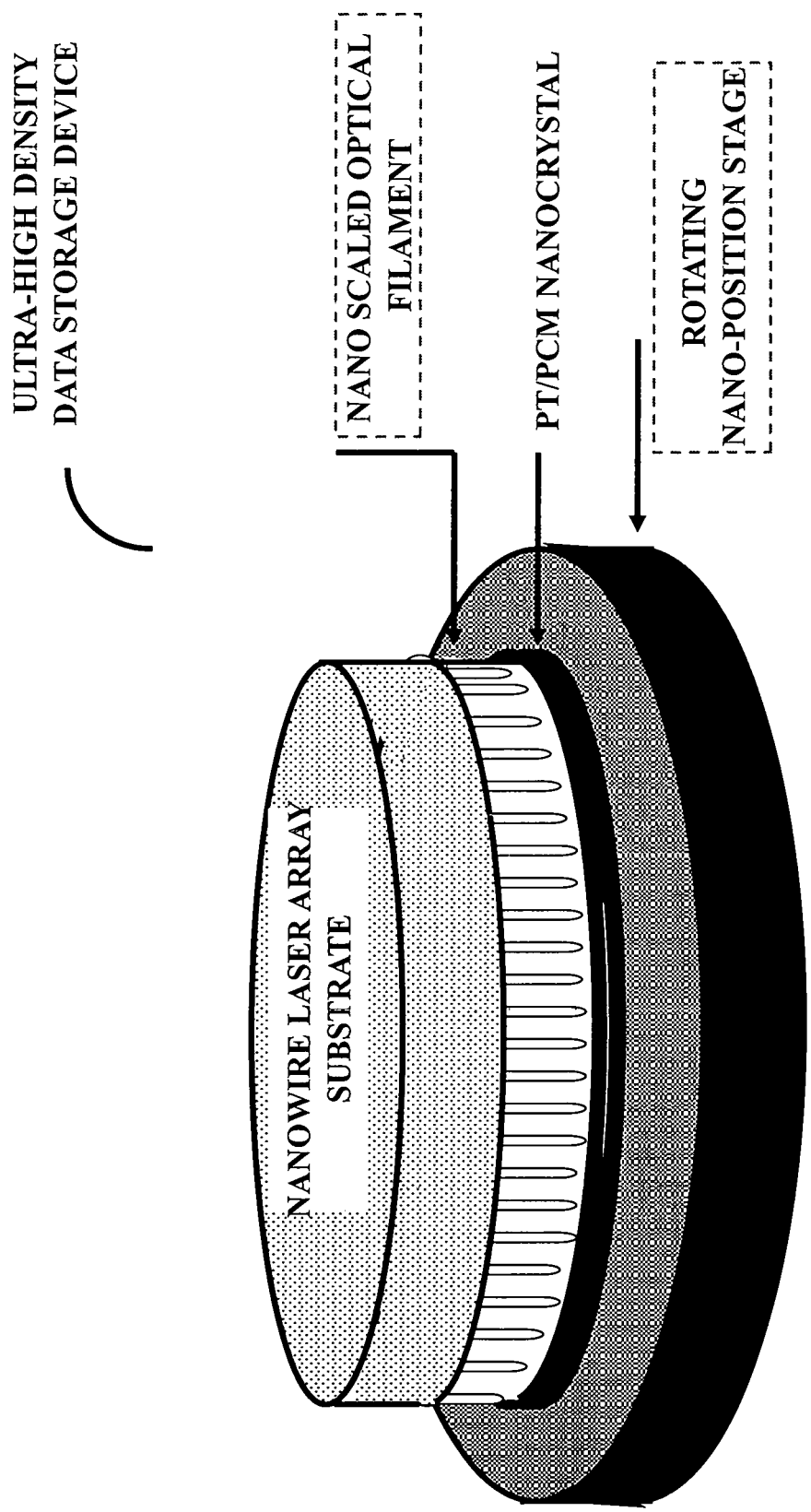

FIG. 29A illustrates an embodiment of an ultrahigh density data storage device.

FIGS. 29B-29E illustrate components for the ultrahigh density data storage device.

Three-Dimensional/Holographic Display

FIGS. 30A-30J illustrate ten embodiments of a protruded metal/non-metal nano optical antenna (NOA).

FIGS. 31A-31L illustrate various configurations of blue quantum dots, green quantum dots and red quantum dots.

Figure 31G:
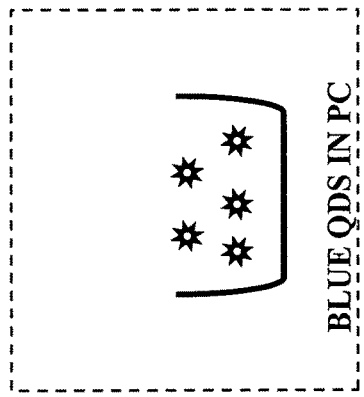
Figure 31H:
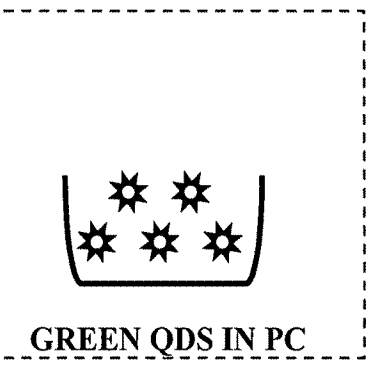
Figure 31I:
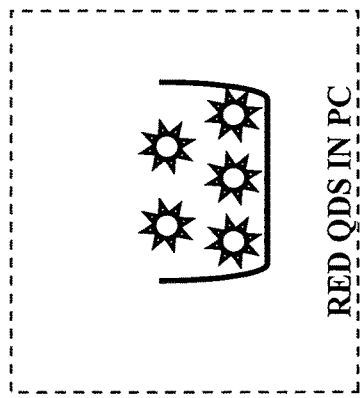
Figure 31J:
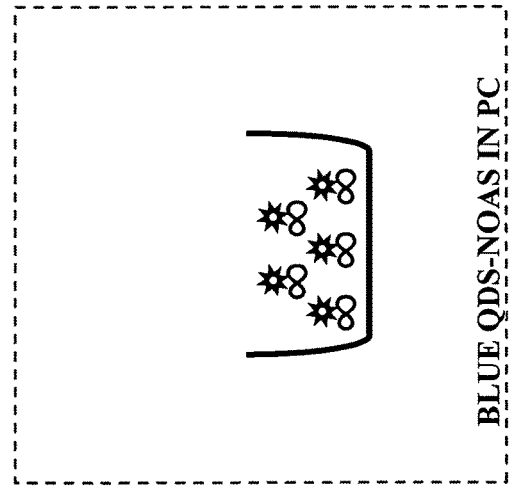
Figure 31K:
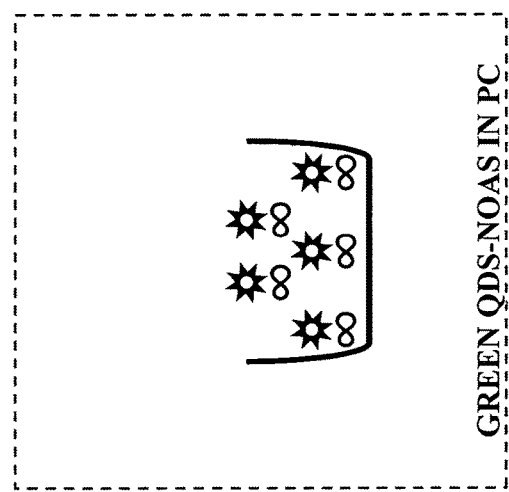
Figure 31L:
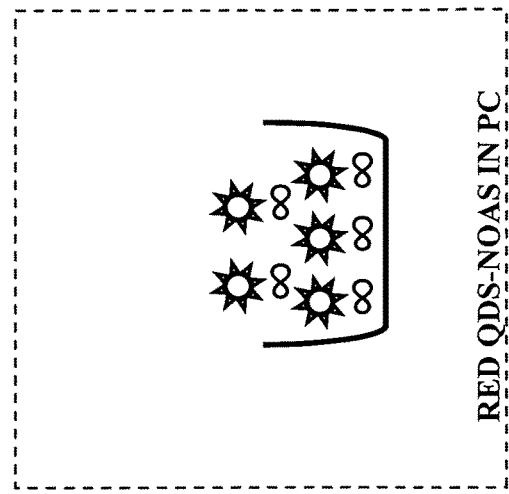
Figures 31M, 31N:
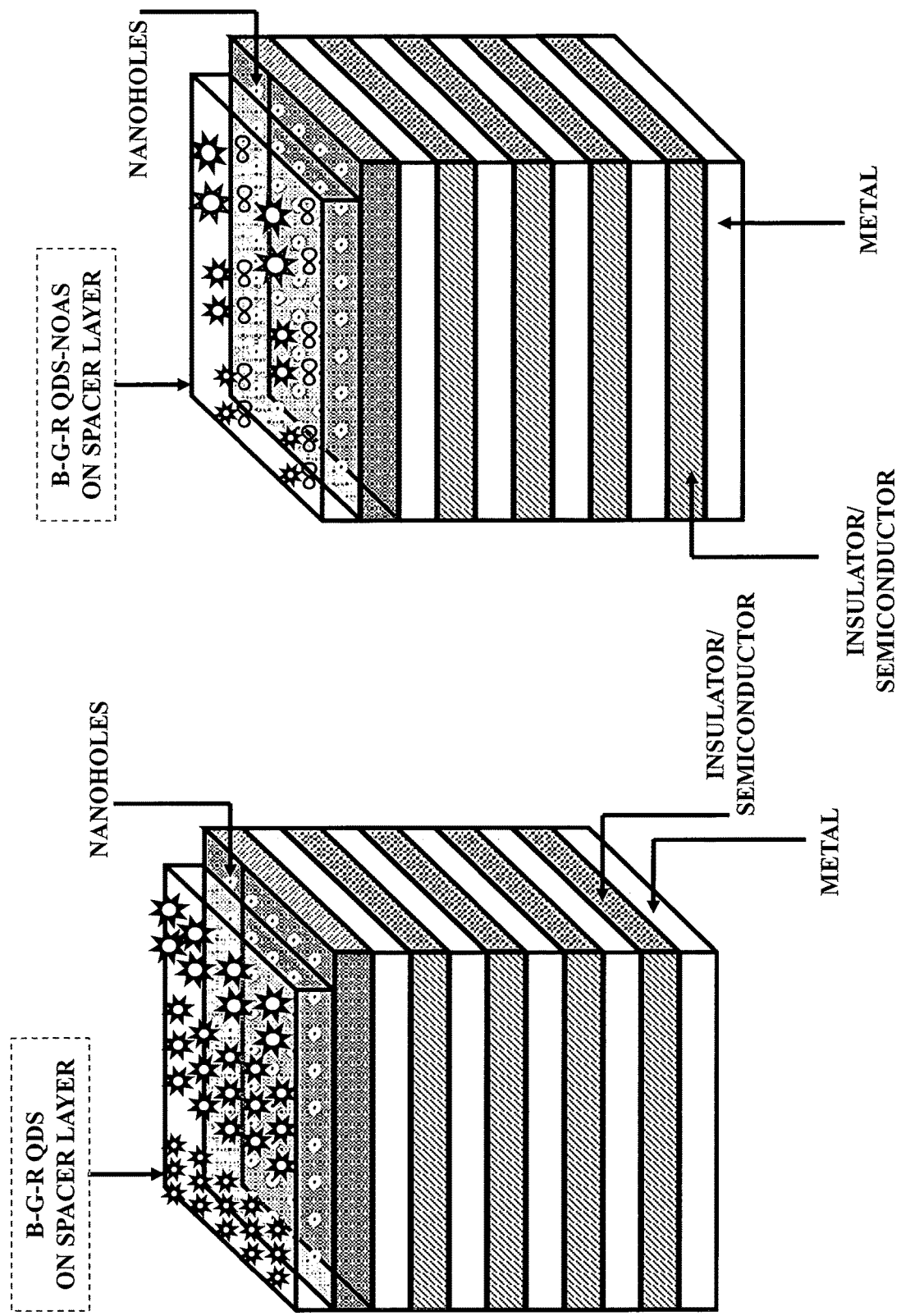

FIG. 31M illustrates a combination of a hyperbolic metamaterial (HMM) and quantum dots (e.g., red/blue/green quantum dots).

FIG. 31N illustrates a combination of a hyperbolic metamaterial and quantum dots (e.g., blue/green/red quantum dots) coupled with protruded metal/non-metal nano optical antenna.

Figure 31O:
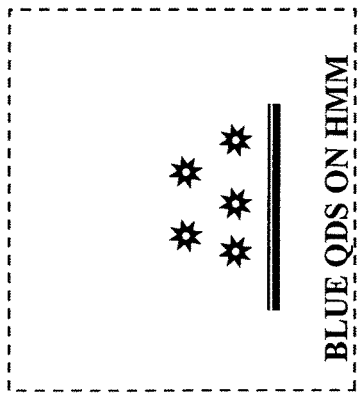
Figure 31P:
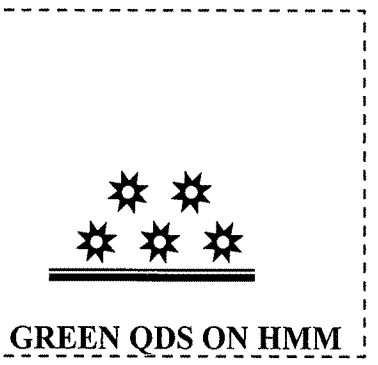
Figure 31Q:
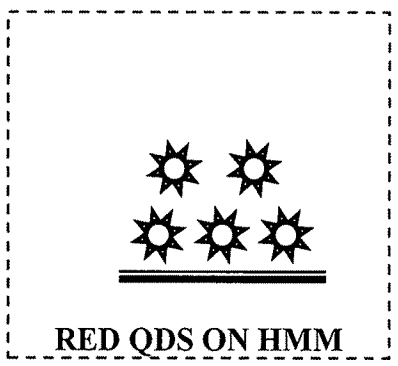

FIGS. 31O-31Q illustrate configurations of blue quantum dots on a hyperbolic metamaterial, green quantum dots on a hyperbolic metamaterial and red quantum dots on a hyperbolic metamaterial respectively.

Figure 31R:
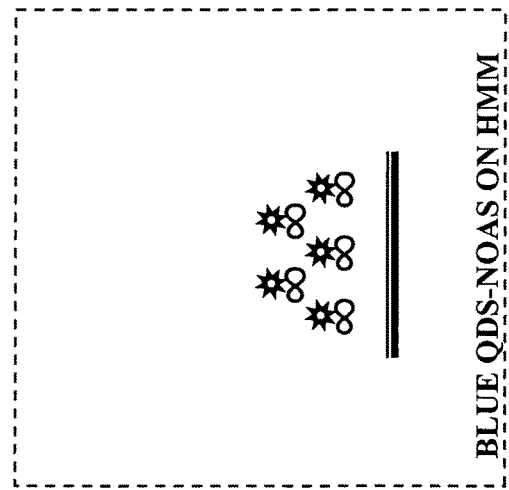
Figure 31S:
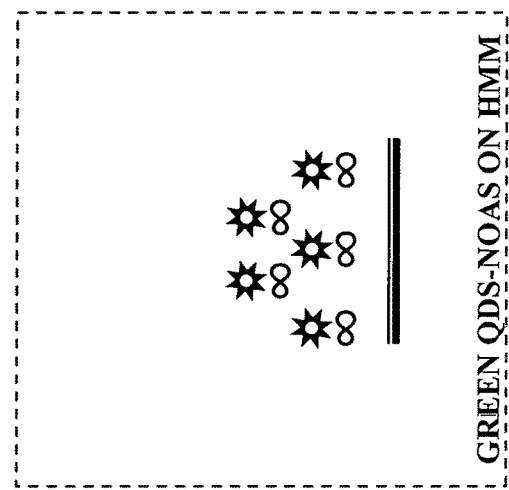
Figure 31T:
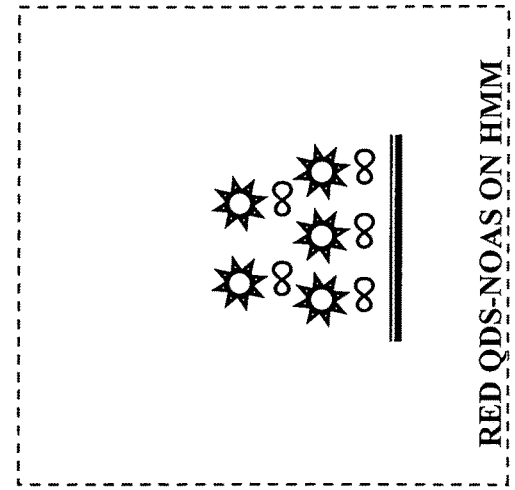

FIGS. 31R-31T illustrate configurations of blue quantum dots (wherein each blue quantum dot is coupled with a protruded metal/non-metal nano optical antenna) on a hyperbolic metamaterial, green quantum dots (wherein each green quantum dot is coupled with a protruded metal/non-metal nano optical antenna) on a hyperbolic metamaterial and red quantum dots (wherein each red quantum dot is coupled with a protruded metal/non-metal nano optical antenna) on a hyperbolic metamaterial respectively.

FIGS. 32A-32G describe/outline five embodiments of an electrically switchable light valve (LV).

Figure 32G:
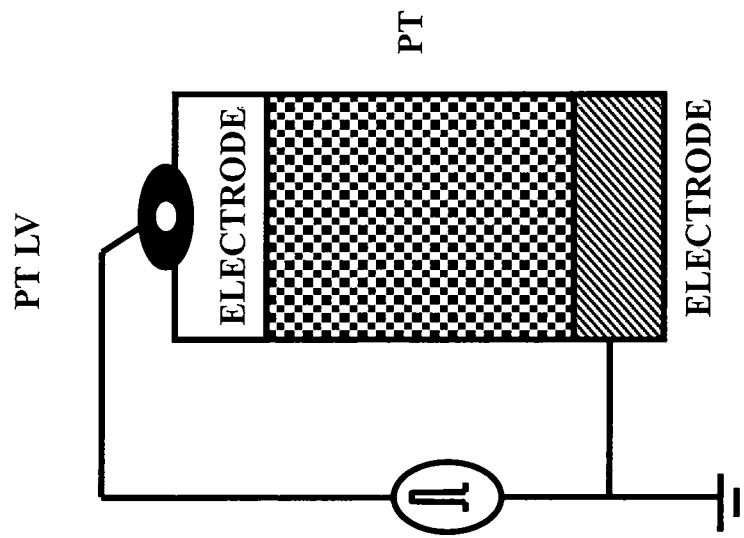
Figure 32F:
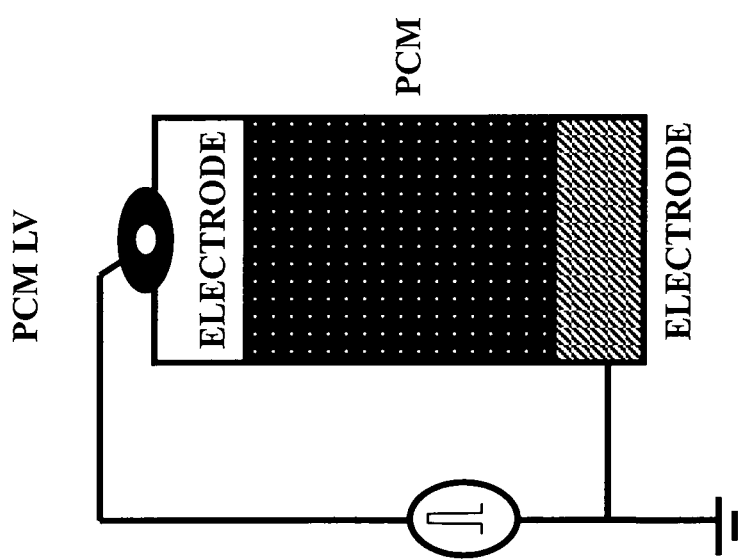

FIGS. 32F-32G illustrate two embodiments of an electrically switchable light valve.

Figure 33:
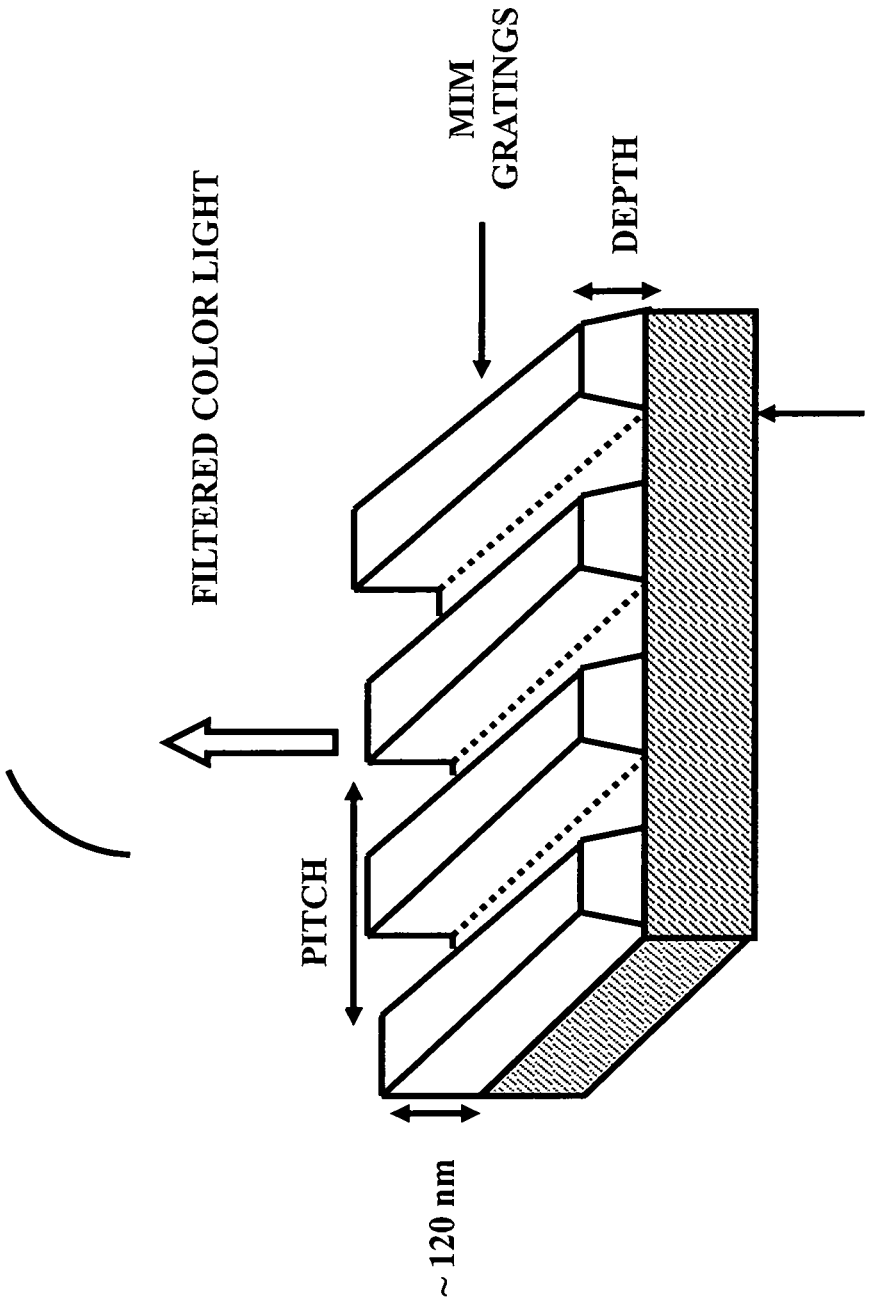

FIG. 33 illustrates an embodiment of a plasmonic optical color filter.

Figure 34A:
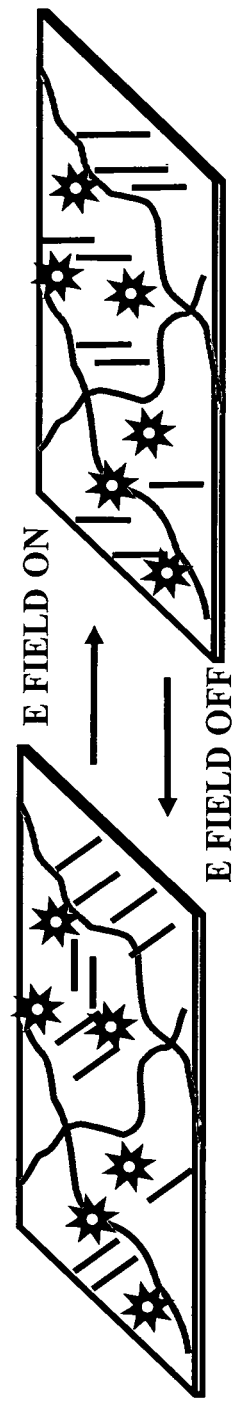
Figure 34B:
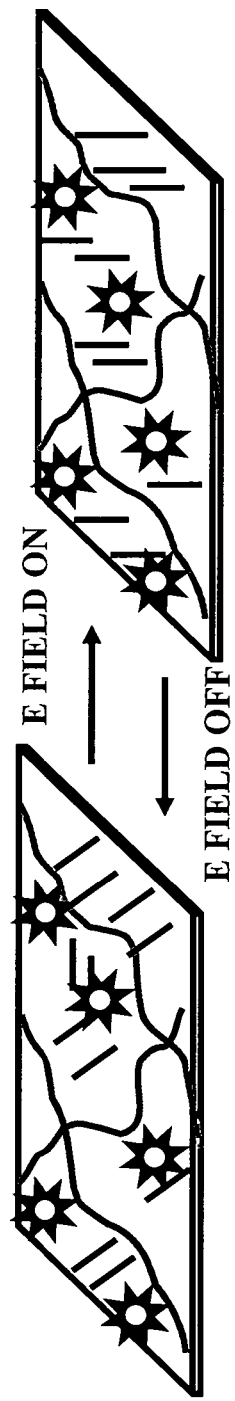
Figure 34C:
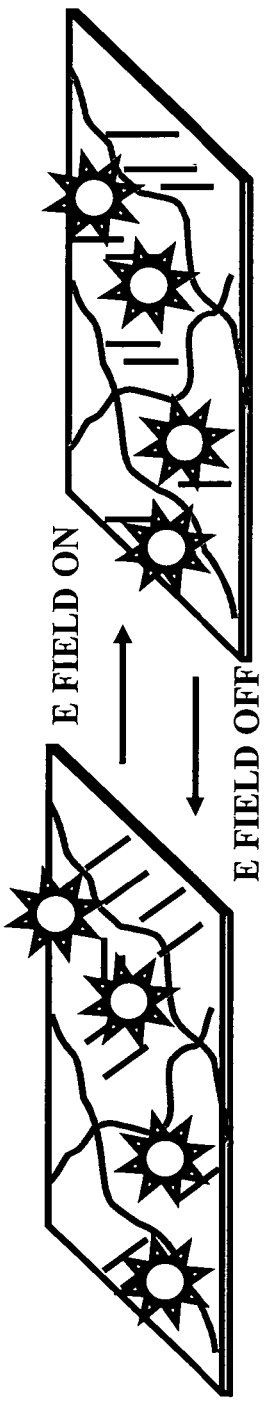

FIGS. 34A-34C illustrate blue quantum dots in an electrically switchable liquid crystal gel (LCG), green quantum dots in an electrically switchable liquid crystal gel and red quantum dots in an electrically switchable liquid crystal gel respectively.

FIGS. 35A-35H illustrate eight embodiments of a pixel of a display, utilizing light emitting diode (LED) backlighting.

FIGS. 36A-36G illustrate materials and design/fabrication/construction for an embodiment of an ultraviolet (UV)/blue microlight emitting diode (pLED).

FIGS. 37A-37H illustrate eight embodiments of a micropixel of a display, utilizing ultraviolet/blue microlight emitting diodes on each sub pixel.

Figure 38:
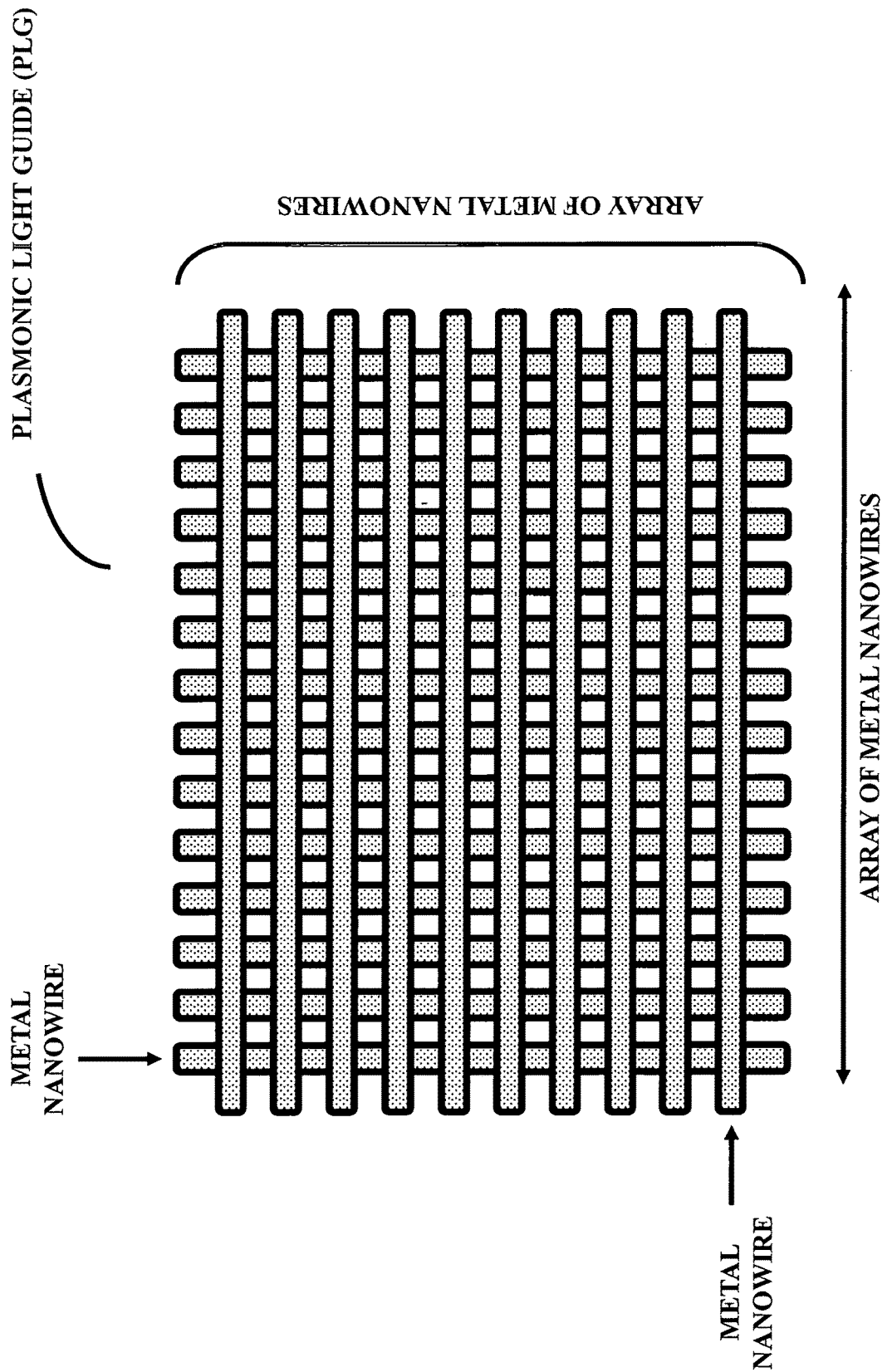
Figure 39A:
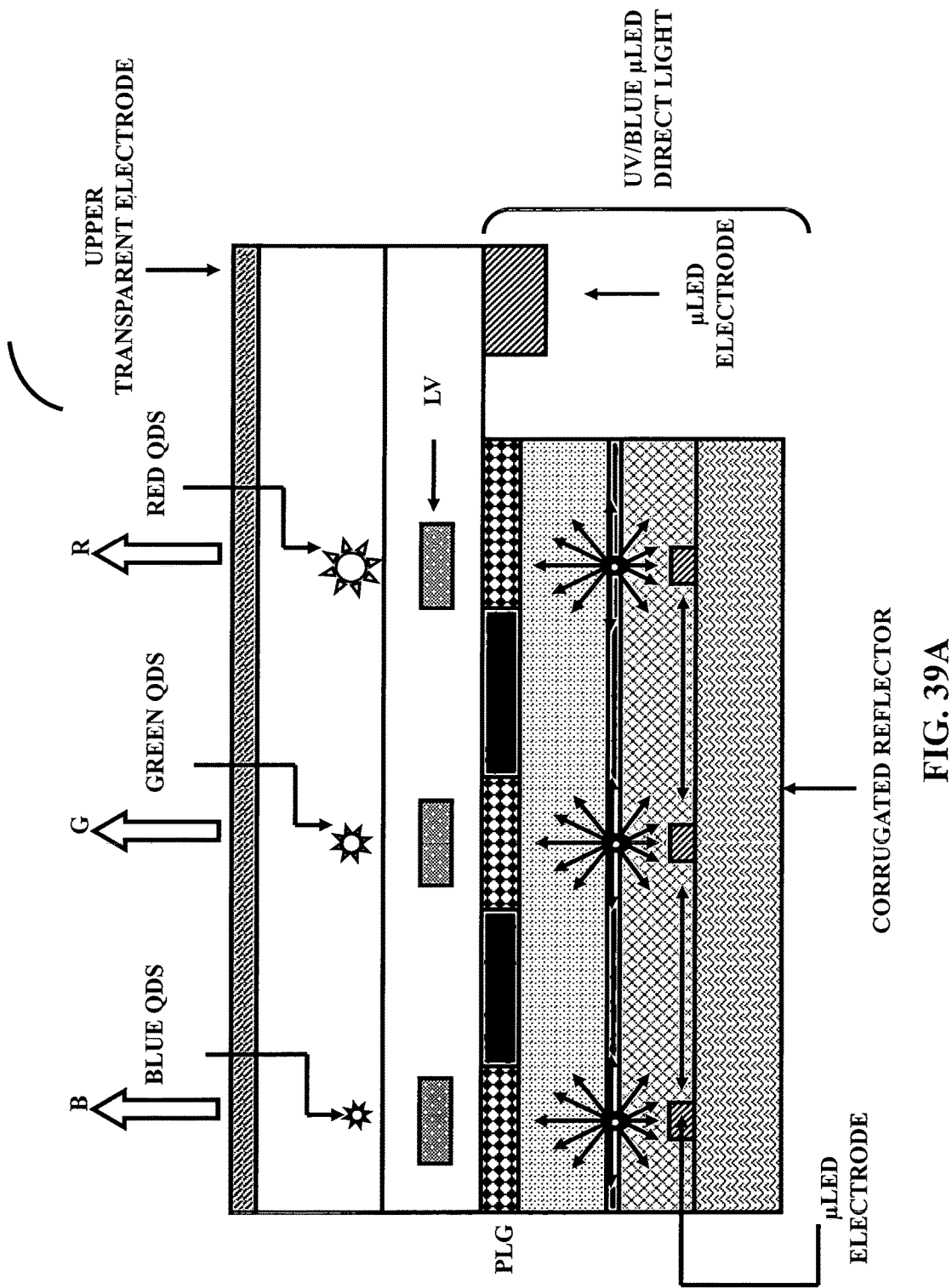
Figure 39B:
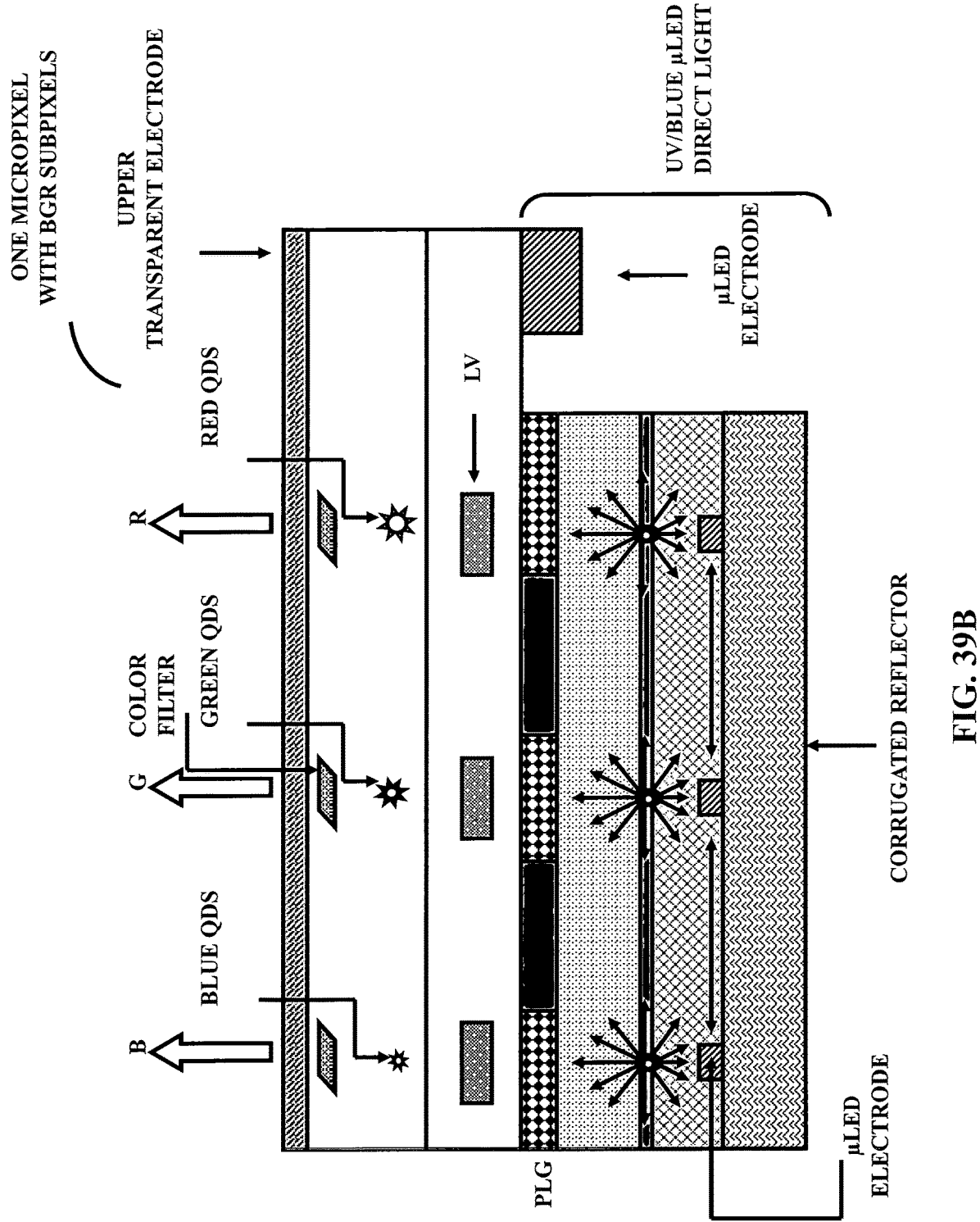
Figure 39C:
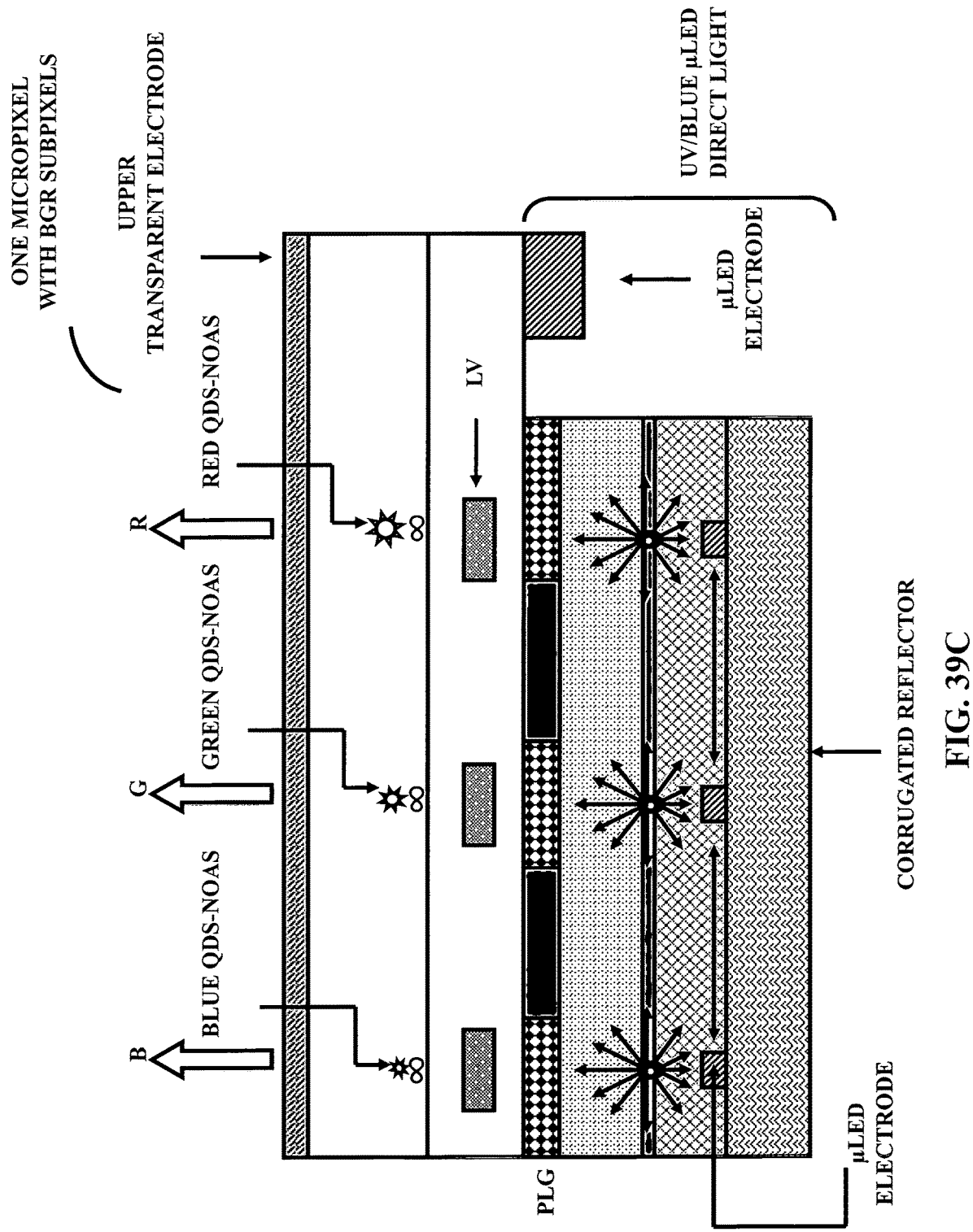
Figure 39D:
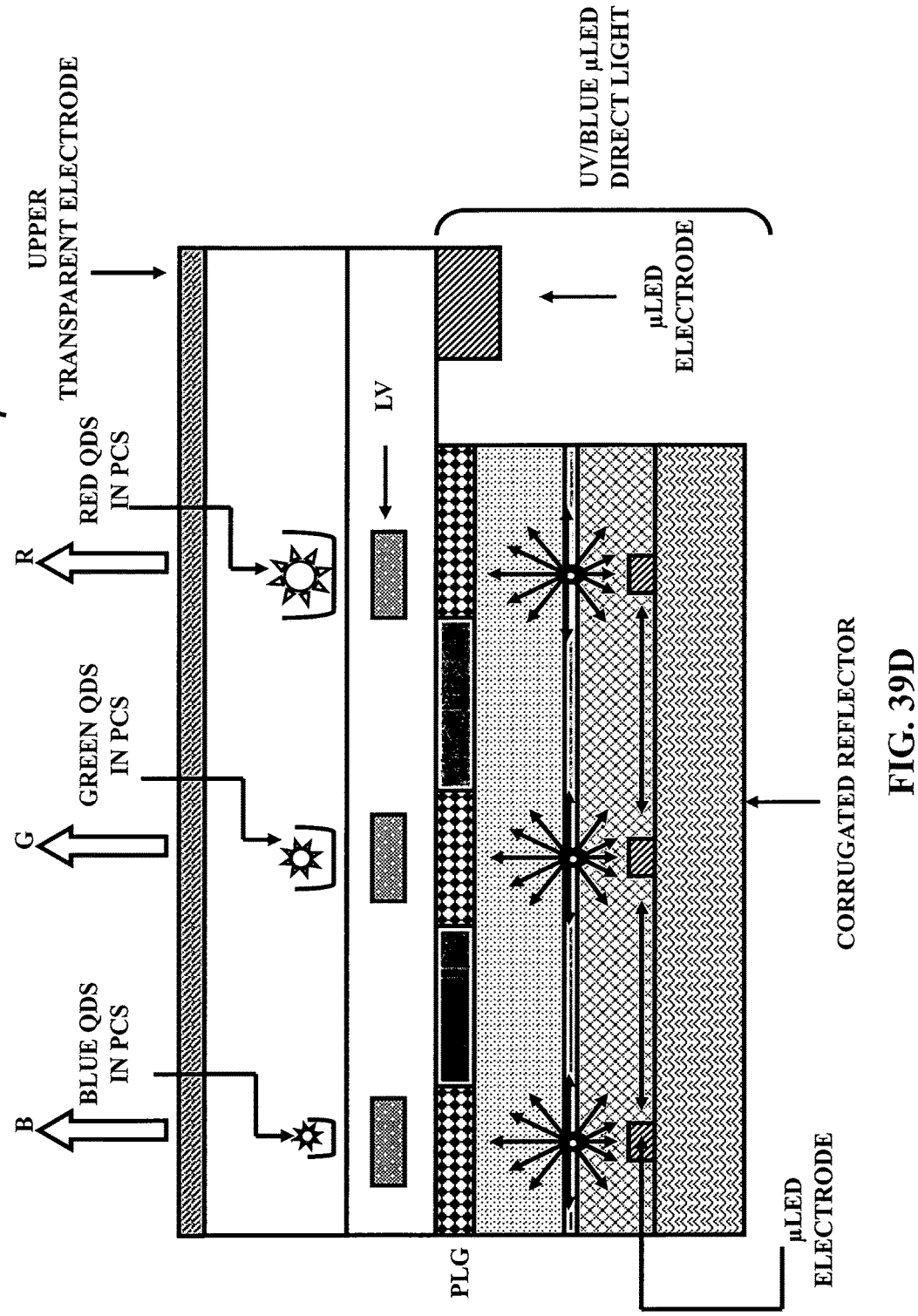
Figure 39E:
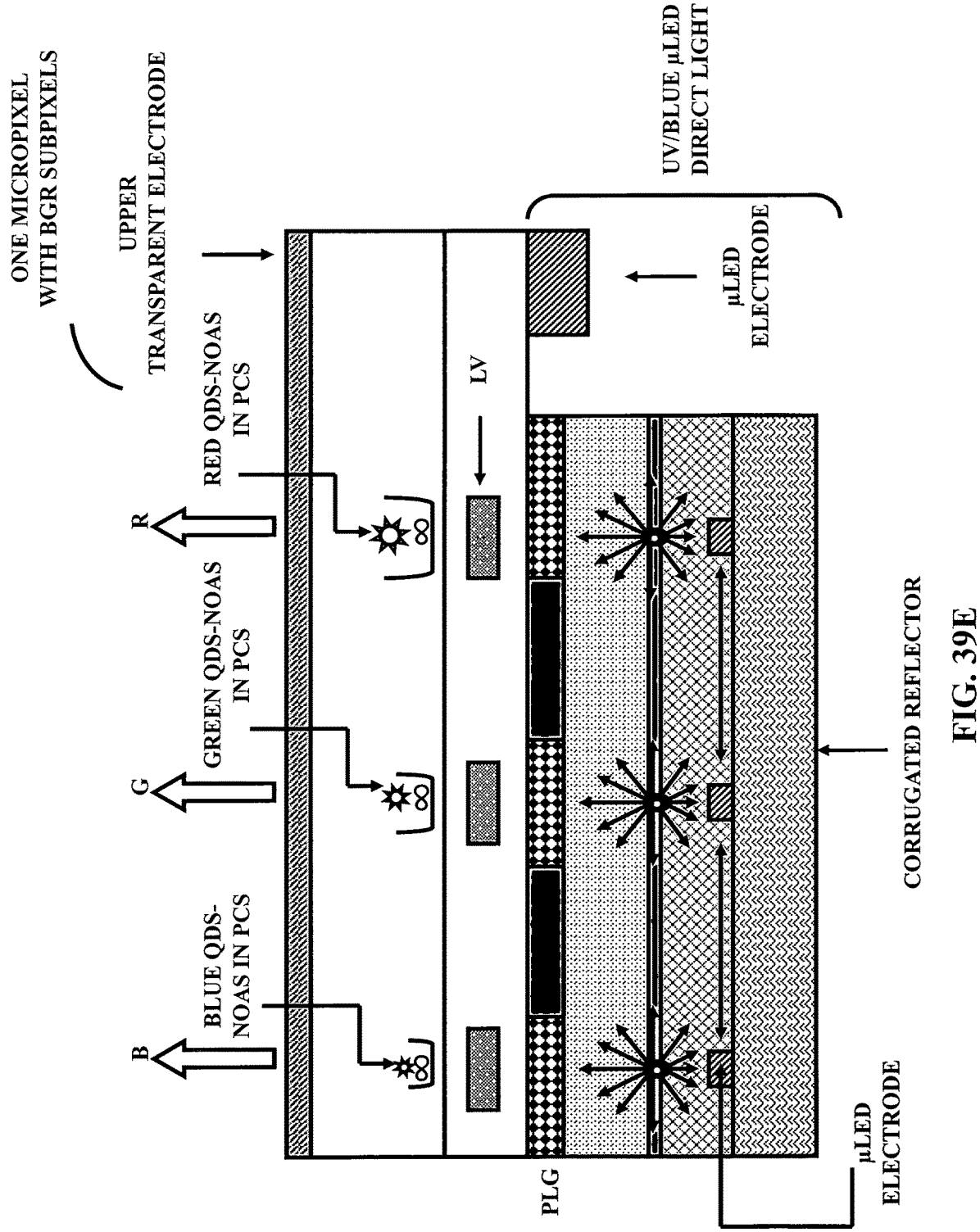
Figure 39F:
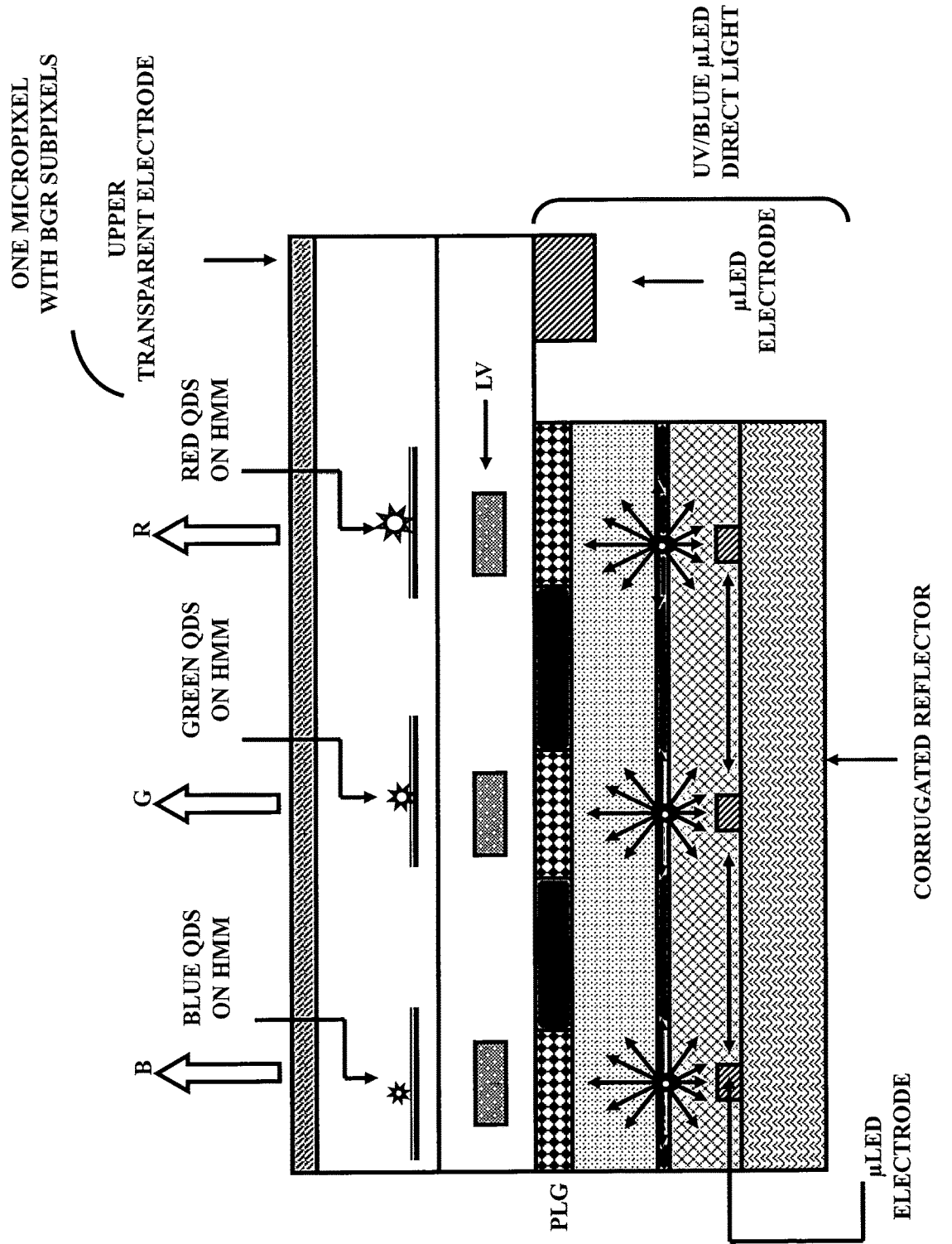
Figure 39G:
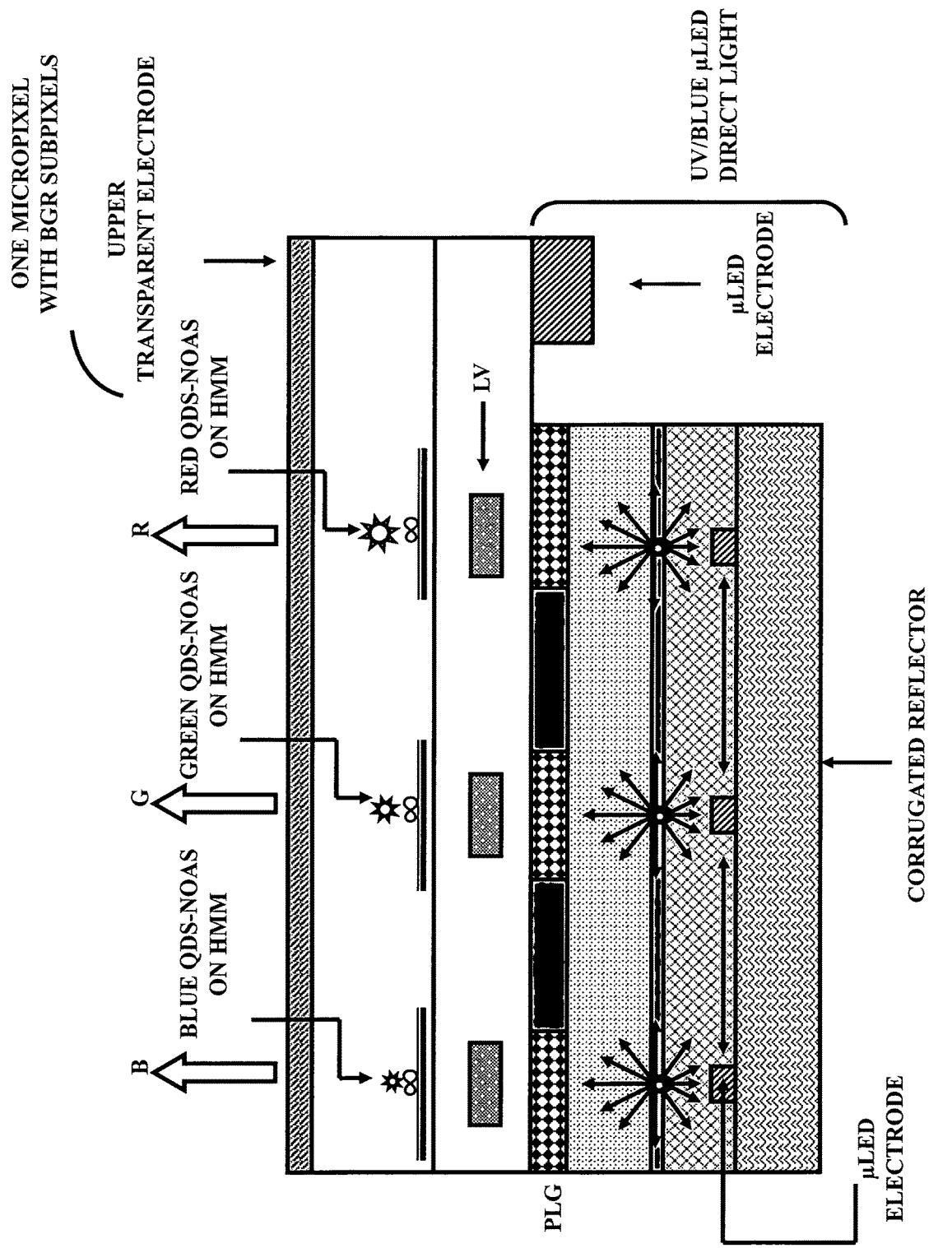
Figure 39H:
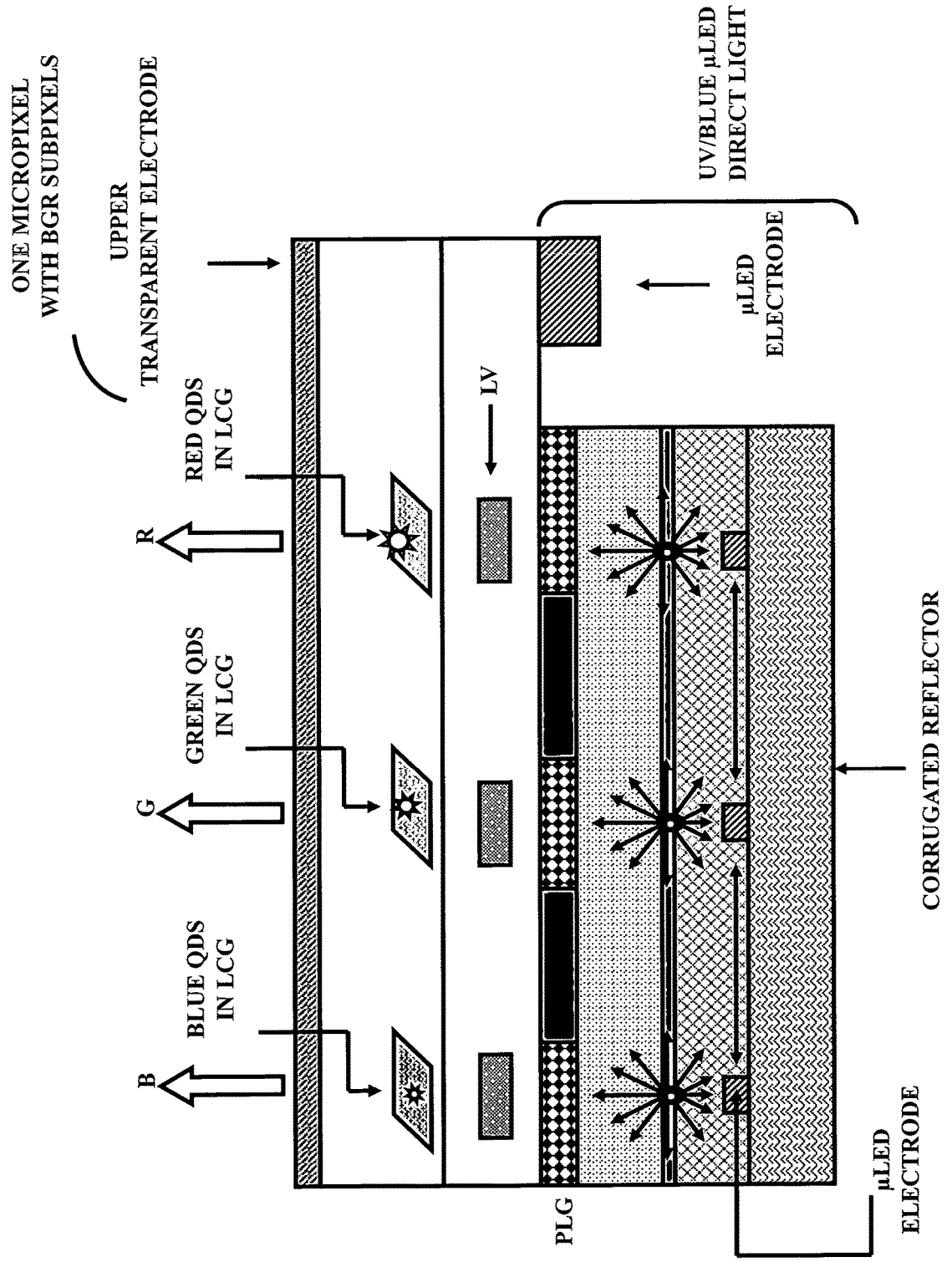

FIG. 38 illustrates a plasmonic light guide (PLG).

FIGS. 39A-39H illustrate eight embodiments of a micropixel of a display, utilizing ultraviolet (UV)/blue microlight emitting diodes and plasmonic light guides on each subpixel.

Figures 40A, 40B:
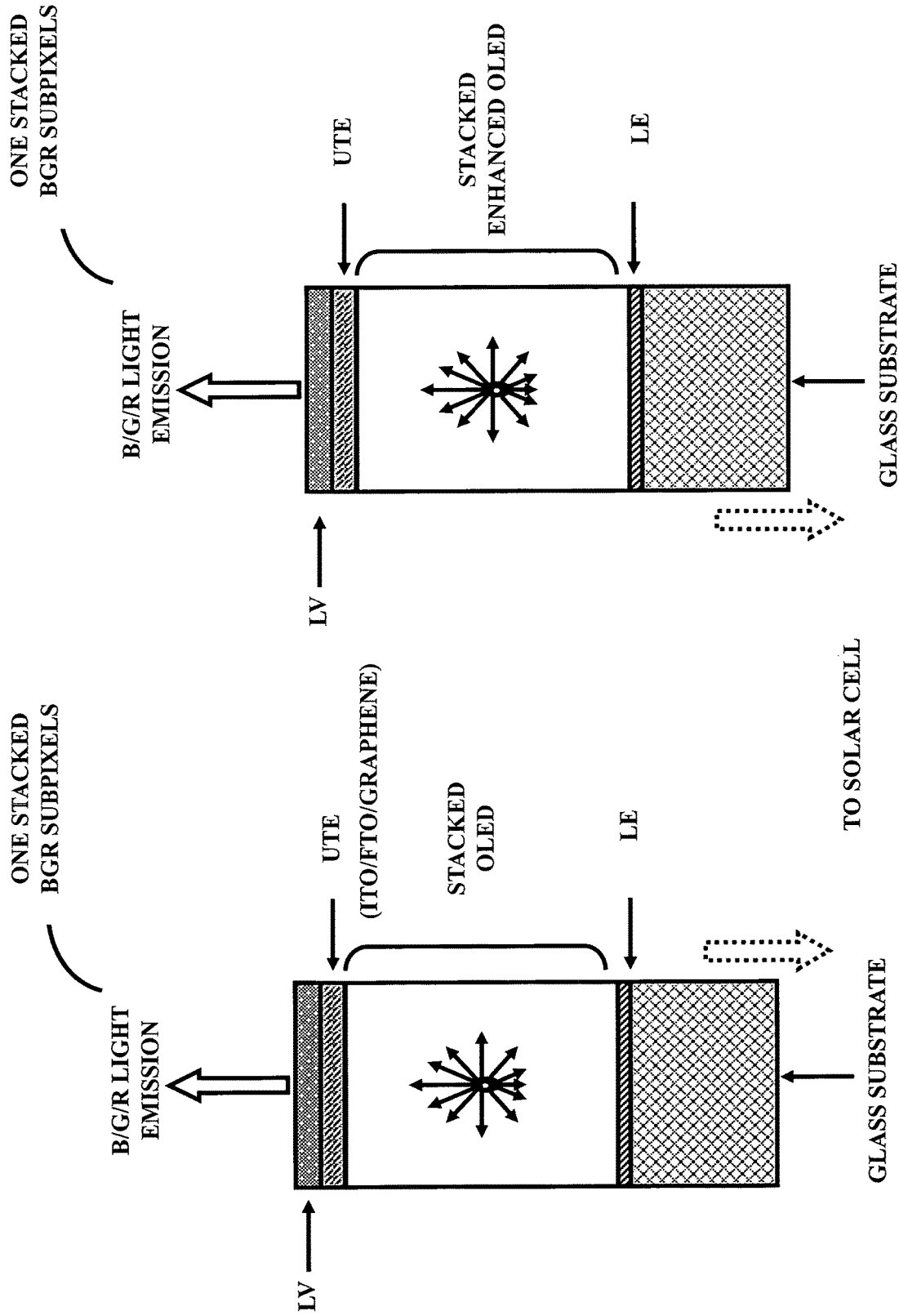
Figure 40C:
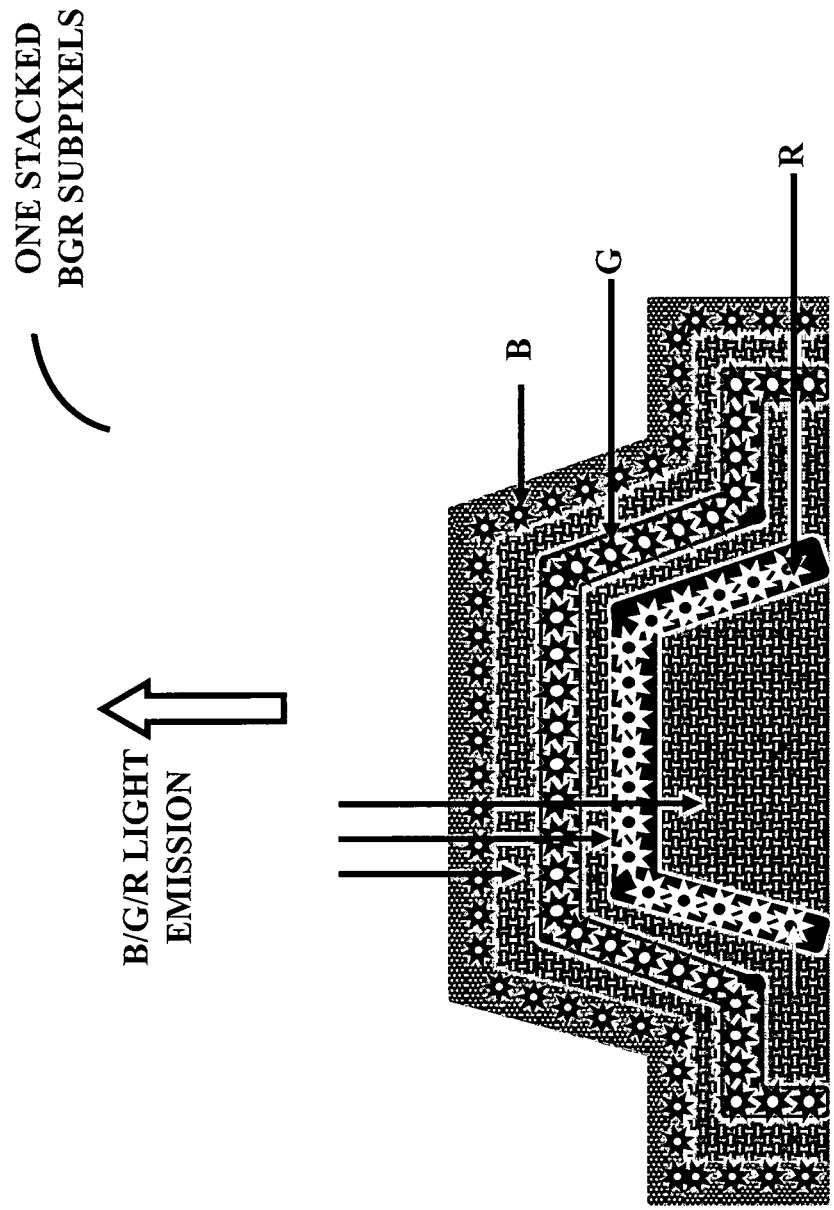

FIGS. 40A-40C illustrate two embodiments of a micropixel of a display, utilizing vertically stacked organic light emitting diodes (OLED).

Figure 41A:
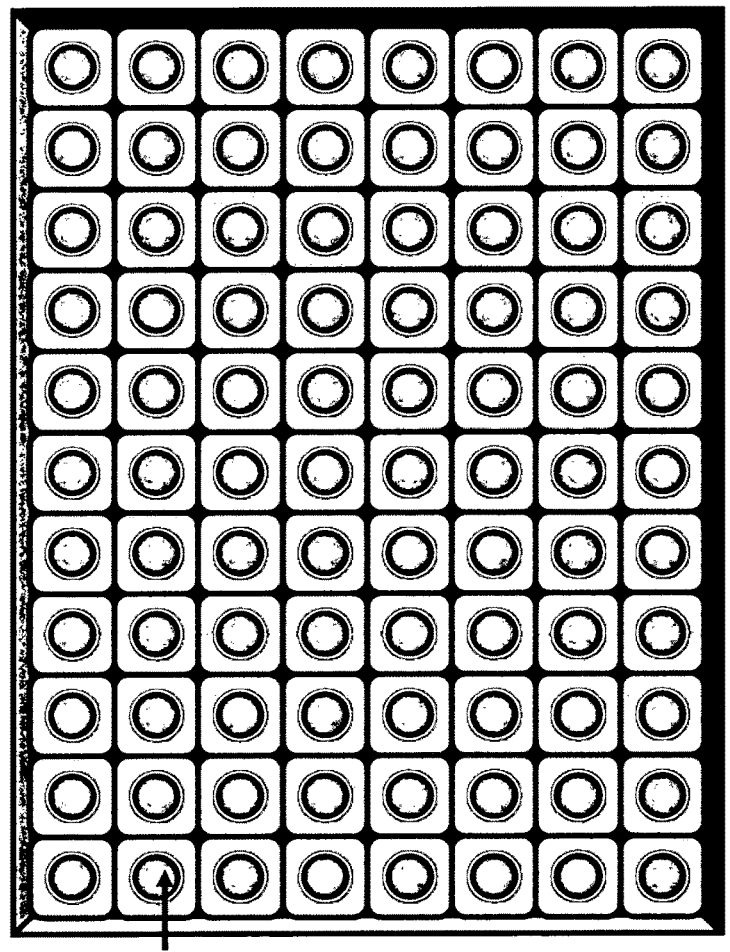

FIG. 41A illustrates an embodiment of a two-dimensional array of micropixels of a display.

Figure 41B:
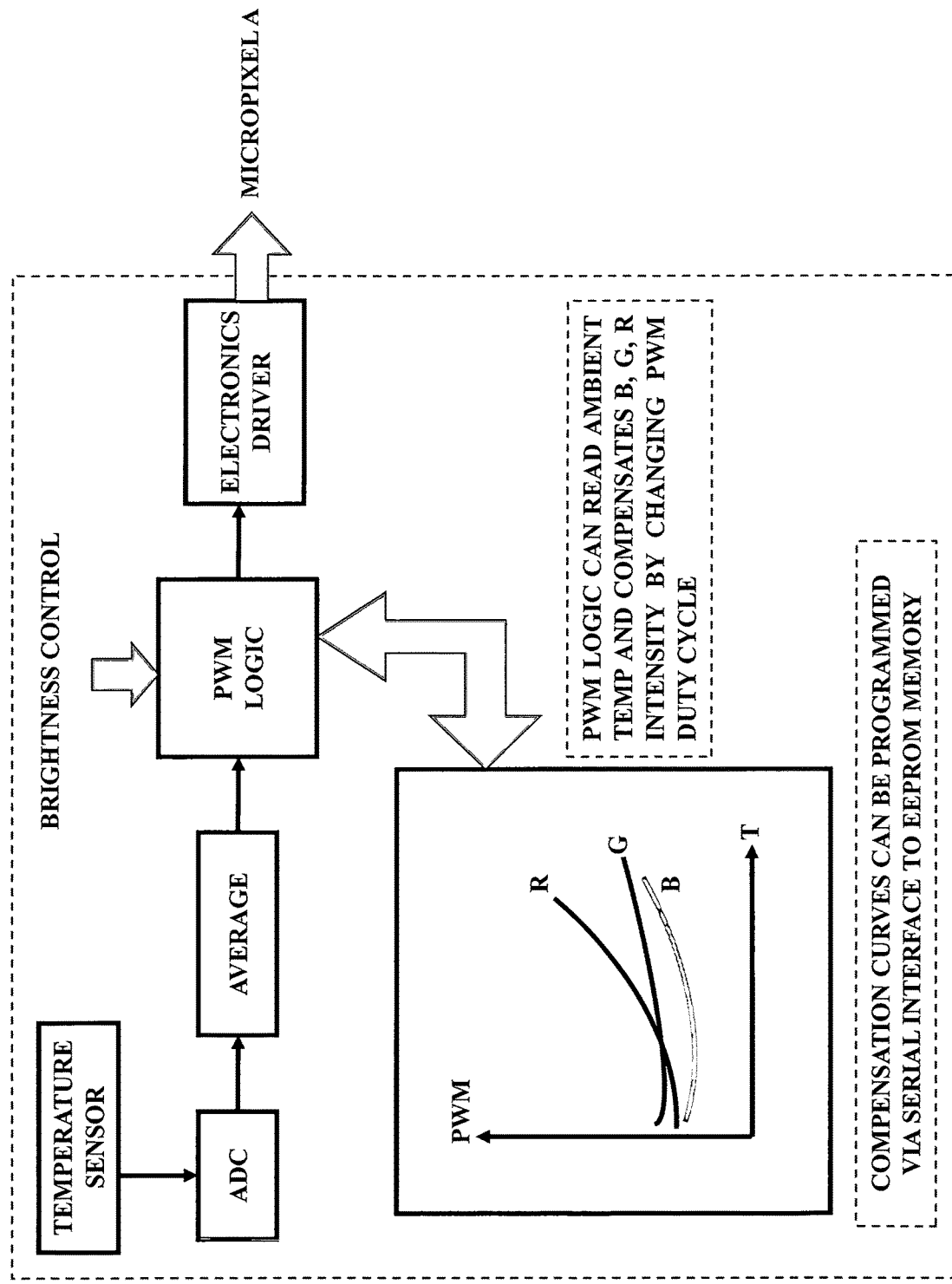

FIG. 41B illustrates an embodiment of an electronic control of the micropixel of a display.

FIG. 42A-42B illustrates an embodiment of integration, micropixels, cameras/phototransistors and the Super System on Chip.

Figure 43A:
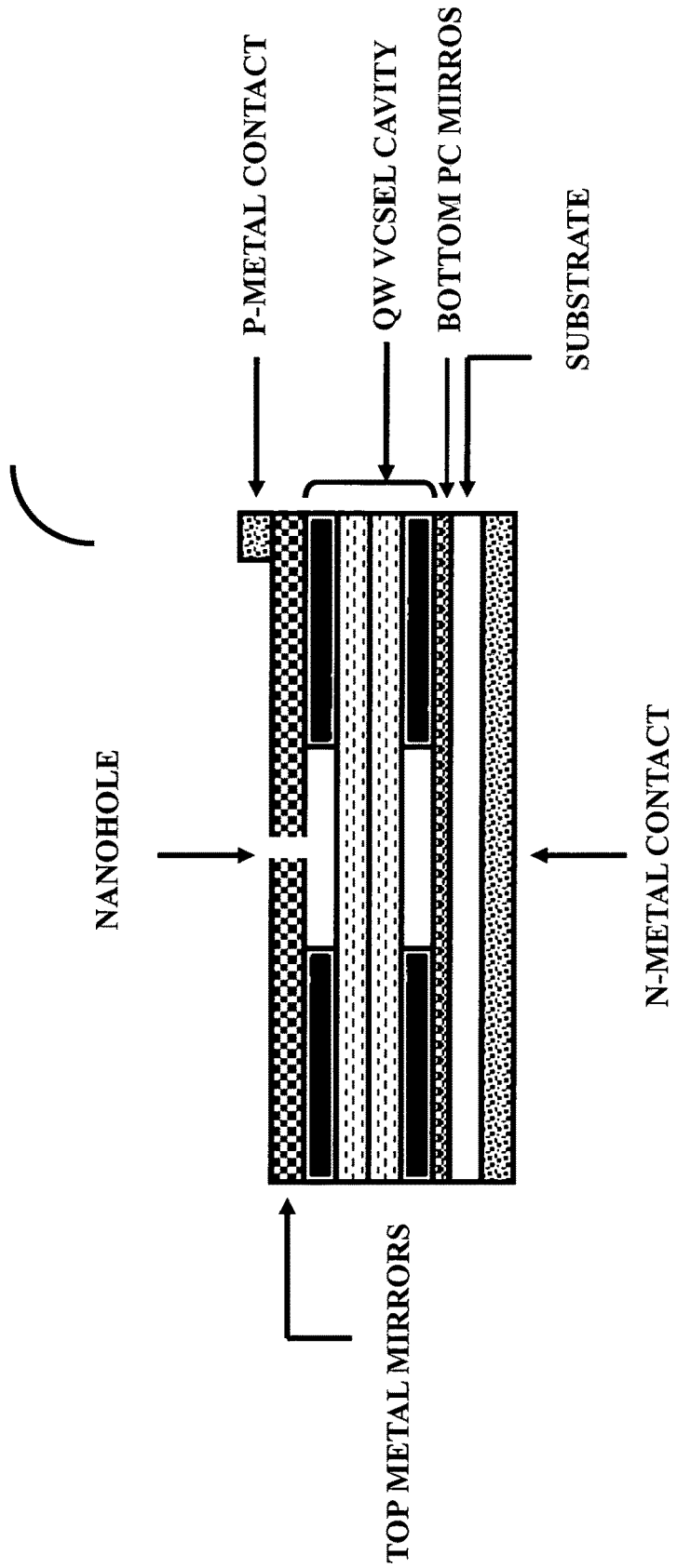
Figure 43B:
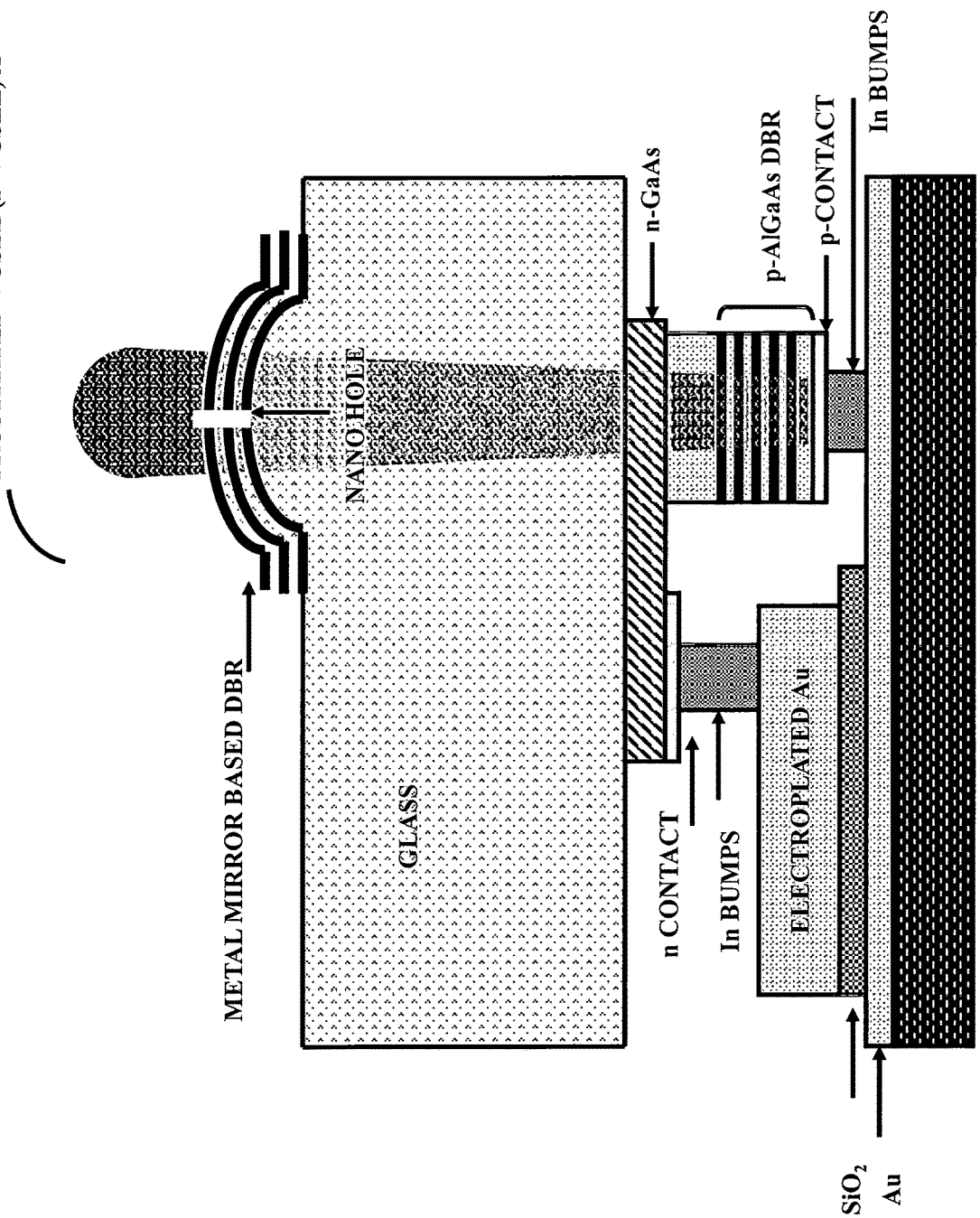

FIGS. 43A-43B illustrate an embodiment of a frustrated vertical cavity surface emitting laser (F-VCSEL).

Figure 43C:
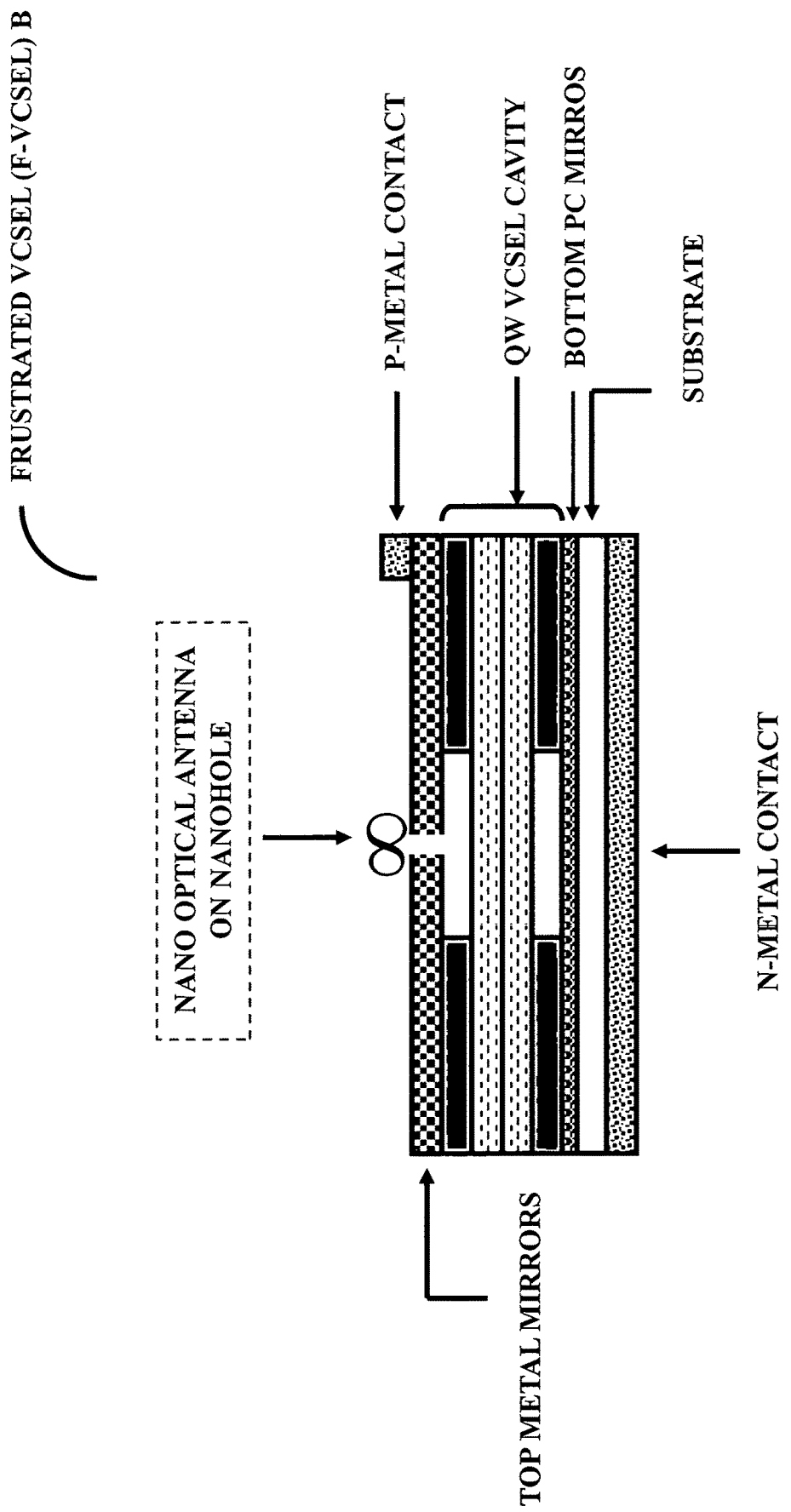
Figure 43D:
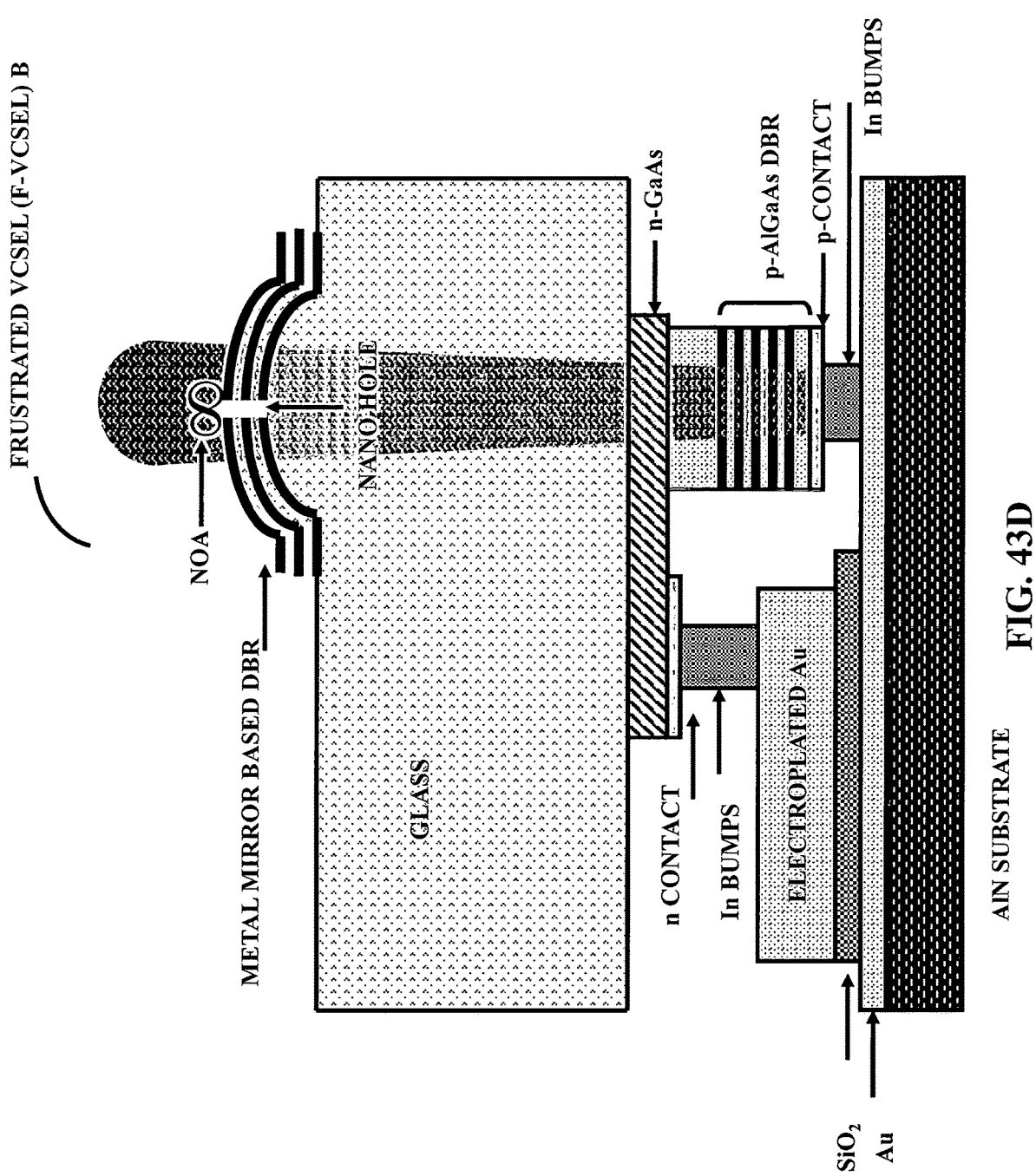

FIGS. 43C-43D illustrate an embodiment of a frustrated vertical cavity surface emitting laser integrated with a protruded metal/non-metal nano optical antenna.

FIGS. 44A-44H illustrate eight embodiments of a micropixel of a display, utilizing a frustrated vertical cavity surface emitting laser or frustrated vertical cavity surface emitting laser integrated with a protruded metal/non-metal nano optical antenna on each subpixel.

Figure 45:
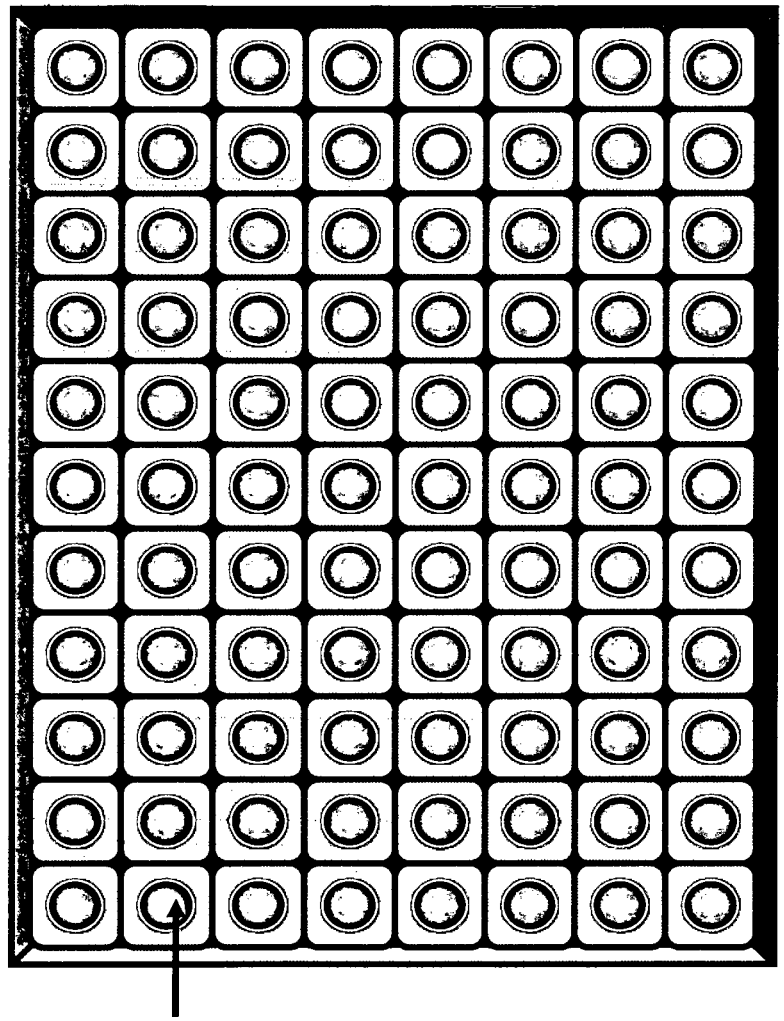

FIG. 45 illustrates another embodiment of a two-dimensional array of micropixels of a display.

FIGS. 46A-46D illustrate four additional embodiments to enable a micropixel of a display.

Figure 47A:
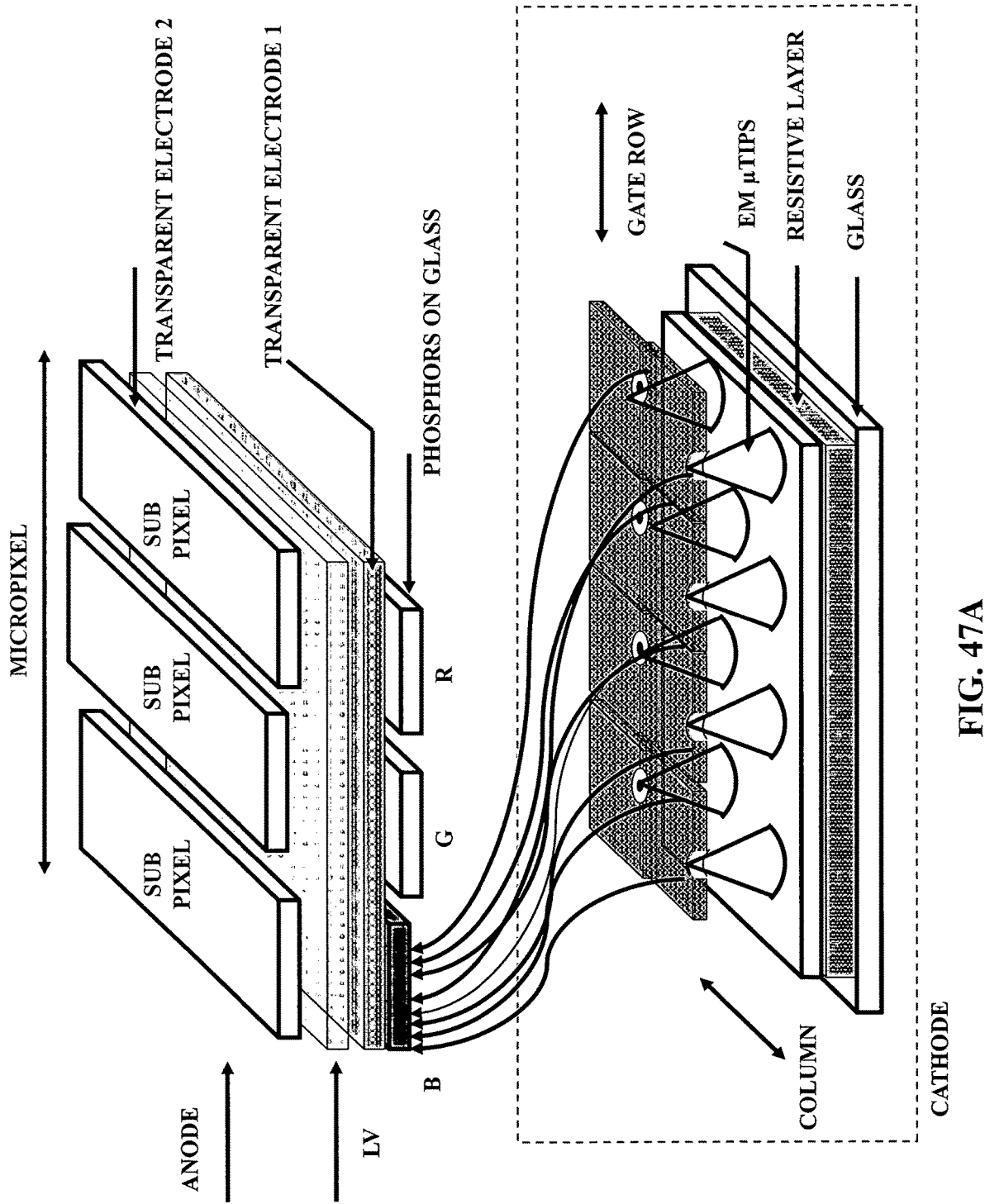
Figure 47B:
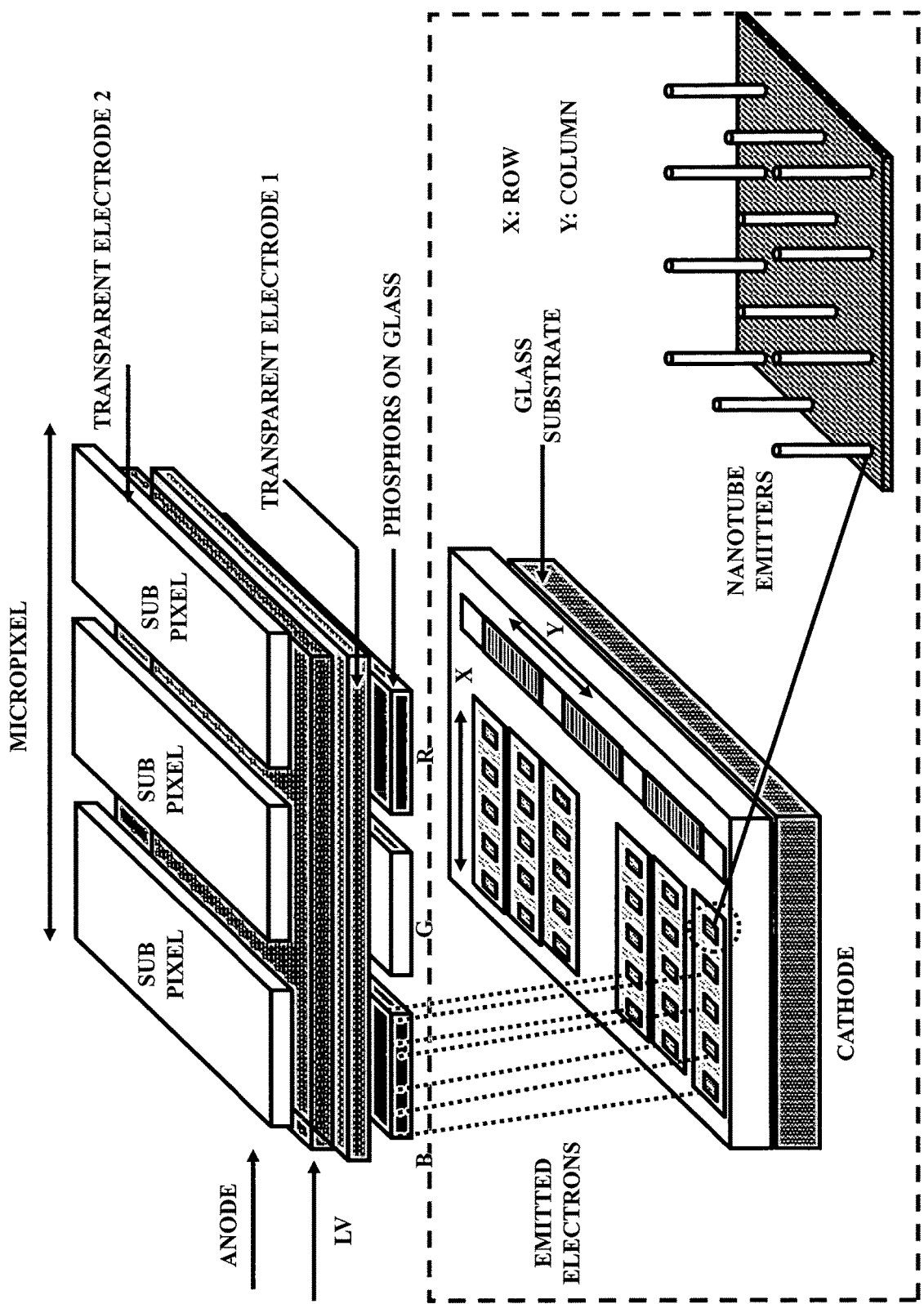

FIGS. 47A-47B illustrate two additional embodiments to enable a micropixel of a display.

Figure 48A:
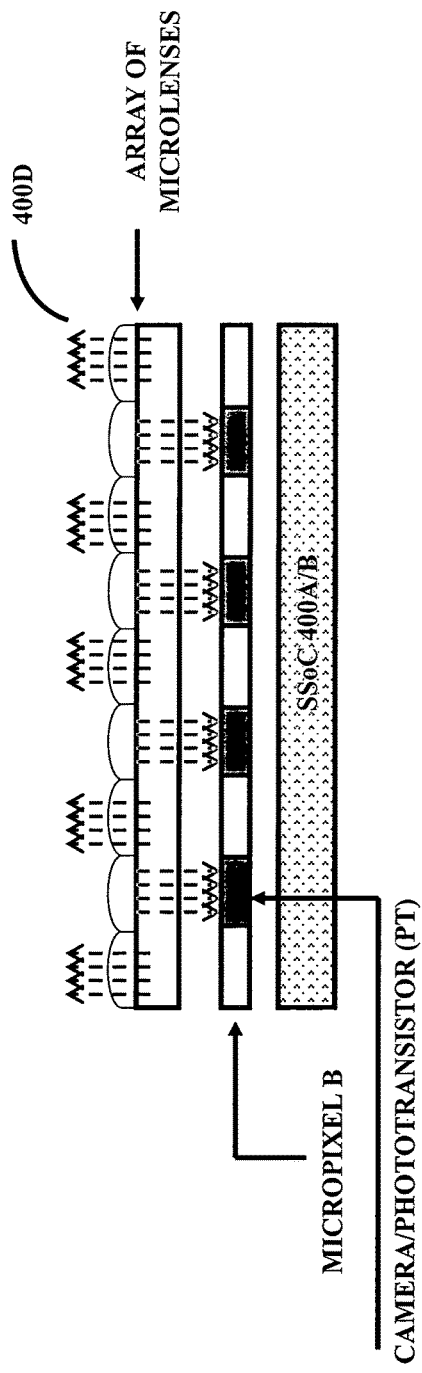
Figure 48B:
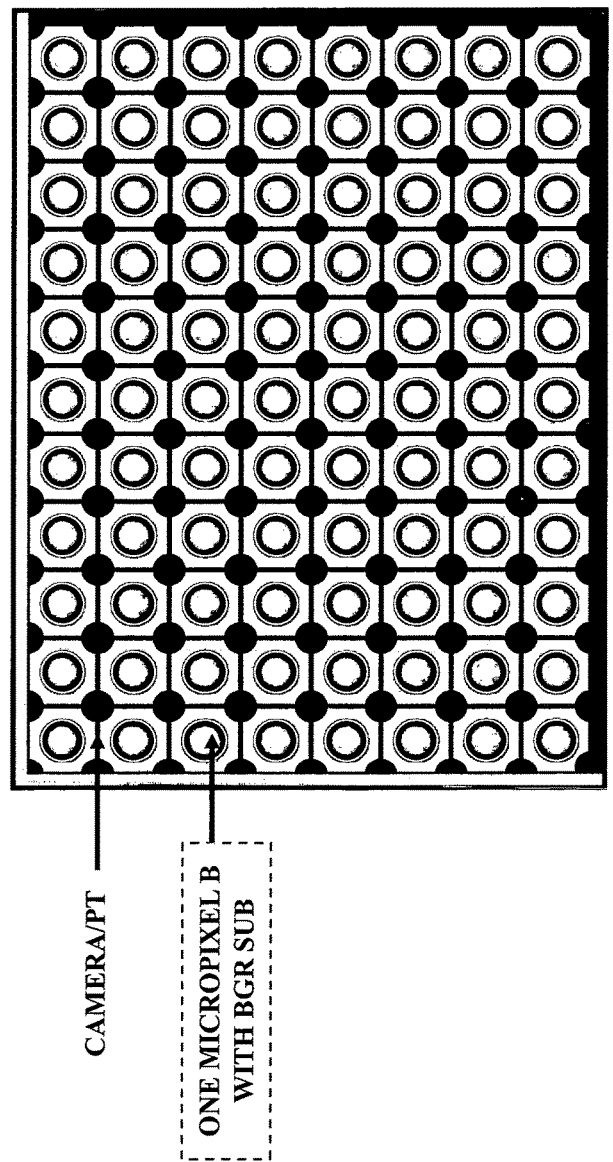

FIGS. 48A-48B illustrate an embodiment of integration, micropixels, cameras/phototransistors and the Super System on Chip.

Figure 49:
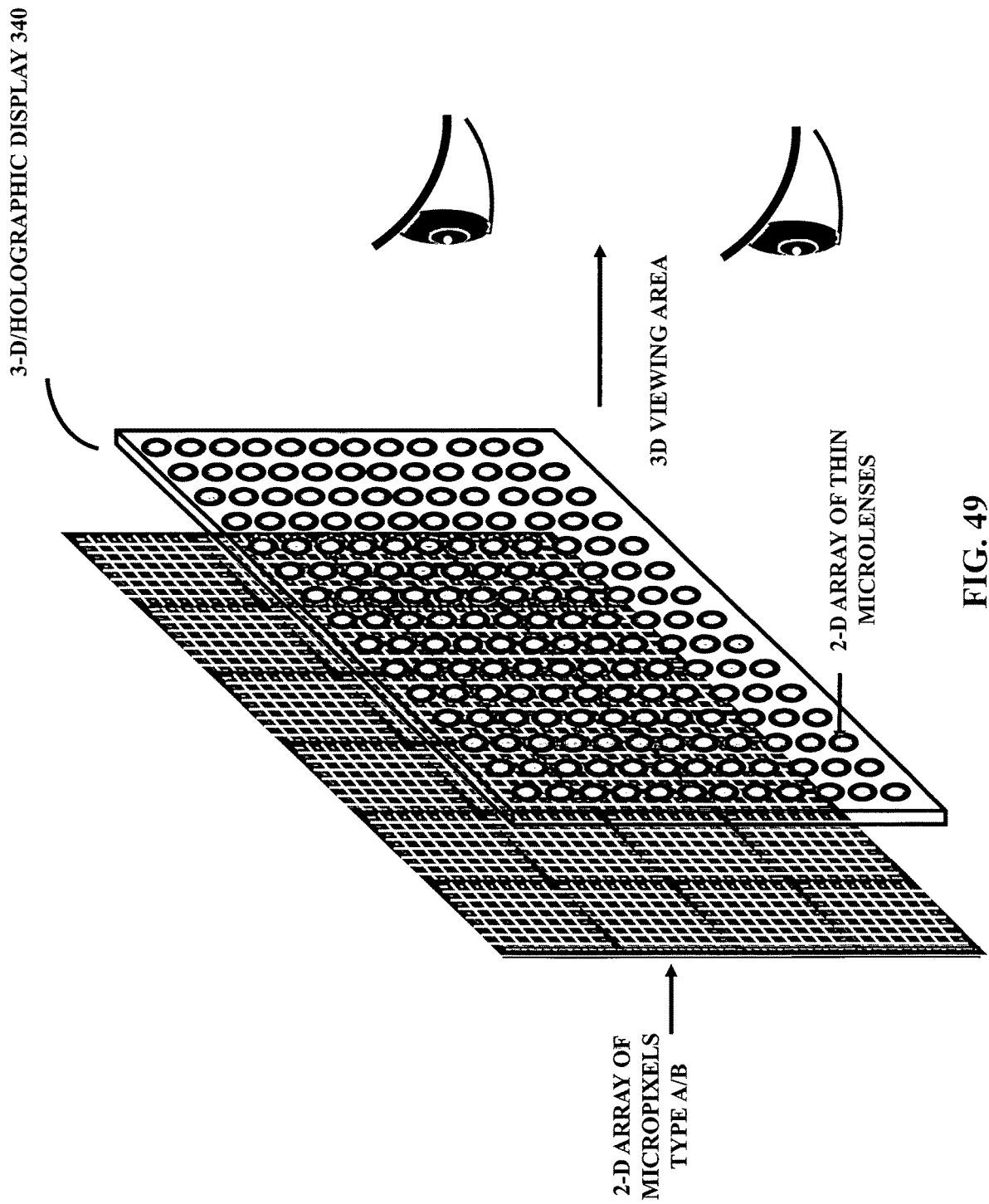

FIG. 49 illustrates an embodiment of a three-dimensional/ holographic display.

Microprojector

Figure 50A:
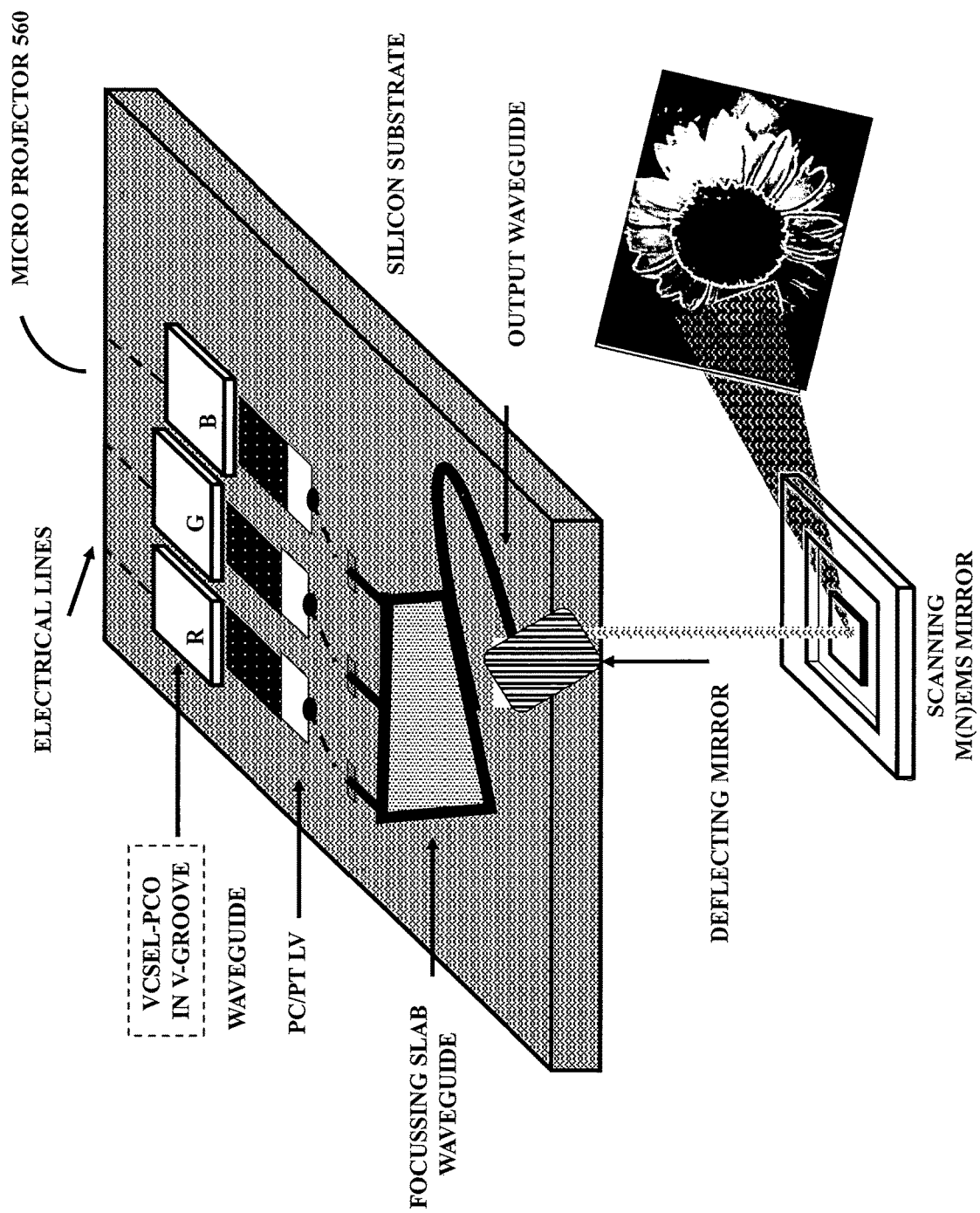
Figure 50B:
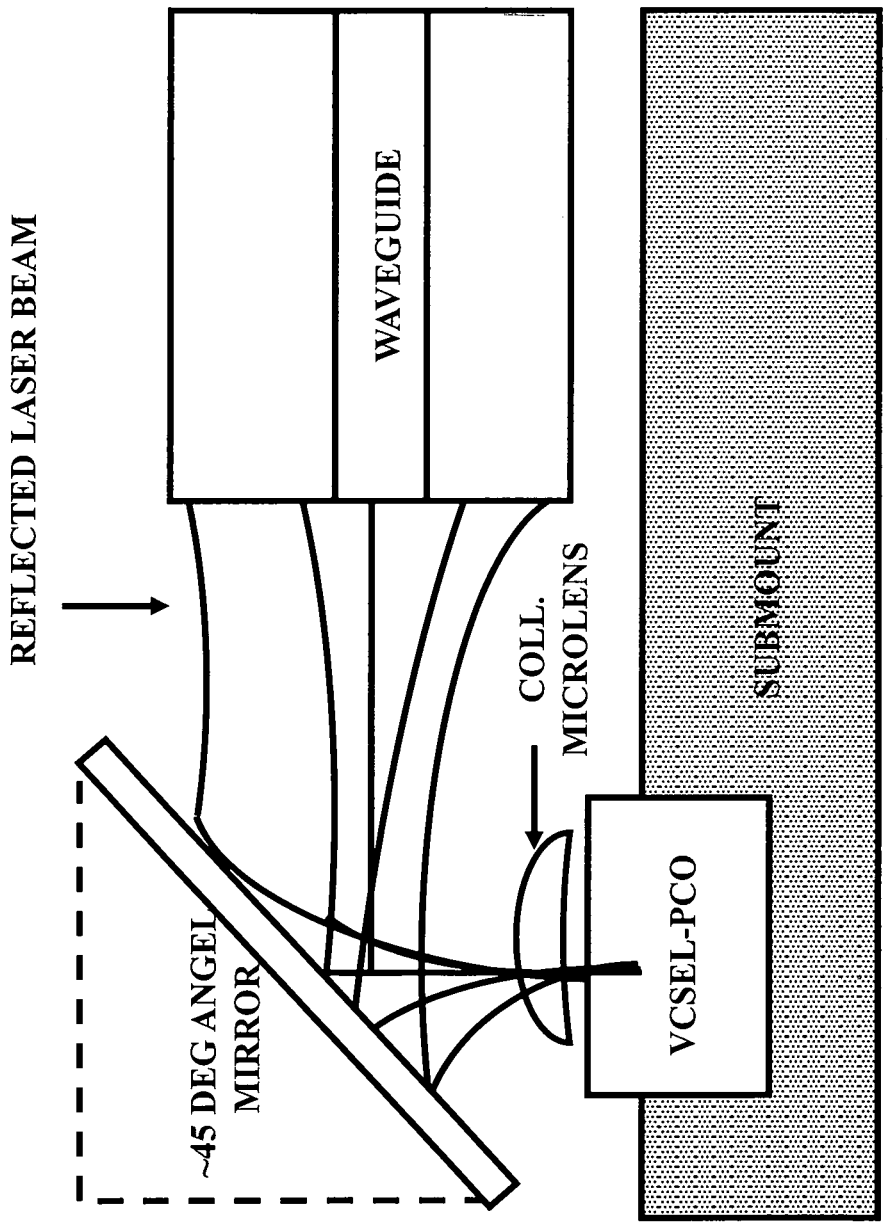
Figure 50C:
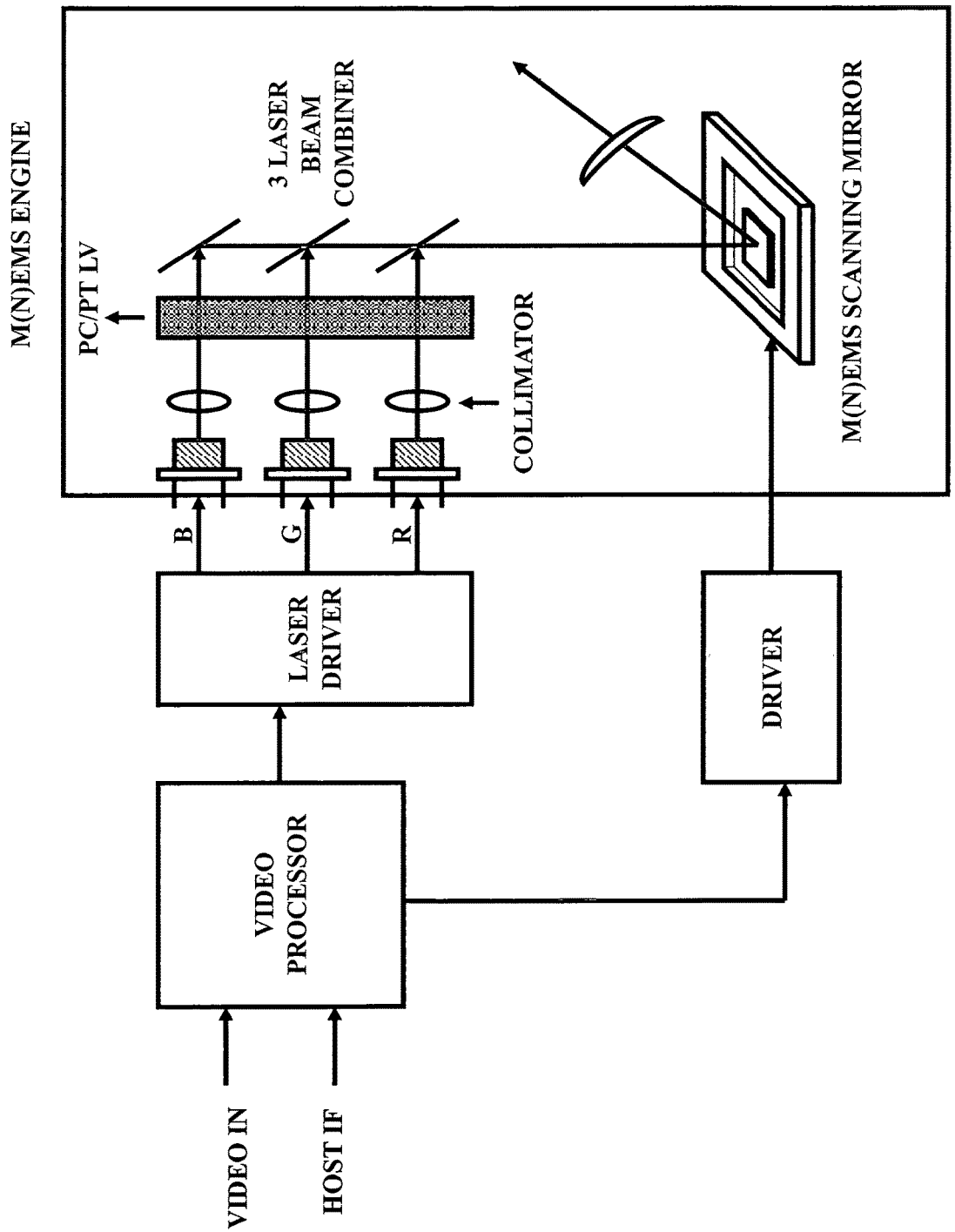

FIGS. 50A-50C illustrate an embodiment of a microprojector.

FIGS. 51A-51D illustrate four embodiments of an optical engine.

FIGS. 52A-52D illustrate two embodiments of another optical engine.

Figure 53:
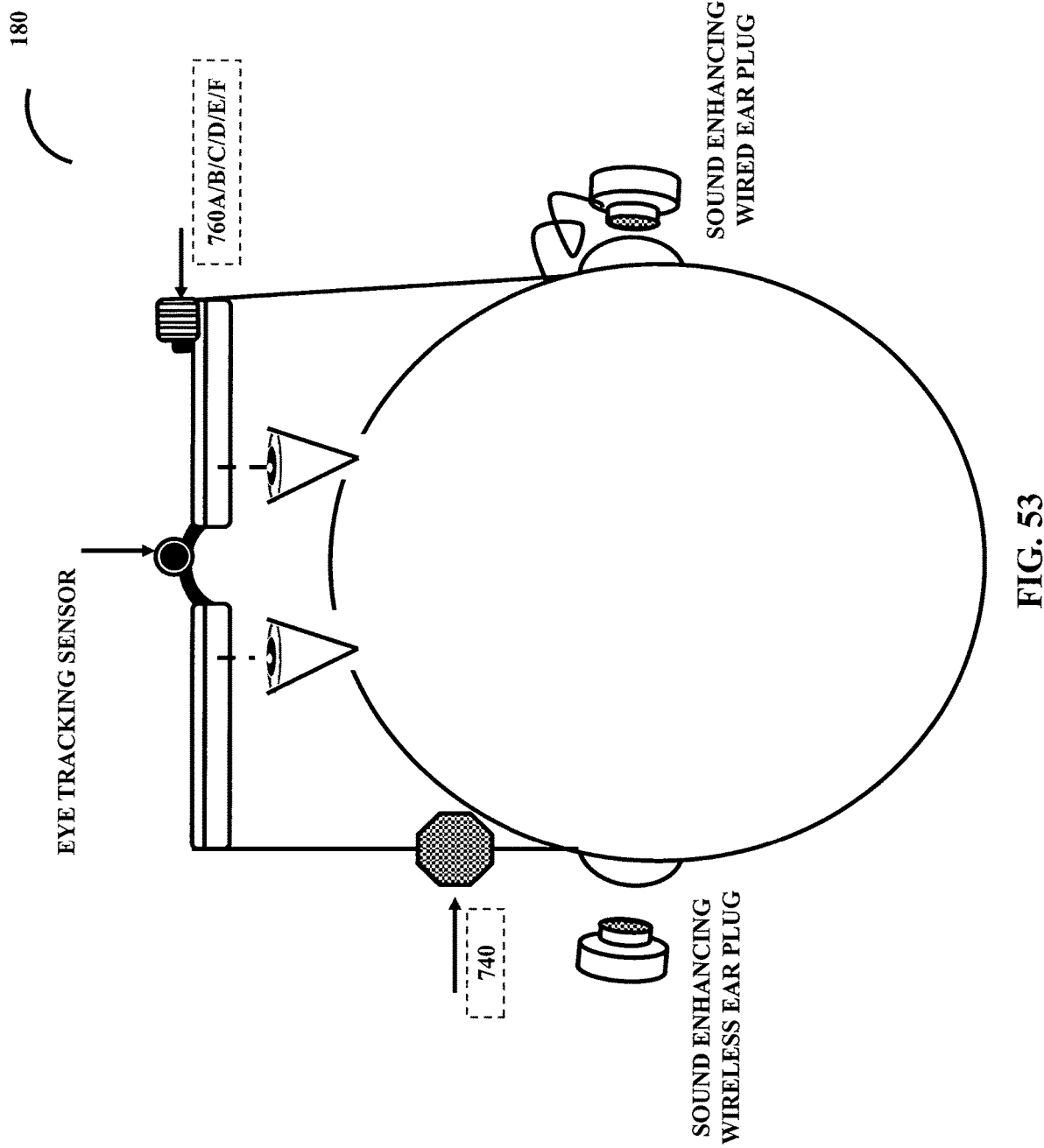

FIG. 53 illustrates an embodiment of an intelligent wearable augmented reality personal assistant device.

Point-of-Care Diagnostics

FIGS. 54A-54C represent various configurations of a generic representation of a biomarker binder.

Figure 55C:
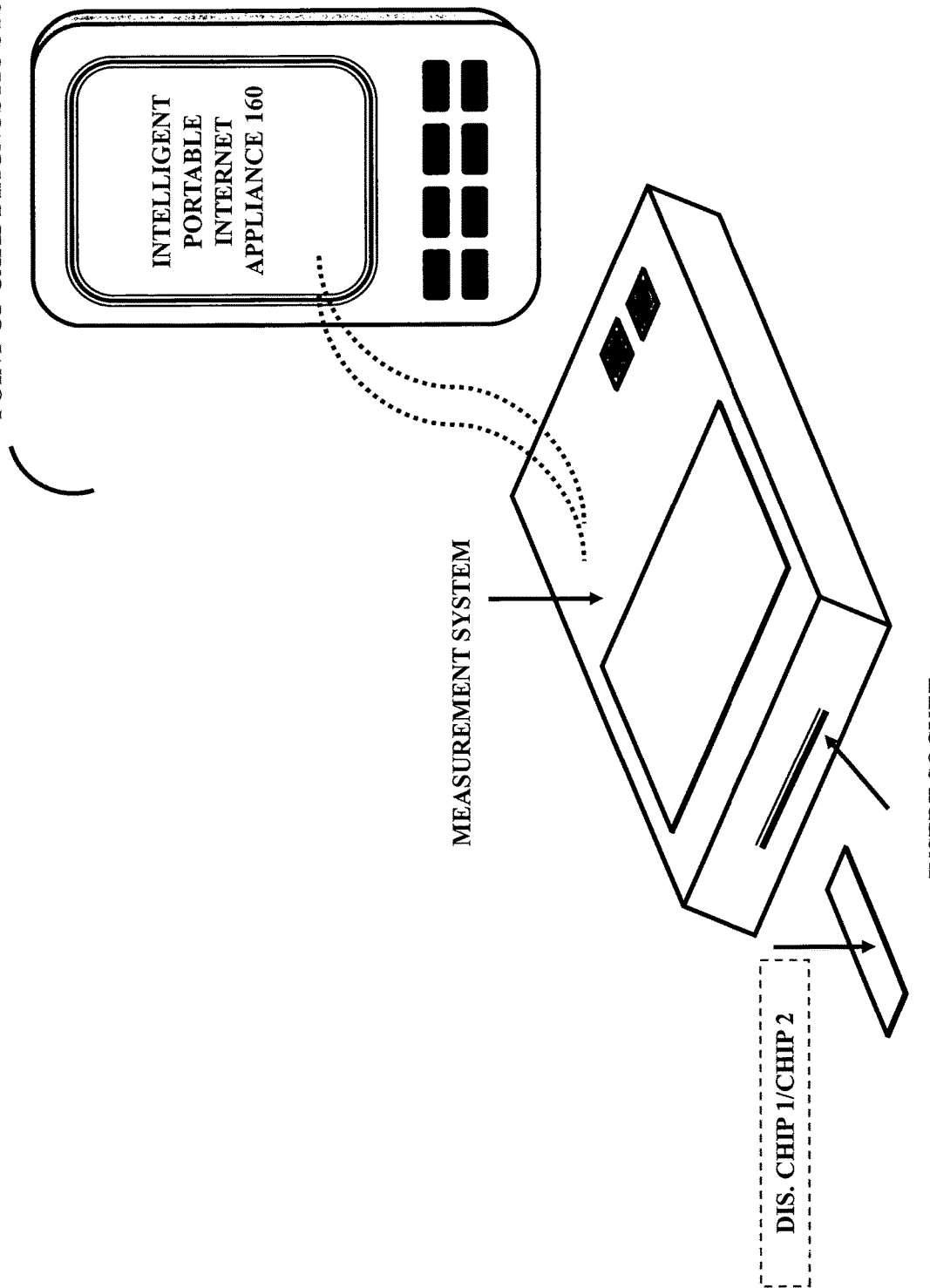

FIGS. 55A-55C illustrate an embodiment of a point-of-care diagnostic system.

Wearable Personal Health Assistant Device

FIGS. 56A-56L illustrate an embodiment of a wearable personal health assistant device.

Figure 57A:
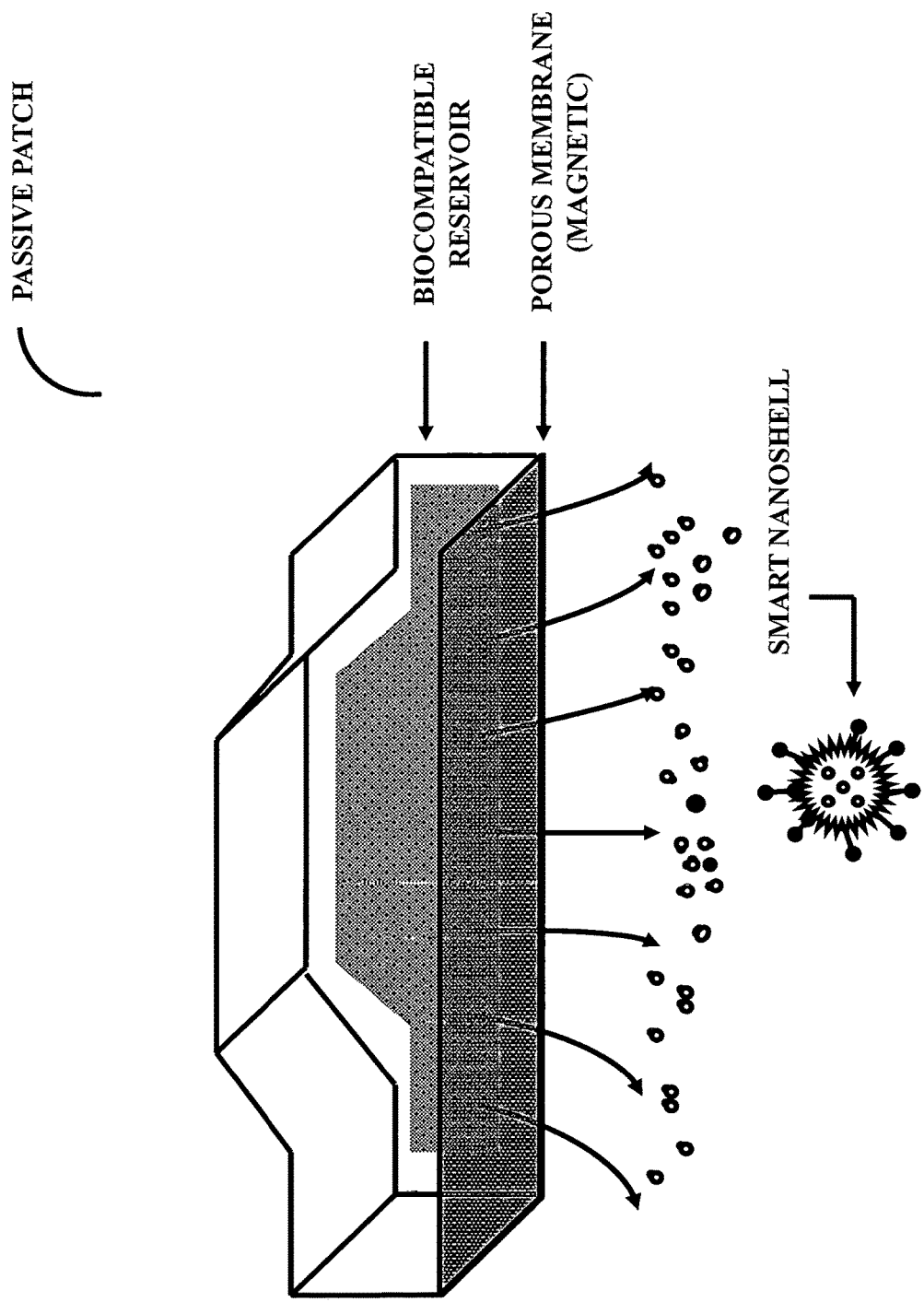

FIG. 57A illustrates an embodiment of a passive patch.

FIGS. 57B-57H illustrate an embodiment of an active patch.

Figure 57B:
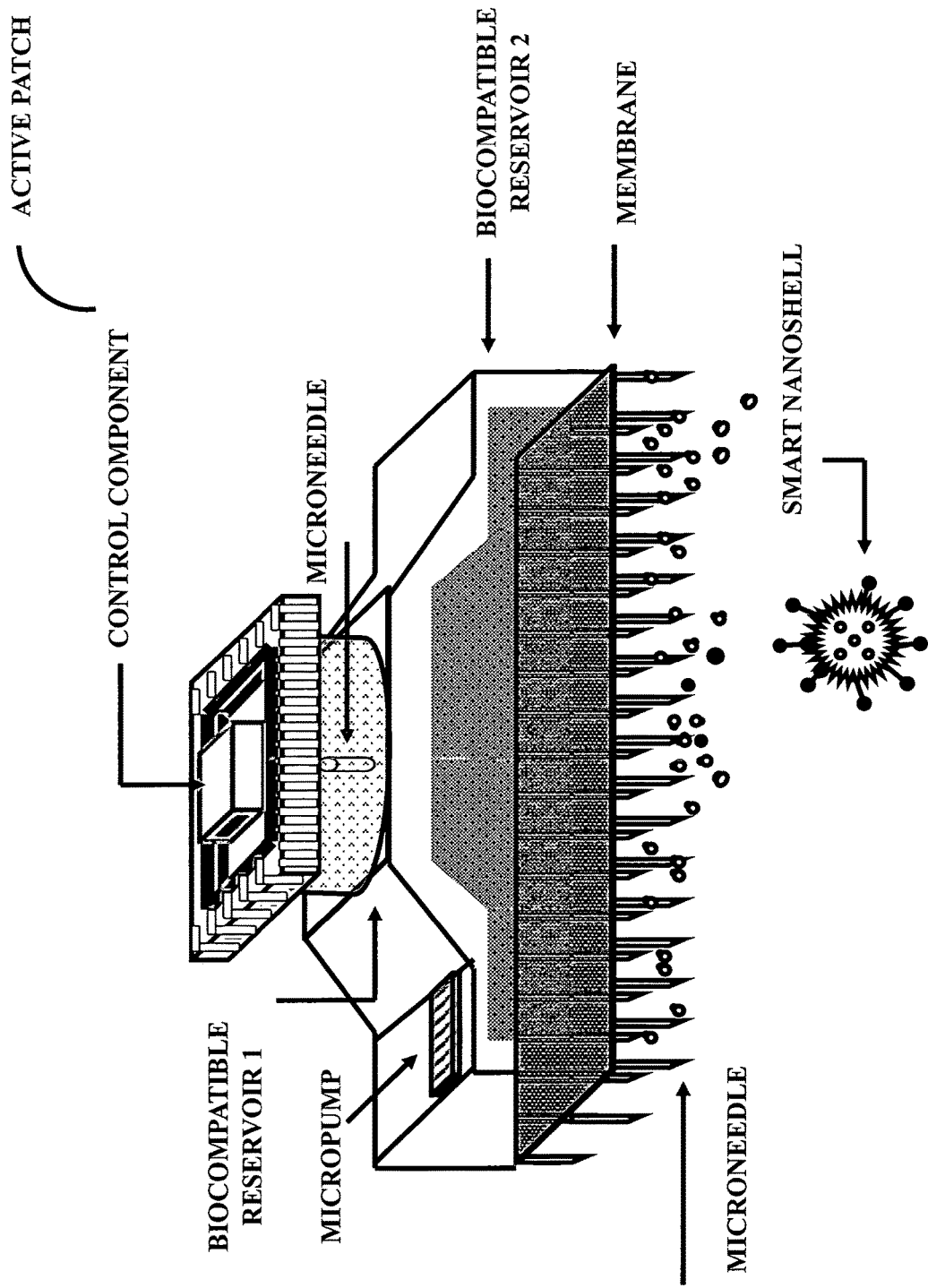
Figure 57F:
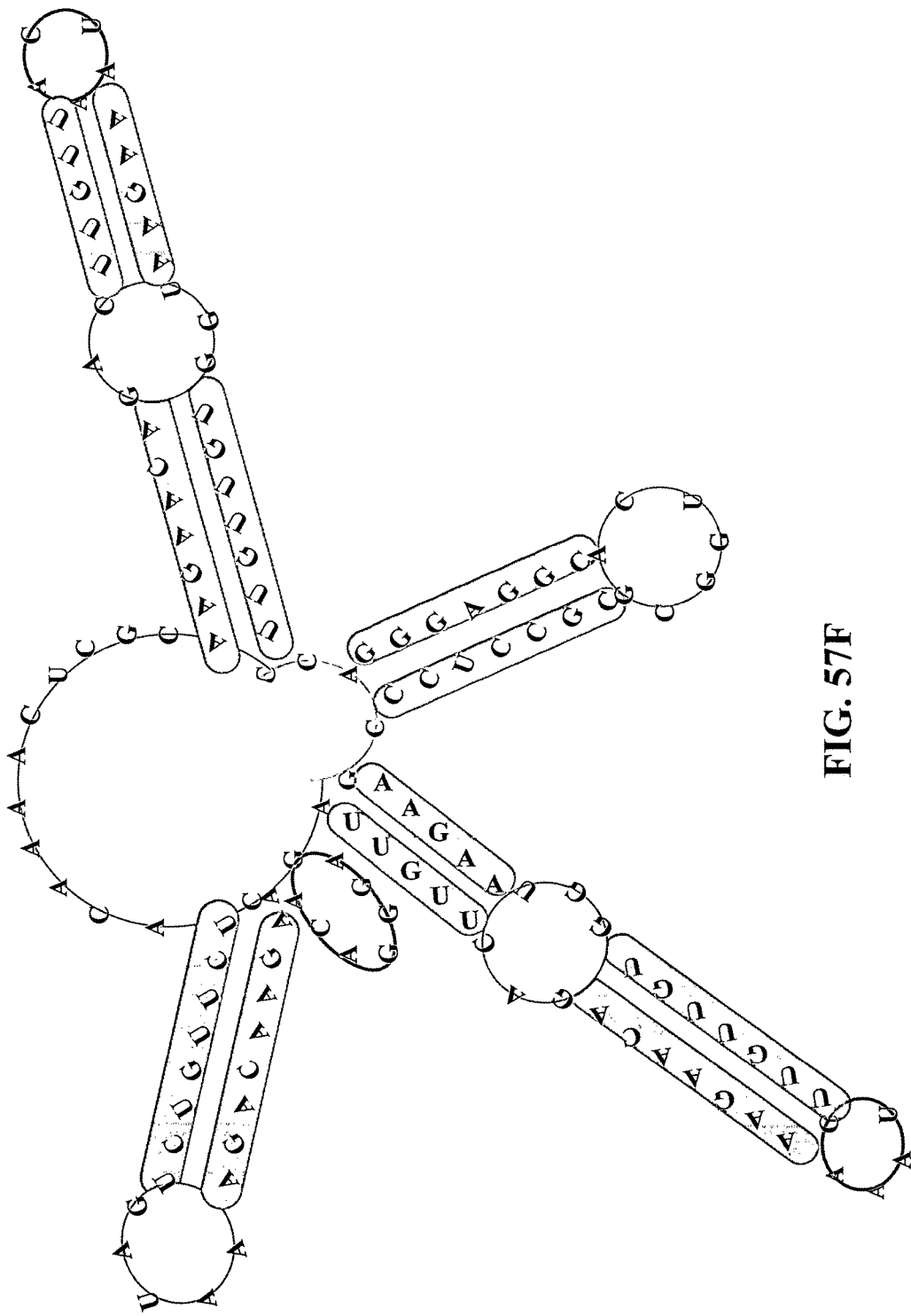
Figure 57G:
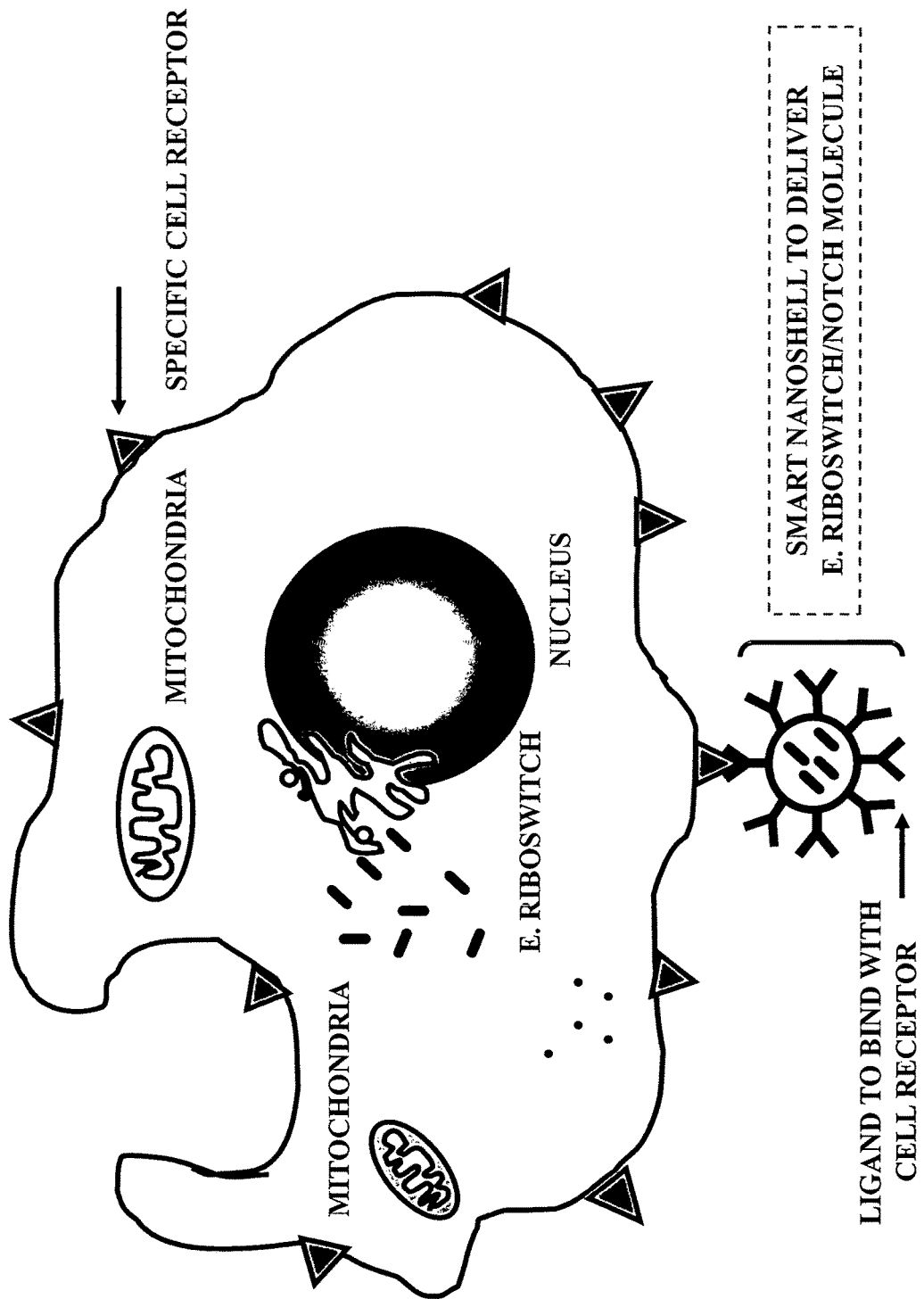
Figure 57H:
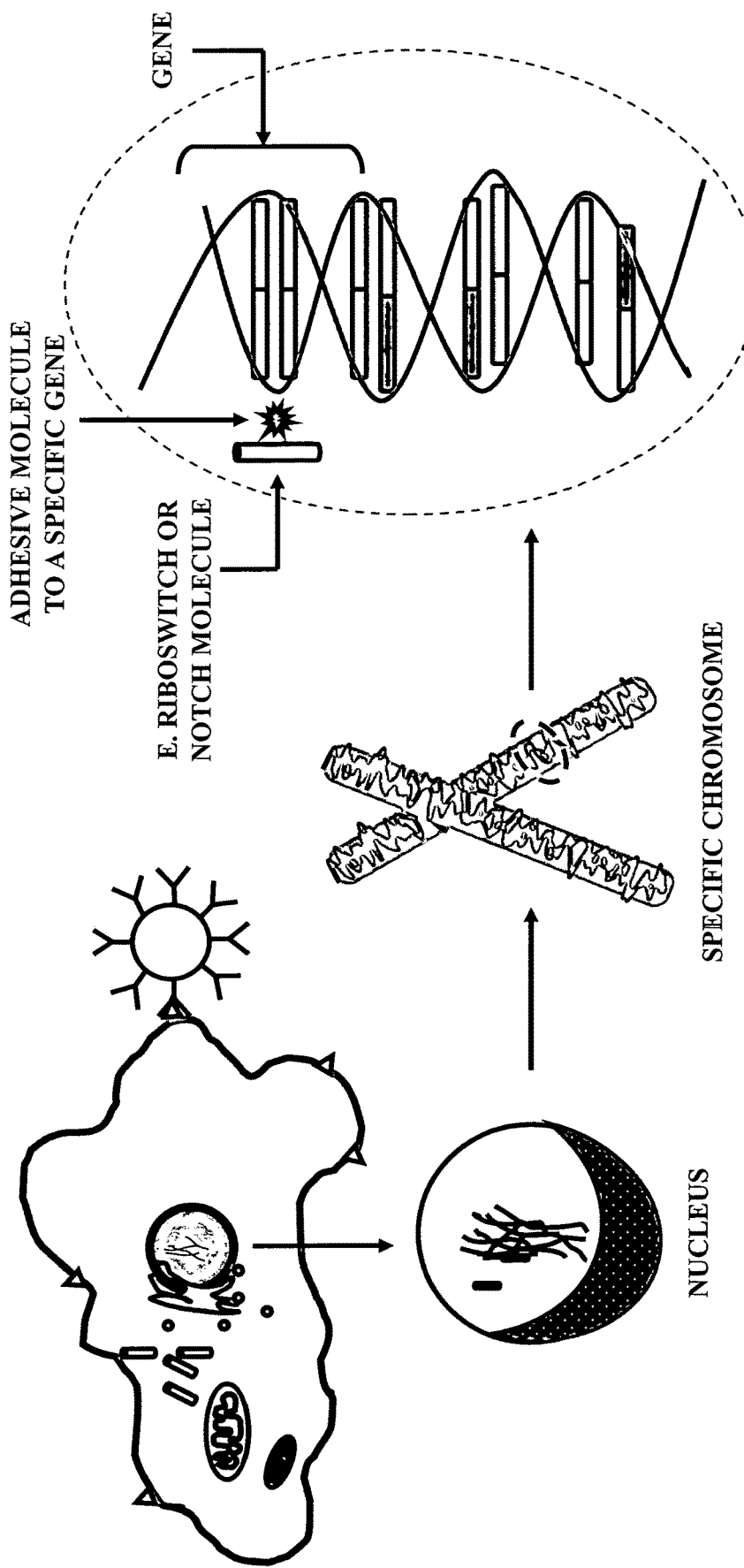
Figure 57I:
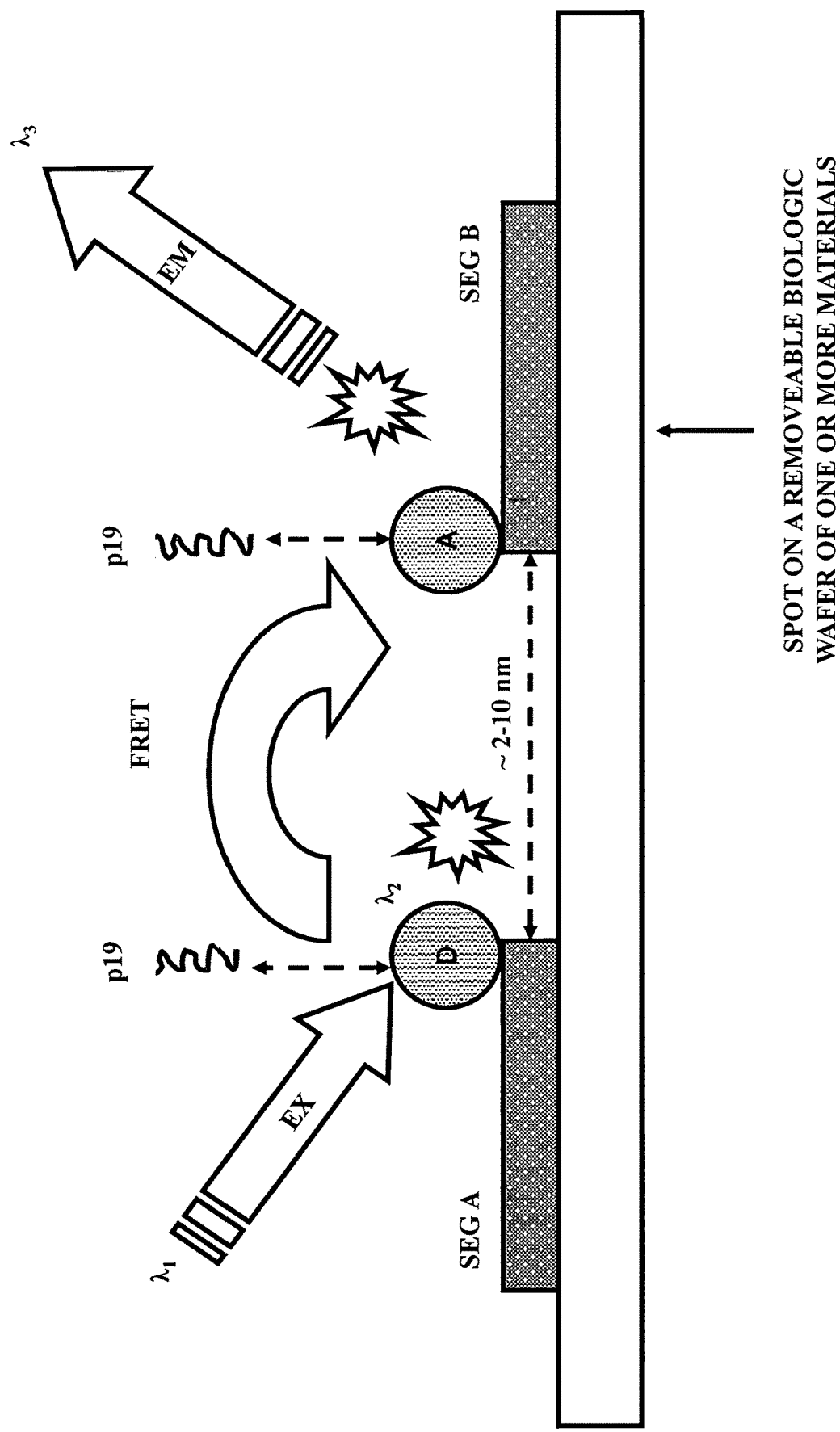

FIG. 57I illustrates an embodiment of Förster/Fluorescence Resonance Energy Transfer (FRET) between a donor fluorophore and an acceptor fluorophore.

Figure 57J:
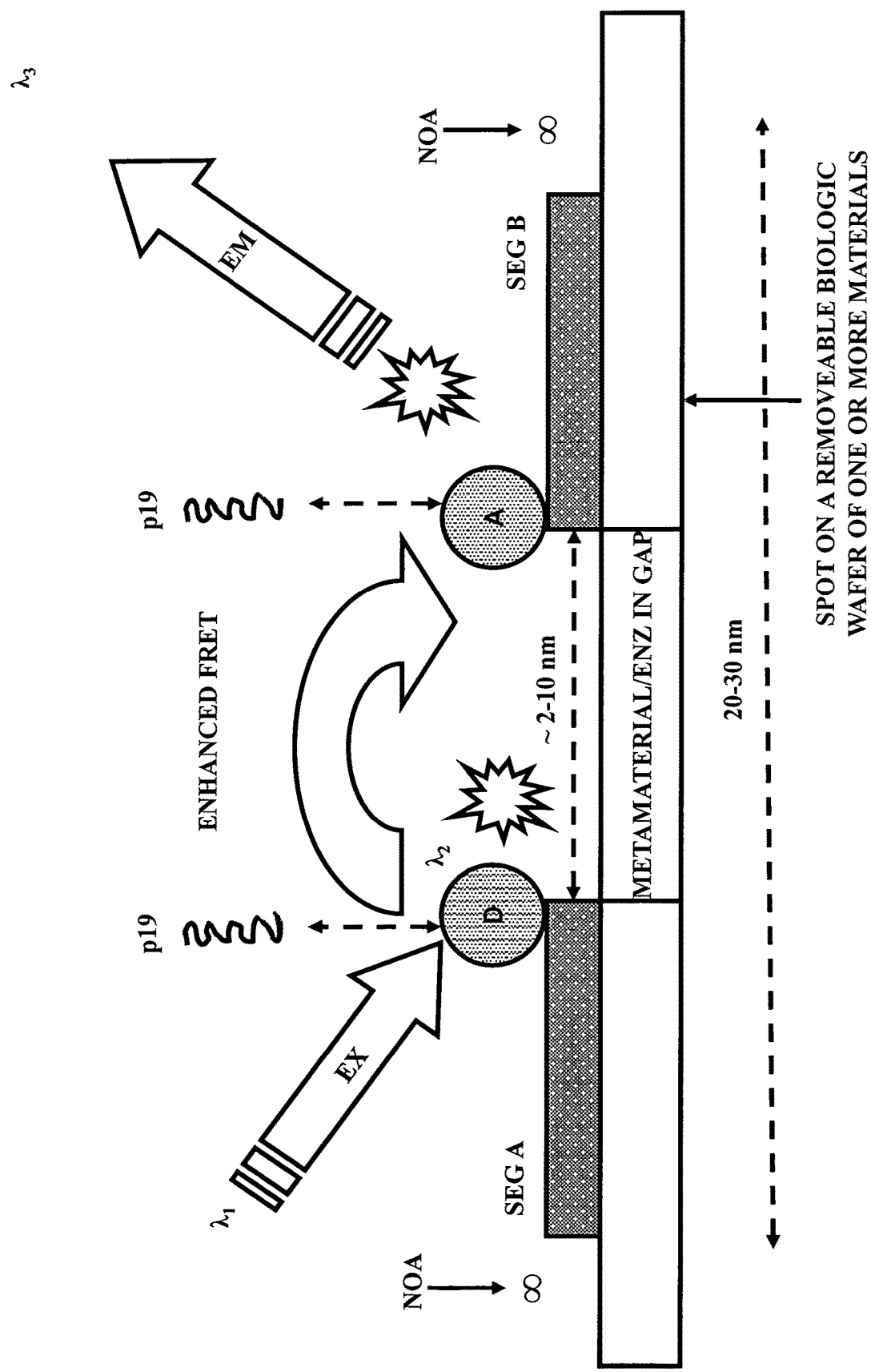
Figure 57K:
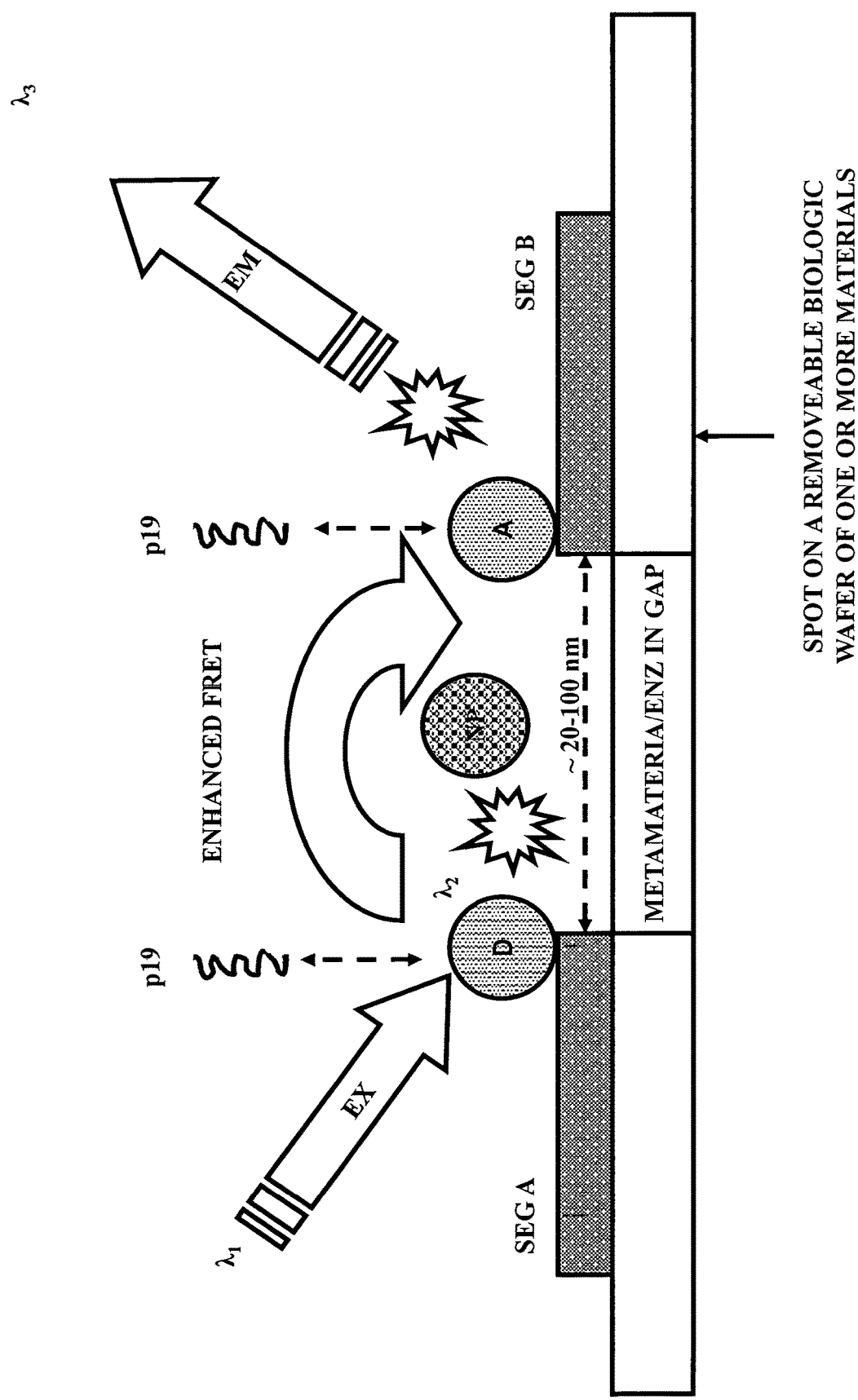

FIGS. 57J-57K illustrate two embodiments of plasmonic enhanced Förster/Fluorescence Resonance Energy Transfer between a donor fluorophore and an acceptor fluorophore.

Figure 57L:
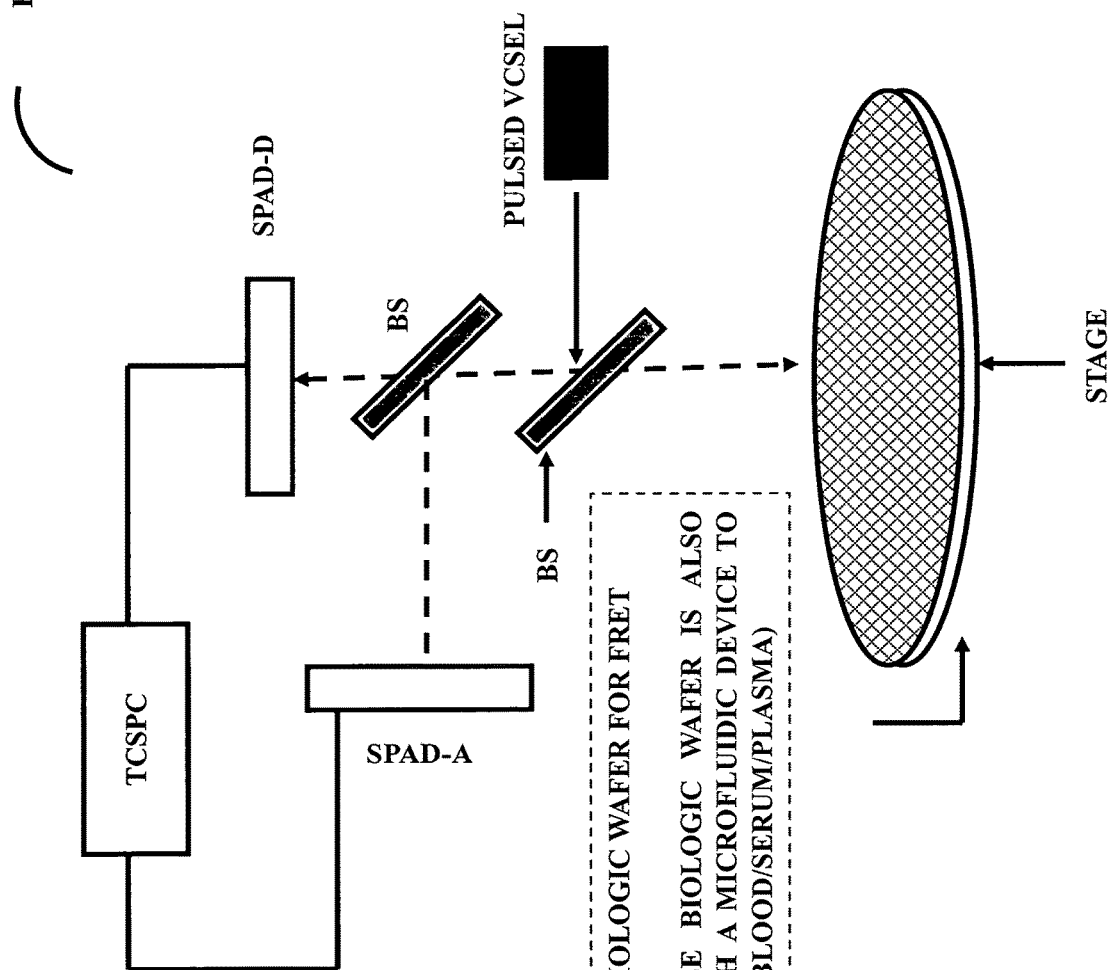

FIG. 57L illustrates an embodiment of a biomarker detection system utilizing Förster/Fluorescence Resonance Energy Transfer, as illustrated in FIGS. 57I, 57J and 57K.

Figure 57M:
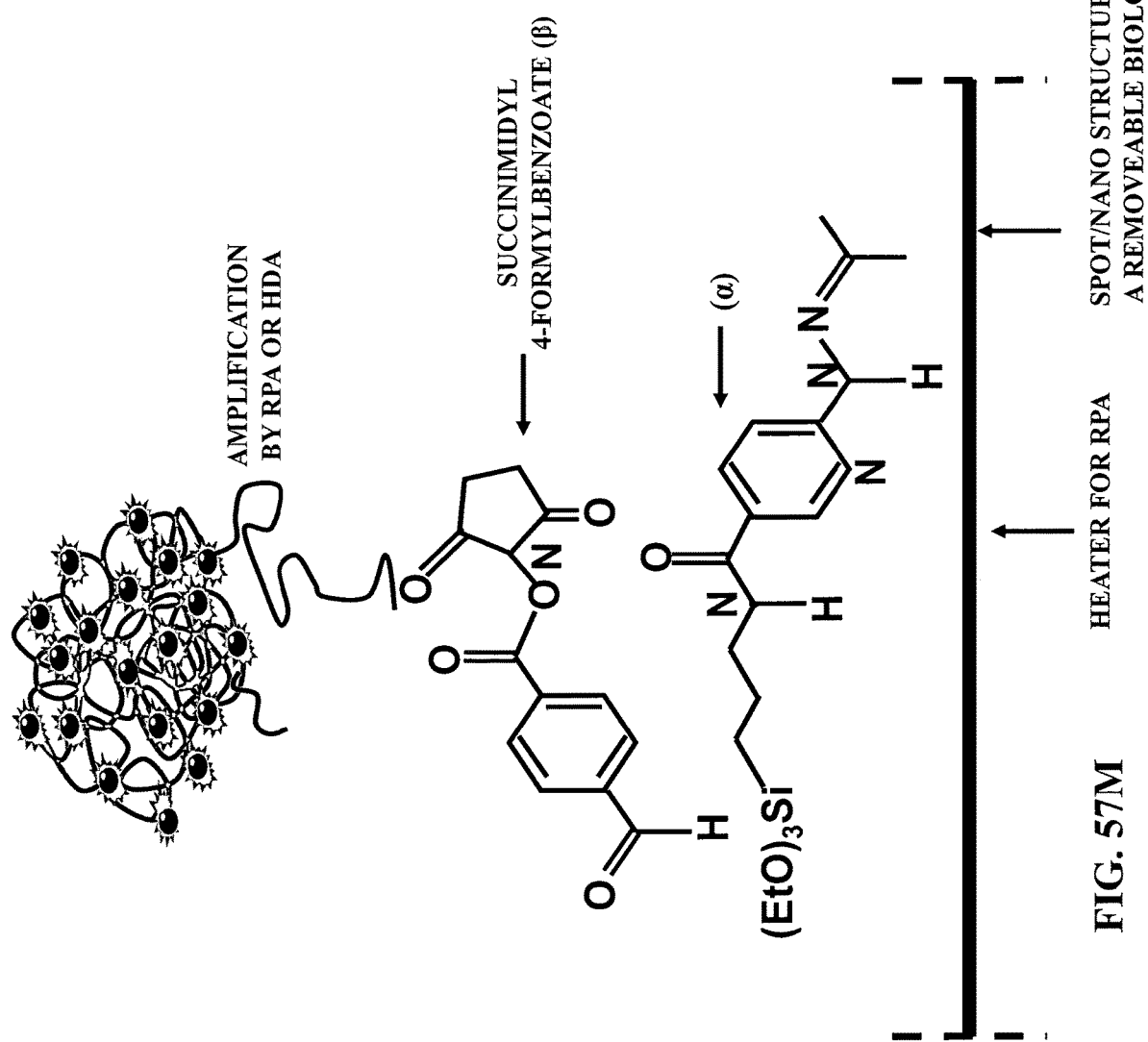

FIG. 57M illustrates an embodiment of amplified biomarker binder-biomarker coupling integrated with fluorophores.

Figure 57N:
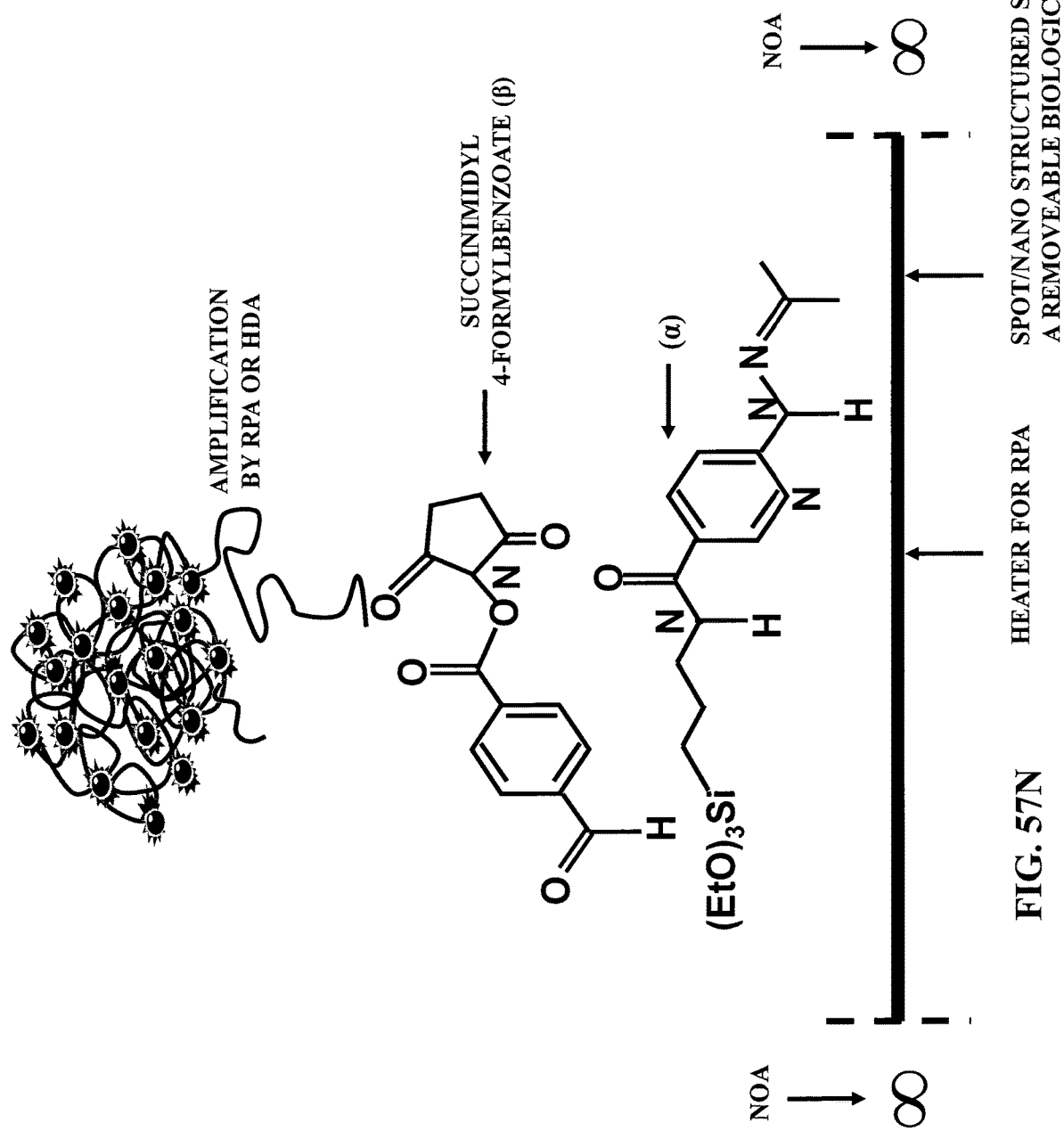

FIG. 57N illustrates an embodiment of plasmonic enhanced and amplified biomarker binder-biomarker coupling integrated with fluorophores.

Figure 57O:
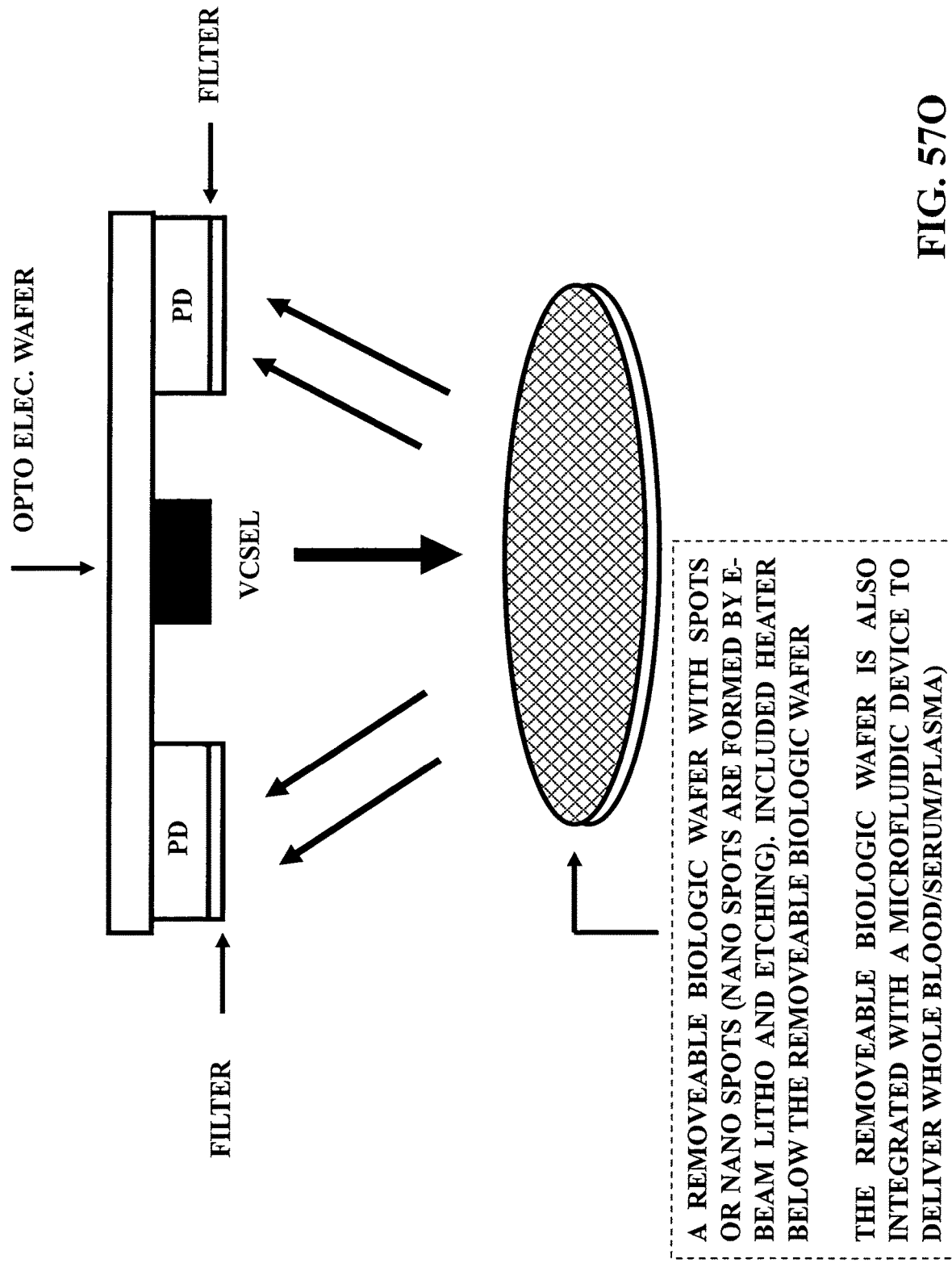
Figure 57P:
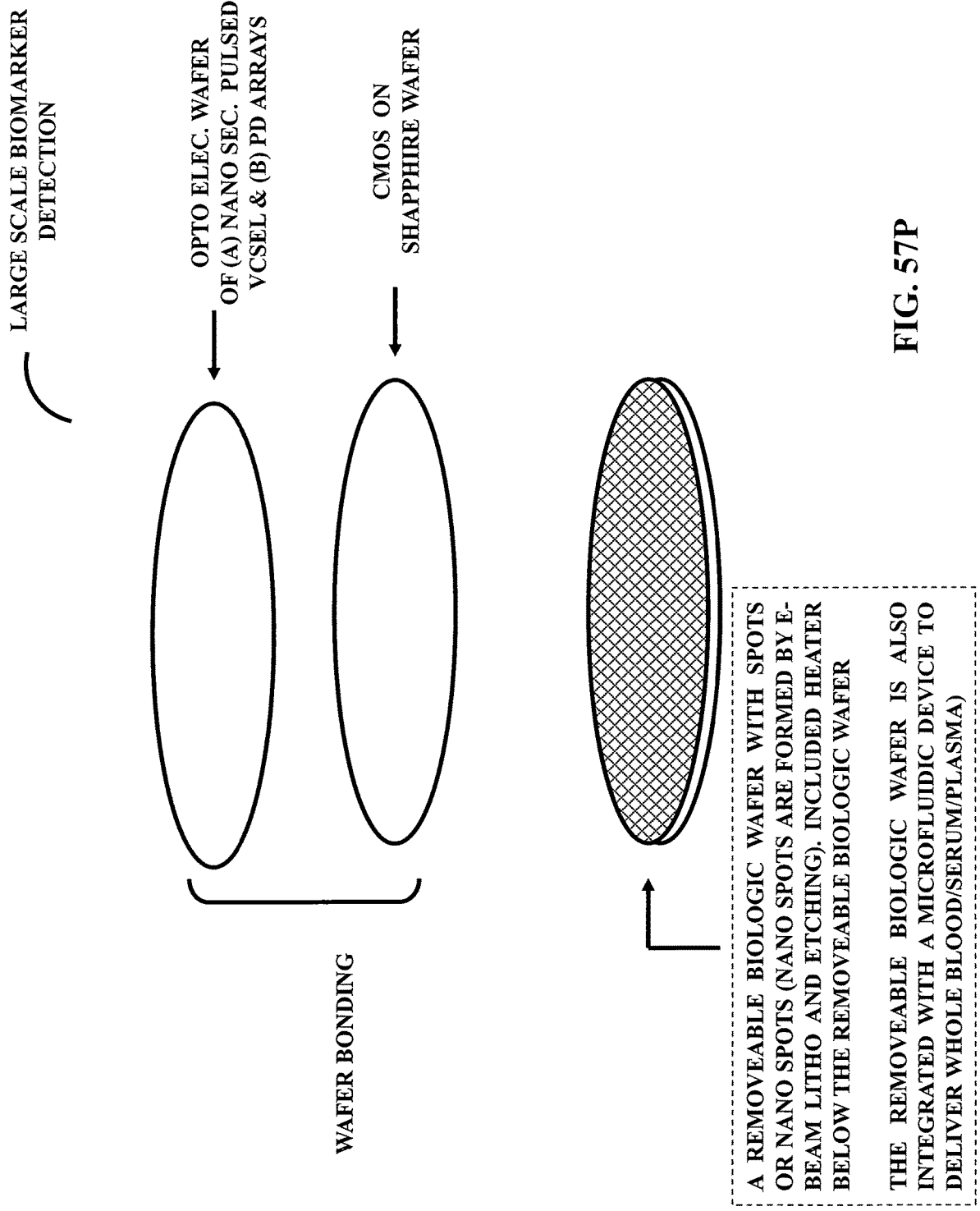

FIGS. 57O-57P illustrate two embodiments of wafer scale detection of (amplified or amplified and plasmonic enhanced) biomarker binder-biomarker coupling integrated with fluorophores.

Figure 57Q:
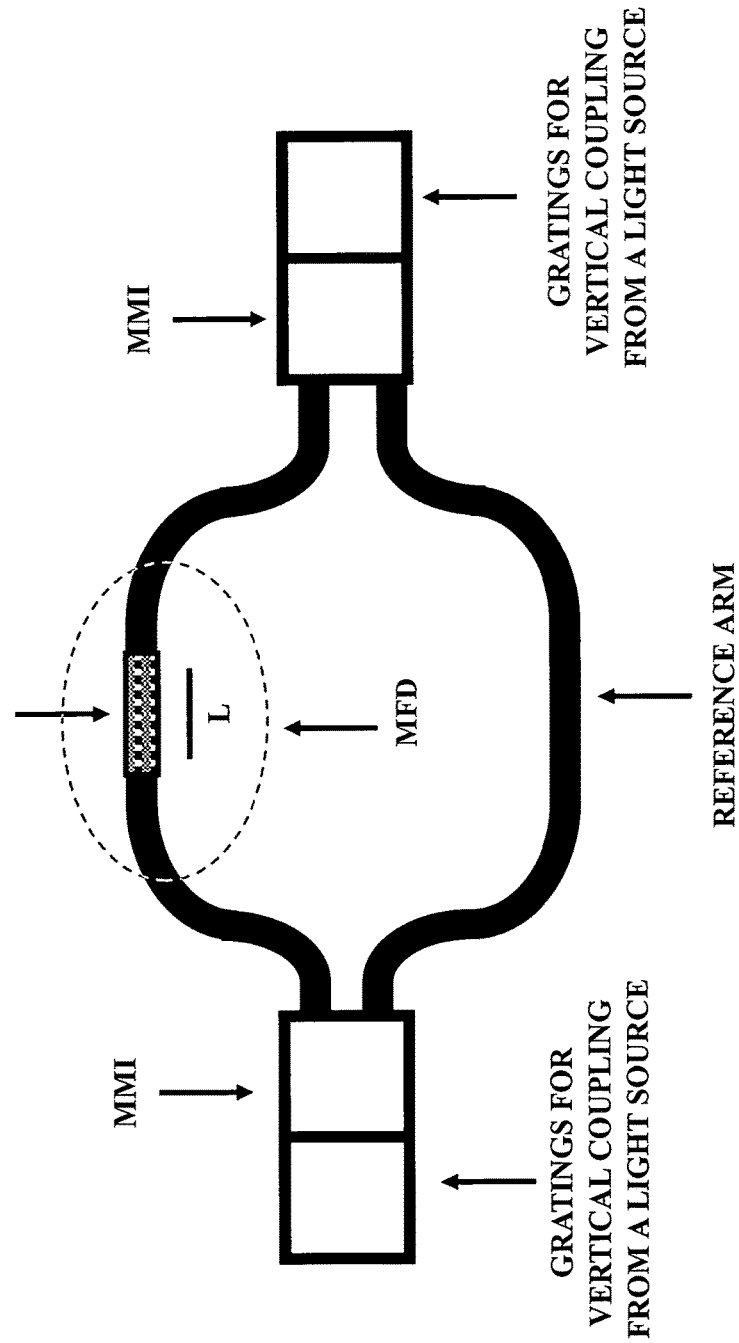
Figure 57R:
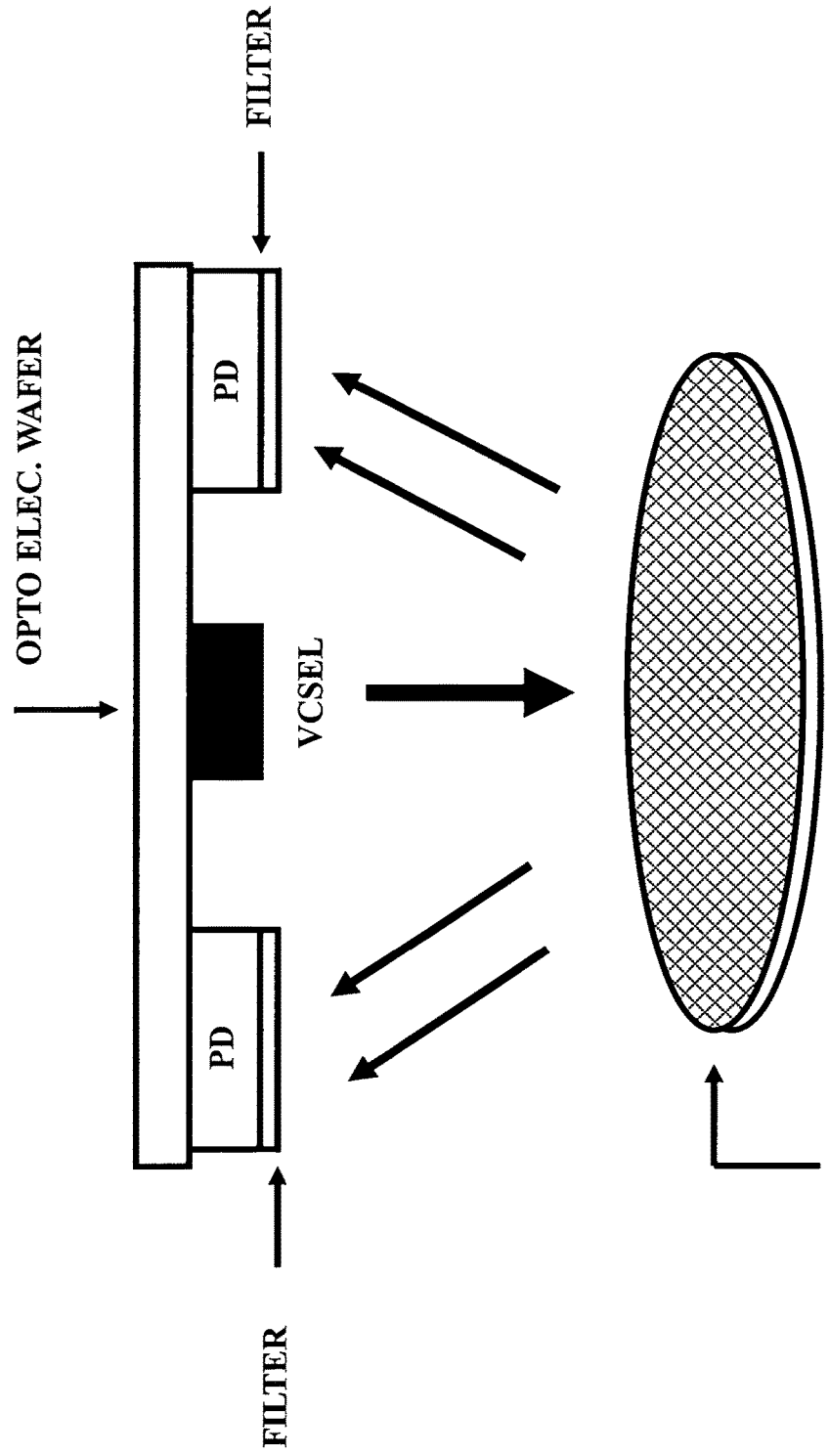
Figure 57S:
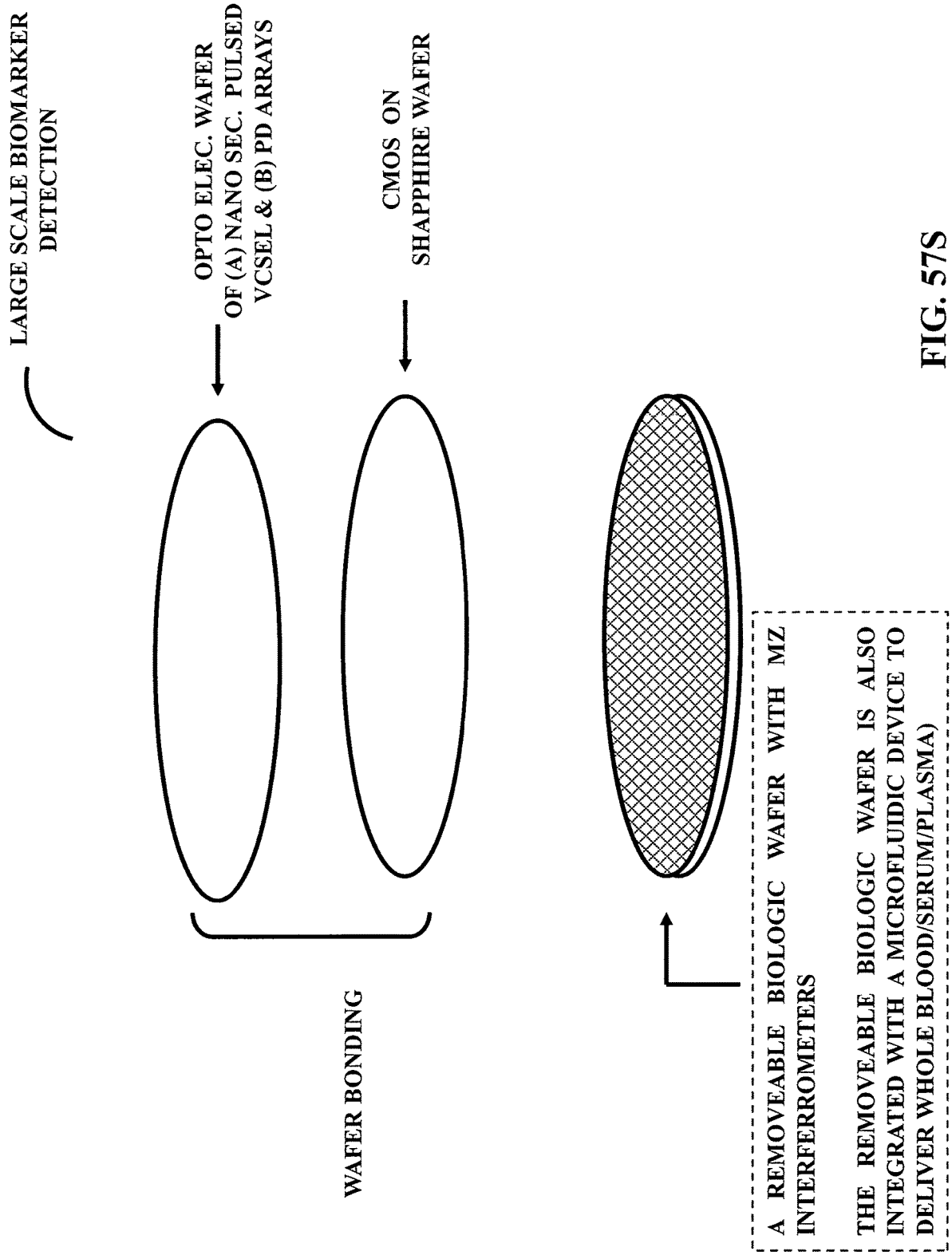

FIGS. 57Q-57S illustrate an embodiment of wafer scale detection of biomarker binder-biomarker coupling, utilizing asymmetric Mach-Zehnder Interferometers (MZIs).

Figure 57T:
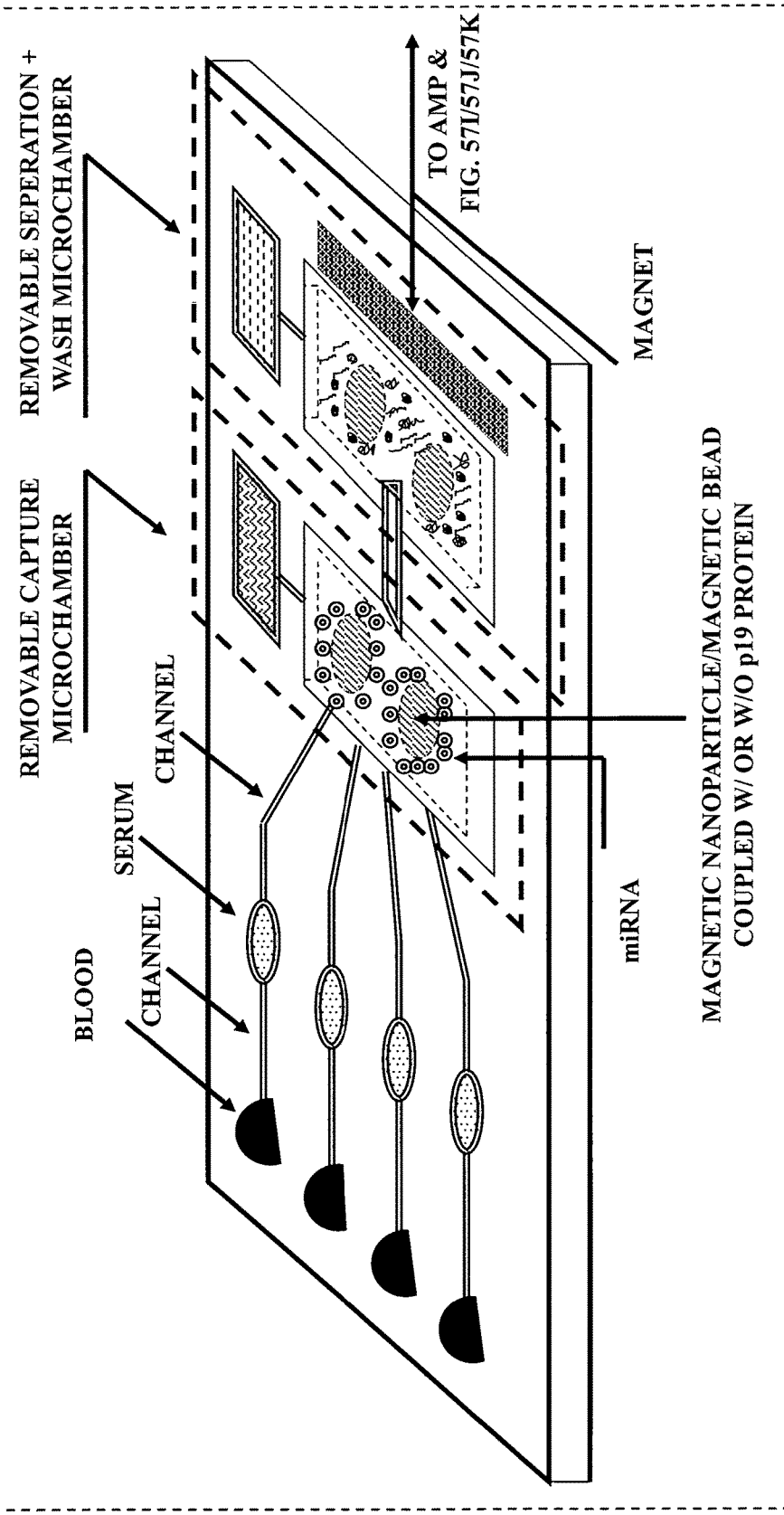

FIG. 57T illustrates an embodiment of a microfluidic based miRNA capture system.

Diagnostic System

FIGS. 58A-58F illustrate an embodiment of an early diagnostic system A.

FIGS. 59A-59J illustrate an embodiment of an early diagnostic system B.

FIGS. 60A-60F illustrate an electro-optical embodiment of a deoxyribonucleic acid (DNA) sequencing system.

Figure 60A:
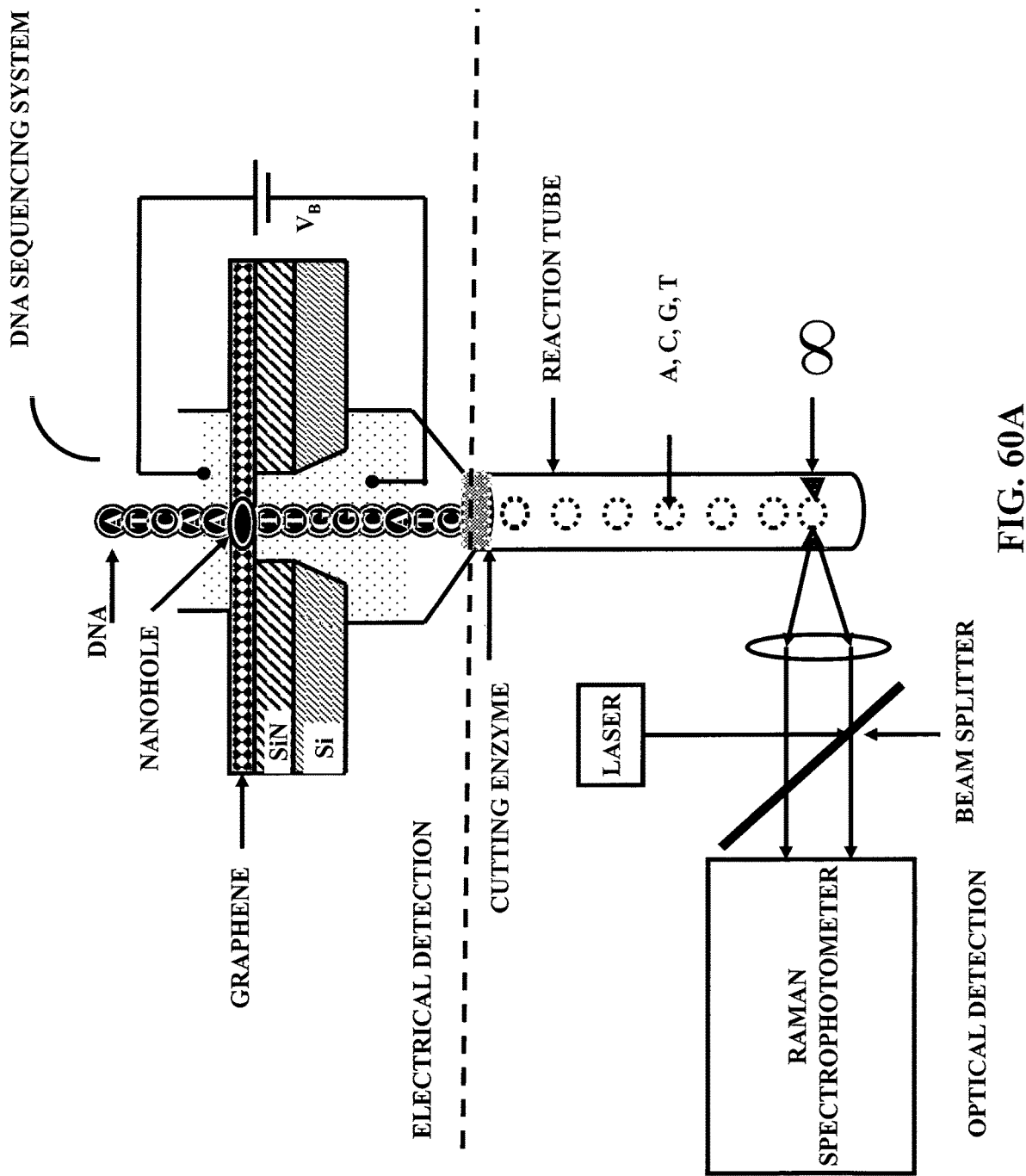
Figure 60B:
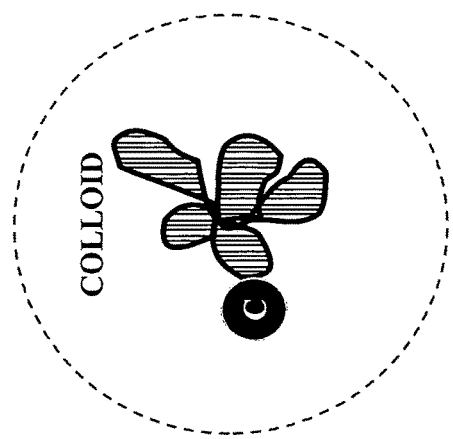
Figure 60C:
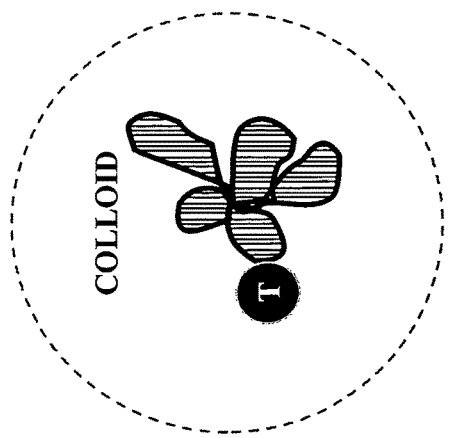
Figure 60D:
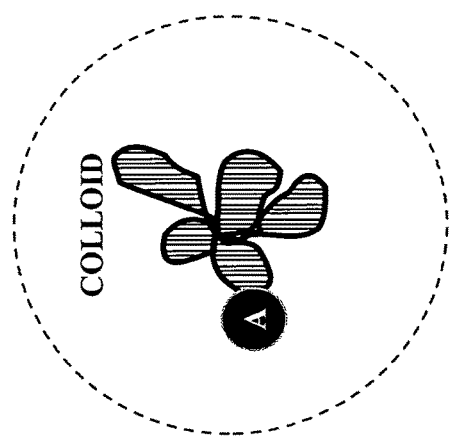
Figure 60E:
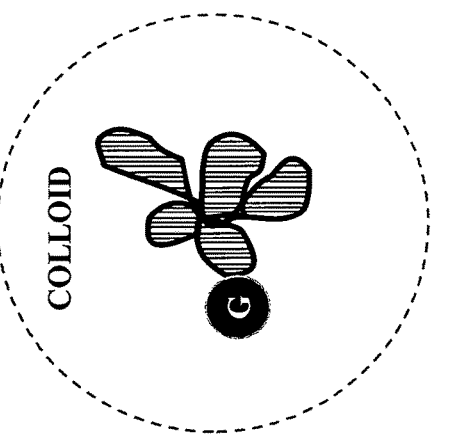
Figure 60F:
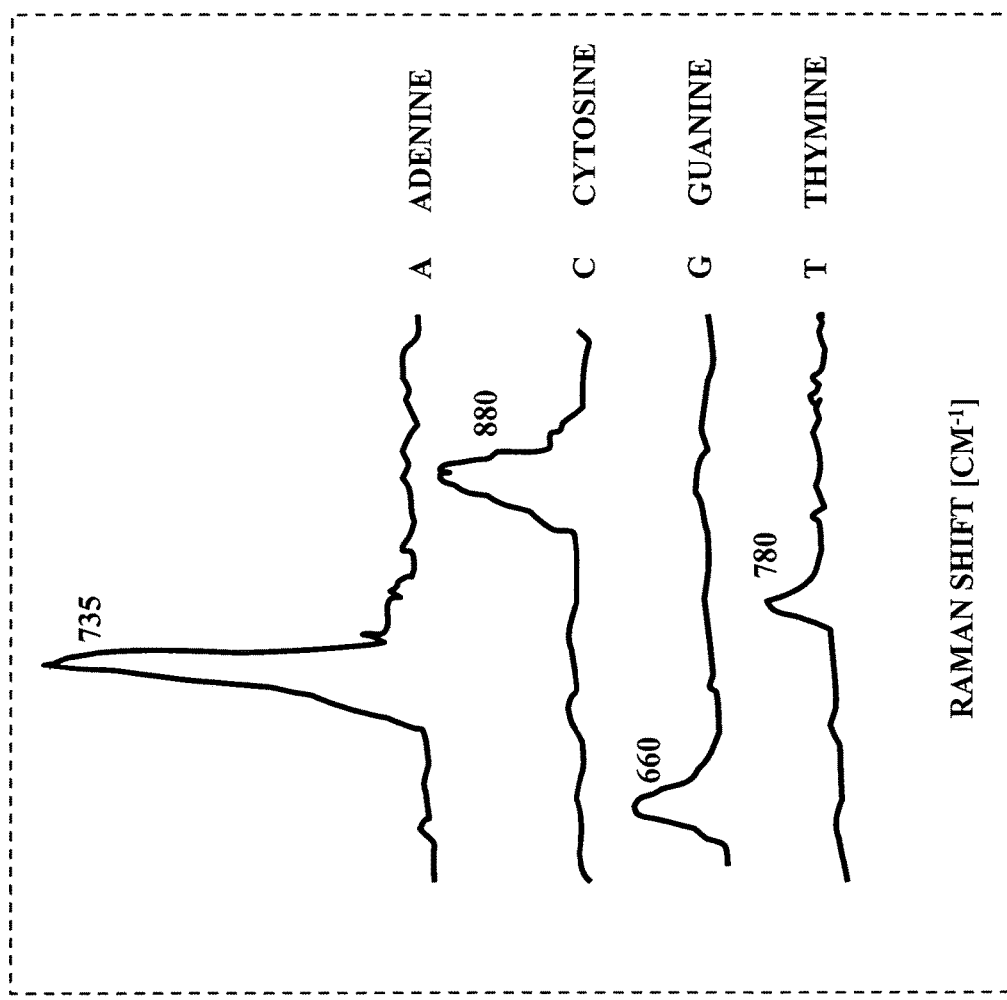
Figure 60G:
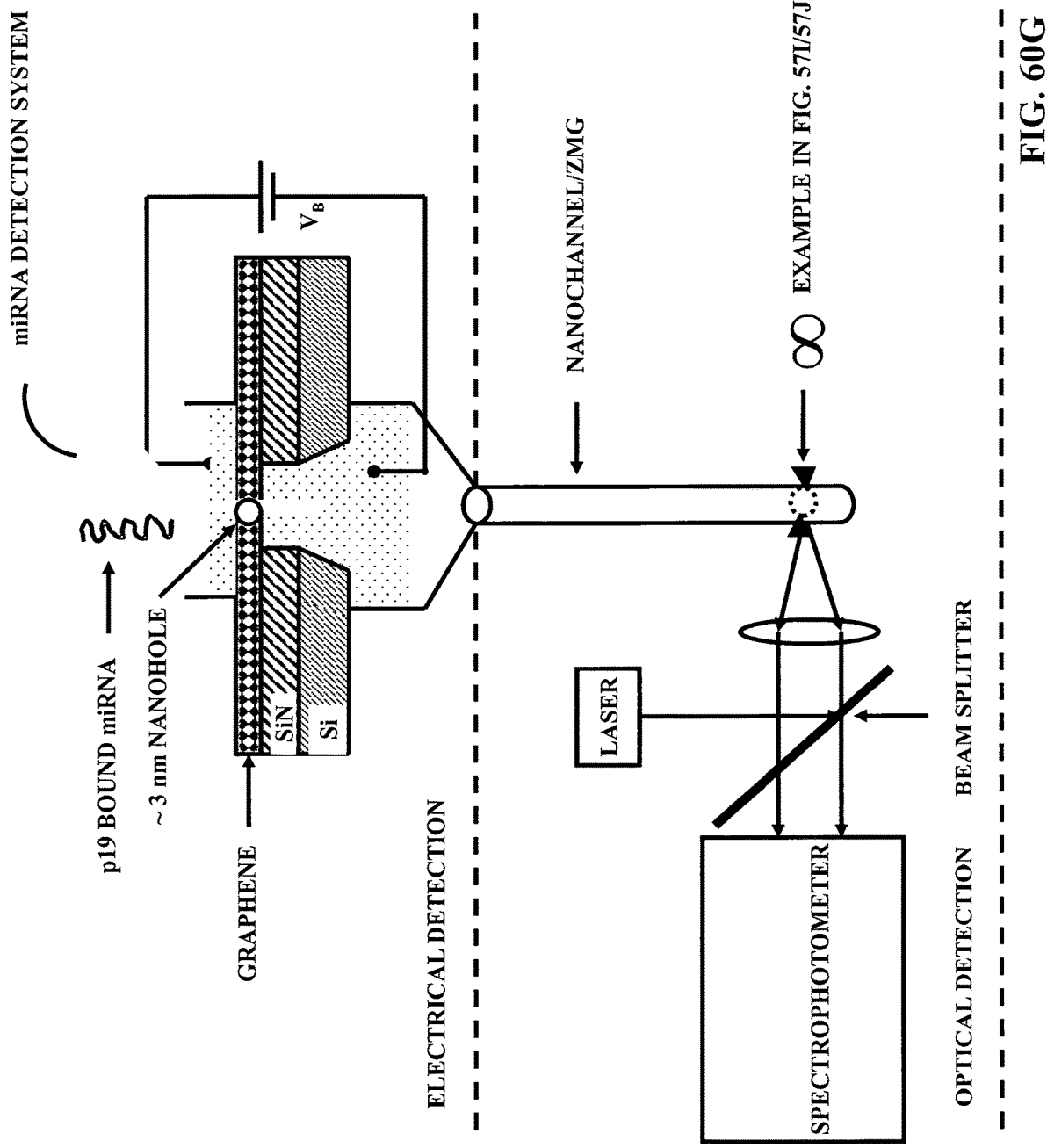

FIG. 60G illustrates an electro-optical embodiment of miRNA detection system.

Figure 61A:
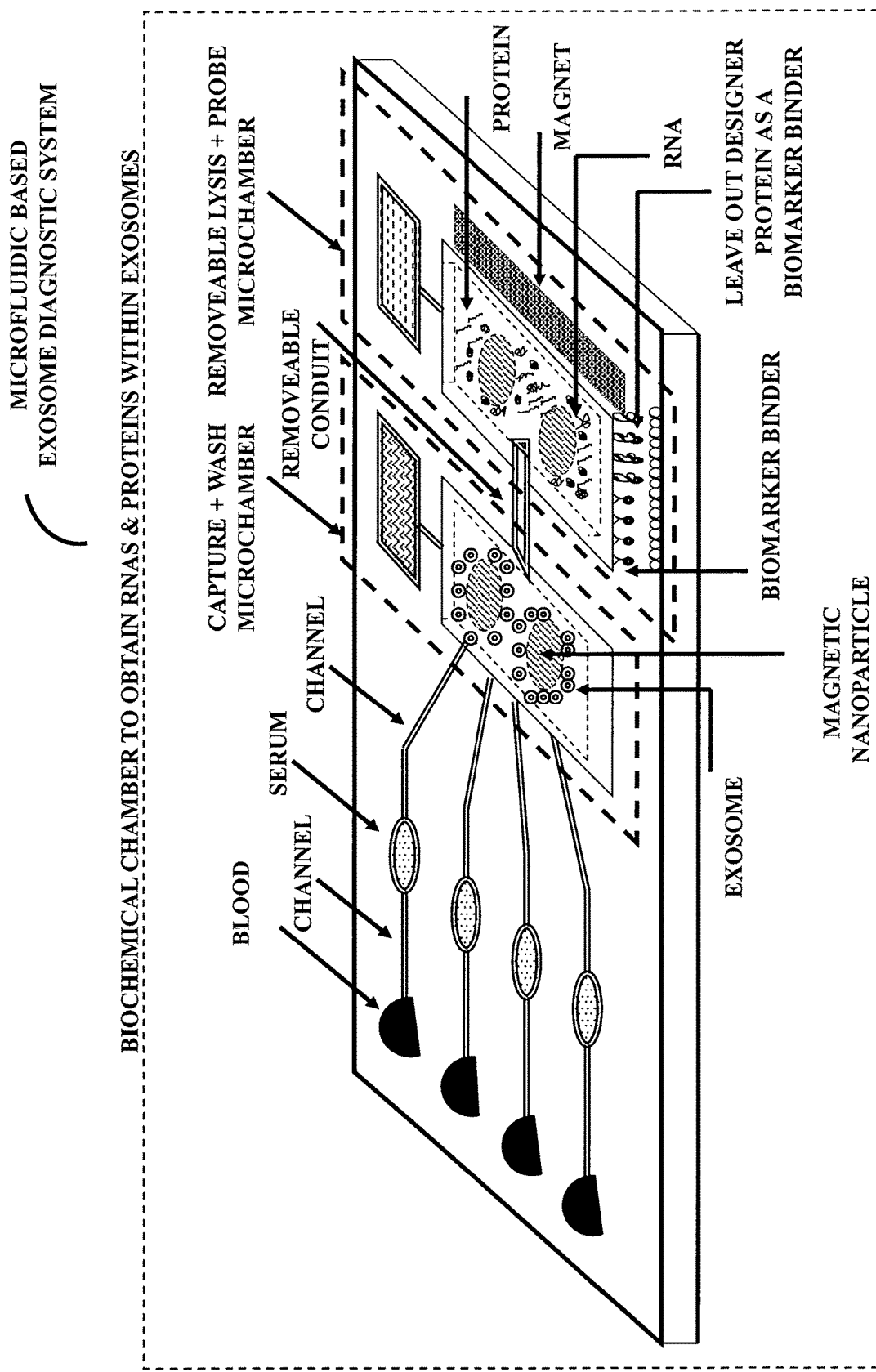
Figure 61B:
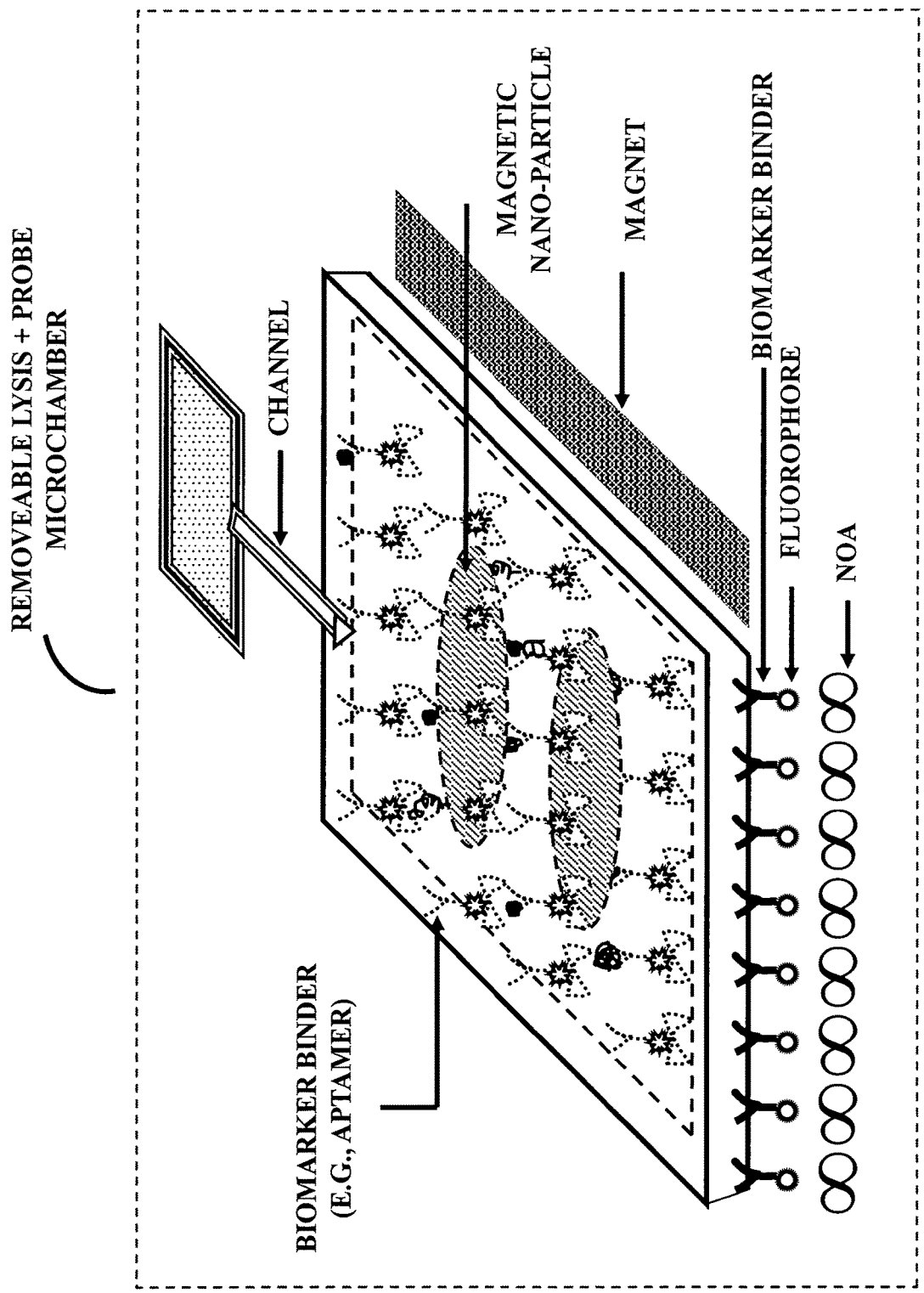
Figure 61C:
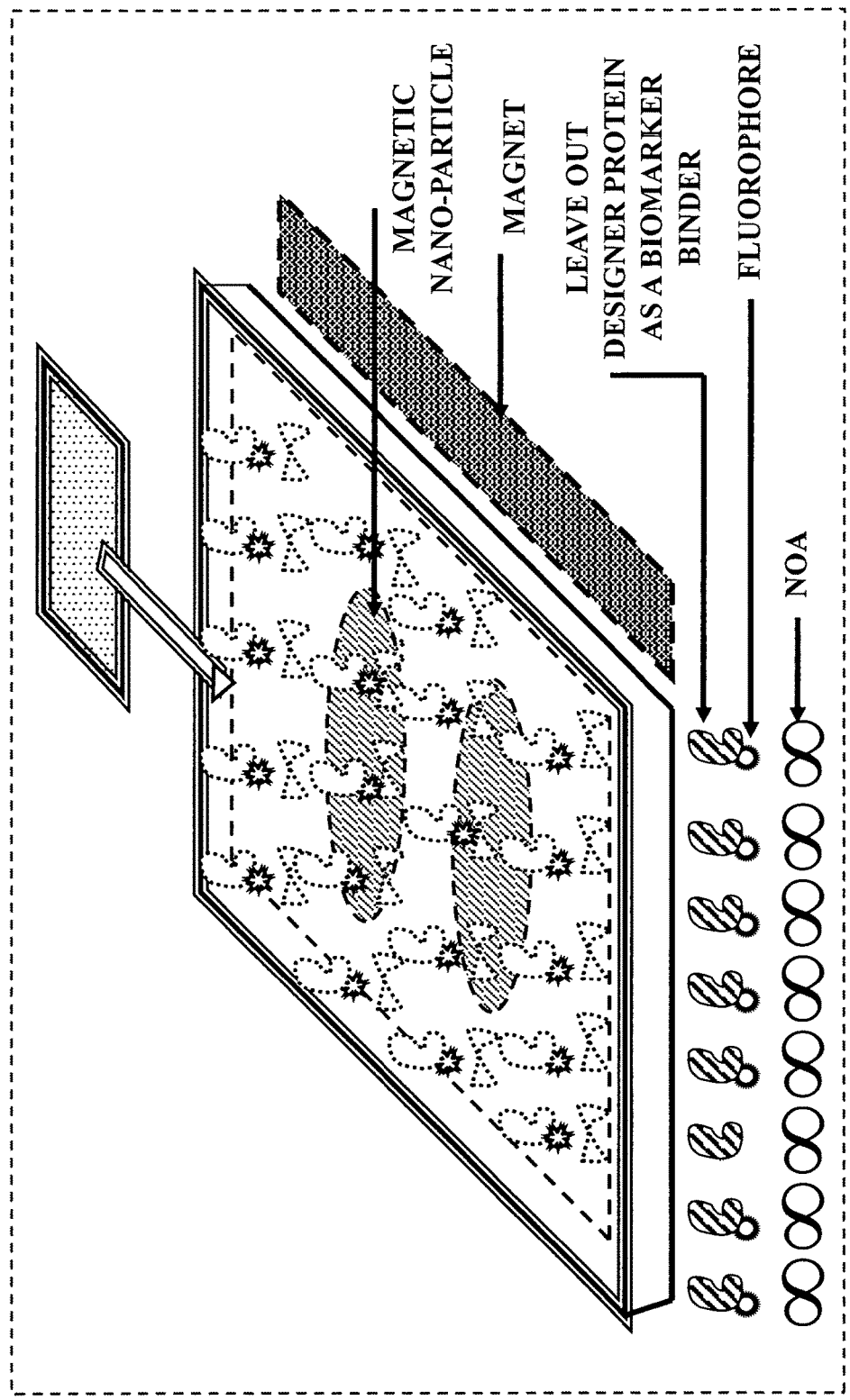

FIGS. 61A-61C illustrate an embodiment of a microfluidic based exosome diagnostic system.

Micro/Nano Three-Dimensional Printer

Figure 62A:
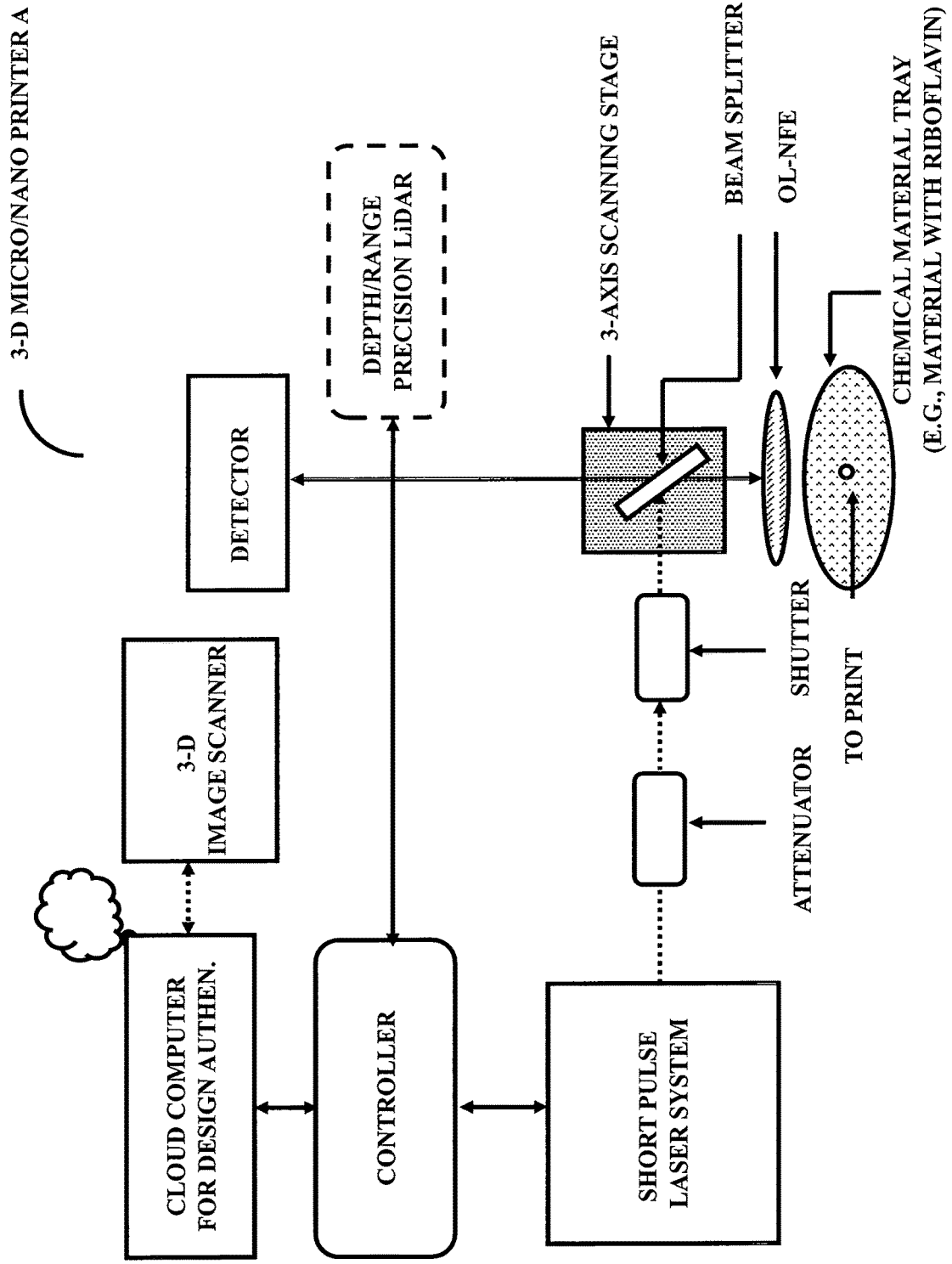
Figure 62B:
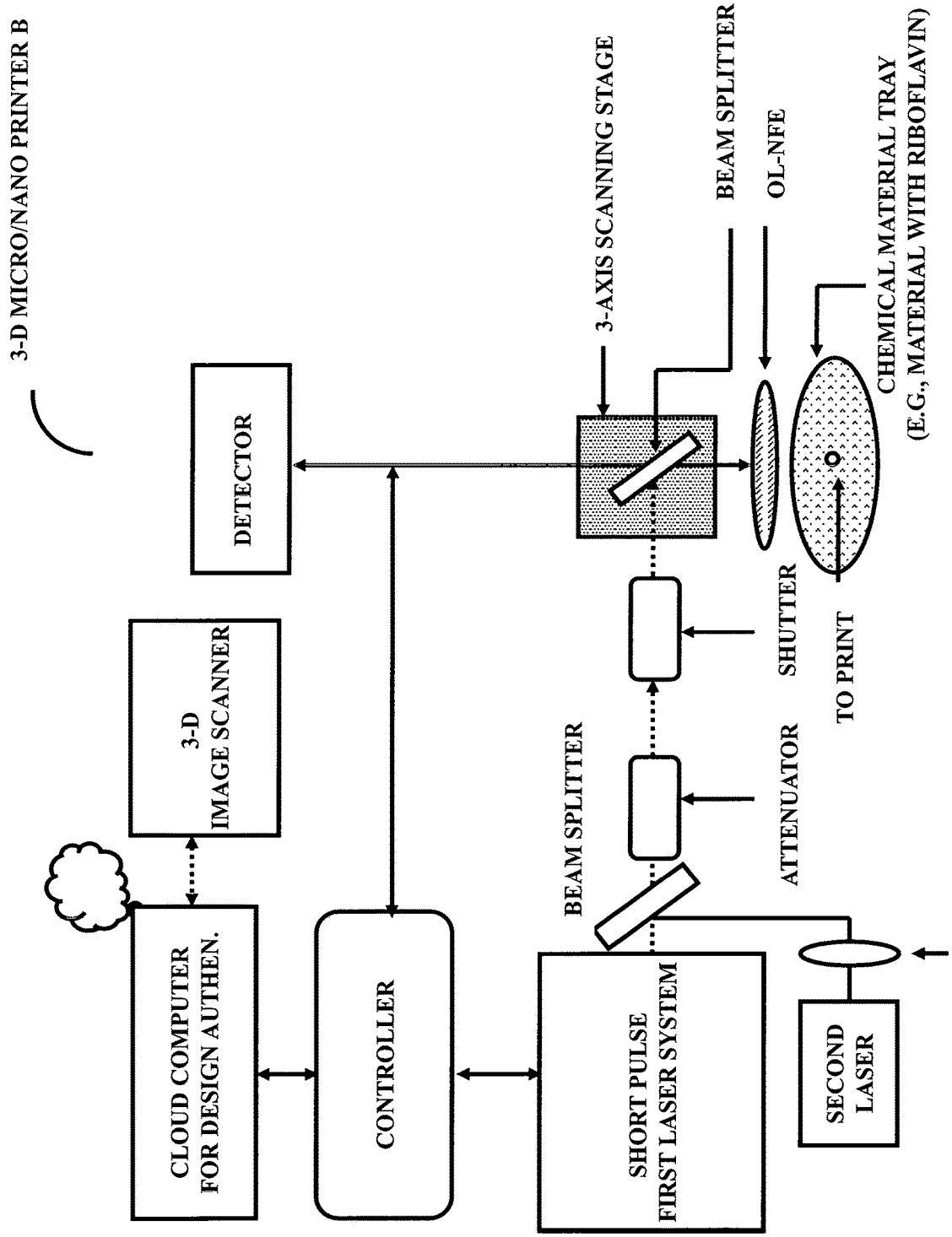

FIGS. 62A-62B illustrate two embodiments of a three-dimensional micro/nano printer.

Personal Human Operating System

Figure 63A:
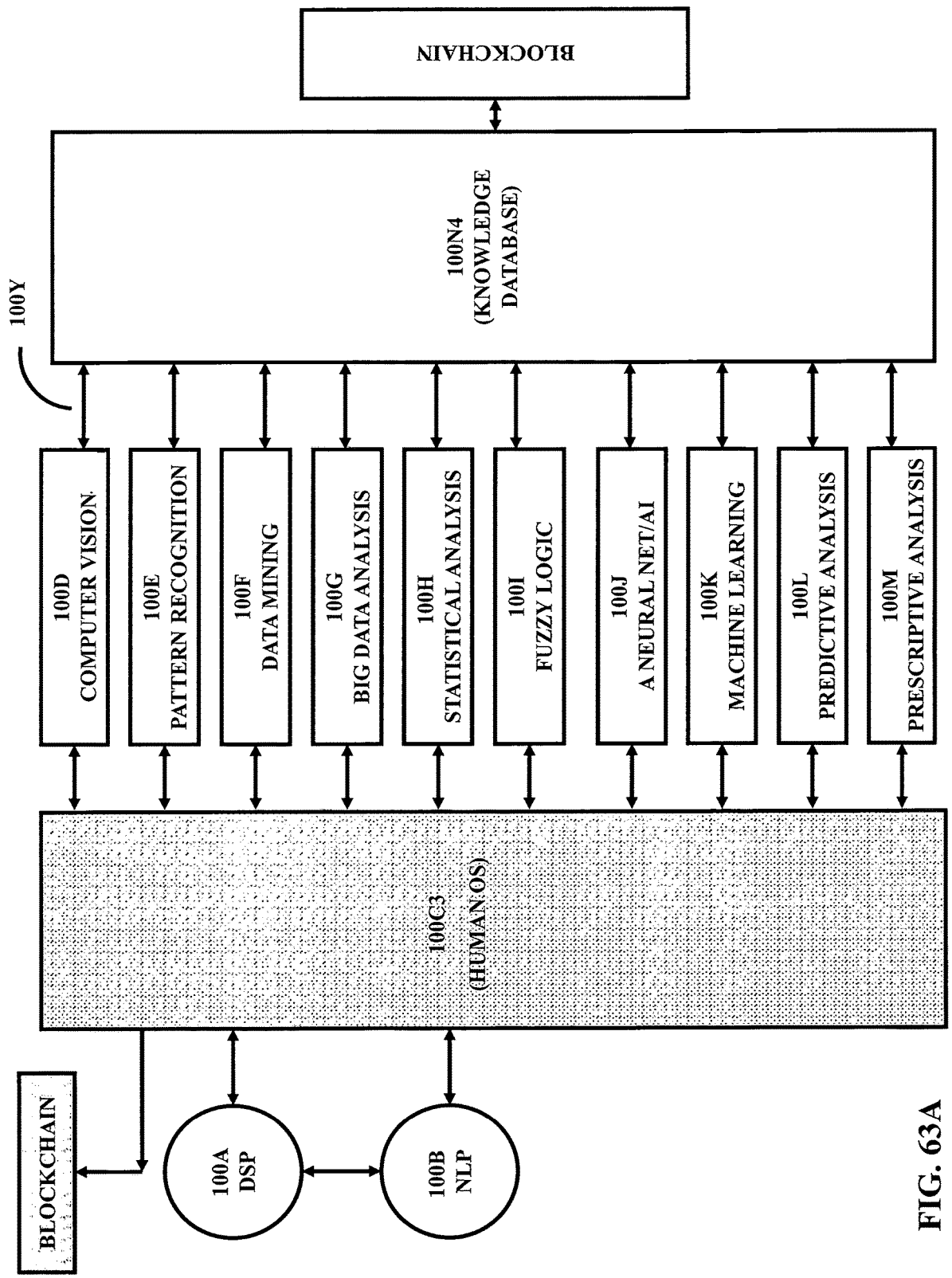
Figure 63B:
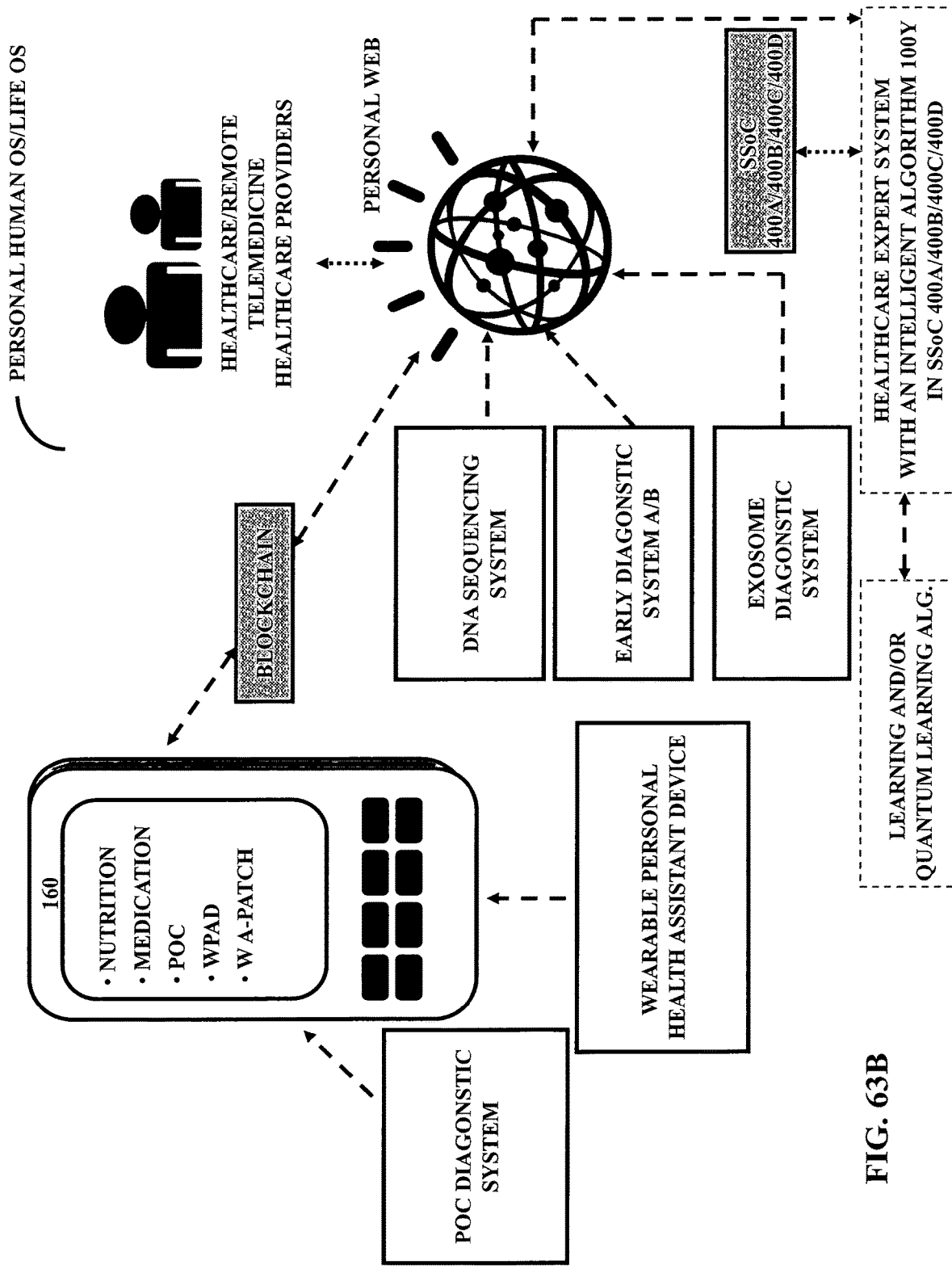

FIGS. 63A-63B illustrate an embodiment of a Personal Human Operating System.

Figure 63C:
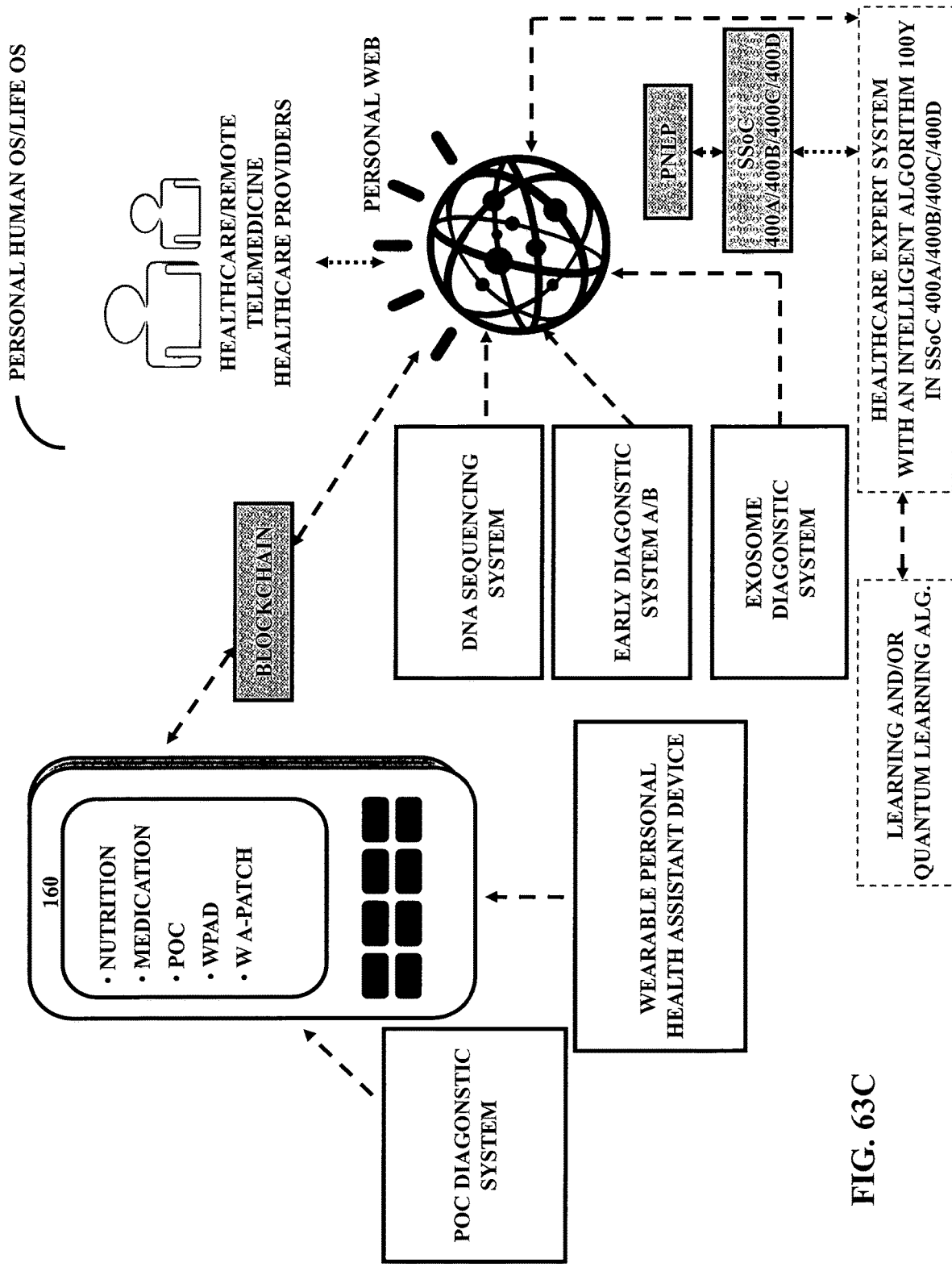

FIG. 63C illustrates another embodiment of a Personal Human Operating System, utilizing a photonic neural learning processor (PNLP).

Figure 63D:
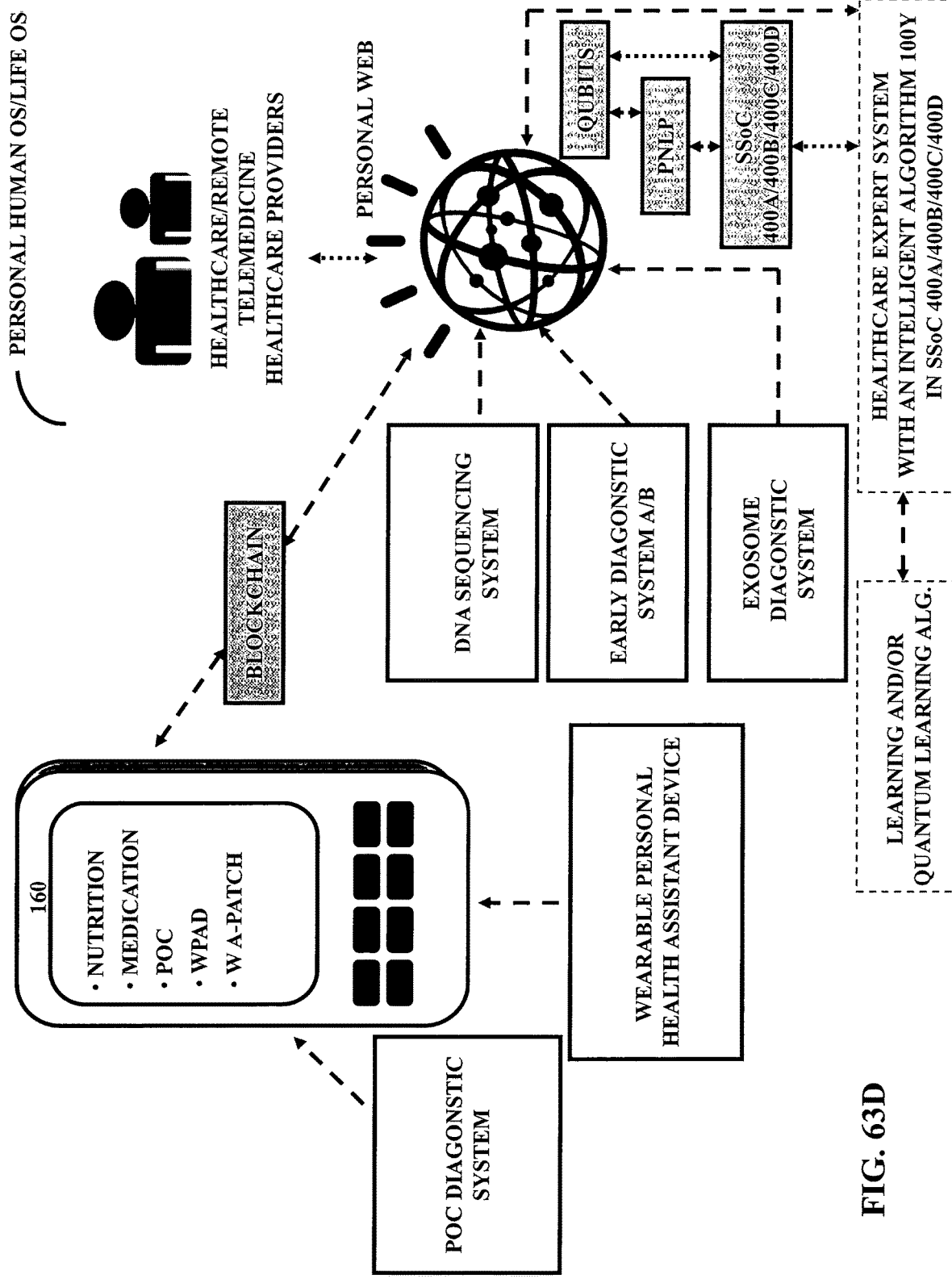

FIG. 63D illustrates another embodiment of a Personal Human Operating System, utilizing a photonic neural learning processor, coupled with one or more quantum bits (qubits).

Figure 64A:
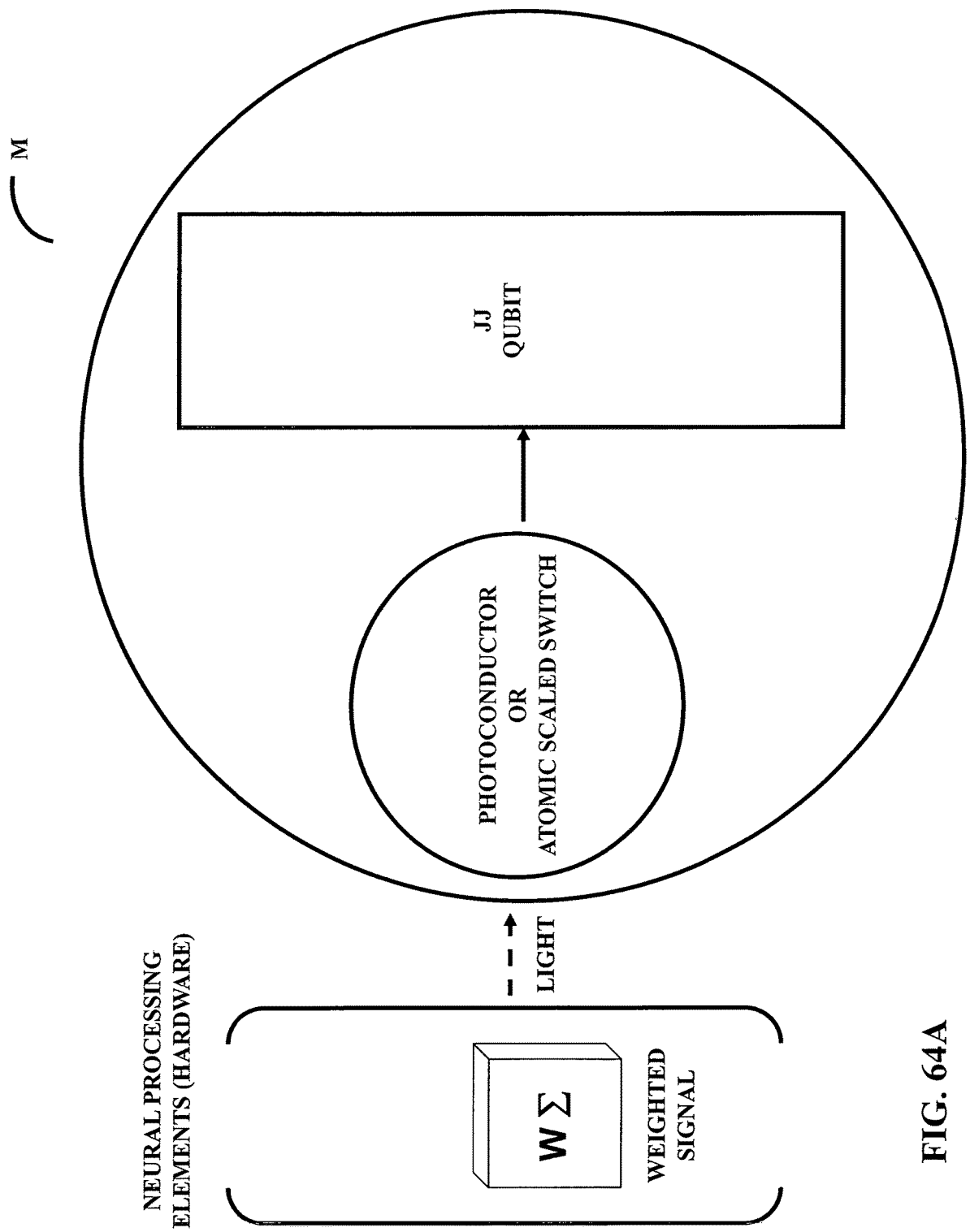

Large Scale Network of Coupling (Electro-Optical/Optical) of Light Signal (Activated by Weighted Electrical Signals from Neural Processing Hardware Elements) with Qubits FIG. 64A illustrates an embodiment (identified as M) of electro-optical coupling of a light signal (only activated by weighted electrical/optical signals from neural processing hardware elements) with a qubit based on Josephson junction (JJ).

Figure 64B:
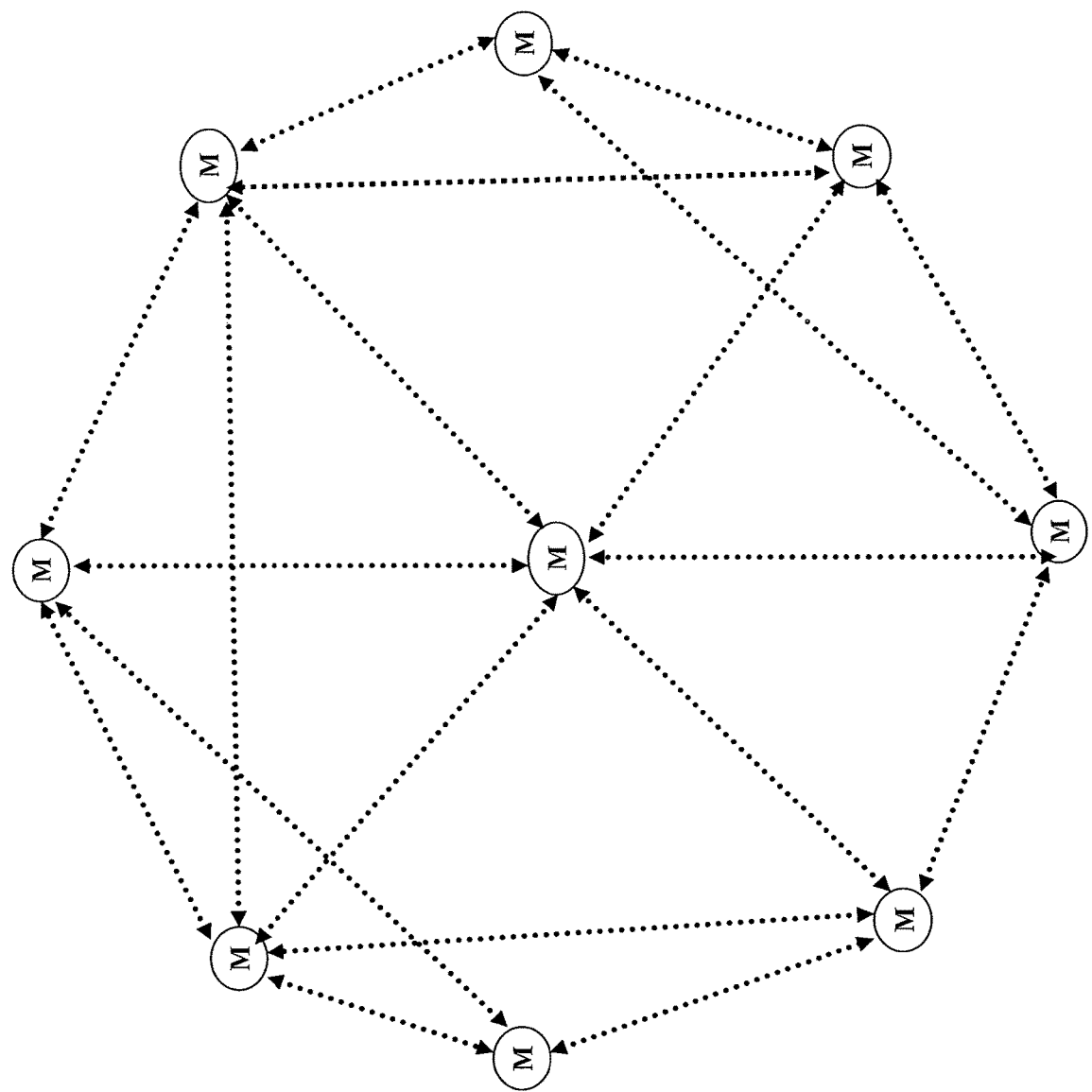

FIG. 64B illustrates a large scale network of the above configuration (in FIG. 64A).

Figure 64C:
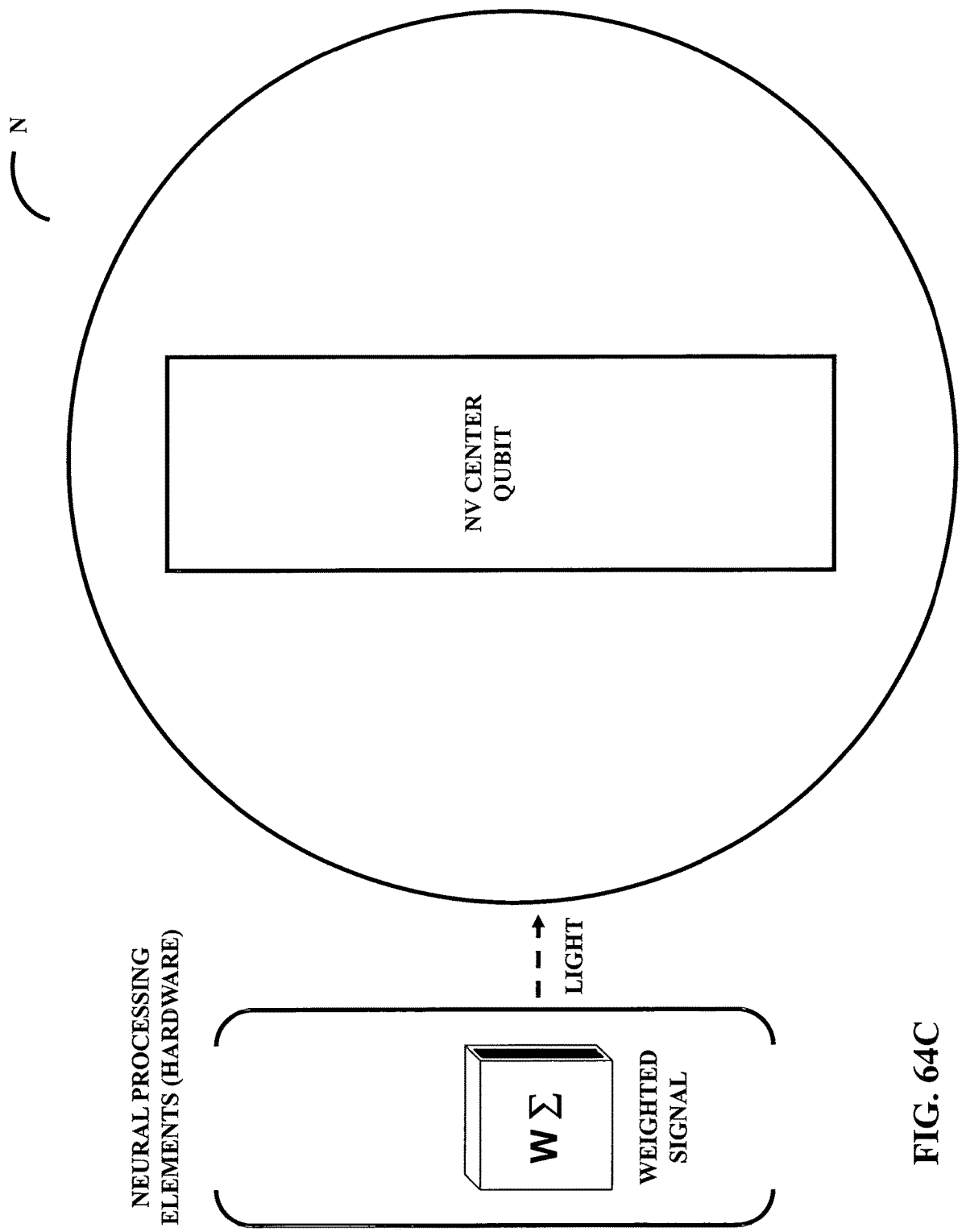
Figure 64D:
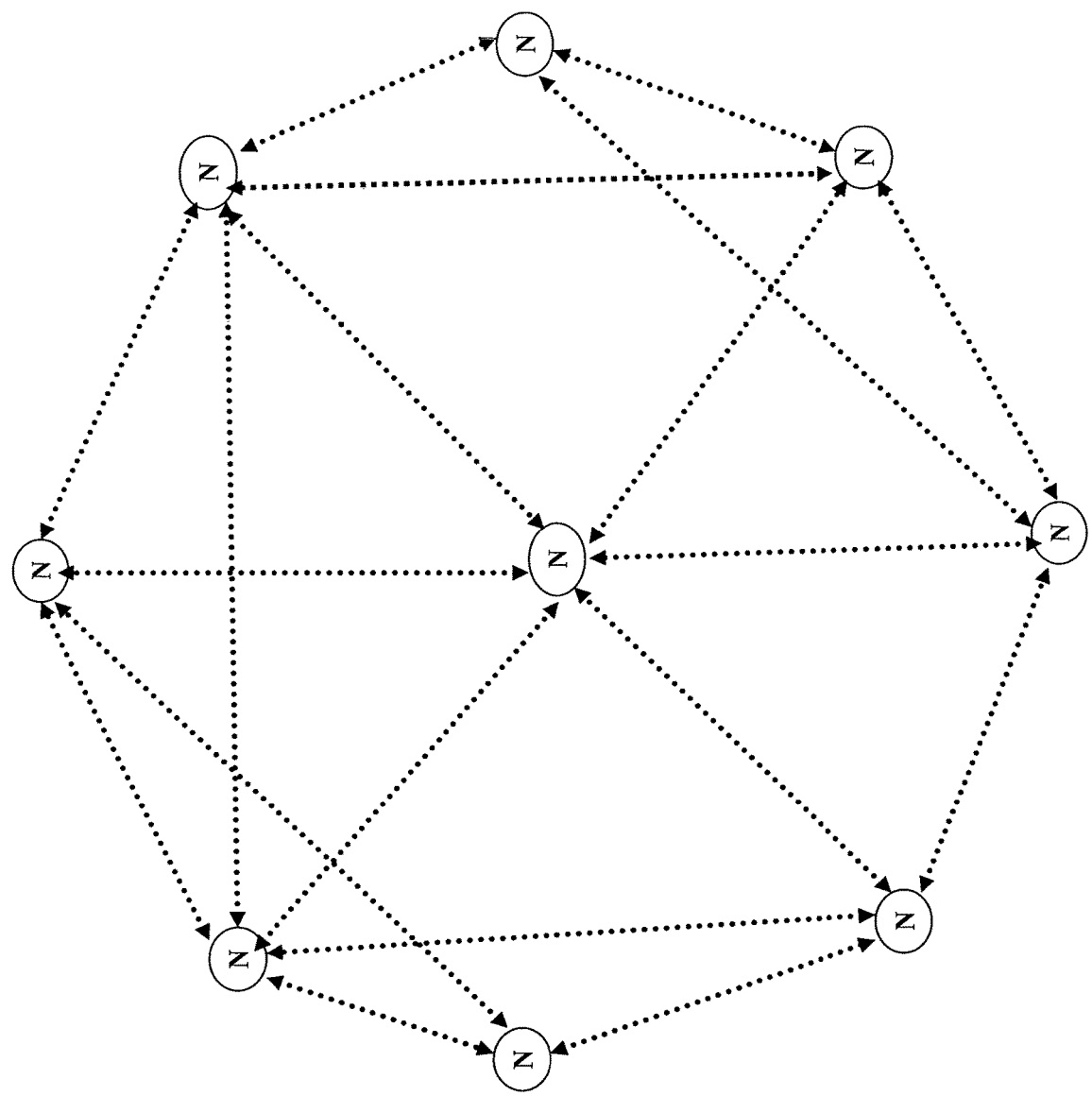

FIG. 64C illustrates another embodiment (identified as N) of optical coupling of a light signal (only activated by weighted electrical/optical signals from neural processing hardware elements) with a qubit based on a nitrogen vacancy center in diamond crystal FIG. 64D illustrates a large scale network of the above configuration (in FIG. 64C).

Figure 64E:
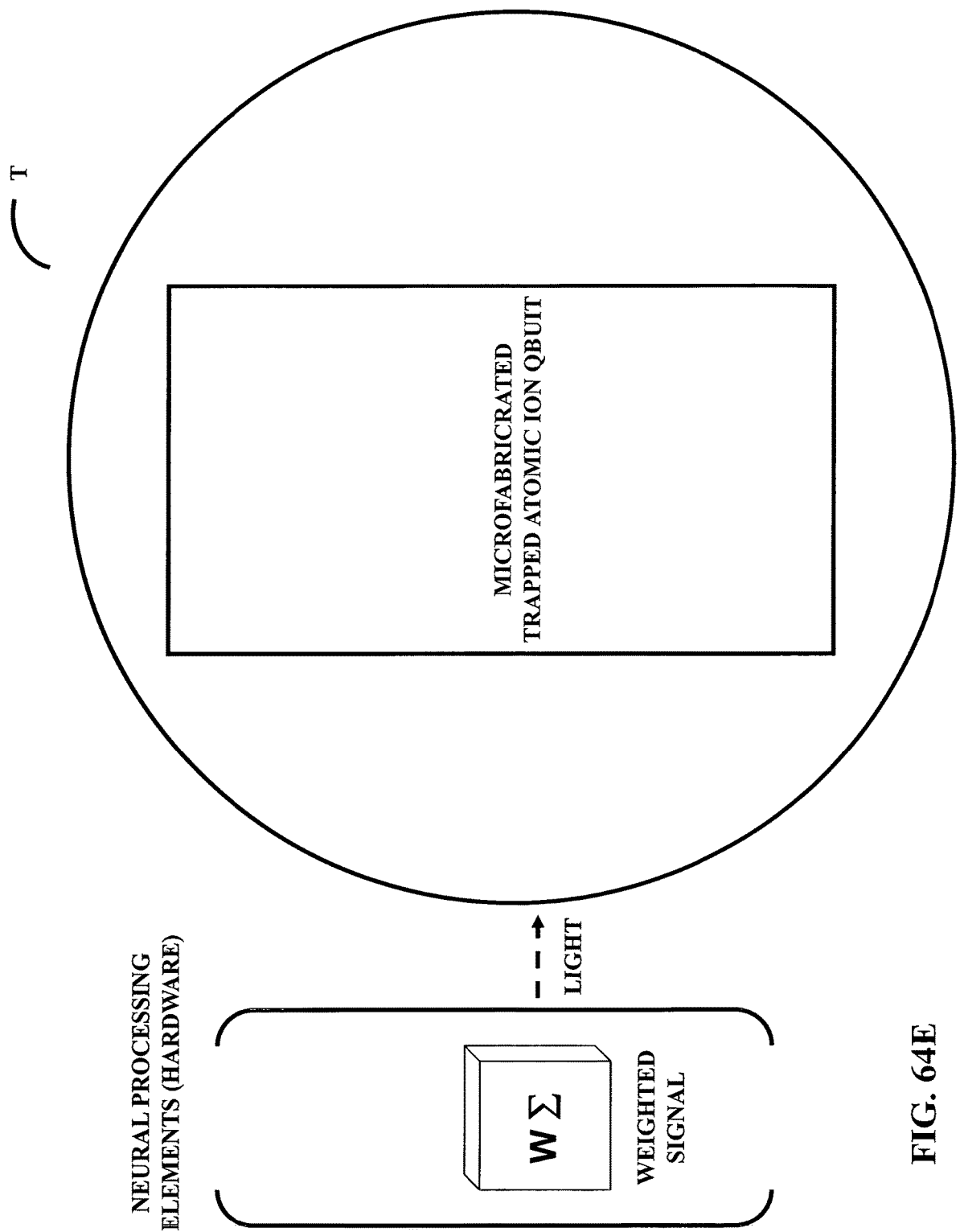

FIG. 64E illustrates another embodiment (identified as T) of optical coupling of a light signal (only activated by weighted electrical/optical signals from neural processing hardware elements) with a qubit based on trapped atomic ion.

Figure 64F:
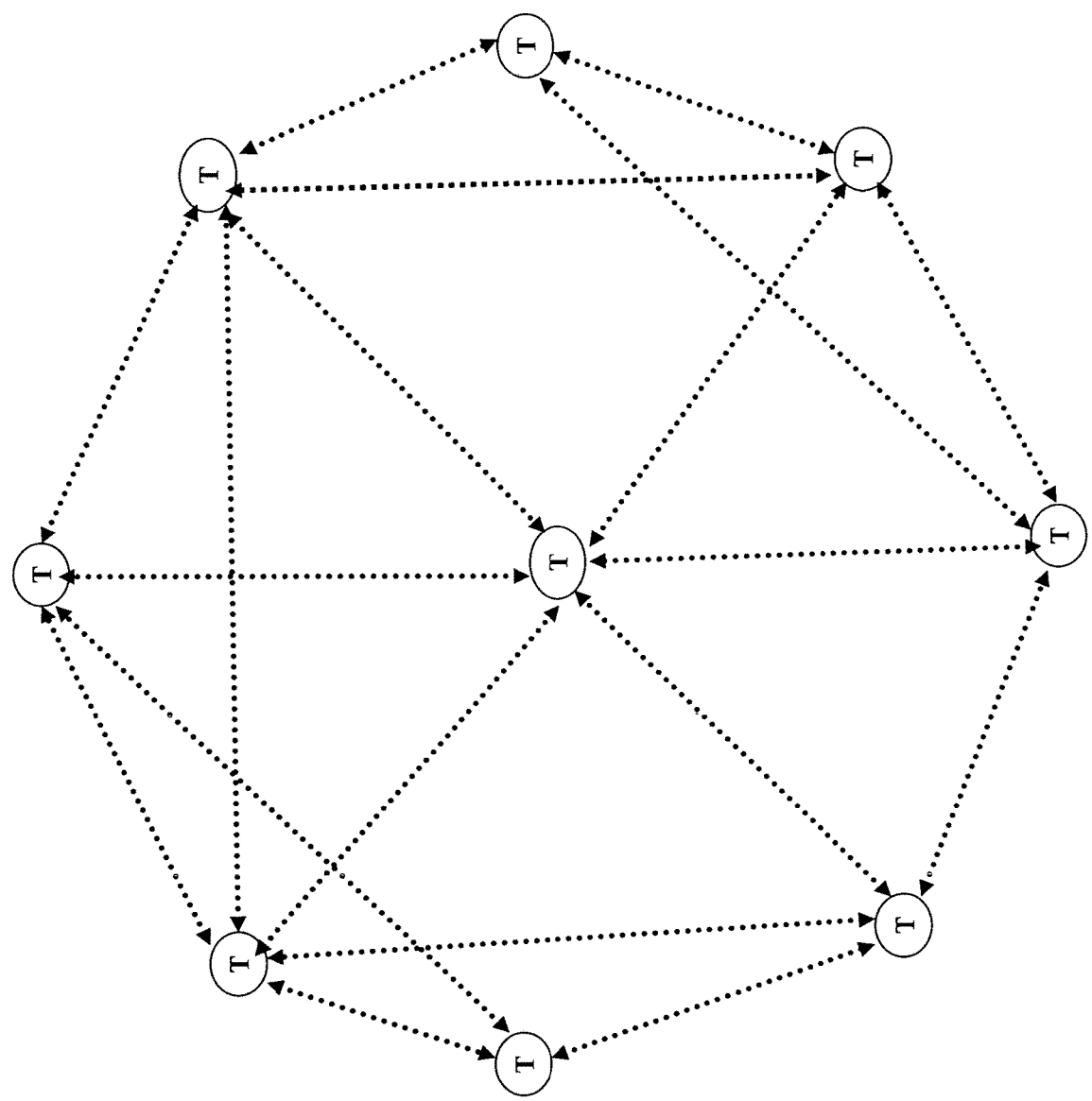

FIG. 64F illustrates a large scale network of the above configuration (in FIG. 64E).

Figure 64G:
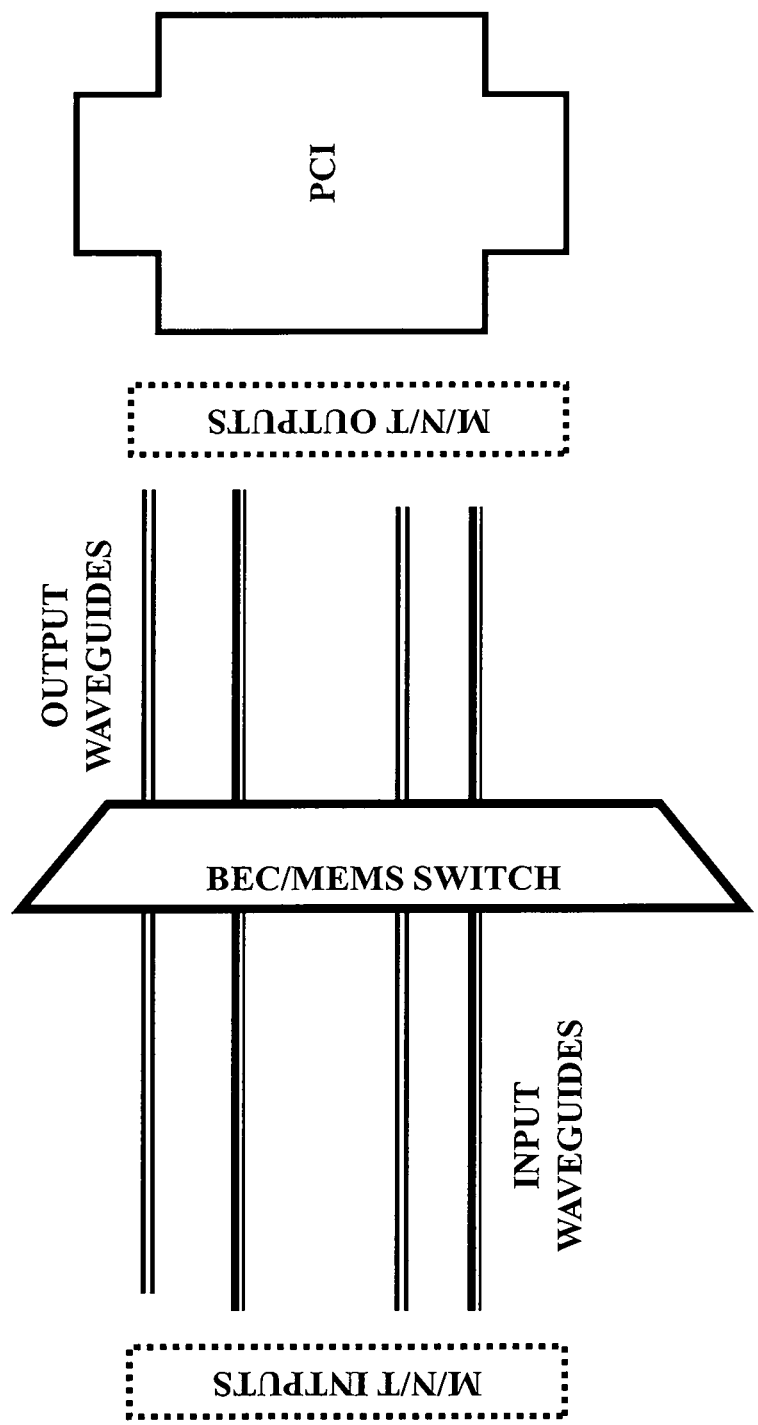

FIG. 64G illustrates integration of above M/N/T with an ultrafast optical switch (e.g., Bose-Einstein condensate (BEC) switch), input waveguides, output waveguides and photon counting imager (PCI).

Figure 65A:
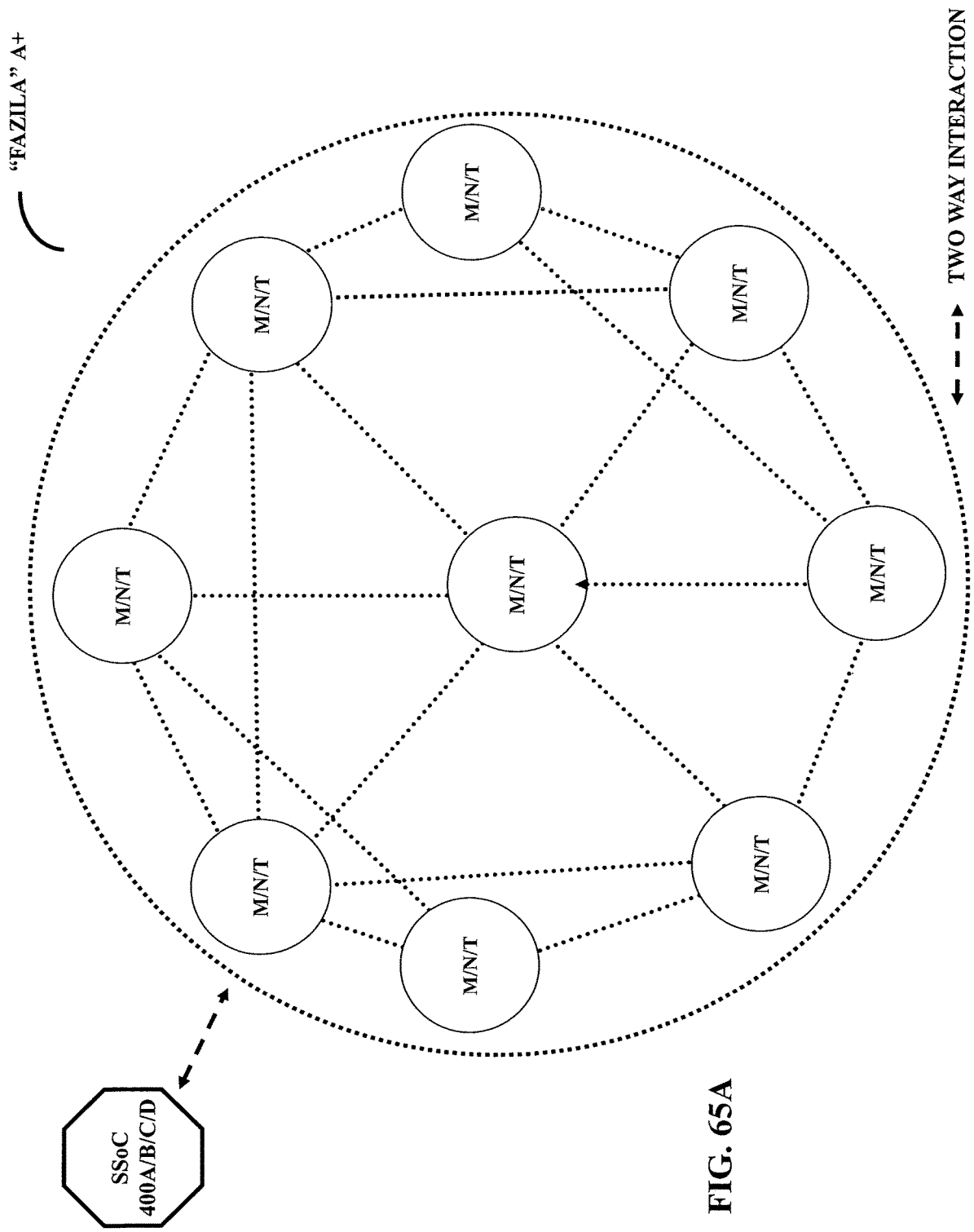

Integration/Coupling of (Above) Coupled Qubits (M/N/T) with Super System on Chip/Photonic Neural Learning Processor FIG. 65A illustrates integration/coupling of the above coupled qubits M/N/T with the Super System on Chip.

Figure 65B:
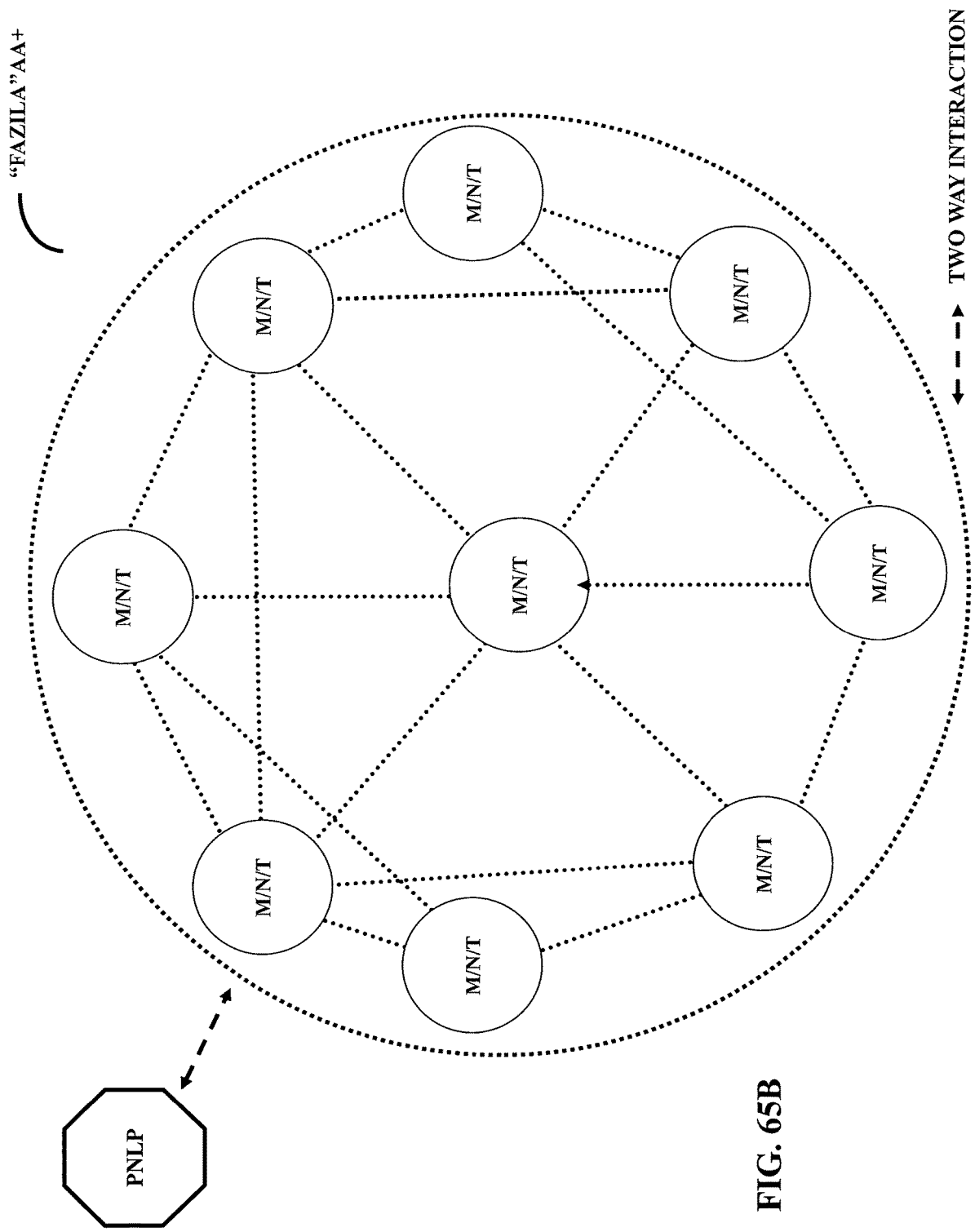

FIG. 65B illustrates integration/coupling of the above coupled qubits M/N/T with a photonic neural learning processor.

Figure 65C:
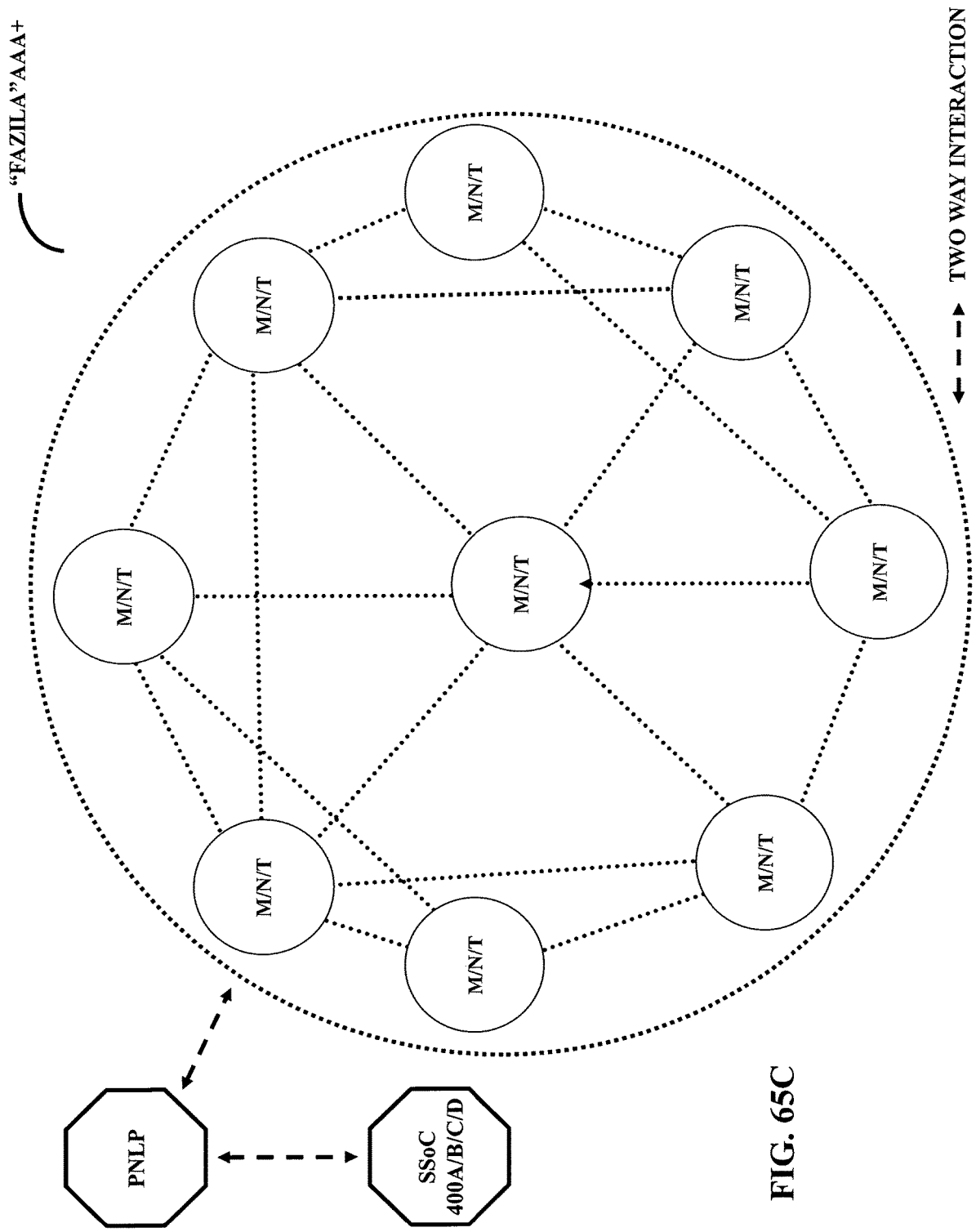

FIG. 65C illustrates integration/coupling of the above coupled qubits M/N/T with a photonic neural learning processor, wherein the photonic neural learning processor is coupled with the Super System on Chip.

DETAILED DESCRIPTION OF THE DRAWINGS

Figure 1A:
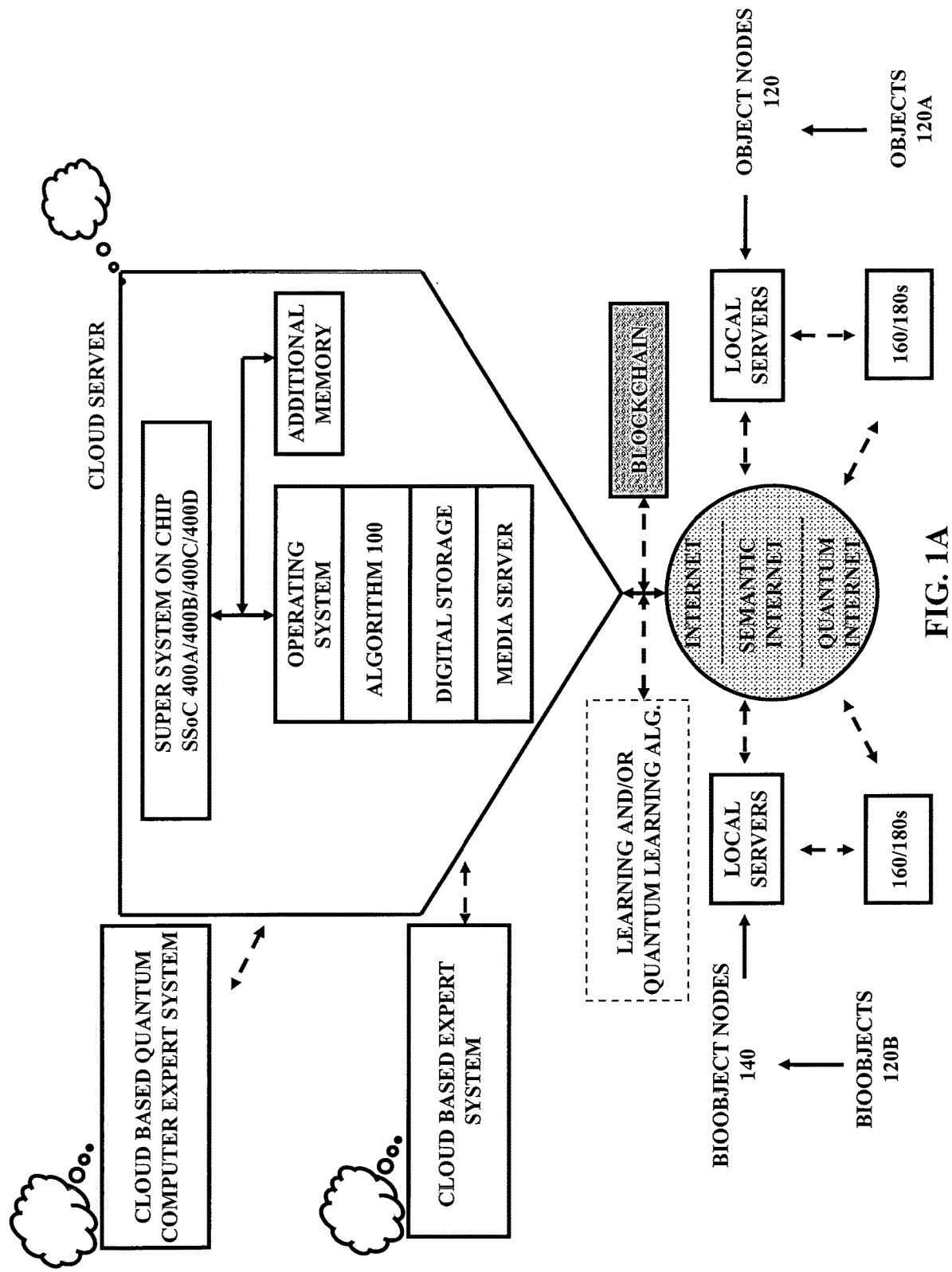
FIG. 1A illustrates an embodiment of interactions/communications among local servers (connecting with objects, object nodes, bioobjects, bioobject nodes, intelligent portable internet appliances and intelligent wearable augmented reality personal assistant devices), an intelligent algorithm in a cloud server, a cloud expert system, a cloud quantum computer expert system and the internet (including a semantic internet and/or a quantum internet).
Intelligent Algorithm

FIG. 1A illustrates interactions of objects 120As, bioobjects 120Bs, object nodes 120s, bioobject nodes 140s, local servers, an intelligent algorithm 100, a cloud expert system, an internet (including a semantic internet and/or a quantum internet), intelligent portable internet appliance 160 and/or intelligent wearable augmented reality personal assistant device 180. An intelligent vehicle can be connected with the objects 120A via the object nodes 120.

Additionally, the internet (including the semantic internet and/or the quantum internet) includes a learning algorithm/quantum learning algorithm. A learning algorithm/quantum learning algorithm (including deep learning/meta-learning and self-learning) combines multiple nonlinear processing layers, using simple elements operating in parallel and inspired by biological nervous systems. It consists of an input layer, several hidden layers and an output layer. The layers are interconnected via neuron like nodes, with each hidden layer using the output of the previous layer as its input.

Biometric Security Implementation (e.g., Fingerprint, Voice Print, Facial Recognition, Iris Scan), Hardware Authentication (e.g., baking authentication into the user's hardware. Downloading an app onto the user's phone and then verifying for the phone's Bluetooth signal to verify the user's computer location with respect to Bluetooth signal) and Data Encryption (e.g., encryption keys with public/private key infrastructure can be Lattice based or Multivariate based or Hash based or Coding based or never repeating pattern and they are generally quantum computing resistant cryptography) can be included with the internet (including the semantic internet and/or the quantum internet).

The internet (including the semantic internet and/or the quantum internet) is coupled with a public/consortium/private blockchain.

A blockchain does not have a single point of failure. Furthermore, with a blockchain technology, data can be stored in a decentralized and distributed manner. Instead of residing at a single location, data can be stored in an open source distributed ledger. In order to make updates to a particular piece of data, the owners of that data must add a new block of the data on top of the previous block of the data, creating a specific chain or sequence of codes. Thus, every single alteration or change to any piece of data is tracked and no data is lost or deleted because participants in blockchain can always look at previous versions of a block to identify what is different in the latest version. This distributed record-keeping can detect blocks that have incorrect or false data, preventing loss, damage and corruption. Thus, it renders mass data hacking or data tampering much more difficult, because all participants in the blockchain (network) can see that the ledger had altered in some way in real time/near real time. Thus, a blockchain can enable security of sensitive information.

With regards to data immutability, it is important to consider how a blockchain can fit side by side with the data privacy laws—the right to be forgotten in a blockchain technology, wherein the blockchain technology guarantees that nothing will be erased is a challenge, but there are at least two (2) solutions. One solution is to encrypt the personal information written in the system to ensure that, when the time comes, forgetting the keys will ensure that sensitive information is no longer accessible. Another solution is to focus on the value of blockchain to provide unalterable evidence by writing the hash of transactions to it, while the transactions themselves can be stored outside of the system. This maintains the integrity of transactions, while enabling the ability to erase the transactions, leaving only traces of forgotten information in the blockchain.

Additionally, a learning algorithm/quantum learning algorithm (including deep learning/meta-learning and self-learning) can be coupled/integrated with a topological data analysis (TDA) or a clustering algorithms to analyze a massive set of data (e.g., Big Data). Topological data analysis is an approach to the analysis of a large volume of data, utilizing techniques from topology (e.g., shape of datasets). Topological data analysis can enable the geometric features of a large volume of data, utilizing topology Extraction of information from a large volume of data that is high-dimensional, incomplete and noisy is generally challenging. But, topological data analysis provides a general framework to analyze a large volume of data in a manner that is insensitive to the particular metric chosen and provides dimensionality reduction and robustness to noise. One of the advantages of topological analysis is low dimensional representation of higher dimensional connectivity.

The internet (including the semantic internet and/or the quantum internet) includes a built-in search engine and personal data storage.

The World Wide Web is made with computers but for people. The websites use natural language, images and page layout to present information in a way that is easy for a user to understand, but the computers themselves really can't make sense of any information and cannot read relationships or make decisions like people can. The semantic internet can help computers read and use the web. Metadata added to web pages can make the existing World Wide Web machine readable, so computers can perform more of the tedious work involved in finding, combining and acting upon information on the web.

The intelligent algorithm 100 is at a cloud server. The cloud server includes a Super System on Chip 400A/400B/400C/400D. The Super System on Chip 400A/400B/400C/400D can comprise one or more digital processors, one or more memristors and one or more memory components. The Super System on Chip 400A/400B/400C/400D can further electrically couple with a digital storage device, additional memory components and a media server and they can be managed by an embedded operating system algorithm. The cloud server can be connected with a cloud expert system and a cloud quantum computer expert system.

Figure 1B:
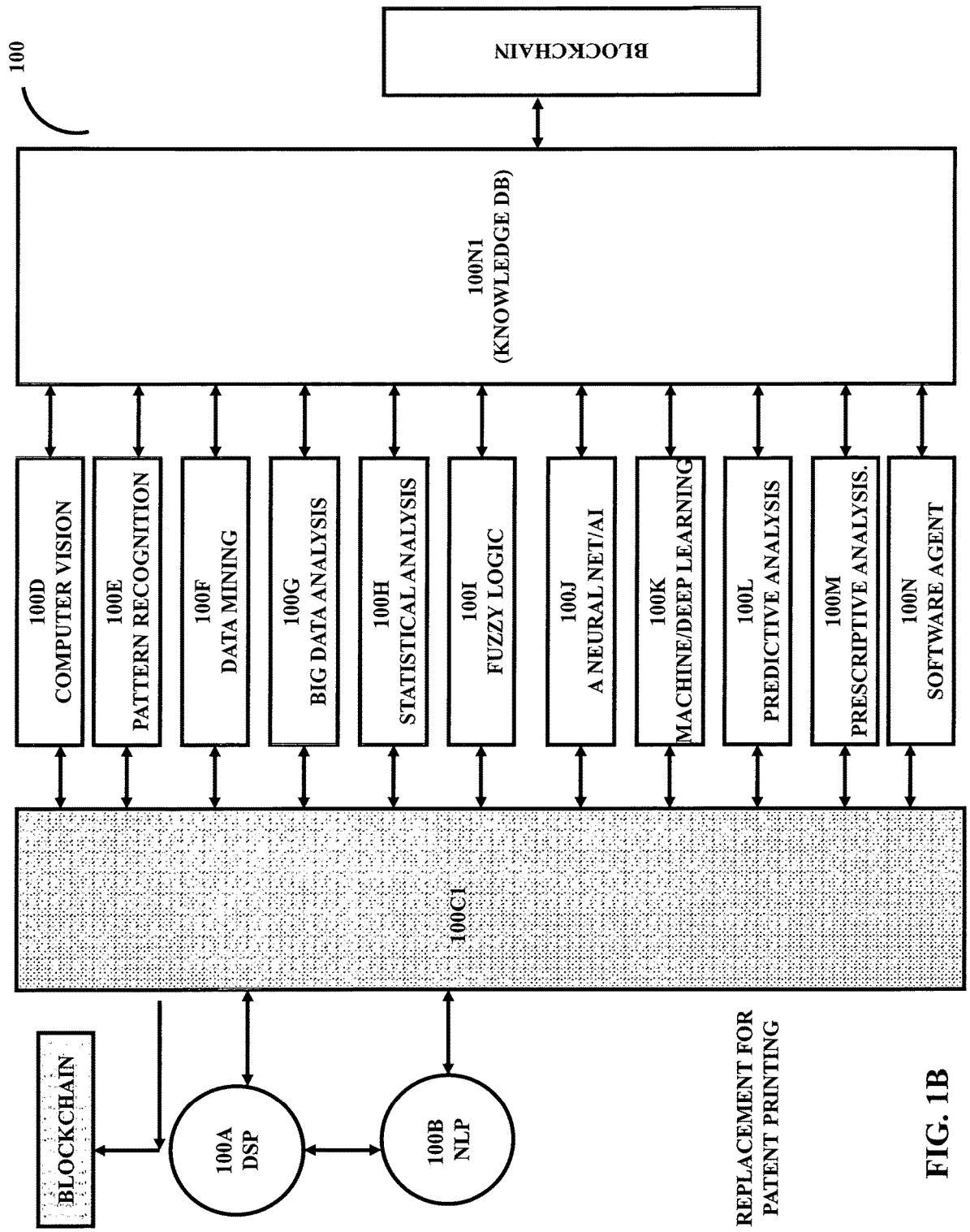
FIG. 1B illustrates an embodiment (in block diagram) of an intelligent algorithm.

FIG. 1B illustrates the intelligent algorithm 100: The intelligent algorithm 100 includes a digital security protection (DSP) algorithm submodule 100A, a natural language processing (NLP) algorithm submodule 100B and an application specific algorithm submodule 100C (the application specific algorithm submodule 100C1 is coupled with a public/consortium/private blockchain). The application specific algorithm submodule 100C1 and a knowledge database 100N1 (the knowledge database 100N1 is coupled with a public/consortium/private blockchain) are coupled with a computer vision algorithm submodule 100D, a pattern recognition algorithm submodule 100E, a data mining algorithm submodule 100F, Big Data analysis algorithm submodule 10G, a statistical analysis algorithm submodule 100H, a fuzzy logic (including neuro-fuzzy) algorithm submodule 100I, an artificial neural network/artificial intelligence algorithm submodule 100J, a machine learning (including deep learning/meta-learning and self-learning) algorithm submodule 100K, a predictive analysis algorithm submodule 100L, a prescriptive algorithm module 100M and a software agent algorithm submodule 100N.

The fusion of a neural network algorithm and fuzzy logic algorithm is neuro-fuzzy, which can enable both learning as well as approximation of uncertainties. The neuro-fuzzy algorithm can use fuzzy inference engine (with fuzzy rules) for modeling uncertainties, which is further enhanced through learning the various situations with a radial basis function. The radial basis function consists of an input layer, a hidden layer and an output layer with an activation function of hidden units. A normalized radial basis function with unequal widths and equal heights can be written as:

$$\psi_i(x)(\text{softmax}) = \frac{\exp(h_i)}{\sum\limits_{i=1}^{n} \exp(h_i)}$$

$$h_i = \left(-\sum_{l=1}^{2} \frac{(X_l - u_{il})^2}{2\sigma_l^2}\right)$$

X is the input vector, uil is the center of the ith hidden node (i=1, . . . , 12) that is associated with the lth (l=1, 2) input vector, σi is a common width of the ith hidden node in the layer and softmax (hi) is the output vector of the ith hidden node. The radial basis activation function is the softmax activation function. First, the input data is used to determine the centers and the widths of the basis functions for each hidden node. Second, it is a procedure to find the output layer weights that minimize a quadratic error between predicted values and target values. Mean square error can be defined as:

$$MSE = \frac{1}{N}\sum_{k=1}^{N}((TE)_k^{exp} - (TE)_k^{cal})^2$$

The connections between various algorithm submodules of the intelligent algorithm 100 can be similar to synaptic networks to enable deep learning/meta-learning and self-learning of the intelligent algorithm 100.

Meta-learning can enable a machine some human-level mental agility. It may be useful for achieving machine intelligence at human-level.

Details of the digital security protection have been described/disclosed in U.S. non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

Fuzzy means not clear (blurred). A fuzzy logic is a form of approximate reasoning, that can represent variation or imprecision in logic by making use of natural language (NL) in logic. The key idea of the fuzzy logic rule is that it uses a simple/easy way to secure the output(s) from the input(s), wherein the outputs can be related to the inputs by if-statements.

Fuzzy set theory is a generalization of the ordinary set theory. A fuzzy set is a set whose elements belong to the set with some degree of membership p. Let X be a collection of objects. It is called universe of discourse. A fuzzy set A∈X is characterized by membership function μA(x), which represents the degree of membership, degree of membership maps each element between 0 and 1. It is defined as: A={(x, $\mu_A(x)$)); x∈X}.

Figure 1C:
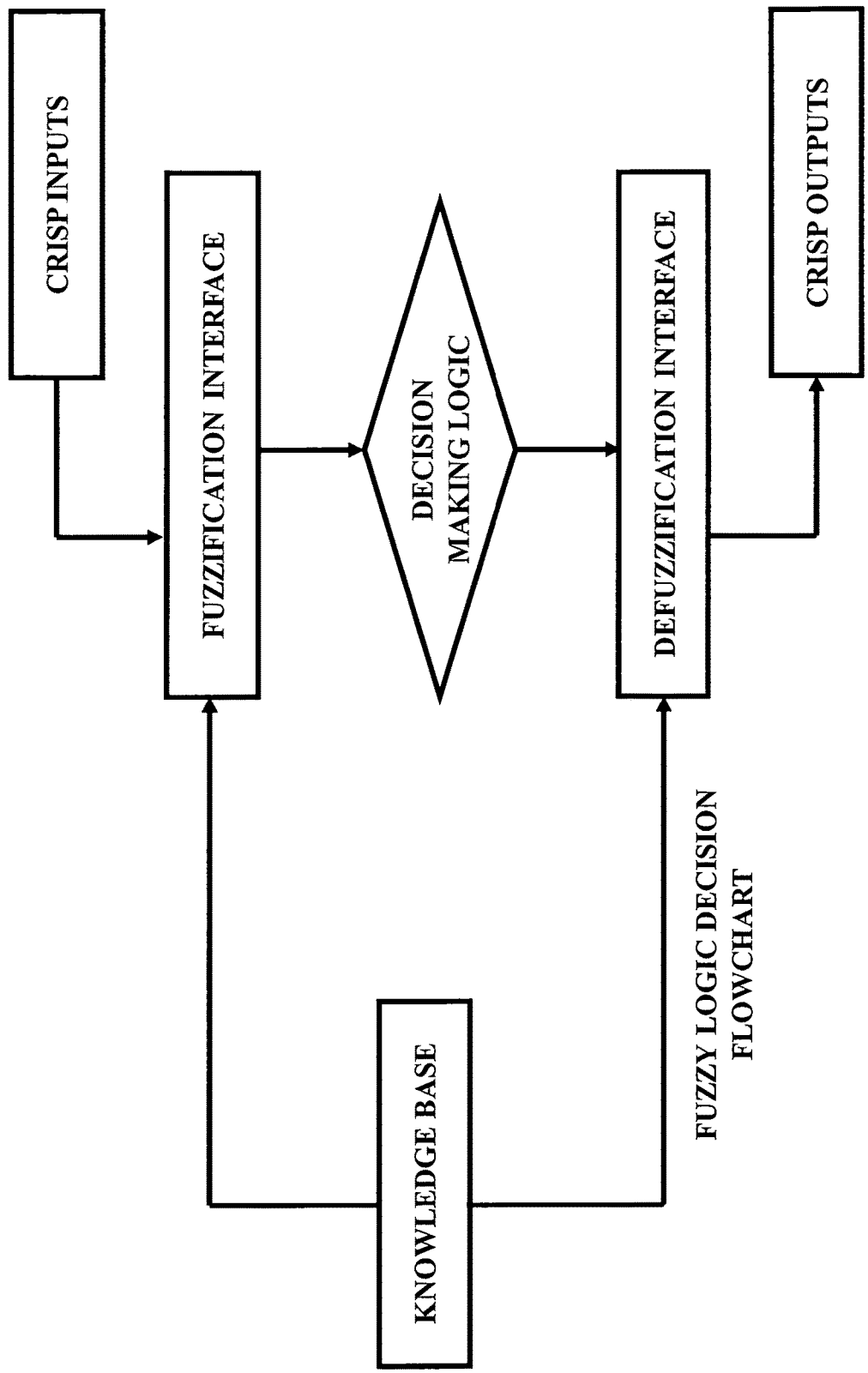
FIG. 1C illustrates an embodiment (in block diagram) of a fuzzy logic rule of the intelligent algorithm.

In FIG. 1C, crisp inputs are fed into a fuzzification interface. The fuzzification interface algorithm submodule is coupled with (a) a knowledge base and (b) a decision-making logic algorithm submodule. The decision-making logic algorithm submodule is coupled with a defuzzification interface algorithm submodule. The defuzzification interface algorithm submodule is coupled with a fuzzy logic decision flow chart. The defuzzification interface algorithm submodule creates crisp outputs.

Figure 1D:
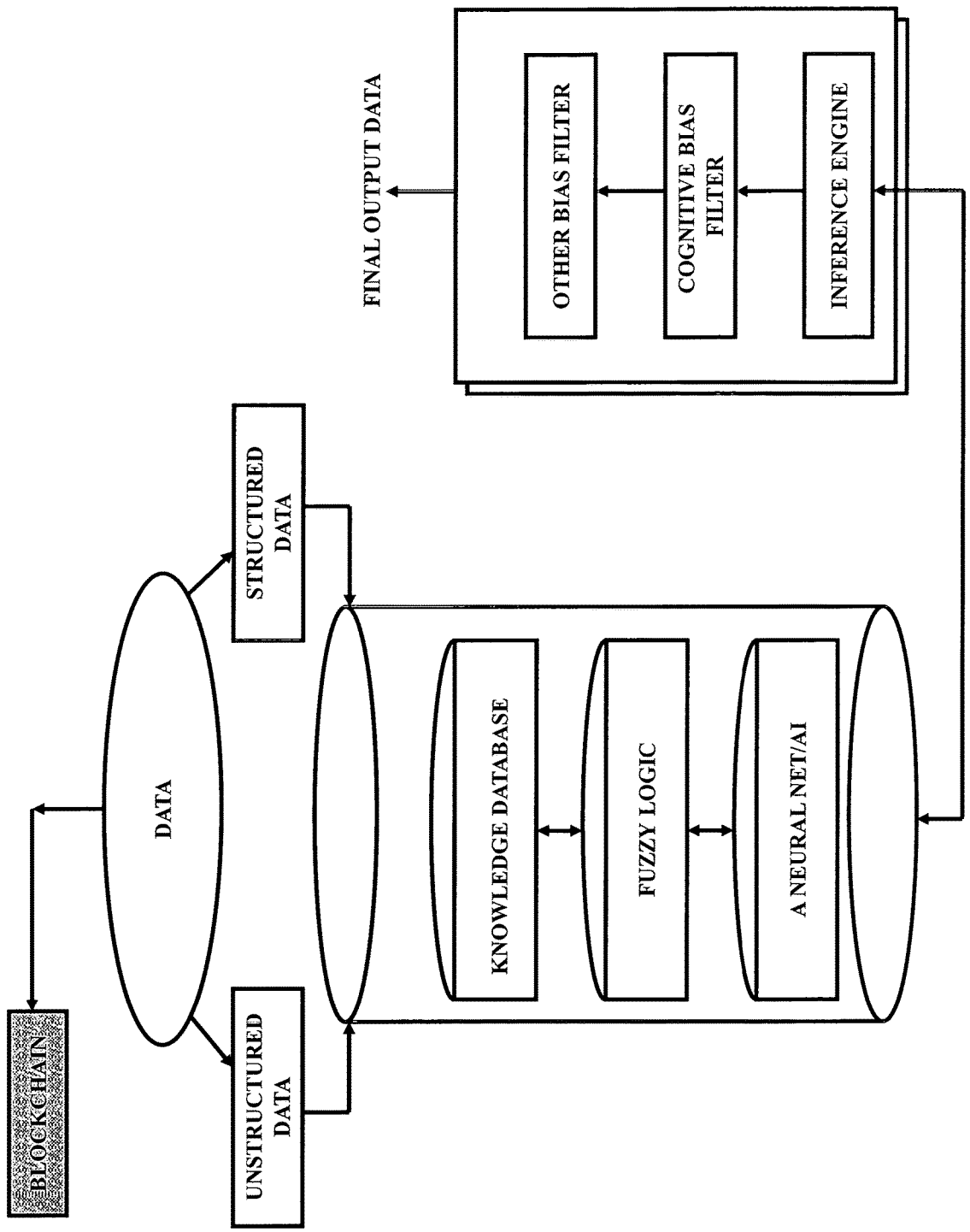
FIG. 1D illustrates an embodiment (in block diagram) of a knowledge extraction rule of the intelligent algorithm.

FIG. 1D illustrates a knowledge extraction rule of the algorithm 100. Both the structured inputs and unstructured inputs are coupled with a public/consortium/private blockchain. Both the structured inputs and unstructured inputs are configured through (a) a knowledge database submodule, (b) a fuzzy logic (including neuro-fuzzy) algorithm submodule, (c) an artificial neural network/artificial intelligent algorithm submodule, (d) an inference engine algorithm submodule, (e) a cognitive bias filter submodule and (f) finally other bias filter submodules to create an output data.

Figure 1E:
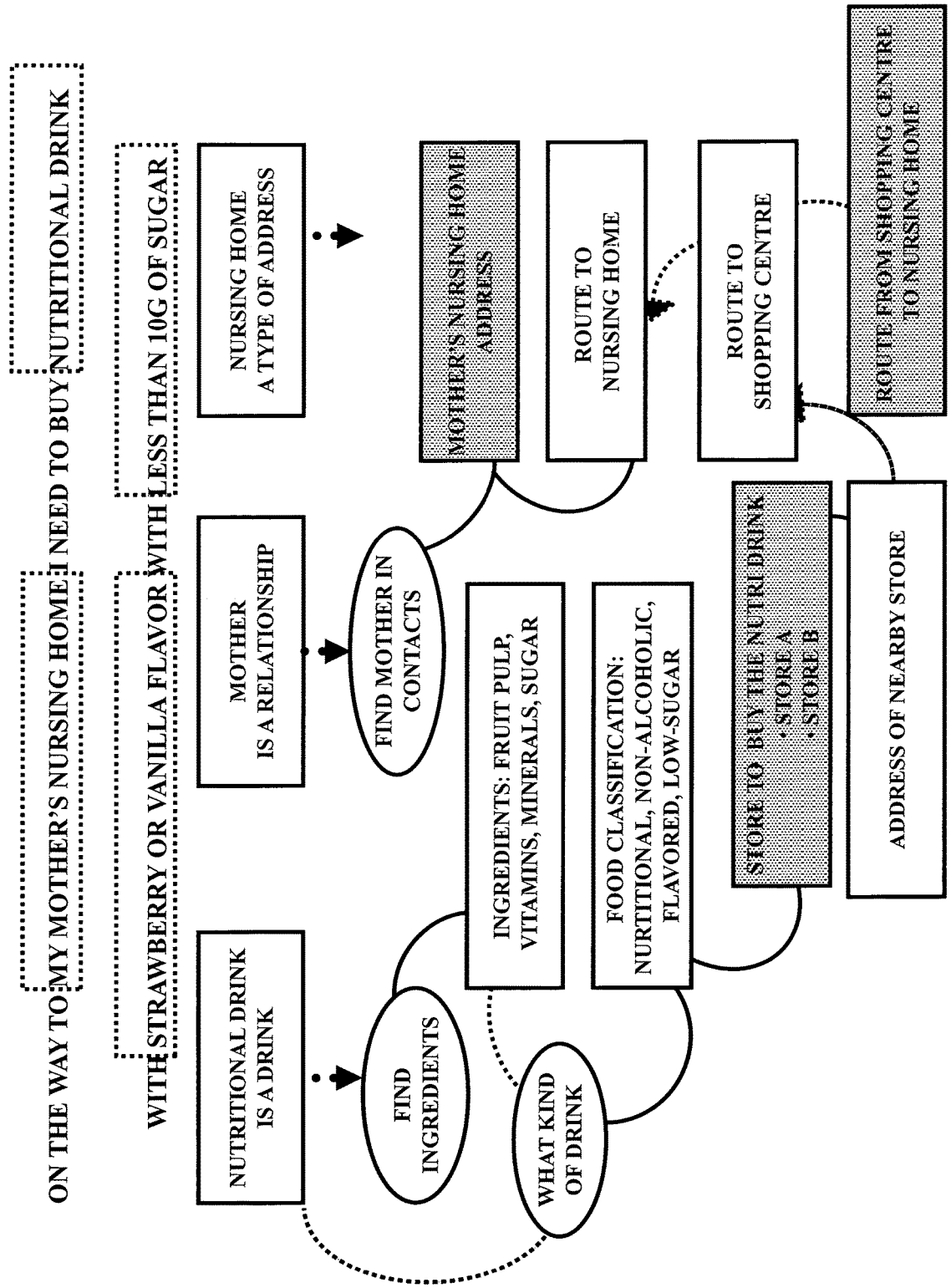
FIG. 1E illustrates an example application of the intelligent algorithm.
Object (Sensor) Enabled Social Commerce

FIG. 1E illustrates an example application of the intelligent algorithm 100. A user has to bring a low sugar nutritional drink of either strawberry or vanilla to the user mother's nursing home. The intelligent algorithm 100 understands by breaking down the natural language commands into relationship based elements and executing each element such as (a) who is the mother of a user? (b) where is the user mother's nursing home? (c) what is a low sugar nutritional drink? (d) what is a flavor? (e) what is a strawberry flavor? (f) what is a vanilla flavor? (g) where is a suitable store to buy such a low sugar strawberry or vanilla flavored nutritional drink? (e) how to drive to the user mother's nursing home from such a suitable store, after purchasing the low sugar strawberry or vanilla flavored nutritional drink?

The intelligent algorithm 100 can then recommend an actionable solution(s) to the user.

In another application, the intelligent portable internet appliance 160 and/or intelligent wearable augmented reality personal assistant device 180 can contain rich data of the user's activities, including who the user knows (phone/social networking contact lists), who the user talks to (logs of phone calls, texts and e-mails), where the user goes (global positioning system data, Wi-Fi logs, geotagged/bokodes tagged photos) and what the user does (indoor position system, apps he/she uses, payment he/she makes and accelerometer data). Utilizing the above rich data with the intelligent algorithm 100, personal predictive analytics (social graph) of the user can be built.

Bokodes are tiny barcodes which can encode binary data, the view angle and the distance of a viewer from a thing. A camera positioned up to four meters away can capture and decode all information. Bokodes can give a robust estimate of geotagged photos.

Figure 2A:
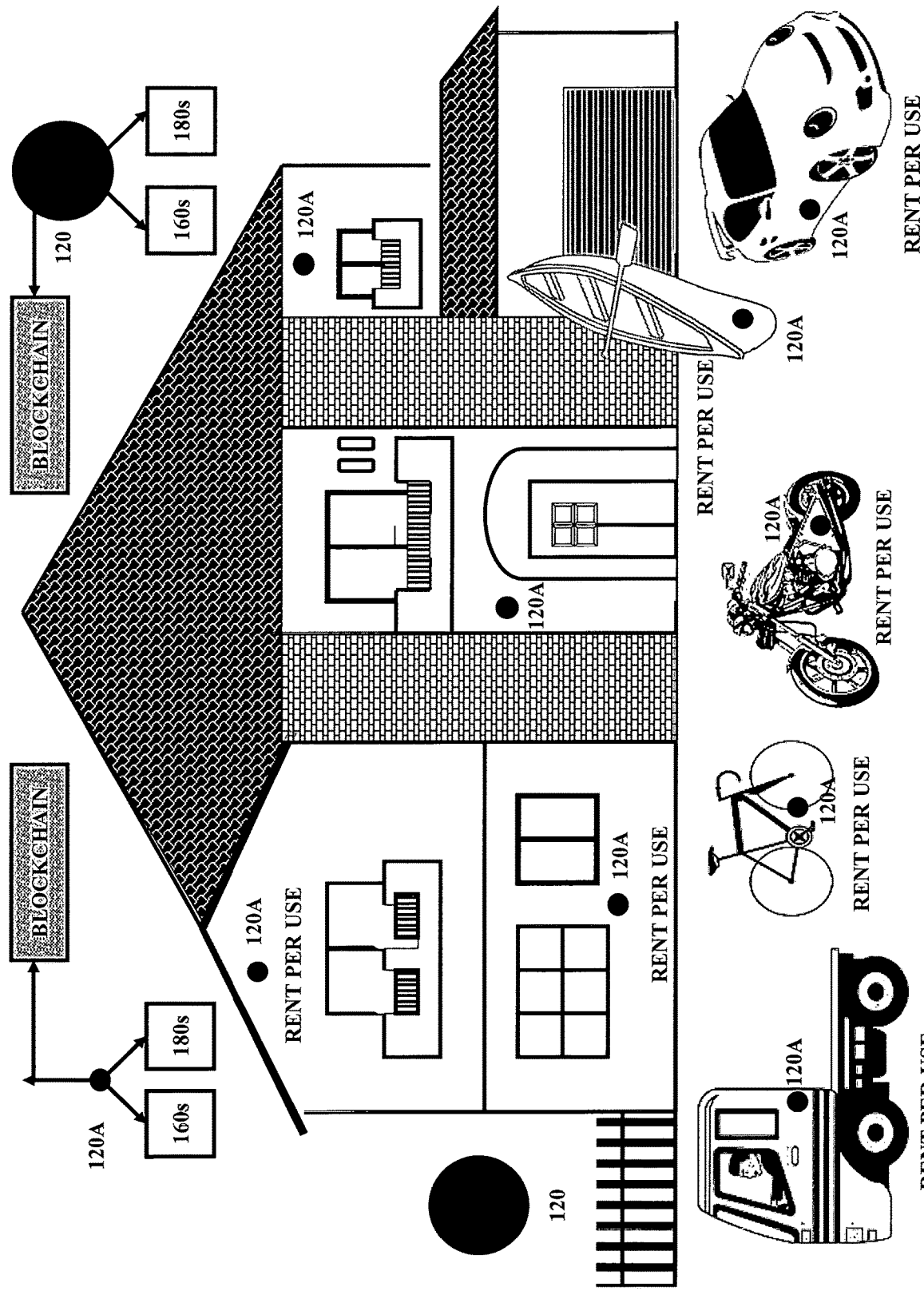
FIG. 2A illustrates an embodiment of object(s) enabled peer-to-peer social commerce.

FIG. 2A illustrates peer-to-peer social commerce, enabled by the application algorithm submodule 100C, objects 120As and object nodes 120s. The objects 120As and object nodes 120s are coupled with a public/consortium/private blockchain.

Figure 2B:
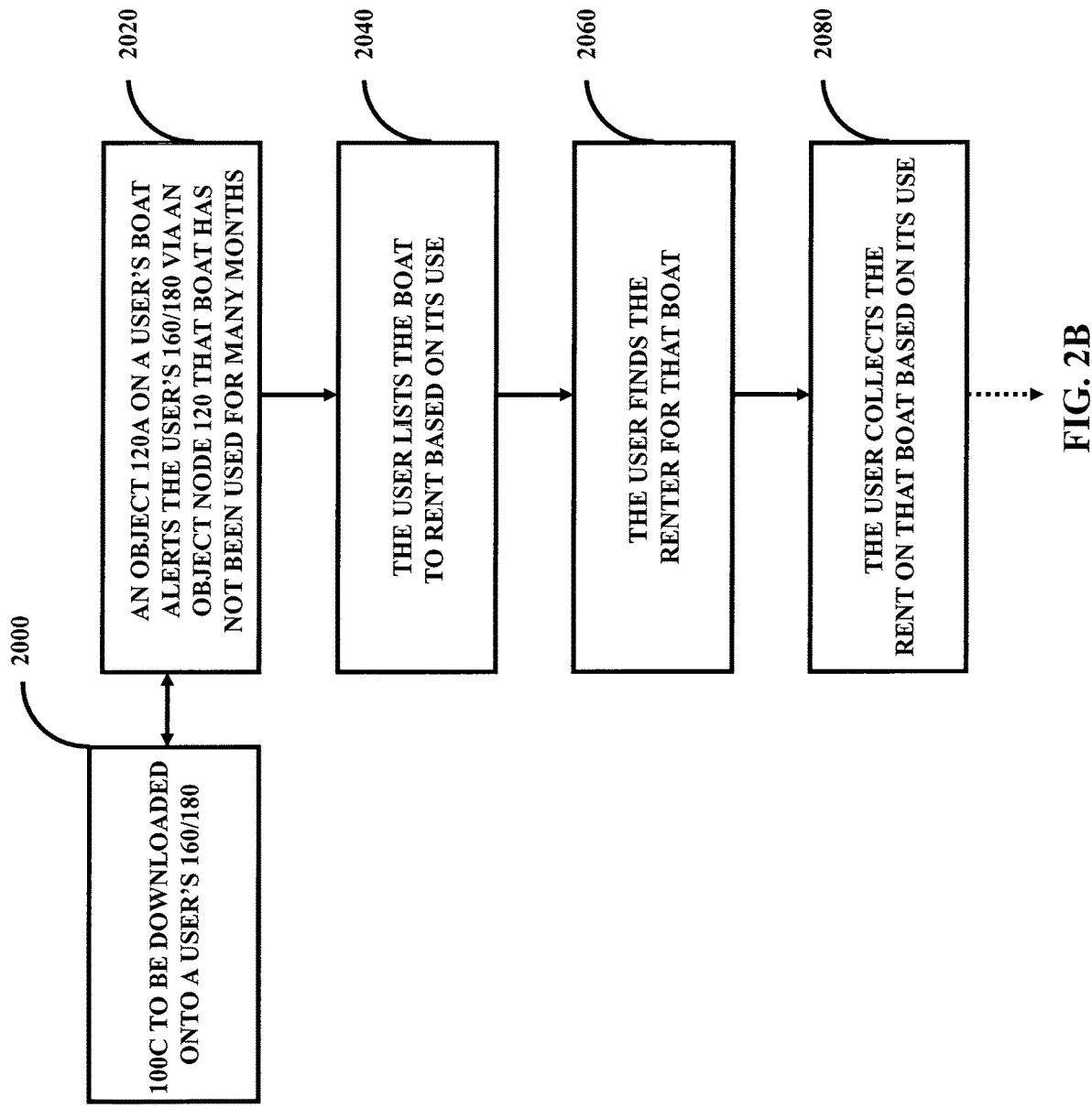
FIGS. 2B-2C illustrate an embodiment of methods of peer-to-peer social commerce, enabled by the objects, object nodes, intelligent algorithms, intelligent portable internet appliances and/or intelligent wearable augmented reality personal assistant devices.
Intelligent Vehicle

In FIG. 2B, in step 2000, the application algorithm submodule 100C can be downloaded onto the intelligent portable internet appliance 160 and/or intelligent wearable augmented reality personal assistant device 180. In step 2020, an object 120A alerts the intelligent portable internet appliance 160 and/or intelligent wearable augmented reality personal assistant device 180 of the user via the object node 120 that the user's boat has not been used for many months. In step 2040, the user lists that unused boat for rent based on its use, utilizing the application algorithm submodule 100C. In step 2060, the user finds a renter for that unused boat, utilizing the application algorithm submodule 100G. In step 2080, the user collects the rent on that unused boat based on its use.

Figure 2C:
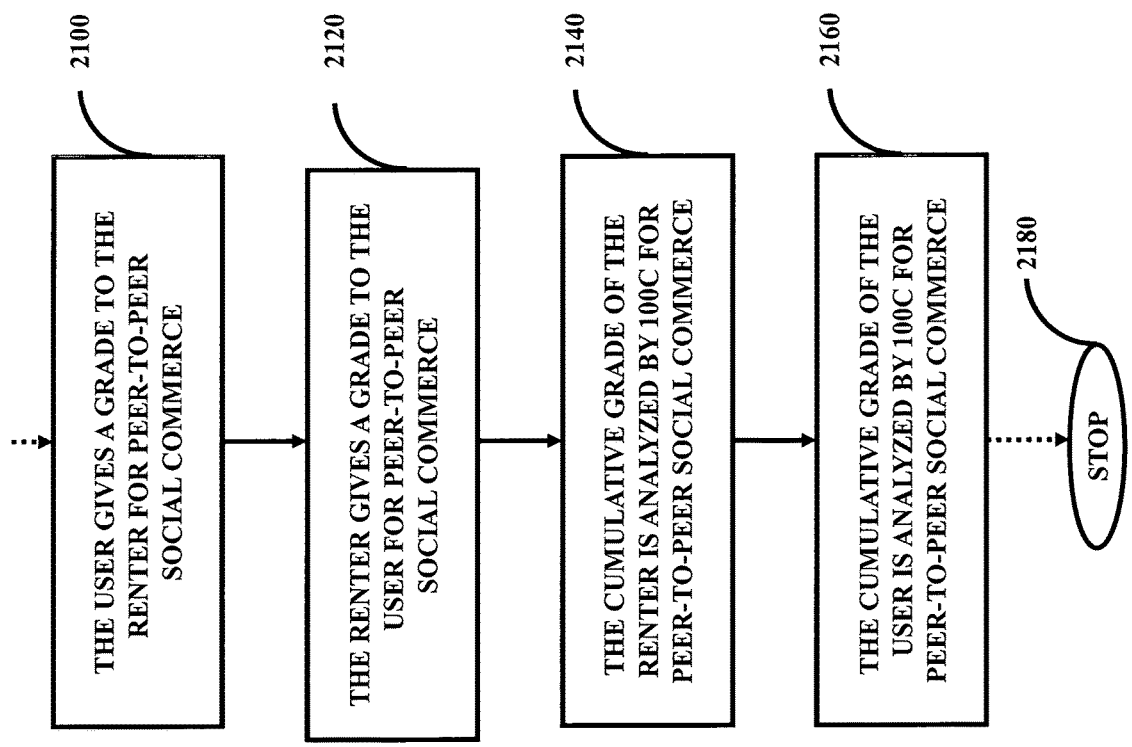

In FIG. 2C, continuing in step 2100, the user gives grades to the renter for peer-to-peer social commerce. In step 2120, the renter gives grades to the user (boat owner) for peer-to-peer social commerce. In step 2140, the cumulative grade of the renter is analyzed for future peer-to-peer social commerce. In step 2160, the cumulative grade of the user (boat owner) is analyzed for future peer-to-peer social commerce. Step 2180 denotes stop.

Figure 3A:
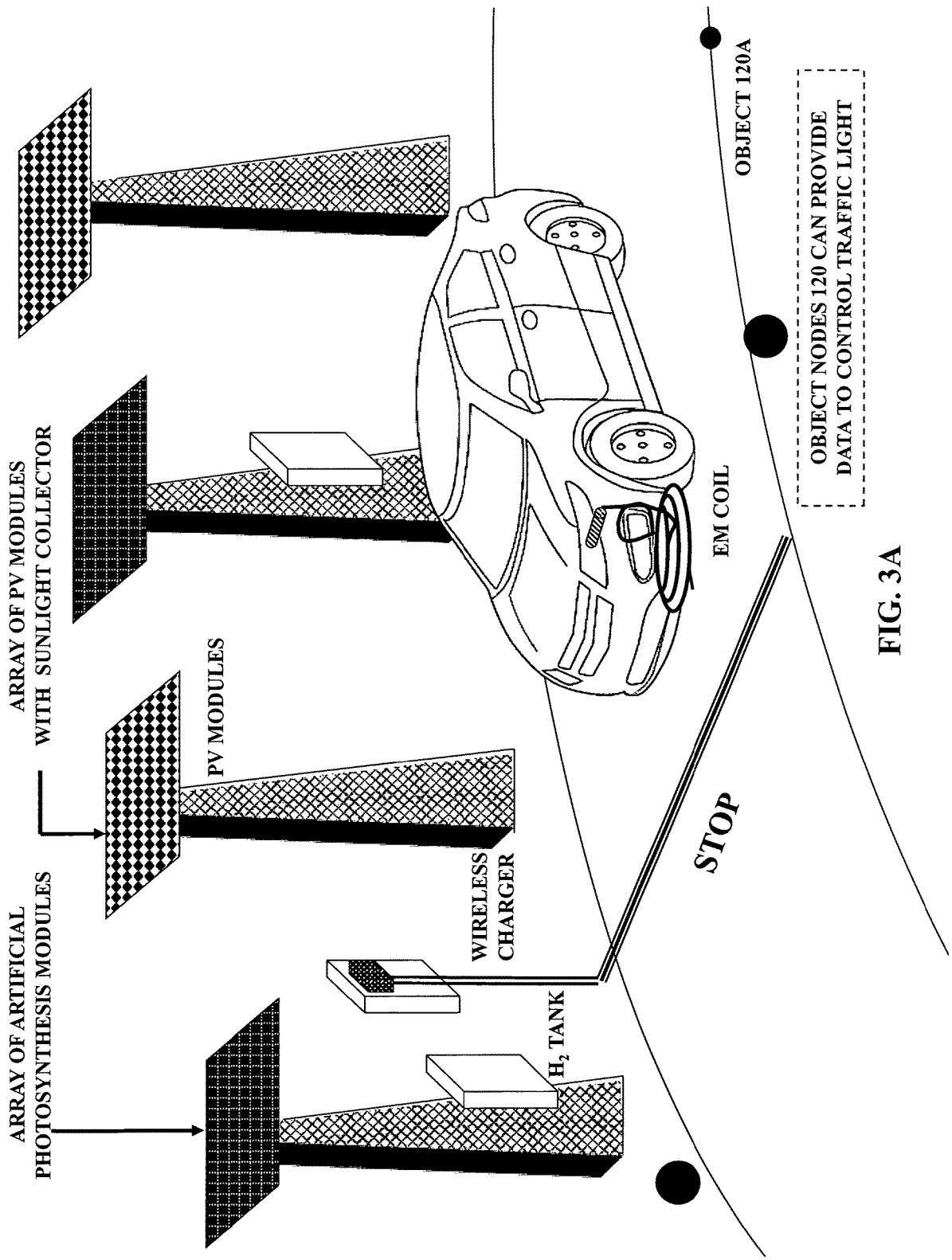
FIG. 3A illustrates an embodiment of a roadway with objects, object nodes photovoltaic modules and artificial photosynthesis modules to enable electromagnetic (wireless) charging to an intelligent vehicle.

FIG. 3A illustrates electromagnetically (wirelessly) charging of an intelligent vehicle. The intelligent vehicle's battery/ultracapacitor (e.g., an ultracapacitor can be based on hydrophilic polymer or nanostructured (e.g., carbon nanotubes/grapheme nanotubes) or nano-textured electrodes) can electromagnetically (wirelessly) charge from underneath the roadway. The intelligent vehicle is capable of interacting/communicating with the object nodes 120 on the roadway, wherein the object nodes 120, for example, can provide data (input) to control a traffic light. FIG. 3A also illustrates a roadway, wherein at least one side of the roadway can be fabricated/constructed with photovoltaic modules and/or artificial photosynthesis modules to provide electromagnetic (wireless) charging and hydrogen to the intelligent vehicle.

Figure 3B:
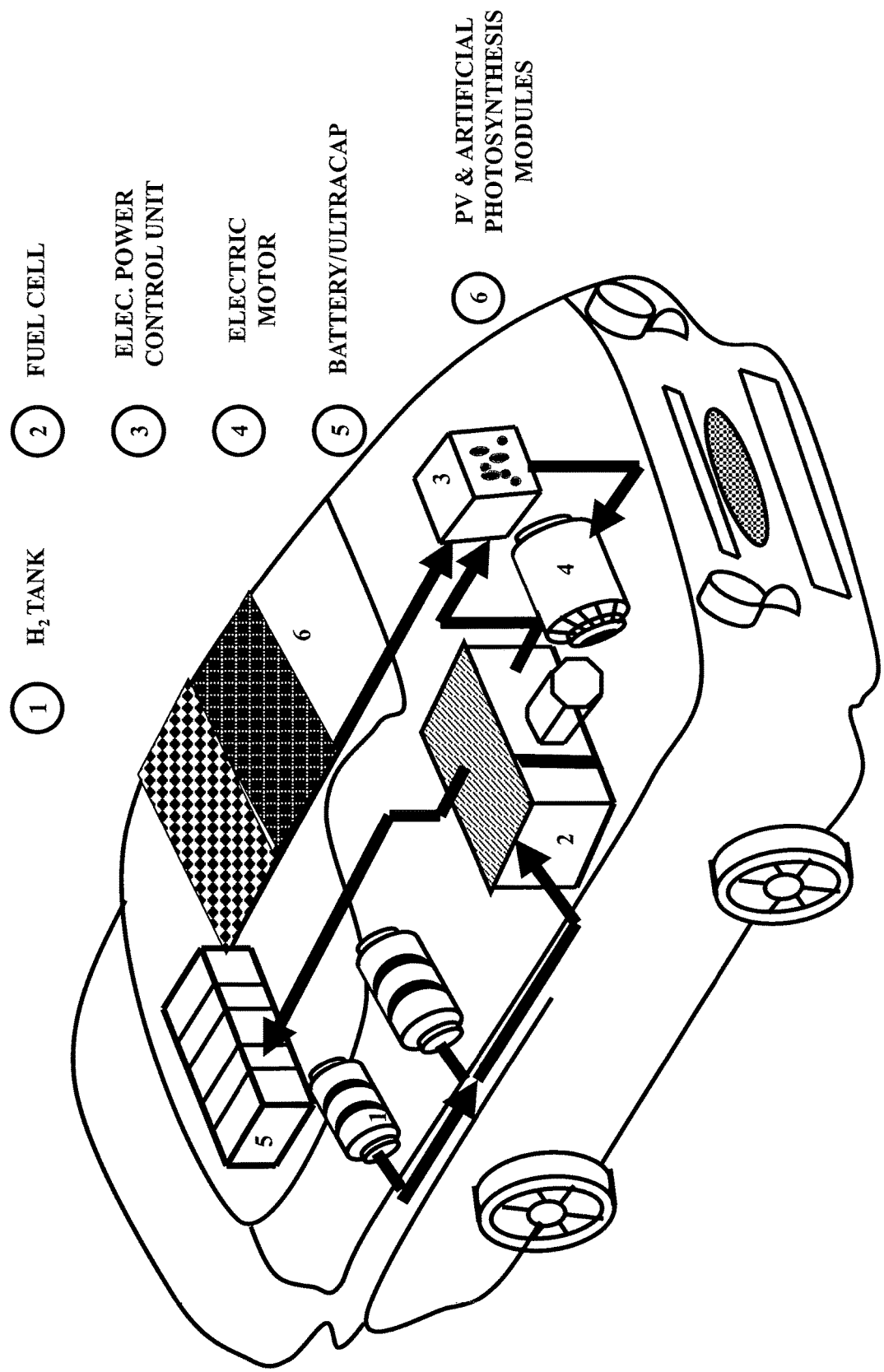
FIG. 3B illustrates an embodiment of the intelligent vehicle.

FIG. 3B illustrates the intelligent vehicle, which can comprise principal subsystems such as: high efficiency photovoltaic modules, artificial photosynthesis modules, an ultracapacitor/battery and a hydrogen fuel cell. Furthermore, the intelligent vehicle can be fabricated/constructed, utilizing graphene/graphene-like material with carbon-fiber reinforced epoxy resin, as the intelligent vehicle body's material and a curved display device. Additionally, graphene/graphene-like material in the intelligent vehicle's body can be integrated with one or more ultracapacitors.

An ultracapacitor fabricated/constructed out of carbon (or graphene/graphene-like material or a mixture of graphene/graphene-like material and carbon nanotube or carbon nanorods) can be coated onto conductive plates, wherein the conductive plates are immersed in an electrolyte solution.

Furthermore, an ultracapacitor can include a surface active ionic liquid (SAIL). It should be noted that an ultracapacitor is a supercapacitor.

Figure 3C:
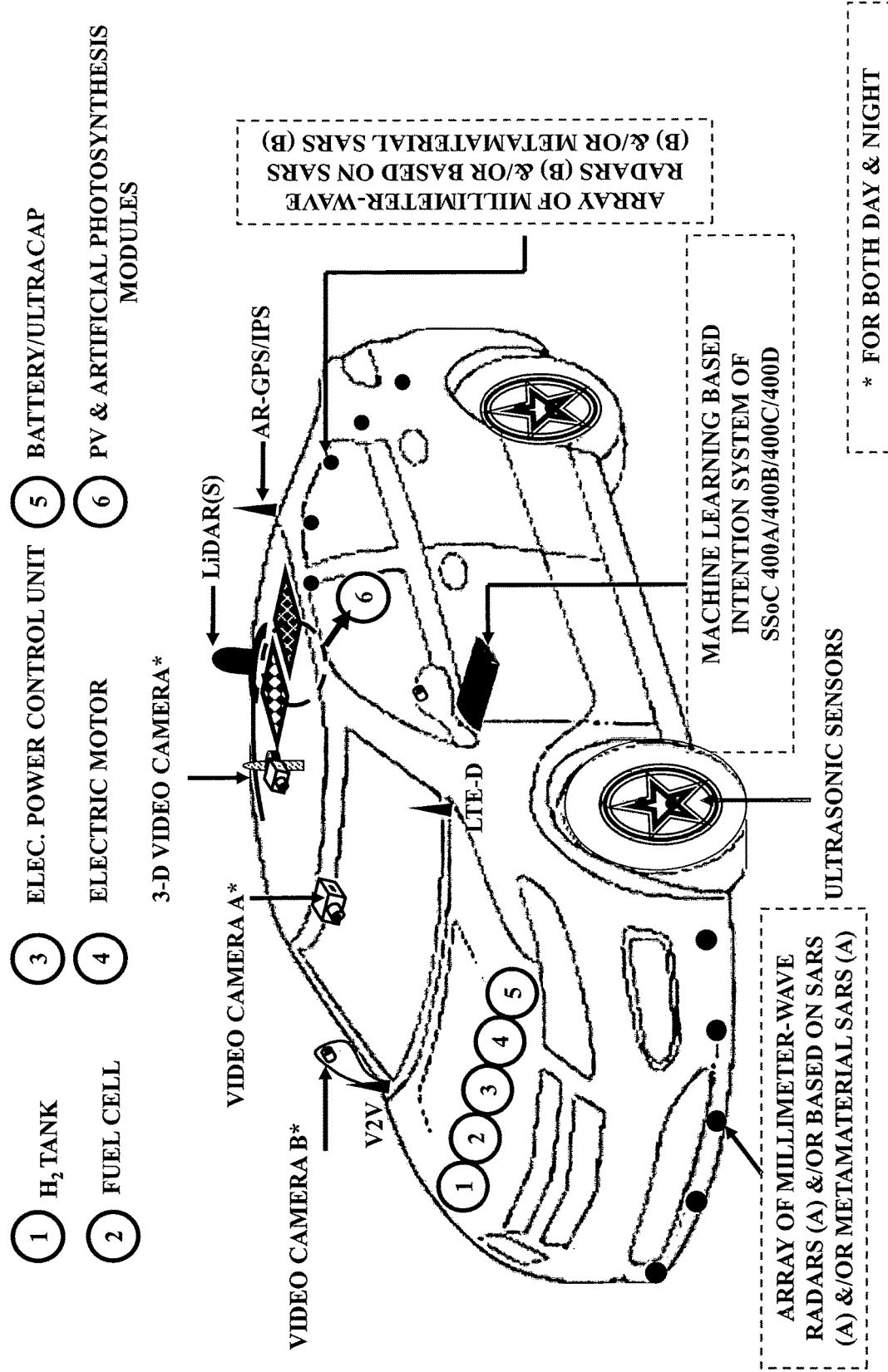
FIG. 3C illustrates an embodiment of key components/ subsystems of the intelligent vehicle.

FIG. 3C illustrates the intelligent vehicle, which is configured with a machine learning (including deep learning/meta-learning and self-learning) algorithm based near real time/real time intention system of the Super System on Chip 400A/400B/400C/400D.

The intelligent vehicle includes high efficiency photovoltaic modules, artificial photosynthesis modules, a battery/ultracapacitor, a hydrogen fuel cell, an array of millimeter-wave radars, a light detection and ranging subsystems (e.g., frequency modulated continuous wave (or quasi-continuous of about microsecond pulse duration) optical phased array), a LTE-Direct radio, vehicle to vehicle (V2V) communication, an augmented reality enhanced global positioning system (AR-GPS), an augmented reality enhanced indoor positioning system (AR-IPS), video cameras (for day and night), a three-dimensional orientation video camera (for day and night), ultrasonic sensors and other sensors (e.g., anti-lock braking systems, anti-collision sensor system, passenger air bags and real time fuel consumption sensor). Additionally, the communication network of the intelligent vehicle can be coupled with a large scale network of memristors (or memory resistors, wherein each memory resistor switch can remember its state of resistance based on its history of applied voltage and/or current).

The outputs of a large scale network of memristors extremely difficult to predict based on various inputs-making it secure from external cyber cloning/hacking. Additionally, the array of camera pixels of the video camera or the three-dimensional orientation video camera can be coupled with an array of photovoltaic (PV) cells and/or an array of display pixels.

The light detection and ranging technology subsystem can be coupled or integrated with the millimeter-wave chipset to communicate at a speed higher than 5G.

The light detection and ranging technology subsystem generally does not work well in harsh weather conditions—such as rain/fog/snow. But, the millimeter-wave radar (e.g., about 75 to 110 GHz range) utilizing silicon-germanium (SiGe) or radio frequency complementary metal oxide semiconductor (RF-CMOS) process technology may be relatively unaffected by any weather condition (including harsh weather conditions—such as rain/fog/snow).

Furthermore, one or more 79-140 GHz high resolution (based on Synthetic Aperture Radar's principle) radars can also be utilized. The range of each high resolution radar can be enhanced by multiple inputs-single output (MISO) sensors or multiple inputs-multiple outputs (MIMO) sensors arranged in a circular manner or frequency modulated continuous wave signal, wherein the frequency modulated continuous wave signal is coupled with a large array of antennas. Furthermore, 79-140 GHz high resolution radar can be either analog or digital and capable of beamforming and beam steering.

Metamaterials can be fabricated/constructed with an artificial periodic structure. It is the configurations of these periodic structures that result in unnatural material characteristics, including the modification of a material's electrical permittivity (s) and magnetic permeability (p). By designing the configuration of the periodic structures, the dispersion, refraction and reflection of an electromagnetic wave can be controlled.

Figure 3D:
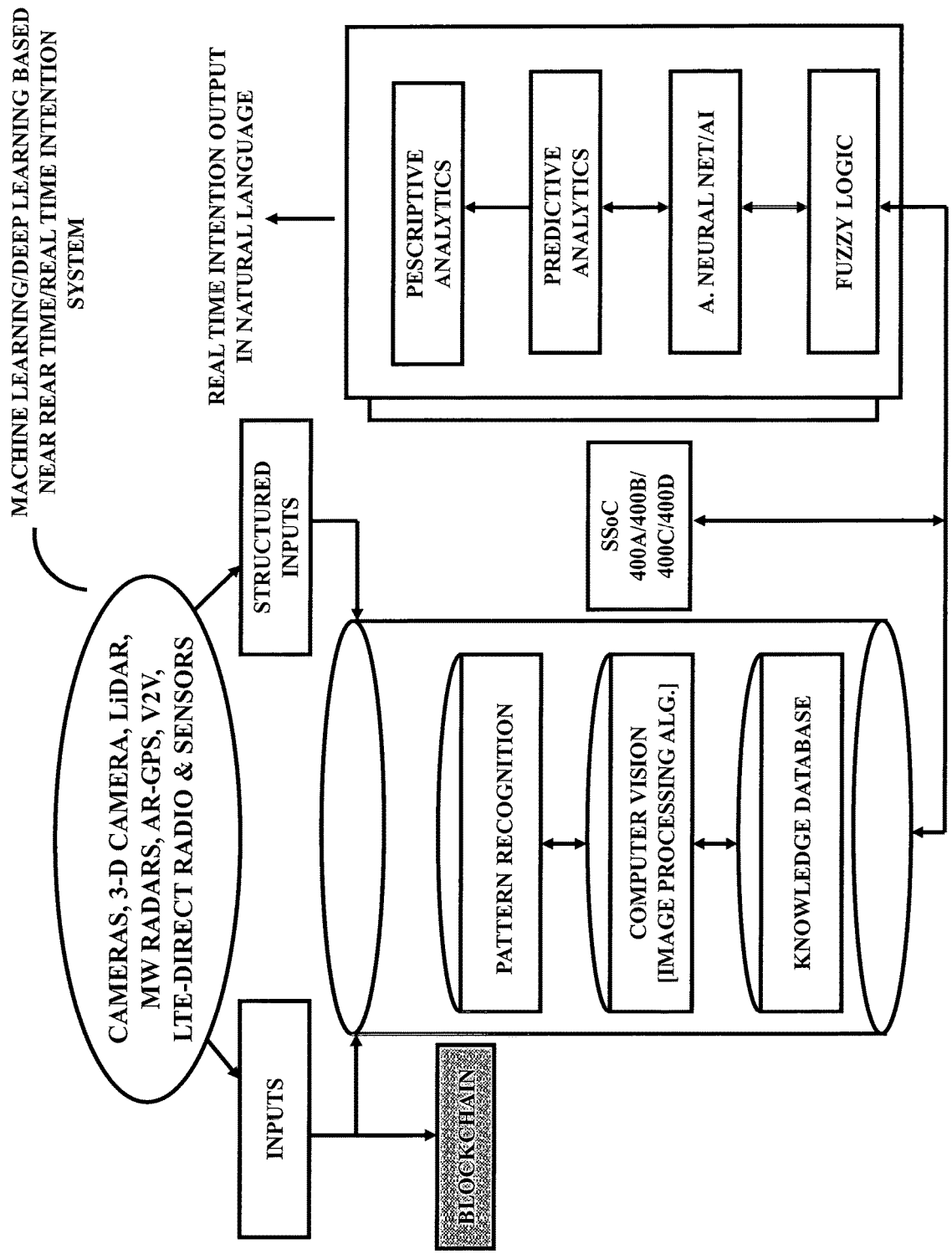
FIG. 3D illustrates an embodiment of a machine learning (including deep learning/meta-learning and self-learning) algorithm based intention system (coupled with a public/consortium/private blockchain—a distributed ledger) of the intelligent vehicle.
Figure 3E:
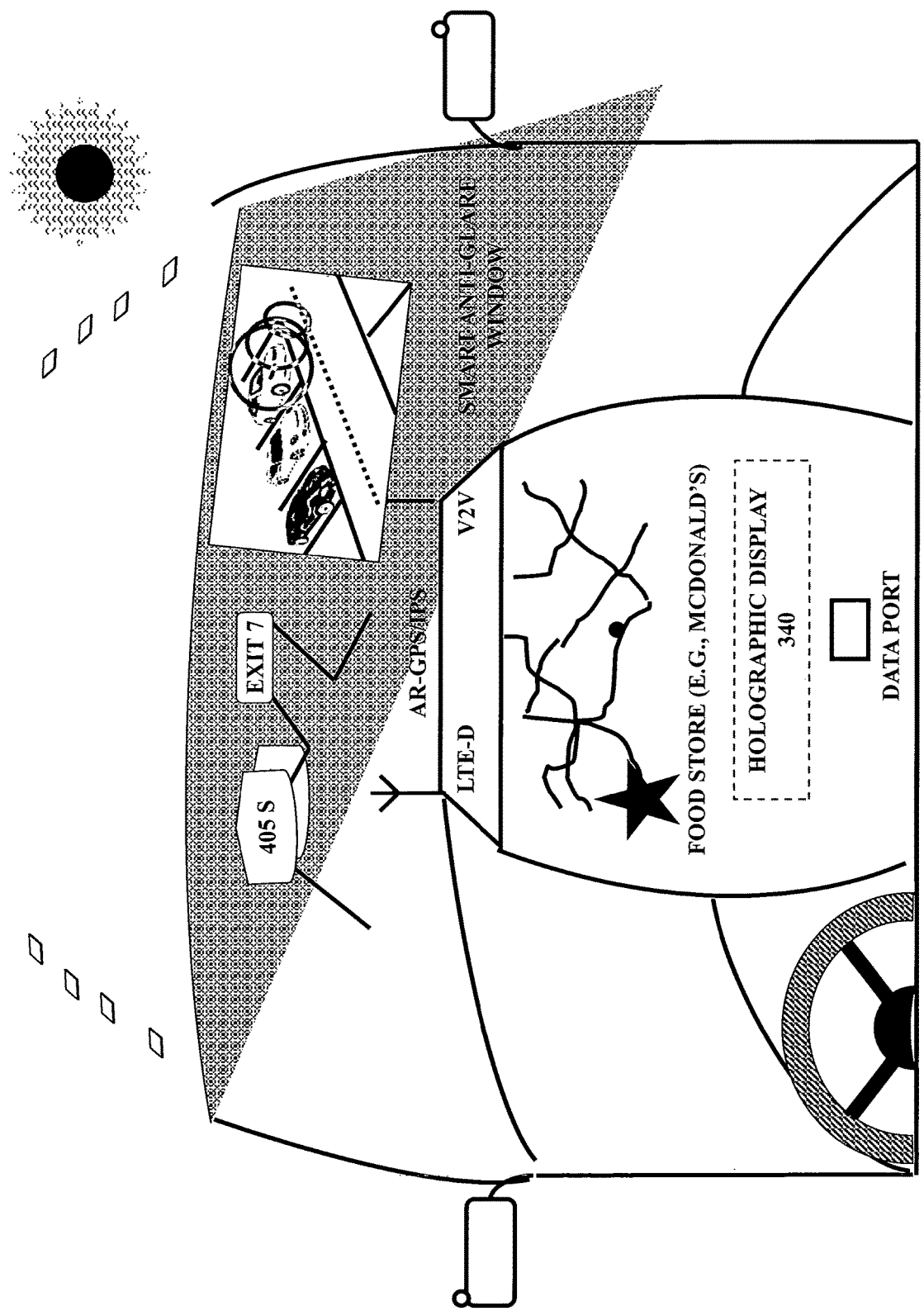
FIGS. 3E-3J illustrate other components/subsystems of the intelligent vehicle.
Figures 3F, 3G:
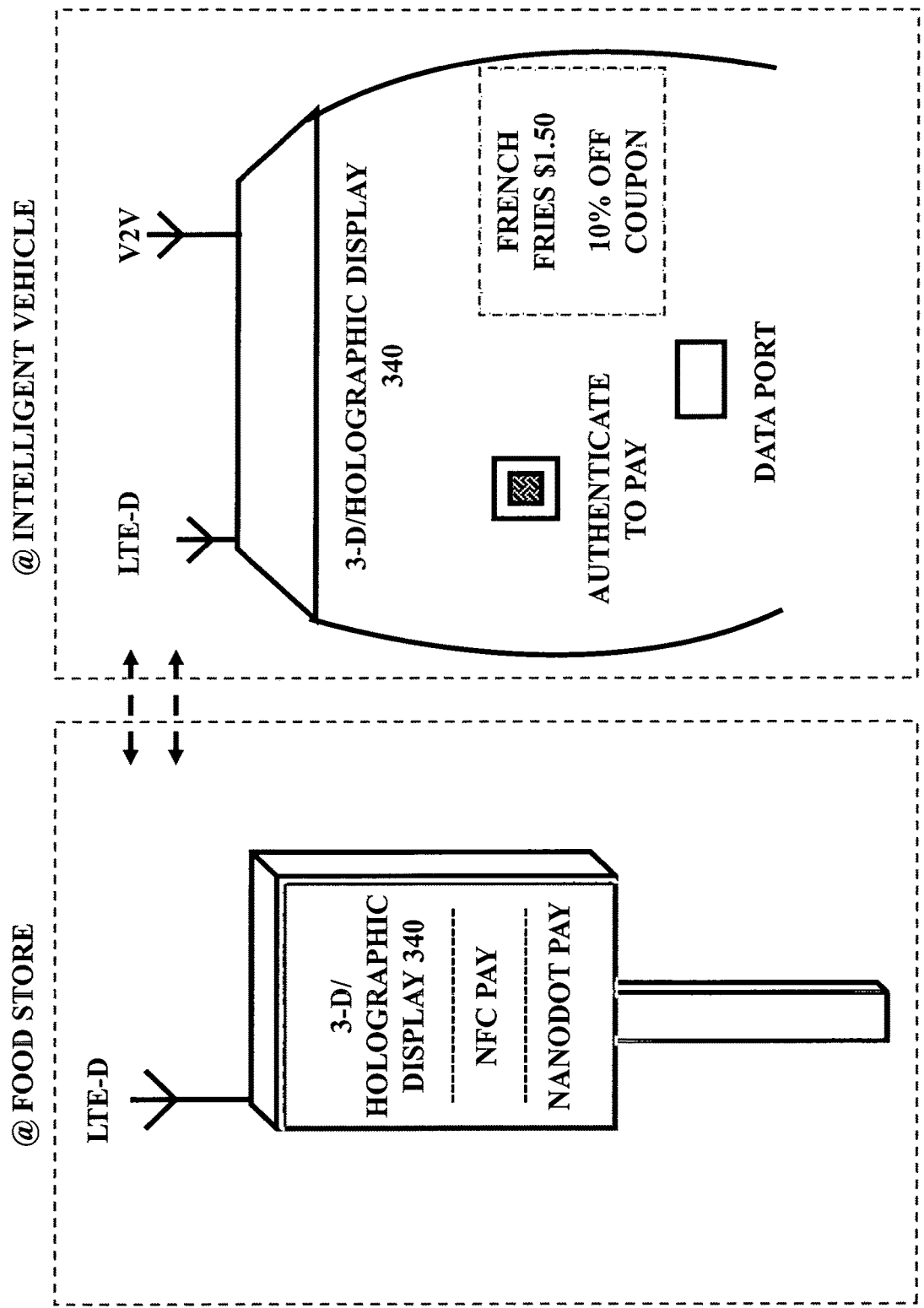
Figure 3H:
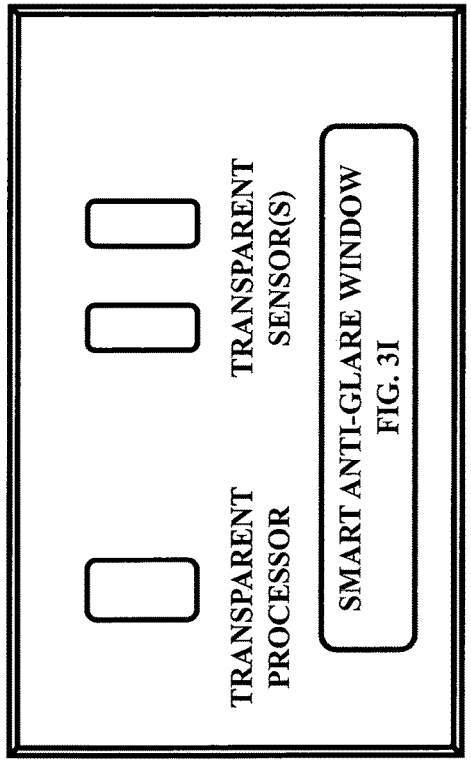
Figure 3I:
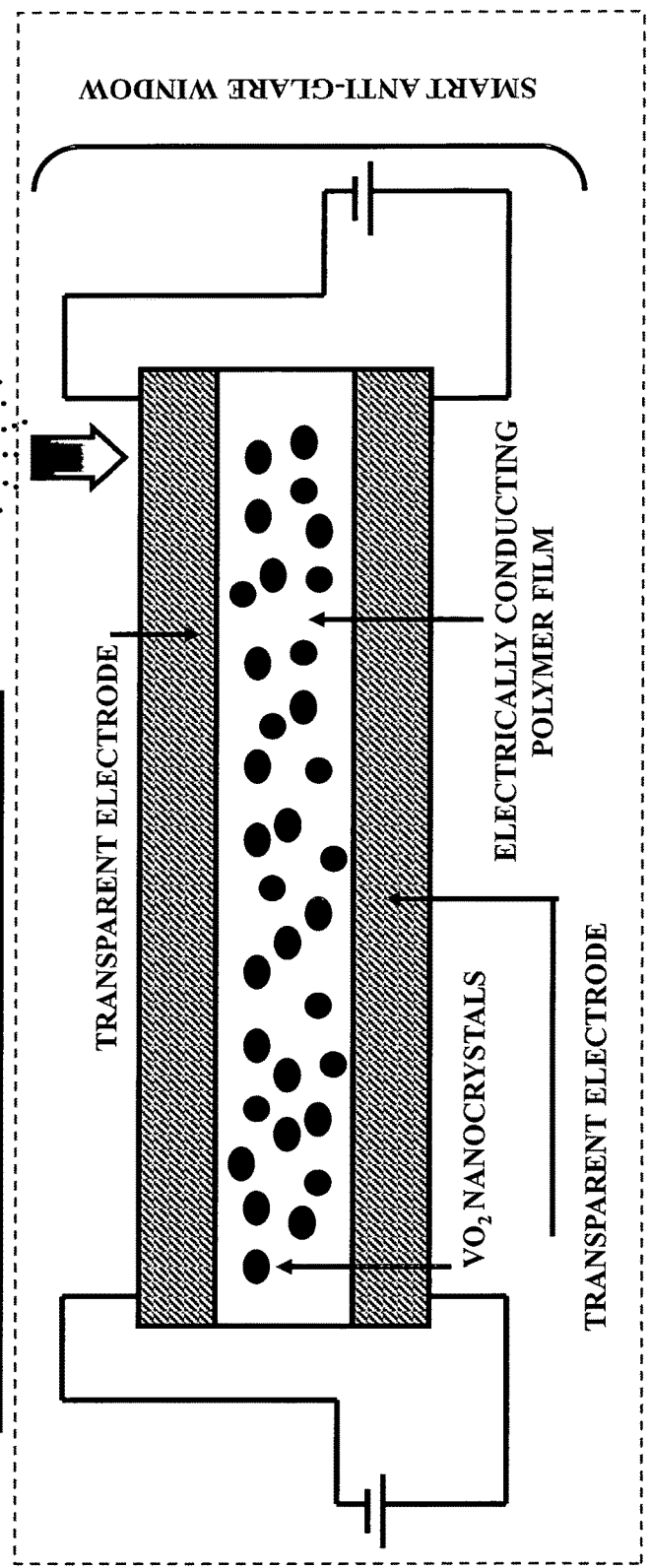
Figure 3J:
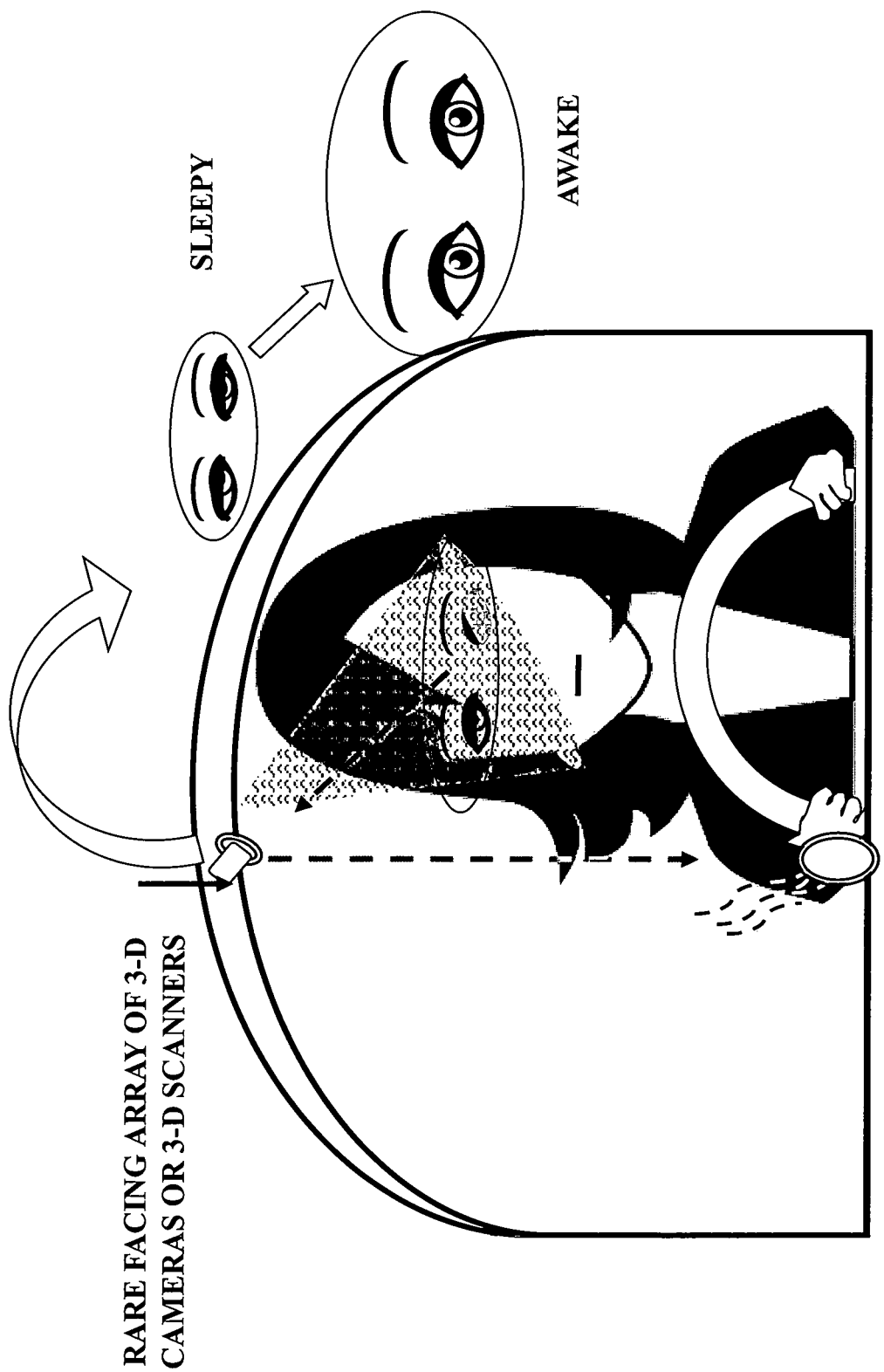
Figure 3K:
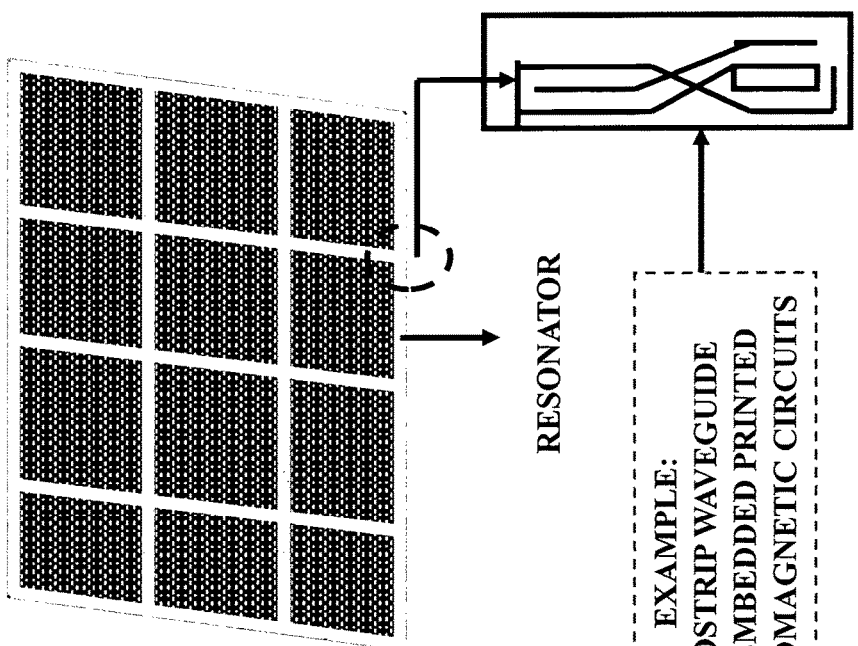
FIG. 3K illustrates an embodiment of a high resolution radar comprising metamaterials.

As illustrated in FIG. 3K, a high resolution radar (based on Synthetic Aperture Radar's principle) can be fabricated/constructed by dynamically controlled electromagnetically specific metamaterial surface, which consists of a periodic array of resonators, wherein each resonator (consisting of embedded/printed electromagnetic circuits) can receive and transmit/broadcast at a specific microwave frequency. Electromagnetic properties of each resonator can be electrically tuned (or programmed to change electromagnetic properties in response to electric currents in embedded/printed electromagnetic circuits) to control each pattern of radiation precisely. The overall radiation pattern for two-dimensional/three-dimensional imaging is the superposition of the radiation pattern from each resonator.

Additionally, the millimeter-wave radar or high resolution radar (based on Synthetic Aperture Radar's principle) or high resolution radar (based on Synthetic Aperture Radar's principle) with metamaterial can be capable to penetrate ground in all weather conditions.

By sending electromagnetic pulses (e.g., very high frequency (VHF)) up to 10 feet below the ground and detecting the reflected electromagnetic pulses bouncing off from dirt, rocks and snow, a near real time/real time three-dimensional roadmap coupled with a global positioning system/an augmented reality enhanced global positioning system can be constructed. The near real time/real time three-dimensional map can be coupled or integrated with the Super System on Chip 400A/400B/400C/400D and/or the artificial eye.

Furthermore, the Super System on Chip 400A/400B/400C/400D and/or the artificial eye can be coupled with a computer vision algorithm and/or an artificial intelligence algorithm and/or an artificial neural network algorithm and/or a machine learning (including deep learning/meta-learning and self-learning) algorithm for ultrafast data processing, image processing/image recognition, deep learning/meta-learning and self-learning.

The Super System on Chip 400A/400B/400C/400D and/or the artificial eye can be coupled with a hardware security component (HSC). The hardware security component can encrypt communication and prevent the spread of malicious/manipulated software code. It can also secure boot and check that software is authentic, trusted and unaltered.

The hardware security component can be coupled with a physical un-clonable function device (PUFD) to reduce any risk of cyber security, wherein the physical un-clonable function device includes a two-dimensional (crossbar) array of memristors.

In some light detection and ranging applications, a 905 nm laser and a corresponding wavelength's photodiode are proper. However, 1550 nm or higher wavelength is eye safe. For example, a time-of-flight direct flash light detection and ranging subsystem can be realized by (a) a high power superluminescent diode (SLD) or a high power edge emitting/surface emitting laser, (b) a collimating lens, (c) a two-dimensional array of bandpass filters for incident wavelength, (d) a two-dimensional array of image sensors for incident wavelength and (e) a Light-to-Distance System on Chip (L-D SoC). The details of a Light-to-Distance System on Chip are discussed in later paragraphs.

For example, a scanning light detection and ranging subsystem can be realized by coupling (a) a high power pulsed fiber laser or a master oscillator (e.g., a distributed feedback laser (DFB))-integrated with a single pass tapered power amplifier (T-PA) (MOPA), (b) a collimating lens, (c) a wide angle three-dimensional scanner or a one-dimensional (1-D)/two-dimensional array of scanning mirrors (e.g., a digital mirror device (DMD) manufactured by Texas Instrument), (d) an one/two-dimensional array of bandpass filters for incident wavelength, (e) a one-dimensional (e.g., 1×32)/two-dimensional array of avalanche photodetectors (e.g., each photodiode has an active area of about 100 microns) for incident wavelength and (f) a Light-to-Distance System on Chip.

Instead of the wide angle three-dimensional scanner or an one-dimensional/two-dimensional array of scanning mirrors, a single surface emitting photonic crystal (PC) (pulsed) laser or a two-dimensional array of surface emitting photonic crystal (E-PC) (pulsed) lasers, wherein each surface emitting photonic crystal (pulsed) laser can provide a pulse in nanoseconds or in sub-nanoseconds. In this configuration, photonic crystals are electrically controlled by multiple electrodes.

Furthermore, the high power laser diode can be wavelength specific to filter out background stray light.

A high power (1000 watts) master oscillator power amplifier based short pulse fiber laser includes (a) a 980 nm pump laser module, (b) a master oscillator power amplifier module and (c) an actively doped fiber.

Alternatively, a high power short pulsed laser can be based on chirped pulse amplification (CPA), wherein a short laser pulse is expanded to larger pulse width, amplified at intensities that are below the amplifier damage threshold and compressed in air or vacuum to a narrow pulse width.

Furthermore, a master oscillator power amplifier can include a modulator (e.g., phase/intensity/frequency) for accurate ranging.

Also, multiple power amplifiers can be coherently combined for higher (exit) optical power.

For example, a non-mechanically moving light detection and ranging subsystem can be realized by coupling (a) a high power narrow linewidth (less than 200 Hz) frequency modulated pulsed laser (e.g., a distributed feedback laser integrated with a single pass power amplifier), (b) a first 1×N ultrafast optical switch for transmission, (c) an array of N 3-port optical circulators, (d) an array of N beam collimating lenses, (e) a second 1×N ultrafast optical switch for reception, (f) an array of N balanced photodiodes (BPDs) and (g) a Light-to-Distance System on Chip.

This non-mechanically moving light detection and ranging subsystem can be considered as a frequency modulated continuous wave (or quasi-continuous) light detection and ranging subsystem. In this case, the frequency of the laser is ramped linearly in time and the time delay associated with the round trip time to the target produces a beat signal with the frequency proportional to range. Up-down frequency ramps can be used to unambiguously distinguish both target range and target velocity.

For example, an optical phased array based light detection and ranging chip can be fabricated/constructed as a photonic integrated circuit, integrating (a) a low relative intensity noise (RIN), mod-hop free, ultra-narrow linewidth (less than 50 Hz), wavelength tunable high power 1550 nm laser, (b) a low-loss waveguide, (c) a semiconductor optical (pre) amplifier/erbium doped waveguide based (pre) amplifier, (d) a 1×N power splitter (or a star (optical) coupler), (e) 1×M multimode interference (optical) coupler (MMI), (f) an array of thermal/electro-optic phase shifters, (g) an array of semiconductor optical (post) amplifiers/erbium doped waveguide based (post) amplifiers for optical power equalization, (h) an array of vertical grating (e.g., second-order gratings) (optical) couplers to direct the phased laser beams toward the direction of a target, (i) a graded index lens/diffractive optical elements (DOE), (j) an array of waveguide (e.g., germanium waveguide) photodiodes and (k) a Light-to-Distance System on Chip.

It should be noted that vertical grating (optical) couplers are special purpose grating (optical) couplers.

The optical phased array can be thermal-optical or liquid crystal (LC) based/liquid crystal waveguide based.

Alternatively, many passive optical components can be fabricated/constructed utilizing silicon on insulator (SOI)/silicon on silicon nitride substrate and then can be co-packaged with active components (e.g., lasers, semiconductor optical amplifiers and photodiodes).

Alternatively, an array (one-dimension/two-dimension) of vertical grating (optical) couplers can be replaced by an array (one-dimensional/two-dimensional) of nanoscaled passive antennas (e.g., V-shaped/Yagi-Uda) to direct the laser beams toward a target direction, wherein the nanoscaled antennas are evanescently coupled to an underlying waveguide, which is guiding and distributing the laser beam.

An array emitters at spacing is larger than $\lambda/2$, with $\lambda$ as the wavelength of the optical field in the medium of propagation can create side lobes. Thus, each emitter with an enormously decreased footprint and spacing (e.g., plasmonic/nanoscaled antennas) may be required to eliminate unwanted side lobes. It is desirable to have the maximum dimension of the nanoscaled antenna between 2 nm to 1000 nm.

A non-uniform spacing of the emitters may be used to suppress unwanted side lobes.

Alternatively, an array (one-dimension/two-dimension) of vertical grating (optical) couplers can be replaced by an array (one-dimension/two-dimension) of actively controlled nanoscaled antennas (e.g., actively controlled nanoscaled antennas of vanadium dioxide ($VO_2$)) to direct the laser beams toward a target direction, wherein the actively controlled nanoscaled antennas are evanescently coupled to an underlying waveguide, which is guiding and distributing the laser beam.

To achieve coherent emitters, a 10-element array of vanadium dioxide slot nanoantennas (about 30 nm wide, about 300 nm long at 100 nm spacing) may be fed by a single narrow linewidth laser via a multimode interference coupler (or by an array of phase locked/injection locked narrow linewidth lasers). A 10-element array of vanadium dioxide slot nanoantennas can enable about ±20° angle. Vertical stacked layers (separated by silicon dioxide thin-film(s)/polymer layer(s)) of a 10-element array of vanadium dioxide slot nanoantennas can be coupled with a narrow linewidth laser and this configuration can enable about ±20° angle in horizontal axis and vertical axis to enable three-dimensional optical phase array. Furthermore, an individual vanadium dioxide slot nanoantenna can be electrically controlled (about 10 nanoseconds switching time) by via metal electrodes/transparent graphene nanoheaters, coupled through metallized via holes. Alternatively an individual vanadium dioxide slot nanoantenna can be optically controlled (about 1 nanosecond switching time) by via waveguides and a laser (e.g., a 1550 nm laser).

Alternatively, an acoustic wave from a piezoelectric transducer can scatter (like gratings) a guided laser light in a waveguide enabling a photonic-phononic waveguide based optomechanical antenna (OMA) or optoacoustical antenna (OAA). An array of these optomechanical antennas or optoacoustical antennas can steer a laser beam in two-dimension.

Generally, a Light-to-Distance System on Chip can include (a) a supply clock circuit, (b) a timing sequencer circuit, (c) a control circuit of 1550 nm laser(s), (d) a synchronization circuit of 1550 nm laser(s), (e) an analog signal conditioner circuit, (f) an analog-to-digital conversion circuit, (g) a time-to-digital conversion circuit, (h) a first (general) signal processing circuit, (i) a second (specific) signal processing circuit to determine distance output and (j) a diagnostic circuit.

Frequency change can be utilized to calculate velocity of an object. Similarly, a Light-to-Distance/Velocity System on Chip (L-D/V SoC) can include (a) a supply clock circuit, (b) a timing sequencer circuit, (c) a control circuit of 1550 nm laser(s), (d) a synchronization circuit of 1550 nm laser(s), (e) an analog signal conditioner circuit, (f) an analog-to-digital conversion circuit, (g) a time-to-digital conversion circuit, (h) a first (general) signal processing circuit, (i) a second (specific) signal processing circuit to determine distance output, (j) a third (specific) signal processing circuit to determine velocity output and (k) a diagnostic circuit.

To reduce glare of two head lights from the intelligent vehicle, each head light can include a light source (e.g., laser/light emitting diode) and a digital mirror device (e.g., Texas Instrument's DLP5531-Q1), wherein the digital mirror device can be programmed to project light on the road, not anywhere else.

The light detection and ranging subsystem and/or high resolution radar and/or metamaterial based high resolution radar can be coupled with a gyro sensor (for stability), a global positioning system (GPS), an augmented reality enhanced global positioning system and an augmented reality enhanced indoor positioning system.

Tracking a moving target is a computationally intensive process that can take seconds, making the technology unreliable for avoiding impending collisions, without the integration of the Super System on Chip 400A/400B/400C/400D for ultrafast data processing, image processing/image recognition, deep learning/meta-learning and self-learning.

The light detection and ranging subsystem and/or high resolution radar and/or metamaterial based high resolution radar can be integrated with a digital signal processor.

The light detection and ranging subsystem and/or high resolution radar and/or metamaterial based high resolution radar can be coupled or integrated with the Super System on Chip 400A/400B/400C/400D and/or the artificial eye. The Super System on Chip 400A/400B/400C/400D can enable ultrafast data processing, image processing/image recognition, deep learning/meta-learning and self-learning.

Furthermore, the Super System on Chip 400A/400B/400C/400D and/or the artificial eye can be coupled with a computer vision algorithm and/or an artificial intelligence algorithm and/or an artificial neural network algorithm and/or a machine learning (including deep learning/meta-learning and self-learning) algorithm for ultrafast data processing, image processing/image recognition, deep learning/meta-learning and self-learning.

For example, the artificial eye can be fabricated/constructed utilizing a very large scale integration of the atomic scaled switches. Photocurrent is induced in a photoconductive layer (which is coupled between a metal electrode and a solid-electrolyte electrode) by light irradiation. The photocurrent reduces metal ions with positive charges in the solid-electrolyte electrode and this precipitates as metal atoms to form an atomic scaled metal connection between the metal electrode and the solid-electrolyte electrode-operating as an atomic scaled switch, turned on by light irradiation and/or an applied electrical activation (e.g., voltage).

FIG. 3D illustrates a machine learning (including deep learning/meta-learning and self-learning) algorithm based near real time/real time intention system of the Super System on Chip 400A/400B/400C/400D.

The Super System on Chip 400A/400B/400C/400D can enable ultrafast data processing, image processing/image recognition, deep learning/meta-learning and self-learning.

Alternatively, by creating more than 10 to 1,000 mini-circuits within a field programmable gate array (FPGA), effectively the field programmable gate array with or without traditional central processing units (CPU) can be turned into 10 or 1,000-core processors with each core processor working on its own instructions in parallel and such a configuration may be utilized instead of the Super System on Chip 400A/400B/400C/400D.

The near real time/real time structured and unstructured inputs from cameras, three-dimensional cameras, light detection and ranging subsystems, millimeter wave radars, high resolution radars, an augmented reality enhanced global positioning system, vehicle to vehicle communication, a LTE-Direct radio and sensor(s) can be correlated through a computer vision algorithm submodule, a pattern recognition algorithm submodule, a data mining algorithm submodule, Big Data analysis algorithm submodule, a statistical analysis algorithm submodule, a fuzzy logic (including neuro-fuzzy) algorithm submodule, an artificial neural network/artificial intelligence algorithm submodule, a machine learning (including deep learning/meta-learning and self-learning) algorithm submodule, a predictive analysis algorithm submodule, a software agent algorithm submodule and a natural language processing algorithm submodule to create an intention output (in natural language) in near real time/real time-thus, a pattern of actions of the intelligent vehicle can be predicted in the near real time/real time.

For example, the machine learning (including deep learning/meta-learning and self-learning) algorithm based near real time/real time intention system of the Super System on Chip 400A/400B/400C/400D can be sensor-aware and/or context-aware and it can alert the user (driver) of the intelligent vehicle about the intention of other users (drivers of other intelligent vehicles) in proximity.

The intelligent vehicle includes or couples with an intelligent subsystem, wherein the intelligent subsystem is sensor-aware and/or context-aware, wherein the intelligent subsystem is coupled by (i) a wireless/sensor network with an object 120A and an internet appliance and/or (ii) a biosensor network with a bioobject 120B, wherein the internet appliance includes a microprocessor/microcontroller and a radio transceiver, wherein the intelligent subsystem includes

- a radio transceiver/electromagnetic induction module/sensor module,
- an internet protocol address and an algorithm, wherein the algorithm is selected from group consisting of the following a user specified safety control algorithm, an authentication algorithm of the user, an in-situ diagnostics algorithm of the intelligent subsystem and a remote diagnostics algorithm of the intelligent subsystem, wherein the above algorithm includes a first set of instructions, stored in a non-transitory media of the intelligent subsystem and
- a learning algorithm or an intelligence rendering algorithm (e.g., the social wallet 100N2/natural language activated/voice activated "Fazila" as described in FIG. 10A or an algorithm as described in FIG. 1B (which can be coupled with Super System on Chip 400A/400B/400C/400D of the intelligent subsystem for ultrafast data processing, image processing/image recognition, deep learning/meta-learning and self-learning), stored in the non-transitory media of the intelligent subsystem or a cloud data storage) for providing intelligence (to the intelligent subsystem) in response to the user's interest or preference.

The intelligent subsystem can provide an automatic search on internet in response to the user's interest or preference (via inputs of voice/text commands).

It should be noted that the social wallet can be web based, as an application or as an electronic module (hardware) and the social wallet electronic module (hardware) can be realized as the intelligent subsystem.

Details of the social wallet (e.g., as an application in FIG. 1A of U.S. non-provisional patent application Ser. No. 13/448,378 or as an electronic module (hardware)) have been described/disclosed in U.S. Non-Provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

Details of an intelligent subsystem have been described/disclosed in U.S. non-provisional patent application Ser. No. 14/014,239 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Aug. 29, 2013 and in its related U.S. non-provisional patent applications (with all benefit provisional patent applications) are incorporated in its entirety herein with this application.

The intelligent vehicle can also couple with an object (e.g., Internet of Things (IoT)), wherein an object is described/disclosed in previous paragraph.

Details of the objects have been described/disclosed in U.S. non-provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

Furthermore, the machine learning (including deep learning/meta-learning and self-learning) algorithm based near real time/real time intention system can be connected with a cloud quantum computer for near real time/real time risk/scenario analysis.

The machine learning (including deep learning/meta-learning and self-learning) algorithm based near real time/real time intention system of the Super System on Chip 400A/400B/400C/400D can be applied to both semi-autonomous intelligent vehicles and autonomous intelligent vehicles.

FIG. 3E illustrates an application of the intelligent algorithm submodule 100C of the intelligent vehicle for locating a nearby food store (e.g., McDonald's) utilizing an augmented reality enhanced global positioning system.

FIG. 3F illustrates a subsystem (at the food store) with an LTE-Direct radio, a three-dimensional/holographic display, and a near field communication radio based payment system/nanodots based payment system.

The LTE-Direct radio can enable (a) wireless devices to communicate directly or discover services in 500-meter proximity without any cellular reception (b) the distribution of customer-profiled advertising/coupons (e.g., vehicle/customer recognition) with instant updates. On-demand near real time delivery of goods can be realized by utilizing a LTE-Direct radio and a global positioning system.

FIG. 3G illustrates an application of interactions of the intelligent vehicle with a food store via the three-dimensional/holographic display, LTE-Direct radio and near field communication radio based/nanodots based payment system.

FIG. 3H illustrates a smart anti-glare window (of the intelligent vehicle) integrated with a transparent processor and an array of transparent sensors (e.g., an outside light intensity/temperature/rain sensor). The transparent processor and the transparent sensors can be fabricated/constructed with indium-gallium-zinc oxide or zinc-tin oxide semiconductor material.

FIG. 3I illustrates an electrically switchable smart anti-glare window. Vanadium dioxide is a transparent insulator at room temperature. But after its phase transition temperature, vanadium dioxide is reflective and opaque, thus temperature determines if vanadium dioxide is an insulator or a metal. Vanadium dioxide nanoparticles embedded within transparent electrically conducting polymeric films (with transparent electrodes on the transparent electrically conducting polymeric films) can act as a smart anti-glare window, when heated electrically. Alternatively, vanadium dioxide thin-film can be utilized, instead of vanadium dioxide nanoparticles. The smart anti-glare window can be coated with thin-films to protect the user (the driver of the intelligent vehicle) from harmful UV rays. A large area smart anti-glare window can be printed by a nanotransfer printing method.

Additionally, any relevant information from the internet connection of the intelligent vehicle and/or intelligent portable internet appliance 160 and/or intelligent wearable augmented reality personal assistant device 180 can be augmented and projected via a head-up display (HUD) onto the smart anti-glare window, wherein the head-up display includes a microprojector 560, as described in FIG. 50A. The head-up display can respond/recognize voices, gestures or read an item or a person in the user's field of view, wherein a decoder is configured to convert the said reading of the item or the person into text or an image, taking into account the context of driving.

Details of the augmented reality personal assistant device 180 are illustrated in FIG. 53.

FIG. 3J illustrates an application of an array of eye-facing cameras/three-dimensional scanner to monitor the user's eye opening and closing patterns. If the user is sleepy, then an electronics system integrated with the array of eye-facing cameras/three-dimensional scanner can alert the user (the driver of the intelligent vehicle).

FIG. 3K illustrates a high resolution radar (based on Synthetic Aperture Radar's principle), which can be fabricated/constructed by dynamically controlled electromagnetically specific metamaterial surface. The metamaterial surface consists of a periodic array of resonators, wherein each resonator (consisting of embedded/printed electromagnetic circuits) can receive and transmit/broadcast at a specific microwave frequency. Electromagnetic properties of each resonator can be electrically tuned (or programmed to change electromagnetic properties in response to electric currents in embedded printed electronic circuits) to control each pattern of radiation precisely. The overall radiation pattern for two-dimensional/three-dimensional imaging is the superposition of the radiation patterns from each resonator.

Additionally, the millimeter-wave radar or high resolution radar or a high resolution radar with metamaterial can be capable to penetrate ground in all weather conditions.

The frequency modulated continuous wave (or quasi-continuous) light detection and ranging subsystem can enable faster acquisition, better resolution, better dynamic range and longer distance measurement capability, compared to a time-of-flight direct flash light detection and ranging subsystem.

The frequency modulated continuous wave (or quasi-continuous) light detection and ranging subsystem can be a coherent subsystem. Alternatively, homodyne/heterodyne coherent light detection and ranging subsystem can be considered.

The frequency modulated continuous wave (or quasi-continuous) light detection and ranging subsystem can be Synthetic Aperture based. A Synthetic Aperture based light detection and ranging subsystem can be integrated with a computational camera. The computational camera can be a standalone device. The computational camera may be considered as a femotosecond time-of-flight light detection and ranging subsystem.

Figure 3L:
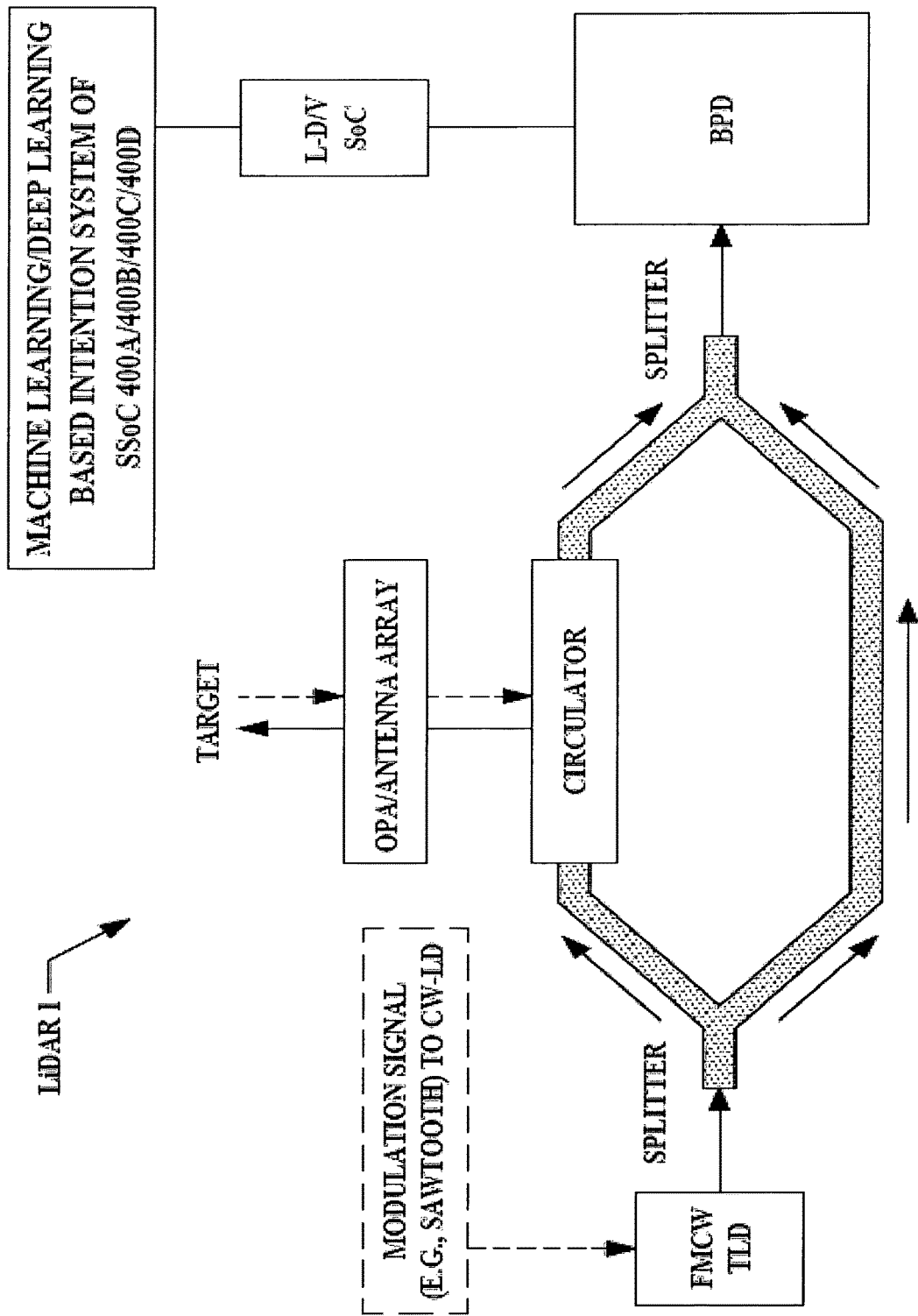
FIG. 3L illustrates an embodiment of a frequency modulated continuous (or quasi-continuous) wave light detection and ranging subsystem (FMCW-LiDAR).

FIG. 3L illustrates a frequency modulated continuous wave (or quasi-continuous) light detection and ranging subsystem, wherein a frequency modulated continuous wave (or quasi-continuous) tunable narrow linewidth light source (providing a frequency (e.g., a sawtooth) modulated light signal), a balanced photodiode (where a beat frequency is generated), a 3-port optical circulator (or a triplexer optical element) can be optically coupled with a Mach-Zehnder type interferometer. The 3-port optical circulator is optically coupled with an optical phased array or an array of antennas.

The balanced photodiode can be electro-optically coupled with a Light-to-Distance/Velocity System on Chip.

The Light-to-Distance/Velocity System on Chip can be coupled with the machine learning (including deep learning/ meta-learning and self-learning) algorithm based Intention System of the Super System on Chip 400A/400B/400C/ 400D, utilizing the algorithm 100 in FIG. 1B.

Thus, Target Distance=(Beat frequency*Speed of Light in Free Space)/(2*Frequency of Laser Modulation).

In an optical phased array, the frequency modulated continuous wave (or quasi-continuous) light beam is phase modulated by an array of phase modulators, then the phase modulated light beams (from the array of phase modulators) are beam steered by the optical phased array.

Alternatively, instead of the optical phased array, an array of antennas/vertical grating (optical) couplers/holographic optical elements (HOEs)/mirrors/collimating lenses can be utilized for beam steering toward the target.

It should be noted that the frequency modulated continuous (or quasi-continuous) wave light beam can be based multiple distinct wavelengths (e.g., based on wavelength division multiplexing (WDM)).

Figure 3M:
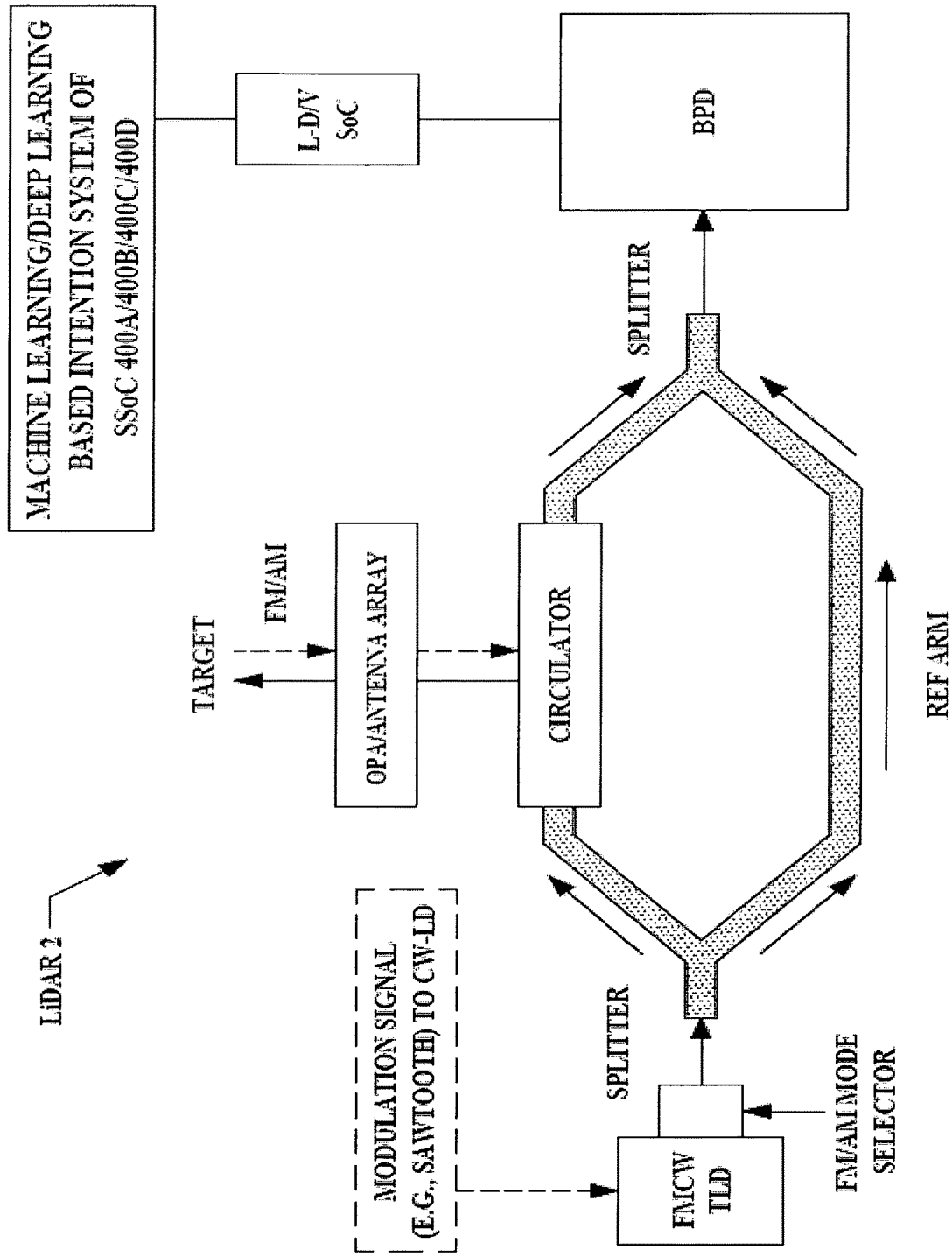
FIG. 3M illustrates an embodiment of a frequency modulated continuous (or quasi-continuous) wave light detection and ranging subsystem with a selector device to select either frequency modulation (FM) or amplitude modulation (AM).

FIG. 3M is similar to FIG. 3L, except modified/enhanced by a mode selector device to select either frequency modulation or amplitude modulation.

Figure 3N:
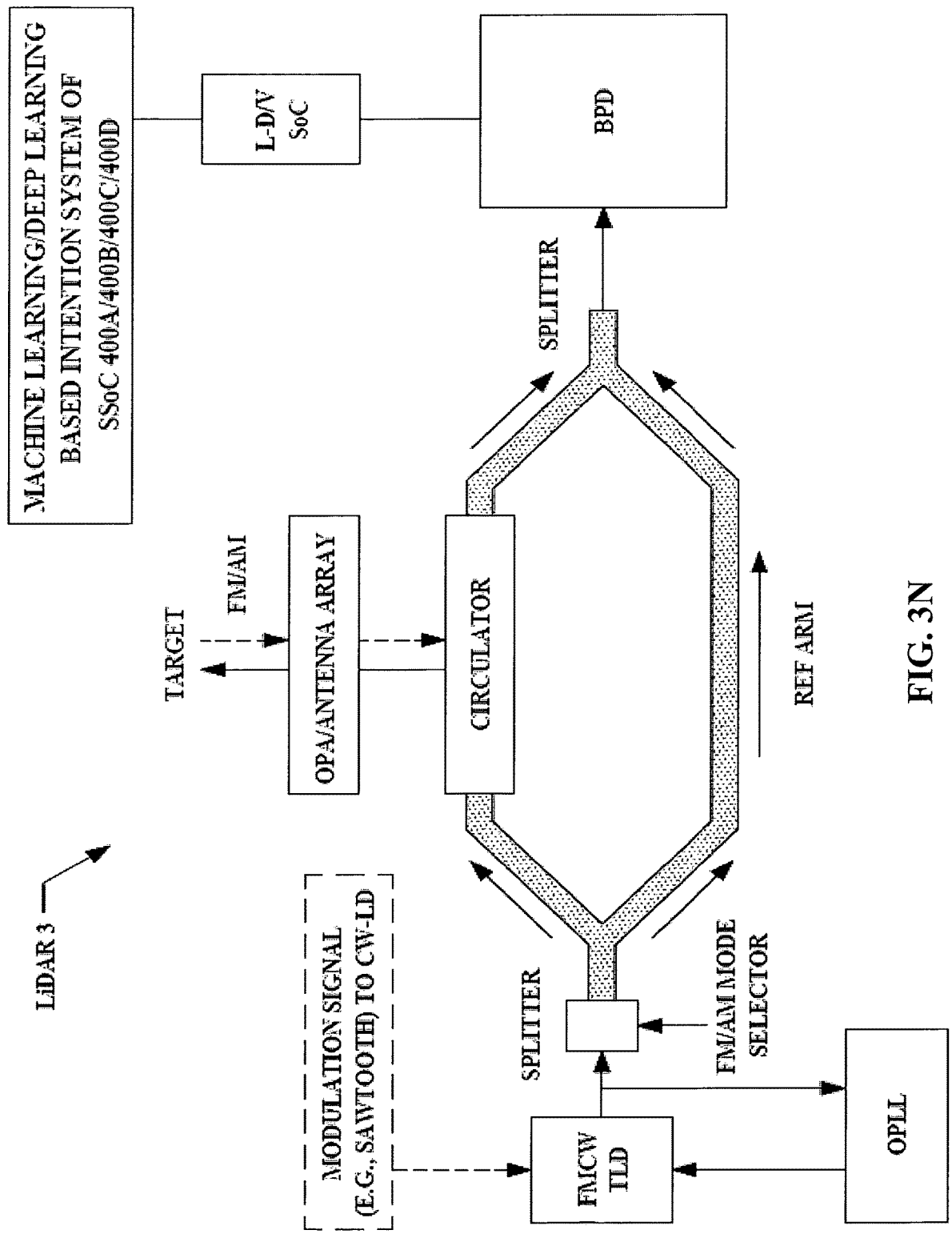
FIG. 3N illustrates an embodiment of a frequency modulated continuous (or quasi-continuous) wave light detection and ranging subsystem with a selector device (to select either frequency modulation or amplitude modulation) and an optical phase-locked loop (OPPL).

FIG. 3N is similar to FIG. 3M, except modified/enhanced by an optical phase-locked loop.

The linearity of the frequency modulation of a frequency modulated continuous wave (or quasi-continuous) tunable light source is a critical factor. The linearity of the frequency modulation of a frequency modulated continuous wave (or quasi-continuous) tunable light source may be improved by an optical phase-locked loop.

Figure 3O:
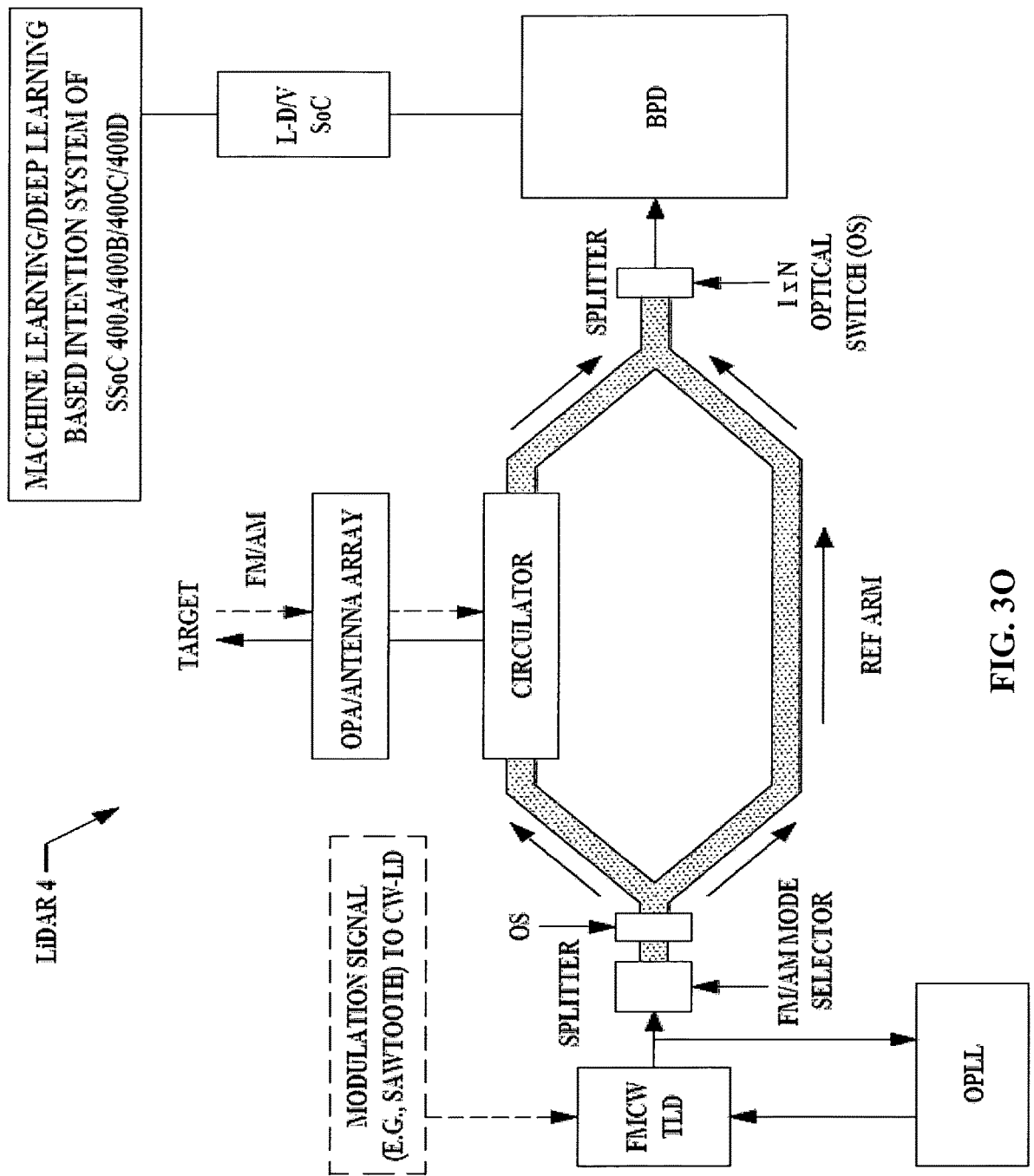
FIG. 3O illustrates an embodiment of a frequency modulated continuous (or quasi-continuous) wave light detection and ranging subsystem with a selector device (to select either frequency modulation or amplitude modulation), an optical phase-locked loop and two (2) 1×N optical switches.

FIG. 3O is similar to FIG. 3N, except modified/enhanced by a 1×N optical switch and an array of balanced photodiodes.

The 1×N optical switch can be based on two-waveguides based directional (optical) coupler/three-waveguides based directional (optical) coupler/Mach-Zehnder type interferometer.

To reduce size and electrical power consumption of the 1×N optical switch, it can include one-dimensional/two-dimensional photonic crystals.

For low-insertion loss and high extinction ratio, one-dimensional/two-dimensional photonic crystals may be useful.

The 1×N optical switch can be an ultrafast optical switch incorporating a phase transition material (e.g., vanadium dioxide) or a phase change material (e.g., $Ge_2Sb_2Te_5$ (GST), $Ge_2Sb_2Se_4Te_1$ (GSST) or $Ag_4In_3Sb_{67}Te_{26}$ (AIST)) or a non-linear polymer with Kerr effect (e.g., p-Toluene Sulfonate (PTS)) or lithium niobate thin-film.

Furthermore, by fusing data from multiple light detection and ranging subsystems and multiple far infrared thermal cameras, a real time 360-degrees angular image/three-dimensional map of (recognized) objects can be constructed. The real time 360-degrees angular image/three-dimensional map (of recognized objects) can be coupled with natural language activated/voice activated "Fazila" as described in FIG. 10A or an algorithm 100 as described in FIG. 1B to provide near real time/real time intelligence. The three-dimensional map can compare road conditions at various times.

Figure 3P:
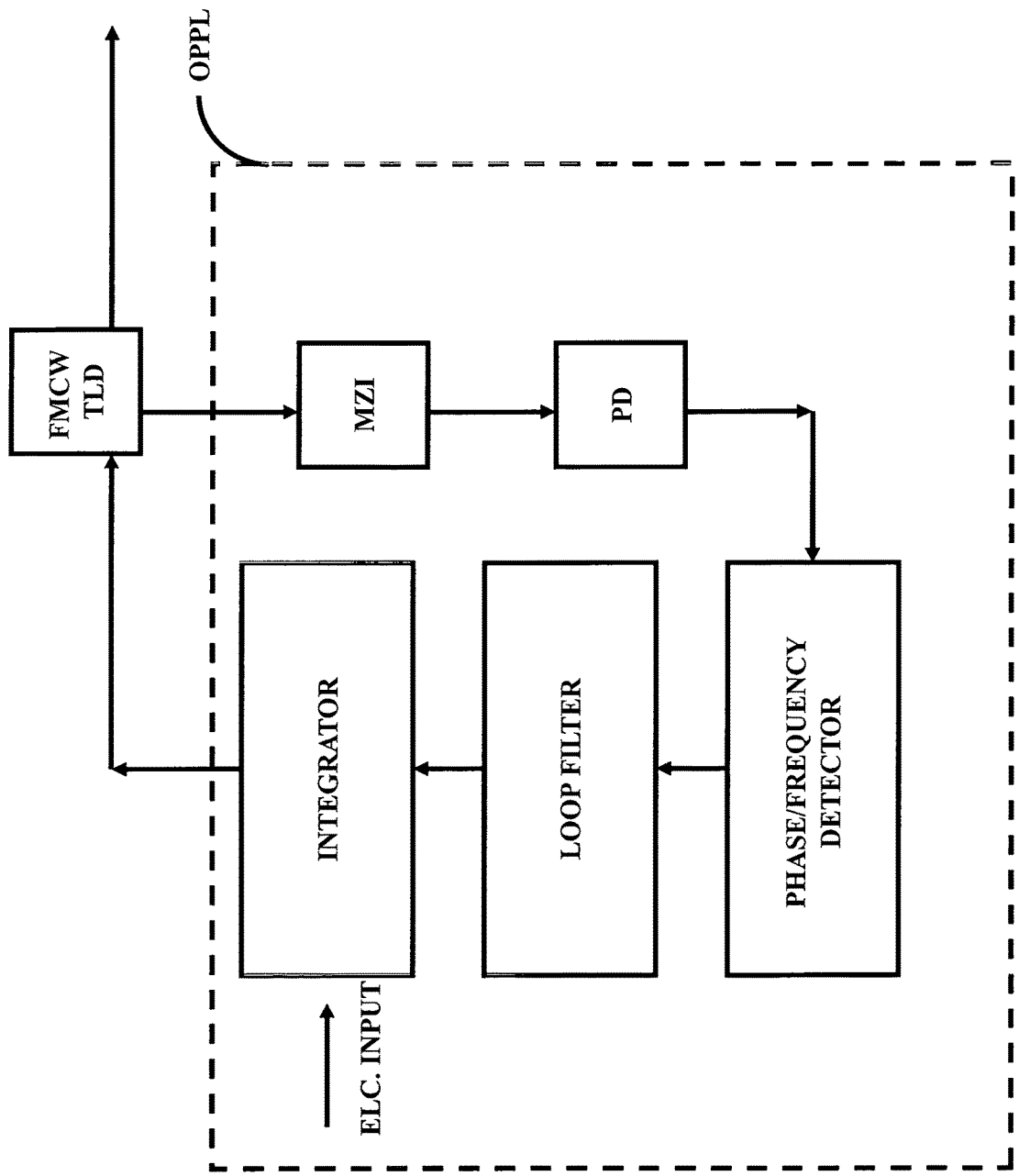
FIG. 3P illustrates a block diagram of an optical phase-locked loop.

FIG. 3P illustrates a block diagram of the optical phase-locked loop. The optical phase-locked loop consists of a phase-frequency detector, which is coupled with a loop filter, wherein the loop filter is then coupled with an integrator (the integrator is receiving an electrical input (e.g., voltage). The output of the integrator is fed into a frequency modulated continuous wave (or quasi-continuous) tunable laser. A portion of the output of the frequency modulated continuous wave (or quasi-continuous) tunable laser is coupled with a Mach-Zehnder interferometer, which is then coupled with a photodiode. The output of this photodiode is coupled with the phase-frequency detector.

By reducing the length of the electrical wires and optical fibers in the feedback path, the dynamics of the optical phase-locked loop can be improved to suppress the higher frequency errors. Furthermore, close integration of the electronic circuits with photonic integrated circuits/devices can enable sophisticated control mechanisms, three-dimensional imaging with micrometer level precision for three-dimensional copy machine, corneal imaging and robotic microsurgery.

Figure 3Q:
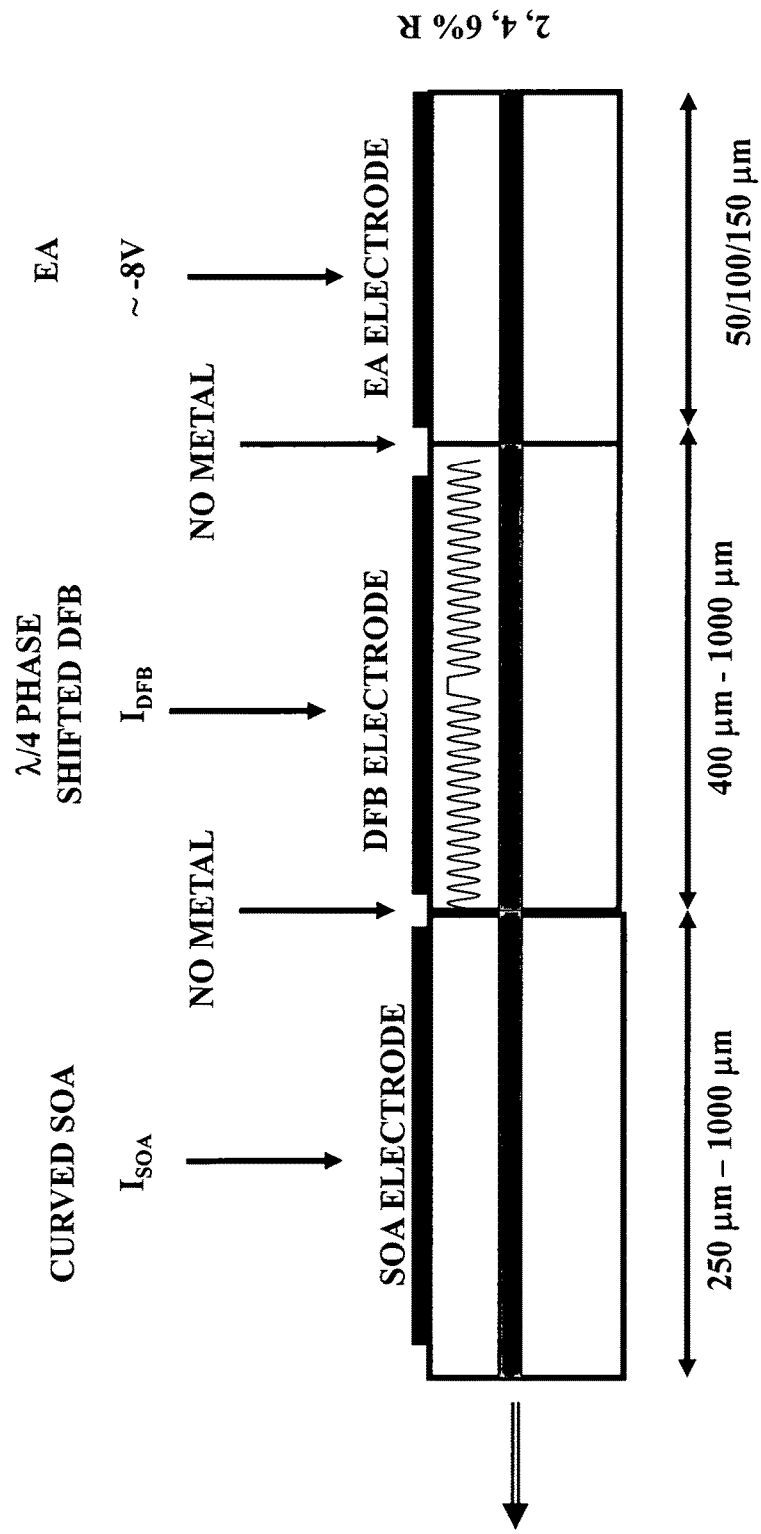
FIG. 3Q illustrates a block diagram of a high power wavelength tunable diode/semiconductor (W-TLD) laser.

FIG. 3Q illustrates a block diagram of a three-section high power wavelength high power wavelength tunable (about 8 nm) diode/semiconductor laser. It consists of an electro-absorption modulator (of about 50/100/150 microns in length) near the rear facet (with about 2% reflectivity), followed by a λ/4 phase shifted distributed feedback laser (of about 400 microns in length) in the middle and then a curved semiconductor optical amplifier (of about 250 microns in length) near the front facet. The front facet has an ultra low reflectivity coating. All three sections are suitably electrically biased and separated (by etching a slot) to eliminate any electrical short.

Figure 3R:
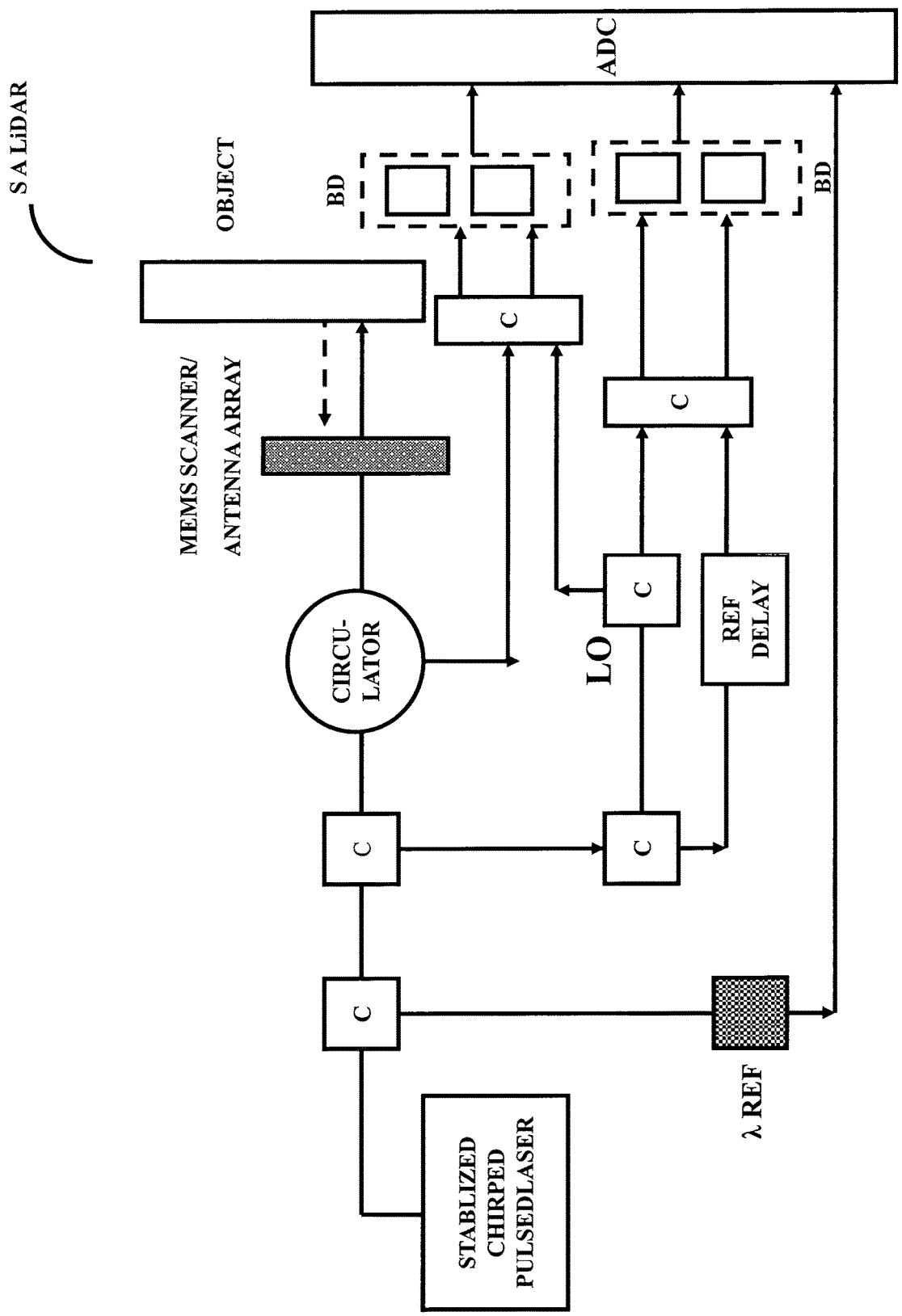
FIG. 3R illustrates a block diagram of a Synthetic Aperture based light detection and ranging subsystem.

FIG. 3R illustrates a Synthetic Aperture based light detection and ranging subsystem. The Synthetic Aperture based light detection and ranging subsystem includes a pulsed laser (e.g., a pulsed laser of 4 μs-pulse width at 1 KHz repetition rate, wherein each pulse has 200 μJ of laser energy). In FIG. 3R a stabilized chirped laser (the output of which can be amplified by an erbium doped fiber amplifier (EDFA), if needed) is coupled with optical (optical) couplers (identified by C) and a 3-port optical circulator. The 3-port optical circulator is then coupled with a microelectromechanical systems (MEMS) based scanner or an array of antennas in the direction of an object. The (optical) couplers are coupled with a wavelength reference, a reference delay and a local oscillator (identified by LO). Finally (optical) couplers (identified by C) are coupled with balanced photodiodes, wherein the balanced photodiodes are coupled with an analog-to-digital converter (identified by ADC).

Figure 3S:
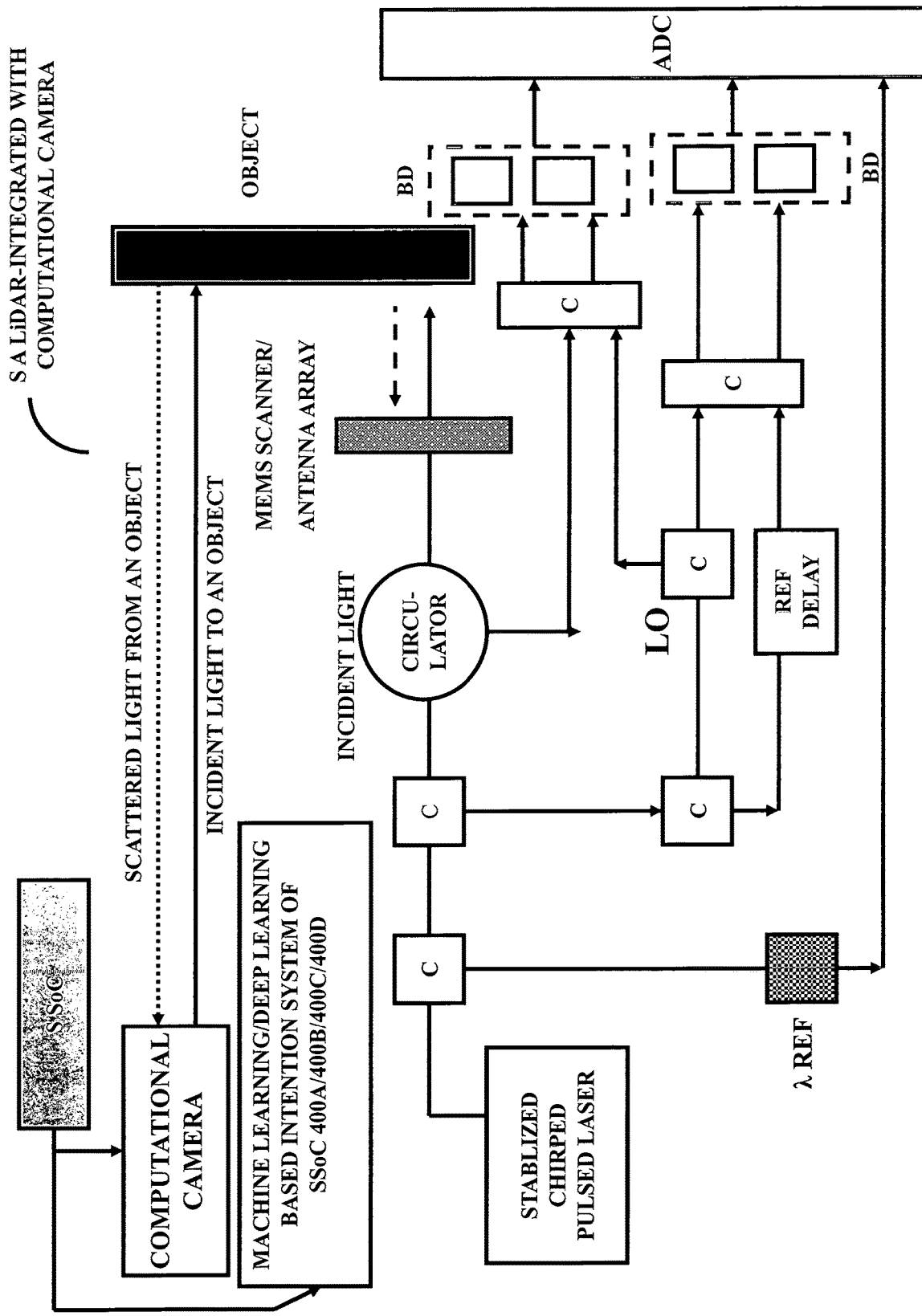
FIG. 3S illustrates a block diagram of a Synthetic Aperture based light detection and ranging subsystem integrated/coupled with a computational camera.

FIG. 3S illustrates a Synthetic Aperture based light detection and ranging subsystem integrated with a computational camera.

Figure 3T:
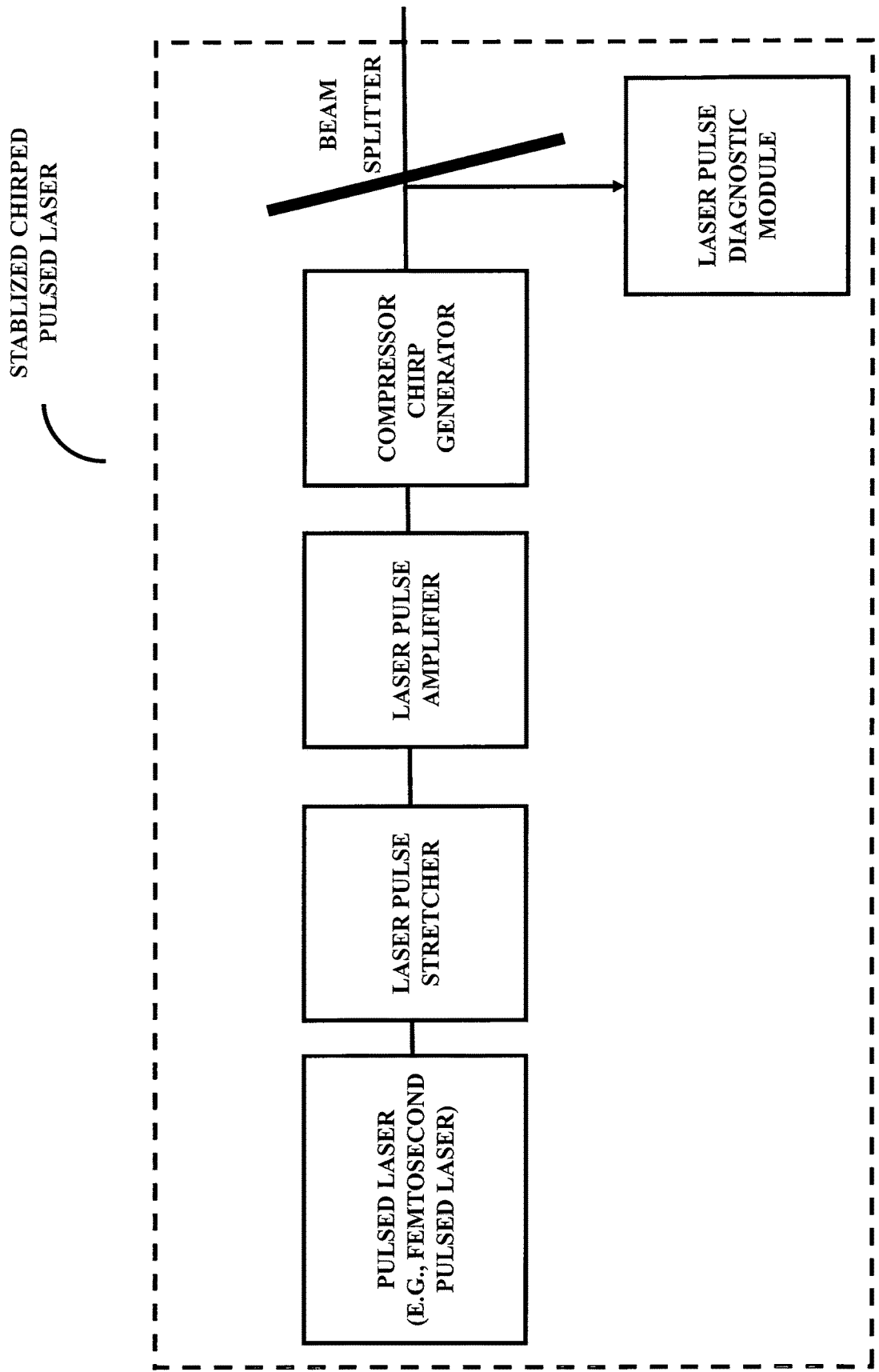
FIG. 3T illustrates a block diagram of a stabilized chirped pulsed laser module.

FIG. 3T illustrates a block diagram of a stabilized chirped pulsed laser module. In FIG. 3T, a pulsed laser is coupled with a laser pulse stretcher, which is then coupled with a laser pulse amplifier. The laser pulse amplifier is coupled with a compressor chirp generator. The output of the compressor chirp generator is divided by a beam splitter. One output of the beam splitter is toward the object and another output from the beam splitter is coupled with a laser pulse diagnostic module.

A pulsed laser will periodically emit light in the form of optical pulses in ultra-short time duration, rather than a continuous wave (CW). The duration or pulse width of the pulsed laser can range from 10's of nanoseconds to 10's of picoseconds. There are several things to consider with the properties and characteristics of the pulsed laser, such as peak power (which is the maximum amount of power that a single pulse delivers), average power, pulse width and pulse energy.

Gain-switching is a technique by which a laser can be made to produce pulses of light of extremely short duration of the order of picoseconds. For example, a quantum well AlGaAs/InGaAs laser with a very large ratio of active layer thickness to optical confinement factor can result in single, high-energy short (about 10-100 picoseconds) single optical pulses. This will require an injection current pulse of ~10 Amp and pulse duration of 1.5-2 nanoseconds. A narrow asymmetric waveguide design is a way of implementing such a structure while maintaining good far-field properties of the single emitted mode.

A modulated diode laser is a continuous laser system in which its output optical power can be manipulated in accordance to an input signal triggering it. One of the most common application for a modulated diode laser is to input a periodic analog or digital signal, such that it will be modulated between an "on" state and "off" state. The main difference between the modulated laser and pulsed laser is the modulated laser is simply turning on and off periodically. A pulsed laser will release burst of energy periodically. A modulated laser will only turn on to a set maximum output power, regardless how quickly or slowly the laser is modulating between the on and off states.

FIG. 3U consists of FIG. 3U1, FIG. 3U2, FIG. 3U3 and Figure U4.

FIG. 3U1 illustrates a standalone computational camera 1. The computational camera may be considered as a nanosecond/picosecond time-of-flight (ToF) light detection and ranging subsystem. In FIG. 3U1, a discrete pulsed laser (e.g., pulsed optically pumped vertical cavity surface emitting laser (VCSEL) or a discrete gain-switched semiconductor laser) and a two-dimensional array of single photon avalanche diodes (SPADs) of InGaAs/InP or germanium on silicon are utilized. The discrete pulsed laser can be coupled with a spatial light modulator (SLM), if needed and a diffractive/refractive optics based beam expander. The single photon avalanche diode may require cooling by a thermoelectric cooler (TEC).

By shaping the spatial wavefront through a spatial light modulator, the pulsed laser beam can propagate through a strongly scattering medium (e.g., fog/rain/snow) without lateral diffusion. Furthermore, the backscattering of the pulsed laser beam can be suppressed. A spatial light modulator can modulate amplitude, phase or polarization of the pulsed laser beam in space and time. The spatial light modulator can consists of 40 pairs of InGaAs/GaAs/GaAsP multiple-quantum wells embedded in an asymmetric Fabry-Perot (FP) cavity formed by highly reflective back distributed Bragg reflectors and moderate reflective top distributed Bragg reflectors. The computational camera can include an algorithm for image reconstruction to detect an object in any weather condition (including harsh weather conditions—such as rain/fog/snow) or around the corner (not in line-of-sight).

The pulsed laser of the standalone computational 1 can have a full width at half maximum (FWHM) rise time of an optical pulse or a full width at half maximum fall time of an optical pulse from about 0.01 nanoseconds to about 10 nanoseconds. The full width at half maximum is given by the difference between the two extreme values of an independent variable at which a dependent variable is equal to half of its maximum value. In other words, the full width at half maximum can describe the width of a bump on a curve or function. It is given by the distance between points on the curve at which the function reaches half its maximum value. For Gaussian function $e^{-x^2/(2\sigma^2)}$, the full width at half maximum is $2\sqrt{2\ln 2}\sigma$.

However, it should be noted that to observe around the corner (non line-of-sight) by the standalone computational camera 1, pulsed laser of the standalone computational 1 should have a full width at half maximum rise time of an optical pulse or a full width at half maximum fall time of an optical pulse at less than 1 nanosecond.

The fast rise/fall time can be realized by incorporating using a laser incorporating a laser structure integrated with a voltage controlled modulator and/or a saturable absorber (SA).

The saturable absorber is generally 20 microns, 40 microns, or 100 microns in length. The saturable absorber can be realized by ion implantation of a laser structure. The saturable absorber can be an actively biased waveguide or an unbiased electrically isolated (from the main laser structure) waveguide.

It should be noted that the saturable absorber realized in the form an unbiased electrically isolated (from the main laser structure) waveguide may require bulk active layers (as opposed to quantum well layers) otherwise similar to gain section of the laser structure.

It should be noted that there can be (a) a diffuser/diverging lens after the collimated laser beam to capture the entire field of view of the object and (b) an imaging lens (for the scattered laser beam from the object) prior to the two-dimensional array of single photon avalanche diodes. The diffuser/diverging lens can be refractive optics based or diffractive optics based.

It should be noted that instead of a discrete pulsed laser, an array of pulsed lasers can be utilized. The laser beam from each pulsed laser in the array of pulsed laser can be collimated.

A first prism can deflect a first collimated laser beam (from a first pulsed laser) down and the second prism can deflect the first laser beam upward toward the center. Finally, the third prism can deflect the first collimated laser beam parallel to and under the second collimated undeviated laser beam.

Thus, utilizing a set of right angle deflections, the shape of the laser beam from an array of pulsed laser can be changed from rectangular shape to square shape or to a desired shape for higher composite pulsed laser output power (from an array of lasers) by a beam shaping optical subsystem. Thus, the beam shaping optical subsystem can include one or more prisms.

Furthermore, prisms can be replaced by flat mirrors or a metamaterial surface for beam deflection with minimum loss of output power from the array of pulsed lasers.

Furthermore, this scheme may enable redundancy of a pulsed laser. The failure of a pulsed can be detected by a photodiode, placed behind each pulsed laser.

Alternatively, bare unprocessed indium phosphide based epitaxial materials/layers on indium phosphide substrate can be bonded onto a silicon wafer. Then indium phosphide substrate can be removed and then InGaAs/InP based single photon avalanche diode can be fabricated/constructed. Conventional gold metal based contact on indium phosphide based epitaxial materials/layers can be replaced by nickel based alloyed contact compatible with complementary metal-oxide-semiconductor fabrication on silicon. This scheme can eliminate direct (chip-to-wafer bonding) of InGaAs/InP based single photon avalanche diode chip with the wafer of complementary metal-oxide-semiconductor fabrication on silicon.

The array of single photon avalanche diodes and the pulsed laser can be coupled with the Super System on Chip 400A/400B/400C/400D, which is then coupled with a machine learning (including deep learning/meta-learning and self-learning) algorithm based intention system.

Alternatively, a single electrically controlled photonic-crystal (pulsed) laser or a two-dimensional array of electrically controlled photonic crystal (pulsed) lasers can be utilized, wherein each electrically controlled photonic-crystal (pulsed) laser can provide a pulse in nanoseconds or in sub-nanoseconds.

It should be noted that a discrete pulsed electrically pumped vertical cavity surface emitting laser has limited output power, however can be scaled in arrays with tens to thousands of pulsed electrically pumped vertical cavity surface emitting lasers on one single wafer for higher power density at a pulse duration in nanoseconds or sub-nanoseconds.

Gain-switching utilizes the structure with an extremely large equivalent spot size. In dynamic behavior, the use of extremely large equivalent spot size results in enhanced gain-switching and eventually in an efficient picosecond operation mode. This principle can work with bulk, quantum well and vertical cavity surface emitting laser.

Alternatively, a picoseconds high optical output power pulsed laser can be a mode locked (e.g., passively mode locked) integrated external-cavity surface emitting laser. It can contain a highly reflective bottom distributed Bragg reflector, a quantum-well/quantum dot absorber, a pump distributed Bragg reflector and a gain region of multiple quantum-well/quantum dot layers and an antireflection section and it is optically pumped approximately at an 45 degrees angle. But, it can be electrically pumped also.

For example, an optically pumped mode locked integrated external-cavity surface emitting laser is an ultrafast semiconductor disk laser, where the saturable absorber can be integrated in the semiconductor gain structure. But, the absorber needs to be protected from the pump excitation and thus, the absorber should be located beneath the gain structure and separated by a pump-reflecting mirror.

Furthermore, a transparent wafer based mode locked integrated external-cavity surface emitting laser structure can enable higher exit output power and wafer-level integration of an output (optical) coupler with etched mirrors (facets) and electrical pumping of the gain section of the mode locked integrated external-cavity surface emitting laser.

An ammonium hydroxide dip, followed by $(NH4)_2S_x$ and KrF pulsed laser (at a low intensity) treatments or alternatively, argon/nitrogen ion beam treatment on etched mirrors (facets), then deposition of about 2 nm of silicon/amorphous silicon/hydrogenated amorphous silicon/zinc selenide and 20 nm of aluminum oxide under vacuum can reduce surface defects. The ion beam energy, the ion beam density, the ion beam exposure time and the composition of the background gas mixture are critical in argon/nitrogen ion beam treatment. Typically, the entire etching of mirrors (facets) and passivation process of mirrors (facets) can be performed under ultrahigh vacuum (UHV) to reduce any possibility of surface oxidation prior to passivation. Alternatively, regrowth of passivation material (e.g., semi-insulating indium phosphide) around the etched mirrors (facets) can reduce surface defects.

For heat dissipation, a mode locked integrated external-cavity surface emitting laser can be attached/bonded to a heat spreader (e.g., a diamond heat spreader).

For reduction of costs, a vertical cavity surface emitting laser at 850 nm wavelength and two-dimensional array of single photon silicon avalanche diodes at 850 nm wavelength can be utilized. But for the reduced reflection, 1550 nm wavelength may be ideal.

FIG. 3U2 illustrates another embodiment of a standalone computational camera 2. This is similar to the embodiment illustrated in FIG. 3U1, except there is an additional metamaterial surface for ultrafast laser beam steering. Furthermore, instead of the metamaterial surface, an array of phase modulators (either electrically controlled, as described in FIG. 3V1 or optically controlled, as described in FIG. 3V2) can be utilized. It should be noted that instead of a discrete pulsed laser, an array of pulsed lasers can be utilized and the parallel beam from the array of pulsed lasers can be shaped from rectangular to square by right angle prisms/rotators/ metamaterial surface.

FIG. 3U3 illustrates another embodiment of a standalone computational camera 3. A high peak (e.g., 2 to 10 watts) power Wavelength tunable (multi-wavelength) pulsed laser (TL) (e.g., with wavelength span at 850 nm+/−20 nm or 1550 nm+/−20 nm and pulse duration in nanoseconds or sub-nanoseconds) is coupled in a hybrid master oscillator power amplifier configuration. However, the wavelength tunable laser is optically isolated from the power amplifier by an isolator. The output of the power amplifier is coupled with a 1×N cyclic arrayed waveguide router (wherein the optical energy of different wavelengths is uniformly distributed to N output waveguides). The N output waveguides (each output waveguide can be integrated with a semiconductor optical amplifier) of the cyclic arrayed waveguide router (cyclic AWG) are coupled with N 3-port optical circulators. Each 3-port optical circulator has three (3) ports, the first port of the 3-port optical circulator is optically coupled with the output waveguide of the 1×N cyclic arrayed waveguide router, the second port of the 3-port optical circulator is optically coupled with a single photon avalanche diode and the third port of the 3-port optical circulator is optically coupled with a diverging lens for viewing a stationary or moving target and an imaging lens. The single photon avalanche diode is detecting the scattered light from a stationary or moving target.

Each single photon avalanche diode and the high peak power wavelength tunable pulsed laser are coupled with the Super System on Chip 400A/400B/400C/400D, which is then coupled with a machine learning (including deep learning/meta-learning and self-learning) algorithm based intention system.

Alternatively, a modulated optical signal (from a wavelength tunable (multi-wavelength) continuous wave laser) may be utilized in lieu of a pulsed optical signal (from a wavelength tunable (multi-wavelength) pulsed wave laser). The modulation scheme may contain a suitable modulation pattern (e.g., Hamiltonian codes). The single photon avalanche diode will then detect the (incident) modulation pattern, which can be shifted in time, upon scattering from a stationary or moving target.

FIG. 3U4 illustrates an embodiment of a high power (e.g., up to 100 watts) wavelength tunable pulsed laser module. The output beam of a first (wavelength) tunable pulsed (e.g., about 1 nanosecond or 10-100 picoseconds) laser diode 1 (e.g., a distributed feedback laser/gain-switched laser/FIG. 3Q) can be collimated by a collimating lens 1, propagated through a 60 dB isolator 1 to a special purpose non-polarizing beam splitter (Special BS) 1. Similarly, the output beam of a second (wavelength) tunable pulsed (e.g., about 1 nanosecond or 10-100 picoseconds) laser diode 2 (e.g., a distributed feedback laser/gain-switched laser/FIG. 3Q) can be collimated by a collimating lens 2, propagated through a 60 dB isolator 2 to a non-polarizing beam splitter (BS) 2.

Alternatively, the first wavelength tunable pulsed laser diode 1 and the second wavelength tunable pulsed laser diode 2 can be optically coupled with a Y-branched waveguide (optical) coupler or a multimode interference (MMI) (optical) coupler, eliminating both the special purpose non-polarizing beam splitter 1 and non-polarizing beam splitter 2.

The special purpose non-polarizing beam splitter (Special BS) 1 allows the output laser beam (of the wavelength tunable pulsed laser diode 2) from the non-polarizing beam splitter (BS) 2 to pass through and both the output laser beams (of the wavelength tunable pulsed laser diodes 1 and 2) are reflected by a non-polarizing beam splitter 3, then collimated by a collimating lens 3 and passed through an electrically biased tapered power amplifier integrated with an electrically biased optical gate (OG). The output laser beam of the tapered power amplifier is collimated by a collimating lens 4 and passed through a 60 dB isolator 3. Furthermore, the output laser beam can be coupled with a volume Bragg gratings for wavelength stability and the whole module namely the high power (wavelength) tunable pulsed laser module can be temperature stabilized by a thermoelectric cooler.

Furthermore, a high power pulsed laser can be a Febry Perot broad area laser diode or broad area laser diodes with on-chip V-junction angled (e.g., about 15 degrees angle) waveguide cavity. The angled waveguide can also include photonic crystals or microstructures.

Alternatively, a modulated optical signal (from a wavelength tunable (multi-wavelength) continuous wave laser) may be utilized in lieu of a pulsed optical signal (from a wavelength tunable (multi-wavelength) pulsed wave laser) and in this case an optical modulator (which is not shown in FIG. 3U4) will be integrated after the 60 dB isolator in the optical path.

The high power (wavelength) tunable pulsed laser module can be miniaturized utilizing a silicon optical bench.

It should be noted that a collimating lens/receiving lens can be a metamaterial lens. A metamaterial lens consists of an ultrathin (about 1 micron in thickness) flat surface that is covered with an array of nanoscaled pillars or holes. As incident light hits these elements, many of its properties (e.g., polarization, intensity, phase and direction of propagation) changes.

Furthermore, the laser material structure and/or gallium nitride laser driver can be bonded onto the high heat dissipating silicon carbide (SiC) by atomic diffusion bonding. The in plane laser device can be realized by an etched laser facet (mirror). The out plane laser device can be realized by an etched laser facet (mirror) and vertical gratings coupler. For example, the atomic diffusion bonding for the laser material structure on silicon carbide is described below:

The top layer of the laser material on indium phosphide substrate and the top surface of a temporary silicon substrate can be coated with tungsten of about 5 nm thick for atomic diffusion bonding inside a bonding system at about 10 kPa pressure at room temperature.

Indium phosphide substrate is removed in dilute hydrochloric acid (HCl).

Underside exposed layer of the laser material structure and the top surface of a silicon carbide substrate can be coated with tungsten of about 5 nm thick for atomic diffusion bonding inside a bonding system at about 10 kPa pressure at room temperature.

The temporary silicon substrate is removed in potassium hydroxide (KOH) solution.

Exposed tungsten is removed by plasma etching in $CF_4$ gas.

These steps complete the transfer of the laser material structure onto the silicon carbide substrate for in plane laser device by an etched laser facet (mirror) or the out plane laser device by an etched laser facet (mirror) and vertical gratings coupler.

Similarly, gallium nitride material can be transferred onto the silicon carbide substrate for electrical circuit fabrication. Thus, the common silicon carbide substrate can be utilized for fabricating/constructing laser device and electrical circuit. It should be noted that similar scheme can be utilized to bond lithium niobate thin film on a silicon on insulator substrate—for a composite silicon photonic substrate.

FIG. 3V consists of FIG. 3V1, FIG. 3V2 and FIG. 3V3.

A single photon avalanche diode detector is a reverse biased avalanche photodiode (APDs) biased above the avalanche breakdown voltage in the Geiger mode. In this mode, a single incident photon can generate an electron-hole pair to initiate a self-sustaining avalanche, rapidly generating a readily detectable current pulse. After each detection event, the avalanche current must be quenched to restore the detector in the quiescent state to detect the next single photon. Indium-Gallium-Arsenide/Indium-Phosphide (In-GaAs/InP) can enable near room temperature operation single-photon avalanche diode. The single photon avalanche diode detector can be integrated with thin-film optical filter, if needed.

One embodiment is to combine the low-noise silicon single photon avalanche multiplication with the infrared wavelength detection/absorption by a thick (~3000 nm) germanium (Ge) layer.

FIG. 3V1 illustrates such an embodiment. There is a layer of n+ silicon on a high resistance silicon substrate. The layer of n+ silicon has n+ metal (positive) metal contacts. There is a silicon multiplication layer on n+ silicon layer. The silicon multiplication layer has ion implanted p+ regions. There is an epitaxial seed layer (about 200 nm) of germanium on the silicon multiplication layer. On the epitaxial seed layer of germanium, there is a thick (about 3000 nm) germanium layer for infrared wavelength detection/absorption and then followed by p+ germanium layer. It should be noted that germanium on silicon growth is difficult to due to the lattice mismatch. However, germanium on silicon single photon avalanche diode can enable near room temperature operation and reduced after pulsing compared to InGaAs/InP single photon avalanche diode.

Furthermore, the layer of p+ germanium has embedded/patterned light absorbing nanostructures with p+ metal (negative) metal contacts in mesa device architecture and it includes an optical filter.

FIG. 3V2 illustrates a two dimensional array of single photon avalanche diodes in fully parallel processing.

The array of single photon avalanche diodes can be fabricated/constructed, utilizing three-dimensional stacking, wherein a read-out electronic circuitry is just below the plane of the single photon avalanche diodes and the read-out electronic circuitry is coupled with the upper single photon avalanche diodes and a lower printed electronic circuitry by via holes.

Germanium-on-silicon single photon avalanche diode can be compatible with a conventional complementary metal-oxide-semiconductor or complementary metal-oxide-semiconductor+ memristors process technology. Complementary metal-oxide-semiconductor+ memristors process circuit can be fabricated, wherein memristors are integrated onto a complementary metal-oxide-semiconductor+ memristors process platform-enabling a neuromorphic architecture.

A three-dimensional image sensor based on the single photon avalanche diode detectors through silicon via and backside illuminated devices can be realized. Furthermore, such a three-dimensional image sensor can be integrated/co packaged with complementary metal-oxide-semiconductor device/System on Chip or complementary metal-oxide-semiconductor+ memristors device/System on Chip or the Super System on Chip 400A/400B/400C/400D FIG. 3V3 consists of FIG. 3V3.1, FIG. 3V3.2 and FIG. 3V3.3.

FIG. 3V3.1 illustrates integration of an image sensor (based on single photon avalanche diodes-including single photon avalanche diodes fabricated/constructed on indium phosphide or germanium-on-silicon material) with a complementary metal-oxide-semiconductor integrated circuit (of control and read-out electronics).

For example, the integration can be vertical integration utilizing low-temperature direct wafer bonding/indium bump bonding.

FIG. 3V3.2 illustrates integration of an image sensor (based on single photon avalanche diodes-including single photon avalanche diodes fabricated/constructed on indium phosphide or germanium-on-silicon material) with a complementary metal-oxide-semiconductor integrated circuit (of control and read-out electronics) plus a two-dimensional/three-dimensional array of memristors/a two-dimensional/three-dimensional network of memristors.

FIG. 3V3.3 illustrates integration of an image sensor (based on single photon avalanche diodes-including single photon avalanche diodes fabricated/constructed on indium phosphide or germanium-on-silicon material) with a complementary metal-oxide-semiconductor integrated circuit (of control and read-out electronics) plus the Super System on Chip 400A/400B/400C/400D (as described in later paragraphs) for ultrafast image processing/image recognition, deep learning/meta-learning and self-learning.

It should be noted that a 90 nm complementary metal-oxide-semiconductor fabrication/process technology can enable about 1 million density of a two-dimensional array of image sensors (based on single photon avalanche diodes-including single photon avalanche diodes fabricated/constructed utilizing germanium-on-silicon).

The array of pulsed lasers and single photon avalanche diodes can be coupled with the Super System on Chip 400A/400B/400C/400D (as described in later paragraphs) for ultrafast data processing, image processing/image recognition, deep learning/meta-learning and self-learning.

FIGS. 3W1-3W4 illustrate four (4) embodiments of packaging of a computational camera.

FIG. 3W1 illustrates an embodiment, wherein the p-metal of a pulsed laser (P LD) is mounted on a thermally conducting metallized heat spreader (HS) (e.g., aluminum nitride/diamond). All sides of the thermally conducting metallized heat spreader can be metallized. A eutectic gold tin solder (in multilayer thin-films) can be deposited on the top surface of the thermally conducting metallized heat spreader. The thermally conducting metallized heat spreader is placed onto a carrier substrate (CS). The carrier substrate is in the front cutout section of a first printed circuit board (PCB) for the pulsed laser. The carrier substrate has slots for mounting a fast axis collimating lens (FAC), a slow axis collimating lens (SAC), a volume Bragg gratings (VBG) and a diffuser (D) by UV curable epoxy.

It should be noted that a spatial light modulator may be utilized prior to the diffuser (D).

The carrier substrate can be electrically coupled with the first printed circuit board by a low inductance interconnect metal (e.g., ultrasonically welded copper metal bar of about 4 mm wide and 0.3 mm thick).

Generally, ultrasonic welding is the use of high frequency vibration to produce a solid state weld between two components held in proximity (close) contact. It has high reliability due to a low energy cold (no heating) process within a short process time, without any intermetallic phase/thermal expansion mismatch and it enables high ampacity compared to wire bond. The n-side metal of the pulsed laser is electrically coupled with the first printed circuit board by a short flexible circuit (e.g., Molex rigid flex circuit bonded onto n-side metal by epoxy) to realize a low inductance interconnect.

The first printed circuit board has gallium nitride (GaN) field effect transistors (FETs) based integrated circuit, which is driven by a driver integrated circuit.

It is possible to control the thermal stress in gallium nitride layer on a silicon substrate by inserting an aluminum nitride and an aluminum gallium nitride (AlGaN), as intermediate layers. Furthermore, use of a silicon nitride interlayer can reduce the density of threading dislocations, by encouraging threading dislocations to bend into the (0001)-plane and move laterally where they annihilate with dislocations of opposite Burgers vector.

Furthermore, the silicon substrate can be replaced by a composite substrate including a bulk substrate of silicon, followed by a diamond thin/thick film of 1-50 microns in thickness and then followed by a silicon thin-film of 0.5-2 microns in thickness. The above substrate can be identified as diamond-on-silicon.

Thus, gallium nitride field effect transistors can be fabricated/constructed, utilizing a substrate like silicon, silicon-on-diamond, silicon carbide or diamond.

It should be noted that the diamond substrate can (i) reduce an thermal impedance (° C./W) by as much as 60% and (ii) increase power density (of gallium nitride field effect transistors) by 3-fold compared to the silicon carbide substrate. The gallium nitride field effect transistors based integrated circuit can provide current at about 250 amp with a full width at half maximum rise time/fall time of an electrical pulse current between 1 ns and 10 ns.

Alternatively, the carrier substrate can have a first metallized stepped vertical structure eliminating the heat spreader completely and a second metallized stepped vertical structure. The first metallized stepped vertical structure and the second metallized stepped vertical structure are separated in dimension and electrically isolated. However, the first metallized stepped vertical structure is electrically connected to the first contact at bottom of the carrier substrate by a metallized via hole(s) and the second metallized stepped vertical structure is electrically connected to the second contact at bottom of the carrier substrate by a metallized via hole(s).

The first metallized stepped vertical structure is for p-metal down bonding/mounting of the pulsed laser/array of lasers. The second metallized stepped vertical structure is for an extremely short and very wide wedge/ribbon bond to n-metal of the pulsed laser/array of lasers.

There may be more than one extremely short and very wide wedge/ribbon bonds to minimize inductance.

The carrier substrate can be further electrically coupled to a printed circuit board (PCB) by an interposer. An interposer is an electrical interface routing device, which can spread or reroute a connection from one electrical interface to another electrical interface.

Similarly, FIG. 3W1 contains a second printed circuit board for an array of the single photon avalanche diode detectors and an imaging lens. However, the array of the single photon avalanche diode detectors and the imaging lens can be placed onto a separate carrier substrate. The array of the single photon avalanche diode detectors can be bonded onto a complementary metal oxide semiconductor-electronic integrated circuit via indium bumps, wherein the above stack can be temperature controlled/cooled by a thermoelectric cooler for higher performance, especially the single photon avalanche diode detector is based on indium phosphide material.

The first printed circuit board and the second printed circuit board are electrically coupled with the Super System on Chip 400A/400B/400C/400D.

The carrier substrate, the first printed circuit board, the second printed circuit board and the Super System on Chip 400A/400B/400C/400D (for ultrafast data processing, image processing/image recognition, deep learning/meta-learning and self-learning) can be housed in a hermetically sealed enclosure.

The hermetically sealed enclosure can be thermally coupled with a finned heat sink/finned heat sink with a fan. Furthermore, the hermetically sealed enclosure has two (2) transparent metal coated glass windows for pulsed heating to defrost or deice.

FIG. 3W2 is similar to FIG. 3W1, except the short flexible circuit interconnect is replaced by a mechanical clamp between the first printed circuit board and a metal (e.g., copper) holder, placed on top of the n-metal to realize a low inductance metal interconnect. Furthermore, many wide (e.g., each 2 mm wide) and thick (e.g., each 0.2 mm thick) gold heavy wedge/ribbon bonds may also be suitable to realize a low inductance metal interconnect.

FIG. 3W3 is similar to FIG. 3W1, except it has an array of pulsed lasers, followed by an array of collimating lenses (CLA) and a beam shaper (BSP) to shape the laser beam to a composite square profile from a rectangular profile from the array of pulsed lasers.

FIG. 3W4 is similar to FIG. 3W3, except the short flexible circuit interconnect is replaced by a mechanical clamp between the first printed circuit board and a metal (e.g., copper) holder, placed on top of the n-metal of the array of pulsed laser to realize a low metal inductance interconnect.

With an advanced fabrication/construction technology of an etched facet/mirror, far away from the p-metal, on a semiconductor surface, an edge step of a suitable dimension can be fabricated/constructed all the way to the n+ substrate. The edge step can be passivated and planarized by a spin on glass (SOG). A large diameter via hole(s) to the n+ substrate can be fabricated/constructed and completely filled with eutectic n-metal (AuGe—Ni)—Au. In this configuration both p-metal and n-metal contacts can be bonded by flip-chip technology eliminating wire bonds completely, enabling faster optical signal (less than 5 ns optical pulse width) at 10-20 KHz repetition rate.

FIG. 3W5 illustrates an embodiment of flip chip mounting a pulsed laser of a computational camera directly bonded (utilizing eutectic/epoxy bond) on a complementary metallized pattern of the printed circuit board, wherein n-metal contact is fabricated/constructed by metallized via hole(s), as described in the above paragraph. Furthermore, optical components can be bonded (utilizing epoxy) onto the precise cutout holes of the printed circuit board.

FIG. 3W6 is similar to FIG. 3W5, except it has an array of pulsed lasers, instead of a pulsed laser.

FIG. 3X consists of FIG. 3X1, FIG. 3X2, FIG. 3X3, FIG. 3X4, FIG. 3X5, FIG. 3X6, FIG. 3X7, FIG. 3X8, FIG. 3X9 and FIG. 3X10.

FIGS. 3X1-3X10 illustrate ten (10) embodiments of an integrated detection and ranging subsystem on multi-layer of polymer/spin-on-glass on a substrate (e.g., silicon on insulator), utilizing a three-dimensional photonic integrated circuit based optical phase array.

A (electro optic) phase modulator utilizes a metal electrode/optical element, placed along an optical waveguide. By applying electric voltage on the electrode or the optical signals on the optical element (e.g., a ring resonator), the refractive in the waveguide can be changed in order to control the phase of the light.

For example, an electrically induced phase modulator of a phase transition material-vanadium dioxide is about 375 nm×375 nm in area and about 50 nm in thickness. Similarly, an optically induced phase modulator of a phase transition material-vanadium dioxide is about 250 nm×250 nm in area and about 50 nm in thickness.

The unwanted side lobes can be suppressed when phase modulators are spaced less than λ/2 (1550 nm) distance. A non-uniform spacing of the phase modulators may be used to suppress unwanted side lobes.

FIG. 3X1 illustrates an integrated embodiment of a light detection and ranging subsystem 5 (based on a three-dimensional photonic integrated circuit based optical phase array), utilizing a narrow linewidth laser, which is coupled with a 1×N multimode interference coupler, an array of (electrically controlled) phase modulators, an array of semiconductor amplifiers/variable optical attenuators and an array of vertical couplers (for laser beam steering). The return optical path is coupled with an array of balanced photodiodes (e.g., germanium material photodiodes), which are also coupled with the reference narrow linewidth laser via a multimode interference coupler.

The narrow linewidth laser can be fabricated/constructed by butt coupling a reflective semiconductor amplifier (RSOA) with a spot size converted waveguide, an array of ring resonators (with a heating element on each ring resonator) and a loop mirror.

The array of balanced photodiodes can be coupled with the Light-to-Distance/Velocity System on Chip System on Chip. The Light-Distance/Velocity System on Chip is then coupled with a machine learning (including deep learning/meta-learning and self-learning) algorithm based intention system.

Furthermore, the Light-Distance/Velocity System on Chip can include/couple with a Lorentzian Least Squares Fitting Processor (LLSF Processor) to improve precision and sensitivity beyond the coherence length of the narrow linewidth laser.

FIG. 3X2 illustrates another integrated embodiment of a light detection and ranging subsystem 6 (based on a three-dimensional photonic integrated circuit based optical phase array). This embodiment is similar to the embodiment in FIG. 3X1, except an array of phase modulators are controlled optically (e.g., a phase transition material-vanadium dioxide under optical excitation), instead being controlled electrically.

FIG. 3X3 illustrates another integrated embodiment of a light detection and ranging subsystem 7 (based on a three-dimensional photonic integrated circuit based optical phase array). This embodiment is similar to the embodiment in FIG. 3X1, except the narrow linewidth laser is fabricated/constructed differently, by utilizing an array of multiwavelength/multicolor distributed feedback lasers, coupled with a multimode interference coupler, wherein the multimode interference coupler is coupled with a curved semiconductor optical amplifier. The output of the curved semiconductor optical amplifier is (free-space) coupled with a planar lightwave circuit (PLC). The planar lightwave circuit includes a directional coupler (DC) and high reflectivity coated waveguide for feedback to the array of multiwavelength/multicolor distributed feedback lasers.

FIG. 3X4 illustrates another integrated embodiment of a light detection and ranging subsystem 8 (based on a three-dimensional photonic integrated circuit based optical phase array). This embodiment is similar to the embodiment in FIG. 3X3, except an array of phase modulators are controlled optically, instead being controlled electrically.

FIG. 3X5 illustrates another integrated embodiment of a light detection and ranging subsystem 9 (based on a three-dimensional photonic integrated circuit based optical phase array). This embodiment is similar to the embodiment in FIG. 3X1, except the narrow linewidth laser is based on a distributed feedback laser, which is optically coupled with a whispering gallery microresonator/high Q microresonator via a half pitch graded index lens.

FIG. 3X6 illustrates another integrated embodiment of a light detection and ranging subsystem 10 (based on a three-dimensional photonic integrated circuit based optical phase array). This embodiment is similar to the embodiment in FIG. 3X5, except an array of phase modulators are controlled optically, instead being controlled electrically.

FIG. 3X7 illustrates another integrated embodiment of a light detection and ranging subsystem 11 (based on a three-dimensional photonic integrated circuit based optical phase array). This embodiment is similar to the embodiment in FIG. 3X1, except the narrow linewidth laser is based on an external cavity laser.

An external cavity laser can provide narrow linewidth. Generally, the external cavity laser can consist of an external cavity, a semiconductor gain chip (with an anti-reflection coating on both facets of the semiconductor gain chip) and a volume holographic Bragg grating (VHBG). This is similar to a conventional extended cavity diode laser but with the external cavity replacing one of the mirrors. Here, the external cavity acts as a mirror and the resonant feedback is re-injected into the gain chip if the frequency of the extended cavity diode laser matches the resonance frequency of the external cavity. As the light travels back and forth inside the external cavity before feeding back to the gain chip, this configuration effectively enables a very long cavity to ensure an ultra-narrow linewidth (less than 50 Hz) laser.

FIG. 3X8 illustrates another integrated embodiment of a light detection and ranging subsystem 12 (based on a three-dimensional photonic integrated circuit based optical phase array). This embodiment is similar to the embodiment in FIG. 3X7, except an array of phase modulators are controlled optically, instead being controlled electrically.

FIG. 3X9 illustrates another integrated embodiment of a light detection and ranging subsystem 13 (based on a three-dimensional photonic integrated circuit based optical phase array). This embodiment is similar to the embodiment in FIG. 3X8, except it utilizes, electrically controlled nanoscaled antennas (for both phase control and laser beam steering) of phase transition/phase change material. It is desirable to have the maximum dimension of the nanoscaled antenna between 2 nm to 1000 nm.

FIG. 3X10 illustrates another integrated embodiment of a light detection and ranging subsystem 14 (based on a three-dimensional photonic integrated circuit based optical phase array). This embodiment is similar to the embodiment in FIG. 3X9, except it utilizes, optically controlled nanoscaled antennas (for both phase control and laser beam steering) of phase transition/phase change material. It is desirable to have the maximum dimension of the nanoscaled antenna between 2 nm to 1000 nm.

Generally the array of antennas can be either one-dimensional or two-dimensional. The array of antennas actively can be actively controlled by an external stimulus (e.g., an electrical (voltage/current) or optical or terahertz signal).

For example, a nanoscaled slot antenna element can consist of 30 nm wide etched slot into a metal (e.g., gold) thin-film of about 40 nm thickness. The metal thin-film can be deposited on a phase transition (e.g., vanadium dioxide) thin-film of about 25 nm thickness. The length of the slots can be about 300 nm. The spacing between adjacent nano-slot centers is about 100 nm. The phase transition thin-film can be deposited on a suitable base substrate (e.g., alumina, diamond, lithium niobate, silicon, silicon on insulator).

The larger laser beam steering angle may be possible by optimizing the geometric parameters of the antenna elements and utilizing non-identical antenna elements.

The angular steering of laser beam range can be extended by decreasing the period between the emitting elements to sub-wavelength dimensions at the cost of individual control of each single emitter.

Generally, a phase transition material is a solid material (e.g., vanadium dioxide), wherein its lattice structure can change from a particular form to another form, still remaining crystal-graphically solid. But, a phase change material is a material (e.g., $Ge_2Sb_2Te_5$ (GST), $Ge_2Sb_2Se_4Te_1$ (GSST) or $Ag_4In_3Sb_{67}Te_{26}$ (AIST)), wherein its phase can change from a solid to liquid, or its phase can change from an amorphous to crystalline, or crystalline to amorphous.

Furthermore, a phase transition material (e.g., vanadium dioxide) may generate an optical loss; an alternative phase change material (e.g., $Ge_2Sb_2Te_5$ (GST), $Ge_2Sb_2Se_4Te_1$ (GSST) or $Ag_4In_3Sb_{67}Te_{26}$ (AIST)) can be utilized.

It should be noted that the multiple optical components of the LiDAR 1 in FIG. 3L, LiDAR 2 in FIG. 3M, LiDAR 3 in FIG. 3N, LiDAR 4 in FIG. 3O, LiDAR 5 in FIG. 3X1, LiDAR 6 in FIG. 3X2, LiDAR 7 in FIG. 3X3, LiDAR 8 in FIG. 3X4, LiDAR 9 in FIG. 3X5, LiDAR 10 in FIG. 3X6, LiDAR 11 in FIG. 3X7, LiDAR 12 in FIG. 3X8, LiDAR 13 in FIG. 3X9 and LiDAR 14 in FIG. 3X10 can be optically coupled by photonic wire bond (PWB) waveguides on a common master platform substrate (e.g., of aluminum nitride (AlN) ceramic or a combination of copper, aluminum nitride and copper platform).

Photonic wire bonding is a technique in which photonic waveguides are written with an ultrafast laser into a photoresist material via two-photon lithography, producing freespace photonic wires that can optically connect disparate optical components on a common platform, just as electronics can be connected via conventional metal wire bonding on a printed circuit board. Photonic integrated circuits and waveguides can be placed on a common platform substrate using a standard pick-and-place machine. The optical coupling between the photonic integrated circuits and waveguides can be embedded into a photosensitive resist. The positions of the optical coupling structure within the photosensitive resist are detected using three-dimension machine vision techniques with sub-100 nm accuracy. The shape of the photonic wire bond waveguides are designed according to the recorded imaged positions of optical structures and defined by two-photon lithography. Unexposed photoresist can be removed and the photonic wire bond waveguides are embedded in a low-index cladding material.

For example, a master platform can be copper of about 0.125 mm thickness, followed by aluminum nitride of about 0.25 mm to 0.4 mm thickness, followed by about 0.125 mm thickness of copper. The master platform can consists of a stepped pad, slots for optical mounting and metallized via holes for electrical connections. The master platform can be also a heat spreader.

The light detection and ranging subsystems, as described in previous paragraphs can enable LiDAR-on-Chip, on a silicon-on-insulator substrate/silicon-on-silicon nitride substrate. Ultimately, the light detection and ranging subsystem(s), as described in previous paragraphs shall be hermetically sealed to protect from environment.

FIG. 3Y consists of FIG. 3Y1 and FIG. 3Y2.

FIG. 3Y1 illustrates a diagram for ultrafast laser beam steering utilizing a metamaterial surface (e.g., material of vanadium dioxide) and a laser (e.g., a mode locked laser). This metamaterial can be tunable (electrically or optically) and/or time-varying and/or space-varying.

FIG. 3Y2 illustrates another diagram for ultrafast laser beam steering utilizing a metamaterial surface and a photonic crystal (broad area) semiconductor laser. The vertical stack configuration of the photonic crystal (broad area) semiconductor laser includes an active layer and photonic crystal layer sandwiched by an upper cladding layer and a lower cladding layer. The light emission from the photonic crystal (broad area) semiconductor laser can be steered by a metamaterial surface. However, the photonic crystal (broad area) semiconductor laser can be replaced by a vertical cavity surface emitting laser.

A metamaterial surface can consist of a two-dimensional array of resonant metasurface unit cells (fabricated/constructed on a material with electrically tunable dielectric constant). By controlling the electrical stimulus (voltage or current) to each individual metasurface unit cell, the resonance frequency can be adjusted. Also the phase of the transmitted electromagnetic wave through the unit cell can be also controlled-enabling the manipulation of the phase front of the transmitted electromagnetic wave through the metasurface for laser beam steering.

The material with electrically tunable dielectric constant can be a phase transition material/phase change material/liquid crystal/graphene.

It should be noted that ultrafast beam steering can be obtained, utilizing (a) an electric field for triggering insulator-to-metal phase transition in a particular phase transition material-vanadium dioxide or (b) terahertz for triggering a phase change in a particular phase change material-$Ag_4In_3Sb_{67}Te_2$ (AIST).

The optical phase conjugation can operate like a dynamic holography. In optical phase conjugation, light is always reflected straight back the way it came from, no matter what the angle of incidence is. This reflected conjugate wave therefore propagates backwards through a distorting medium—such as rain/fog/snow and essentially un-does any distortion and returns to a coherent beam of parallel rays traveling in the exact opposite direction. This along with Huygen's principle of wave propagation can explain the time-reversed reconstruction principles in optical phase conjugation.

Figure 3Z:
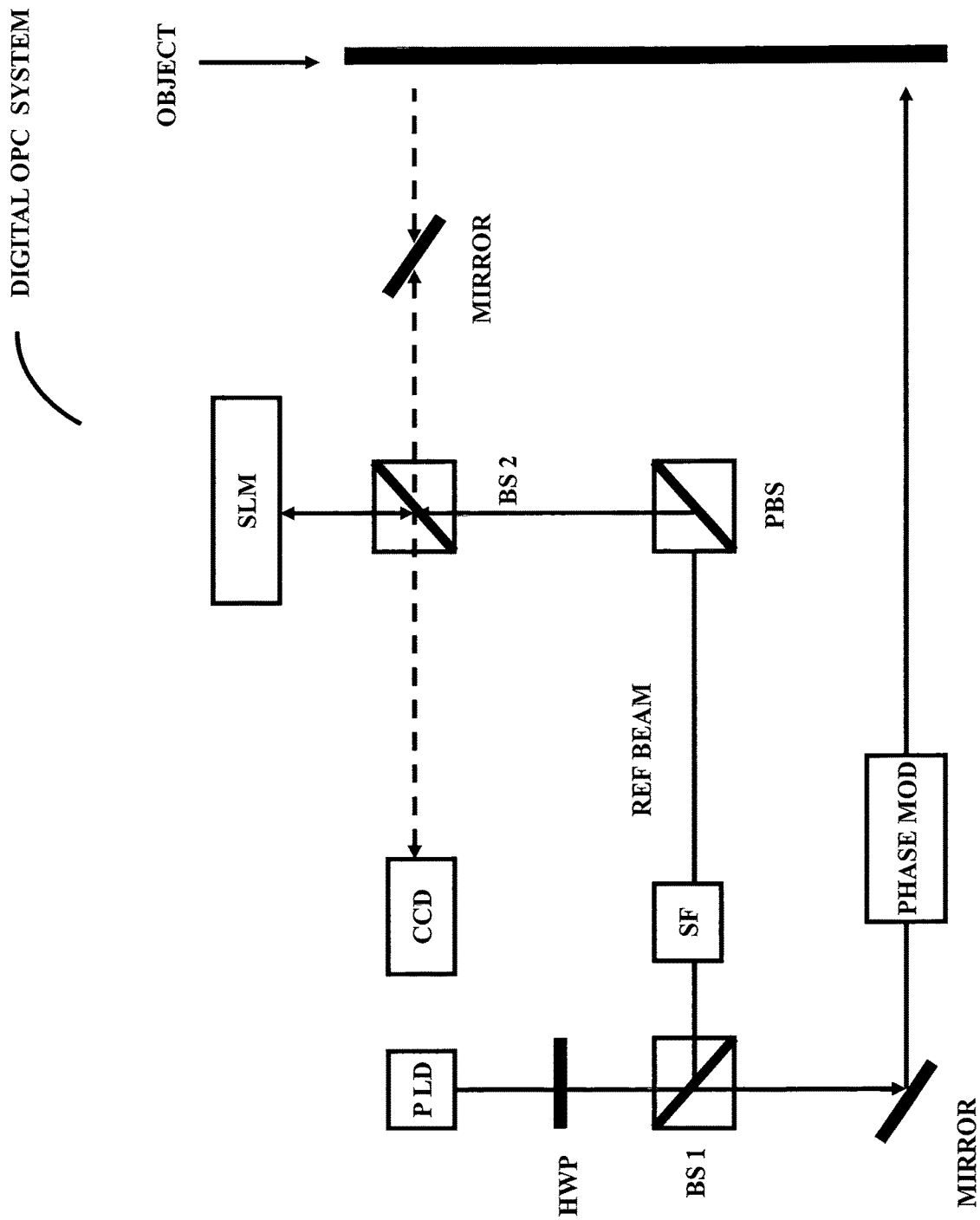
FIG. 3Z illustrates an embodiment to detect an object in any weather condition (including harsh weather conditions—such as rain/fog/snow) by a digital optical phase conjugation (DOPC) system, which can be utilized or integrated with a computational camera.

FIG. 3Z illustrates an embodiment to detect an object in any weather condition (including harsh weather conditions—such as rain/fog/snow) by a digital optical phase conjugation system. The output of the pulsed laser is passing through a half wave plate, then split by a non-polarizing beam splitter (BS) 1. One laser beam is passing through a phase modulator to a stationary or moving target. Another laser beam is passing through a spatial filter and polarizing beam splitter (PBS) toward a non-polarizing beam splitter (BS) 2. The non-polarizing beam splitter (BS) 2 is placed at the symmetry plane between a spatial light modulator and an array of CCD pixels. The scattered light from a stationary or moving target is also passing through the non-polarizing beam splitter (BS) 2. The pixel size of a spatial light modulator is larger than that of a CCD pixel. But, a lens can be utilized to enlarge the CCD pixel. The orientation of the array of CCD pixels and the spatial light modulator is of critical importance in the digital optical phase conjugation system. Furthermore, the digital optical phase conjugation system can be integrated with the computational camera, as described in previous paragraphs.

In general, but not limited to, the intelligent vehicle system (including a robotic/self-driving vehicle system) for self-intelligence, sensor-awareness, context-awareness and autonomous actions, remembering the patterns and movements can include:
(a) a Super System on Chip 400A/400B/400C/400D for ultrafast data processing, image processing/image recognition, deep learning/meta-learning and self-learning, wherein the Super System on Chip 400A/400B/400C/400D includes:
(i) a processor-specific electronic integrated circuit,
(ii) an array or a network of memristors for neural processing, and
(iii) a photonic component or a photonic integrated circuit, wherein the photonic component includes an optical waveguide, wherein the processor-specific electronic integrated circuit in said (i), the array or the network of memristors in said (ii), and the photonic component or the photonic integrated circuit in said (iii) of the Super System on Chip 400A/400B/400C/400D are interconnected or coupled in two-dimension or three-dimension electrically and/or optically (e.g., by optical wavelength division multiplexing and/or optical time division multiplexing), wherein the Super System on Chip 400A/400B/400C/400D is coupled with a digital signal processor and/or an artificial eye, wherein the artificial eye includes light activated and/or electrically activated switches
Furthermore, for example, the machine learning (including deep learning/meta-learning and self-learning) algorithm based near real time/real time intention system of the Super System on Chip 400A/400B/400C/400D can be sensor-aware and/or context-aware and it can alert the user (driver) of the intelligent vehicle about the intention of other users (drivers of other intelligent vehicles) in proximity,
(b) a detection system, wherein the detection system includes (i) or (ii) or (iii), as listed below,
(i) a radar or a radar comprising metamaterials or a ground penetrating radar,
(ii) a four-dimensional (4-D) light detection and ranging subsystem to measure distance and/or velocity, wherein the four-dimensional light detection and ranging subsystem is hermetically sealed. The four-dimensional (4-D) light detection and ranging subsystem can include one or more narrow linewidth (less than 200 Hz) lasers and one or more photodiodes/balanced photodiodes. However, it should be noted that the one laser can be a semiconductor diode laser or a master oscillator power amplifier (MOPA) or a fiber laser,
(iii) a computational camera, or one or more cameras, wherein the computational camera includes one or more pulsed lasers, wherein the one pulsed laser can be a semiconductor diode laser or a master oscillator power amplifier (MOPA) or a fiber laser, wherein the one pulsed laser may be optically coupled with a spatial light modulator wherein the one pulsed laser has a full width at half maximum rise time of an optical pulse or a full width at half maximum fall time of an optical pulse from 0.01 nanoseconds to 10 nanoseconds, wherein the computational camera further includes one or more single photon avalanche diodes, wherein the one pulsed laser is electrically coupled with an integrated circuit including gallium nitride transistors, wherein a full width at half maximum rise time of an electrical pulse current or wherein a full width at half maximum fall time of the electrical pulse current of the integrated circuit including gallium nitride transistor's is between 1 nanosecond and 10 nanoseconds, wherein the detection system can be coupled with a sub-terahertz imaging system. The computational camera can couple with or include a real time image reconstruction algorithm to detect an object in a harsh weather or around a corner. A sub-terahertz imaging system can transmit a signal at a sub-terahertz wavelength and measure the absorption and reflection of the scattered signal (from an object) at the sub-terahertz wavelength by a two-dimensional array of receivers, wherein each receiver consists of a heterodyne detector. The signal from the two-dimensional array of receivers can be coupled with a processor to recreate an image of the object. The output signals of the two-dimensional array of receivers can be used to calculate the distance of the object and combining/steering the output signals of the two-dimensional array of receivers can be used to image of the object, wherein the Super System on Chip 400A/400B/400C/400D is coupled with the detection system.

The detection system can be coupled with or includes an artificial intelligence/machine learning/deep learning (e.g., neural networks based deep learning)/fuzzy logic (including neuro-fuzzy logic) algorithm.

The detection system can be also coupled with or includes a near real time map or an augmented reality enhanced near real time map.

The four-dimensional light detection and ranging subsystem or the computational camera can be coupled with a gyro sensor or a global positioning system or an augmented reality enhanced global positioning system.

The four-dimensional light detection and ranging subsystem or the computational camera can be in a hermetically sealed housing. They can be housed in a side mirror or a head light of the intelligent vehicle system.

However, the hermetic sealed housing may include both a diverging lens and an imaging lens, placed at the exterior of the hermetic sealed housing.

The hermetic sealed housing with a front cover glass surface (placed at the exterior of the hermetic sealed housing) may require cleaning (from just) and defrosting/deicing. The defrosting/deicing can be realized efficiently and quickly by very rapid pulsed current based heating (of heat flux of 10 to 100 watts/$cm^2$) on a transparent metal coating (e.g., indium tin oxide or index matched indium tin oxide) on the front cover glass surface (placed at the exterior of the hermetic sealed housing).

Alternatively, the diverging lens and the imaging lens can be coated with a transparent metal coating on the outer front surface for very rapid pulsed heating in order to quickly defrost/deice.

The four-dimensional light detection and ranging subsystem can be a coherent/Synthetic Aperture based coherent subsystem.

The four-dimensional light detection and ranging subsystem can include a stabilized chirped pulsed laser or an optical phase-locked loop.

The four-dimensional light detection and ranging subsystem can be either frequency modulation or amplitude modulation.

The four-dimensional light detection and ranging subsystem can include a two-dimensional/three-dimensional optical phased array for laser beam steering.

The optical phased array for laser beam steering can include one or more semiconductor optical amplifiers or variable optical attenuators.

The four-dimensional light detection and ranging subsystem can include an array of nanoscaled antennas, wherein each nanoscaled antenna is passively uncontrolled or actively controlled for laser beam steering.

As discussed before, to achieve coherent emitters, a 10-element array of vanadium dioxide slot nanoantennas should be fed by a single narrow linewidth laser via a multimode interference coupler (or by an array of phase locked/injection locked narrow linewidth lasers). A 10-element array of vanadium dioxide slot nanoantennas can enable about ±20° angle. Vertical stacked layers (separated by a silicon dioxide/polymer layer) of a 10-element array of vanadium dioxide slot nanoantennas can be coupled with a narrow linewidth laser and this configuration can enable about ±20° angle in horizontal axis and vertical axis to enable three-dimensional optical phase array.

Furthermore, an individual vanadium dioxide slot nanoantenna can be electrically controlled (about 10 nanoseconds switching time) by via metal electrodes/transparent graphene nanoheaters, coupled through metallized via holes. Alternatively an individual vanadium dioxide slot nanoantenna can be optically controlled (about 1 nanosecond switching time) by via waveguides and a laser (e.g., a 1550 nm laser).

The three-dimensional optical phased array for laser beam steering can include a first (optical) layer of a first optical material and a second (optical layer) of a second optical material, wherein the first (optical) layer includes an array of (nanoscaled) antennas of a phase transition/phase change/transition metal dichalcogenide (TMDC) material (the transition metal dichalcogenide material is a high second harmonic (SH) generation material) on the first optical material, wherein the second (optical) layer includes an array of (nanoscaled) antennas of a phase transition/phase change/second harmonic generation material on the second optical material, wherein the first (optical) layer of the first optical material and the (second) optical layer of the second optical material are isolated by an electrically insulating layer, wherein the first optical material and the second optical material can be similar or dissimilar in optical properties. It is desirable to have the maximum dimension of the nanoscaled antenna between 2 nm to 1000 nm.

It may be necessary to utilize some chemical mechanical polishing to ensure sufficiently flat/planar surfaces and to accurately align the first (optical) layer with the second (optical) layer via a self-aligned vertical stacking process.

For example, a first silicon nanomembrane can be transfer printed onto a suitable substrate (e.g., silicon on insulator substrate for many vertical stacks). A dielectric layer for waveguide, a phase transition/phase change layer for (nanoscaled) antennas (e.g., dipole/slot) and metallization on the phase transition/phase change layer and edge metal bond pads can be deposited and fabricated. A spin-on dielectric, such as spin-on-glass (SOG) or polyimide can be coated as a separation layer. It may be necessary to utilize some chemical mechanical polishing of the separation layer to ensure sufficiently flat/planar surface. A second silicon nanomembrane can be transfer printed.

Via holes (dry etching through the separation layer) can used to contact the metallization (for electrical coupling) on the phase transition/phase change layer. Alternatively, slanted etched waveguides, surface gratings and mirrors can be fabricated (for optical coupling) on the phase transition/phase change layer.

The above fabrication steps can be repeated to realize multiple vertical layers, wherein each vertical layer is coupled by a single narrow linewidth laser via a multimode interference coupler (or by an array of phase locked/injection locked narrow linewidth lasers) to realize a three-dimensional optical phase array.

Because a phase transition material (e.g., vanadium dioxide) may generate an optical loss, an alternative phase change material (e.g., $Ge_2Sb_2Te_5$ (GST), $Ge_2Sb_2Se_4Te_1$ (GSST) or $Ag_4In_3Sb_{67}Te_{26}$ (AIST)) can be utilized. Alternatively, a transition metal dichalcogenide material (e.g., $MoS_2$) of monolayer/nanoscaled thickness on top of about 50 nm thick metal (e.g., gold) rod with dimensions of about 20 nm by 30 nm can be arrayed (in one-dimension/two-dimension) to form an optical phased arrayed antenna. A transition metal dichalcogenide material can exhibit high second harmonic generation in monolayer/nanoscaled thickness. In practice, a transition metal dichalcogenide material is a second harmonic generation material.

The four-dimensional light detection and ranging subsystem can include a metamaterial surface for laser beam steering.

The four-dimensional light detection and ranging subsystem can include an array of optomechanical antennas or an array of optoacoustical antennas for laser beam steering.

The four-dimensional light detection and ranging subsystem can include an optical switch or an array of holographic optical elements or an array of collimating lenses or a 3-port optical circulator.

The four-dimensional light detection and ranging subsystem can include a laser of a distinct wavelength/tunable wavelength/narrow linewidth. The narrow linewidth laser can be coupled with a processor for Lorentzian least squares fitting to enhance a coherence length of the narrow linewidth laser.

The computation camera can include a germanium-on-silicon single photon avalanche diode, which may be optically coupled with a light absorbing nanostructure. The single photon avalanche diode can be electrically coupled with the Super System on Chip 400A/400B/400C/400D.

The single photon avalanche diode can be electrically coupled with a complementary metal-oxide-semiconductor circuitry. The complementary metal-oxide-semiconductor circuitry can be coupled with an array or a network of memristors.

The single photon avalanche diode can be electrically coupled with an electronic circuitry in a vertically stacked arrangement.

The pulsed laser of the computational camera can be intimately coupled (with reduced inductance) with a laser driver consisting of gallium nitride transistors to realize a current pulse of 1-10 ns full width at half maxima pulse width. In practice, the trailing edge should not have a long tail. The trailing edge should be no more than full width at half maxima pulse width.

The single photon avalanche diode of the computational camera can be electrically coupled with an electronic circuitry in a vertically stacked arrangement.

The pulsed laser of the computational camera can be intermediately coupled with a laser driver consisting of gallium nitride transistors.

The computational camera can include a three-dimensional dynamic real time image reconstruction algorithm to detect an object in a harsh weather or around a corner.

The three-dimensional image reconstruction algorithm can iterate (via parallel computational processing) between depth, reflectivity and background updates, by applying a gradient step followed by a denoiser. For example, the depth update can include a gradient step and a point cloud denoising. The reflectivity update can include a reflectivity step and a point cloud denoising. The background update can include an imaging step and a point cloud denoising.

The computational camera can include an optical phase conjugation system, wherein the optical phase conjugation system consists of a spatial light modulator an imaging device and a laser.

The four-dimensional light detection and ranging subsystem and/or the computational camera and/or the sub-terahertz imaging system and/or the bio-inspired camera can be monolithically integrated or co-packaged on a common substrate. The sub-terahertz imaging system includes a transmitter at a sub-terahertz wavelength and one or more receivers at the sub-terahertz wavelength.

The Super System on Chip 400A/400B/400C/400D can be coupled with a hardware security component, wherein the hardware security component includes an array of memristors.

The Super System on Chip 400A/400B/400C/400D can be coupled with one or more qubits or a photonic neural learning processor, wherein the photonic neural processor includes an interferometer or a laser, wherein the photonic neural learning processor can be also coupled with one or more qubits.

The Super System on Chip 400A/400B/400C/400D can be coupled with a set of instructions in an artificial intelligence algorithm/artificial neural network algorithm/machine learning algorithm, stored in a non-transitory memory component.

The Super System on Chip 400A/400B/400C/400D can be coupled with a set of instructions in computer vision algorithm/image processing algorithm, stored in a non-transitory memory component.

The Super System on Chip 400A/400B/400C/400D can be coupled with a set of instructions in natural language processing, stored in a non-transitory memory component.

The detection system can be coupled with a sub-terahertz imaging system, wherein the sub-terahertz imaging system includes a transmitter at a sub-terahertz wavelength and one or more receivers at the sub-terahertz wavelength, wherein the one receiver consists of a heterodyne detector.

The intelligent vehicle system can include a camera, wherein the camera is a video camera/three-dimensional orientation video camera/ultrafast camera/bio-inspired camera, wherein the bio-inspired camera includes one or more photodetectors to detect an intensity of light in a wide dynamic range.

The intelligent vehicle system can include a body material of graphene integrated with carbon-fiber reinforced epoxy resin or a body material of graphene-like material integrated with carbon-fiber reinforced epoxy resin, or a body material of synthetic silk integrated with carbon-fiber reinforced epoxy resin, wherein the body material is integrated with one or more ultracapacitors or supercapacitors, wherein the one ultracapacitor/supercapacitor can be charged by electromagnetic induction.

The intelligent vehicle system can include a photovoltaic module and/or a photosynthesis module, wherein the photovoltaic module can include a nanostructured surface/nanostructured material.

The intelligent vehicle system can be hydrogen fuel cell powered.

The intelligent vehicle system can include a Long-Term Evolution-Direct communication subsystem or a vehicle-to-vehicle communication subsystem.

The intelligent vehicle system can include a viewing window, wherein light transmission through the viewing window is electrically tunable.

The intelligent vehicle system can include a first head light and a second head light, wherein the first head light includes a first micromirror and a first light emitting diode, wherein the second head light includes a second micromirror and a second light emitting diode.

The intelligent vehicle system can include a proximity payment subsystem, wherein the proximity payment subsystem includes a near-field communication device.

The intelligent vehicle system is sensor-aware or context-aware.

It should be noted that thermal load of the pulsed laser depends on the pulse duration and the pulse repetition rate. The pulsed laser can be bonded p-metal side down onto a metallized heat spreader (e.g., metallized boron arsenide ($B_{12}As_2$) semiconductor/aluminum nitride ceramic/copper diamond composite (DMCH) ceramic).

The heat spreader can be then bonded in near proximity to a pulsed laser driver circuitry (consisting of transistors based on gallium nitride material).

The heat spreader can be a multilayer stack of two or more electrically insulating ceramics (e.g., aluminum nitride and copper diamond composite) with suitable thicknesses, thermal expansion coefficients and thermal conductivities to reduce effective thermal stress and effective thermal resistance.

The wafer of two or more electrically insulating ceramics can be bonded (wafer bonding) to create the multilayer stack of two or more electrically insulating ceramics.

The heat spreader can be a multilayer stack of one or more electrically insulating ceramic (e.g., aluminum nitride and copper diamond composite) and a metal (e.g., copper) with suitable thicknesses, thermal expansion coefficients and thermal conductivities to reduce effective thermal stress and effective thermal resistance. For example, a heat spreader can be copper of about 0.125 mm thickness, followed by about 0.25 mm to 0.4 mm thickness of aluminum nitride, followed by about 0.125 mm thickness of copper.

Alternatively, one or more ceramic layers can be deposited by microwave plasma-assisted chemical vapor deposition (plasma-CVD) and/or molecular beam epitaxy (MBE) onto another ceramic base substrate. For example, aluminum nitride can be deposited by microwave plasma-assisted chemical vapor deposition (Plasma-CVD) from hexakis (dimethylamido)dialuminum-$Al_2(N(CH_3)_2)6$.

Alternatively, one or more ceramic layers can be printed from a suitable liquid slurry consisting of a ceramic powder(s) and a polymer(s), utilizing ultraviolet (UV) light based stereolithography/three-dimensional printing and subsequent post three-dimensional printing high temperature annealing in a suitable gas mixture.

For example, in the case of an indium phosphide (InP) material based pulsed laser, the top layer for the pulsed laser bonding (e.g., p-metal contact down) can be about 400 microns thick semiconductor boron arsenide, followed by about 1600 microns thick AlSiC pyrolytic graphite composite.

Alternatively, in the case of an indium phosphide material based pulsed laser, the top ceramic for the pulsed laser bonding (e.g., p-metal contact down) can be a combination of about 20 microns thick aluminum nitride and about 1000 microns thick copper diamond composite, followed by about 1600 microns thick AlSiC pyrolytic graphite composite.

Alternatively, in the case of an indium phosphide material based pulsed laser, the top layer for the pulsed laser bonding (e.g., p-metal contact down) can be about 400 microns thick semiconductor boron arsenide, followed by about 1600 microns thick Cu—Mo—Cu/AlSiC metal, wherein the 1600 microns thick Cu—Mo—Cu/AlSiC metal (as a base) can include a folded fin or an array of microchannels. However, isolation layers are required to separate the microchannels from the electrical contact to the pulsed laser diode and reduce the CTE value of the cooler to 5-6.5 ppm/K Alternatively, in the case of an indium phosphide material based pulsed laser, the top ceramic for the pulsed laser bonding (e.g., p-metal contact down) can be a combination of about 20 microns thick aluminum nitride and about 1000 microns thick copper diamond composite, then followed by about 1600 microns thick Cu—Mo—Cu/AlSiC metal, wherein the 1600 microns thick Cu—Mo—Cu/AlSiC metal (as a base) can include a folded fin or an array of microchannels.

Alternatively, in the case of an indium phosphide material based pulsed laser, the top layer for the pulsed laser bonding (e.g., p-metal contact down) can be about 400 microns thick semiconductor boron arsenide, followed by about 400 microns thick Cu—Mo—Cu/AlSiC metal, followed by a folded fin, followed by a structure encapsulating a thermally sensitive phase change material, then followed by about 1600 microns thick Cu—Mo—Cu/AlSiC metal, wherein the 1600 microns thick Cu—Mo—Cu/AlSiC metal (as a base) can include an array of microchannels.

Alternatively, in the case of an indium phosphide material based pulsed laser, the top ceramic for the pulsed laser bonding (e.g., p-metal contact down) can be a combination of about 20 microns thick aluminum nitride and about 1000 microns thick copper diamond composite, followed by about 400 microns thick Cu—Mo—Cu/AlSiC metal, followed by a folded fin, followed by a structure encapsulating a thermally sensitive phase change material, then followed by about 1600 microns thick Cu—Mo—Cu/AlSiC metal, wherein the 1600 microns thick Cu—Mo—Cu/AlSiC metal (as a base) can include an array of microchannels.

Alternatively, in the case of an indium phosphide material based pulsed laser, the top layer for the pulsed laser bonding (e.g., p-metal contact down) can be about 400 microns thick semiconductor boron arsenide, followed by about 400 microns thick Cu—Mo—Cu/AlSiC metal, followed by a folded fin, followed by a structure encapsulating a thermally sensitive phase change material, then followed by about 1600 microns thick Cu—Mo—Cu/AlSiC metal/AlSiC pyrolytic graphite composite (as a base).

Alternatively, in the case of an indium phosphide material based pulsed laser, the top layer for the pulsed laser bonding (e.g., p-metal contact down) can be about 400 microns thick semiconductor boron arsenide, followed by about 400 microns thick Cu—Mo—Cu/AlSiC metal, followed by a folded fin, then followed by about 1600 microns thick Cu—Mo—Cu/AlSiC metal/AlSiC pyrolytic graphite composite (as a base).

Alternatively, in the case of an indium phosphide material based pulsed laser, the top ceramic for the pulsed laser bonding (e.g., p-metal contact down) can be a combination of about 20 microns thick aluminum nitride and about 1000 microns thick copper diamond composite, followed by about 400 microns thick Cu—Mo—Cu/AlSiC metal, followed by a folded fin, followed by a structure encapsulating a thermally sensitive phase change material, then followed by about 1600 microns thick Cu—Mo—Cu/AlSiC metal/AlSiC pyrolytic graphite composite (as a base).

Alternatively, in the case of an indium phosphide material based pulsed laser, the top ceramic for the pulsed laser bonding (e.g., p-metal contact down) can be a combination of about 20 microns thick aluminum nitride and about 1000 microns thick copper diamond composite, followed by about 400 microns thick Cu—Mo—Cu/AlSiC metal, followed by a folded fin, then followed by about 1600 microns thick Cu—Mo—Cu/AlSiC metal/AlSiC pyrolytic graphite composite (as a base).

Alternatively, in the case of an indium phosphide material based pulsed laser, the top ceramic for the pulsed laser bonding (e.g., p-metal contact down) can be a 1000 microns thick aluminum nitride, followed by about 400 microns thick Cu—Mo—Cu/AlSiC metal, followed by a folded fin, then followed by about 1600 microns thick Cu—Mo—Cu/AlSiC metal/AlSiC pyrolytic graphite composite (as a base).

Furthermore, 1000 microns thick aluminum nitride can act as an optical bench for mounting a beam shaping lens, a volume holographic Bragg grating and a laser driver.

Various combinations of the above thermal configurations are possible to reduce thermal stress, thermal resistance and to increase heat transfer efficiently.

Furthermore, instead of boron arsenide semiconductor, a metal matrix composite (MMC) material with tailored coefficient of expansion (4-8 ppm/K) and thermal conductivity (>450 W/m K), specifically those based on diamond particles (with thermal conductivity between 1000 and 2000 W/mK) can be utilized.

Cu—Mo—Cu has tunable thermal properties and its properties are illustrated below:

| Cu—Mo—Cu Composition | Density (g/cm3) | CTE (ppm/K) | Thermal Conductivity W/m.K | |
|---|---|---|---|---|
| | | | On Plane | Thru Plane |
| 14:72:14 | 9.88 | 5.6 | 200 | 170 |
| 1:4:1 | 9.75 | 6.0 | 220 | 180 |
| 1:3:1 | 9.66 | 6.8 | 244 | 190 |
| 1:2:1 | 9.54 | 7.8 | 260 | 210 |
| 1:1:1 | 9.32 | 8.8 | 305 | 250 |

Furthermore, Cu—Mo—Cu may be replaced by W—Cu and its properties are illustrated below:

| Physical Properties | W90-Cu10 | W85-Cu15 | W80-Cu20 | W75-Cu25 |
|---|---|---|---|---|
| Composition (Wt % W) | 90% | 85% | 80% | 75% |
| Density at 20° C. (g/cm3) | 17.0 | 16.3 | 15.6 | 14.9 |
| CTE at 20° C. (ppm/K) | 6.5 | 7.0 | 8.3 | 9.0 |
| Thermal Conductivity (W/mK) | 180 | 190 | 200 | 220 |

Furthermore, the ceramic heat spreader can consists of an array of vertical thermal vias to enhance vertical thermal conduction.

The array of microchannels can utilize an electrically insulated liquid coolant (e.g., HFE-7100) that boils as it flows through the array of microchannels. Hoverer, it should be noted that narrower diameter microchannels is useful for efficient heat transfer.

A phase change material (PCM) can store thermal energy by the phase change from solid to liquid.

Additionally, an array of microchannels can be spatially coupled with an array of microjets, which (a microjet) utilizes small jets of high velocity fluid for cooling. The microjet impinges directly on the surface to be cooled. The momentum of the jet suppresses the thermal boundary layer at the surface, producing very high heat transfer coefficients in the impingement zone. The combination of the array of microchannels and the array of microjets is a hybrid micro-cooling system.

Generally, the above thermal design configurations can be applied to any high heat dissipating device.

Additionally, the array of microchannels can be carefully fabricated/constructed (or even embedded with the heat spreader) within the Super System on Chip 400A/400B/400C/400D or optics to chip multichip module (MCM) for efficient thermal management.

Additionally, thermal management can be performed by an application specific microcontroller/processor with a thermistor chip and an algorithm consisting of a feedback control/feed forward control/a combination of feedback and feed forward/predictive control.

The predictive control is generally designed by the minimization of a cost function in which the change of the manipulated variable and the next values of the controlled variable are evaluated. The prediction of the controlled variable at the present time k over a horizon p is based on a nonparameterized (e.g. impulse response) or a parameterized system model.

Figure 4A:
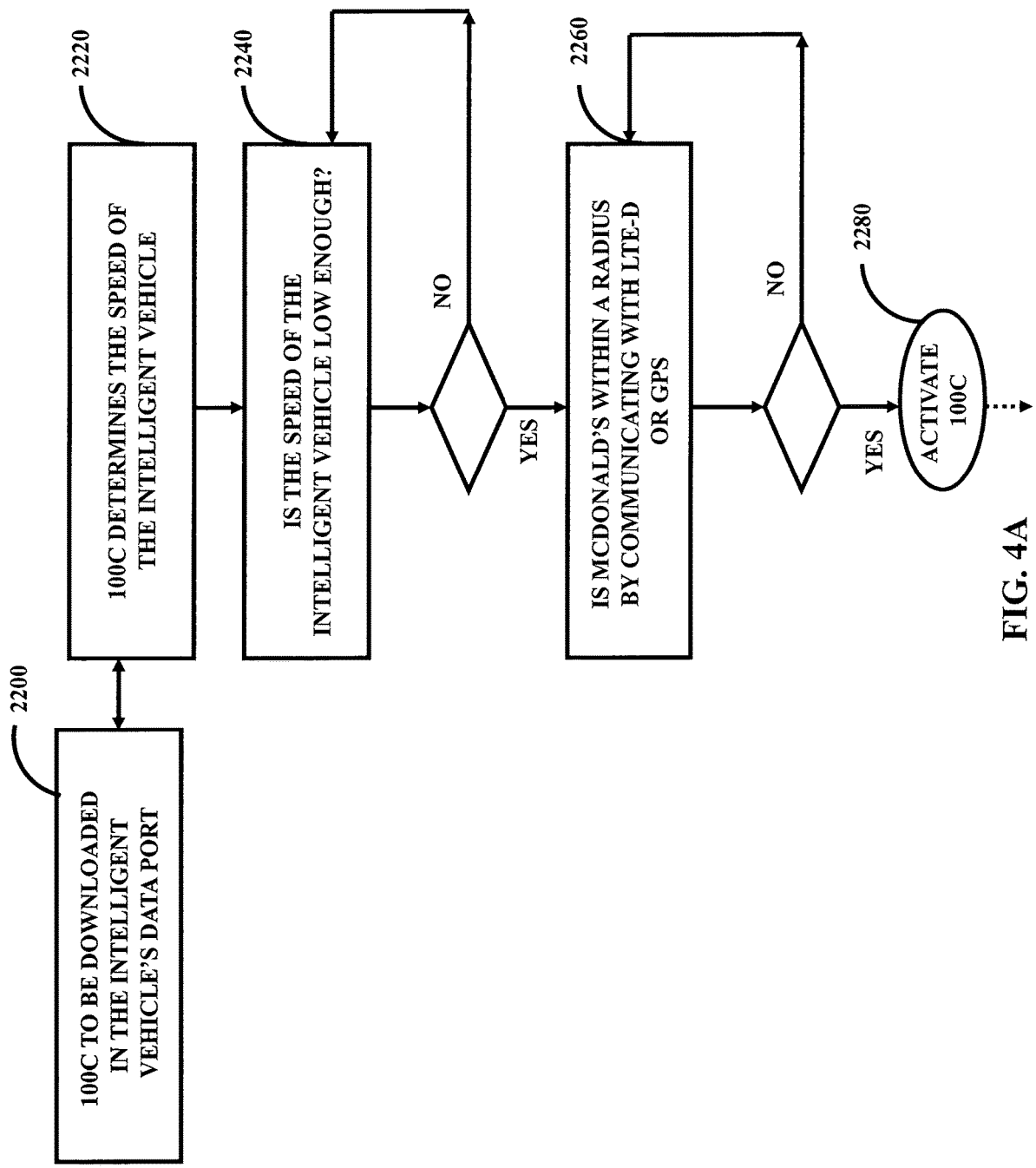
FIGS. 4A-4H illustrate an application of an intelligent algorithm of the intelligent vehicle.

In FIG. 4A, in step 2200, 100C can be downloaded in the intelligent vehicle's data port. In step 2220, 100C determines the speed of the intelligent vehicle. In step 2240, 100C determines if the speed of the intelligent vehicle is low enough, then 100C allows proceeding to step 2260; otherwise 100C reiterates the previous step. In step 2260, 100C determines if McDonald's is in close proximity to the intelligent vehicle by utilizing the LTE-Direct radio and/or global positioning system, then 100C allows proceeding to step 2280, where the core application of 100C is activated.

Figure 4B:
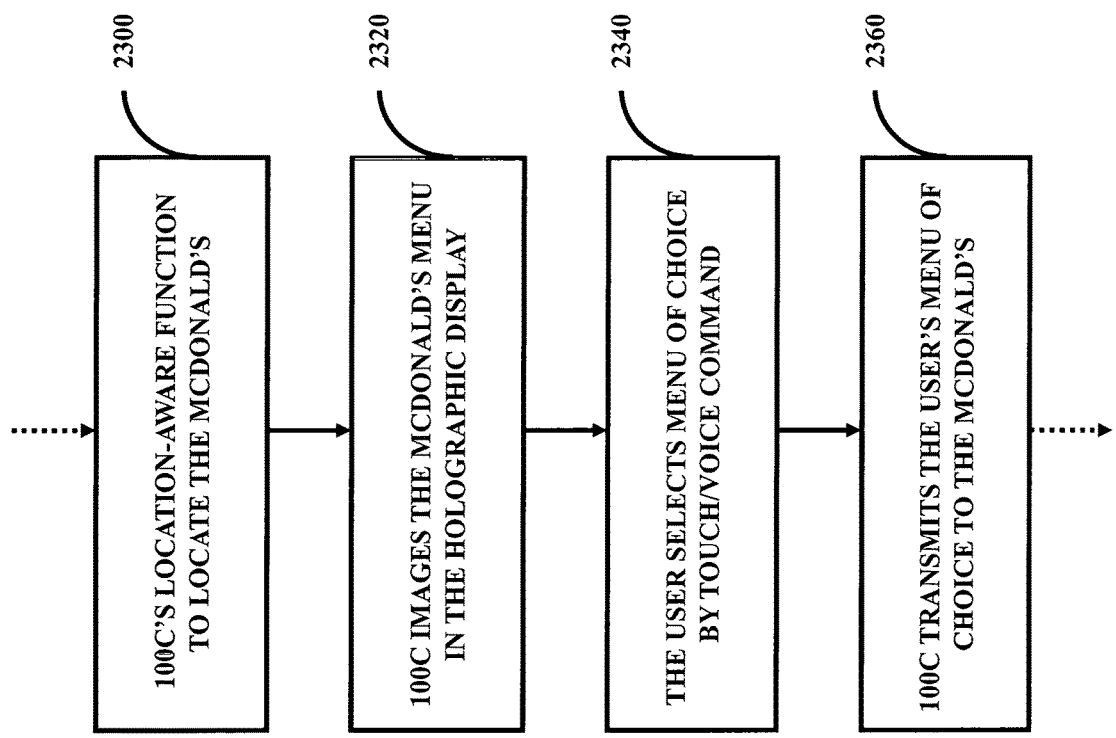

In FIG. 4B, continuing in step 2300, 100C further enables a location-aware function to locate the McDonald's. In step 2320, 100C images McDonald's menu on the intelligent vehicle's three-dimensional/holographic display. In step 2340, the user selects his/her food items from the McDonald's menu by touch/voice command. In step 2360, 100C transmits his/her choice of the McDonald's menu to the McDonald's.

Figure 4C:
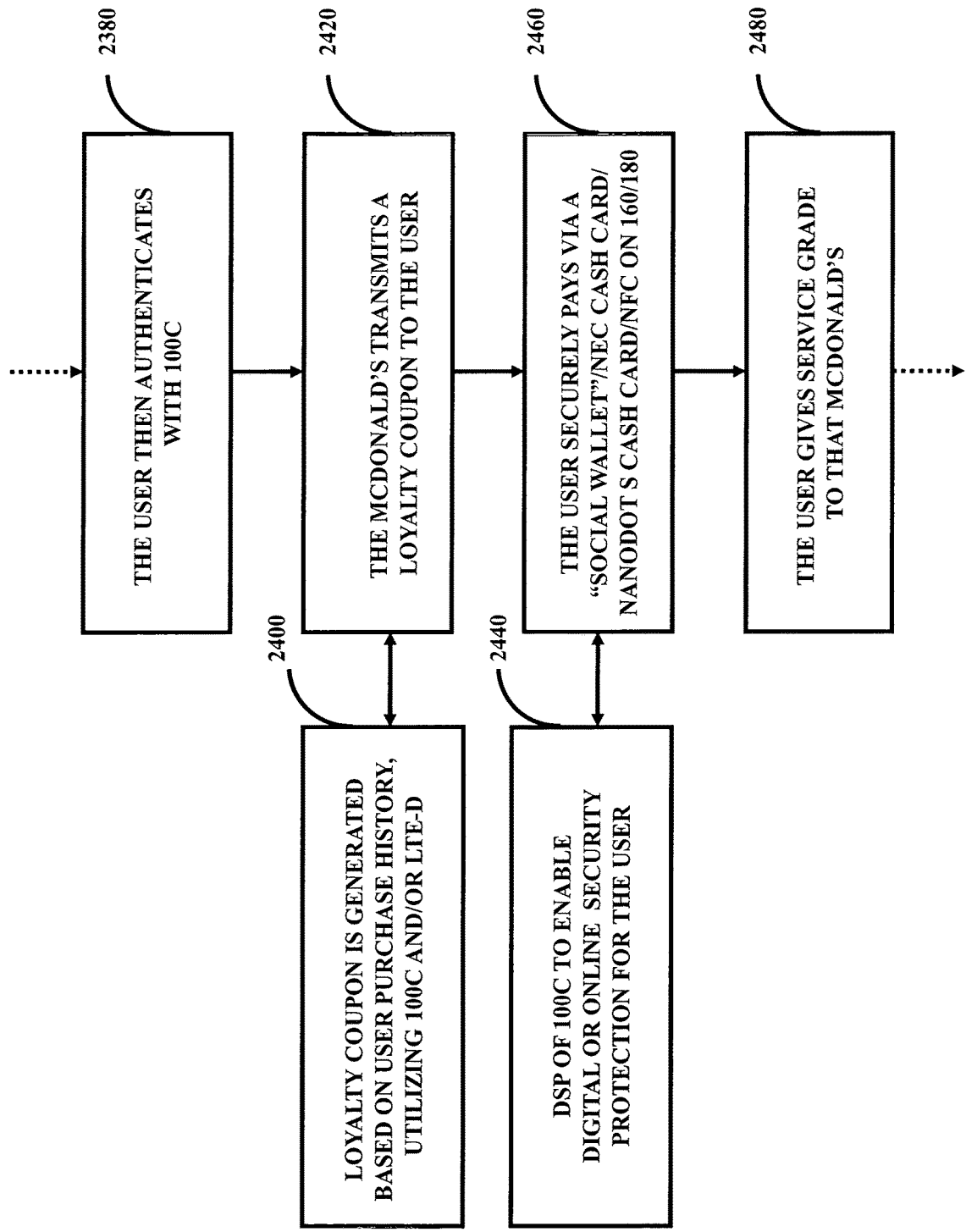

In FIG. 4C, continuing in step 2380, the user authenticates (via biometric confirmation) himself/herself with 100C. In step 2400, a loyalty coupon for the user is generated by McDonald's, utilizing 100C and/or an LTE-Direct radio. In step 2420, McDonald's transmits a loyalty coupon to the user. In step 2440, the digital security protection of 100C provides digital or online security protection for the user. In step 2460, the user securely pays for his/her food items using a social wallet/near field communication radio cash card/nanodots cash card or near field communication radio of intelligent portable internet appliance 160/intelligent wearable augmented reality personal assistant device 180. In step 2480, the user gives a service grade (feedback) to the McDonald's for the service rendered.

Figure 4D:
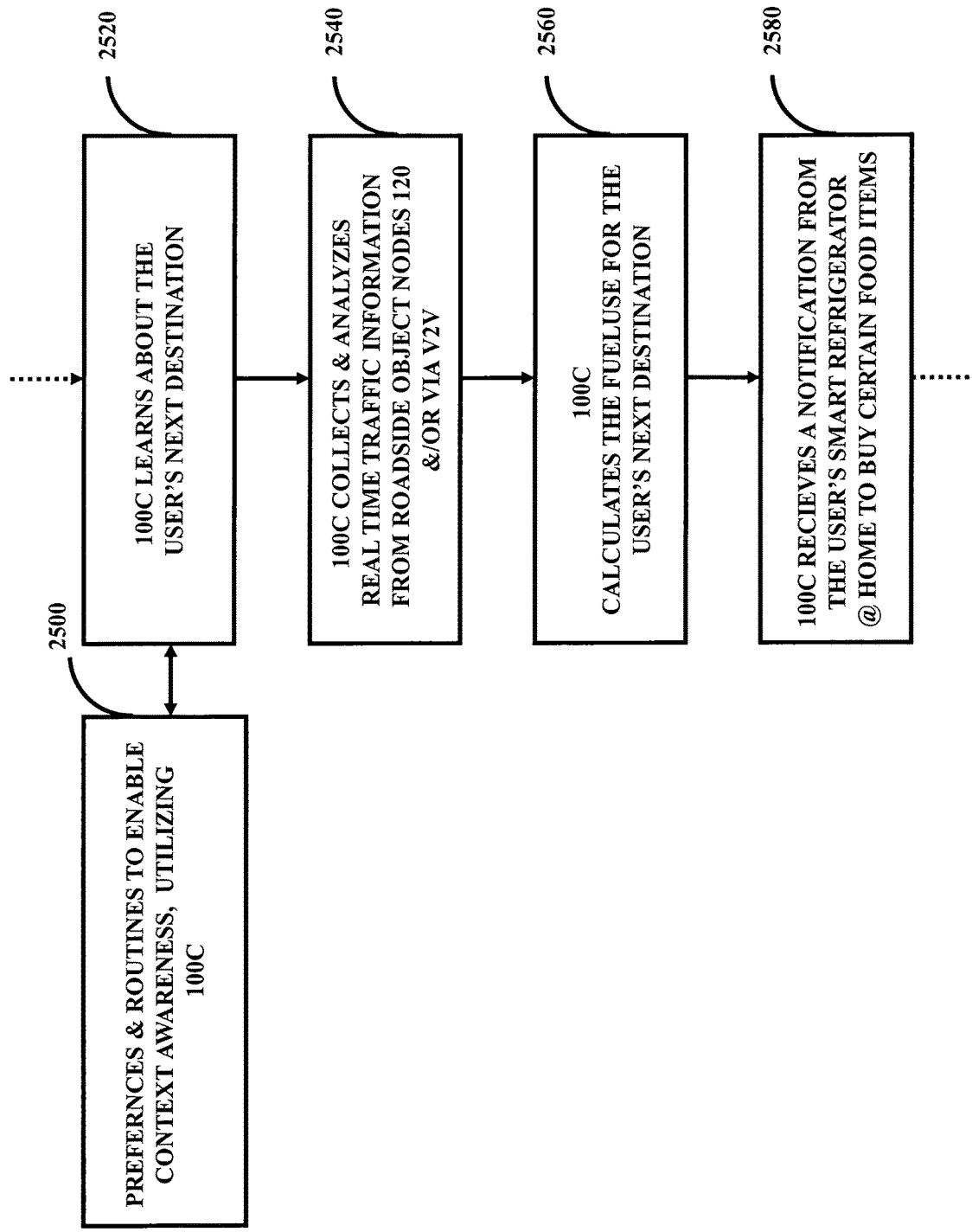

In FIG. 4D, continuing in step 2500, the user's preference and routines are utilized by 100C to enable context awareness. In step 2520, 100C contextually learns the user's next destination. In step 2540, 100C collects and/or analyzes near real time/real time traffic information from object nodes 120 at the roadside and/or via vehicle-to-vehicle communication. In step 2560, 100C calculates the fuel consumption for the user's next destination. In step 2580, 100C receives a notification from the user's smart refrigerator at his/her home to buy certain food items.

Figure 4E:
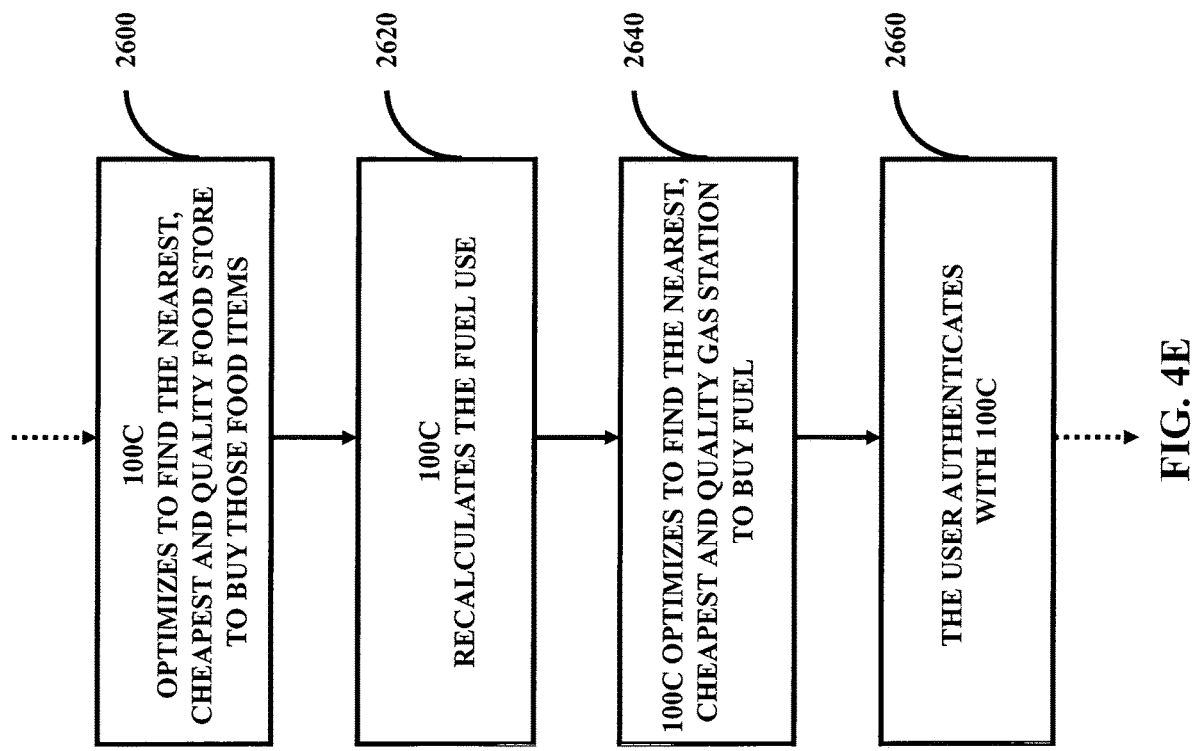

In FIG. 4E, continuing in step 2600, 100C optimizes to find the nearest cheapest and quality food store to buy those food items. In step 2620, 100C recalculates the fuel consumption. In step 2640, 100C optimizes to find the nearest cheapest and quality gasoline station store to buy fuel. In step 2660, the user authenticates (via biometric confirmation) himself/herself with 100C.

Figure 4F:
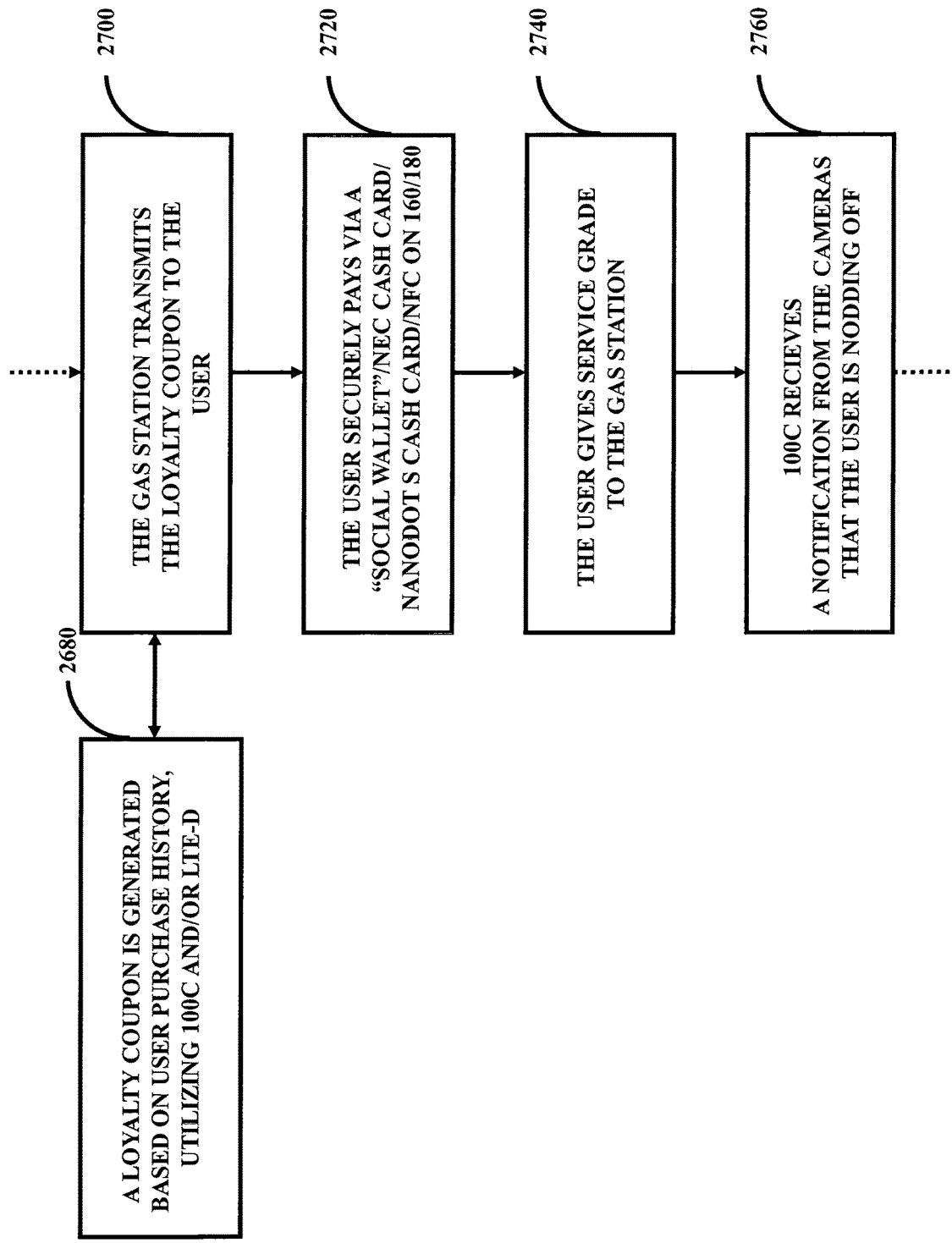

In FIG. 4F, continuing in step 2680, a loyalty coupon for the user is generated by the gasoline station, utilizing 100C and/or the LTE-Direct radio. In step 2700, the gasoline station transmits the loyalty coupon to the user. In step 2720, the user securely pays for gas using a social wallet/near field communication radio cash card/nanodots cash card or near field communication radio of intelligent portable internet appliance 160/intelligent wearable augmented reality personal assistant device 180.

In step 2740, the user gives a service grade to the gasoline station for the service rendered. In step 2760, 100C receives a notification from an array of eye-facing cameras that the user is nodding off.

Figure 4G:
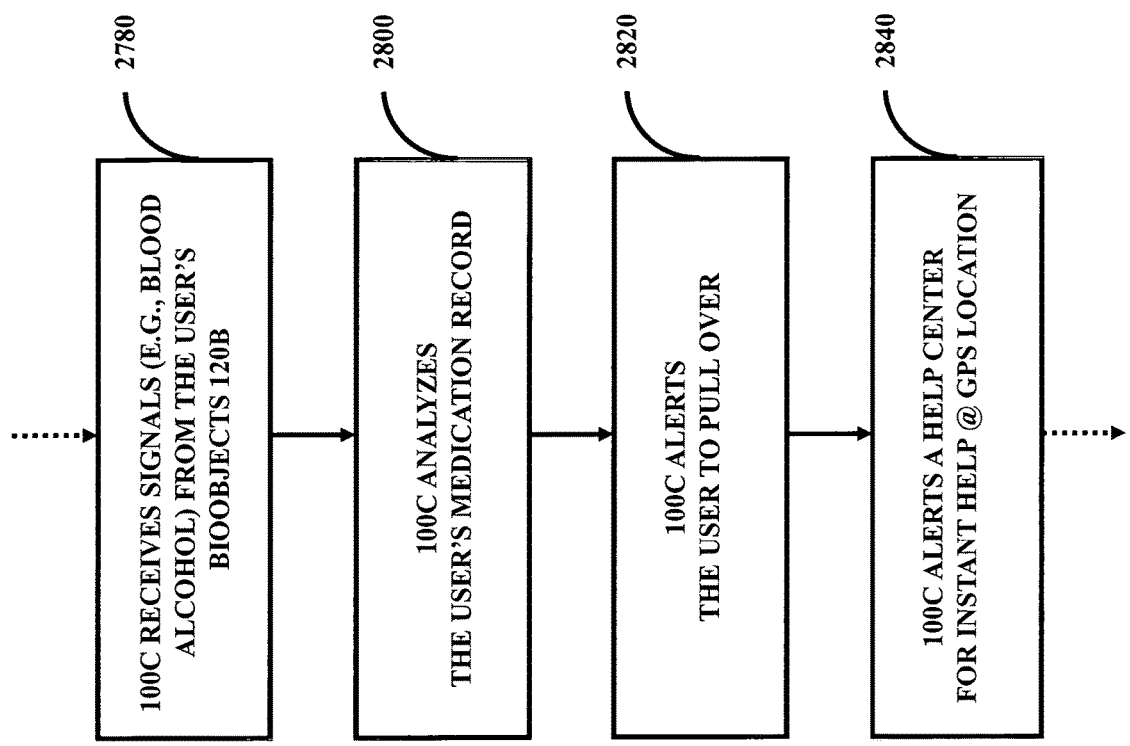
Figure 56A:
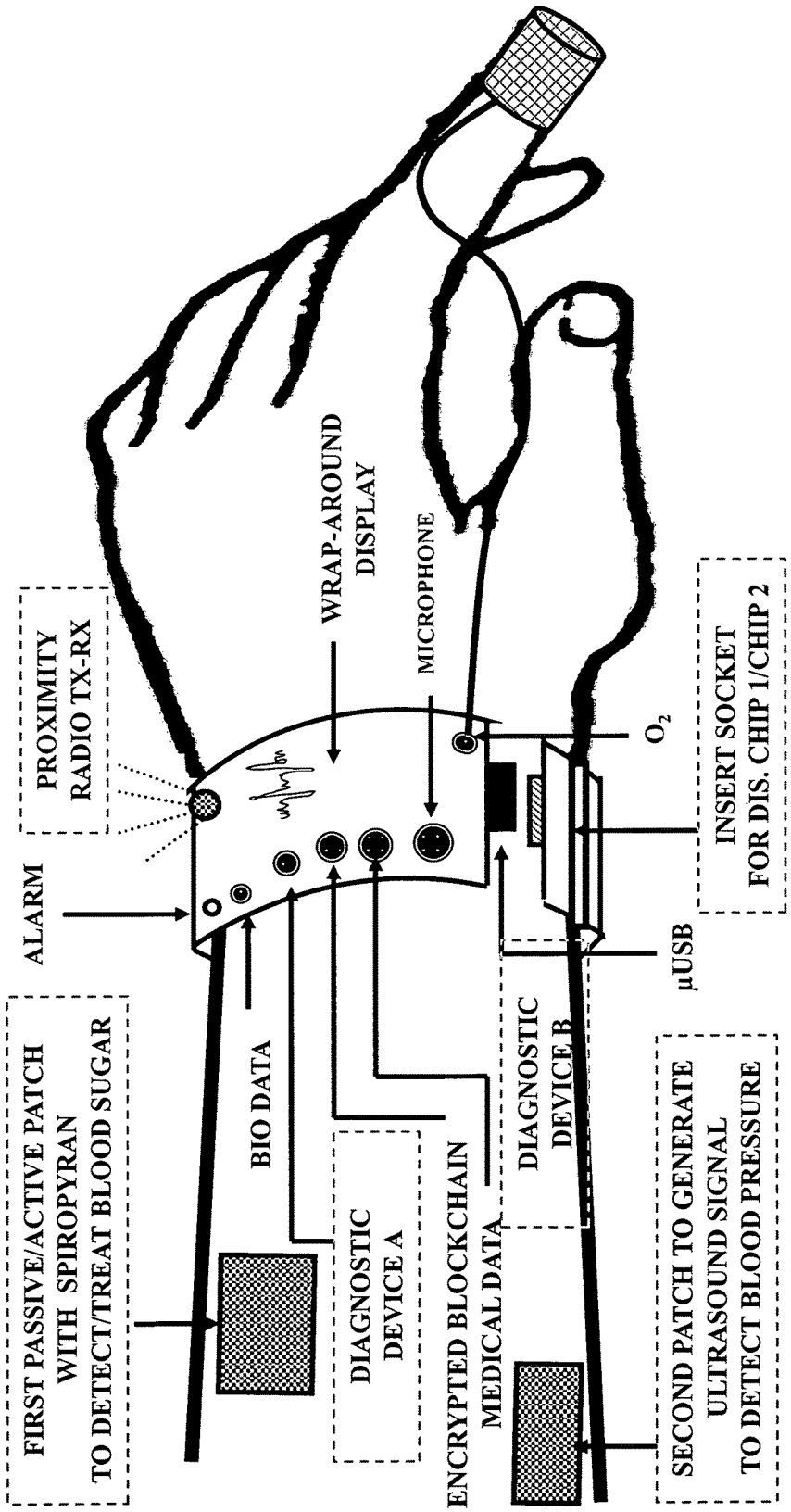
Figure 56B:
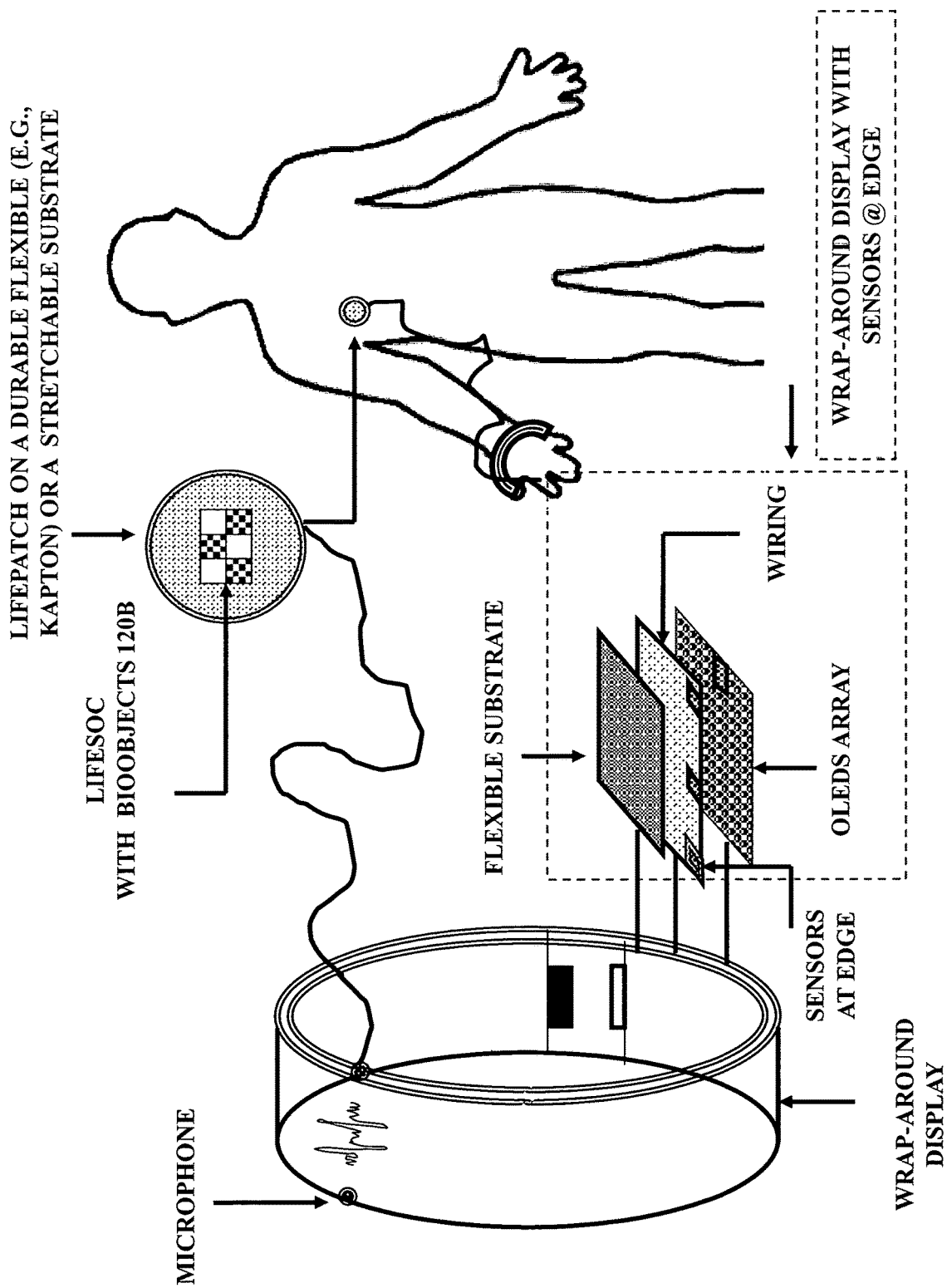

In FIG. 4G, continuing in step 2780, 100C receives vital signals (e.g., alcohol level in blood or blood pressure or sudden dizziness) from the user's bioobjects 120Bs. In step 2800, 100C analyzes the user's medication record, as recorded by the wearable personal health assistant device (FIG. 56A). In step 2820, 100C alerts the user to pull over from the road. In step 2840, 100C alerts a help center, identifying the user's vehicle's location (by global positioning system).

Figure 4H:
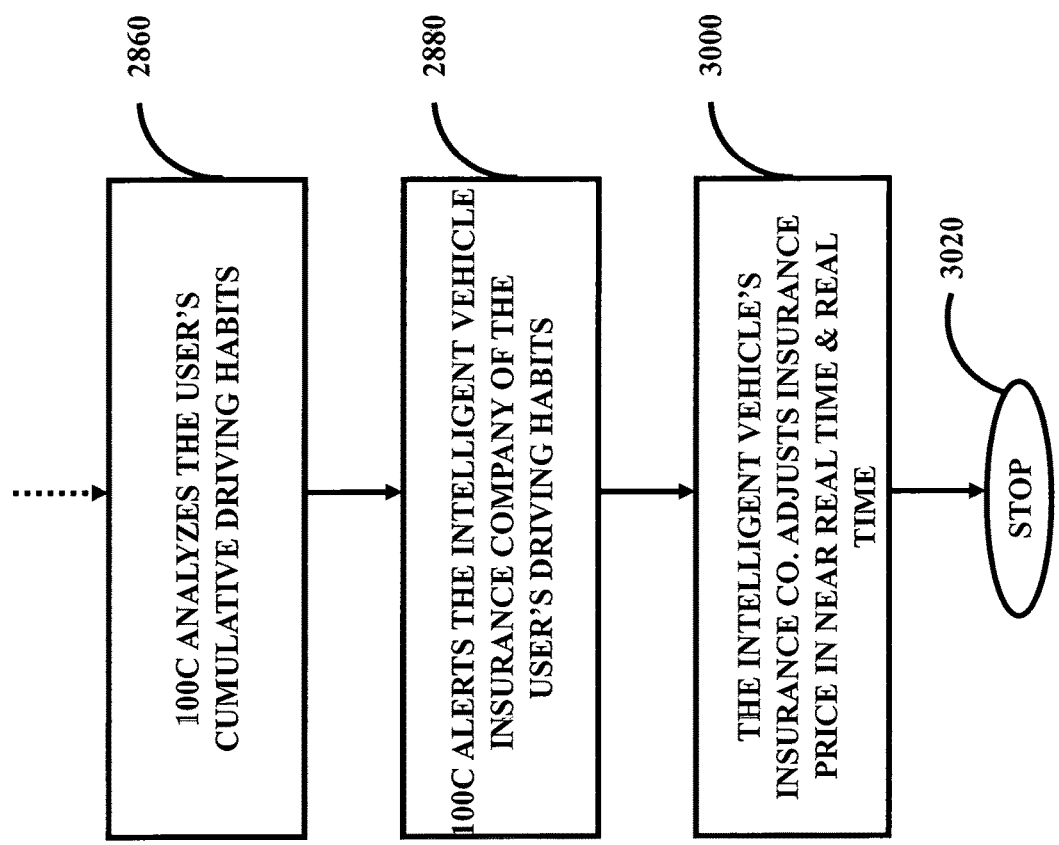

In FIG. 4H, in step 2860, 100C analyzes the user's cumulative driving habits by securing data from the intelligent vehicle. In step 2880, 100C notifies the intelligent vehicle's insurance company regarding the user's driving habits. In step 3000, the intelligent vehicle's insurance company adjusts the insurance price in near real time/real time. Step 3020 denotes a conclusion of this application.

The intelligent algorithm 100 includes an application specific algorithm submodule 100C. There are other applications of the intelligent algorithm 100, for example (a) by converting detailed photo images of real properties using a computer vision based application specific algorithm submodule 100C, the value of the real property may be estimated and (b) by converting Monte Carlo enhanced discounted free cash flow (MC-DCF) to an application specific algorithm submodule 100C, the intrinsic value of a stock may be estimated.

FIG. 5A illustrates a sunlight concentrator assembly, utilizing an array of prisms-further focusing onto a right-angle prism and a mechanically moveable stage.

FIG. 5B illustrates a sunlight concentrator assembly, which is optically coupled with a photovoltaic module via a right angle focal prism. The photovoltaic module has an array of vertical waveguides (fabricated/constructed by a femtosecond laser) connecting with an array of integrated solar cells, wherein each integrated solar cell is wavelength matched for a specific (slice of) spectrum of sunlight.

FIG. 5C illustrates an integrated solar cell, which is wavelength matched for a specific spectrum of sunlight. The integrated solar cell has embedded light trapping nanostructures and includes a tandem 3-junction solar cell plus an amorphous silicon solar cell at the bottom.

Additionally, a tandem 3-junction solar cell can include silicon quantum dots and/or germanium quantum dots for carrier multiplication in order to enable a higher efficiency solar cell. Alternatively, perovskite-copper indium gallium diselenide (CIGS) tandem or perovskite-multicrystalline silicon (Si) tandem can be utilized instead of tandem 3-junction solar cells. Solar cells for both blue spectrum and green spectrum can be coated with pentacene organic thin-film to increase the conversion efficiency by about 5%.

FIG. 5D illustrates embedded light trapping nanostructures on the outside and inside of an integrated artificial photosynthesis-photovoltaic module based energy generation system.

FIG. 5E illustrates an integrated artificial photosynthesis-solar cell module, wherein the artificial photosynthesis module includes embedded light trapping nanostructures on the outside and inside, nanoshells with photocompounds inside, a porous platinum-graphene-multiwall carbon nanotube (MW-CNT) membrane with embedded photocompounds (e.g., LHC-II) or photocompounds in a carbon nanotube.

A photoanode can be based on InGaN material. A photocathode for water splitting can be based on platinum-multiwall carbon nanotube/$N_2P$-multiwall carbon nanotube/multiwall carbon nanotube coated with Laccase enzyme. The artificial photosynthesis module is the tandem 3-junction solar cells (plus an amorphous silicon solar cell at the bottom).

FIG. 6 illustrates an application of photovoltaic and artificial photosynthesis modules at home.

Figure 7A:
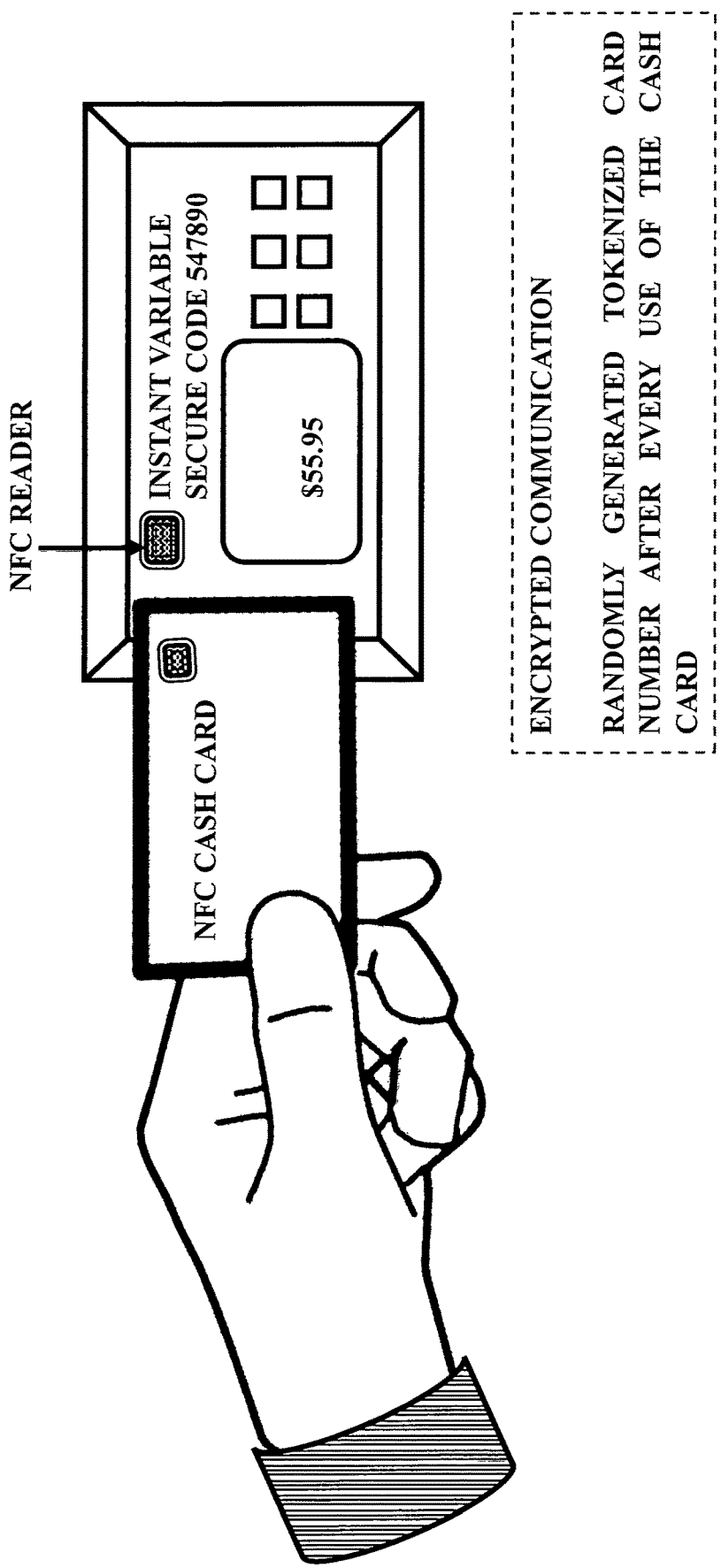

FIG. 7A illustrates a near field communication based cash card, where the cash card is integrated with at least (a) a near field communication chip and (b) a first biometric sensor (e.g., finger vein sensor). The actual number of the cash card is tokenized, never revealed at all. When the first biometric sensor clearly identifies the user and the cash card securely communicates with a near field communication radio reader at a point of sale payment system via 256-bit strong encryption, then the display (device) at the point of sale payment system displays an instant unique variable code. The user has to input the instant unique variable code and his/her own unique password(s) into the point of sale payment system. The cash card transmits a 16-digit token and unique cryptogram to the point of sale payment system, then to a MasterCard/Visa network. The MasterCard/Visa network swaps the 16-digit token and unique cryptogram and further analyzes other identifications on the cash and information from digital security protection algorithm submodule 100A (FIG. 1B) before authorizing or rejecting the purchase within milliseconds.

The point of sale payment system can be provisioned or enabled by a second biometric sensor, in case of any malfunction of the first biometric sensor. The instant variable code for the user varies at each point of sale transaction.

Figure 7B:
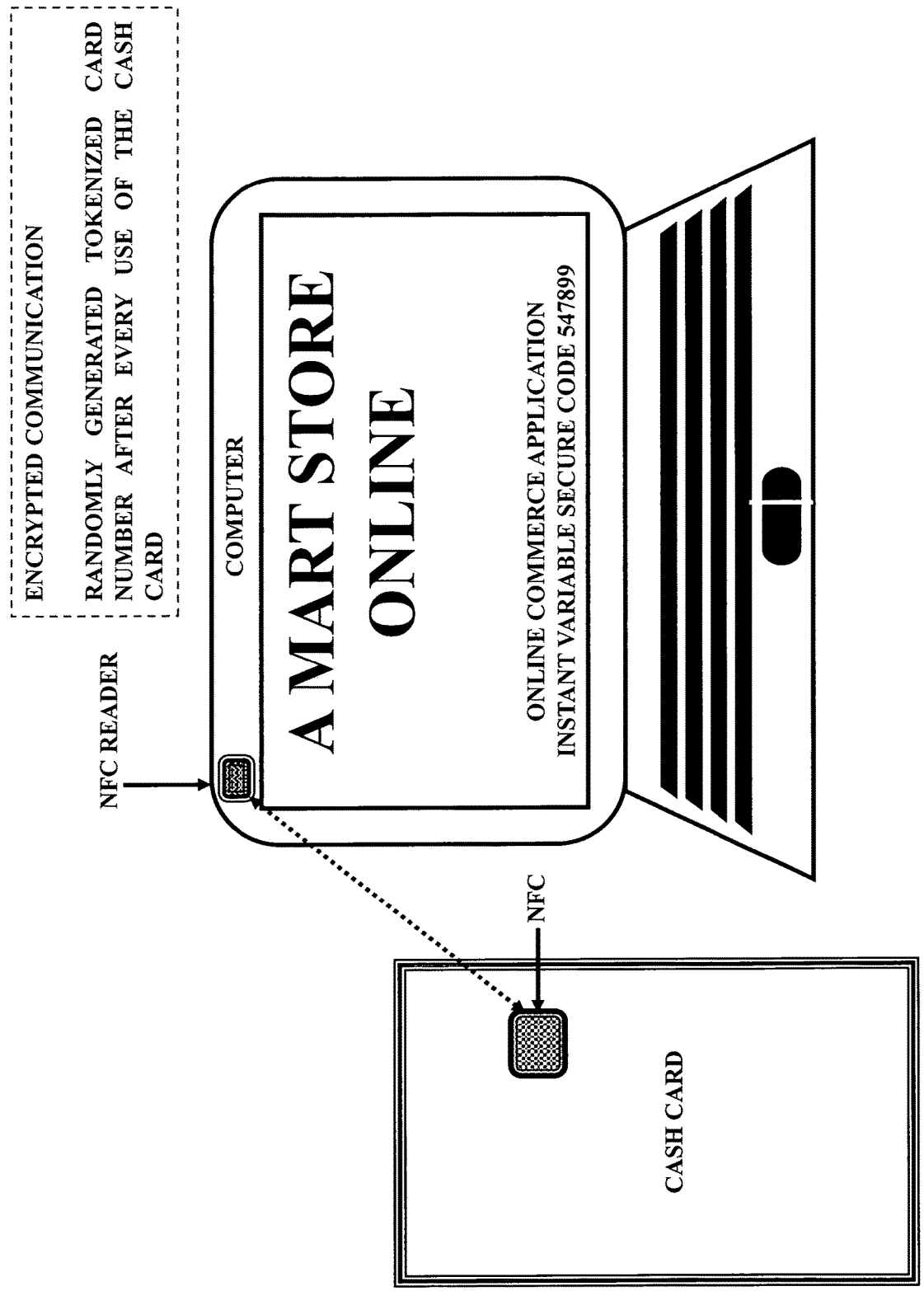

Similar to FIG. 7A, FIG. 7B illustrates the near field communication based cash card for the online/internet purchases utilizing a computer, which includes a near field communication reader.

Figure 7D:
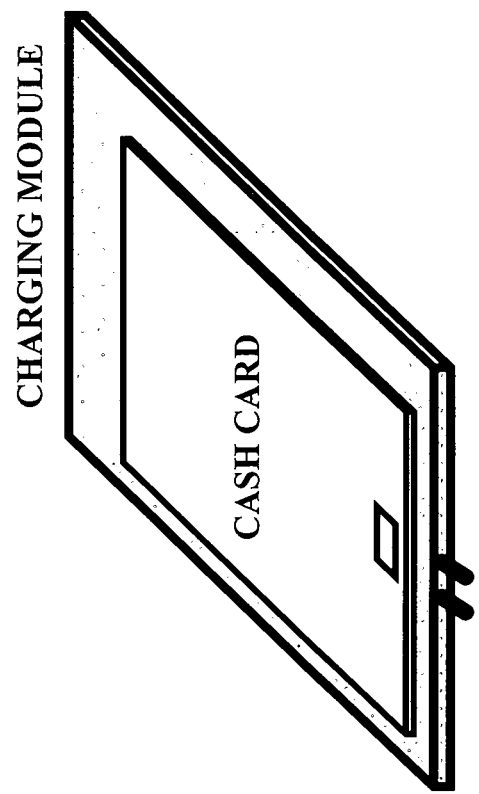
Figure 7C:
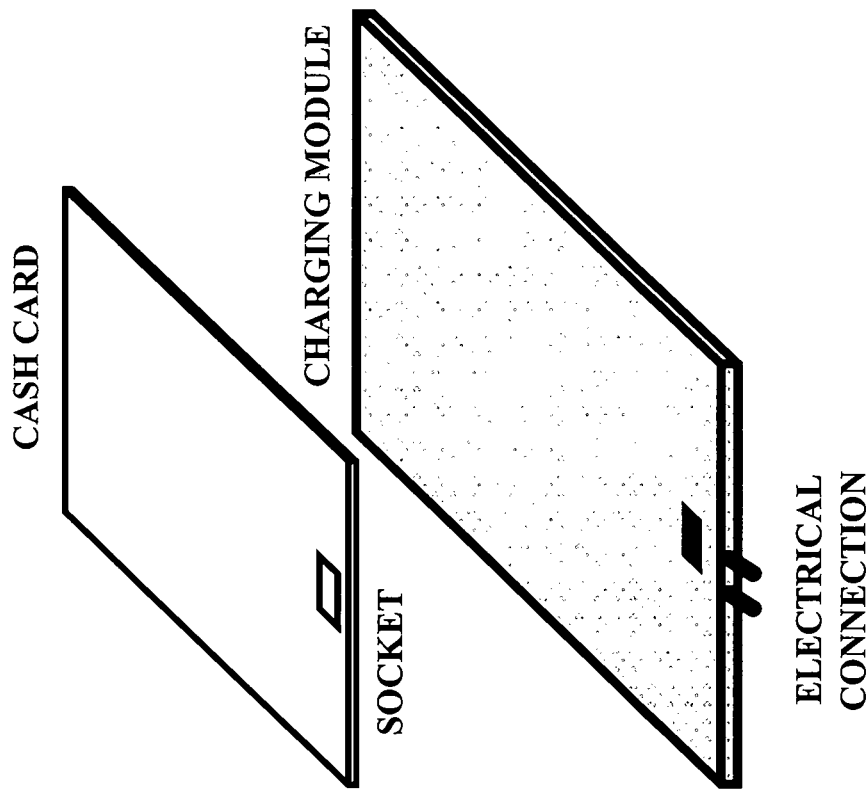

FIG. 7C and FIG. 7D illustrate a wired charging configuration of the cash card.

Figure 7E:
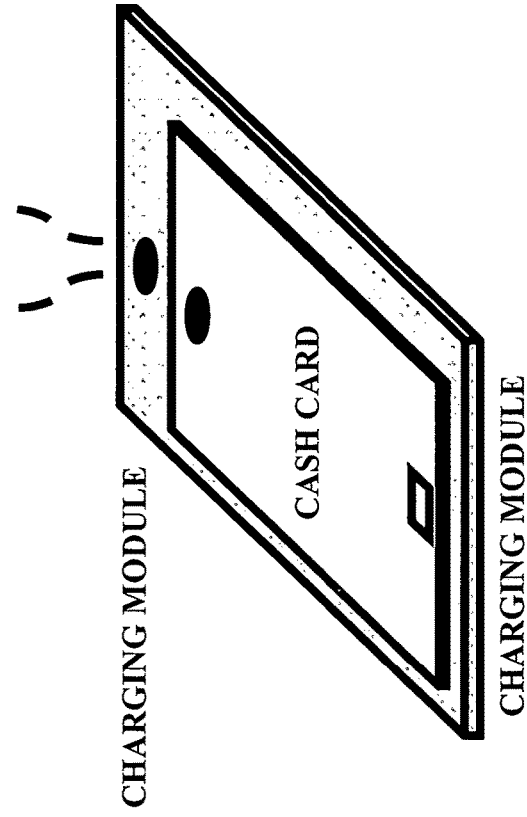
Figure 7E:
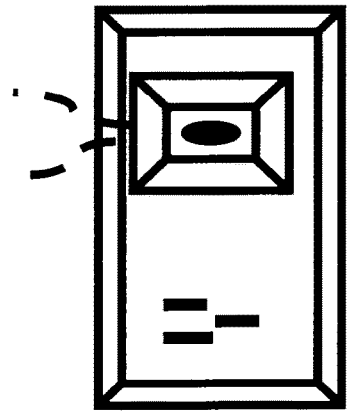

FIG. 7E illustrates a wireless charging through air configuration of the cash card.

FIG. 8A illustrates a cash card, where the cash card is integrated with at least (a) millions of nanodots (e.g., ceramic nanodots) and (b) a first biometric sensor (e.g., finger vein sensor). The cash card can communicate with a single photon reader at the point of sale via unbreakable quantum physics based encryption. The actual number of the cash card is tokenized, never revealed at all. When the first biometric sensor clearly identifies the user and the cash card securely communicates with the nanodots communication reader at a point of sale payment system via unbreakable quantum physics based encryption, then the display (device) at the point of sale payment system displays an instant unique variable code. The user has to input the instant unique variable code and his/her own unique password(s) at the point of sale payment system. The cash card transmits a 16-digit token and unique cryptogram to the point of sale payment system, then to a MasterCard/Visa network. The MasterCard/Visa network swaps the 16-digit token and unique cryptogram and further analyzes other identifications on the cash card and information from digital security protection algorithm submodule 100A (FIG. 1B) before authorizing or rejecting the purchase within milliseconds.

The point of sale payment system can be provisioned or enabled by a second biometric sensor, in case of any malfunction of the first biometric sensor. The instant variable code for the user varies at each point of sale transaction.

Similar to FIG. 8A, FIG. 8B illustrates the nanodots based cash card for the online/internet purchase utilizing a computer, which includes a single photon reader.

FIG. 8C illustrates the scattering of single photons from a single photon source at room temperature (e.g., diamond semiconductor with defect centers) by millions of nanodots and the scattered photons are detected by a single photon avalanche diode (e.g., a Geiger mode avalanche photodiode (Gm-APD)).

FIG. 9A illustrates a cash card on a bendable-flexible substrate (e.g., a plastic/polymer substrate), which can integrate a photovoltaic cell, a rechargeable thin-film battery, a power management chip, a light emitting diode (LED), a first biometric (e.g., a finger print/vein sensor) sensor, a cash card specific System on Chip (integrated with a processor, a memory component, a secure element and a storage component) and a near field communication radio (with its antenna). The cash card as in FIG. 9A can integrate a rewritable magnetic strip.

A fingerprint sensor can be fabricated/constructed by combining colloidal crystals with a rubbery material, wherein colloidal crystals can be dissolved in a suitable chemical leaving air voids in the rubbery material, thus creating an elastic photonic crystal. The fingerprint sensor emits an intrinsic color, displaying three-dimensional ridges, valleys and pores of the user's fingerprint, when pressed. The cash card specific System on Chip with a specific algorithm and camera can be utilized to compare the user's previously captured/stored fingerprint. A non-matching fingerprint would render the cash card instantly unusable.

Details of the optical fingerprint sensor have been described/disclosed in U.S. non-provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 and in its related U.S. non-provisional patent applications (with all benefit provisional patent applications) are incorporated in its entirety herein with this application.

FIG. 9B illustrates the cash card B, which is the cash card A with the addition of a surface mountable low-profile camera or copper indium selenide (CIS) based flexible camera and a second biometric sensor (e.g., a sensor to recognize voice).

FIG. 9C illustrates the cash card C, which is the cash card B with the addition of a Bluetooth LE communication radio (with its antenna).

FIG. 9D illustrates the cash card D, which is the cash card C with the addition of a display (e.g., an E-Ink display).

It should be noted that any code number (e.g., a card verification value number) on the cash card A or cash card B or cash card C can be dynamically reconfigured/changed, as the cash card A or cash card B or cash card C contains a cash card specific System on Chip (integrated with a processor, a memory component, a secure element and a storage component).

Thus, the cash card A or cash card B or cash card C with any dynamically reconfigured/changed code number can reduce fraud related to any transaction.

FIG. 9E illustrates the cash card E, which is the cash card D with the addition of a large number of nanodots (e.g., ceramic nanodots).

The cash card can have electromagnetic coils in its interior for receiving electrical power wirelessly at a close proximity to the intelligent portable internet appliance 160 or the intelligent wearable augmented reality personal assistant device 180.

The cash card can be integrated with the intelligent portable internet appliance 160 or the intelligent wearable augmented reality personal assistant device 180 or the social wallet.

Utilizing the cash card, the user can securely purchase/rent a product/service.

The user can register for a secure short text message payment service by sending/verifying a short text message with a web portal of the cash card (wherein the web portal is configured with intelligent algorithms) in order to create a virtual cash card account. Upon verification of the (a) user's unique pin number, (b) user's unique biometric identification (e.g., finger vain sensor/voice), (c) user required reply within a specified timeout period for a one time random key provided (from the web portal of the cash card) and (d) a digital security protection algorithm submodule 100A (within "Fazila" as described in FIG. 10A), the user can also securely purchase/rent a product/service by a short text message (as the cash card is integrated with the intelligent portable internet appliance 160 or the intelligent wearable augmented reality personal assistant device 180). The digital security protection algorithm submodule 100A can be coupled with a social wallet.

The social wallet (e.g., 100N2/natural language activated/voice activated "Fazila" as described in FIG. 10A or an algorithm as described in FIG. 1B (which can be coupled with the Super System on Chip 400A/400B/400C/400D for ultrafast data processing, image processing/image recognition, deep learning/meta-learning and self-learning) can enable a near real time/real time focal point convergence of various applications or functions with one integrated user identification. APIs of many service links can be created by import.io and converged into the one integrated user identification. For example, after properly authenticating the user's profile via suitable biometric verification, the user can open a digital bank account entirely online. The digital bank account with a search box can enable the user to type in queries in a question-answer format (e.g., "how much did I spend on travel last week?"). Furthermore, the question-answer format can be enhanced by a fuzzy logic (including neuro-fuzzy) algorithm.

Patterns of various applications or functions of a single user can be incorporated in the personal web. The personal web can make life easier in automating routine actions/decisions for the user. The personal web can relate to (a) social (people, the user interacts with and the content the user exchanges in the social networks), (b) location (the user checks into), (c) product (the things the user buys on Amazon or eBay, the movies the user watches on Snapchat/Netflix/YouTube or the hotels the user books online) and (d) interest (the sort of things the user searches for on Google/You Tube or the things the user like on Facebook)—thus the personal web can reveal a lot about the user. Building a statistical history, learning and relearning about the user data of social, location, product and interest, the usefulness of a personal web can be enhanced. For example, the personal web can be configured to know what time the user wants/anticipates to wake up at, even before the user sets an alarm. It knows the user's route to work and monitors traffic along the way, guiding the user through the most efficient route. Before the user's lunch break, the user can get food recommendations based on his/her past eating habits and current health conditions. When the user gets home, a smart thermostat has heated the home to the user's preferred temperature and a smart TV has remembered that the user loves to watch the evening news with CBS Dan Rather after work.

Furthermore, the usefulness of the personal web can be enhanced by connecting with sensors, wherein the sensors are also connected with the distributed internet/distributed semantic internet (coupled with a public/consortium/private blockchain) and/or intelligent portable internet appliance 160 and/or the intelligent wearable augmented reality personal assistant device 180.

The user has multiple passwords, identifications, services and devices. But security across them is fragmented. The digital security protection algorithm submodule 100A can sort through contextual, situational and historical data to verify the user's identity on different devices including the user's identity with biometric data in near real time/real time. The digital security protection algorithm submodule 100A can learn about the user's social graph and make an inference about the user behavior that is out of the norm or may be due to someone stealing that user's identity. Based on the user's social graph, the digital security protection algorithm submodule 100A will know the user intimately, for example if a particular user is a vegetarian, but someone is buying a non-vegetarian food with the user's credit card, the digital security protection algorithm submodule 100A will automatically close the credit card in question. Thus, online security is based on intimacy with the user's social graph; rather than a collection of various fragmented passwords.

Furthermore, the one integrated user identification can be embedded with the digital security protection algorithm 100A.

A social graph of a user, enabled by (a) sensors (e.g., a location determination module-indoor positioning system/global positioning system), (b) individual data patterns of the user, (c) an algorithm for generating the user's social graph with machine transformations, wherein the algorithm for generating the composite social graph with machine transformations can be stored in a local data storage unit of the intelligent portable internet appliance 160 and/or the intelligent wearable augmented reality personal assistant device 180 and/or a cloud based data storage unit of the social wallet.

The near real time/real time snapshots/holographic snapshots (e.g., images/videos) of the contextual world around the user can be color enhanced/edited/geotagged/personalized (e.g., personalized with emoji/emoticon) by utilizing an algorithm(s). The user's (or the user's one integrated user identification) social graph and/or social geotag can be linked with a virtual avatar.

The near real time/real time snapshots/holographic snapshots (e.g., images/videos) by a camera (e.g., camera of the intelligent portable internet appliance 160/intelligent wearable augmented reality personal assistant device 180) can be instantly recognized (with or without much information about the snapshots/holographic snapshots) or color enhanced or edited/geotagaged/personalized by utilizing an algorithm(s). Furthermore, near real time/real time snapshots/holographic snapshots can be integrated with the virtual avatar (and the virtual avatar can be coupled with a public/consortium/private blockchain) and shared via the internet or a cloud based data storage unit of the social wallet via the intelligent portable internet appliance 160 or the intelligent wearable augmented reality personal assistant device 180.

Alternatively, the user can store his/her social graph and/or social geotag in his/her personal cloud via a microcomputer (e.g., Raspberry Pi) with properly implemented cryptography (e.g., lattice based encryption, which can hide data inside complex algebraic structures) and personal authentication (e.g., face/voice recognition).

The user can auction/monetize his/her social graph with or without social geotag by utilizing an auction algorithm(s) or opt out. The price of the user's social graph with or without social geotag can be based on the utility function of his/her social graph and/or social geotag to an advertiser- thus enabling user centric distributed personal web and democratizing the distributed internet.

Details of the personal web and auctioning/monetizing the user's social graph have been described/disclosed in U.S. non-provisional patent application Ser. No. 15/731,577 entitled "OPTICAL BIOMODULE FOR DETECTION OF DISEASES AT AN EARLY ONSET, filed on Jul. 3, 2017 and in its related U.S. non-provisional patent applications (with all benefit provisional patent applications) are incorporated in its entirety herein with this application.

Furthermore, the user can securely host/store his/her own files and data (which can be used at any place, any time and any device) in his/her personal cloud via a microcomputer. Such a microcomputer can enable secure communication (e.g., Bitmail) and connect with other systems/subsystems/objects/biological objects via a personal network (e.g., Wi-Fi). Instead of talking to a centralized e-mail mail server at Google, Bitmail can distribute messages across networks of peer users, encrypting Bitmail's address and content automatically. Furthermore, peer users can help store and only deliver Bitmail to the intended recipient user. Bitmail can obscure the sender's identity and an alternate Bitmail address can send Bitmail on the user's behalf. Additionally, this can enable online payment, protecting privacy of the user via the user's virtual avatar (which can be coupled with a public/consortium/private blockchain). Through the user's virtual avatar, the user just would need to supply/apply a fragment of information necessary to receive a service (e.g., purchasing an item). Furthermore, intelligence from the user's social graph and/or social geotag can be realized by an intelligent learning set of instructions, which can include: a computer vision algorithm and/or an artificial intelligence algorithm and/or an artificial neural network algorithm and/or a machine learning (including deep learning/meta-learning and self-learning) algorithm for ultrafast data processing, image processing/image recognition, deep learning/meta-learning and self-learning.

The intelligent learning set of instructions (described in FIGS. 1B-IE) can provide an automatic search on the internet (e.g., on a remote browser) in response to the user's interest/preference/input. The remote browser can be coupled with an array of memristors, as described in pervious paragraphs. Furthermore, the intelligent learning set of instructions (described in FIGS. 1B-IE) can be coupled with the Super System on Chip 400A/400B/400C/400D.

It should be noted that the intelligent learning set of instructions can include a quantum computer enhanced machine learning (including deep learning/meta-learning and self-learning) algorithm and such realized intelligence can enable targeted advertisement to the user/user's virtual avatar.

A composite social graph of many users, enabled by (a) sensors (e.g., a location determination module-indoor positioning system/global positioning system), (b) collective data patterns, (c) the intelligent learning set of instructions for generating the composite social graph with machine transformations, wherein the composite social graph can be stored in a local data storage unit of the intelligent portable internet appliance 160 and/or the intelligent wearable augmented reality personal assistant device 180 and/or a cloud based data storage unit of the social wallet.

The composite social graph may include location, web tracking, message/e-mail, social media/message, near real time/real time bidding/auction, online purchase and online/digital banking.

A method of extracting intelligence and prediction from the composite social graph can utilize a topological data analysis algorithm submodule, a computer vision algorithm submodule, a pattern recognition algorithm submodule, a data mining algorithm submodule, Big Data analysis algorithm submodule, a statistical analysis algorithm submodule, a fuzzy logic (including neuro-fuzzy) algorithm submodule, an artificial neural network/artificial intelligence algorithm submodule, a machine learning (including deep learning/meta-learning and self-learning) algorithm submodule, a predictive analysis algorithm submodule, a software agent algorithm submodule and a natural language processing algorithm submodule.

This one-time random key is sent to the user via a short text message (from the web portal of the cash card) and it will be received only by the user.

Loss of the short text message will lead to a transaction failure, while a delayed short text message may increase the time required for the transaction to complete. However, this may affect only a small number of transactions.

"Fazila" is described in FIG. 10A. FIG. 10A illustrates the intelligent algorithm 100X. The intelligent algorithm 100X includes a digital security protection (DSP) algorithm submodule 100A, a natural language processing algorithm submodule 100B, and an application specific algorithm submodule 100C2 (e.g., Short Text Message Payment). The application specific algorithm submodule 100C2 and the user's social graph 100N2 are coupled with a computer vision algorithm submodule 100D, a pattern recognition algorithm submodule 100E, a data mining algorithm submodule 100F, Big Data analysis algorithm submodule 100G, a statistical analysis algorithm submodule 100H, a fuzzy logic (including neuro-fuzzy) algorithm submodule 1001, an artificial neural network/artificial intelligence algorithm submodule 100J, a machine learning (including deep learning/meta-learning and self-learning) algorithm submodule 100K, a predictive analysis algorithm submodule 100L, a prescriptive analysis algorithm submodule 100M and a software agent algorithm submodule 100N. The application specific algorithm submodule 100C2 (e.g., Short Text Message Payment), the user's social graph 100N2 and the user's social wallet 100N3 are coupled a public/consortium/private blockchain.

The connections between various algorithm submodules of the intelligent algorithm 100X can be similar to synaptic networks to enable deep learning/meta-learning and self-learning of the intelligent algorithm 100X. Furthermore, "Fazila", as described in FIG. 10A can be coupled with special purpose learning computer hardware/processor or the Super System on Chip 400A/400B/400C/400D.

An application of "Fazila", as described in FIG. 10A is to estimate a user's own credit score, wherein all payments and bills of the user is passing through the social wallet, wherein each payment and bill may be coupled with a public/consortium/private blockchain. Furthermore, "Fazila", as described in FIG. 10A can be coupled with special purpose learning computer hardware/processor or the Super System on Chip 400A/400B/400C/400D. The user's own credit score may account the user's education, social profile, payment history, debt-to-income ratio and other credit-related relevant factors. The user's own credit score can recommend the user regarding spending habits (budgeting and/or credit score enhancement) in near real time/real time, based on the personalization of the user's profile. Additionally, the social wallet can enable online payment, online real money transfer between users and online virtual money transfer between users, protecting privacy of the user via the user's virtual avatar. Through the user's virtual avatar, the user just would need to supply/apply a fragment of information necessary to receive a service (e.g., purchasing an item).

Furthermore, the user can anonymously purchase products/services/pay online without revealing the user's true identity.

For example, the user could ask for a one-time password (OTP) for his/her Amazon account by clicking Amazon icon on the user's intelligent portable internet appliance (e.g., as illustrated in FIGS. 14A-14B). Amazon can look up the user's digital certificate (coupled with blockchain) on the blockchain and return an one-time password to the user's intelligent portable internet appliance. The one-time password will be encrypted so that it cannot be seen by anyone else, except the intended user. The user can then login to Amazon using the blockchain identity and the one-time password and anonymously purchase products/services/pay (e.g., paying from a credit/debit card coupled with the user's blockchain identity) online without revealing the user's true identity. The user can collect product at a delivery box coupled with the user's blockchain identity.

Details of the social wallet enabling online payment, online real money transfer between users and online virtual money transfer between users have been described/disclosed in U.S. non-provisional patent application Ser. No. 13/448, 378 entitled "SYSTEM AND METHOD FOR INTELLIGENT SOCIAL COMMERCE", filed on Apr. 16, 2012 (U.S. Pat. No. 9,697,556, issued on Jul. 4, 2017) and in its related U.S. non-provisional patent applications (with all benefit provisional patent applications) are incorporated in its entirety herein with this application.

Furthermore, intelligence from the user's social graph and/or social geotag can be realized by an intelligent learning set of instructions, which can include: a computer vision algorithm and/or an artificial intelligence algorithm and/or an artificial neural network algorithm and/or a machine learning (including deep learning/meta-learning and self-learning) algorithm for ultrafast data processing, image processing/image recognition, deep learning/meta-learning and self-learning.

Instead of the verification of the user's unique biometric identification, the user can utilize a near field communication enabled cash card to authenticate himself/herself with the near field communication enabled intelligent portable internet appliance 160 or the near field communication enabled intelligent wearable augmented reality personal assistant device 180.

FIG. 10B illustrates a near field communication enabled cash card to authenticate the user with the near field communication enabled intelligent portable internet appliance 160.

FIG. 10C illustrates a secure payment system between users and merchants, utilizing a clearing system of short text messages. The clearing system can be coupled with an expert system, which can be further coupled with the Super System on Chip 400A/400B/400C/400D, which includes an intelligent algorithm 100X. The above secure payment system can also enable peer-to-peer lending/peer-to-peer social commerce between users.

It should be noted that other forms of text message can be utilized instead of the short text message.

FIG. 10D illustrates a universal and secure application of the cash card A/B/C/D/E, for example, with respect to digital signature, biometric identification, digital certificate, e-mail access, internet access, digital purse, electronic shopping, secure short text message based purchase, electronic loyalty program and physical access.

FIG. 11 illustrates the object 120A. The object 120A integrates various tiny components in a System on Chip or System on Package. Tiny components are fabricated/constructed for extremely low power consumption. A tiny component 200 includes a tiny processor 200A, a tiny memory 200B and a tiny operating system (Tiny OS) 200C. The tiny component 200 is electrically coupled with a tiny data storage component 220, a tiny solar cell 240, a tiny battery 260, a tiny sensor 280 and an extremely low power tiny wireless component 300. The tiny sensor 280 can be fabricated/constructed for a specific purpose. The tiny solar cell 240 can be fabricated/constructed on top of the tiny battery 260. The extremely low power tiny wireless transmitter component 300 can be a tiny antenna. The object 120A can be electromagnetically powered from an ambient Wi-Fi network. Various versions of the object 120A are also possible within the spirit of this invention.

FIG. 12A illustrates the bioobject 120B. FIG. 12A is similar to FIG. 11, except the tiny sensor 280 is replaced by a tiny biosensor 320. The tiny biosensor 320 can be fabricated/constructed for a specific (e.g., glucose) purpose. The tiny solar cell 240 can be fabricated/constructed on top of the tiny battery 260. The extremely low power tiny wireless transmitter component 300 can be a tiny antenna.

FIG. 12B illustrates another embodiment of the bioobject 120B, which integrates the tiny battery 260, the extremely low power tiny wireless transmitter component 300 and the tiny biosensor 320. The tiny biosensor 320 can be fabricated/constructed for a specific sensing purpose. The tiny solar cell 240 can be fabricated/constructed on top of the tiny battery 260. The extremely low power tiny wireless transmitter component 300 can be a tiny antenna.

FIG. 12C illustrates another embodiment of the bioobject 120B, which can be a biodegradable nanoshell (encapsulating turn-on fluorophores) decorated with ligand A and ligand B to bind two specific receptors of a specific biological cell. Polymer groups shy away from water, which can cause them to aggregate and quench their fluorescence, but when polymer groups are far apart, they shine. Turn-on fluorophores are based on such polymers. Upon binding with the specific biological cell, the nanoshell releases encapsulated turn-on fluorophores. pH within cancer cells is about 6.6 (more acidic) compared to 7.4 pH of normal cells. Alternatively, turn-on fluorophores can be encapsulated within pH-sensitive biodegradable calcium phosphate nanoshells to release within cancer cells. When optically excited by a light source (e.g., light emitting diode/laser) and when turn-on fluorophores are within the specific biological cell, fluorescence can be detected by an ultrasensitive detector (e.g., indium gallium arsenide avalanche photodiode/electron-multiplying charge coupled device/charge coupled device/complementary metal oxide semiconductor). This embodiment can be suitable for in-vivo cancer diagnostics by fluorescence, if the bioobject 120B (e.g., biodegradable nanoshell) is encapsulated within a biocompatible package.

For in-vivo diagnostics, the light source can be coupled with an optical fiber. The end of the optical fiber can be fabricated/constructed with a protruded metal/non-metal nano optical antenna (FIGS. 30A-30J) to enhance light intensity and/or a nano optical focusing device to focus below the Abbey's diffraction limit (FIGS. 29D-29E).

Additionally, $Mn^{2+}$ ions can be encapsulated within the pH-sensitive biodegradable calcium phosphate nanoshell or any suitable nanoshell to release $Mn^{2+}$ in cancer cells. $Mn^{2+}$ in cancer cells can be utilized as an enhanced MRI contrast agent.

For a cancer therapeutic application, a functionalized (e.g., one/two ligands to chemically bind/couple with one type/two types of cell receptors) smart nanoshell encapsulating a light sensitive compound can be injected into the bloodstream and absorbed selectively by cancer cells. When the treated cancer cells are exposed to laser (coupled with an optical fiber), highly reactive oxygen molecules can be produced to destroy cancer cells.

Figure 29B:
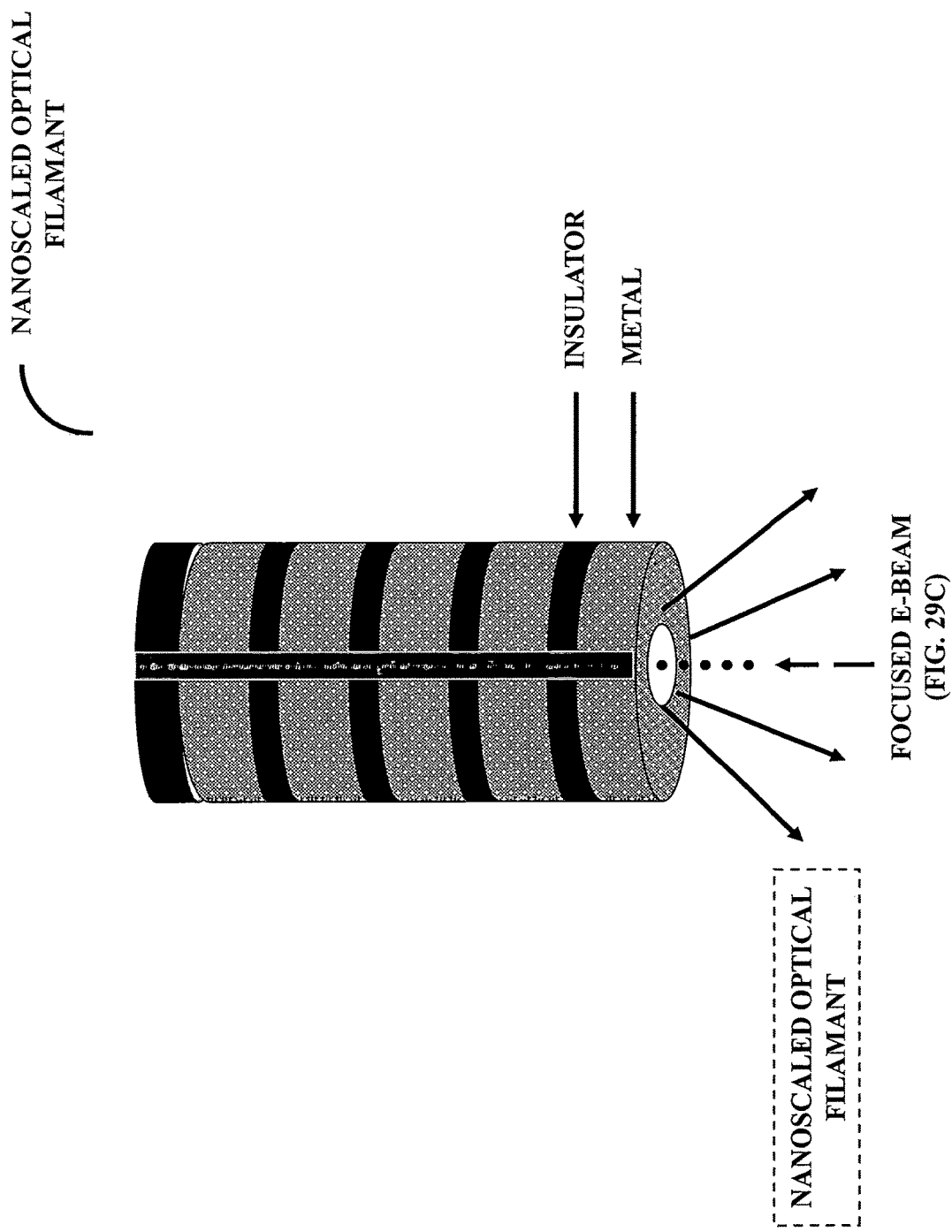
Figure 29C:
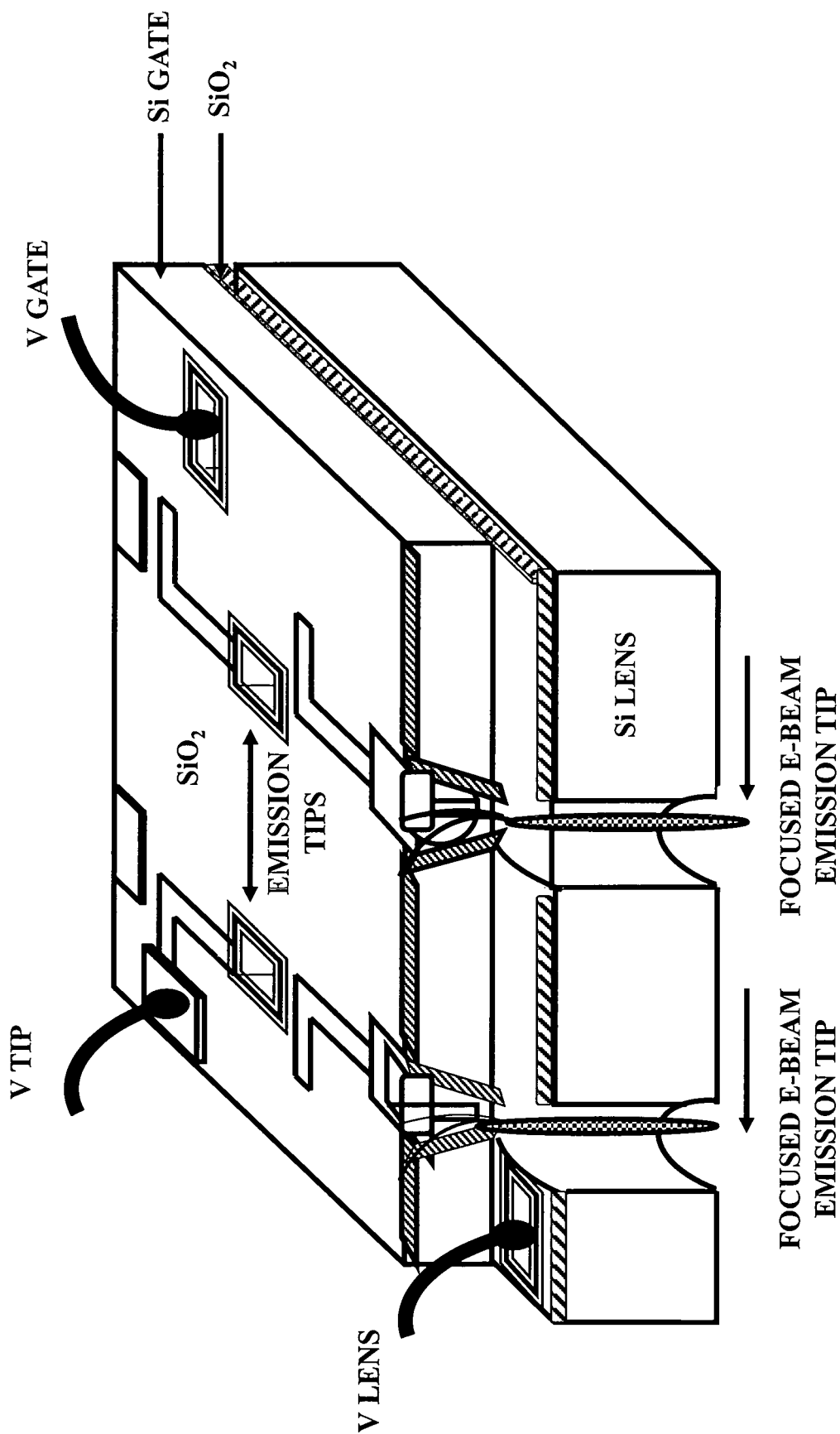
Figures 29D, 29E:
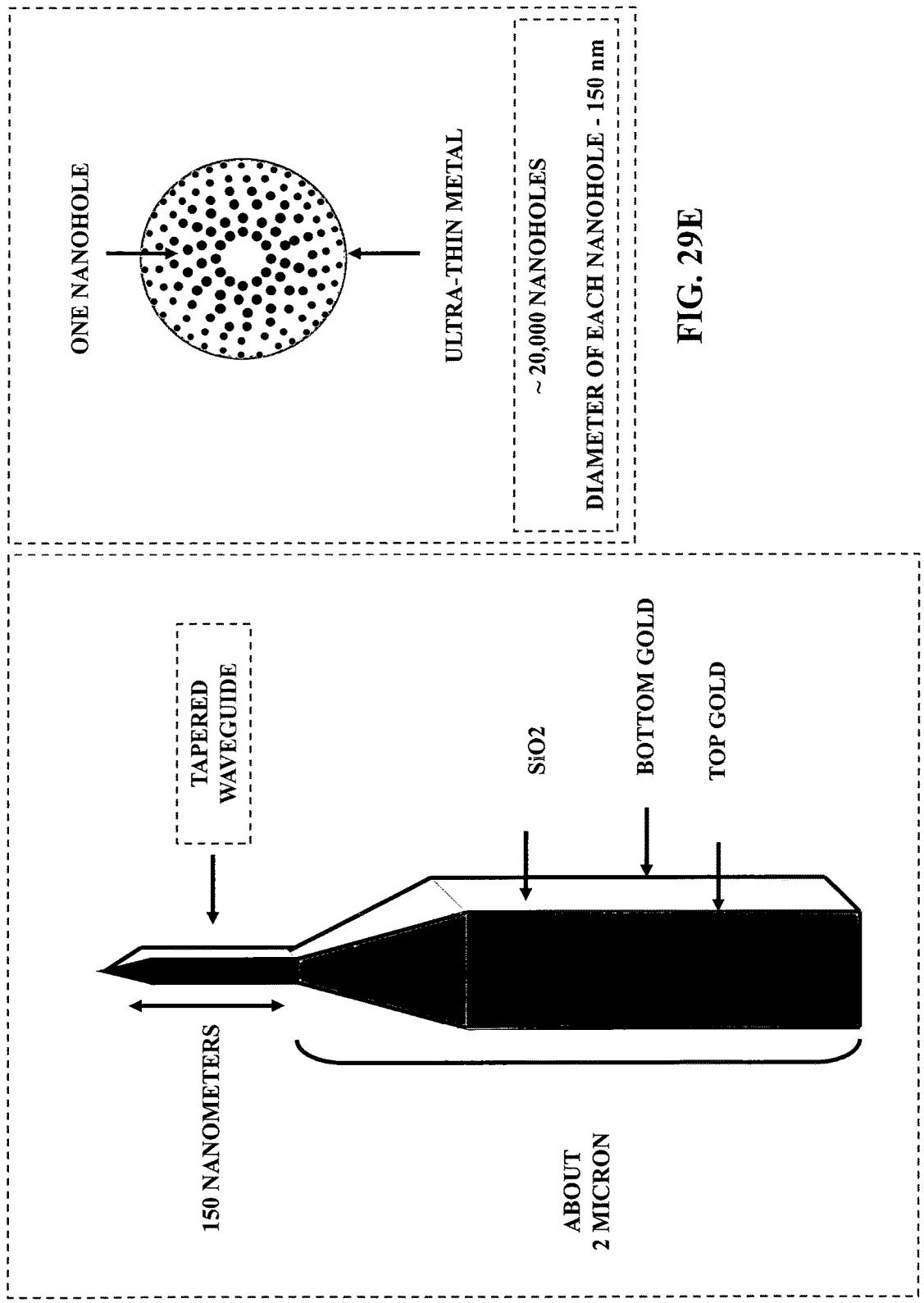
Figure 30A:
Figure 30A:
Figure 30B:
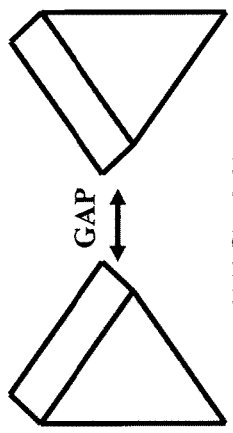
Figure 30D:
Figure 30C:
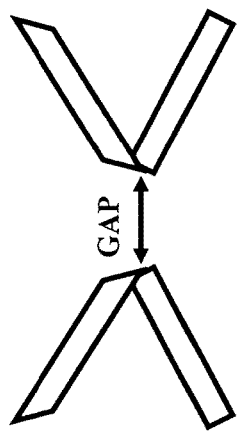
Figure 30E:
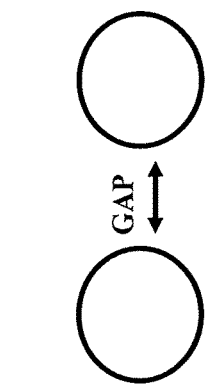
Figure 30F:
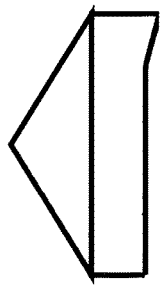
Figure 30H:
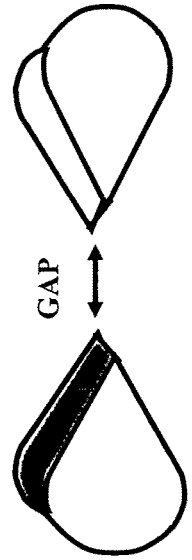
Figure 30G:
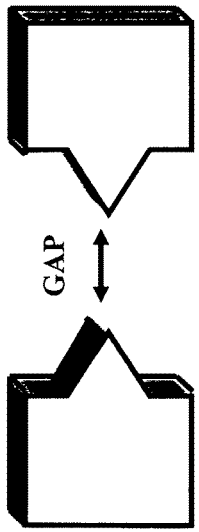
Figure 30I:
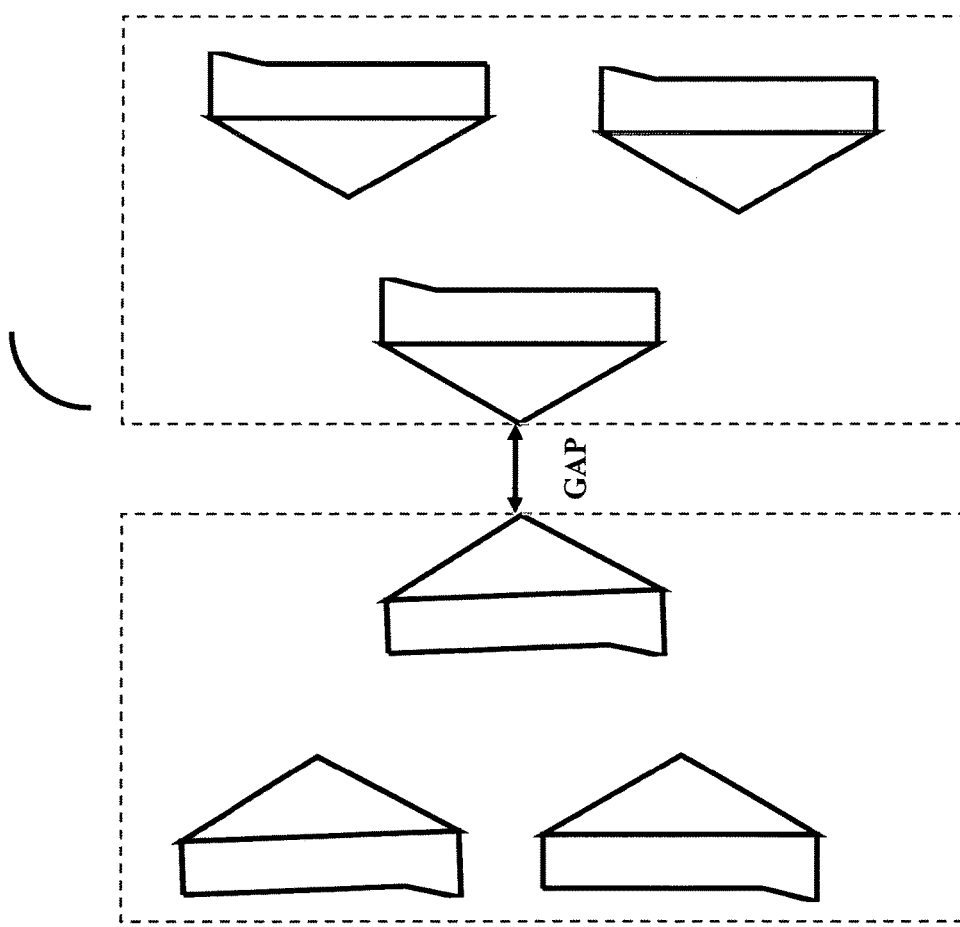
Figure 30J:
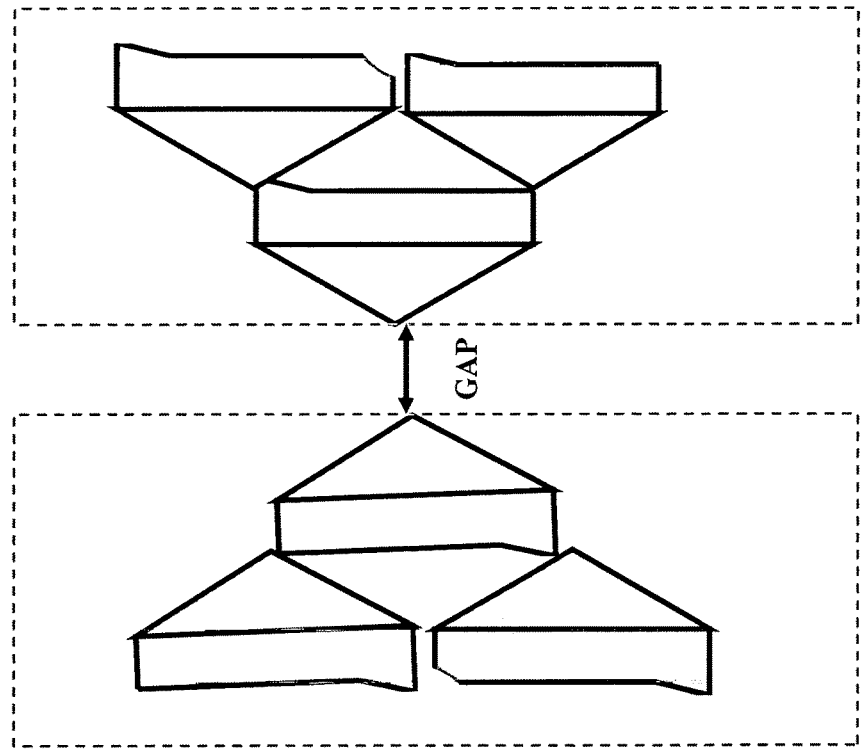

The end of the optical fiber can be fabricated/constructed with a protruded metal/non-metal nano optical antenna (FIGS. 30A-30J) to enhance light intensity and/or a nano optical focusing device to focus below the Abbey's diffraction limit (FIGS. 29D-29E).

Similarly, for a cancer therapeutic application, a functionalized (e.g., one/two ligands to chemically bind/couple with one type/two types cell receptors) smart nanoshell encapsulating cerium fluoride ($CeF_3$) nanoparticles can be injected into the bloodstream and absorbed selectively by cancer cells. When the treated cancer cells are exposed to X-ray/pulsed terahertz radiation, highly reactive oxygen molecules can be produced to destroy cancer cells.

FIG. 13 illustrates interactions/communications among the bioobjects 120Bs, the bioobject node 140 with the intelligent portable internet appliance 160, intelligent wearable augmented reality personal assistant device 180 and healthcare/remote/telemedicine healthcare providers. The bioobject 120B can be implanted within a human body.

For example, the bioobject 120B can measure and transmit the user's heart rhythm periodically. If the user's heart rhythm is perceived to be abnormal (compared with the user's normal heart rhythm) then the intelligent portable internet appliance 160/intelligent wearable augmented reality personal assistant device 180 can communicate automatically for emergency 911 (indicating the user's location by a global/indoor positioning system) help without any human input.

FIG. 14A illustrates the intelligent portable internet appliance 160 and the key components of 160 (in block diagram) are listed below in Table 1

TABLE 1

| Component | Description |
| --- | --- |
| 100 | Algorithm |
| 340 | Three-Dimensional/Holographic Display |
| 380 | Communication Radio* (WiMax/LTE) |
| 400A/B/C/D | Super System On Chip (Can Be Coupled With An Artificial Eye) |
| 420 | Operating System Algorithm |
| 440 | Security & Authentication Algorithm |
| 460 | Time Shift & Place Shift Device |
| 480 | Surround Sound Microphone |
| 500 | Front Facing High Resolution Camera(s) @ Low Light Level |
| | Front Facing High Resolution Camera(s) @ Low Light Level Can Be Coupled With An Artificial Eye(s) |
| | Front Facing High Resolution Camera(s) @ Low Light Level May Consist Of CMOS Camera Sensor(s) With Integrated Metasurface Built-On Top Of CMOS Camera Sensor(s) |
| 520 | Back Facing High Resolution Camera(s) @ Low Light Level |
| | Back Facing High Resolution Camera(s) @ Low Light Level Can Be Coupled With An Artificial Eye(s) |
| | Back Facing High Resolution Camera(s) @ Low Light Level May Consist Of CMOS Camera Sensor(s) With Integrated Metasurface Built-On Top Of CMOS Camera Sensor(s) |
| 540 | High Resolution Camcorder @ Low Light Level (Can Be Coupled With An Artificial Eye) |
| 560 | Microprojector |
| 580 | Proximity Radio* (Near Field Communication/Bluetooth LE) TxRx |
| 600 | Personal Area Networking Radio 1* (Bluetooth/Wi-Fi) TxRx |
| 620 | Personal Area Networking Radio 2* (Ultrawide Band/Millimeter-Wave) TxRx |
| 640 | Positioning System (Global Positioning System* & Indoor Positioning System) |
| 660 | Universal Communication Interface (UCI) |
| 680 | Electronic Personal Assistant |
| 700 | Electrical Powering Device (Solar Cell + Battery + Ultracapacitor) With Wireless Charging Option |
| 720 | Stylus |

[*With Radio Specific Antenna] [TxRx Means Transceiver]

The intelligent portable internet appliance 160 can enable wireless electrical charging or over the air electrical charging (electromagnetically charging through air). A power base station can be plugged into the electrical wall plug/socket. The power base station can emit low-frequency (4 MHz to 10 MHz) electromagnetic radiation. A power harvesting circuit on an electrical contact area of the intelligent portable internet appliance 160 can resonate at the same frequency emitted by the power base station. When the electrical contact area of the intelligent portable internet appliance 160 comes in close proximity to the power base station, the electrical contact area of the intelligent portable internet appliance 160 can absorb the energy via electromagnetic coupling-thus enabling electromagnetically charging through air.

Similarly, the intelligent portable internet appliance 160 can enable wireless electrical charging or over the air electrical charging (electromagnetically charging through air) with another intelligent portable internet appliance 160.

The intelligent portable internet appliance 160 can project light beam(s) through a permeable front panel to simulate a dial pad Details of the electronic personal assistant and stylus to write on a display have described/disclosed in U.S. non-provisional patent application Ser. No. 13/448,378 entitled "SYSTEM AND METHOD FOR INTELLIGENT SOCIAL COMMERCE", filed on Apr. 16, 2012 and its related U.S. non-provisional patent applications (with all benefit provisional patent applications) are incorporated in its entirety herein with this application.

A universal communication interface can integrate animation, animated GIF, drawings, emotions, gestures (hand/eye), location data, text, voices, voice snippets and videos.

The universal communication interface can be further enhanced by "Fazila" as described in FIG. 10A Solar cells can be fabricated/constructed on top of the battery, integrated with an ultracapacitor.

The intelligent portable internet appliance 160 is sensor aware and context aware, as it is wirelessly connected/sensor connected with objects 120As, object nodes 120s, bioobjects 120Bs and bioobject nodes 140s.

FIG. 14B illustrates another version of the intelligent portable internet appliance (denoted as 160A), which includes the three-dimensional/holographic display 340, a stretchable display 360 (embedded with inkjet printed transparent processor(s) and memristors) and a communication radio 380. The stretchable display 360 can be reconfigured into two viewing windows, denoted as 360A and 360B. The two viewing windows can display different images.

Alternatively, a display or a holographic display can be foldable, which can be constructed from a graphene sheet and/or an organic light-emitting diode connecting/coupling/interacting with a printed organic transistor and a rubbery conductor (e.g., a mixture of carbon nanotube/gold conductor and rubbery polymer) with a touch/multi-touch sensor.

A foldable display can replace the stretchable display 360.

Details of the foldable display have been described/disclosed in U.S. non-provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 and in its related U.S. non-provisional patent applications (with all benefit provisional patent applications) are incorporated in its entirety herein with this application.

It should be noted that the stretchable display 360 can be a wraparound display that continues over the edge of the intelligent portable internet appliance 160/160A onto the rear of the intelligent portable internet appliance 160/160A.

FIG. 15A illustrates transition metal oxide (TMO) layers, very large-scale integration (VLSI) of photonic integrated circuits layers and very large-scale integration of electronic integrated circuits (EIC) layers within a digital processor 400A.

FIG. 15B illustrates a top view of FIG. 15A.

FIG. 15C illustrates a completed wafer with (a) electronic integrated circuits, (b) photonic integrated circuits, utilizing III-V semiconductor epitaxial layers on silicon and (c) transition metal oxide devices.

Gradually tapered silicon waveguides (on silicon) connecting with polymer waveguides (on silicon) can enable large-scale integration of photonic integrated circuits and electronic integrated circuits. Various photonic components can be integrated utilizing an asymmetric twin-waveguide (ATG) structure.

Details of the large-scale integration of photonic integrated circuits and electronic integrated circuits have been described/disclosed in U.S. non-provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

FIG. 15D illustrates a top view of a two-dimensional material (e.g., molybdenum disulphide/graphene)-transition metal oxide material (X) heterostructure based transistor devices. Furthermore, instead of a single two-dimensional material, two or more two-dimensional materials of designer properties can be utilized.

FIG. 15E illustrates a cross-section view of FIG. 15D.

FIG. 15F illustrates a top view of a two-dimensional material-phase transition material (Y) heterostructure based transistor devices. A phase change material can be utilized instead of a phase transition material.

FIG. 15G illustrates a cross-section view of FIG. 15F.

A topological insulator is an insulator in the bulk interior, but conducting at the edges without any heat dissipation. A special normal insulator can be switched (e.g., either electrically or optically by a laser) to a topological insulator (material state) at a room temperature. Such switchable topological insulator can electrically connect a source metal and a drain metal of a transistor. For example, an electrically switchable (room temperature) topological insulator is a two-dimensional (atomically thin) $Na_3Bi$ or $Bi_xSe(1-x)$ or $Bi_2Se_3$ or an atomically thin layer of bismuth atoms on insulating silicon carbide substrate (bismuthene).

Alternatively, attracted pairs of electron and holes in two (2) atomically thin semiconductors (a first semiconductor is carrying electrons and the second semiconductor is carrying holes) can enable (room temperature) exciton superfluid of an energy efficient exciton transistor without any heat dissipation.

FIG. 16A illustrates 400A4, a two-dimensional integration of memristors. Memristors (e.g., based on transition metal oxide material/ferroelectric material/phase change material/phase transition/amorphous silicon material) are formed at the intersections of row metal electrodes and column metal electrodes. A particular transition metal oxide-tantalum oxide can be very stable/reliable under a large number of electrical pulses. A particular phase change material-$Ag_4In_3Sb_{67}Te_{26}$ (AIST) switches between a disordered amorphous phase A and another disordered amorphous phase B in a sub-picosecond time-scale, when excited by picosecond pulses (e.g., about 500 kV/cm peak field strength at a repetition rate of about 30 Hz for about 30 seconds). Such phase change switching occurs at lower electric field strength/energy level and can enable an ultrahigh speed non-volatile memristor (as switching from the disordered amorphous phase B to the disordered amorphous phase A requires an application of a short burst of heat, which can be provided electrically/optically).

Memristor is a non-linear resistive and switching device with an inherent memory similar to a synapse. Both are two-terminal devices whose conductance can be modulated by an external stimulus with the ability to store (memorize) new information. Memristor can bring data closer to a processor, without a lot of electrical power consumption, as a biological neural system does. Also, memristors can create neuron-like voltage spikes to enable neuromorphic circuits.

Alternatively, photonic synapse mimicking the biological neural synapse can be based on a tapered optical waveguide (e.g., silicon nitride optical waveguide) with discrete phase change/phase transition material islands on top of the tapered optical waveguide and a 3-port optical circulator-optically coupling the photonic synapse (in one port), the post-neuron (in another port) and the weighing pulses and pre-neuron (in another port).

A photonic integrated circuit of many (e.g., 100) photonic synapses can include both input diffraction (optical) couplers and output diffraction (optical) couplers-thus enabling a photonic neural learning processor.

Additionally, a photonic neural learning processor (can be useful for machine learning (including deep learning/meta-learning and self-learning) and/or image/pattern recognition and/or Big Data analysis) can be fabricated/constructed for example, utilizing a cascaded configuration of interferometers (e.g., Mach-Zehnder type interferometers), 3-db (optical) couplers and waveguide based phase shifters. Heat applied to the waveguide base phase shifter(s) can direct light beams to change its shape. It should be noted that interferometer(s) and/or waveguide based phase shifter(s) can be fabricated/constructed, utilizing a phase change/phase transition material for faster response to an external stimulus (e.g., heat or voltage) and/or integrated with saturable absorbers (e.g., graphene integrated saturable absorber). To reduce thermal cross-talk between the heating elements, thermal isolation trenches can be fabricated/constructed between the heating elements. Alternatively, the photonic neural learning processor can be fabricated/constructed for example as a network(s) of wavelength tunable/selective laser-integrated with an external modulator, when the external modulators are activated by an action of weighted electrical signals (from an array of memristors or by converting optical signals of distinct wavelengths from ring resonators/fast tunable ring resonators (e.g., fast tunable ring resonators incorporating vanadium dioxide thin-film/quantum dot) based add/drop filters). The above network(s) can also utilize a network(s) of optical switches/fast optical switches. It should be noted that the photonic neural learning processor can be a standalone subsystem. Such a system on chip or an artificial neural network based system on chip can enable cognitive/artificial neural like computing. Furthermore, a system on chip or an artificial neural network system based on chip can include ultrafast graphene transistors of modified band structure: silicon carbide (substrate)—preciously positioned/intercalated magnetic metal ions (e.g., rare-earth metal ions) below graphene-graphene. Furthermore, a system on chip or an artificial neural network based system on chip can integrate the photonic neural learning processor via a network(s) of waveguides (including a waveguide(s) of chalcogenide glass material), thus enabling a hybrid electrical-photonic neural learning processor.

Details of the memristor have been described/disclosed in U.S. non-provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

Alternatively, a circularly/elliptically polarized optical pulse(s) from a first pulsed laser of a first optical intensity (e.g., 0.1 mV/cm strength) at a first wavelength (e.g., infrared) on an atomically thin layer/monolayer/thin-film of a two-dimensional material (e.g., tungsten diselenide) can put electrons of the two-dimensional material into a first pseudospin state (e.g., computing Von Neumann state 1) and then a linearly polarized optical pulse(s) from a second pulsed laser of a second optical intensity (e.g., 10 mV/cm strength) at a second wavelength (e.g., terahertz—for example coupling a femtosecond laser device with a non-linear material) can put electrons of the two-dimensional material into a second pseudospin state (e.g., computing Von Neumann state 2) in femtoseconds. The first optical intensity is different from the second optical intensity and the first wavelength is different from the second wavelength.

Such ultrafast switching from the first pseudospin state/computing Von Neumann state 1 (e.g., emitting detectable light of clockwise circular polarization) to the second pseudospin state/computing Von Neumann state 2 (e.g., emitting detectable light of counter clockwise circular polarization) can enable a unique building block of an ultrafast (clock speed) digital optical processing element.

Furthermore, the two-dimensional material can be epitaxially (e.g., atomic layer epitaxy/molecular beam epitaxy) grown/deposited (e.g., chemical/ion beam/physical vapor deposition)/three-dimensionally printed on a first substrate (e.g., boron nitride), where the first substrate is transparent to the incident wavelength.

For example, the first substrate can be a silicon/silicon-on-insulator/silicon-on-sapphire, which is transparent to an infrared wavelength. The first substrate can be utilized for epitaxially growing/depositing/three-dimensional printing the two-dimensional material (also etching an array of microscaled/nanoscaled spots of the two-dimensional material).

An array of the microscaled/nanoscaled spots can be arrayed into a two-dimensional configuration. Additionally, a vertical hetrostructure stack of the two-dimensional material and an array of the microscaled/nanoscaled spots can be arrayed into a three-dimensional configuration.

Alternatively, an ultrafast photonic neural learning processor can be fabricated/constructed when a network(s) of the first pulsed lasers and second pulsed lasers are activated by an action of weighted electrical signals (from an array of memristors or by converting optical signals of distinct wavelengths from ring resonators/fast tunable ring resonators (e.g., fast tunable ring resonators incorporating vanadium dioxide thin-film/quantum dot) based add/drop filters).

Furthermore, the photonic neural learning processor can integrate network(s) of waveguides (including a waveguide(s) of chalcogenide glass), thus enabling a hybrid electrical-photonic neural learning processor.

A qubit has the odd property that it can be in superposition, meaning it's in two different states at the same time: The bits in a Von Neumann computer can represent either zero or one, but a qubit can represent both zero and one at the same time. For this reason, a string of only 16 qubits can represent 64,000 different numbers simultaneously. It is because a quantum computer can in principle evaluate all possible solutions to the same problem in parallel that increases in computational speed exponentially. But one of the difficulties in building a quantum computer is that superposition of states can be very fragile. Any interaction (e.g., a material defect/vibration/fluctuating electric fields/ noise) with its environment can cause a subatomic particle to snap into just one of its possible states. Photons are much more resistant to outside influences than subatomic particles, but that also makes them harder to control over the course of a computation, a quantum computer needs to repeatedly alter the states of qubits.

Additionally, there may be superposition of the first pseudospin state and second pseudospin state-enabling an ultrafast qubit at a normal temperature. An array of such qubits at microscaled/nanoscaled spacing (only limited by diffraction/near-field diffraction) can enable an optical quantum computer at a normal temperature.

Furthermore, a compact optical configuration can be realized by fabricating/constructing a network of silicon nitride waveguides on top of a second substrate. The network of silicon nitride waveguides can route light. Above the silicon nitride waveguides, a layer (about 1 micron in thickness) of silicon dioxide thin-film or an electrically activated optically tunable material based thin-film can be fabricated/constructed. On top of the silicon dioxide thin-film or electrically activated optically tunable material based thin-film on the second substrate, there are transparent/indium tin oxide/niobium electrodes, integrated with tiny openings in the electrodes to allow light (which is guided via silicon nitride waveguides) to pass through to activate/configure a qubit on the first substrate. Beneath the tiny openings in the transparent/indium tin oxide/niobium electrodes, the waveguides in silicon nitride break into a series of sequential ridges to act as diffraction gratings in order to direct light down through the holes and concentrate the light into a beam narrow enough to activate/configure a qubit on the first substrate, as described in previous paragraph. Furthermore, integration of a surface normal light modulator (e.g., a graphene based surface normal spatial light modulator) with the diffraction gratings can also be realized.

A single microscaled/nanoscaled spot (only limited by diffraction/near-field diffraction) of the two-dimensional material can be formed on a waveguide (on the second substrate), wherein the waveguide can be utilized to propagate both circularly/elliptically polarized optical pulse(s) of the first wavelength at time t=0 and linearly polarized optical pulse(s) of the second wavelength at time $t=t_1$, which can be sequenced in time domain.

Furthermore, in some configuration the first substrate can be integrated/co-packaged with the second substrate. In some configuration the first substrate can be same as the second substrate.

Alternatively, qubits on the first substrate can be realized by entangled impurity ions, implanted (at a precise depth) into a nanoscaled (about 50 nm in diameter single crystal) phase transition material. The phase transition material can be grown or fabricated/constructed on yttria-stabilized zirconia (YSZ) with refractive index of 2.110 at 1550 nm. Photoluminescence (which can be enhanced by a pair of nanoscaled optical antennas (as illustrated in FIGS. 30B, 30C, 30E, 30F, 30G and 30H) of particular wavelength the impurity ions within the nanoscaled single crystal phase transition material can be obtained by exciting by the light of suitable wavelength through the hole as described above and detected by a photodiode. However, the photoluminescence wavelength of the impurity embedded within the nanoscaled single crystal phase transition material (e.g., samarium nickelate ($SmNiO_3$) or vanadium dioxide ($VO_2$)) one can be detuned, upon the phase transition of the phase transition material by an external stimulus (e.g., an electrical/optical/terahertz stimulus). The first substrate may be cooled to preserve the qubits for sufficient amount of time.

Alternatively, qubits on the first substrate can be realized by entangled nitrogen-vacancy (NV) color centers. The first substrate can include an array (or a network) of optical waveguides (e.g., single mode/multi-mode optical waveguides) of a diamond single-crystal by optical/electron-beam lithography and ion-beam milling/reactive-ion/wet etching. The above array (or the network) of optical waveguides can be coupled to an array of optical fibers.

A nitrogen-vacancy color center is a nitrogen (contamination) impurity molecule in the diamond (carbon) lattice located adjacent to an empty lattice site or a vacancy. A nitrogen-vacancy color center can be created utilizing a single-crystal diamond with inherently contaminated with about 2 PPM (parts per million) nitrogen impurity molecules and a first laser pulse (e.g., from a femtosecond laser).

The first pulse can be activated to create an empty lattice site or a vacancy. Then a second laser pulse can be activated to move/push the newly created empty lattice site or the vacancy toward the nitrogen molecule (contamination) impurity molecule until a fluorescence signal from the newly formed nitrogen-vacancy color center is detected. The intensity of the first laser pulse can be higher than the intensity of the second laser pulse.

Each optical waveguide can include one or more such nitrogen-vacancy color centers at specific locations. Each nitrogen-vacancy color center can be located within the gap of a bow tie nanoantenna to enhance the fluorescence signal from the nitrogen-vacancy color center. Furthermore, each nitrogen-vacancy color center can be optically coupled with photonic crystals to enhance the fluorescence signal from the nitrogen-vacancy color center. Additionally, each specific location can include a curved lens or a metamaterial lens (e.g., including an array of nanoscaled pillars) for efficient collection of light from each nitrogen-vacancy color center. However, the curved lens or the metamaterial surface may be fabricated/constructed after or before each nitrogen-vacancy color center is formed.

The first substrate can include microwave strip lines to control nitrogen-vacancy color center and electrodes to tune the emission wavelength of the fluorescence signal from each nitrogen-vacancy color center upon excitation from a third laser pulse from the second substrate (the second substrate is described in previous paragraphs). A 532 nm laser (for spatial imaging and stabilizing the local charge environment), a 637 nm laser (for resonant readout) and a microwave signal (for ground-state spin manipulation) can address a single nitrogen-vacancy color center. Thus, spins of the nitrogen-vacancy color center are entangled and can enable a qubit (for quantum computer and/or quantum memory and/or quantum internet). For example, a first microwave signal can put the electronic spins of the nitrogen-vacancy color center into superposition. Then, a radio-frequency signal can put the nitrogen nucleus into a specified spin state. A second lower power microwave signal can entangle the spins of the nitrogen-vacancy color center and they are suitable to perform quantum computation. After the quantum computation is performed, a third microwave signal (with polarization is rotated relative to that of the second microwave signal) can disentangle the nucleus and the nitrogen-vacancy color center. Additionally, utilizing a feedback control system, a nitrogen-vacancy color center qubit can stay in superposition over a long period of time. Additionally, a thin-film of a piezoelectric material coupled with two electrodes can be fabricated/constructed on the first substrate. Consequently, both laser and surface acoustic wave (SAW) can be used to control its quantum state.

It is possible that these qubits can operate at room temperature. But, the first substrate may be cooled at lower temperature (e.g., 4K) so that qubits are not fragile.

The nitrogen vacancy based qubit can be integrated with an input (excitation) laser. The input (excitation) laser is only configured to generate light pulses mimicking a neuron to communicate with many neurons. The input (excitation) laser is only configured to generate light pulses mimicking a neuron to communicate with many neurons.

The input (excitation) laser for the nitrogen vacancy based qubits can be excited only when a network(s) of the first pulsed lasers and second pulsed lasers are activated by an action of weighted electrical signals (from an array of memristors or by converting optical signals of distinct wavelengths from ring resonators/fast tunable ring resonators (e.g., fast tunable ring resonators incorporating vanadium dioxide thin-film/quantum dot) based add/drop filters)—thus coupling nitrogen vacancy based qubits with the Super System on Chip 400A/400B/400C/400D (including the neural learning processor of the Super System on Chip 400A/400B/400C/400D, wherein the neural learning processor consists of an array or a network of memristors, arranged in either in two-dimension or in three-dimension) and/or the photonic neural learning processor.

Furthermore, nitrogen-vacancy color center based qubit can be replaced by a defect center in a two-dimensional material (e.g., hexagonal boron nitride (h-BN)).

For some of the defects in a two-dimensional material, the intensity of the emitted light may change with a magnetic field, which controls the spin and the spin controls the number of photons emitted from the defects in a two-dimensional material. This change in number of photons can be utilized as a qubit (potentially) at room temperature. This configuration can enable a portable nuclear magnetic resonance (NMR) imaging device (like a stethoscope). Quantum mechanical spins due to defects in a two-dimensional material can create a faint radio frequency signal. This faint radio frequency signal can be converted into an electrical signal utilizing an electrical circuit, consisting of capacitor (C), inductance (L) and resistor (R). The electrical circuit can be coupled with an ultrathin/nanoscaled (e.g., 10-20 nm thick) membrane. The ultrathin/nanoscaled membrane can form an external cavity. The resonance frequency (by laser excitation) of the external cavity may change minutely due to nanoscaled deformation of the ultrathin/nanoscaled membrane and the minute change (the original frequency of the laser and frequency change due to signals quantum mechanical spins). However, the quantum mechanical spins due to defects in a two-dimensional material may change in the presence of hydrogen molecules in a biological material and thus the quantum mechanical spins can be detected for in vivo and ex vivo diagnostic applications.

These defects in a two-dimensional material can be systematically organized/created by a first laser pulse and second laser pulse. The first laser can be activated to create a defect center in a two-dimensional material. Then a second laser pulse can be activated to move/push the newly created defect center until a fluorescence signal from the newly formed defect center is detected under a suitable magnetic field. The intensity of the first laser pulse can be higher than the intensity of the second laser pulse.

Furthermore, a compact optical configuration can be realized by fabricating/constructing a network of silicon nitride waveguides on top of a second substrate. The network of silicon nitride waveguides can route light. Above the silicon nitride waveguides, a layer (about 1 micron in thickness) of silicon dioxide thin-film or an electrically activated optically tunable material based thin-film can be fabricated/constructed. On top of the silicon dioxide thin-film or electrically activated optically tunable material based thin-film on the second substrate, there are transparent/indium tin oxide/niobium electrodes, integrated with tiny openings in the electrodes to allow light (which is guided via silicon nitride waveguides) to pass through to activate/configure a qubit on the first substrate. Beneath the tiny openings in the transparent/indium tin oxide/niobium electrodes, the waveguides in silicon nitride break into a series of sequential ridges to act as diffraction gratings in order to direct light down through the holes and concentrate the light into a beam narrow enough to activate/configure a qubit on the first substrate, as described in previous paragraph. Furthermore, integration of a surface normal light modulator (e.g., a graphene based surface normal spatial light modulator) with the diffraction gratings can also be realized.

Many (e.g., 100) qubits may be controlled by a commercially available multi-channel activation and readout control system (e.g., Zurich Instruments' Quantum Computing Control System (QCCS)). The readout of such qubits are performed by a photodetector and then digitized by a pulse counter.

FIG. 16B illustrates 400A5, a three-dimensional integration of memristors.

FIG. 16C illustrates 400A6, which is a three-dimensional integration of a memristor with various versions of a digital processor (based on 400A1/400A2/400A3).

Additionally the above 400A6 in FIG. 16C, which is a three-dimensional integration of a memristor with a digital processor, wherein the digital processor can include transistors based on a topological insulator or exciton (superfluid), as discussed in previous paragraphs.

FIG. 16D illustrates 400A7, which is a three-dimensional integration of a memristor and a digital memory with various versions of a digital processor (based on 400A1/400A2/400A3).

Additionally the above 400A7 in FIG. 16D, which is a three-dimensional integration of a memristor with a digital processor, wherein the digital processor can include transistors based on a topological insulator or exciton (superfluid), as discussed in previous paragraphs.

Furthermore, the digital processor can also be based on ferroelectric or carbon nanotube material. A carbon nanotube can be utilized as an electrode in 400A4/400A5/400A6/400A7 and as an interconnecting material in 400A5/400A6/400A7.

Details of the three-dimensional interconnecting material, as carbon nanotube have been described/disclosed in U.S. non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

FIG. 17A illustrates how a memristor would respond/switch with fixed amplitude serial input pulses.

FIG. 17B illustrates how a memristor would respond/switch with multiple weighted amplitude parallel input pulses.

FIG. 17C illustrates interactions of memristors with various nodes A, B, C, D, E and F. The node can be a processing node.

FIG. 18A illustrates a ferroelectric digital memory fabricated/constructed on a digital processor (based on 400A1/

400A3/400A3) in a vertical stacking configuration. This configuration is denoted as 400A8.

FIG. 18B illustrates a digital memory (as illustrated in FIGS. 19A-19C) fabricated/constructed on a digital processor (based on 400A1/400A3/400A3) in a vertical stacking configuration. This configuration is denoted as 400A9.

In a von Neumann computer, computation occurs in orders of magnitude faster than accessing memory. Applications in computer can spend over 50% of all computing cycles waiting for data to arrive from memory. This problem is the memory bottleneck. To mitigate this memory bottleneck, generally a microprocessor uses a hierarchical memory system with small and fast memory close to the microprocessor (i.e., caches) and large yet slower memory farther away from the microprocessor. A predictive memory prefetcher algorithm (enabled by an artificial intelligence algorithm and/or an artificial neural network based learning algorithm and/or a machine learning (including deep learning/meta-learning and self-learning) algorithm) can predict when to fetch what data into cache to reduce the memory bottleneck and enable predicting memory access patterns efficiently.

FIG. 19A illustrates a nanoscaled vanadium oxide/phase change material based digital memory. The nanoscaled vanadium oxide/phase change material is sandwiched between a carbon nanotube bottom electrode (carbon nanotube is fabricated/constructed on silicon dioxide on silicon) and a top electrode. This digital memory embodiment is denoted as 400M1.

FIG. 19B illustrates nanoscaled vanadium oxide/phase change material based digital memory, wherein the bottom electrode and top electrode are platinum. This digital memory embodiment is denoted as 400M2. Furthermore, a particular phase change material-$Ag_4In_3Sb_{67}Te_{26}$ (AIST) switches between a disordered amorphous phase A and another disordered amorphous phase B in a sub-picosecond time-scale, when excited by picosecond electrical pulses (e.g., about 500 kV/cm peak field strength at a repetition rate of about 30 Hz for about 30 seconds). Such phase change switching occurs at lower electric field strength/energy level and can enable an ultra-high speed non-volatile memristor (as switching from the disordered amorphous phase B to the disordered amorphous phase A requires an application of a short burst of heat, which can be provided electrically/optically).

FIG. 19C illustrates another nanoscaled vanadium oxide based digital (ferroelectric) memory, wherein the nanoscaled vanadium oxide is sandwiched between a thermal silicon dioxide ($SiO_2$) and atomic layer deposited (ALD) silicon dioxide. This digital memory embodiment is denoted as 400M3. Vanadium oxide can be vanadium dioxide or vanadium sesquioxide ($V_2O_3$) or other vanadium oxide composition.

But, there are other memory types such as—the ferroelectric FET (FeFET), Nanotube RAM, Phase-Change Memory, ReRAM and Spin-Orbit Torque MRAM (SOT-MRAM) can be utilized. For the ferroelectric FET, lead-zirconium-titanate (PZT) or lead-zirconium-titanate integrated with an ultra-thin film (~25 nm) of zinc oxide or hafnium dioxide ($HfO_2$) or hafnium zirconium dioxide ($HfZrO_2$) can be utilized and for example, $TiN/HfZrO_2/$IGZO capacitor can be fabricated/constructed. It should be noted that the ferroelectric FET can be utilized as a memristor.

FIGS. 20A-20F illustrate step by step electrical interconnections of 400A6/400A7/400A8/400A9 and additional digital memories (e.g., DRAM), if needed for performance and digital storage. They are electrically connected by metallized via holes.

Figures 20A, 20B:
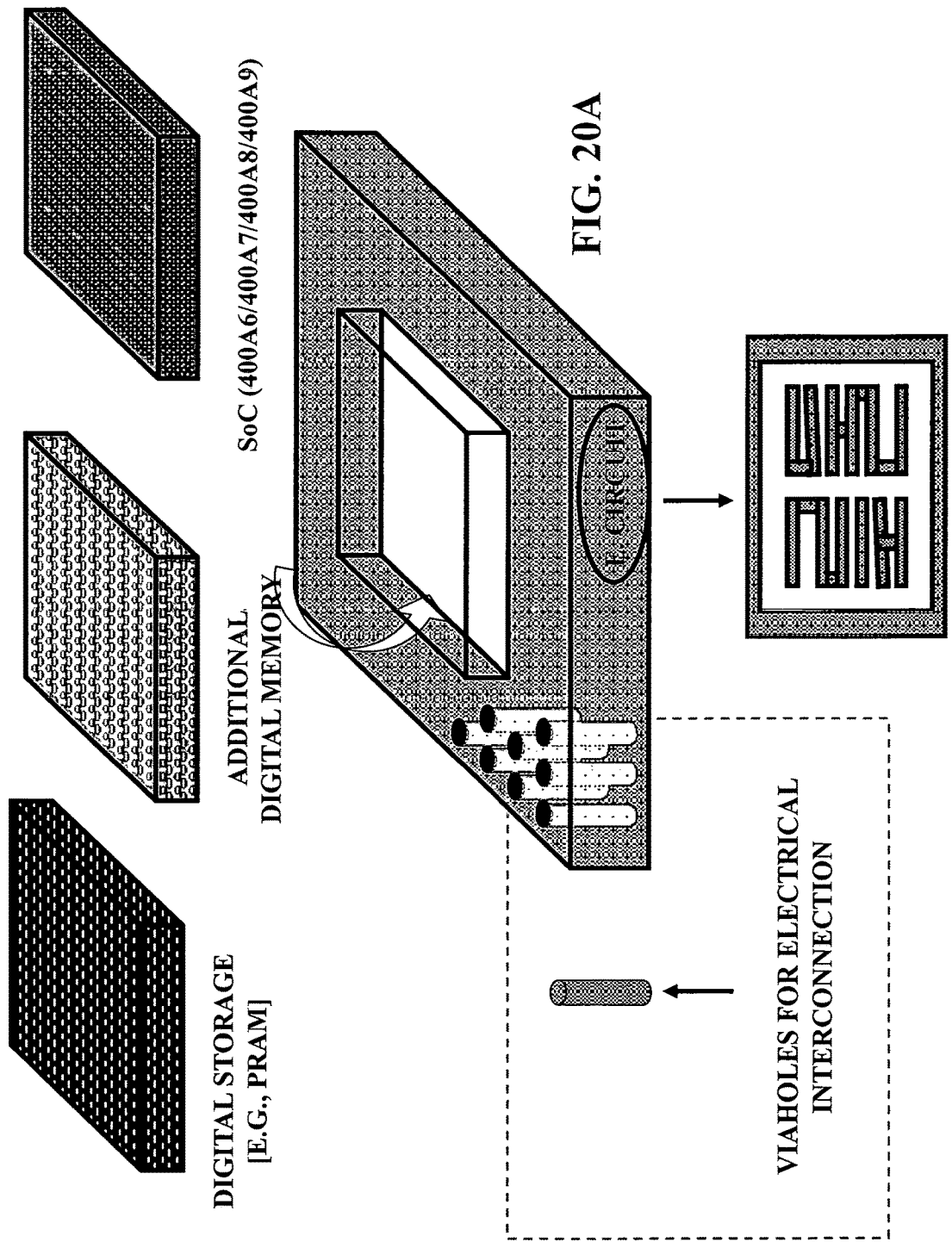
Figure 20C:
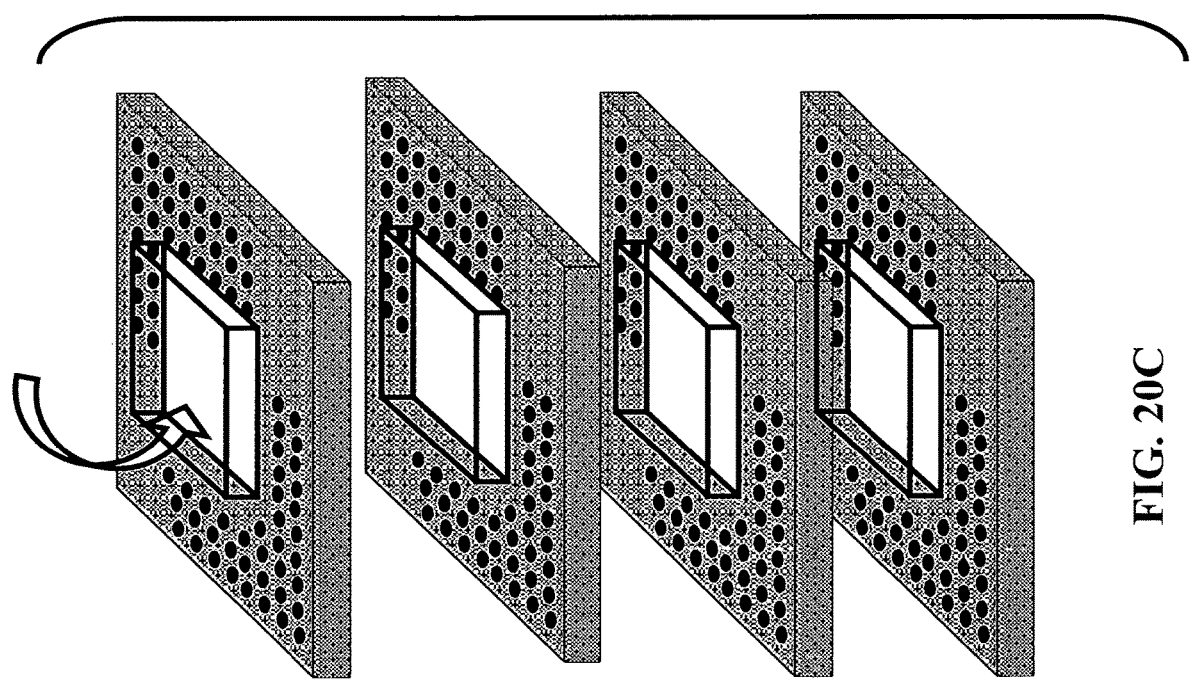
Figure 20D:
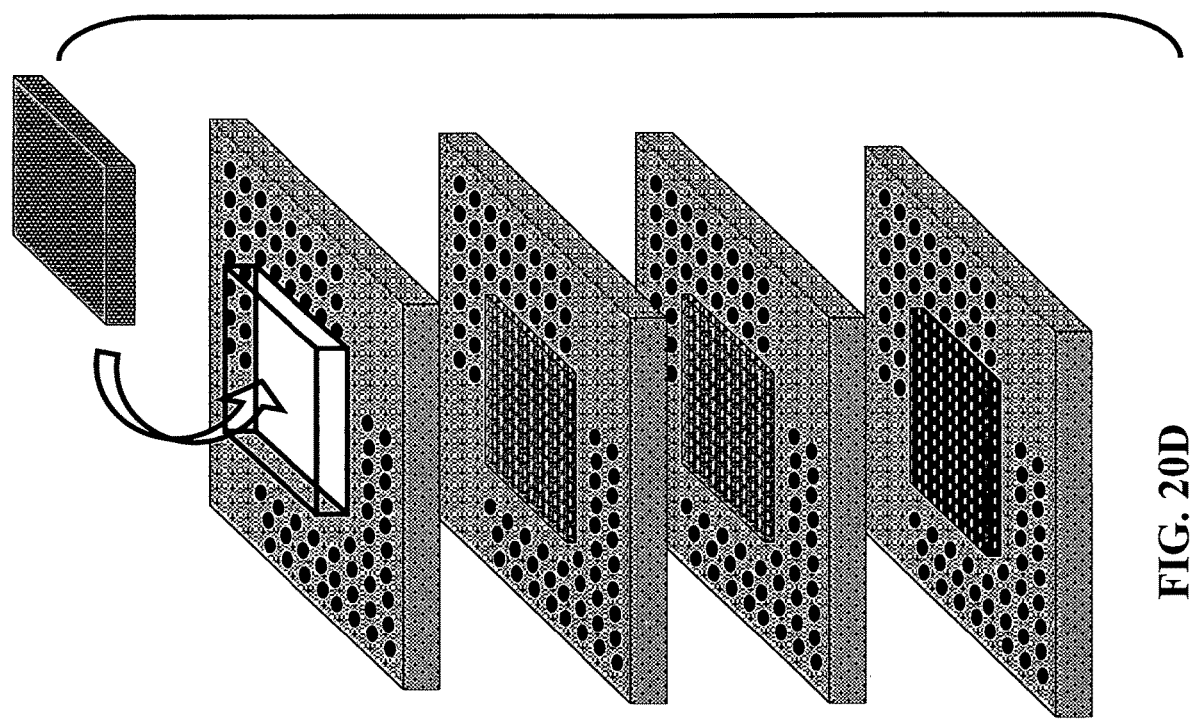
Figure 20E:
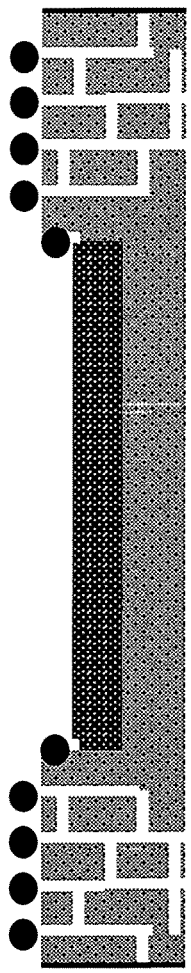
Figure 20F:
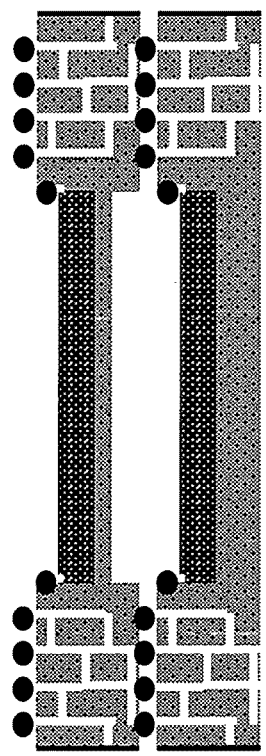
Figure 20G:
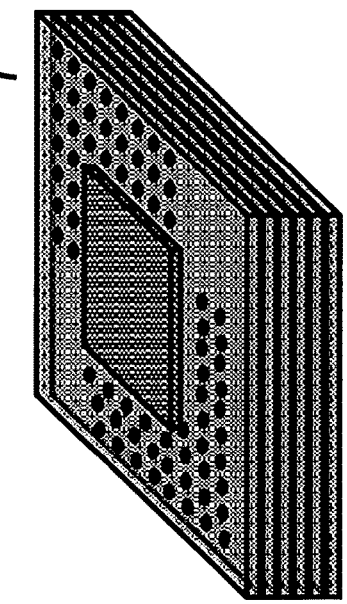

FIG. 20G illustrates the Super System on Chip 400A, utilizing electrical interconnections.

Figure 21A:
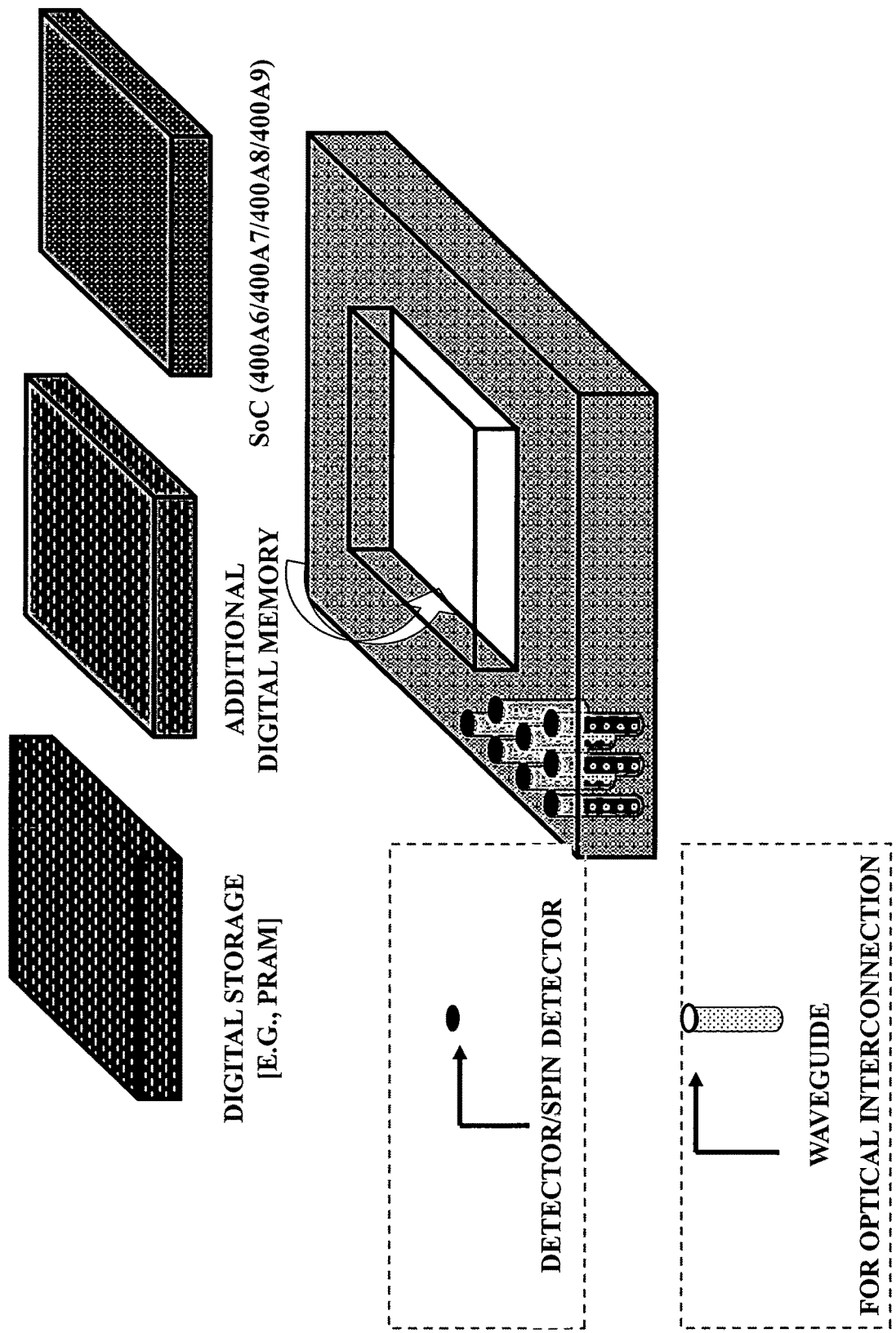
Figure 21B:
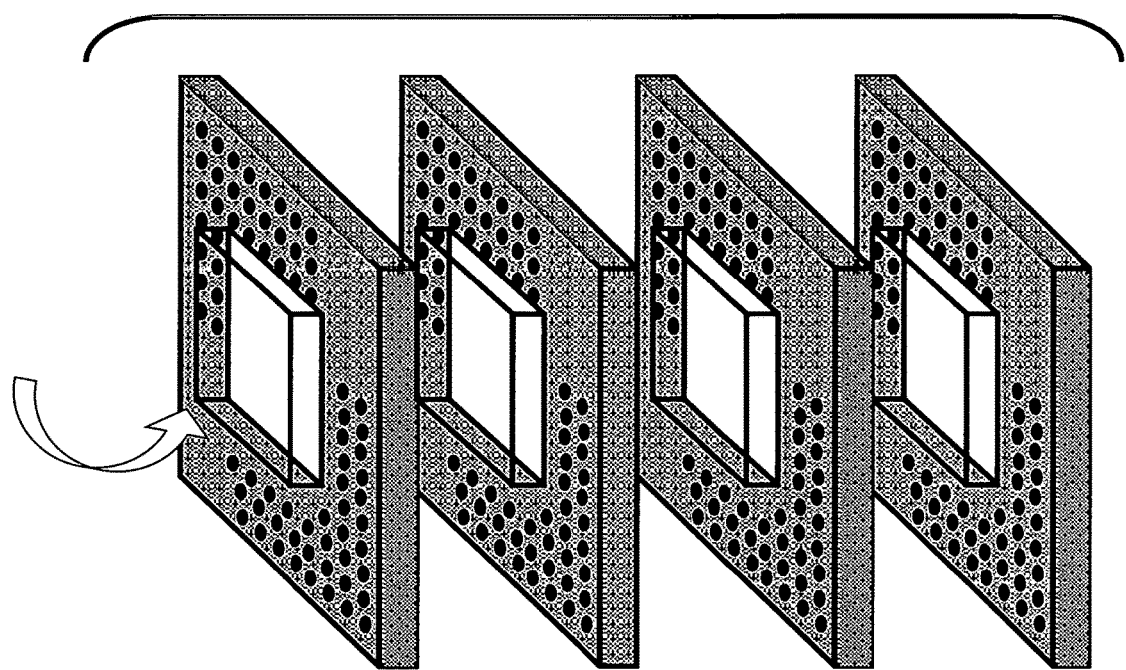

FIGS. 21A-21C illustrate step by step optical interconnections of 400A6/400A7/400A8/400A9 and additional digital memories, if needed for performance and digital storage. They are optically connected by light sources, waveguides and detectors. The light source can be a modulated vertical cavity surface emitting laser/modulated photonic crystal reflector vertical cavity surface emitting laser (PC-VCSEL)/directly modulated nanolaser/directly modulated light emitting diode/directly modulated spin laser. The detector can be a photodetector/spin detector.

FIG. 21D illustrates the Super System on Chip 400B, utilizing optical interconnections.

The Super System on Chip 400A/400B can enable the storage and processing of information simultaneously and it is capable of learning/relearning for self-intelligence, sensor-awareness, context-awareness and autonomous actions, remembering the patterns and movements.

FIG. 22A illustrates a cross-sectional view of a modulated vertical cavity surface emitting laser, which is monolithically integrated with an electro-optic modulator to enable 40 Gbits/s or higher bit rate optical signals.

Details of the vertical cavity surface emitting laser integrated with an electro-optic modulator have been described/disclosed in U.S. non-provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

FIG. 22B illustrates a cross-sectional view of a modulated photonic crystal reflector vertical cavity surface emitting laser, which is monolithically integrated with an electro-optic modulator to enable 40 Gbits/s or higher bit rate optical signals. Here, reflectors of a vertical cavity surface emitting lasers are substituted by two photonic crystal reflectors.

FIG. 23 illustrates a cross-sectional view of a directly modulated nanolaser, which is integrated with the protruded metal/non-metal nano optical antenna at the exit facet. A thin silicon dioxide insulating layer separates the protruded metal/non-metal nano optical antenna from the exit facet to avoid an electrical short. Details of the protruded metal/non-metal nano optical antenna have been described/disclosed in FIGS. 30A-30J.

FIG. 24 illustrates a directly modulated two-dimensional material (e.g., tungsten diselenide or molybdenum disulphide) based wavelength tunable light emitting diode, integrated with a plasmonic light guide (PLG). The plasmonic light guide can enable efficient light output from the light emitting diode. The plasmonic light guide is illustrated in FIG. 38.

FIGS. 25A-25B illustrate a spin controlled vertical cavity surface emitting laser, wherein the vertical cavity includes photonic crystal distributed Bragg reflectors (PC-DBR).

Figure 26A:
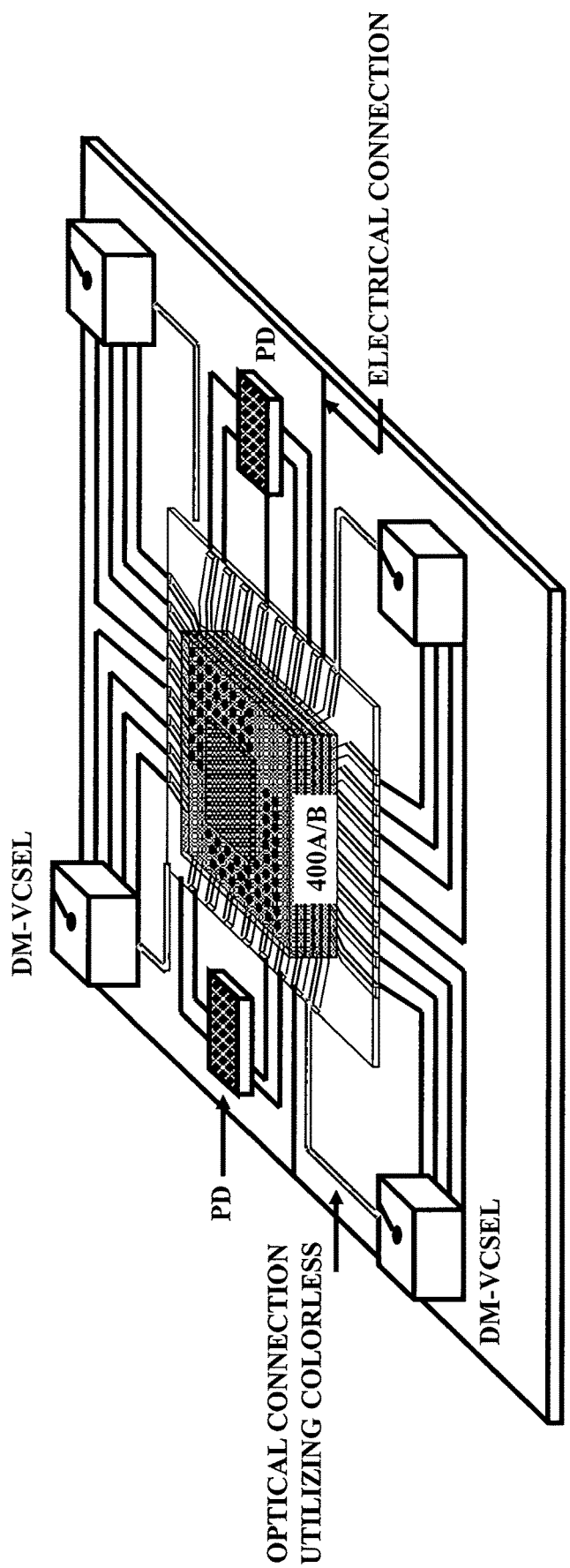

FIG. 26A illustrates wavelength non-specific (colorless) optical connections of 400A/400B, utilizing directly modulated lasers (e.g., directly modulated vertical cavity surface emitting lasers) and photodiodes.

Figure 26B:
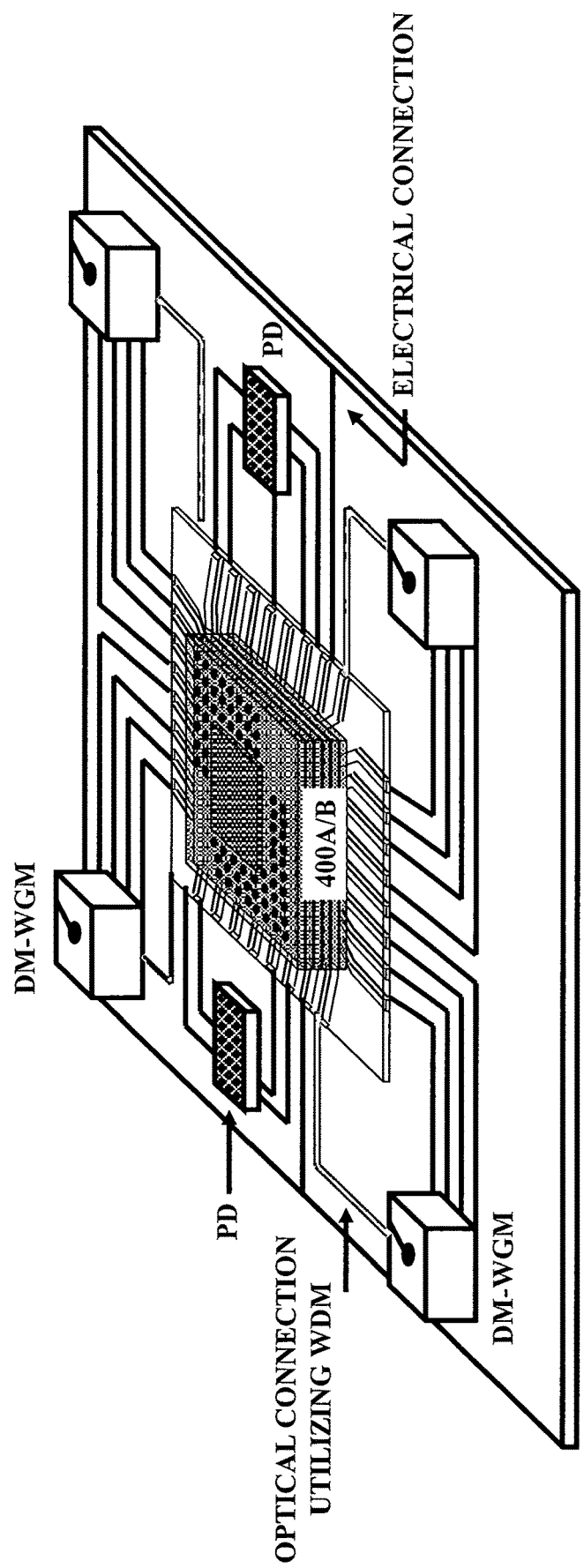

FIG. 26B illustrates a wavelength division multiplexed optical connection of 400A/400B, utilizing directly modulated lasers (e.g., directly modulated wavelength specific whispering gallery mode lasers) and photodiodes.

Figure 26C:
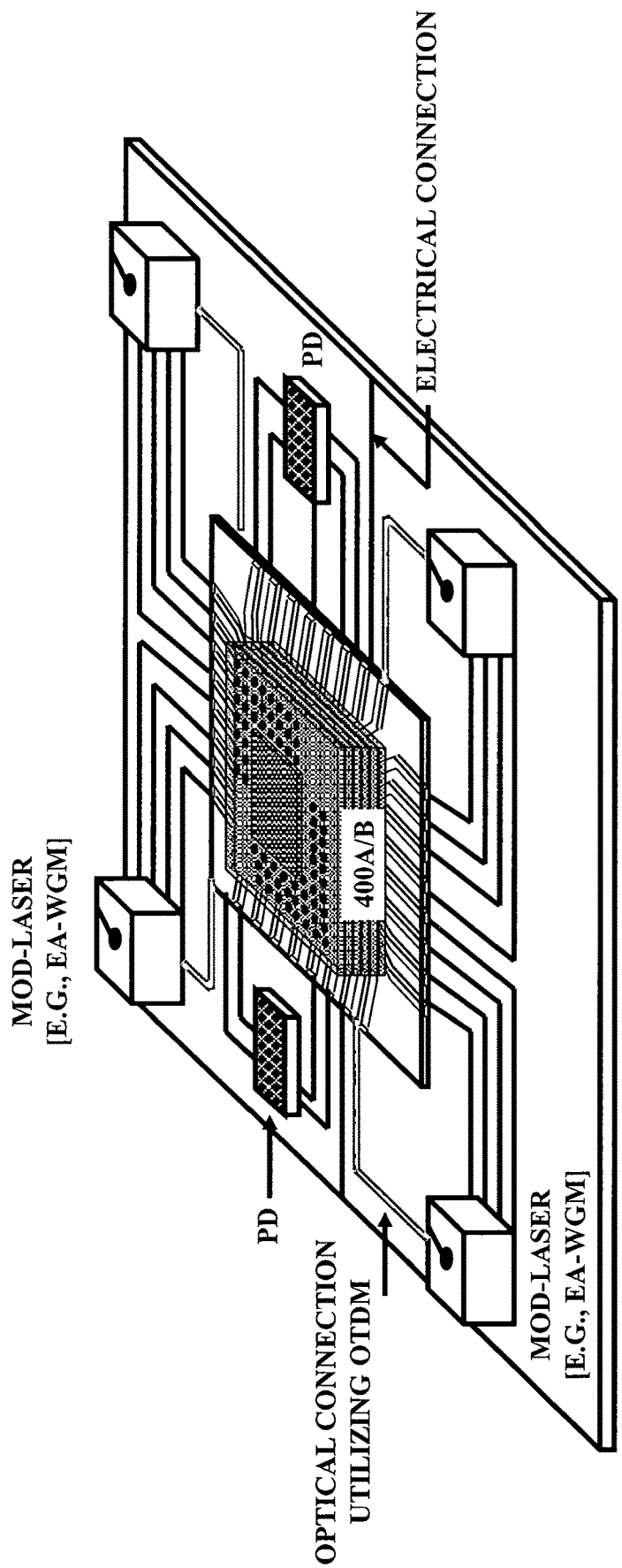

FIG. 26C illustrates an optical time division multiplexed optical connection (OTDM) of 400A/400B, utilizing modulated lasers (e.g., electro-absorption modulated whispering gallery mode lasers) and photodiodes.

Figure 26D:
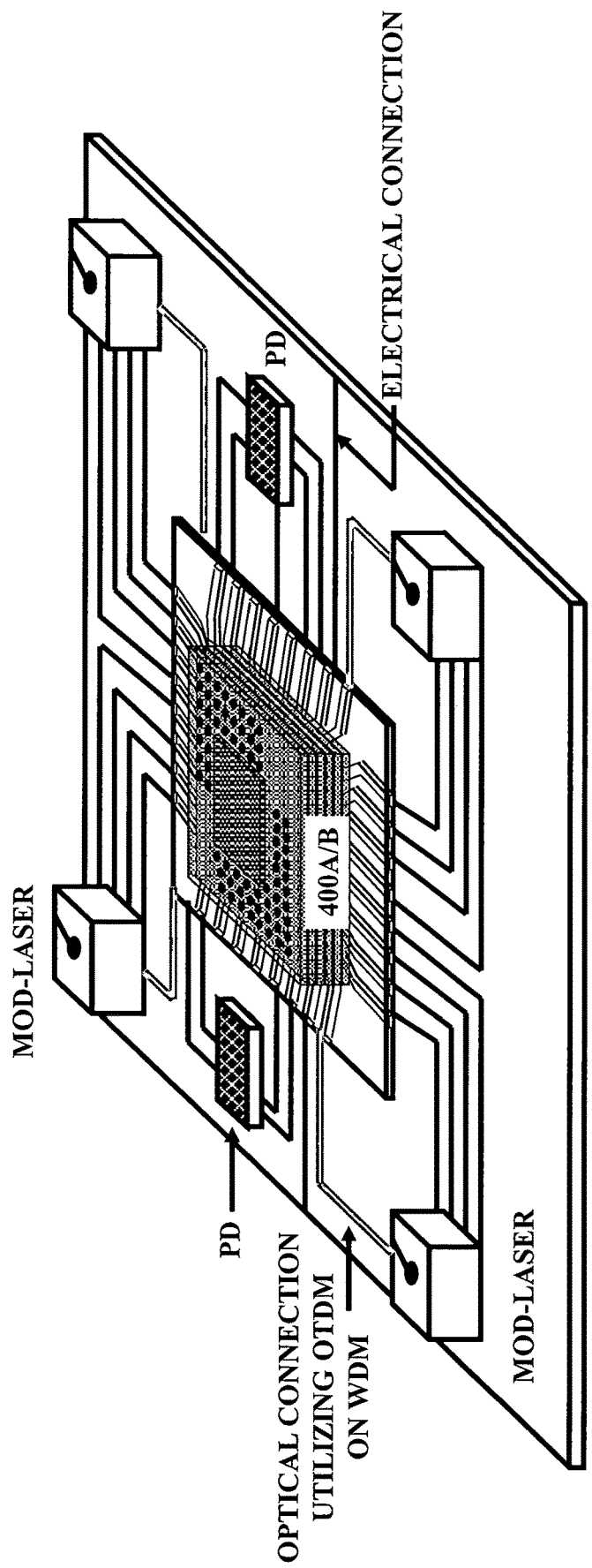

FIG. 26D illustrates an optical time division multiplexed optical connection on wavelength division multiplexing of 400A/400B, utilizing lasers (e.g., electro-absorption modulated wavelength specific whispering gallery mode lasers) and photodiodes.

FIG. 27A illustrates optical interconnections (in planar configuration) of multiple 400As/400Bs on an opto-electronic circuit board, wherein an optical switch (with nanoseconds in switching time) and/or all-optical random-access memory (O-RAM) can be utilized.

An all-optical random-access memory utilizes optical cavities in an indium-gallium arsenide strip buried in gallium arsenide that represent a 1 or 0 by either passing or blocking light. It acts as an optical memory for about a microsecond because the indium-gallium arsenide strip changes its refractive index when exposed to a laser. The optical signal that all-optical random-access memory is trying to remember, will be blocked or passed, depending on the state of the strip. A second pulse of laser on a control section of the indium-gallium arsenide strip reverses its state.

FIG. 27B illustrates that in case of a very sharp (e.g., ~90° angle) optical waveguide, photonic crystals can guide optical signals around the sharp bend from one optical waveguide to another optical waveguide.

FIG. 28A illustrates optical interconnections (in vertical configuration) for the Super System on Chip 400A/400B, enabled by ultralow threshold lasers, high-bit rate modulators, two-dimensional photonic crystal wavelength multiplexers, optical switches (with nanoseconds in switching time), two-dimensional photonic crystal wavelength demultiplexers and waveguide photodiodes.

Electronics scale in capacities with space division multiplexing, by adding parallel wires to a bus, while optical signal scale in capacities with wavelength division multiplexing, by adding parallel wavelengths to a single optical waveguide. Therefore, an array of microring resonator modulators (as translators) can be utilized to convert space division multiplexed electronic signals to wavelength division multiplexed optical signals.

Electrical signals of the Super System on Chip 400A/400B are then transferred to an array of ultralow threshold multi-wavelength lasers (e.g., a heater on a microscaled whispering gallery mode laser or a heater on a nanoscaled active area (FIGS. 28C-28D) can be an ultralow threshold multi-wavelength laser). High-bit rate optical signals from modulators on multiple wavelengths are multiplexed by a two-dimensional photonic crystal wavelength combiner/multiplexer and then switched by an N×M optical switch (FIGS. 28E-28F). Then the multiplexed optical signal of the N×M optical switch is presented to the photonic crystal wavelength demultiplexer and then demultiplexed (separated) high-bit rate optical signals to waveguide photodiodes. The outputs of the waveguide photodiodes/graphene (on silicon on insulator waveguide) photodiodes are electrically connected through the metallized via holes to another Super System on Chip 400A/400B.

FIG. 28B is similar to FIG. 28A, except the N×M optical switch has a first all-optical random-access memory at each input and second all-optical random-access memory at each output of the N×M optical switch.

The high bit-rate modulator can be an electro-absorption or Mach-Zehnder type modulator. Additionally, the high-bit rate modulator can be based on barium titanate material. The photodiodes can be based on photonic crystals. To reduce size, multi-mode interference Mach-Zehnder (MMI-MZ) wavelength multiplexers/demultiplexers can be utilized.

Optical components can be adhesively bonded onto silicon-on-insulator substrate (with polymer waveguides) by DVS-bis-benzocyclybutene. Then the above silicon-on-insulator substrate can be flip-chip bonded onto an array of solder bumps forming connections between the optical components and an electronic circuit.

FIG. 28C illustrates a wavelength specific ultralow threshold laser, utilizing a heater directly on a buried hetrostructured (BH) nanoscaled quantum well indium phosphide (InP) active region (about 3 microns×0.2 microns×0.2 microns in area and 300 nm in thickness) with its lateral P-i-N junction configuration. The front side can be coated with 2 microns' thick spin-on-glass (SOG). The indium phosphide substrate can be removed and oxygen plasma can be utilized to bond and transfer the nanoscaled quantum well indium phosphide active region with its lateral P-i-N junction to a silicon substrate. After bonding to the silicon substrate, an air-bridge structure, current blocking trenches (of width 215 nm), an array of photonic crystals (air holes), n-metal contact and p-metal contact can be fabricated/constructed. The air bridge enables isolation for the nanoscaled quantum well indium phosphide active region. The carrier confinement of the nanoscaled active region is due to its buried hetrostructure. The optical confinement of the nanoscaled active region is due to the array of photonic crystals (air holes). Light from the quantum well indium phosphide active region can be propagated horizontally, utilizing a grating (optical) coupler, then to a tapered silicon waveguide.

FIG. 28D illustrates the nanoscaled active region. Its wavelength can be tuned by changing current to the nanoscaled active region.

Vanadium dioxide is an insulator/Mott insulator until it hits about 150 degrees Fahrenheit, then it turns electrically conducting. FIG. 28E illustrates a directional (optical) coupler vanadium dioxide thin-film (e.g., about 25 nm in thickness, 275 nm in width and 4,500 nm in total length) based optical switch on a substrate (e.g., a silicon on insulator/silicon carbide/diamond). To reduce filamentation related hot spots in vanadium dioxide thin-film, the length of vanadium dioxide thin-film can be segmented into a smaller (e.g., 200 nm) segment. When electrode 1 on vanadium dioxide thin-film is activated, the optical signal at the input port 1 can exit from the output port 2 rapidly. Similarly, when electrode 2 on vanadium dioxide thin-film is activated, the optical signal at the input port 2 can exit from the output port 1 rapidly.

The vanadium dioxide thin-film can be placed just on the waveguide itself or in the close proximity to the waveguide via optical coupling. The vanadium dioxide thin-film can be doped with a trace amount of a dopant (e.g., germanium/grapheme/tungsten) to modulate the phase transition temperature and/or thermal conductivity in the metallic phase. The vanadium dioxide thin-film can be deposited on a seed layer (e.g., ruthenium dioxide ($RuO_2$) or aluminum oxide ($Al_2O_3$). Alternatively, it can be deposited as multi-layers of vanadium dioxide ultrathin-films and titanium dioxide ($TiO_2$) ultrathin-films-as quantum wells. Furthermore, the vanadium dioxide thin-film can be replaced by a thin-film of another phase transition material or a phase change material (PCM) (e.g., germanium-antimony-tellurium/GeSbTe/GST).

Furthermore, the gap between two straight (optical) coupler sections can be as low as 15 nm, instead of 200 nm and the gap can be filled with a material (e.g., germanium/silicon nitride/titanium dioxide/metamaterial).

A method of fabrication/construction of the directional (optical) coupler vanadium dioxide thin-film optical switch is summarized: RF magnetron deposition of vanadium dioxide thin-film on the silicon on insulator substrate, lithographic pattern of the directional (optical) coupler, reactive ion etching of the vanadium dioxide thin-film in CF4 and Ar gases, reactive ion etching of silicon ridge of about 220 nm in depth and lift off of Cr/Au metallization on vanadium dioxide thin-film without any misalignment.

A symmetrical on-off switching time can be obtained by planarization (e.g., utilizing aluminum oxide/hafnium silicate/zirconium silicate/hafnium dioxide/zirconium dioxide thin-film) on the area of the electrode 1 and electrode 2, to reduce resistance-capacitive electrical effects of metallization.

As with the directional (optical) coupler optical switch, the two-photonic crystal (two-dimensional) waveguides can be placed sufficiently close so that the optical modes in each photonic crystal waveguide overlap and interact with each other. The coupling length of a photonic crystal optical switch can be reduced. Hence, the switching time can be reduced.

FIG. 28F illustrates a two-dimensional photonic crystal directional (optical) coupler optical switch, wherein two-dimensional photonic crystals in silicon (in the coupling length region) have a lattice period of air holes that is about 420 nm and a hole diameter that is about 260 nm at 1550 nm wavelength.

The bandwidth of the two-dimensional photonic crystal directional (optical) coupler optical switch can be narrow. However, a two-dimensional photonic crystal Mach-Zehnder optical switch can enable larger bandwidth. In this case, the pitch of the hexagonal photonic crystal lattice can be about 400 nm ("a") and the normalized air hole diameter can be about 0.53 ("d/a").

Metamaterials and/or nanoplasmonic structures endowed with special negative refractive index properties, surrounded by normal materials with positive refractive index properties, as a light (or optical signal(s)) slowing/light (or optical signal(s)) buffering component can slow (even stop) light/optical signal(s) at either input or output of the directional (optical) coupler optical switch or two-dimensional photonic crystal directional (optical) coupler optical switch or two-dimensional photonic crystal Mach-Zehnder optical switch (based the vanadium dioxide ultrathin-film activated by an electrical pulse or a light pulse) for optical processing without any optical-electrical-optical (O-E-O) conversion to read header information of an optical (internet) packet optically. Thus, this can enable an all-optical network. Furthermore, the wavelength or frequency or color of a composite light (or composite optical signal(s)) can slow (even stop) at different spatial points (of metamaterials and/or nanoplasmonic structures endowed with special negative refractive index properties, surrounded by normal materials with positive refractive index properties) to have a trapped effect. The trapped effect can be used for localized intense heating for magnetic storage (which requires a tiny magnetic field by heating), biological imaging and biological (molecular) interaction.

Furthermore, a nanowire of a nonlinear material (e.g., cadmium sulfide) wrapped by a dielectric material, then wrapped by a silver shell at either input or output of the directional (optical) coupler optical switch or two-dimensional photonic crystal directional (optical) coupler optical switch or two-dimensional photonic crystal Mach-Zehnder optical switch (based the vanadium dioxide ultrathin-film activated by an electrical pulse or a light pulse) can change the wavelength or frequency or color of light that passes through it. By confining light within the nonlinear material rather than at the interface between the nonlinear material and the silver shell, light intensity can be maximized, while changing the wavelength or frequency or color of light that passes through it.

Additionally, by applying an electric field across a nanoscaled ring of a nonlinear material (e.g., cadmium sulfide), mixing of optical signals at high on or off ratio can be obtained. Such mixing of optical signals at high on or off ratio can act as an optical transistor.

FIG. 28G illustrates tapering of the input port/output signal ports within a polymer core for efficient optical waveguide to optical fiber coupling.

The slow thermal recovery time can be reduced, if the active area of vanadium dioxide thin-film is nanoscaled and/or current through the material is limited and/or the heat dissipation is rapid (for example, utilizing diamond thin-film).

FIG. 28H illustrates a precise electron pump. The precise electron pump utilizes a silicon quantum dot electrostatic trap to enable precise well-defined electrical current through a circuit. The shape of the quantum dot can be controlled by voltages applied to nearby electrodes. The quantum dot can be filled with electrons and then raised in energy by a process of back-tunneling. All but one of the electrons falling out of the quantum dot goes back into the source lead. Just one electron remains trapped in the quantum dot, which is then ejected into the output lead by tilting the trap. When this is repeated rapidly, it gives a precious current determined solely by the repetition rate and charge of the electron. Such an electron pump can be integrated with the directional (optical) coupler vanadium dioxide thin-film optical switch.

By fabricating/constructing a heat dissipation layer utilizing an ultrathin-film of synthetic diamond/boron arsenide/single walled carbon nanotube/graphene onto electrode 1 and electrode 2 (FIG. 28E) and then flip-chip mounting utilizing a nanoscaled heat spreader onto a highly thermally conducting substrate (e.g., diamond), the slow thermal recovery time can be reduced.

Alternatively, rapid thermal dissipation can be realized by fabricating/constructing a heat dissipation layer utilizing an ultrathin-film of synthetic diamond/boron arsenide/single walled carbon nanotube/graphene below the vanadium dioxide thin-film.

FIG. 28I illustrates a nanoscaled heat spreader, which is a three-dimensional configuration of carbon nanotube and graphene for rapid heat dissipation, wherein vertical heat conduction and/or horizontal heat conduction can be varied by changing the X dimension and Y dimension respectively.

A microscaled ion cloud cooling device/superlattice thermoelectric cooler can be utilized in conjunction with or without the heat dissipation layer and/or nanoscaled heat spreader.

Details of the microscaled ion cloud cooling device and superlattice thermoelectric cooler have been described/disclosed in U.S. non-provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 and in its related U.S.

non-provisional patent applications (with all benefit provisional patent applications) are incorporated in its entirety herein with this application.

Faster optical switching time can be obtained by scaling/segmenting vanadium dioxide thin-film to a smaller area and/or optical activation (e.g., ultrashort pulsed laser activation) rather than electrical activation.

Other chemical compositions of vanadium oxide (e.g., vanadium(III) oxide ($V_2O_3$)) and doped compositions of vanadium oxide can be utilized to enable a higher performance optical switch.

Following permutations and combinations of graphene/graphene quantum dots with vanadium oxide/vanadium oxide quantum dots in Table 2 can be utilized to enable higher performance optical switch.

TABLE 2

| On Silicon (Bottom Layer) | Middle Layer | Top Layer |
|---|---|---|
| ~25 nm Vanadium Dioxide | None | Graphene/Graphene QDs |
| Graphene/Graphene QDs | None | ~25 nm Vanadium Dioxide |
| ~10 nm Vanadium Dioxide | Graphene/Graphene QDs | ~10 nm Vanadium Dioxide |
| Vanadium Dioxide QDs | None | Graphene/Graphene QDs |
| Graphene/Graphene QDs | None | Vanadium Dioxide QDs |
| Vanadium Dioxide QDs | Graphene/Graphene QDs | Vanadium Dioxide QDs |

The process of fabricating/constructing a graphene layer consists of dispersing a graphene oxide (GO) solution in a micropipette, depositing the solution locally and then reducing the graphene oxide to graphene by thermal or chemical treatment.

The optical switch can be integrated with a $\log_2 N$ demultiplexer, which generally consists of rectangular shaped periodic frequency filters in series, wherein the rectangular shaped periodic frequency filters can be formed in a one-dimensional photonic crystal on a ridge waveguide.

In general, but not limited to the Super System on Chip 400A/400B/400C/400D can enable ultrafast data processing, image processing/image recognition, deep learning/meta-learning and self-learning, wherein the Super System on Chip 400A/400B/400C/400D can include embedded microchannels within Super System on Chip 400A/400B/400C/400D for efficient thermal management. These embedded microchannels can utilize an electrically insulated liquid coolant that boils as it flows through the embedded microchannels:
(a) a processor-specific electronic integrated circuit, made of silicon material or silicon-germanium material,
or
a processor-specific electronic integrated circuit, made of a two-dimensional material and a transition metal oxide or a two-dimensional material and a phase change material or a two-dimensional material and a phase transition material,
or
a processor-specific electronic integrated circuit, made of a topological insulator,
or
a processor-specific electronic integrated circuit, made of an exciton (superfluid),
(b) a memory component, made of a nano-scaled phase change material or a nano-scaled phase transition material and/or,
(c) an array of memristors for neural processing, and
(d) a photonic component or a photonic integrated circuit, wherein the photonic component includes an optical waveguide (a photonic crystal based optical waveguide), wherein the processor-specific electronic integrated circuit in said (a), the memory component in said (b), the array of memristors in said (c), and the photonic component or the photonic integrated circuit in said (d) of the Super System on Chip 400A/400B/400C/400D can be interconnected or coupled in two-dimension or three-dimension, electrically or optically (e.g., optically-utilizing either optical wavelength division multiplexing, or optical time division multiplexing). The Super System on Chip 400A/400B/400C/400D can be coupled with an artificial eye, if needed for a particular application. For example, as discussed in previous paragraphs, the artificial eye can be fabricated/constructed utilizing a very large scale integration of the atomic scaled switches. Photocurrent is induced in a photoconductive layer (which is coupled between a metal electrode and a solid-electrolyte electrode) by light irradiation. The photocurrent reduces metal ions with positive charges in the solid-electrolyte electrode and this precipitates as metal atoms to form an atomic scaled metal connection between the metal electrode and the solid-electrolyte electrode-operating as an atomic scaled switch, turned on by light irradiation and/or an applied electrical activation (e.g., voltage). It should be noted that the Super System on Chip 400A/400B/400C/400D can be wafer-scale.

Alternatively, the Super System on Chip 400A/400B/400C/400D can enable ultrafast data processing, image processing/image recognition, deep learning/meta-learning and self-learning, wherein the Super System on Chip 400A/400B/400C/400D can include (embedded microchannels within Super System on Chip 400A/400B/400C/400D for efficient thermal management. These embedded microchannels can utilize an electrically insulated liquid coolant that boils as it flows through the embedded microchannels):
(a) a processor-specific electronic integrated circuit, made of silicon material or silicon-germanium material,
or
a processor-specific electronic integrated circuit, made of a two-dimensional material and a transition metal oxide or a two-dimensional material and a phase change material or a two-dimensional material and a phase transition material,
or
a processor-specific electronic integrated circuit, made of a topological insulator, or
a processor-specific electronic integrated circuit, made of an exciton (superfluid),
(b) a memory component, made of a nano-scaled phase change material or a nano-scaled phase transition material and/or,
(c) an array of memristors for neural processing, and
(d) a photonic component or a photonic integrated circuit, wherein the photonic component includes an optical waveguide (a photonic crystal based optical waveguide),
wherein the processor-specific electronic integrated circuit in said (a), the memory component in said (b), the array of memristors in said (c), and the photonic component or the photonic integrated circuit in said (d) of the Super System on Chip 400A/400B/400C/400D can be interconnected or coupled in two-dimension or three-dimension, electrically or optically (e.g., optically-utilizing either optical wavelength division multiplexing, or optical time division multiplexing), wherein the Super System on Chip 400A/400B/400C/400D can include/couple with a photonic neural learning processor for neural processing, wherein the photonic neural learning processor can include an interferometer or a laser.

The Super System on Chip 400A/400B/400C/400D can be coupled with the artificial eye, if needed for a particular application.

Alternatively, the Super System on Chip 400A/400B/400C/400D can enable ultrafast data processing, image processing/image recognition, deep learning/meta-learning and self-learning, wherein the Super System on Chip 400A/400B/400C/400D can include (embedded microchannels within Super System on Chip 400A/400B/400C/400D for efficient thermal management. These embedded microchannels can utilize an electrically insulated liquid coolant that boils as it flows through the embedded microchannels):

(a) a processor-specific electronic integrated circuit, made of silicon material or silicon-germanium material,
or
a processor-specific electronic integrated circuit, made of a two-dimensional material and a transition metal oxide or a two-dimensional material and a phase change material or a two-dimensional material and a phase transition material,
or
a processor-specific electronic integrated circuit, made of a topological insulator,
or
a processor-specific electronic integrated circuit, made of an exciton (superfluid),
(b) a memory component, made of a nano-scaled phase change material or a nano-scaled phase transition material and/or,
(c) an array of memristors for neural processing, and
(d) a photonic component or a photonic integrated circuit, wherein the photonic component includes an optical waveguide (or a photonic crystal based optical waveguide),
wherein the processor-specific electronic integrated circuit in said (a), the memory component in said (b), the array of memristors in said (c), and the photonic component or the photonic integrated circuit in said (d) of the Super System on Chip 400A/400B/400C/400D can be interconnected or coupled in two-dimension or three-dimension, electrically or optically (e.g., optically-utilizing either optical wavelength division multiplexing, or optical time division multiplexing), wherein the Super System on Chip 400A/400B/400C/400D can be coupled with a hardware security component, wherein the hardware security component includes an array of memristors, wherein the Super System on Chip 400A/400B/400C/400D can be coupled with a photonic neural learning processor for neural processing, wherein the photonic neural learning processor can include an interferometer or a laser. The Super System on Chip 400A/400B/400C/400D can be coupled with artificial eye, if needed for a particular application.

Alternatively, the Super System on Chip 400A/400B/400C/400D can enable ultrafast data processing, image processing/image recognition, deep learning/meta-learning and self-learning, wherein the Super System on Chip 400A/400B/400C/400D can include (embedded microchannels within Super System on Chip 400A/400B/400C/400D for efficient thermal management. These embedded microchannels can utilize an electrically insulated liquid coolant that boils as it flows through the embedded microchannels):

(a) a processor-specific electronic integrated circuit, made of silicon material or silicon-germanium material,
or
a processor-specific electronic integrated circuit, made of a two-dimensional material and a transition metal oxide or a two-dimensional material and a phase change material or a two-dimensional material and a phase transition material,
or
a processor-specific electronic integrated circuit, made of a topological insulator,
or
a processor-specific electronic integrated circuit, made of an exciton (superfluid),
(b) a memory component, made of a nano-scaled phase change material or a nano-scaled phase transition material and/or,
(c) an array of memristors for neural processing, and
(d) a photonic component or a photonic integrated circuit, wherein the photonic component includes an optical waveguide (or a photonic crystal based optical waveguide),
wherein the processor-specific electronic integrated circuit in said (a), the memory component in said (b), the array of memristors in said (c), and the photonic component or the photonic integrated circuit in said (d) of the Super System on Chip 400A/400B/400C/400D can be interconnected or coupled in two-dimension or three-dimension, electrically or optically (e.g., optically-utilizing either optical wavelength division multiplexing, or optical time division multiplexing), wherein the Super System on Chip 400A/400B/400C/400D can be coupled with a hardware security component, wherein the hardware security component includes an array of memristors, wherein the Super System on Chip 400A/400B/400C/400D can be coupled with a photonic neural learning processor for neural processing, wherein the photonic neural learning processor can include an interferometer or a laser. The Super System on Chip 400A/400B/400C/400D can be coupled with an algorithm, stored in a non-transitory memory component for predictive memory prefetching. The Super System on Chip 400A/400B/400C/400D can be coupled with artificial eye, if needed for a particular application.

The above Super System on Chip 400A/400B/400C/400D described in previous paragraphs can include/couple with a digital signal processor.

The above Super System on Chip 400A/400B/400C/400D described in previous paragraphs can include/couple with a wireless chipset (e.g., a Wi-Fi/Wi-Fi(N) chipset).

Alternatively, the above Super System on Chip 400A/400B/400C/400D described in previous paragraphs can include/couple with an ultrahigh speed wireless chipset (e.g., an ultrahigh speed millimeter wave chipset (made of InP based epitaxial material on InP substrate) for peak data rates up to 100 Gbps). The millimeter wave is the frequency bands between 30 GHz to 300 GHz and it has a range of 2 meters (indoor) to 300 meters (outdoor) and it has a latency of about 1 ms.

A System on integrated Super System on Chip 400A/400B/400C/400D can be realized by three-dimensional packaging such as a chip-on-wafer (CoW) stacking which may allow mix-and-match integration of many different known good dies (e.g., a Wi-Fi/ultrahigh speed millimeter wave chipset (e.g., for 5G) and the Super System on Chip 400A/400B/400C/400D) or even stacks of known good dies. The chip-on-wafer stacking is both a face-to-face and face-to-back technology, which can reach up to 1 million bonds per $mm^2$.

Alternatively, bare unprocessed metal-organic chemical vapor deposited (MOCVD) or molecular beam epitaxy (MBE) deposited indium phosphide based materials/layers on indium phosphide substrate can be bonded onto a silicon wafer. Then InP substrate can be removed and then millimeter wave chipset on indium phosphide based materials/layers can be fabricated/constructed.

Alternatively, a System on integrated Super System on Chip 400A/400B/400C/400D can be realized by direct wafer bonding of the metal-organic chemical vapor deposited (MOCVD) or molecular beam epitaxy (MBE) deposited indium phosphide based materials/layers (less than 200 nm) on silicon/silicon-on-insulator/lithium niobate-on-insulator-silicon substrate via an interface layer for monolithic integration of millimeter wave chipset and the Super System on Chip 400A/400B/400C/400D). It should be noted that base indium phosphide is removed in the direct wafer bonding.

Alternatively, a System on integrated Super System on Chip 400A/400B/400C/400D can be realized by direct metal-organic chemical vapor deposition or molecular beam deposition of indium phosphide based materials on silicon/silicon-on-insulator/lithium niobate-on-insulator-silicon substrate for monolithic integration of millimeter wave chipset and the Super System on Chip 400A/400B/400C/400D) via various interface layers to minimize the defect density in indium phosphide based materials/layers.

Furthermore, an antenna-in-package (AiP) solution in LTCC technology can be utilized for an antenna or an array of antennas for a compact standard surface mounted device.

Conventional gold metal based contact on indium phosphide based materials/layers can be replaced by nickel based alloyed contact compatible with complementary metal-oxide-semiconductor fabrication on silicon.

Furthermore, a System on integrated Super System on Chip 400A/400B/400C/400D can integrate lithium niobate photonics technology and/or silicon photonics at the back end of line (BEOL) portion of fabrication.

The silicon photonics can include a tapered waveguide, in which light can enter a tapered waveguide and then it is directed by an adiabatic taper into an underneath waveguide(s) (e.g., a polymer/chalcogenide glass based waveguide) for further electro-optical/optical processing (e.g., optical amplification by a semiconductor optical amplifier)/non-linear optical processing/wave propagation.

Additionally, if needed underneath polymer waveguide(s) can be coupled with an ultrafast (electrically stimulated) nanoseconds optical switch-fabricated/constructed of a phase transition material (e.g., vanadium dioxide) or epitaxially grown barium titanate material. Pockels effect can be strong even in nanoscaled devices of barium titanate material.

The optical switch can include a tapered waveguide, in which light can enter a tapered waveguide and then it is directed by an adiabatic taper into an underneath waveguide(s) (e.g., a polymer/chalcogenide glass based waveguide) for further electro-optical/optical processing (e.g., optical amplification by a semiconductor optical amplifier)/non-linear optical processing/wave propagation.

The above Super System on Chip 400A/400B/400C/400D described in previous paragraphs can include/couple with a vertical cavity surface emitting laser or a photonic crystal based vertical cavity surface emitting laser or a light emitting diode or a waveguide photodiode or an optical switch.

The above Super System on Chip 400A/400B/400C/400D described in previous paragraphs can include/couple with an all-optical random access memory component.

Additionally, the above Super System on Chip 400A/400B/400C/400D described in previous paragraphs can include/couple with an artificial neural network algorithm and/or a machine learning algorithm, stored in non-transitory memory component.

Additionally, the above Super System on Chip 400A/400B/400C/400D described in previous paragraphs can include/couple with a computer vision algorithm and/or an image processing algorithm, stored in non-transitory memory component.

The above Super System on Chip 400A/400B/400C/400D (including the neural learning processor of the Super System on Chip 400A/400B/400C/400D, wherein the neural learning processor consists of an array or a network of memristors arranged in either in two-dimension or in three-dimension) and/or the photonic neural learning processor, as described in previous paragraphs can be coupled with one or more qubits (for quantum processing and/or a quantum memory and/or quantum internet).

Integrating U.S. Non-Provisional patent application Ser. No. 14/014,239 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Aug. 29, 2013 (along with its priority provisional patent applications in 2006), with this current patent application, an application of the Super System on Chip 400A/400B/400C/400D can be as follows:

An intelligent subsystem can be coupled by a wireless network or a sensor network, wherein the intelligent subsystem includes:

(a) the Super System on Chip 400A/400B/400C/400D to enable ultrafast data processing, image processing/image recognition, deep learning/meta-learning and self-learning, (b) a foldable/stretchable/photonic crystals/holographic display, Furthermore, the photonic crystals display can include nanoscaled optical antennas (e.g., denoted by ∞, as in FIGS. 30A-30H)

(c) a radio transceiver or a sensor module, (d) a voice processing module or a voice processing algorithm (module is a collection of electronic/optical/radio frequency components), wherein the voice processing algorithm can be coupled with artificial intelligence algorithm and/or an artificial neural network algorithm and/or fuzzy logic algorithm (e.g., FIGS. 1B-1D), wherein the voice processing algorithm can be stored in a first non-transitory storage media, wherein the intelligent subsystem can be further coupled with or can further include:

(e) a natural language algorithm to understand the voice command in a natural spoken language of a user, wherein the natural language algorithm can be stored in a second non-transitory storage media ((e.g., an storage media of a cloud computer), (f) a learning algorithm or an intelligence algorithm, wherein the learning algorithm or the intelligence algorithm can be based on or can include an artificial intelligence algorithm and/or an artificial neural network algorithm and/or fuzzy logic algorithm (e.g., FIGS. 1B-1D), wherein the learning algorithm or the intelligence algorithm can provide learning or intelligence in response to an interest or a preference of the user, wherein the learning algorithm or the intelligence algorithm can be stored in the second non-transitory storage media (e.g., an storage media of a cloud computer), wherein the first non-transitory storage media and the second non-transitory storage media can be same or different, wherein the foldable/stretchable/photonic crystals/holographic display in (b), the radio transceiver or the sensor module in (c), the voice processing module or the voice processing algorithm in (d), the natural language algorithm in (e) and the learning algorithm or the intelligence algorithm in (f) can be coupled with the Super System on Chip 400A/400B/400C/400D in (a).

The intelligent subsystem can be coupled with the social wallet, wherein the social wallet is coupled with a block-chain.

Additionally, the social wallet can enable online payment, online real money transfer between users and online virtual money transfer between users, protecting privacy of the user via the user's virtual avatar. Through the user's virtual avatar, the user just would need to supply/apply a fragment of information necessary to receive a service (e.g., purchasing an item).

The blockchain enabled social wallet can enhance increased security in mobile payment/peer-to-peer lending/peer-to-peer social commerce, preventing scams like fraud, double-spending, and price gouging. Transactions can be accounted for on a tamper-proof ledger. Furthermore the blockchain can be coupled with a virtual avatar to hide the user identity for anonymity.

The intelligent subsystem described in the previous paragraph, can further include a universal communication interface integrating (i) animation, (ii) animated GIF, (iii) drawings, (iv) emotions, (v) gestures (hand/eye), (vi) location data, (vii) text and (viii) voices/voice snippets/videos. The universal communication interface can be further enhanced by "Fazila" as described in FIG. 10A The intelligent subsystem as described in the previous paragraph can further include an internet firewall or a user-specific security control or a user-specific authentication.

The intelligent subsystem as described in the previous paragraph can further include a biometric sensor or a near-field communication device.

The intelligent subsystem as described in the previous paragraph can further include an ultracapacitor or a fuel-cell.

The intelligent subsystem as described in the previous paragraph can be further coupled with or can further include a search algorithm to provide a search on the internet automatically in response to an interest or a preference of the user, wherein the search algorithm can be stored in the second non-transitory storage media.

The intelligent subsystem as described in the previous paragraph can further include a software as a radio module or an ultra-wideband module or a millimeter wave radio module.

The intelligent subsystem described in the previous paragraph can further include a specific first electronic module: a video compression module, a content over-IP module, a video conference over-IP module, or a three-dimensional video conference over-IP module.

The intelligent subsystem as described in the previous paragraph can further include a specific second electronic module: a voice-to-text conversion module or a text-to-voice conversion module.

The intelligent subsystem as described in the previous paragraph can further include a video compression algorithm, a content over-IP algorithm, a video conference over-IP algorithm, a three-dimensional (3-D) video conference over-IP algorithm, a voice-to-text conversion algorithm or a text-to-voice conversion algorithm.

The intelligent subsystem as described in the previous paragraph can be sensor-aware or context-aware.

FIG. 28J illustrates an embodiment of optics to chip coupling in each input/output, utilizing an ultrahigh (~up to 500 Gbs) speed modulator, a semiconductor optical amplifier and a receiver (a receiver includes a photodiode and an electronic circuitry). In a massively parallel co-packaged multi-chip (optics to chip) module, wherein, each input/output of an electrical chip/electrical component (e.g., a processor/application specific integrated circuits (ASIC)/field programmable gate array/electrical switch (e.g., Broadcom Tomahawk 3)) or the Super System on Chip 400A/400B/400C/400D can be electro-optically coupled by a waveguide, an ultrahigh speed modulator based on a phase transition material (e.g., vanadium dioxide) or a phase change material (e.g., $Ge_2Sb_2Te_5$ (GST), $Ge_2Sb_2Se_4Te_1$ (GSST) or $Ag_4In_3Sb_{67}Te_{26}$ (AIST)) and a receiver.

The modulator can be either ring resonator or Mach-Zehnder interferometer based. The active material of the modulator can be a phase transition/phase change material, which can be stimulated by an electrical/optical/terahertz signal.

The phase transition/phase change switching speed (thereby change in refractive index) can be in the order of picoseconds-even in the order of femtoseconds.

For optical stimulation, the stimulation wavelength $\lambda 2$ can be different than the propagation wavelength $\lambda 1$. In the case of the ring resonator based modulator the nanoscaled (about 200 nm×200 nm in area) patch of a phase transition material (e.g., vanadium dioxide) or a phase change material (e.g., $Ge_2Sb_2Te_5$ (GST), $Ge_2Sb_2Se_4Te_1$ (GSST) or $Ag_4In_3Sb_{67}Te_{26}$ (AIST)) can be stimulated via a waveguide based transformation optical coupler. Furthermore, the waveguide based transformation optical coupler can include nanoscaled holes (of about 100 nm diameter) or photonic crystals (of about 100 nm diameter). The nanoscaled holes or photonic crystals can be air or dielectric filed.

It is expected that there will be optical loss in a phase transition or a phase change material. Such optical loss can be compensated in which light can enter a tapered waveguide and then it is directed by an adiabatic taper into an underneath polymer waveguide(s) (e.g., a polymer/chalcogenide glass based waveguide) on a photonic substrate for further electro-optical/optical processing (e.g., optical amplification by a semiconductor optical amplifier)/non-linear optical processing/wave propagation. Alternatively, the adiabatic taper can be replaced by a photonic wire bond waveguide, enabled by direct-write three-dimensional laser lithography based on two-photon polymerization.

The ultrahigh speed modulator, the receiver and the electrical chip can be electrically coupled to a first packaged substrate by a first array of ball grids. It should be noted that the first packaged substrate can be connected with a second packaged substrate by a second array of ball grids.

Utilizing 128 waveguides, wherein each waveguide is at 500 G per second modulation bandwidth with cumulative throughput of about 51.2 terabit per second and each waveguide can be coupled with a common laser source. Furthermore, wavelength division multiplexing via arrayed waveguide router (AWG) can be utilized in order to reduce number of waveguides.

FIG. 28K illustrates an embodiment of ultrahigh speed modulator. This is an schematic illustration, wherein a ring resonator modulator including a nanoscaled (about 200 nm×200 nm in area) patch of a phase transition material (e.g., vanadium dioxide)/phase change material (e.g., $Ge_2Sb_2Te_5$ (GST), $Ge_2Sb_2Se_4Te_1$ (GSST) or $Ag_4In_3Sb_{67}Te_{26}$ (AIST)) can be stimulated by a wavelength $\lambda 2$ via a waveguide based transformation. optical coupler. The waveguide based transformation optical coupler can include nanoscaled holes (of about 100 nm diameter) or photonic crystals (of about 100 nm diameter). The nanoscaled holes or photonic crystals can be air or dielectric filed. The ring resonator is optically coupled with a silicon waveguide, which is then coupled with an underneath polymer waveguide(s) on a photonic substrate. The stimulation wavelength $\lambda 2$ is different from the propagation laser wavelength $\lambda 1$.

To reduce any joule heating the nanoscaled patch can be coated with about 500 nm of polycrystalline diamond.

The photonic substrate is the coupled with a first packaged substrate by a first array of ball grids. Furthermore, the photonic substrate and the first packaged substrate can be integrated into one substrate. It should be noted that the first packaged substrate can be connected with a second packaged substrate by a second array of ball grids.

In general, but limited to an input/output of an electrical chip/electrical component (a processor/application specific integrated circuits/field programmable gate array/electrical switch) or the Super System on Chip 400A/400B/400C/400D, wherein the input/output of the electrical chip/component or the Super System on Chip 400A/400B/400C/400D can be coupled electrically and/or optically by a modulator, a receiver and a semiconductor optical amplifier, wherein the modulator is either a Mach-Zehnder modulator or a ring resonator modulator, wherein the modulator includes a phase transition material/phase change material, wherein the modulator is activated by an electrical stimulus/optical stimulus/terahertz stimulus, wherein the optical stimulus is provided by a transformation waveguide coupler, wherein the transformation waveguide coupler includes one or more holes (having each hole of about 100 nm in diameter) or a photonic crystal. In a Hyperscaler Data Center (HDC), placing optics next to a switch chip in a (optics to chip) multichip module can simplify high speed serialiser/deserialiser—the circuit that gets data on and off the chip. Thus, there is no need to drive very high speed electrical signals all the way to the front panel's pluggables. This simplifies the printed circuit board design, but significantly constrains the multichip module's overall power consumption/heat dissipation given hundreds of serialiser/deserialiser are used on a reduced area and thus, it will require an array of microchannels and/or microjets for fluid based cooling of the multichip module.

FIG. 29A illustrates an ultrahigh density storage device, utilizing a phase transition/phase change material on a rotating nano positioning stage, wherein the phase transition/phase change material can be excited by an optical filament with a device (FIGS. 29D-29E) to focus below the Abbey's diffraction limit.

FIG. 29B illustrates a nanoscaled optical filament induced on an electronic beam in a metal-insulator configuration.

FIG. 29C illustrates an electron beam created from a focused electron beam emission tip.

FIG. 29D illustrates a tapered waveguide to focus the optical filament below the Abbey's diffraction limit. The waveguide includes an ultrathin (about 100 nm) layer of silicon dioxide sandwiched between two ultrathin (about 30 nm) layers of metal (e.g. aluminum/copper/gold/silver). The waveguide can be tapered adiabatically (over 150 nm) in three dimensions to a singular point.

FIG. 29E illustrates a pattern of nanoscaled holes in an ultrathin (100 nm) metal layer (supported by a transparent substrate) to focus the optical filament below the Abbey's diffraction limit. The pattern includes about 20,000 nanoscaled holes, each hole having about 150 nm in diameter.

Alternatively, instead of scanning with a single (continuous wave/pulsed/ultrashort pulsed) laser, two lasers can be utilized simultaneously. In the first instant a typical laser is using an appropriate wavelength to excite a material. In the second instant is a key second laser, which is focused so that it produces a donut of light overlapping the focal point of the first laser. This configuration can enable the laser to focus below the Abbey's diffraction limit for ultrahigh density storage Quantum dots are tiny light sources with nanoscaled dimensions. They rely on internal electronic transitions which emit a stream of photons, with the color defined by the material, shape and size.

Graphene quantum dots can fluoresce brighter than conventional quantum dots. Graphene quantum dots or quantum dots of a two-dimensional material can be utilized instead of conventional quantum dots. Ultrasound can be utilized to chop up a graphene sheet into atom scale dots. Then, potassium hydroxide can be utilized to enhance the surface area of these atom scale dots.

FIGS. 30A-30J illustrate ten distinct three-dimensional geometrically shaped protruded metal (e.g., aluminum/copper/gold/silver) or non-metal nano optical antennas. The protruded metal/non-metal nano optical antenna can result in enhanced absorption and radiative emission rates, thus leading to higher intrinsic quantum efficiency of a quantum dot. The maximum dimension of the protruded metal/non-metal nano optical antenna can be less than 200 nm. The separation gap in FIGS. 30B, 30C, 30E, 30F, 30G and 30H can be less than 50 nm. The protruded metal/non-metal nano optical antenna can be enclosed within a nanoscaled box. The shape of the nanoscaled box can be arbitrary and/or closed and/or open. The maximum dimension of the nanoscaled box can be less than 400 nm.

Numerous variations and/or modifications in geometrical shapes, tip curvature, dimensions and separation gaps of the protruded metal/non-metal nano optical antenna and nanoscaled box (open or closed) are also possible within the scope of the present invention.

Furthermore, the protruded metal/non-metal nano optical antenna (including its surface and/or tip) can be coated with a two-dimensional material (e.g., graphene).

FIGS. 31A-31C illustrate blue quantum dots, green quantum dots and red quantum dots respectively.

FIGS. 31D-31F illustrate blue quantum dots-protruded metal/non-metal nano optical antennas, green quantum dots-protruded metal/non-metal nano optical antennas and red quantum dots-protruded metal/non-metal nano optical antennas respectively.

Photonic crystals are wavelength scale periodic dielectric microstructures, which create photonic band gaps. Photonic crystals insulate photons similar to the way electrons are insulated in a semiconductor crystal.

FIGS. 31G-31I illustrate blue quantum dots in a photonic crystal, green quantum dots in a photonic crystal and red quantum dots in a photonic crystal respectively. Photonic crystals can be one-dimensional/two-dimensional/three-dimensional.

An original silicon wafer master of a desired photonic crystal design can be fabricated/constructed by laser interference lithography and reactive ion etching. From the original silicon wafer master, many working stamps of a tri-layer material (thin polydimethylsiloxane with Young's modulus of 80 MPa+ soft polydimethylsiloxane+thin glass substrate) can be created utilizing ultraviolet enhanced substrate conformal imprint lithography and inorganic silica sol-gel imprint photoresist. The working stamp of the tri-layer material with silica sol-gel is a suitable transfer mask for printing the desired photonic crystal onto a transparent substrate (to an incident light).

Inkjet printing can be utilized to print quantum dots (in a solution) onto the desired photonic crystal.

Similarly, a working stamp of the tri-layer material with silica sol-gel is a suitable transfer mask for printing the desired photonic crystal with the embedded protruded metal/non-metal nano optical antenna onto a substrate transparent (to an incident light). Two-dimensional and/or three-dimensional colloidal photonic crystals can be fabricated on a large area transparent polymer/semi-interconnected interpenetrating polymer networks (SIPN) substrate by a roll-to-roll Langmuir-Blodgett method, utilizing silica nanospheres (250 nm-550 nm in diameter).

Inkjet printing can be utilized to print quantum dots (from a solution) onto the desired photonic crystal with the embedded protruded metal/non-metal nano optical antenna.

FIGS. 31J-31L illustrate blue quantum dots-protruded metal/non-metal nano optical antennas in a photonic crystal, green quantum dots-protruded metal/non-metal nano optical antennas in a photonic crystal and red quantum dots-protruded metal/non-metal nano optical antennas in a photonic crystal respectively.

FIG. 31M illustrates a hyperbolic metamaterial of alternating n/2 (e.g., n=8/16/20) ultrathin-film of dielectric (e.g., $Al_2O_3$)/semiconductor and n/2 ultrathin-film of metal (e.g., aluminum/copper/gold/silver) on a transparent substrate. Each ultrathin-film of dielectric/semiconductor is about 30 nm in thickness. Each ultrathin-film of metal is about 15 nm in thickness. The top ultrathin-film metal (which is just below an ultrathin-film spacer layer—the spacer layer is not shown in FIG. 31M) can be fabricated/constructed with nanoholes (of about 100 nm in diameter) for light scattering. Incident light can be confined near the top ultrathin-film metal, causing sharp peaks in the fluorescence/reflection spectrum.

Alternatively, a hyperbolic metamaterial of alternating titanium nitride metal and aluminum scandium nitride insulator, each is about 5 to 20 nm in thickness can be utilized. Alternatively, a hyperbolic metamaterial including only insulators can be also utilized.

In FIG. 31M, each quantum dot is placed on a hyperbolic metamaterial.

FIG. 31N is similar to FIG. 31M, except each quantum dot, further coupled with a protruded metal/non-metal nano optical antenna is placed on a hyperbolic metamaterial.

FIGS. 31O-31Q illustrate configurations of blue quantum dots on a hyperbolic metamaterial, green quantum dots on a hyperbolic metamaterial and red quantum dots on a hyperbolic metamaterial respectively.

FIGS. 31R-31T illustrate configurations of blue quantum dots (wherein each blue quantum dot is coupled with a protruded metal/non-metal nano optical antenna) on a hyperbolic metamaterial, green quantum dots (wherein each green quantum dot is coupled with a protruded metal/non-metal nano optical antenna) on a hyperbolic metamaterial and red quantum dots (wherein each red quantum dot is coupled with a protruded metal/non-metal nano optical antenna) on a hyperbolic metamaterial respectively.

FIGS. 32A-32G illustrate a light valve based on thin-film transistor enhanced liquid crystal light (TFT-LCD), microelectromechanical systems, nanoelectromechanical systems (NEMS), piezo-microelectromechanical systems, piezo-nanoelectromechanical systems phase change material (e.g., germanium-antimony-tellurium $Ge_2Sb_2Te_5$) and phase transition material (e.g., vanadium dioxide) respectively. The light valve can either allow or block light to propagate.

Details of the microelectromechanical systems light valve have been described/disclosed in U.S. non-provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

A phase change material switch rapidly between two distinct phases/states with the application of an electric field. However, an electrically switchable light valve based on a phase transition material (sandwiched between two transparent electrodes) can be faster that of a phase change material. The transparent electrode can be indium tin oxide (ITO)/fluorine doped tin oxide (FTO)/graphene.

FIG. 33 illustrates a plasmonic transmission optical color filter based on gratings fabricated/constructed on a metal-insulator-metal structure by ion milling. Typically, the metal (e.g., aluminum) is about 20 nm in thickness and the insulator (e.g., zirconium oxide) is about 100 nm in thickness. By changing the grating pitch, duty cycle and depth, a blue/green/red specific transmission optical color filter can be realized.

However, a multi-layer thin-film transmission optical color filter can be utilized instead of a plasmonic transmission optical color filter.

FIGS. 34A-34C illustrate blue quantum dots in an electrically switchable liquid crystal gel, green quantum dots in an electrically switchable liquid crystal gel and red quantum dots in an electrically switchable liquid crystal gel respectively. The electrically switchable liquid crystal gel can lead to fluorescence emission of higher intensity, when the electric field is off and vice-a-versa.

The light emitting diode backlighting is usually composed of light emitting diodes, coated with a phosphor to give off a white light. In FIGS. 35A-35F, the backlighting is reflected by a substrate coated with high reflecting (HR) thin-film coatings.

Figure 35A:
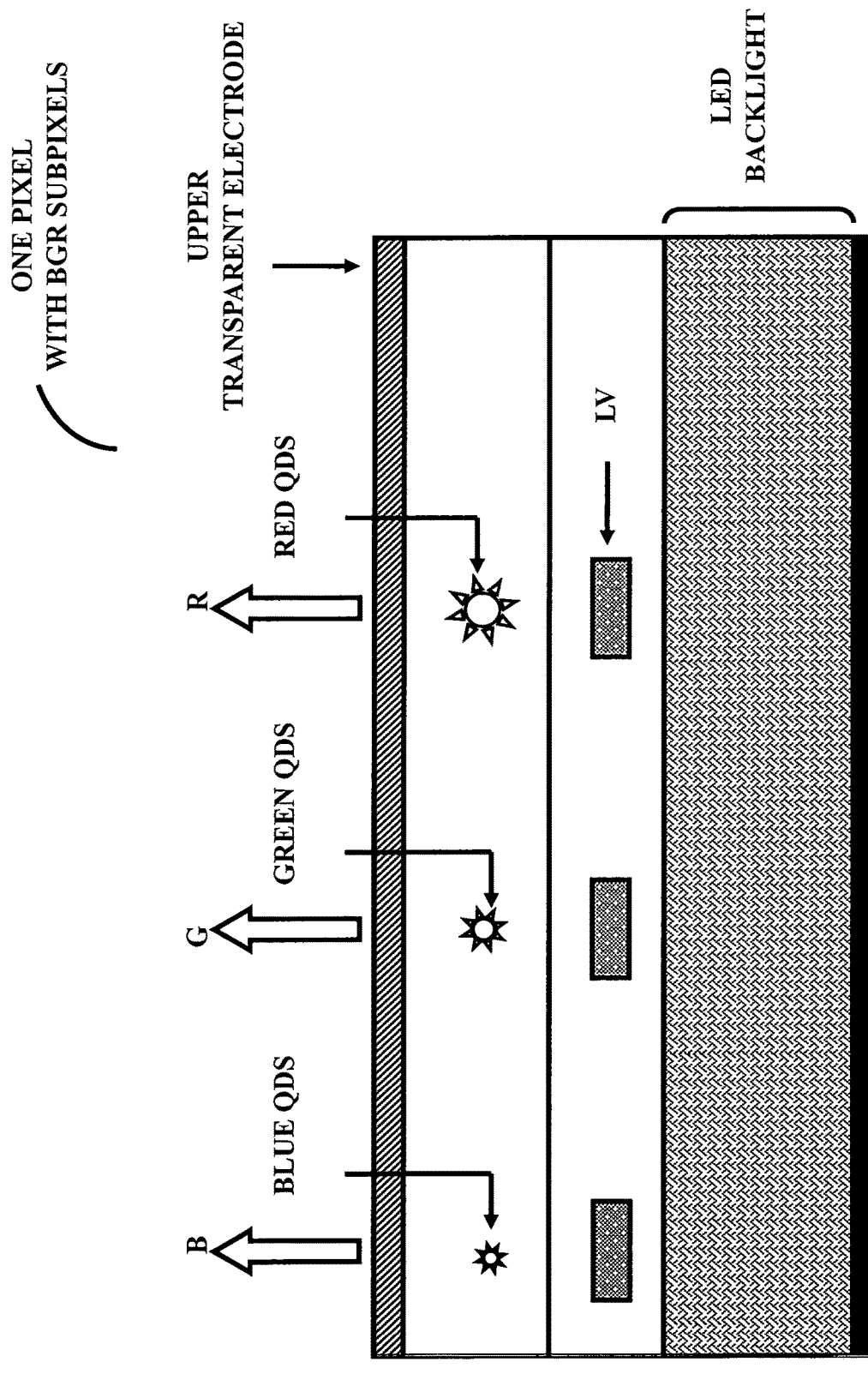

FIG. 35A illustrates one pixel (with a blue subpixel, a green subpixel and a red subpixel), enabled by light emitting diode backlighting, light valves, blue quantum dots, green quantum dots and red quantum dots.

Figure 35B:
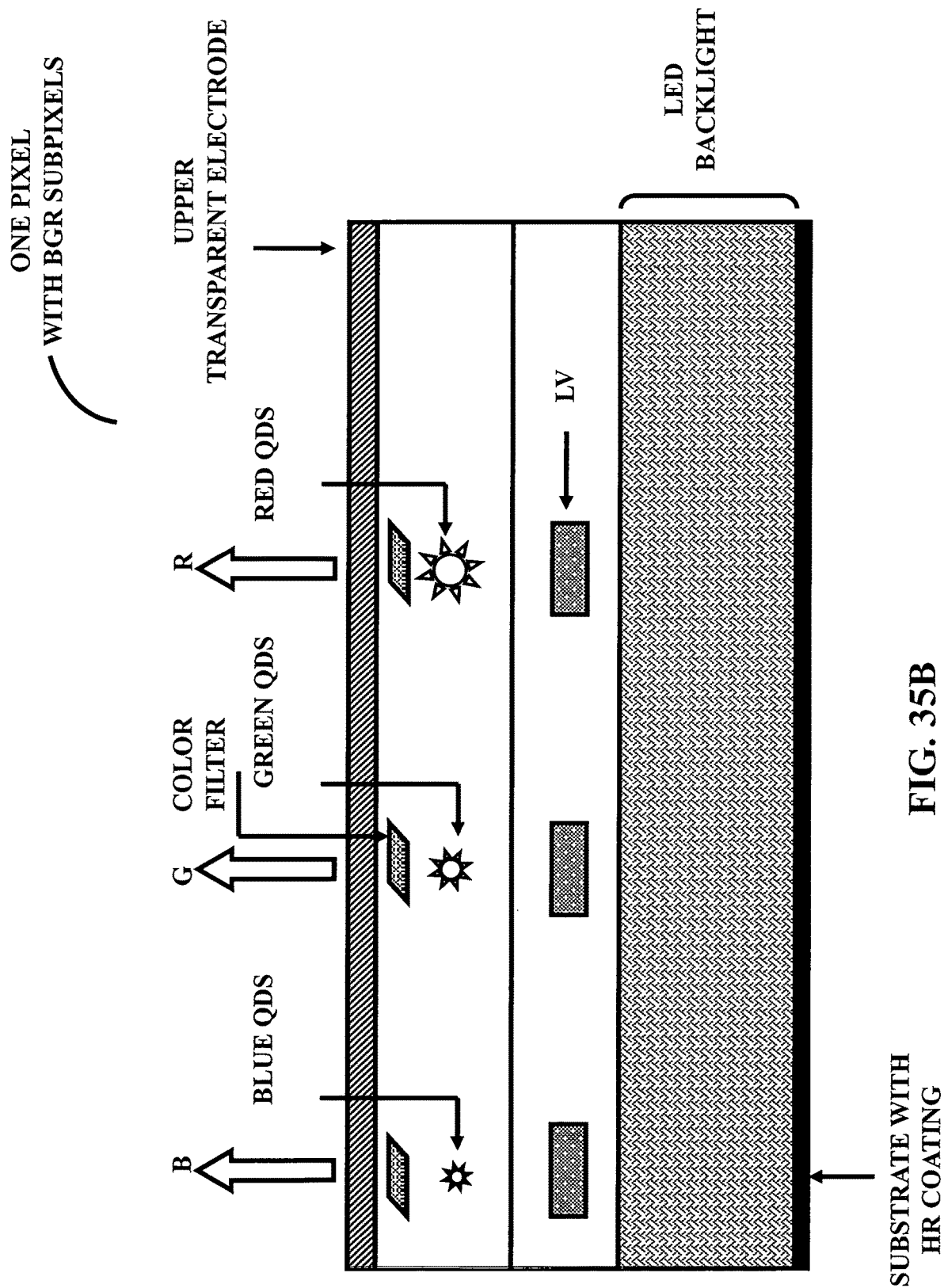

FIG. 35B illustrates one pixel (with a blue subpixel, a green subpixel and a red subpixel), enabled by light emitting diode backlighting, light valves, optical color filters and blue quantum dots, green quantum dots and red quantum dots.

Figure 35C:
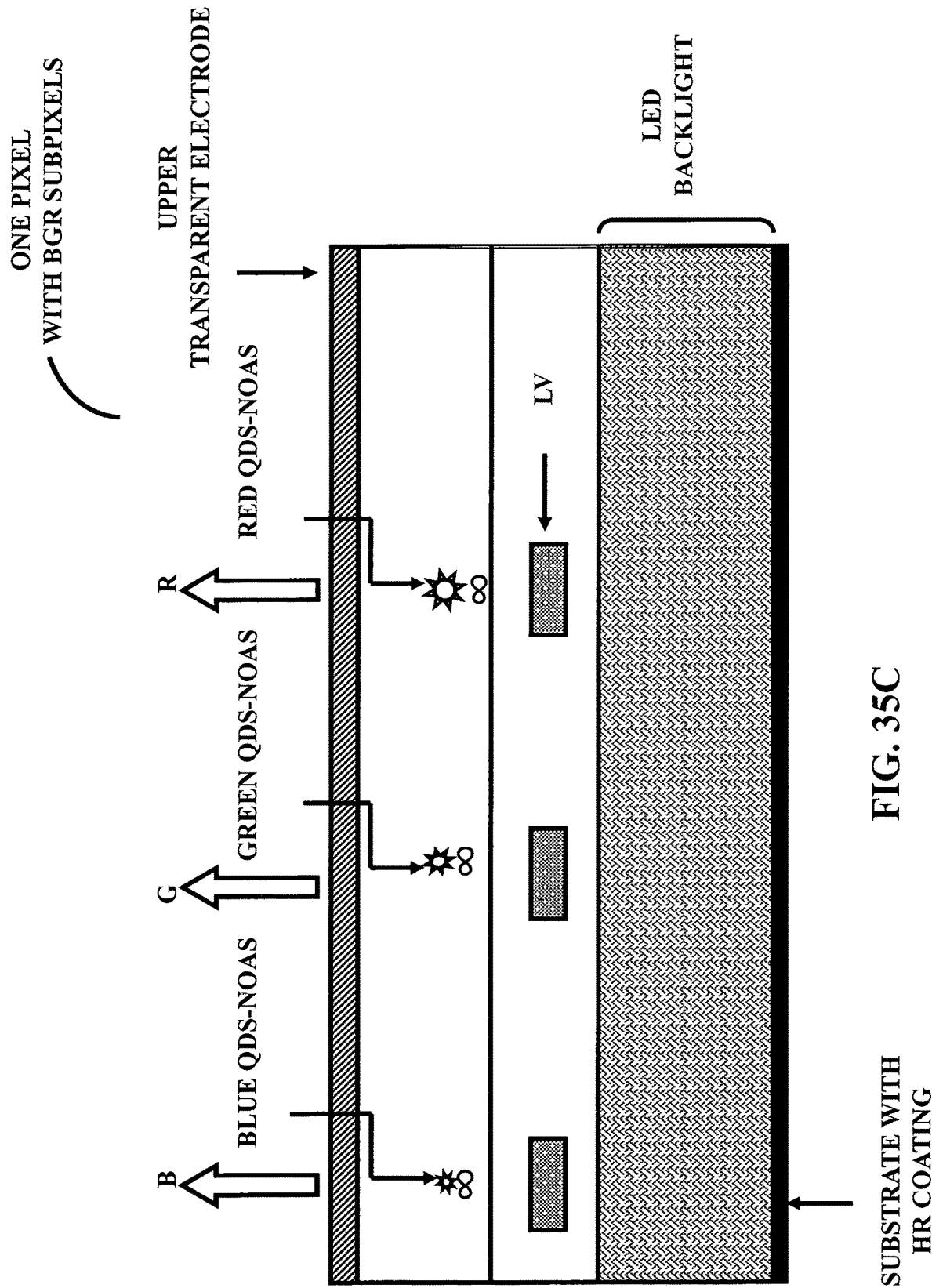

FIG. 35C illustrates one pixel (with a blue subpixel, a green subpixel and a red subpixel), enabled by light emitting diode backlighting, light valves, blue quantum dots-protruded metal/non-metal nano optical antennas, green quantum dots-protruded metal/non-metal nano optical antennas and red quantum dots-protruded metal/non-metal nano optical antennas. Each blue/green/red quantum dot is placed on/near the protruded metal/non-metal nano optical antenna in order to enable plasmonic coupling.

Figure 35D:
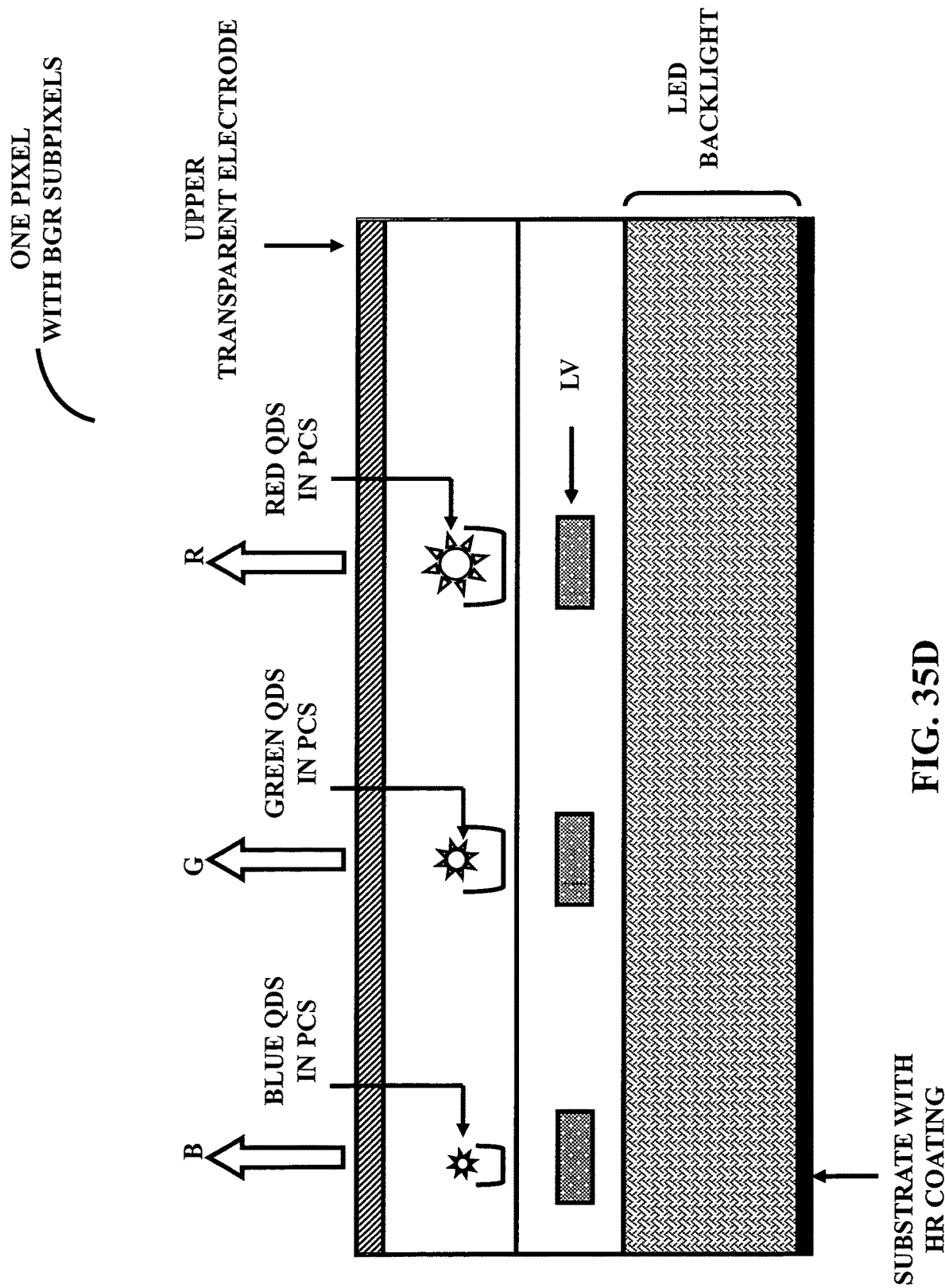

FIG. 35D illustrates one pixel (with a blue subpixel, a green subpixel and a red subpixel), enabled by light emitting diode backlighting, light valves, blue quantum dots in photonic crystals, green quantum dots in photonic crystals and red quantum dots in photonic crystals.

Figure 35E:
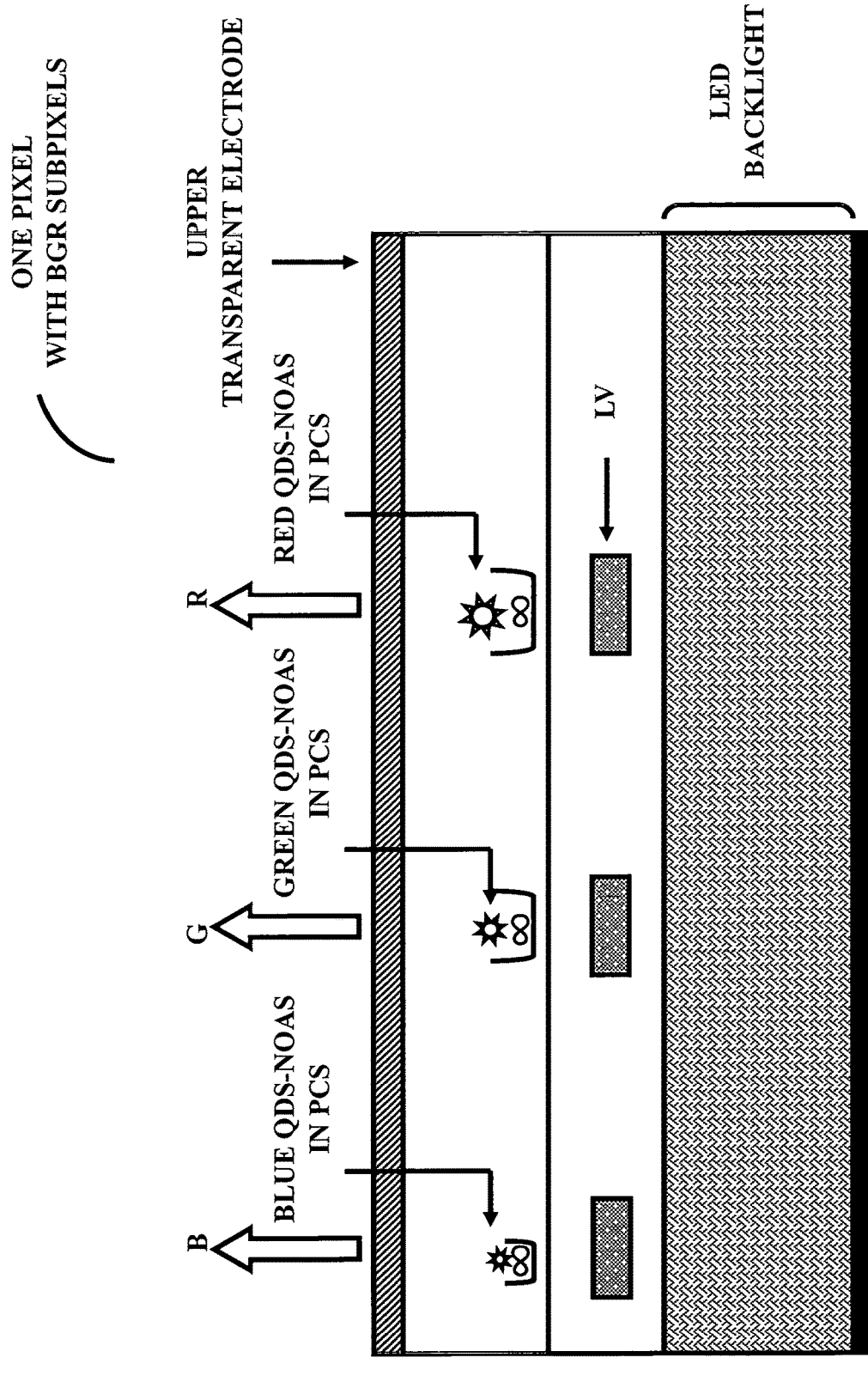

FIG. 35E illustrates one pixel (with a blue subpixel, a green subpixel and a red subpixel), enabled by light emitting diode backlighting, light valves, blue quantum dots-protruded metal/non-metal nano optical antennas in photonic crystals, green quantum dots-protruded metal/non-metal nano optical antennas in photonic crystals and red quantum dots-protruded metal nano optical antennas in photonic crystals.

Figure 35F:
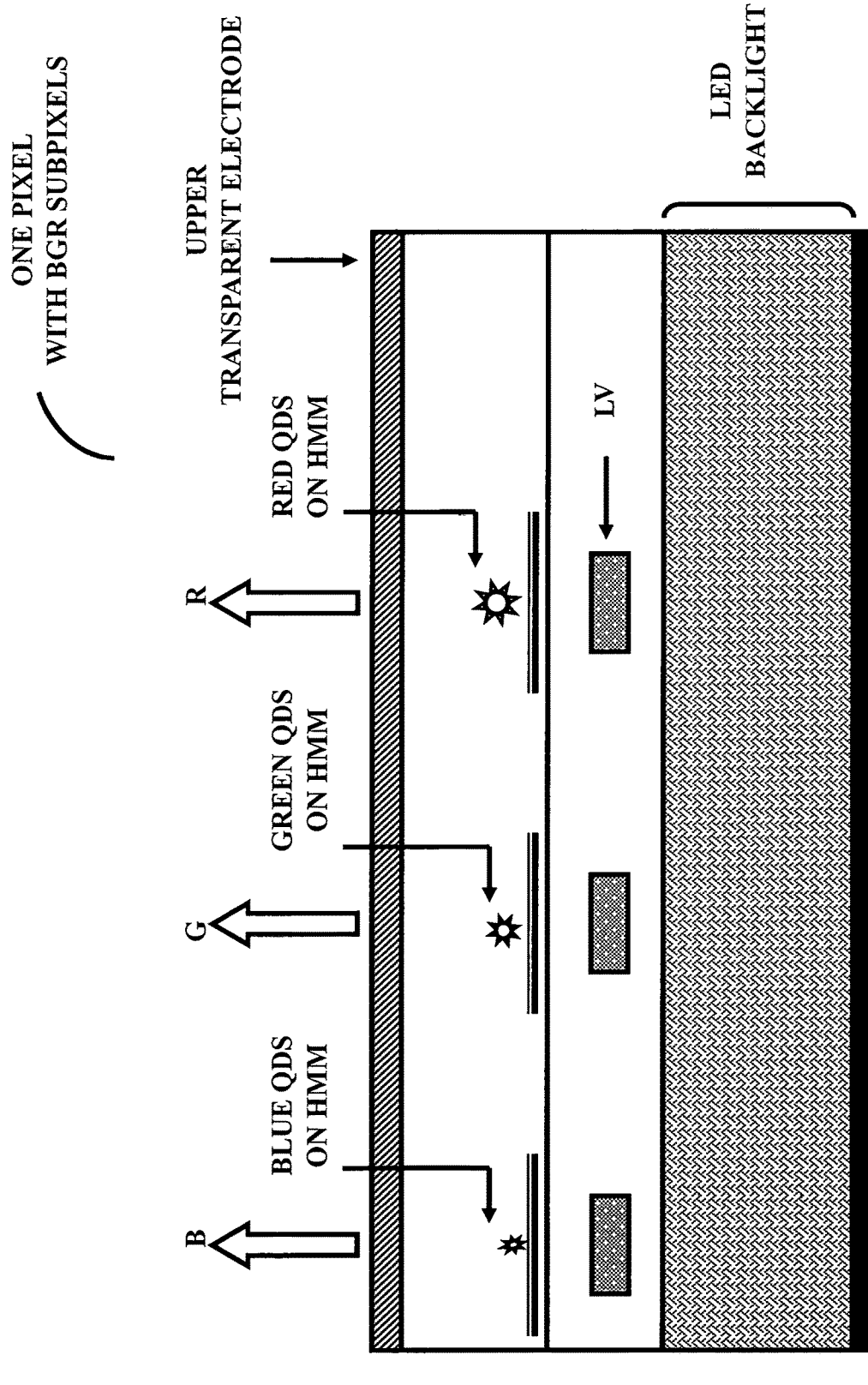

FIG. 35F illustrates one pixel (with a blue subpixel, a green subpixel and a red subpixel), enabled by light emitting diode backlighting, light valves, blue quantum dots on a hyperbolic metamaterial, green quantum dots on a hyperbolic metamaterial and red quantum dots on a hyperbolic metamaterial.

Figure 35G:
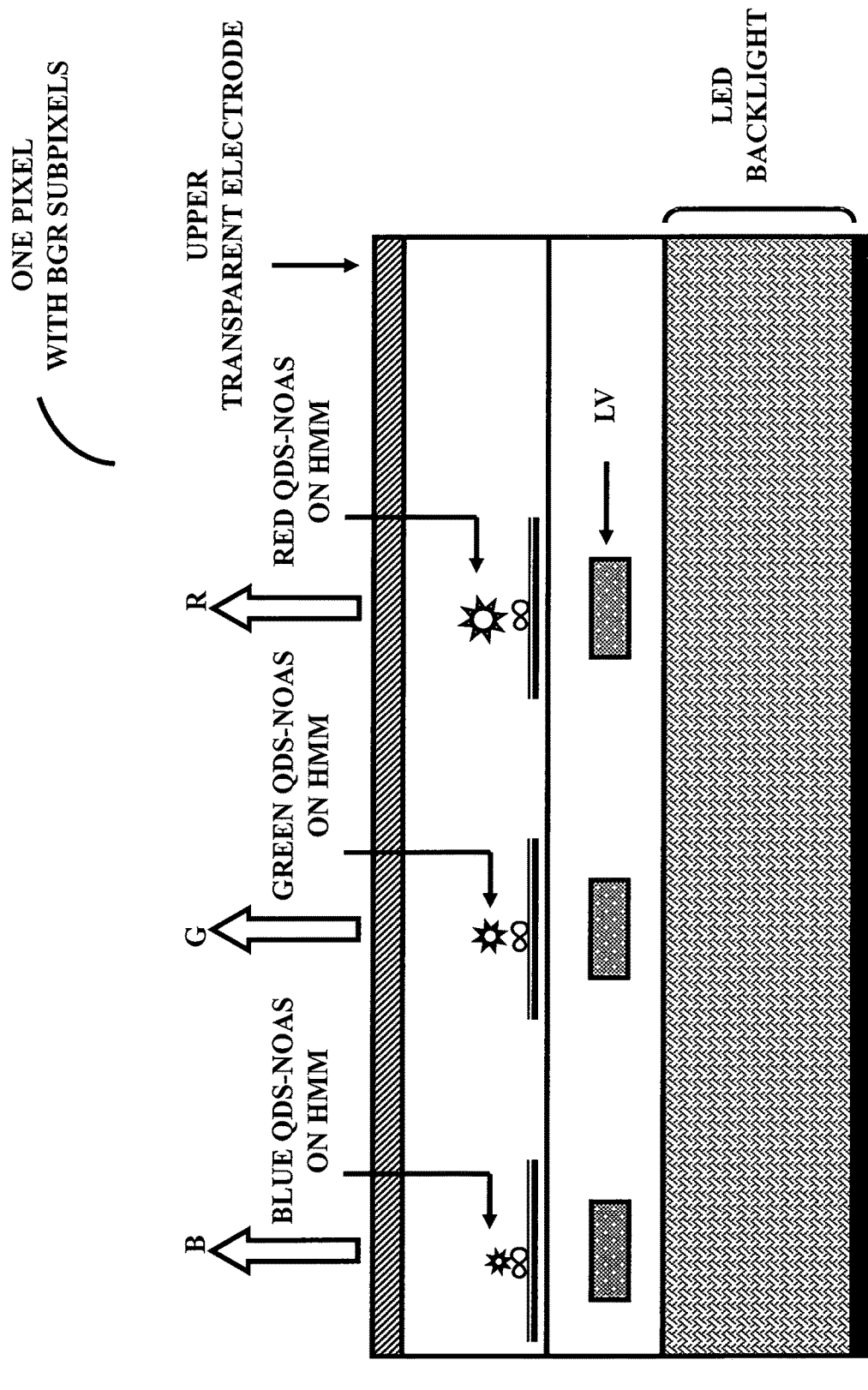

FIG. 35G illustrates one pixel (with a blue subpixel, a green subpixel and a red subpixel), enabled by light emitting diode backlighting, light valves, blue quantum dots-protruded metal/non-metal nano optical antennas on a hyperbolic metamaterial, green quantum dots-protruded metal nano optical antennas on a hyperbolic metamaterial and red quantum dots-protruded metal/non-metal nano optical antennas on a hyperbolic metamaterial.

Figure 35H:
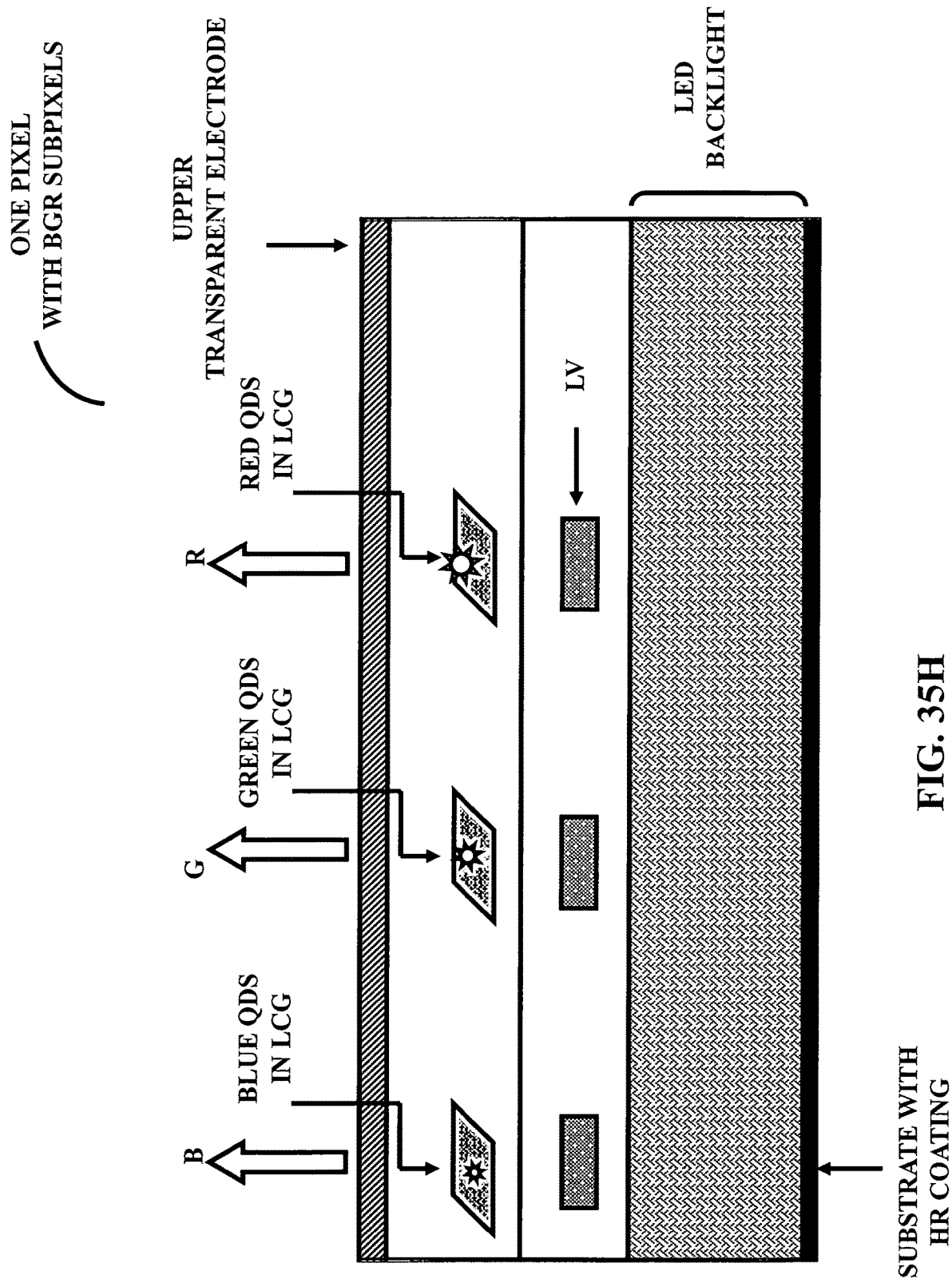

FIG. 35H illustrates one pixel (with a blue subpixel, a green subpixel and a red subpixel), enabled by light emitting diode backlighting, light valves, blue quantum dots in the electrically switchable liquid crystal gel, green quantum dots in the electrically switchable liquid crystal gel and red quantum dots in the electrically switchable liquid crystal gel.

Details of the quantum dots (nanocrystals) and light emitting diode backlighting enabled display have been described/disclosed in U.S. non-provisional patent application Ser. No. 13/448,378 entitled "SYSTEM AND METHOD FOR INTELLIGENT SOCIAL COMMERCE", filed on Apr. 16, 2012 and in its related U.S. non-provisional patent applications (with all benefit provisional patent applications) are incorporated in its entirety herein with this application.

Figure 36A:
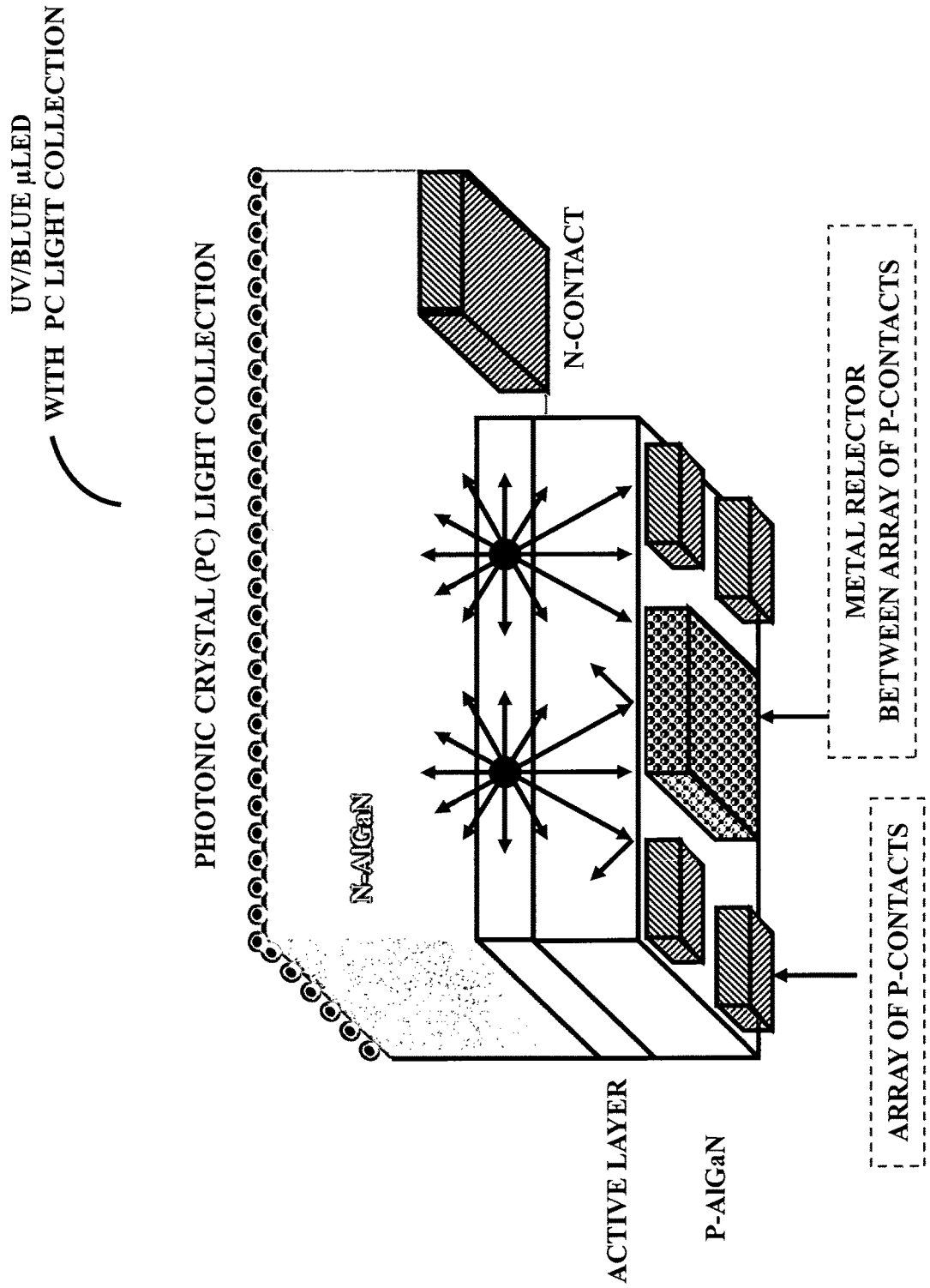

FIG. 36A illustrates a structure for an ultraviolet/blue microlight emitting diode, integrated with photonic crystals light collection optics. The structure has a typical PiN material structure and has an array of p-metal contacts, but the areas between the array of p-metal contacts include a metal (e.g., silver) reflector.

FIG. 36B illustrates typical layer material compositions of an ultraviolet/blue microlight emitting diode.

FIGS. 36C-36F illustrate sequential fabrication (utilizing a substrate lift-off process) for an ultraviolet/blue microlight emitting diode, integrated with the photonic crystals light collection optics.

FIG. 36G illustrates typical dimensions of the photonic crystals light collection optics, where the air hole diameter is about 300 nm and distance between the air holes is about 500 nm.

Figure 37A:
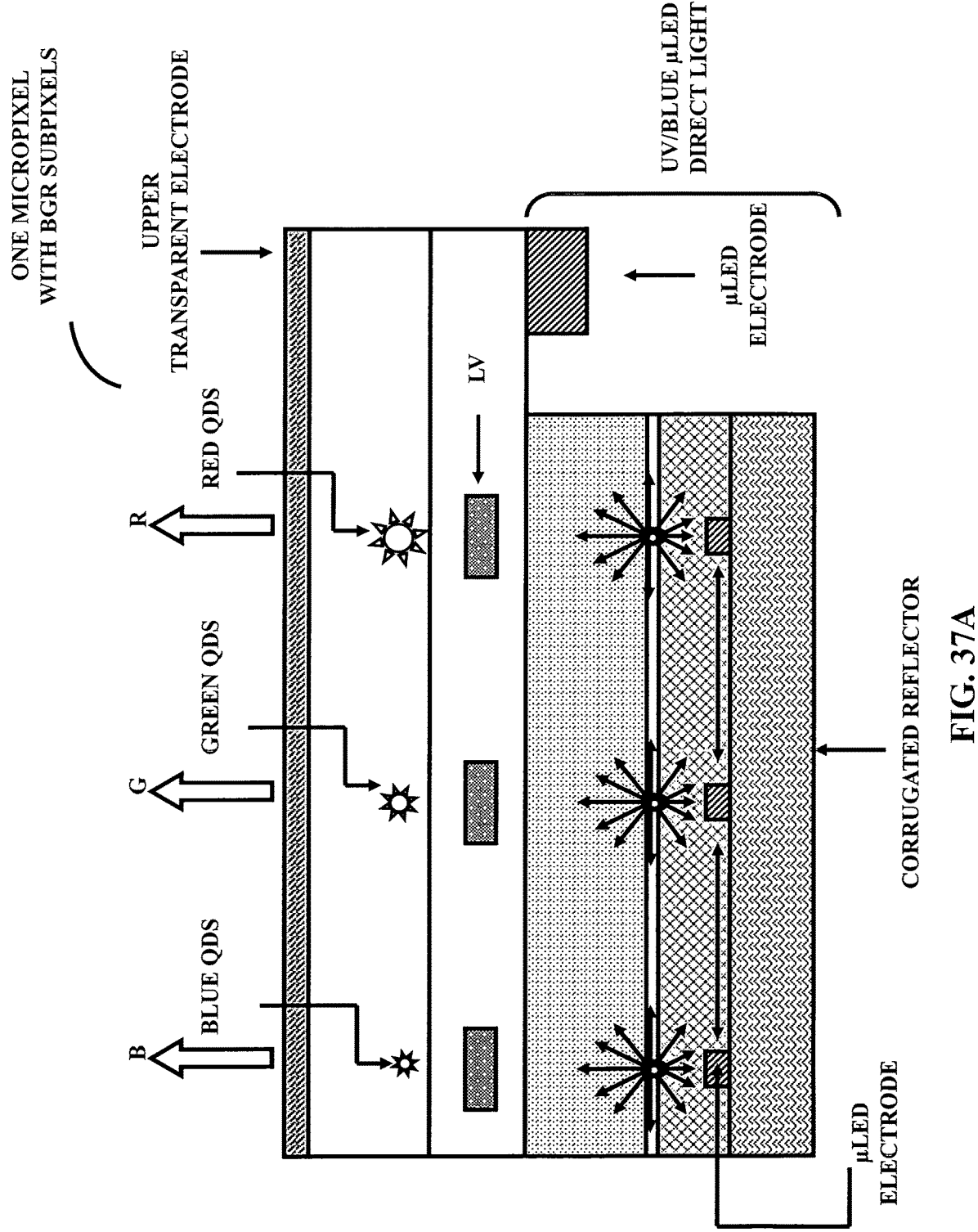

FIG. 37A illustrates one micropixel (with a blue submicropixel, a green submicropixel and a red submicropixel), enabled by ultraviolet/blue microlight emitting diodes, light valves, blue quantum dots, green quantum dots and red quantum dots.

Figure 37B:
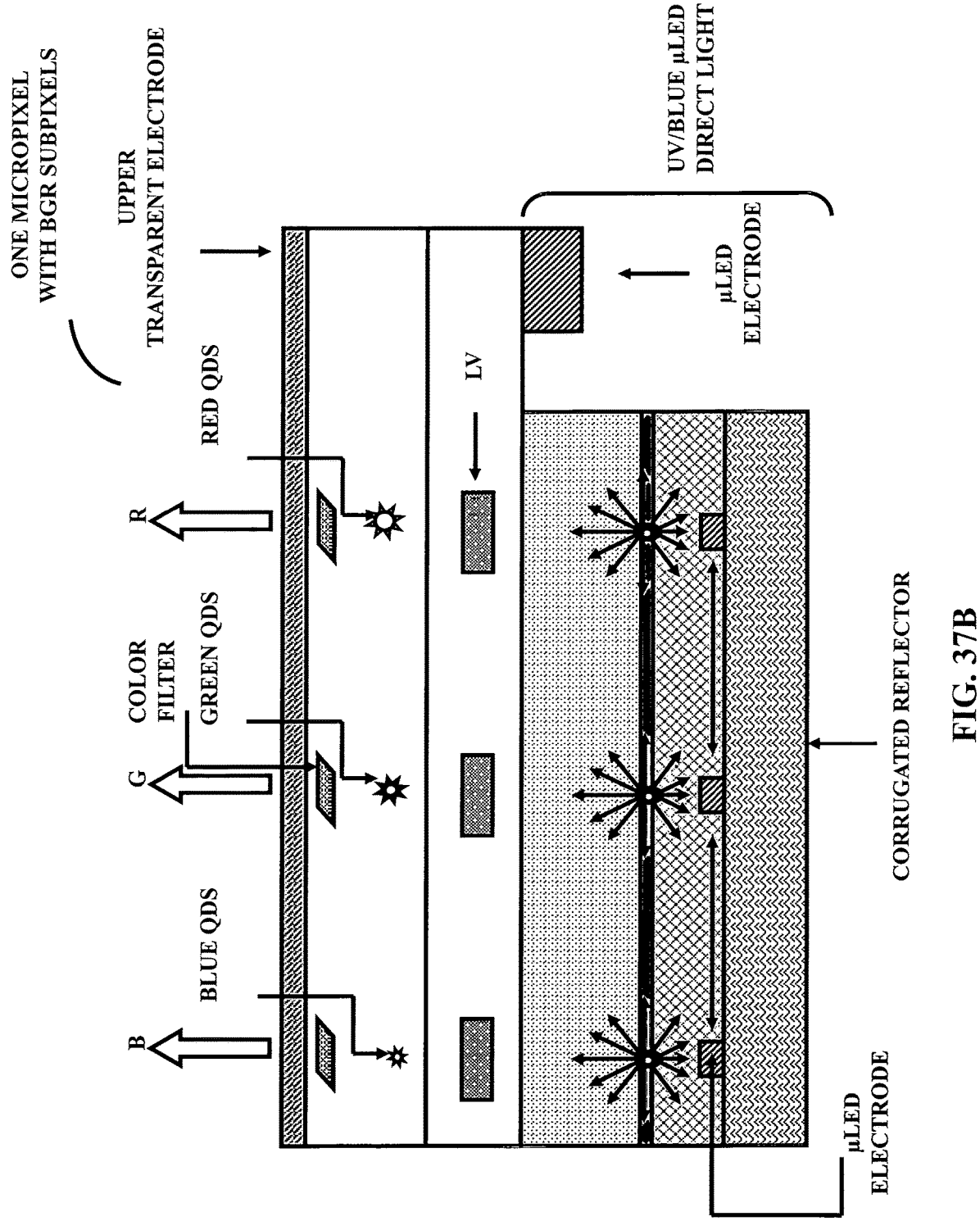

FIG. 37B illustrates one micropixel (with a blue submicropixel, a green submicropixel and a red submicropixel), enabled by ultraviolet/blue microlight emitting diodes, light valves, optical color filters, blue quantum dots, green quantum dots and red quantum dots.

Figure 37C:
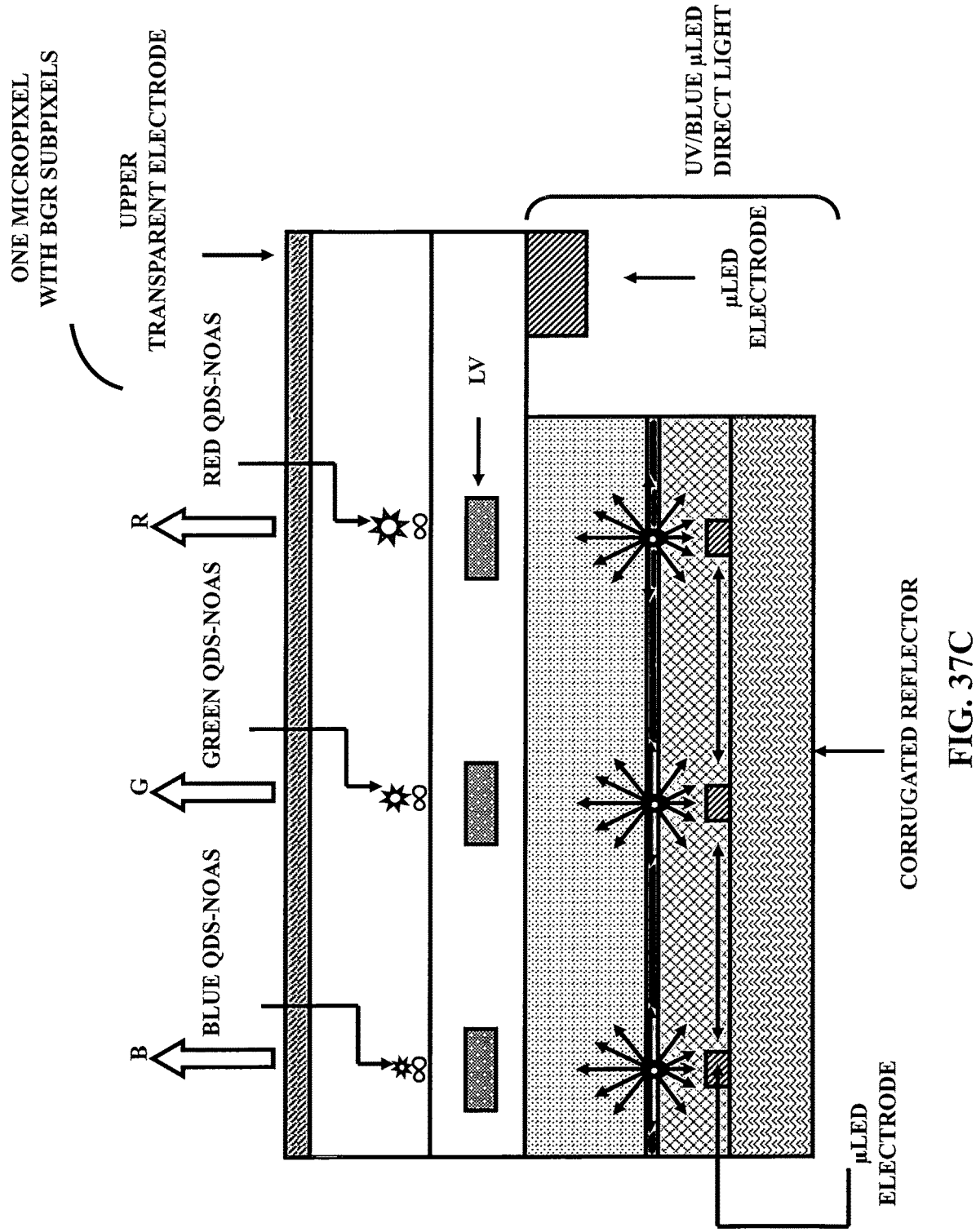

FIG. 37C illustrates one micropixel (with a blue submicropixel, a green submicropixel and a red submicropixel), enabled by ultraviolet/blue microlight emitting diodes, light valves, blue quantum dots-protruded metal/non-metal nano optical antennas, green quantum dots-protruded metal/non-metal nano optical antennas and red quantum dots-protruded metal/non-metal nano optical antennas. Each blue/green/red quantum dot is placed on/near the protruded metal/non-metal nano optical antenna in order to enable plasmonic coupling.

Figure 37D:
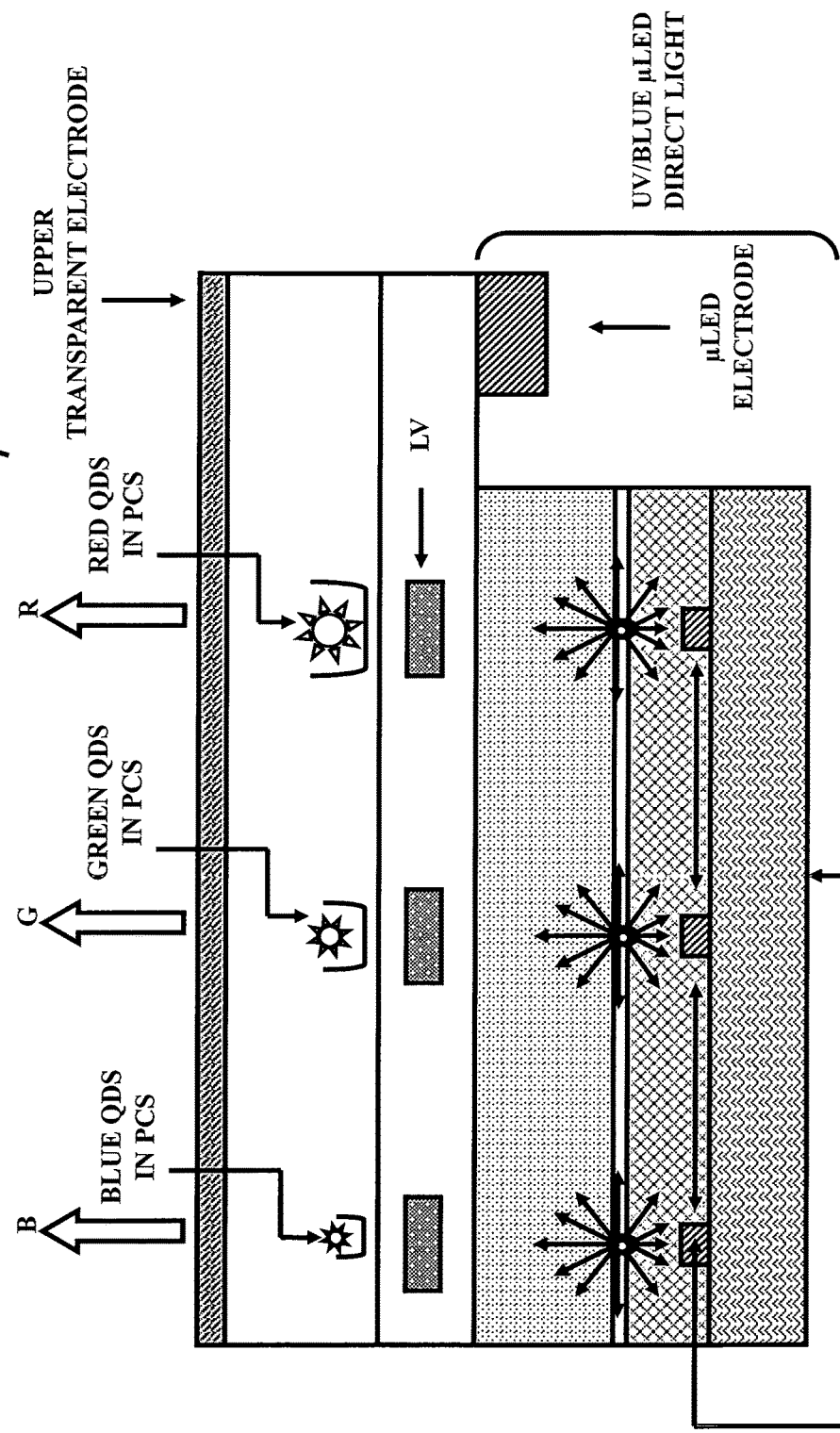

FIG. 37D illustrates one micropixel (with a blue submicropixel, a green submicropixel and a red submicropixel), enabled by ultraviolet/blue microlight emitting diodes, light valves, blue quantum dots in photonic crystals, green quantum dots in photonic crystals and red quantum dots in photonic crystals.

Figure 37E:
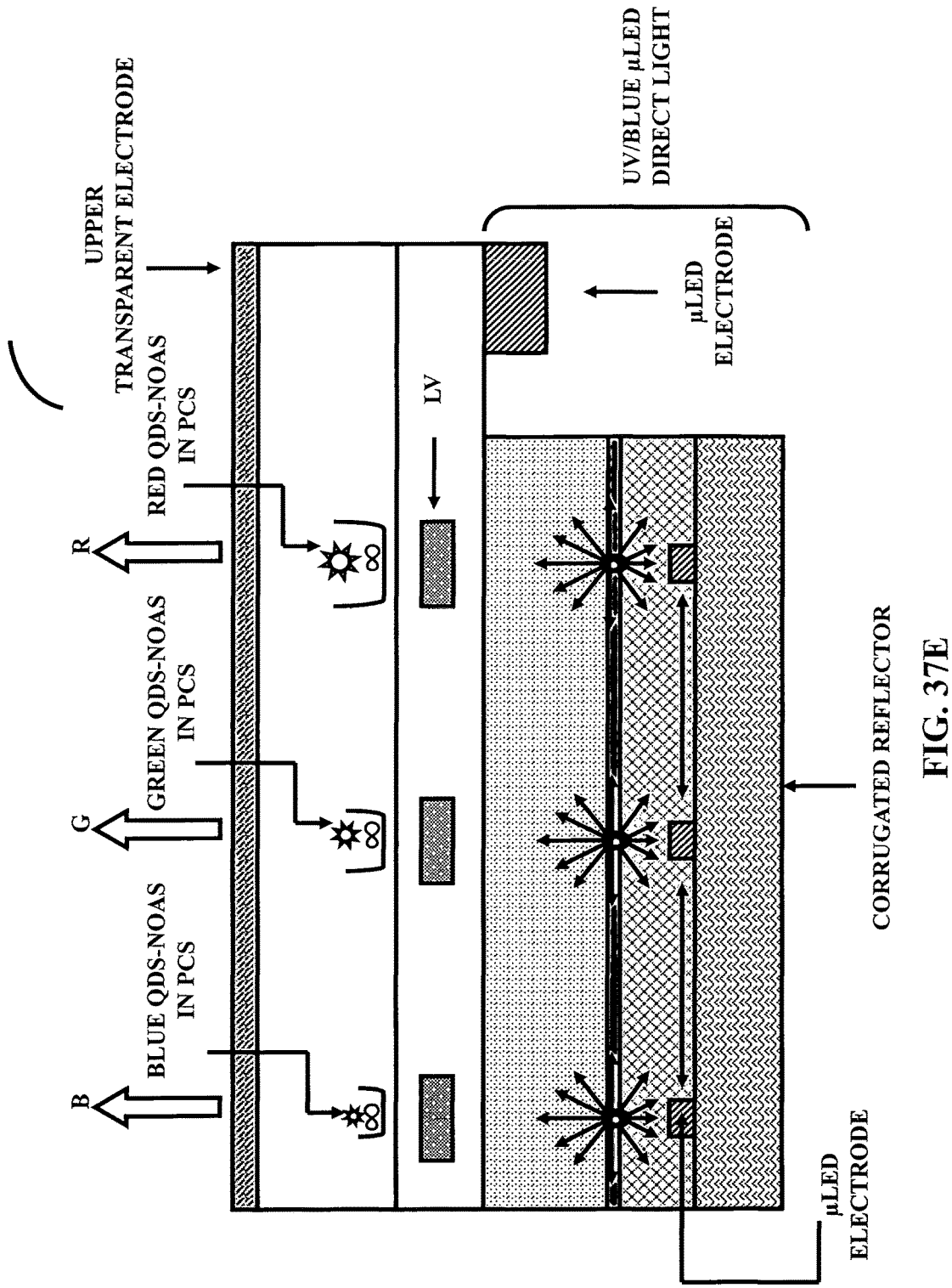

FIG. 37E illustrates one micropixel (with a blue submicropixel, a green submicropixel and a red submicropixel), enabled by ultraviolet/blue microlight emitting diodes, light valves, blue quantum dots-protruded metal/non-metal nano optical antennas in photonic crystals, green quantum dots-protruded metal/non-metal nano optical antennas in photonic crystals and red quantum dots-protruded metal/non-metal nano optical antennas in photonic crystals.

Figure 37F:
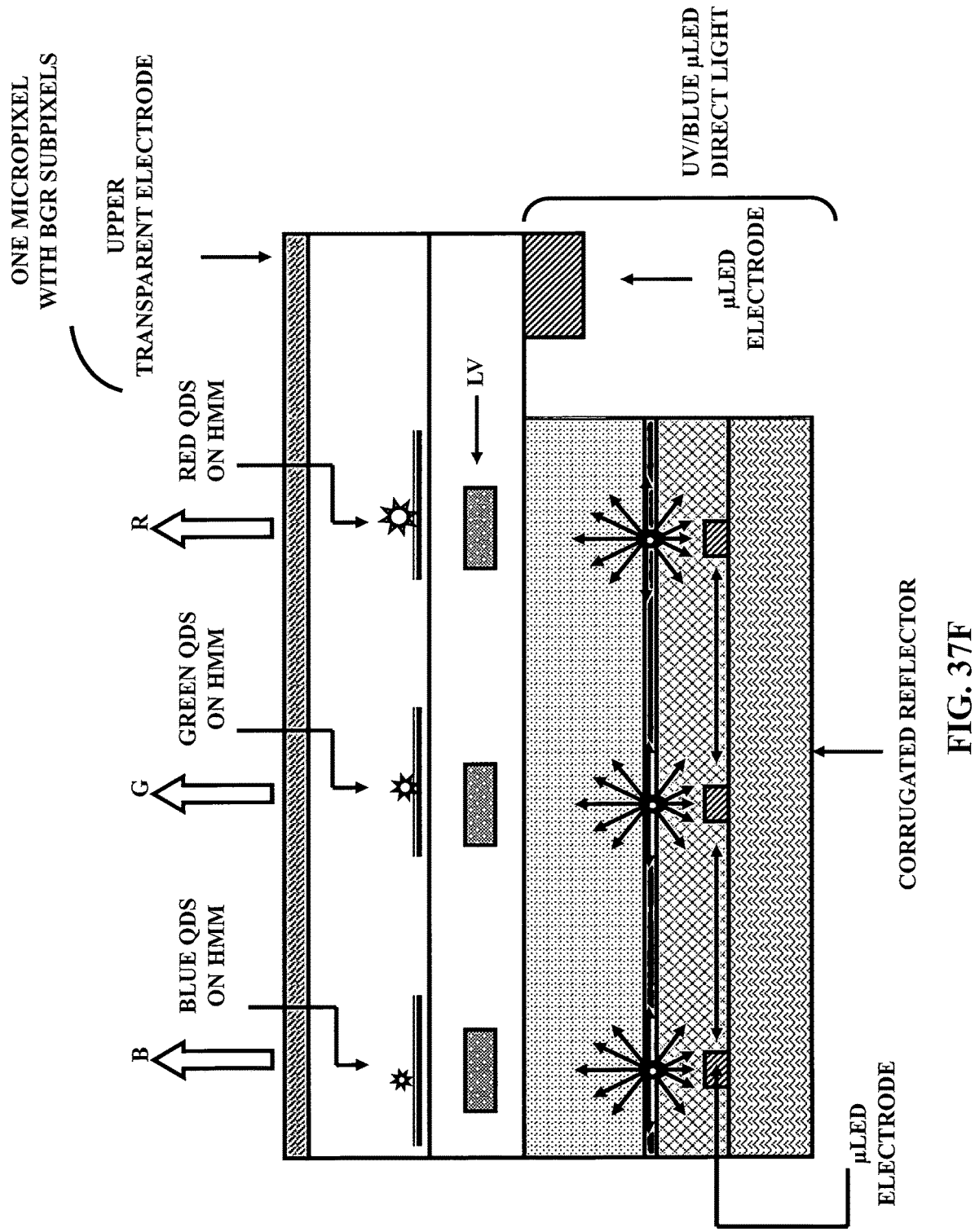

FIG. 37F illustrates one pixel (with a blue subpixel, a green subpixel and a red subpixel), enabled by ultraviolet/blue microlight emitting diodes, light valves, blue quantum dots on a hyperbolic metamaterial, green quantum dots on a hyperbolic metamaterial and red quantum dots on a hyperbolic metamaterial.

Figure 37G:
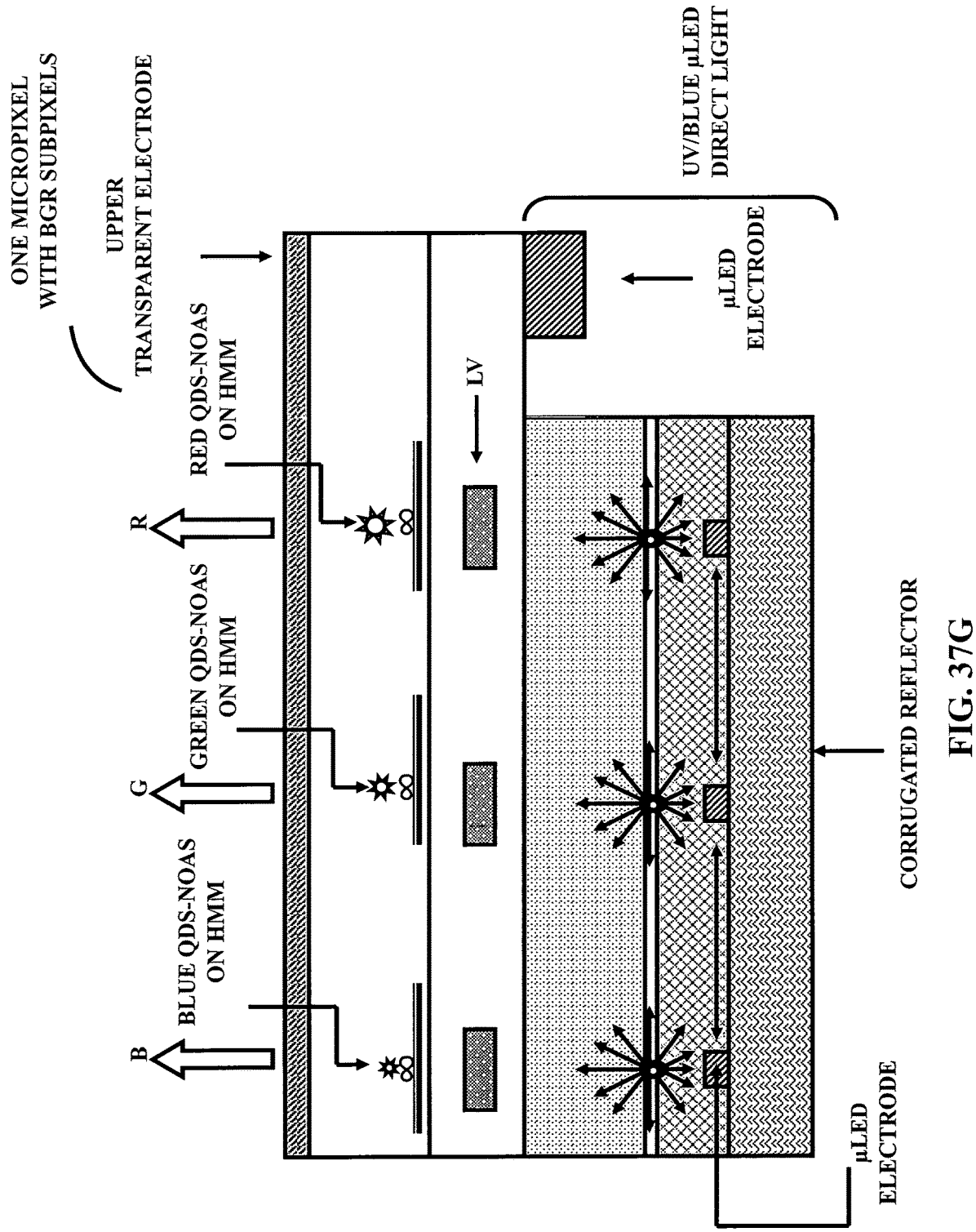

FIG. 37G illustrates one pixel (with a blue subpixel, a green subpixel and a red subpixel), enabled by ultraviolet/blue microlight emitting diodes, light valves, blue quantum dots-protruded metal/non-metal nano optical antennas on a hyperbolic metamaterial, green quantum dots-protruded metal/non-metal nano optical antennas on a hyperbolic metamaterial and red quantum dots-protruded metal/non-metal nano optical antennas on a hyperbolic metamaterial.

Figure 37H:
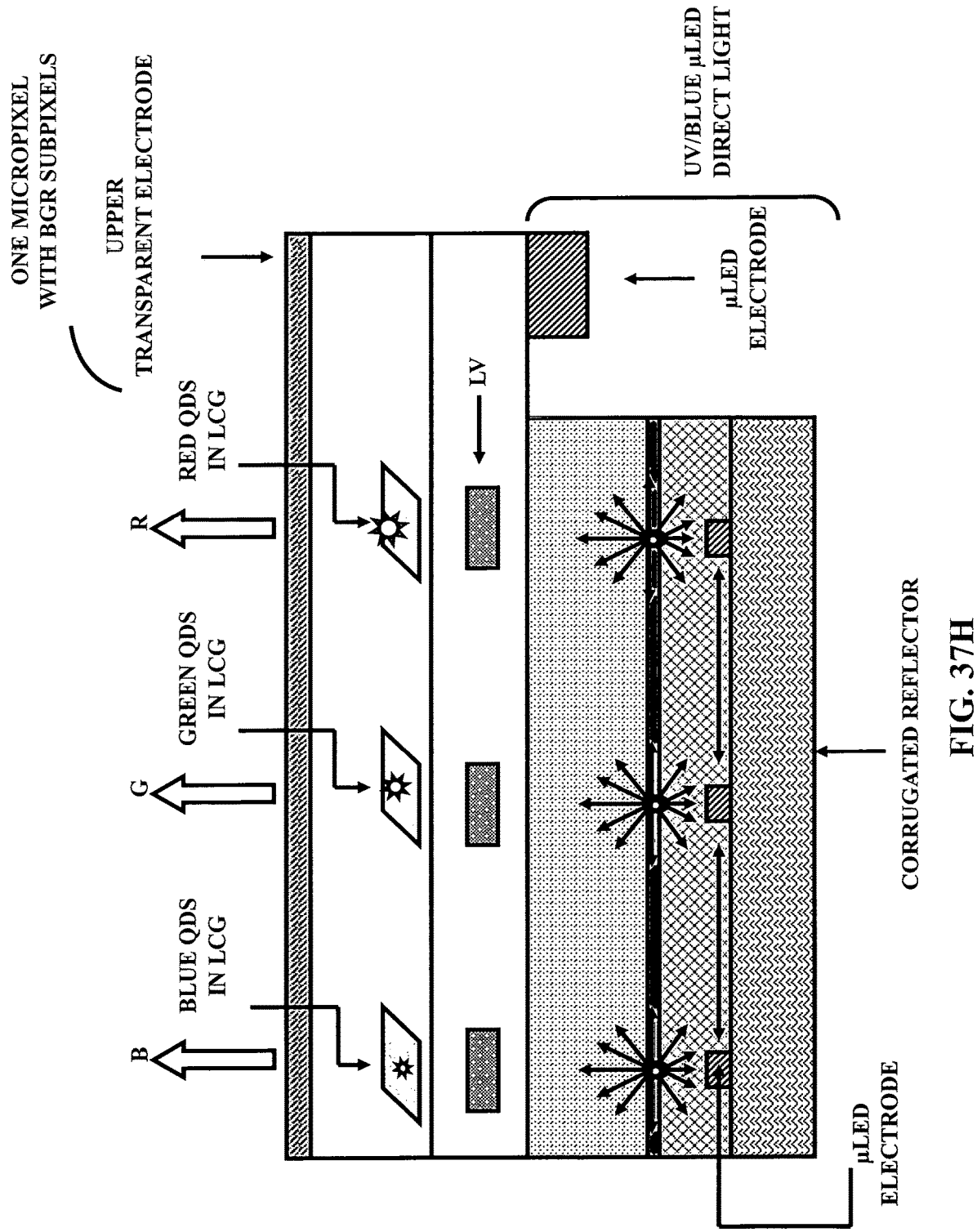

FIG. 37H illustrates one micropixel (with a blue submicropixel, a green submicropixel and a red submicropixel), enabled by ultraviolet/blue microlight emitting diodes, light valves, blue quantum dots in the electrically switchable liquid crystal gel, green quantum dots in the electrically switchable liquid crystal gel and red quantum dots in the electrically switchable liquid crystal gel.

FIG. 38 is a two-dimensional array of metal nanowires and this constitutes a plasmonic light guide (PLG). The plasmonic light guide can enable efficient light output from a light emitting diode.

FIGS. 39A-39G are identical to FIGS. 37A-37F, except the addition of a plasmonic light guide in FIGS. 37A, 37B, 37C, 37D, 37E, 37F, 37G and 37H.

It should be noted that ultraviolet/blue microlight emitting diodes (with photonic crystals light collection optics) can be utilized in FIGS. 37A-37F and FIGS. 39A-39F.

FIG. 40A illustrates vertically stacked blue, green and red organic light emitting diodes (with electrodes on a glass substrate) to act as a micropixel, utilizing a light valve on the upper transparent electrode (e.g., indium tin oxide/graphene). Backward transmitted light through the glass substrate can be collected by a solar cell (e.g., tungsten diselenide solar cell).

FIG. 40B is similar to 40A, except the vertically stacked blue, green and red organic light emitting diodes can be enhanced.

FIG. 40C illustrates an enhancement, where blue, green and red organic light emitting diode materials are mixed with specific sized quantum dots. For example, blue organic light emitting diode material is integrated with blue quantum dots, green light emitting diode material is integrated with green quantum dots and red light emitting diode material is integrated with red quantum dots.

FIG. 41A illustrates two dimensional arrays of micropixels A, wherein one micropixel A has a blue subpixel, a green subpixel and a red subpixel. The micropixel A can be realized with quantum dots, photonic crystals/microlight emitting diodes/microlight emitting diodes (with photonic crystals based light collection optics)/vertically stacked organic light emitting diodes.

FIG. 41B illustrates drive electronics (in block diagram) of the microlight emitting diode for brightness control of a micropixel. Pulse width modulation (PWM) logic can read the ambient temperature and then compensates the intensities of blue, green and red microlight emitting diodes by changing the pulse width modulation's duty cycle. Such compensation curves can be stored in EEPROM memory.

FIG. 42A illustrates a cross section of an integrated device, which includes an array of micropixels A and cameras (e.g., complementary metal oxide semiconductor image sensors)/phototransistors—further co-packaged/monolithically integrated with the Super System on Chip 400A/400B. An array of microlenses is on the top of the array of micropixels and cameras/phototransistors.

The above integration is the Super System on Chip 400C, which can enable the camera to see, store and process information simultaneously and it is capable of learning/relearning for self-intelligence, sensor-awareness, context-awareness and autonomous actions, remembering the patterns and movements.

FIG. 42B illustrates a front view of FIG. 42A.

Details of such integration of camera pixels with the Super System on Chip 400A/400B have been described/disclosed in U.S. non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

FIG. 43A illustrates a frustrated vertical cavity surface emitting laser (F-VCSEL) A, which is similar to FIG. 22B, but the top mirror is metal with a nanohole. The diameter of the nanohole can be less than 5,000 nm. Laser light cannot escape easily, thus frustrated only to escape through the nanohole.

FIG. 43B is packaging of the frustrated vertical cavity surface emitting laser A.

FIG. 43C illustrates a frustrated vertical cavity surface emitting laser B, which is similar to FIG. 43A, except a protruded metal/non-metal nano optical antenna is fabricated/constructed near the nanohole.

FIG. 43D is packaging of the frustrated vertical cavity surface emitting laser B.

Figure 44A:
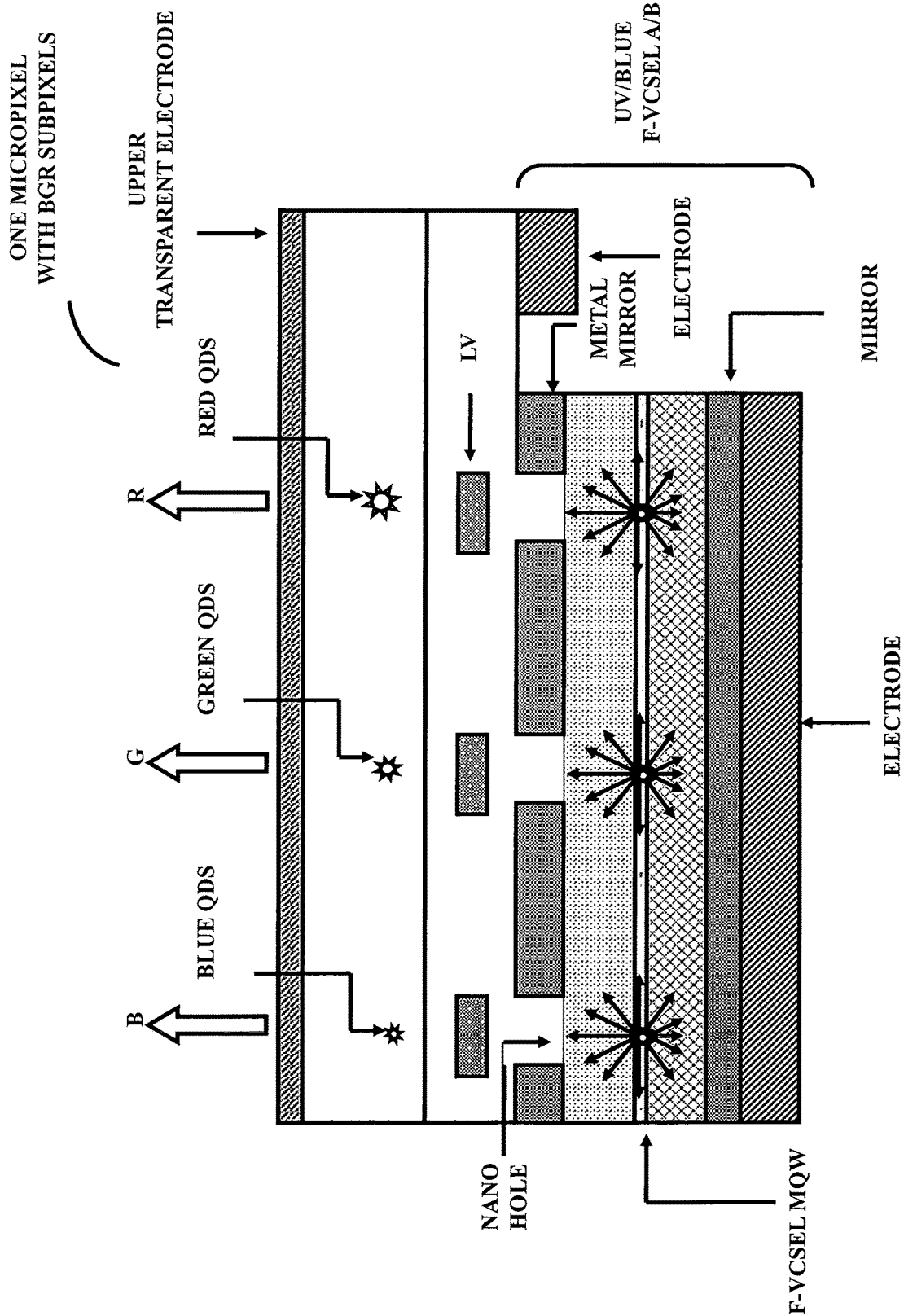

FIG. 44A illustrates one micropixel (with a blue submicropixel, a green submicropixel and a red submicropixel), enabled by frustrated vertical cavity surface emitting lasers A/B, light valves, blue quantum dots, green quantum dots and red quantum dots.

Figure 44B:
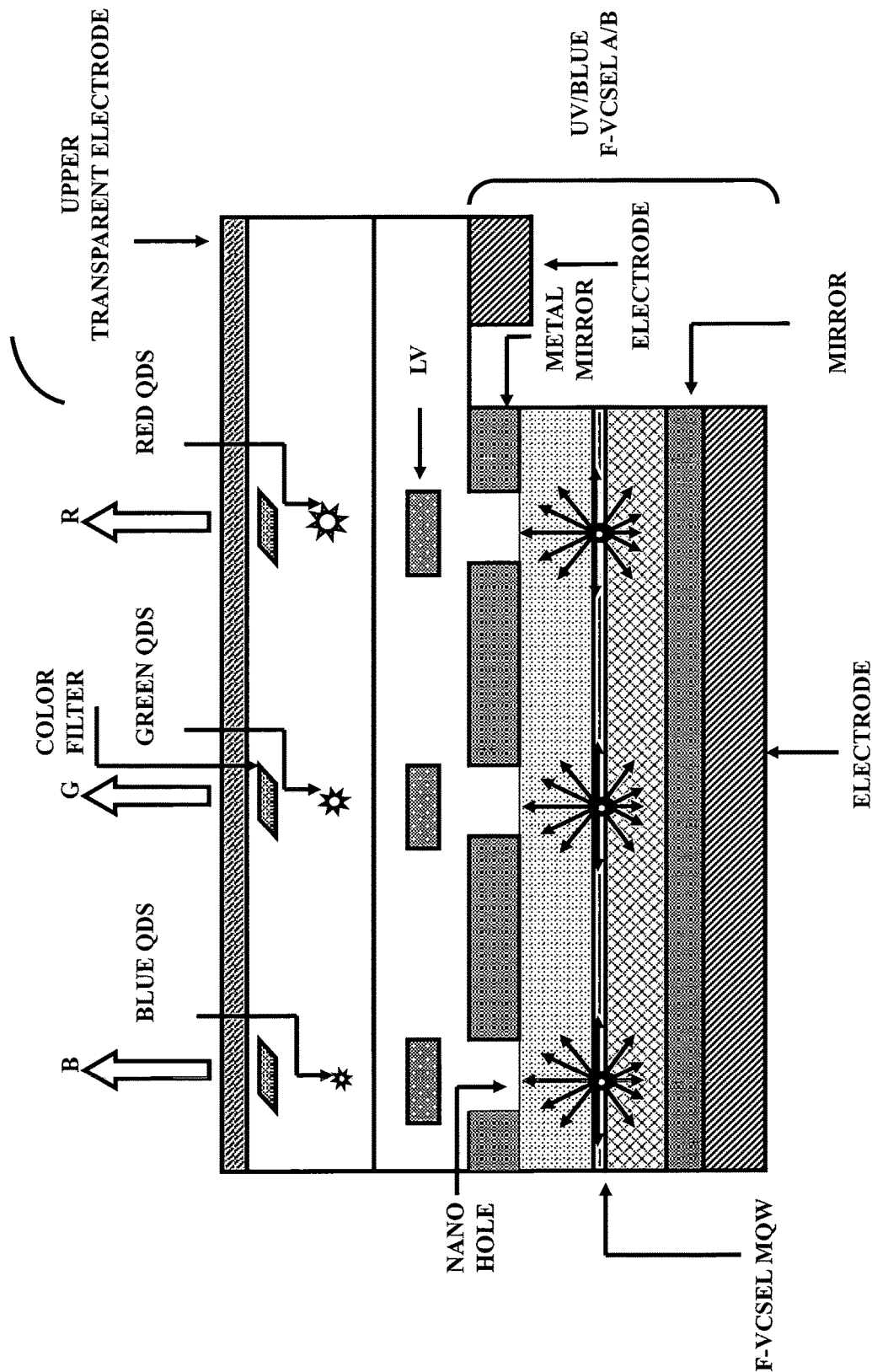

FIG. 44B illustrates one micropixel (with a blue submicropixel, a green submicropixel and a red submicropixel), enabled by frustrated vertical cavity surface emitting lasers A/B, light valves, optical color filters, blue quantum dots, green quantum dots and red quantum dots.

Figure 44C:
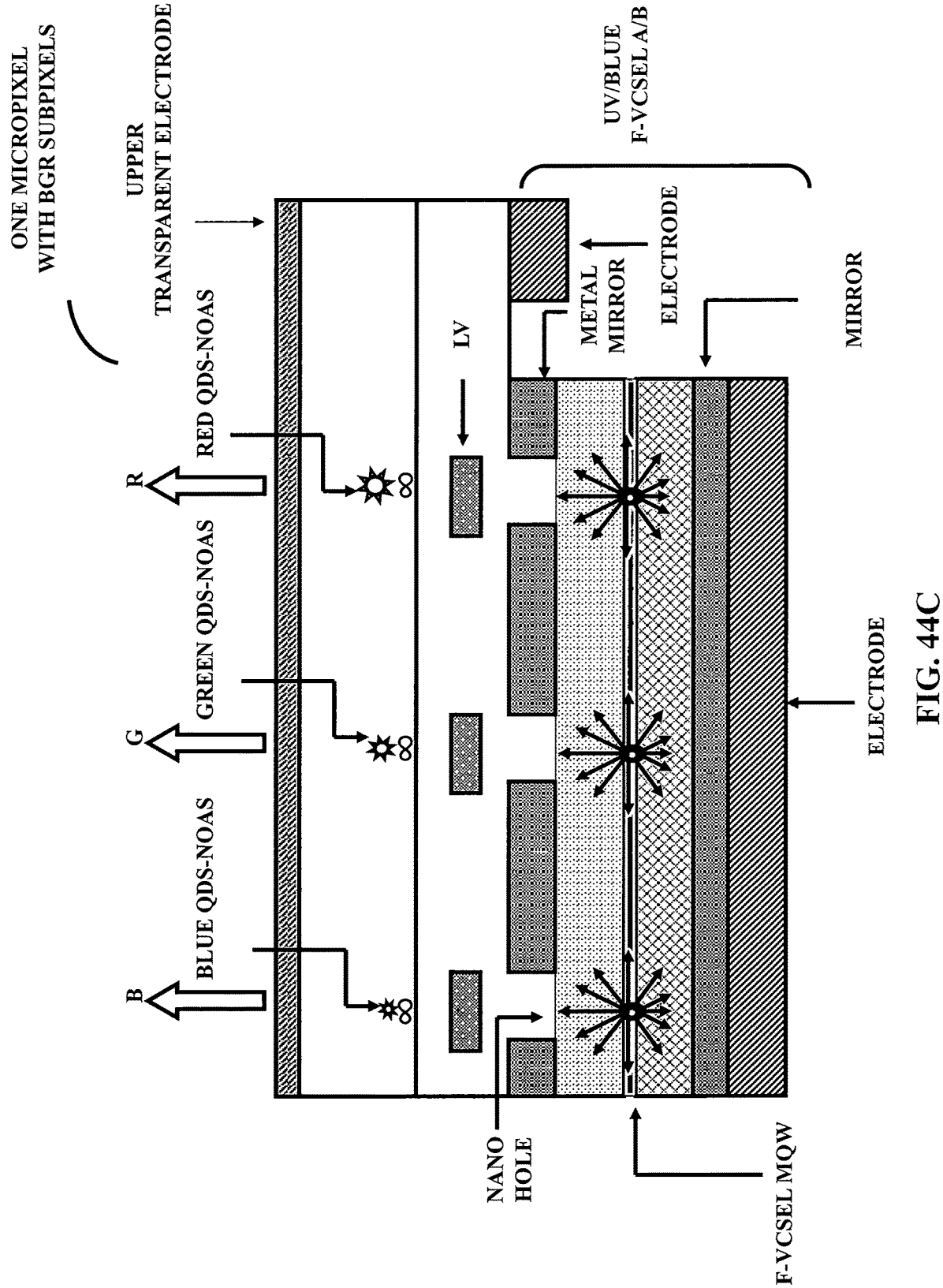

FIG. 44C illustrates one micropixel (with a blue submicropixel, a green submicropixel and a red submicropixel), enabled by frustrated vertical cavity surface emitting lasers A/B, light valves, blue quantum dots-protruded metal/non-metal nano optical antennas, green quantum dots-protruded metal/non-metal nano optical antennas and red quantum dots-protruded metal/non-metal nano optical antennas. Each blue/green/red quantum dot is placed on/near the protruded metal/non-metal nano optical antenna to enable plasmonic coupling.

Figure 44D:
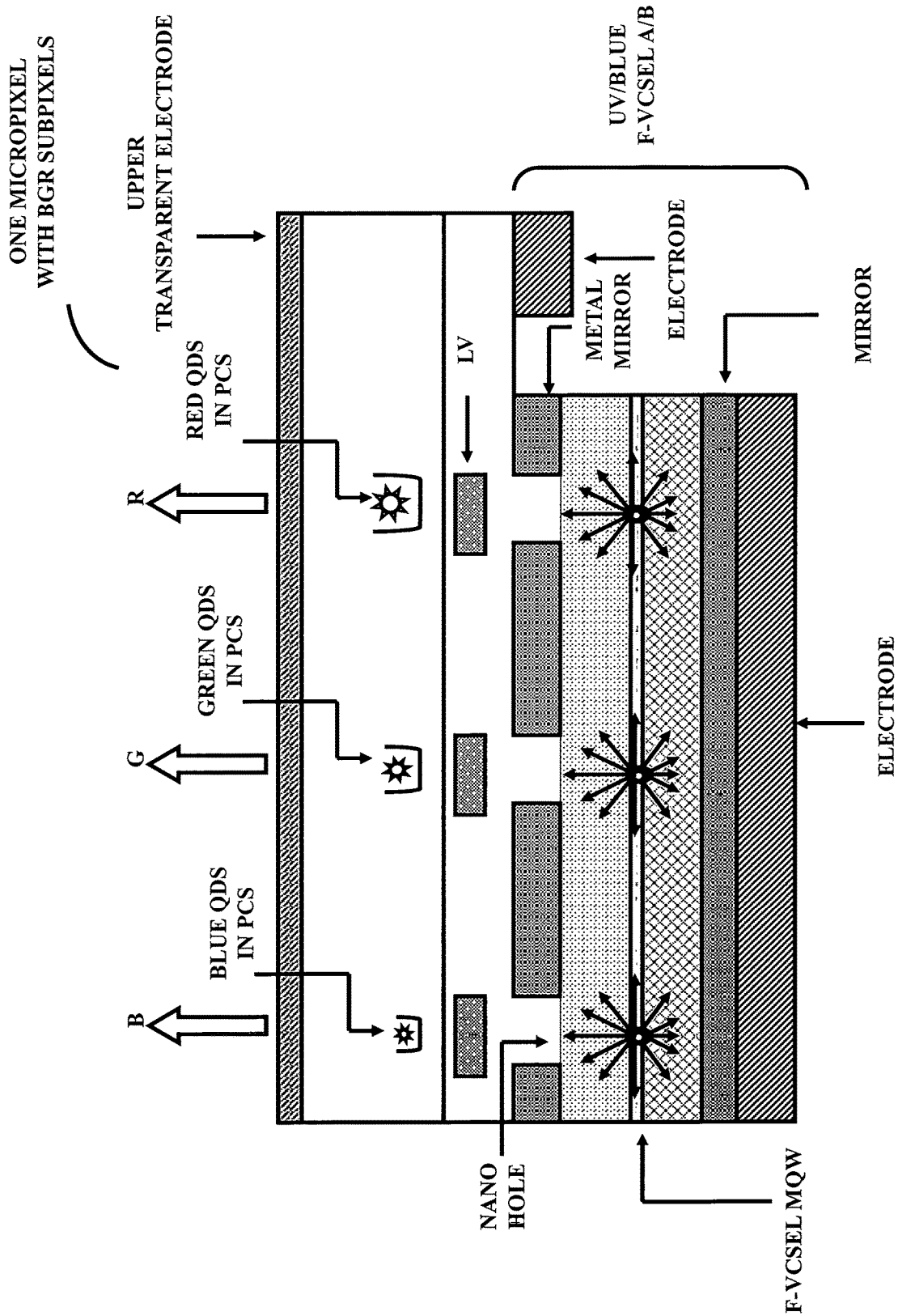

FIG. 44D illustrates one micropixel (with a blue submicropixel, a green submicropixel and a red submicropixel), enabled by frustrated vertical cavity surface emitting lasers A/B, light valves, blue quantum dots in photonic crystals, green quantum dots in photonic crystals and red quantum dots in photonic crystals.

Figure 44E:
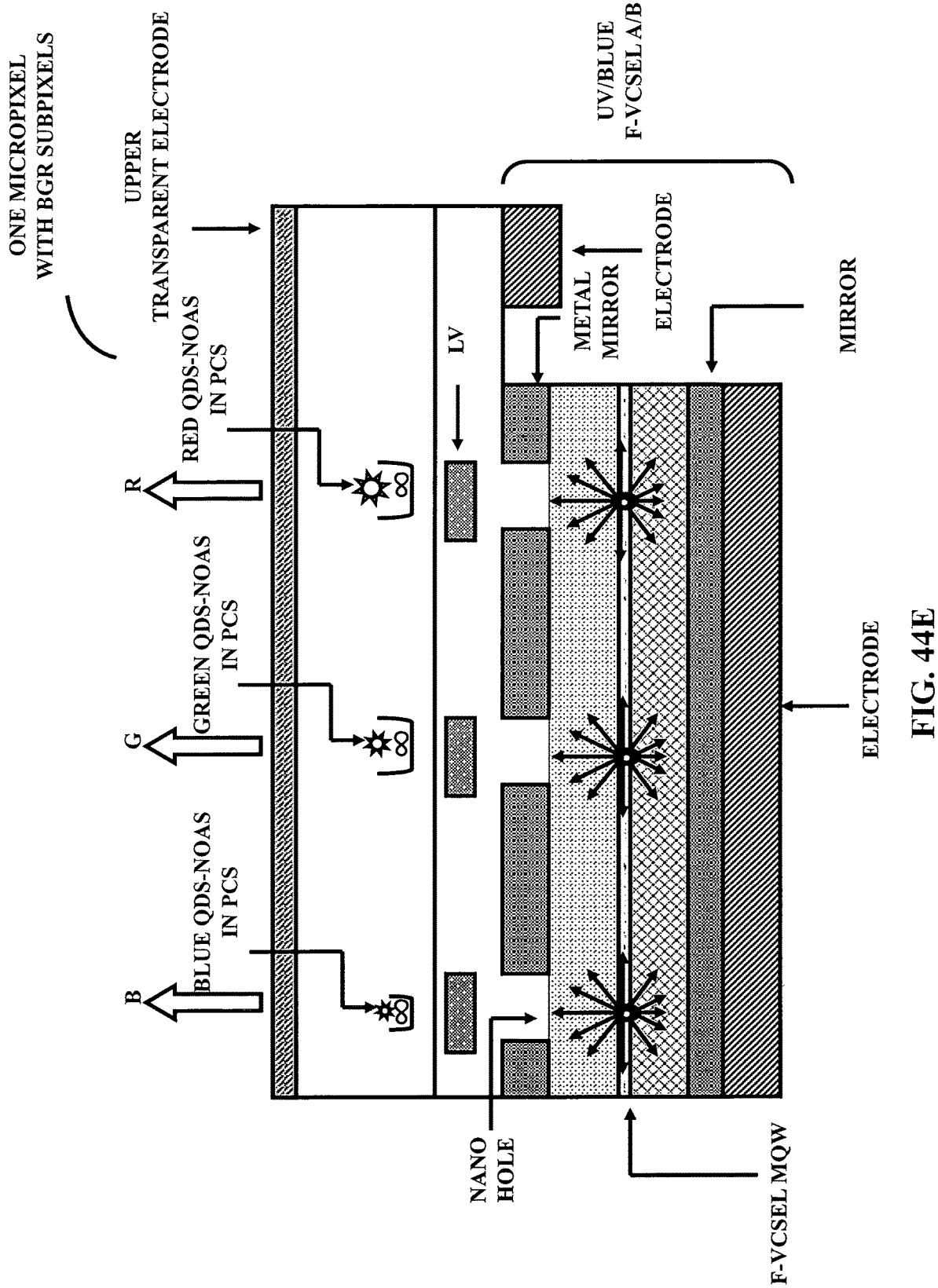

FIG. 44E illustrates one micropixel (with a blue submicropixel, a green submicropixel and a red submicropixel), enabled by frustrated vertical cavity surface emitting lasers A/B, light valves, blue quantum dots-protruded metal/non-metal nano optical antennas in photonic crystals, green quantum dots-protruded metal/non-metal nano optical antennas in photonic crystals and red quantum dots-protruded metal/non-metal nano optical antennas in photonic crystals.

Figure 44F:
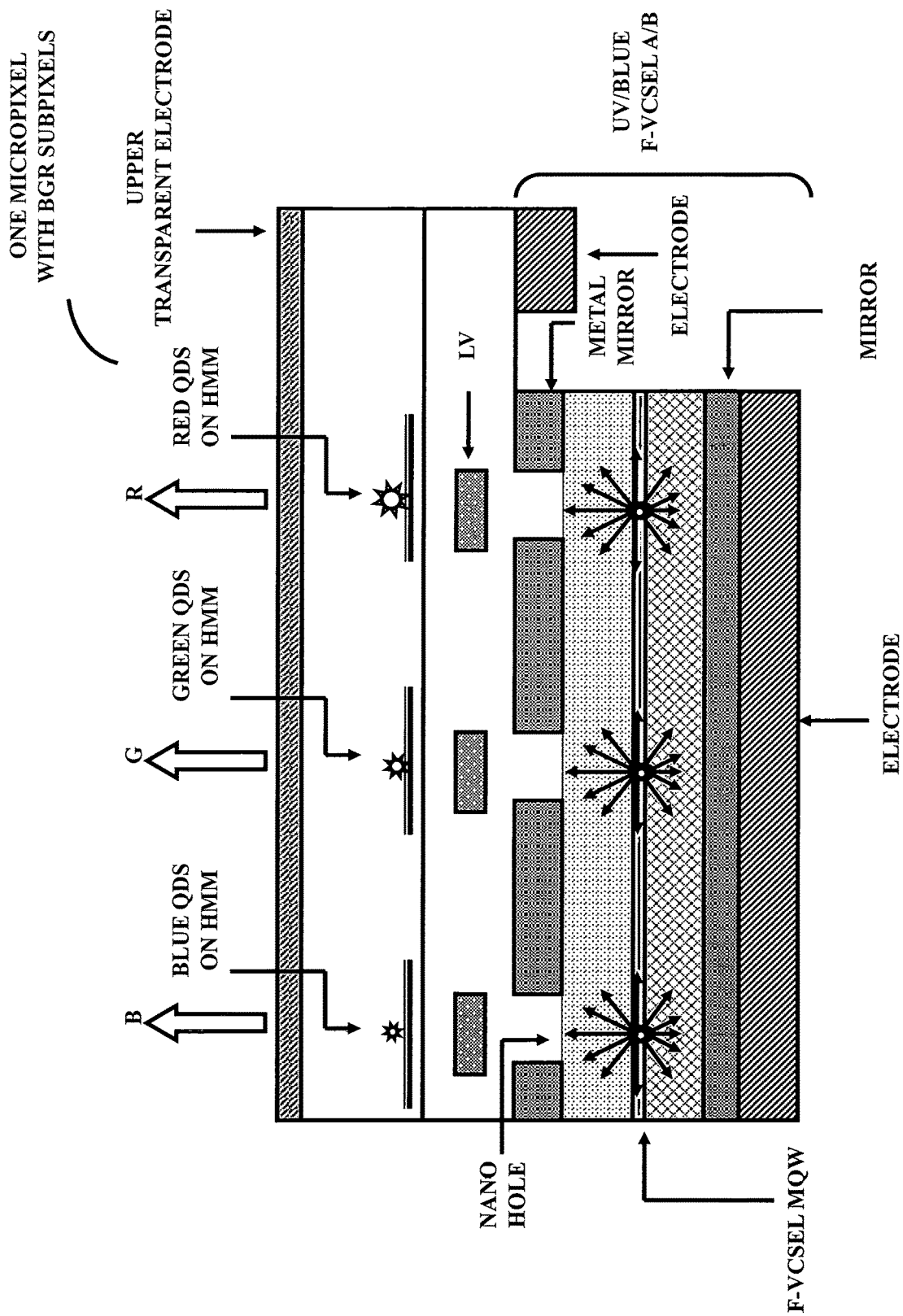

FIG. 44F illustrates one pixel (with a blue subpixel, a green subpixel and a red subpixel), enabled by frustrated vertical cavity surface emitting lasers A/B, light valves, blue quantum dots on a hyperbolic metamaterial, green quantum dots on a hyperbolic metamaterial and red quantum dots on a hyperbolic metamaterial.

Figure 44G:
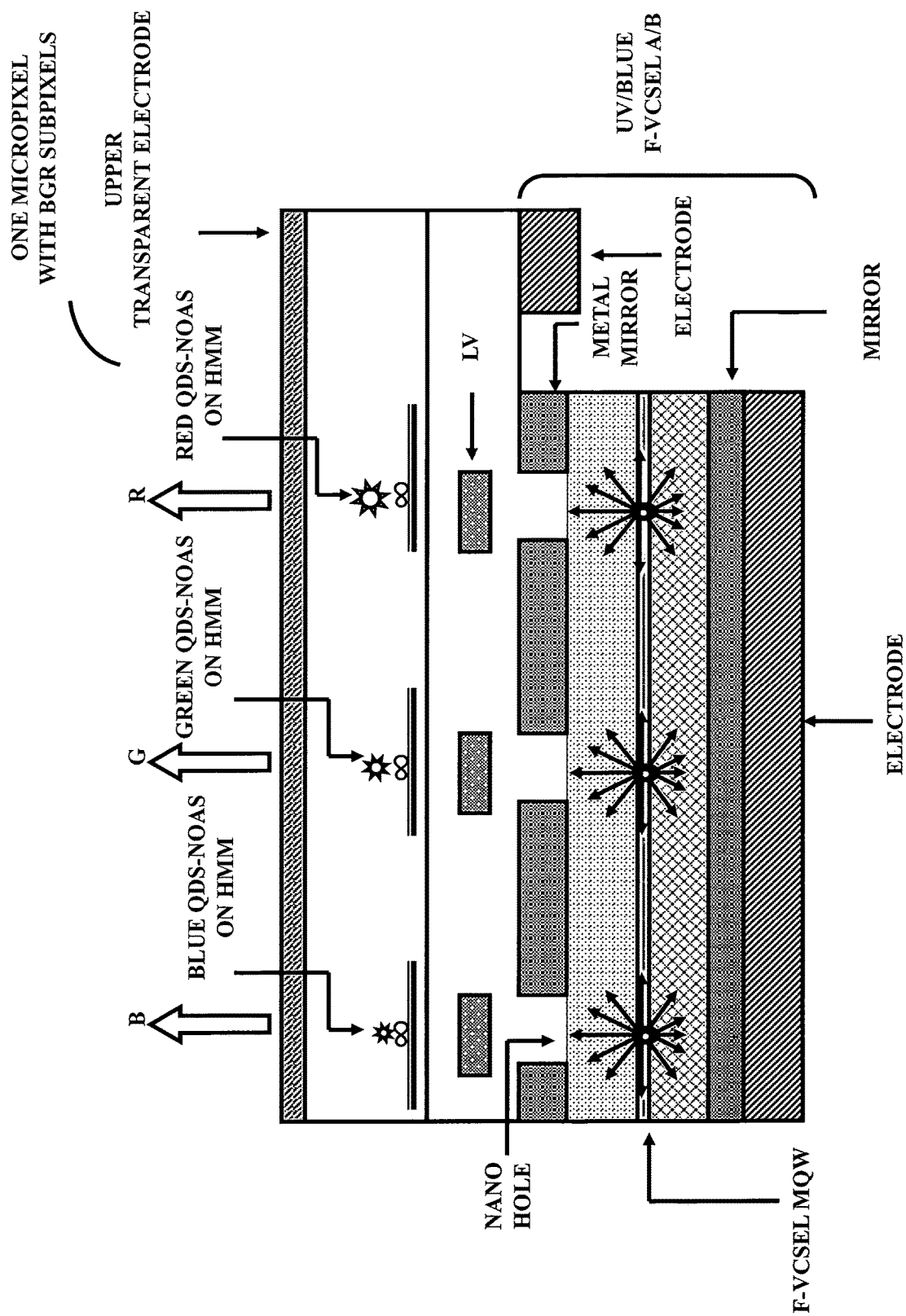

FIG. 44G illustrates one pixel (with a blue subpixel, a green subpixel and a red subpixel), enabled by frustrated vertical cavity surface emitting lasers A/B, light valves, blue quantum dots-protruded metal/non-metal nano optical antennas on a hyperbolic metamaterial, green quantum dots-protruded metal/non-metal nano optical antennas on a hyperbolic metamaterial and red quantum dots-protruded metal/non-metal nano optical antennas on a hyperbolic metamaterial.

Figure 44H:
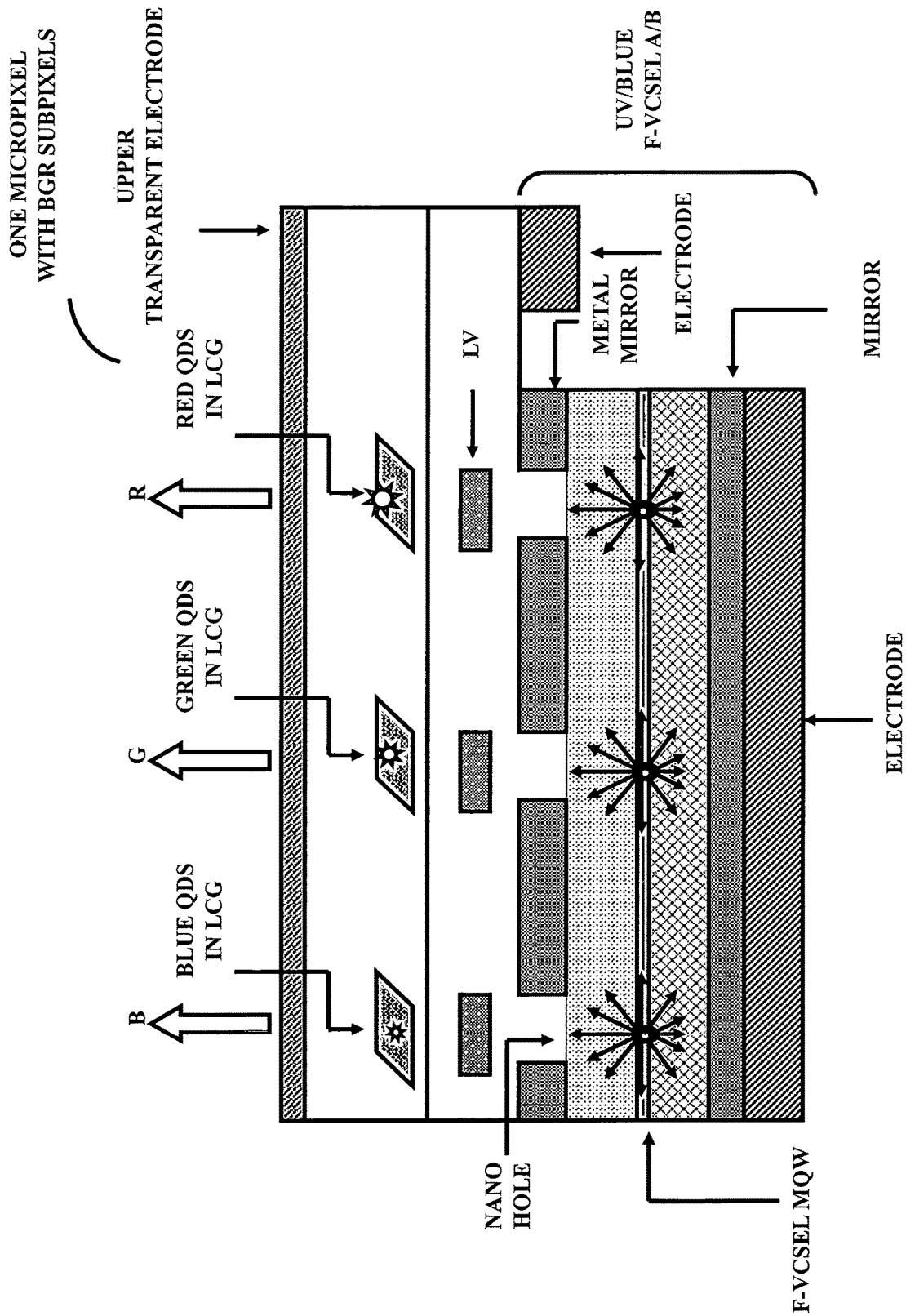

FIG. 44H illustrates one micropixel (with a blue submicropixel, a green submicropixel and a red submicropixel), enabled by frustrated vertical cavity surface emitting lasers A/B, light valves, blue quantum dots in the electrically switchable liquid crystal gel, green quantum dots in the electrically switchable liquid crystal gel and red quantum dots in the electrically switchable liquid crystal gel.

FIG. 45 illustrates two-dimensional arrays of micropixels B, wherein one micropixel B has a blue subpixel, a green subpixel and a red subpixel. The micropixel B can be realized with quantum dots and frustrated vertical cavity surface emitting lasers A/B.

FIG. 46A illustrates a micropixel. Blue quantum dots, green quantum dots and red quantum dots are excited by a stack of light emitting semiconductor layers (epitaxial lifted-off and bonded onto a thin glass substrate).

FIG. 46B is similar to 46A, except blue quantum dots are in a photonic crystal, green quantum dots are in a photonic crystal and red quantum dots are in a photonic crystal.

Figures 46C, 46D:
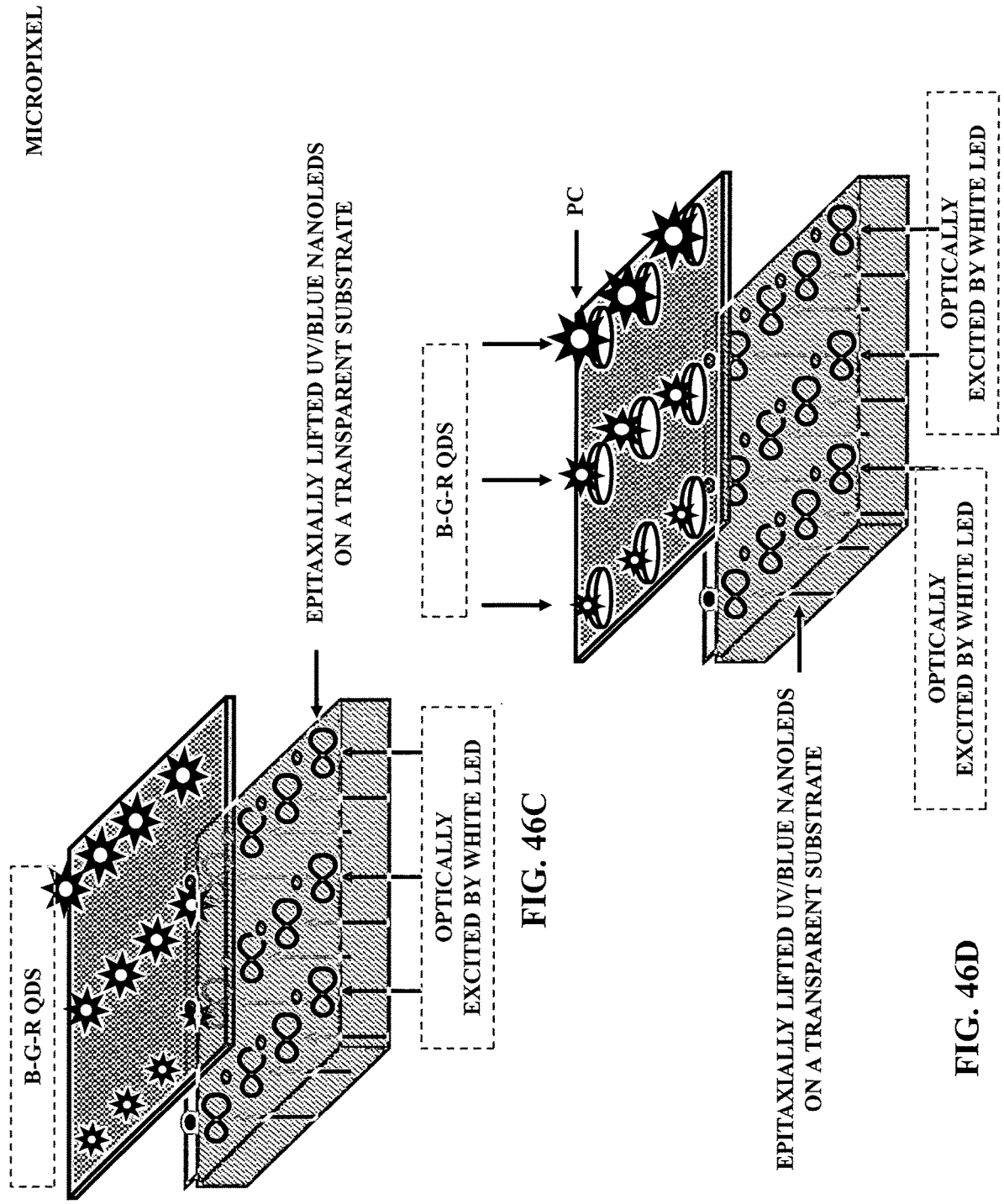

FIG. 46C is similar to FIG. 46A, except blue quantum dots, green quantum dots and red quantum dots are excited by UV/blue nanolightemitting diodes (which are epitaxially lifted from its native semiconductor substrate to a transparent substrate (e.g., glass)).

FIG. 46D is similar to 46C, except blue quantum dots are in a photonic crystal, green quantum dots are in a photonic crystal and red quantum dots are in a photonic crystal.

A UV/blue nanolightemitting diode can be realized by fabricating/constructing (e.g., utilizing electron beam lithography and reactive ion etching) a nanoscaled (e.g., 40 nm in diameter) pillar of a UV/blue light emitting material near or in the gap of the protruded metal/non-metal nano optical antenna. The nanoscaled UV/blue light emitting material can be based on quantum wells or quantum dots.

An ammonium hydroxide dip, followed by $(NH4)_2S_x$ and KrF pulsed laser (at a low intensity) treatments or alternatively, argon/nitrogen ion beam treatment on the walls of a nanoscaled disc, then deposition of about 2 nm of silicon/amorphous silicon/hydrogenated amorphous silicon/zinc selenide and 20 nm of aluminum oxide under vacuum can reduce surface defects. The ion beam energy, the ion beam density, the ion beam exposure time and the composition of the background gas mixture are critical in argon/nitrogen ion beam treatment. Typically, the entire passivation process can be performed under ultrahigh vacuum to reduce any possibility of surface oxidation prior to passivation. Alternatively, regrowth of passivation material (e.g., semi-insulating indium phosphide) around the nanoscaled disc can reduce surface defects. Similarly, this process step/regrowth step can be applied to mirrors (facets)—at least to the exit mirror (facet) of any high power edge emitting laser to reduce catastrophic optical mirror (facet) damage (COMD).

Furthermore, photonic crystals light collection optics can be fabricated/constructed on the exit output surface of the nanoscaled disc for high (light output) extraction efficiency.

Fabrication/construction of the nanolight-emitting diode can be realized as follows: (1) growth of material, (2) electron beam lithography and reactive ion etching of an array of nanoscaled discs, (3) removal of surface oxides on the walls of the nanoscaled discs, (4) selective regrowth of passivation material around the nanoscaled discs, utilizing a dielectric mask, (5) removal of the dielectric mask and (6) precision electron beam lithography and reactive ion etching of protruded metal/non-metal nano optical antenna.

FIG. 47A illustrates a micropixel, utilizing electron emissions from selected (utilizing row and column electrodes) sharp microtips and phosphor layers. The emission from the phosphor layer is controlled by a light valve.

FIG. 47B is similar to 46A, except nanotubes replace sharp microtips.

FIG. 48A illustrates a cross section of an integrated device, which includes an array of micropixels B and cameras (e.g., complementary metal oxide semiconductor image sensors)/phototransistors—further co-packaged/monolithically integrated with the Super System on Chip 400A/400B. An array of microlenses is on top of the array of micropixels and cameras/phototransistors.

The above integration of the Super System on Chip is 400D, which can enable the camera to store and process information simultaneously and it is capable of learning/relearning for self-intelligence, sensor-awareness, context-awareness and autonomous actions, remembering the patterns and movements.

FIG. 48B illustrates a front view of FIG. 48A.

FIG. 49 illustrates a three-dimensional/holographic display 340, utilizing a two-dimensional array of micropixels A/B and an array of microlenses. The three-dimensional/holographic display 340 can be fabricated/constructed in transparent synthetic spinel (magnesium aluminate) instead of glass.

The array of microlenses can be an array of ultrathin flat microlenses (e.g., graphene on glass). The ultrathin flat microlens can be distortion free.

FIG. 50A illustrates a microprojector, enabled by an electrically switchable light valve and a micro (nano) mechanical system based scanning mirror. Blue, green and red photonic crystals light collection optics vertical cavity surface emitting lasers (VCSEL-PCO) are flip-chip mounted within v-grooves in silica on silicon substrate.

The photonic crystals light collection optics vertical cavity surface emitting lasers are rapidly switched to mix a color spectrum by a phase change/phase transition material based light valve. The outputs of the light valve are multiplexed by a focusing slab waveguide and then focused to a micro (nano) mechanical system based scanning mirror by a (about 45-degree angle) deflecting mirror to enable a microprojector.

Any light valve can be utilized instead of the phase change/phase transition material based light valve.

FIG. 50B illustrates guiding of light output from the photonic crystals light collection optics integrated with vertical cavity surface emitting laser into a waveguide. Light from photonic crystals light collection optics integrated with vertical cavity surface emitting lasers is collimated by a microlens and then focused by an about 45-degrees angle mirror.

FIG. 50C illustrates electronics (in block diagram) to drive the microprojector. Outputs of a video processor are inputs to laser driver(s) of the blue/green/red photonic crystals light collection optics vertical cavity surface emitting lasers. Light from photonic crystals light collection optics integrated with vertical cavity surface emitting lasers are collimated, transmitted through the phase change/phase transition material light valve (to control their respective intensities) and then multiplexed by an optical multiplexer. The multiplexed light is incident on the micro(nano)-electro-mechanical systems (M(N)EMS) scanning mirror, which is controlled by a driver. The driver receives input from the video processor.

Figure 51A:
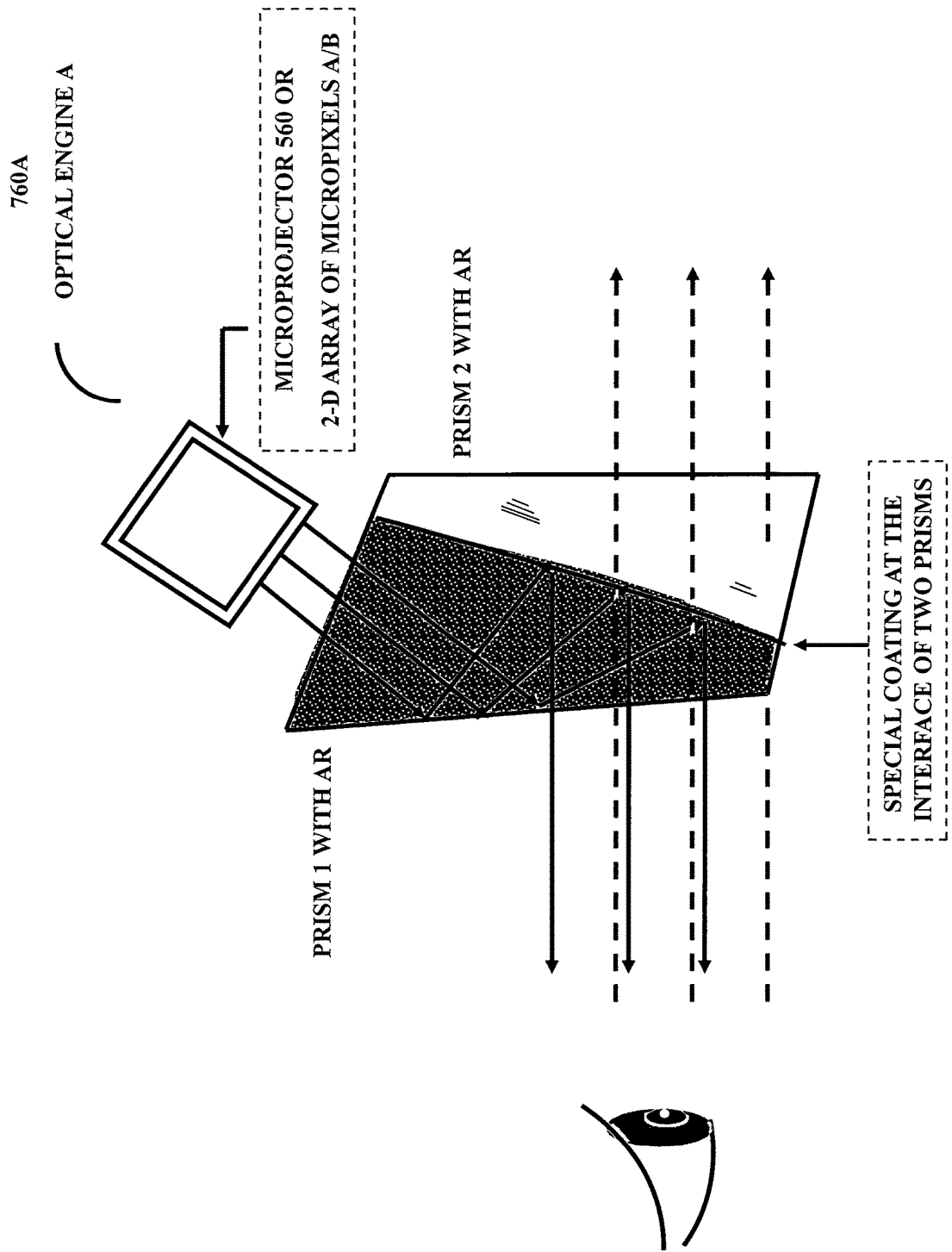

FIG. 51A illustrates an optical engine A, 760A receiving input from the microprojector 560/two-dimensional array of micropixels A/two-dimensional array of micropixels B. The optical engine A, 760A includes two specially shaped prisms. The interface between the two prisms has a thin-film coating to enable reflection of a device/computer generated image and view real events through one eye. The front side of prism 1 and prism 2 can be antireflection (AR) coated.

Figure 51B:
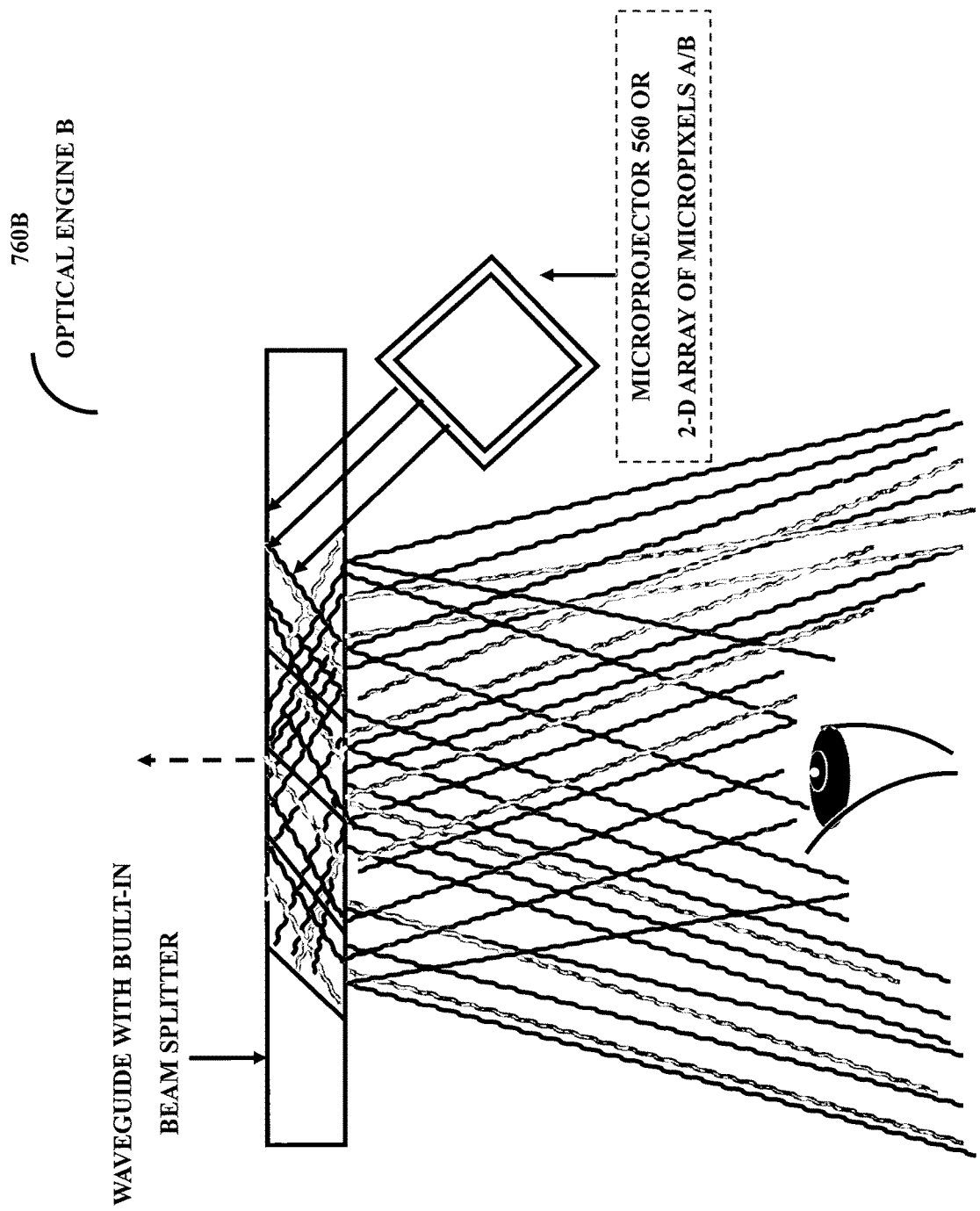

FIG. 51B illustrates another optical engine B, 760B receiving inputs from the microprojector 560/two-dimensional array of micropixels A/two-dimensional array of micropixels B. The optical engine B, 760B includes a waveguide with built-in beam splitter.

Figure 51C:
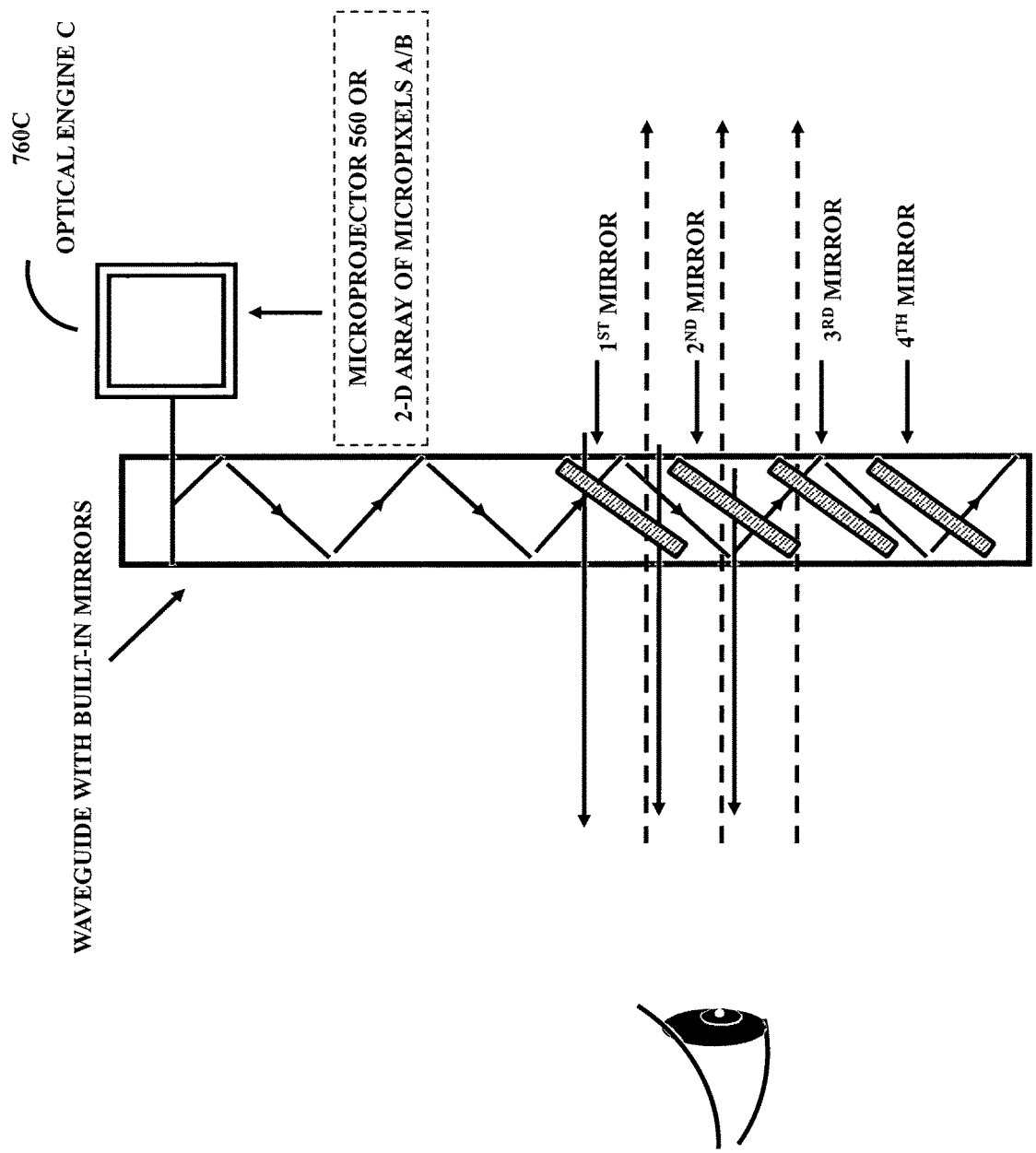

FIG. 51C illustrates another optical engine C, 760C receiving inputs from the microprojector 560/two-dimensional array of micropixels A/two-dimensional array of micropixels B. The optical engine C, 760C includes a waveguide with built-in mirrors.

Figure 51D:
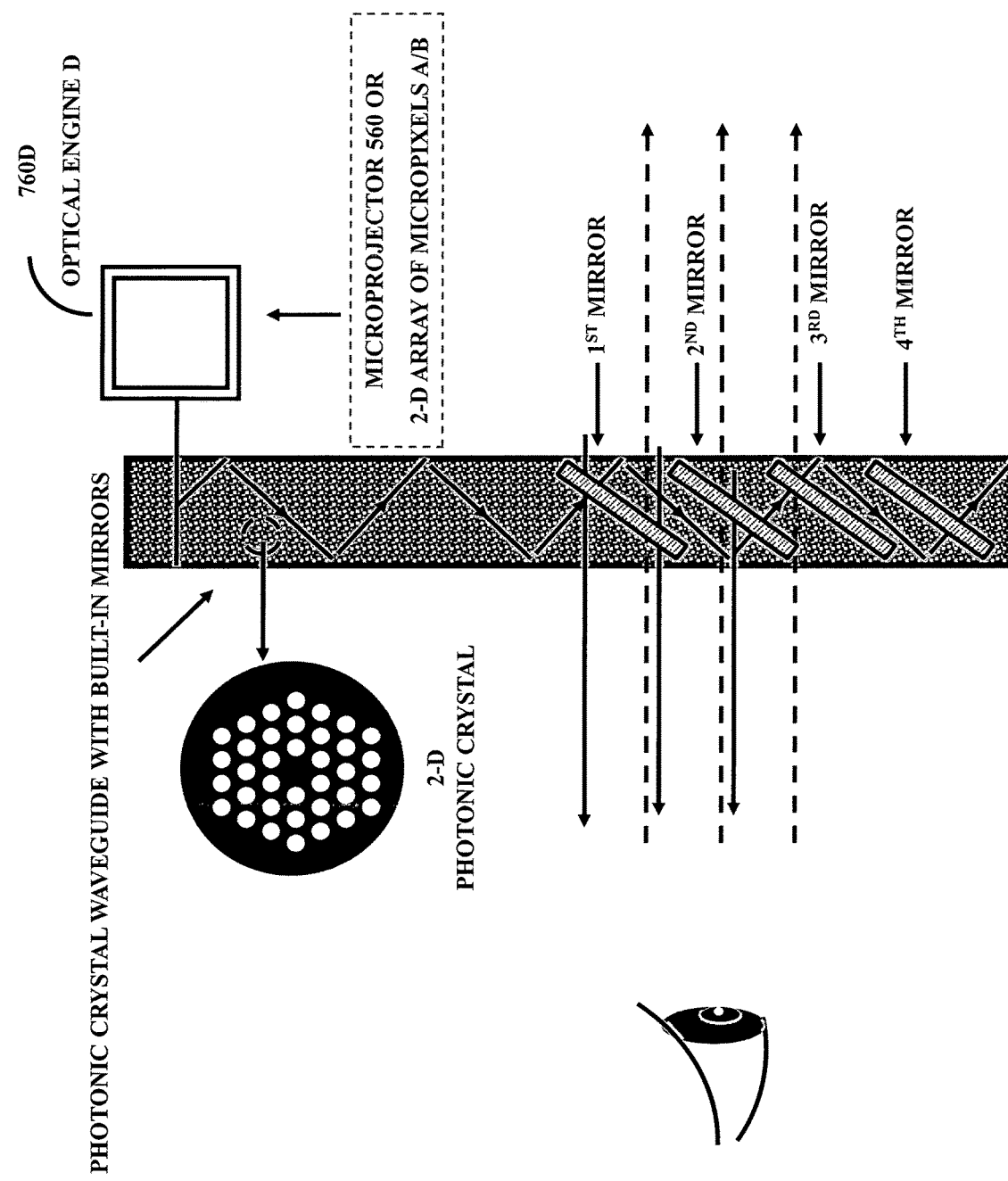

FIG. 51D illustrates another optical engine D, 760D receiving inputs from the microprojector 560/two-dimensional array of micropixels A/two-dimensional array of micropixels B. The optical engine D, 760D includes a two-dimensional photonic crystal (can be fabricated/constructed by nanoimprint lithography) waveguide with built-in mirrors.

The grey area indicates waveguide material (e.g., glass) and the white circles are about 2 to 5 microns diameter air holes in the two-dimensional photonic crystal.

Figure 52A:
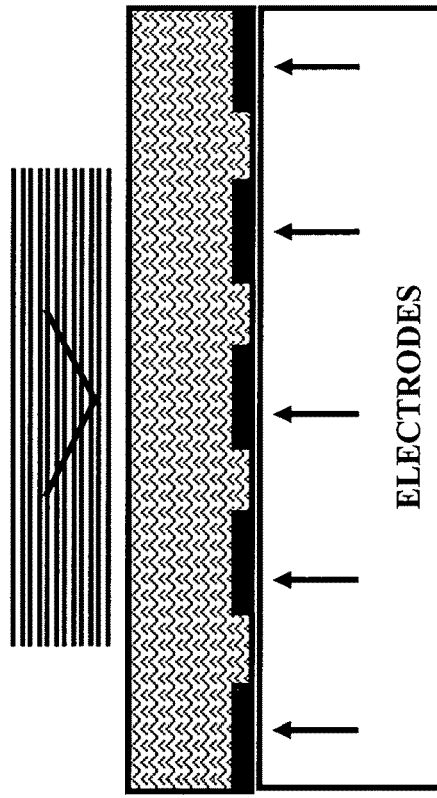
Figure 52B:
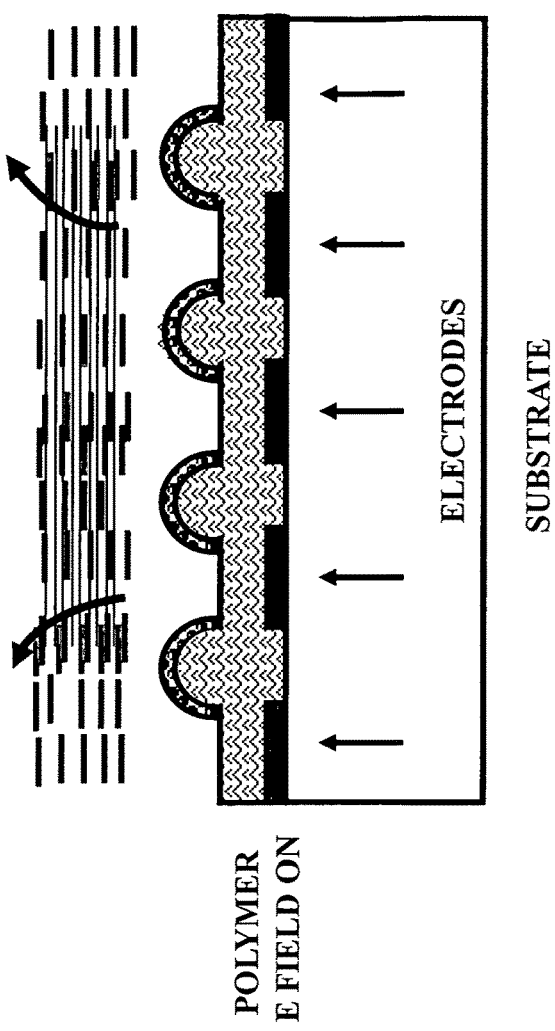

A spatial light modulator is a device that enables spatially varying modulation on a beam of light. FIGS. 52A-52B illustrate a high resolution electrically induced spatial light modulator utilizing about 15 microns thick poly(vinylidene fluoride-trifluoroethylenechlorofluoroethylene)ter polymer film on a transparent substrate.

FIG. 52A illustrates a flat mirror shape of the polymer film without the electric field.

FIG. 52B illustrates a grating(s) shape of the polymer film with the electric field (about 100 volts per micron thickness), as the polymer film shrinks.

Each electrode is about 5 microns in width. The gap between two electrodes is about 15 microns.

Another suitable electro-optic polymer can be utilized instead of poly(vinylidene fluoride-trifluoroethylenechlorofluoroethylene)ter polymer.

Figure 52C:
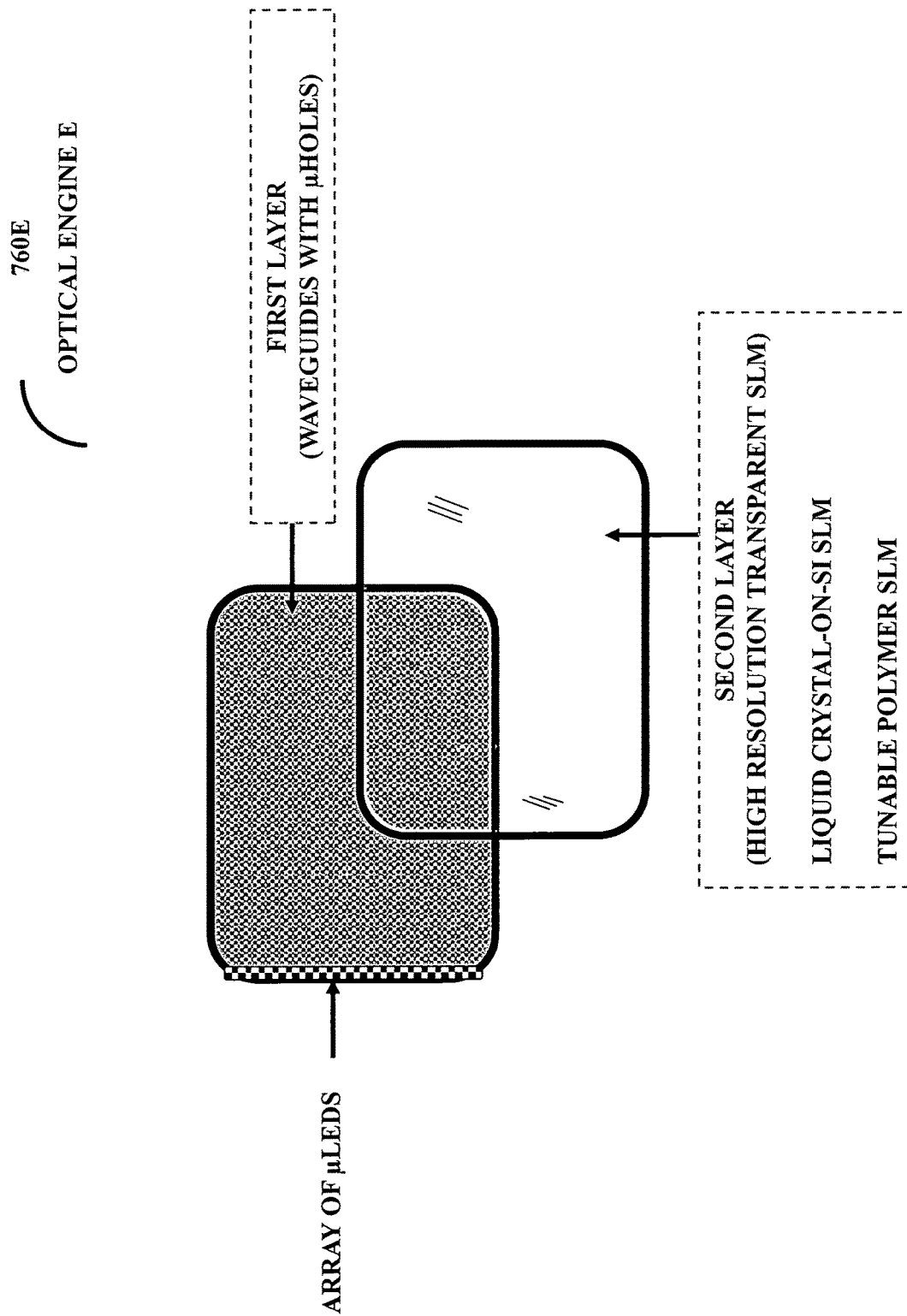

FIG. 52C illustrates another optical engine E, 760E. The optical engine E, 760E includes a first layer with built-in waveguides with microholes and a second layer with a high resolution spatial light modulator (e.g., based on liquid crystal on silicon on insulator (LC-SOI)/electrically activated tunable polymer). The side edge of the first layer is illuminated by an array of microlight emitting diodes, as illustrated previously.

Figure 52D:
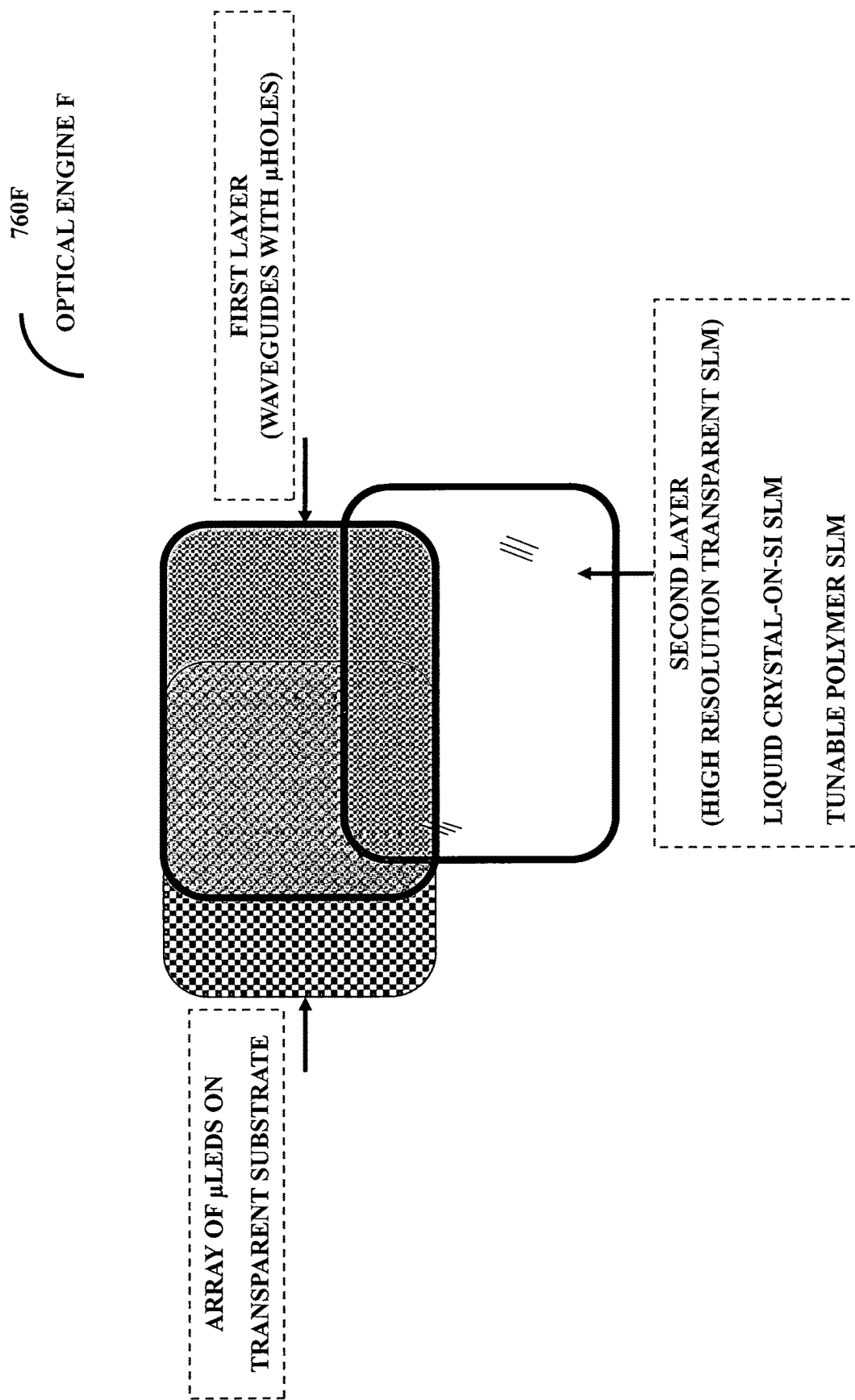

FIG. 52D illustrates another optical engine F, 760F. The optical engine F, 760F includes a first layer with built-in waveguides with microholes and a second layer with a high resolution spatial light modulator. The first layer is directly illuminated by an array of microlight emitting diodes on a transparent substrate.

Augmented reality refers to what a user can perceive through his/her biological senses (e.g., viewing) and the user's perception can be enhanced with device/computer generated input data (e.g., images, sound and video). Augmented reality makes more information available to the user by combining device/computer generated input data to what the user experiences (or views). For example, the user can find a nearby café with the menu of the café translated from a local language to the user's own native language by augmented reality enabled enhancement.

FIG. 53 illustrates an intelligent wearable augmented reality personal assistant device 180, which includes a multichip module system 740, an optical engine 760A/B/C/D/E/F and an eye tracking sensor.

The eye tracking sensor includes an infrared light source and two cameras. The infrared light reflects off the pupil and cornea and the reflections are captured by the two cameras and then processed by an image processing algorithm.

The key components of the multichip module system 740 (in block diagram) are listed below in Table 3.

The intelligent wearable augmented reality personal assistant device 180 can include a wearable electrical power providing patch.

Details of the wearable electrical power providing patch have been described/disclosed in U.S. non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

The front facing high resolution camera-500 and/or the back facing high resolution camera-520 can be coupled with the Super System on Chip 400A/400B/400C/400D and/or the artificial eye.

The Super System on Chip 400A/400B/400C/400D and/or the artificial eye can be coupled with a computer vision algorithm and/or an artificial intelligence algorithm and/or an artificial neural network algorithm and/or a machine learning (including deep learning/meta-learning and self-learning) algorithm and/or a fuzzy logic (including neuro-fuzzy) algorithm for ultrafast data processing, image processing/recognition, deep learning/meta-learning and self-learning.

Thus, enabling a four-dimensional effect on an image captured by image captured by the front facing high resolution camera-500 and/or the back facing high resolution camera-520 of the intelligent wearable augmented reality personal assistant device 180. Thus, enabling a four-dimensional effect (e.g., not only what the front facing high resolution camera-500 and/or the back facing high resolution camera-520 can see, but also how a character/player/event can experience) on an image captured by the front facing high resolution camera-500 and/or the back facing high resolution camera-520 of the intelligent wearable augmented reality personal assistant device 180.

TABLE 3

| Component | Description |
| --- | --- |
| 380 | Communication Radio* (WiMa/LTE) |
| 400A/B/C/D | Super System On Chip (Can Be Coupled With An Artificial Eye) |
| 420 | Operating System Algorithm |
| 440 | Security & Authentication Algorithm |
| 480 | Surround Sound Microphone |
| 500 | Front Facing High Resolution Camera @ Low Light Level (Can Be Coupled With An Artificial Eye) |
| 520 | Back Facing High Resolution Camera @ Low Light Level (Can Be Coupled With An Artificial Eye) |
| 540 | High Resolution Camcorder @ Low Light Level (Can Be Coupled With An Artificial Eye) |
| 580 | Proximity Radio* (Near Field Communication/Bluetooth LE) TxRx |
| 600 | Personal Area Networking Radio 1* (Bluetooth/Wi-Fi) TxRx |
| 620 | Personal Area Networking Radio 2* (Ultrawide Band/Millimeter-Wave) TxRx |
| 640 | Positioning System (Global Positioning System* & Indoor Positioning System) |
| 660 | Universal Communication Interface |
| 700 | Electrical Powering Device (Solar Cell + Battery + Ultracapacitor) With Wireless Charging Option. For Example, Lithium-Ion Battery's Cobalt Oxide Cathode Can Be Coated With Graphene Nanoparticles Or The Cathode Can Be Replaced By Vanadium Disulfide ($VS_2$) Flakes-Which Are Nanoscaled Coated With Titanium Disulfide ($TiS_2$) |

[*With Radio Specific Antenna] [TxRx Means Transceiver]

A universal communication interface can integrate animation, animated GIF, drawings, emotions, gestures (hand/eye), location data, text, voices, voice snippets and videos.

The universal communication interface can be further enhanced by "Fazila" as described in FIG. 10A The intelligent wearable augmented reality personal assistant device 180 is sensor-aware and/or context-aware; as it is wirelessly connected/sensor connected with objects 120A, object nodes 120, bioobjects 120Bs and bioobject nodes 140s.

FIG. 54A represents a generic biomarker binder, which can be an antibody/aptamer/molecular beacon.

FIG. 54B represents a generic biomarker binder chemically coupled with a fluorophore (e.g., a quantum dot fluorophore).

FIG. 54C is similar to FIG. 54B, except the fluorophore (which is coupled with a biomarker binder) is near or within a protruded metal/non-metal nano optical antenna.

FIG. 55A illustrates a disposable diagnostic chip 1. This has an inlet for a drop of blood, an array of capillaries to separate and propagate serum from the blood toward the end of the disposable diagnostic chip 1, where disease specific biomarker binders coupled with fluorophores are embedded. When disease specific biomarkers from the serum chemically bind with biomarker binders, then the disposable diagnostic chip 1 can fluoresce.

Alternatively, gold nanoparticles decorated with disease specific oligonucleotides (or microRNA specific locked nucleic acids (LNAs)) can be embedded in the disposable diagnostic chip 1. When the disease specific oligonucleotides (or microRNA specific locked nucleic acids) recognize complementary disease specific deoxyribonucleic acid/ribonucleic acid strands (including microRNAs) and upon hybridization, color (by chemiluminescence) of the disposable chip 1 can change (which can be detected by a naked eye/spectrophotometer).

Metal (e.g., gold) nanoparticles can also bind with cancer deoxyribonucleic acids-enabling a new blood based test for circulating cancers by detecting a change of color. Furthermore, a substrate including metal nanoparticles of a particular (suitable) shape and particular (suitable) thickness in an ordered array with a particular (suitable) periodicity can emit light of lower wavelength, when excited by light of higher wavelength. If biomolecules bind to the surface of said metal nanoparticles, then intensity of the emitted light of lower wavelength and/or the particular wavelength of the emitted light can change-enabling detection of biomolecules (e.g., cancer deoxyribonucleic acids).

The Recombinase Polymerase Amplification can operate over a convenient temperature range (about 37° C.-42° C.) and it is rapid (10-20 min) and insensitive to temperature variations of about ±1° C. The Recombinase Polymerase Amplification (RPA) (integrating a joule heating element/micro Peltier element on the disposable diagnostic chip 1) can be utilized to amplify of the disease specific deoxyribonucleic acid/ribonucleic acid strands (including microRNAs).

Additionally, a reporter probe (that releases a fluorescent signal when physically separated) can be integrated/chemically coupled with the disease specific deoxyribonucleic acid/ribonucleic acid strands (including microRNAs). In presence of CRISPR-Cas12 (for a single-stranded deoxyribonucleic acid) and CRISPR-Cas13 (for ribonucleic acid), CRISPR-Cas12/CRISPR-Cas13 goes beyond cutting the original deoxyribonucleic acid/ribonucleic acid target respectively and releases enhanced non-specific chemiluminescence signal by cutting other deoxyribonucleic acid/ribonucleic acid respectively. Thus, it can enable rapid diagnostics of a disease (e.g., malaria).

As an alternative or addition to enzyme based amplification, fluorescence amplification can be regarded an effective strategy in bioassay. The integration of plasmonic nanoparticles (e.g., ZnSe—COOH or lanthanide ($Ln^{3+}$) nanoparticles) in proximity of the gold nanoparticles can also significantly enhance photoluminescence.

In case of ZnSe—COOH nanoparticles, the localized surface plasmon resonance (SPR) of gold nanoparticles, the ultraviolet-visible absorption spectrum of gold nanoparticles overlapped with the emission spectrum of ZnSe—COOH nanoparticles-thus generating resonant energy transfer (RET) between gold nanoparticles and ZnSe—COOH nanoparticles.

FIG. 55B illustrates a disposable diagnostic chip 2. FIG. 55B is similar to FIG. 55A, except the fluorophore (coupled with a biomarker binder) is near or within the protruded metal/non-metal nano optical antenna to enhance fluorescence. Within the protruded metal/non-metal nano optical antenna, one or more dielectric (e.g., silica/polymer) nanowires can be fabricated, wherein each dielectric nanowire can be coated with antibodies against a particular type of diseased cells to capture the particular type of diseased cells efficiently. Alternatively, the protruded metal/non-metal nano optical antenna(s) can be replaced by metal nanoparticle(s).

The disposable diagnostic chip 1/disposable diagnostic chip 2 can be fabricated/constructed on a polymer/paper substrate.

FIG. 55C illustrates a measurement system, which has an insertion socket (for the disposable diagnostic chip 1/disposable diagnostic chip 2). The measurement system can detect fluorescence by an ultrasensitive light detector (e.g., indium gallium arsenide avalanche photodiode/charge coupled device/complementary metal oxide semiconductor) when the biomarker binders-biomarkers section is excited by a light source (e.g., a light emitting diode/laser). The measurement system can connect (wired or wirelessly) with the intelligent portable internet appliance 160.

FIG. 56A illustrates an exterior view of a wearable personal health assistant device. This is a computing device with a micro-USB port, a microphone (for voice command) and a proximity radio transceiver and an integrated sensing device for continuous bio data (e.g., (a) body temperature, (b) pulse rate, (c) % oxygen saturation and (d) blood sugar level) recording and reminder. A two-wavelength reflection pulse oximetry can be utilized to measure % oxygen saturation. The wearable personal health assistant device can include a microphone, a proximity radio transceiver (Tx-Rx) module, a wrap-around display and a removable storage device (e.g., a micro USB) encrypting all personal medical data. The encrypted personal medical data is coupled with a public/consortium/private blockchain.

The wearable personal health assistant device can also include a first active/passive patch with spiropyran to detect/treat blood sugar. The first active/passive patch can include polymeric nanoshells encapsulating insulin or long-acting insulin, wherein polymeric nanoshells disintegrate under light activation, after the read-out notification of blood sugar utilizing the first active/passive patch with spiropyran. The wearable personal health assistant device can also include a second patch (e.g., of silicone/hydrogel) with flexible metal wires—producing ultrasound waves to detect blood pressure and other biological/health parameters in a noninvasive manner. The second patch second patch with flexible metal wires—producing ultrasound waves to detect blood pressure can be replaced by capacitive micromachined ultrasonic transducers.

The wearable personal health assistant device can be coupled with an implanted device (e.g., in FIGS. 3B and 3C of Non-Provisional patent application Ser. No. 13/448,378 entitled "SYSTEM AND METHOD FOR INTELLIGENT SOCIAL COMMERCE", filed on Apr. 16, 2012 (U.S. Pat. No. 9,697,556, issued on Jul. 4, 2017) and/or a bio-implanted/bio-indigested energy-efficient microscaled computer.

The bio-implanted/bio-indigested energy-efficient microscaled computer can include a photovoltaic cell, which can be electrically charged/powered by an external infrared illumining beam. The bio-implanted/bio-indigested energy-efficient microscaled computer can also include a microscaled neural processor consisting of memristors.

The bio-implanted/bio-indigested energy-efficient microscaled computer can also include a bidirectional long-range antenna (for example a near field communication antenna) transmitting through flesh and skin.

The wearable personal health assistant device can be integrated with a pulse oximeter, an insertion socket (for the disposable diagnostic chip 1/disposable diagnostic chip 2), an ultrasensitive light detector (for fluorescence measurement), a wearable diagnostic device A and a wearable diagnostic device B.

The wearable personal health assistant device can be electrically coupled with a patch with spiropyran, passive patch, active patch, sensor and LifeSoC. An alarm can remind the user about potential mistakes/conflicts.

Furthermore, the wearable personal health assistant device can be electromagnetically coupled with a patch containing liposomes. Each liposome can encapsulate bioactive molecules/drugs (e.g., insulin/metformin) and magnetic nanoparticles. Upon heating by a high frequency and low intensity magnetic field, the liposome can undergo a phase change from solid to liquid—thus releasing the bioactive molecules/drugs at a time t=0. But, when the high frequency and low intensity magnetic field is turned off, the lipids re-solidify due to reverse phase change, preventing any release of the bioactive molecules/drugs at a time t=t.

Figure 56C:
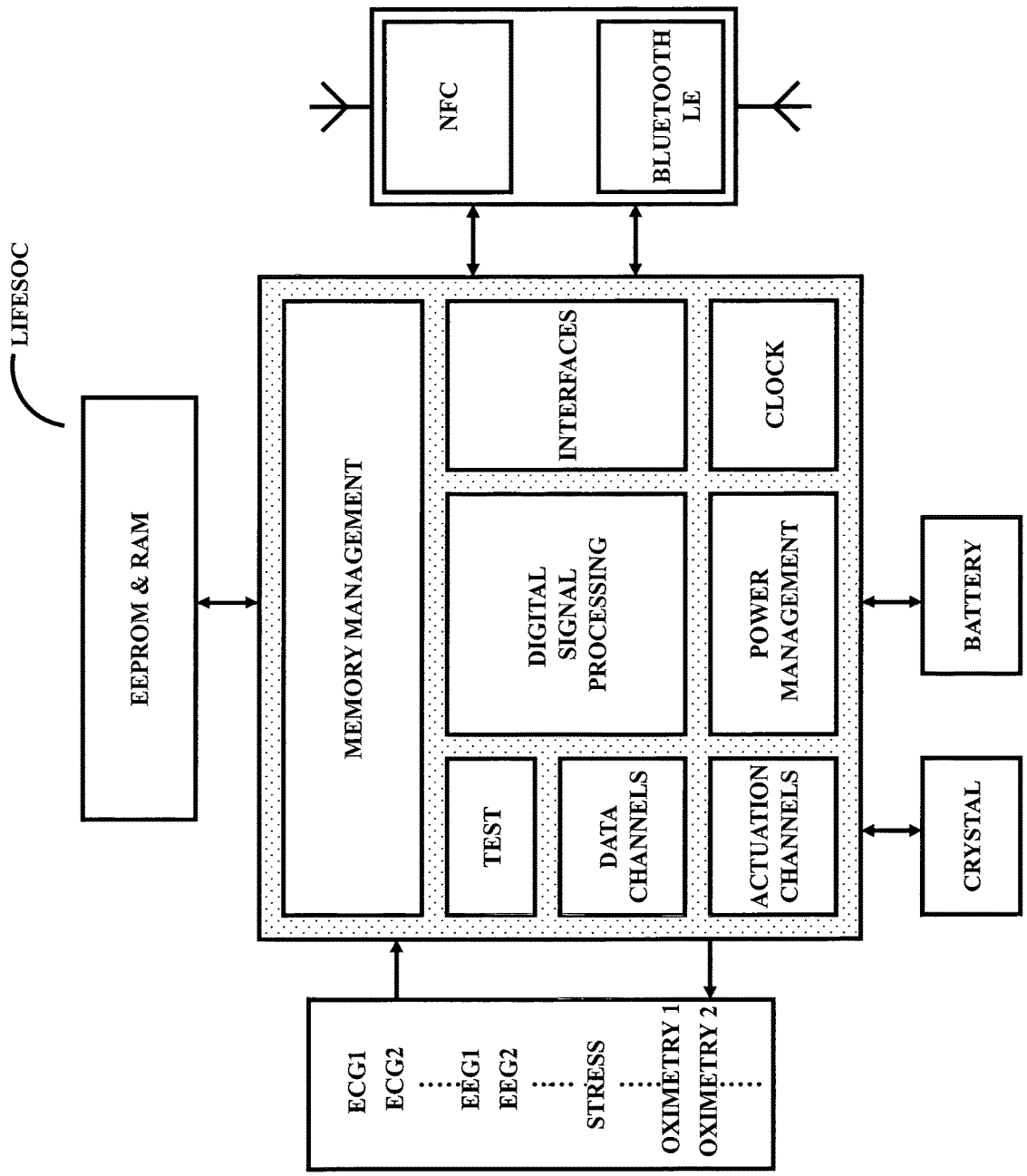
Figure 56D:
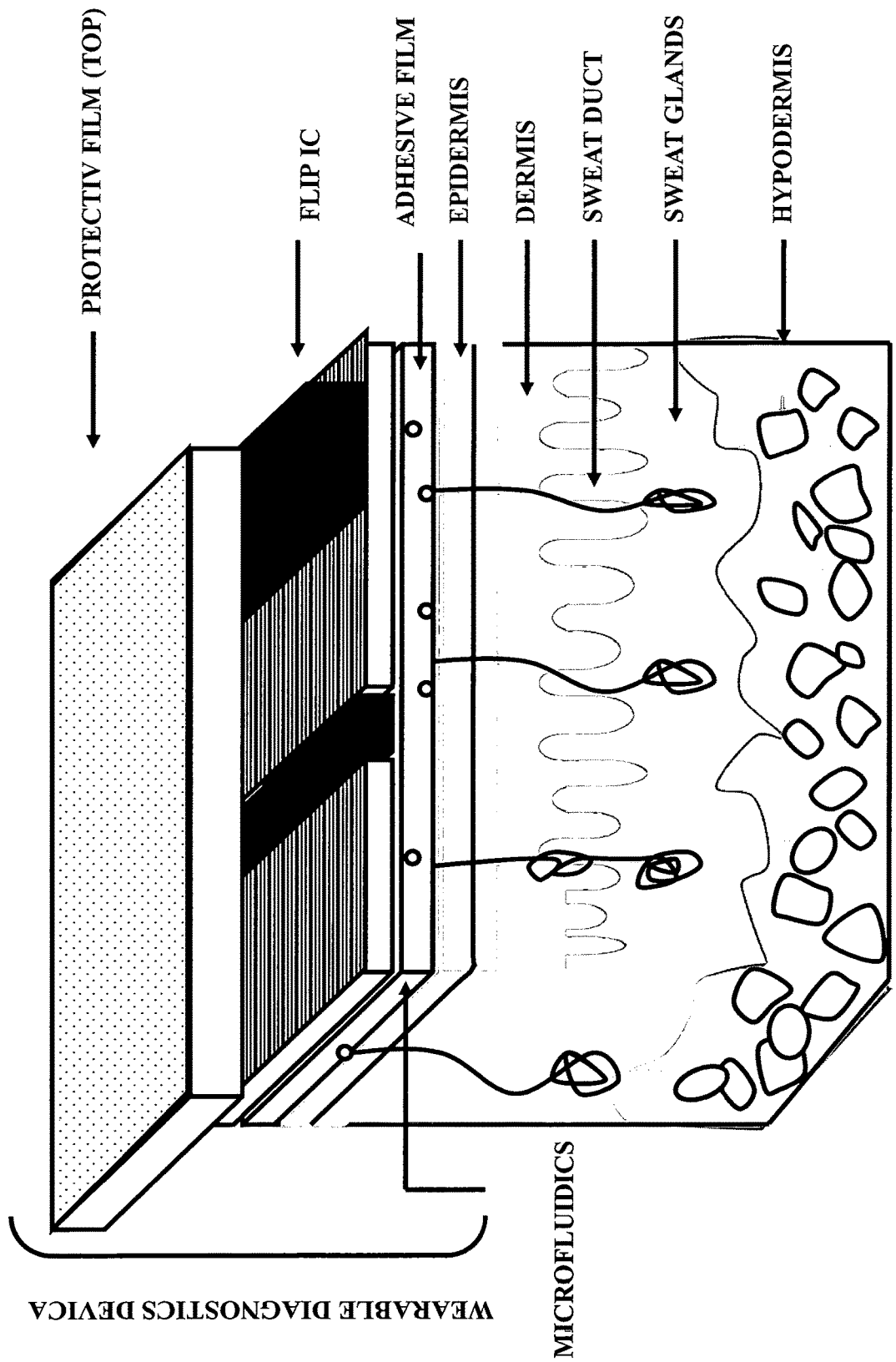
Figure 56H:
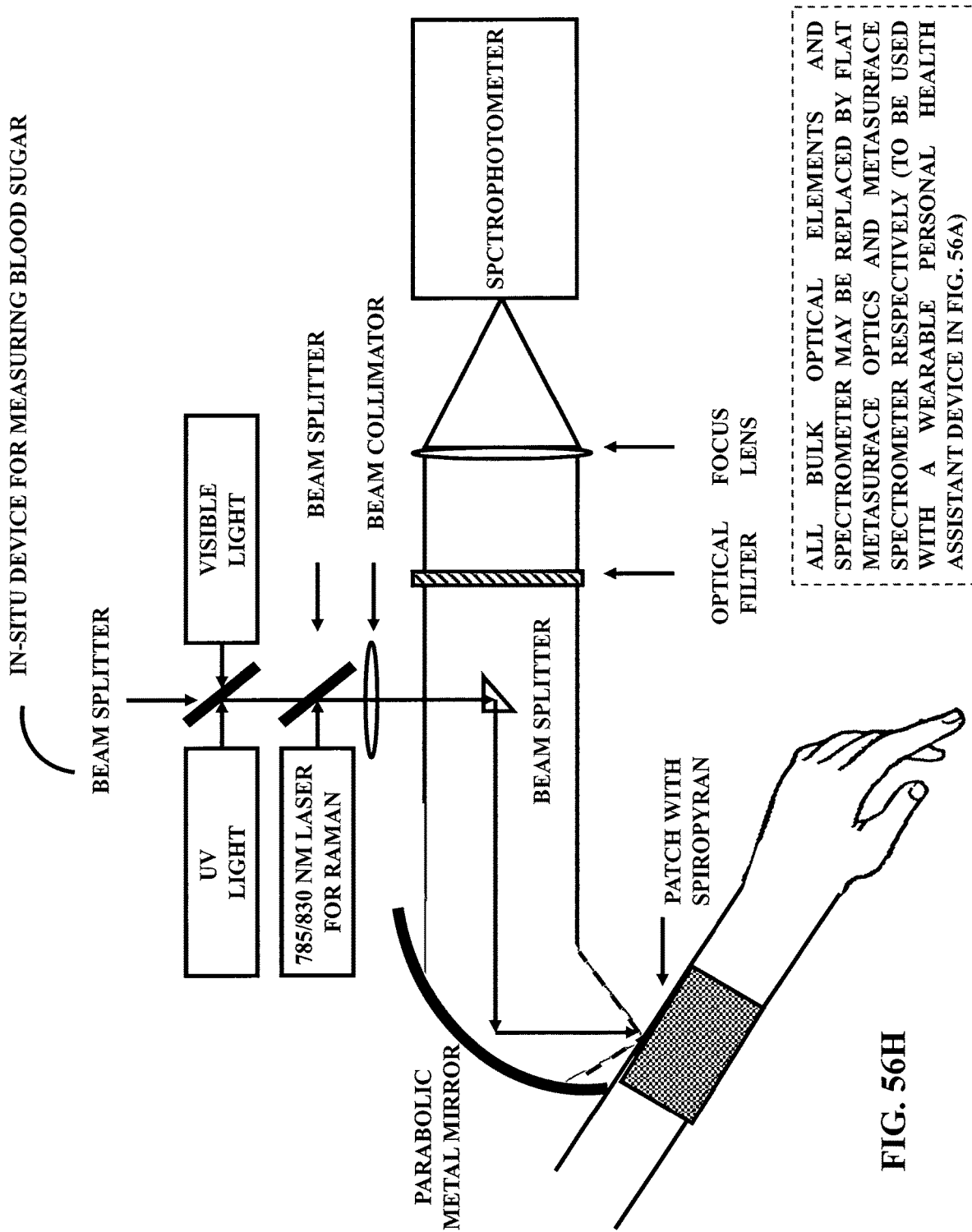

Furthermore, the high frequency and low intensity magnetic field can be turned on/off by a signal from a sensor to detect a particular disease (e.g., blood sugar measurement by the diagnostic device in FIG. 56H or the disposable surface acoustic wave (SAW) chip).

The wearable personal health assistant device can be integrated with a disposable surface acoustic wave chip, which can be decorated/functionalized with disease specific biomarker binders for biomarker. Upon biomarker-biomarker binder coupling on the surface acoustic wave chip, change in shear horizontal-surface acoustic wave (SH-SAW) can be measured to detect a disease.

The wearable personal health assistant device can be integrated with disposable field effect (nanowire) transistors to monitor binding in a completely label free bioassay. For example, peptide nucleic acid (PNA) functionalized silicon nanowires can be incubated with complementary microRNAs (targets) and changes in the resistivity of the silicon nanowires is monitored before and after the binding events. Peptide nucleic acid is deoxyribonucleic acid analogue in which the deoxyribose and phosphate backbone is replaced by a peptide bonding motif.

Details of the field effect (nanowire) transistor have been described/disclosed in U.S. non-provisional patent application Ser. No. 15/731,577 entitled "BIOMODULE TO DETECT A DISEASE AT AN EARLY ONSET", filed on Jul. 3, 2017 and in its related U.S. non-provisional patent applications (with all benefit provisional patent applications) are incorporated in its entirety herein with this application.

The wearable personal health assistant device can be integrated with disposable indium oxide ($In_2O_3$) nanoribbon field effect transistors with gold side gate and electrodes decorated/functionalized with (a) an enzyme glucose oxidase, (b) a natural chitosan film and (c) single-walled carbon nanotubes. When glucose is present in sweat, it interacts with enzyme glucose oxidase-thus setting off a short chain of reactions and generating an electrical signal.

Alternatively, the wearable personal health assistant device can be integrated with disposable organic transistors containing a biomarker binder (e.g., glutathione (GSH)). When the organic transistors coupled/integrated with the biomarker binder is exposed to a biomarker (e.g., glutathione S-transferase (GST) associated with Alzheimer's, breast cancer and Parkinson's) creating a chemical reaction detected by the organic transistors.

Furthermore, the wearable personal health assistant device can be integrated with a disposable organic electrochemical transistors (OECTs) based biosensor decorated with an enzyme, wherein the enzyme is selectively sensitive to either cholesterol or glucose or uric acid.

Alternatively, the high density solid state storage device of the wearable personal health assistant device can be electrically coupled/integrated with a disposable complementary metal oxide semiconductor-electronic integrated circuit (CMOS-EIC), wherein aluminum (Al) metallization layers of the complementary metal oxide semiconductor-electronic integrated circuit wafer are encapsulated by silicon dioxide ($SiO_2$)-planarized and then passivated by a layer of silicon nitride (SiNx) to reduce moisture/humidity related corrosion on aluminum metallization layers. Via holes are etched down to aluminum metallization layers. The complementary metal oxide semiconductor-electronic integrated circuit is coated with titanium/titanium nitride (Ti/TiN) barrier layer. Then via holes are filled with CVD tungsten (W). Tungsten is reactive ion etched back up to tungsten barrier layer. Then tungsten barrier layer is removed by reactive ion etching. A metal layer (e.g., titanium/platinum/gold (Ti/Pt/Au) with gold metallization on top) is lifted off only on tungsten.

The top metal layer provides a surface for immobilization/functionlization of biomarker binders (e.g., single stranded deoxyribonucleic acid and/or deoxyribonucleic acid origami based probe molecules (integrated with an antibody) or locked nucleic acid based probes). Furthermore, the top metal layer can be nanostructured (e.g., about 5 to 25 nm surface roughness) to enhance coupling of the biomarker binders-biomarkers.

It should be noted that microRNAs have a high degree of similarity between the sequences. Some microRNAs vary by a single nucleotide. Locked nucleic acid can be used to enhance the discriminatory power (of the primers and/or probes) to enable excellent discrimination of closely related microRNAs sequences. Locked nucleic acid offers significant improvement in sensitivity and specificity. MicroRNAs are pivotal regulators of cellular processes and cancer biomarkers. Among many methods, electrochemical biosensor has advantages, such as low-cost, small-size, simplicity of construction, ease of use, high sensitivity and selectivity of microRNAs. Their rapid detection at about 1 fM concentration detection limit is possible by Electrochemical Impedance Spectroscopy (EIS) at the electrode/electrolyte interface, (using positively charged gold nanoparticles coupled with disease specific microRNAs/deoxyribonucleic acids) or redox marker(s) or coupling base stacking technology with enzymatic amplification.

The structure of locked nucleic acid is given below. The ribose ring is connected by a methylene bridge between the 2'-O and 4'-C atoms thus, locking the ribose ring in the ideal conformation for Watson-Crick binding. When incorporated into deoxyribonucleic acid/ribonucleic acid oligonucleotide, locked nucleic acids makes the pairing with a complementary nucleotide strand with speed and stability of the resulting duplex.

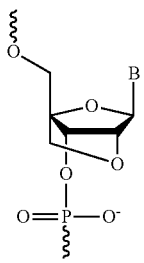

Structure Of Locked Nucleic Acid

The top metal layer can be integrated/included with an electrochemical probe (e.g., $[Ru(NH_3)_6]^{3+}$).

Furthermore, the top metal layer can be integrated/included with (a) a joule heating element/micro Peltier element for the Recombinase Polymerase Amplification and (b) an agent for the Recombinase Polymerase Amplification.

Additionally, the Recombinase Polymerase Amplification can be modified by using electroactive/electrochemical active sequence-specific probes to increase the sensitivity electrical signals from the electrochemical probe, upon the biomarker binder-biomarker (a biomarker(s) in plasma/serum) binding. By altering the Recombinase Polymerase Amplification reagent (e.g., a different primer to target a different nucleotide sequence) various applications are possible.

Furthermore, an addition of a lysis agent (e.g., guanidinium thiocyanate) on the metal layer can enable use of a biomarker(s) in whole blood, without the need of plasma or serum.

Upon the biomarker binder-biomarker binding and amplification, the amplified electrical signals from the electrochemical probe can be detected by the complementary metal oxide semiconductor-electronic integrated circuit. Furthermore, the disposable complementary metal oxide semiconductor-electronic integrated circuit wafer can be replaced by a disposable wafer of silicon-germanium, if cost is not an issue.

Furthermore, the disposable complementary metal oxide semiconductor-electronic integrated circuit based diagnostic device can be a standalone diagnostic device.

Alternatively, a biocompatible substrate (e.g., quartz) with an array of avidin molecules, wherein each avidin molecule is chemically coupled with a biotin molecule, wherein each biotin molecule is chemically coupled with a particularly suitable length poly(ethylene glycol) (PEG) strand, wherein each poly(ethylene glycol) is chemically coupled with a hairpin shaped molecular beacon (MB) or a hairpin shaped locked molecular beacon (LMB) (incorporating locked nucleic acids, a fluorophore and a quencher). Alternatively, the biocompatible substrate can include an array of deoxyribonucleic acid origami based binding sites, utilizing a diamond-like carbon/trimethylsilyl manolayer as a foundation monolayer. The foundation monolayer can be processed into suitable binding sites by (a) electron beam lithography, (b) reactive ion etching, (c) oxygen plasma or ultraviolet-ozone exposure and (d) 100 mM $MgCl_2$ treatment.

Furthermore, binding sites can be preciously positioned utilizing the artificial zinc-finger proteins (ZFPs). Generally, the artificial zinc-finger proteins can bind to wide variety of deoxyribonucleic acid sequences. SNAP-tag is a self-labeling protein tag available in various expression vectors. The deoxyribonucleic acid-binding artificial zinc finger adaptor with SNAP-tag can enable site-selective and efficient assembly of target protein of interest.

Upon binding with a complementary biomarker target, the fluorophore and the quencher of the hairpin shaped molecular beacon or hairpin shaped locked molecular beacon are physically separated—creating an ON (fluorescence) state from a generally OFF (non-fluorescence) state.

Furthermore, to enhance the fluorescence signal, each avidin-biotin-poly(ethylene glycol)-hairpin shaped molecular beacon/hairpin shaped locked molecular beacon based molecular system (within a biosensing pixel) can be positioned horizontally relative to an open space of a three-dimensional protruded structure.

Additionally, the three-dimensional protruded structure can be integrated with a whispering gallery mode microscaled/nanoscaled resonator(s) with a pass-through waveguide for significantly higher detection sensitivity due to change in transmission wavelength (through the waveguide) when (a) the whispering gallery mode microscaled/nanoscaled resonator (e.g., circular shaped/disk shaped/toroidal shaped resonator) is functionalized with disease specific biomarker binders with respect to (b) upon disease specific biomarker binders-biomarkers binding. Furthermore, the whispering gallery mode microscaled/nanoscaled resonator(s) with a pass-through waveguide can be fabricated on a hyperbolic metamaterial surface (as illustrated for example, in FIG. 58D). A high Q microresonator (utilizing a high refractive-index material SiNx/barium titanate (BaTiO$_3$)) or many high Q microresonators in tandem or two-dimensional/three-dimensional photonic crystal) is critical to realize the ultra-high sensitivity. This configuration can enable label free detection of disease specific biomarkers, as opposed to labeled fluorescence signal.

Details of a three-dimensional protruded structure have been described/disclosed in U.S. non-provisional patent application Ser. No. 15/731,577 entitled "BIOMODULE TO DETECT A DISEASE AT AN EARLY ONSET", filed on Jul. 3, 2017 and in its related U.S. non-provisional patent applications (with all benefit provisional patent applications) are incorporated in its entirety herein with this application.

Additionally, each biosensing pixel can include one or more molecular systems.

Each biosensing pixel can be electro-optically coupled with a complementary metal oxide semiconductor image read-out pixel of a complementary metal oxide semiconductor imaging-electronic integrated circuit wafer.

As an example, co-packaged system (of biopixels and complementary metal oxide semiconductor imaging-electronic integrated circuits) can include the following steps-Separating/dicing of a single (complementary metal oxide semiconductor imaging-electronic integrated) die from a complementary metal oxide semiconductor imaging-electronic integrated circuit wafer (about 6 to 12 inches in diameter wafer). Mounting the above single die on another substrate. Passivating the active surface of the above single die. Patterning the active surface of the above single die into an array of optically transparent spots. Functionalizing each optically transparent spots with disease specific biomarker binders (e.g., hairpin shaped locked molecular beacons or molecular beacons). Washing/preparing surface, if needed. Attaching a removable optical excitation subsystem. Attaching a biofluidic container and/or a separate device to provide isolated specific microRNAs and/or attaching a nanohole based deoxyribonucleic acid sequencing device. It should be noted that the above following steps can be modified, if needed.

Details of a biofluidic container (to provide a biomarker fluid), a separate device (to provide isolated specific microRNAs from exosomes) and a nanohole based deoxyribonucleic acid sequencing device have been described/disclosed in U.S. non-provisional patent application Ser. No. 15/731,577 entitled "BIOMODULE TO DETECT A DISEASE AT AN EARLY ONSET", filed on Jul. 3, 2017 and in its related U.S. non-provisional patent applications (with all benefit provisional patent applications) are incorporated in its entirety herein with this application.

Alternatively, an electrical power can be wirelessly transmitted to a LED pixel and a glucose sensor (e.g., a graphene based glucose sensor) on the wearable personal health assistant device through an antenna on the wearable personal health assistant device. This electrical power can activate the LED pixel and the glucose sensor. The LED glows in the normal range of glucose condition. The LED turns off in the high level of glucose condition.

A hydrogel containing pluronic acid with genetically programmed living cells (e.g., genetically programmed bacteria), responding to respond to certain stimuli (molecules) can be utilized as three-dimensional printing ink for a disposable three-dimensional structure (e.g., a tattoo). The wearable personal health assistant device can be integrated with a disposable three-dimensional structure to sense variety of stimuli (molecules) on sweat on skin.

The key components of the wearable personal health assistant device are listed below:

---

Low Power Processor
Digital Memory
Operating System Algorithm
Wrap-around Display
High Density Solid State Data Storage
Microphone
Proximity Radio* (Near Field Communication/Bluetooth LE) TxRx
Universal Communication Interface
Electrical Powering Device (Solar Cell + Battery + Ultracapacitor)
Ultrasensitive Light Detector

---

A universal communication interface can integrate animation, animated GIF, drawings, emotions, gestures (hand/eye), location data, text, voices, voice snippets and videos.

The universal communication interface can be further enhanced by "Fazila" as described in FIG. 10A The micro-USB port can enable transfer of encrypted and public/consortium/private blockchain coupled personal health records, stored in the high density solid state storage device. The disposable diagnostic chip 1/disposable diagnostic chip 2 can be inserted into the insert socket for detection and analysis of fluorescence.

Figure 59B:
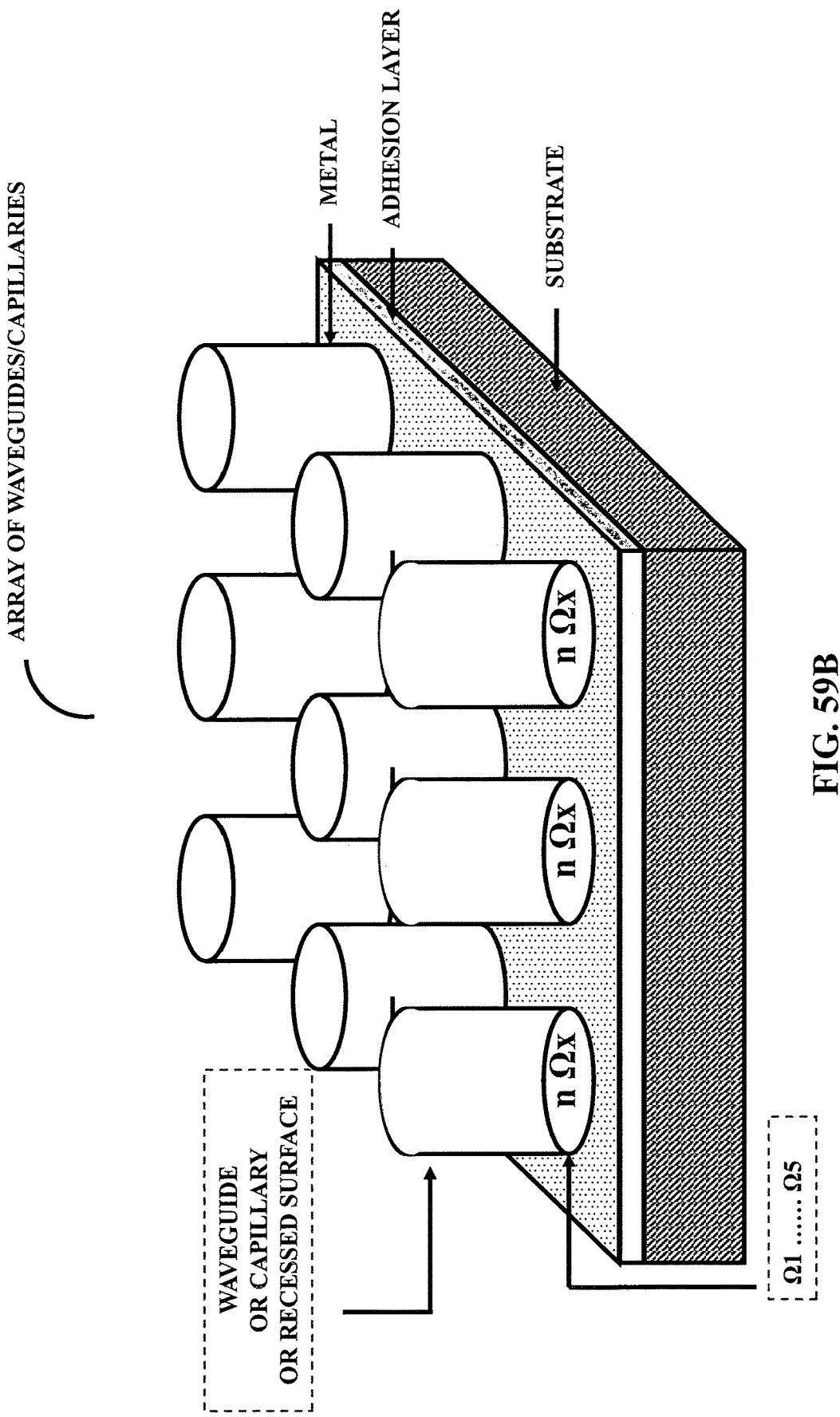

FIG. 59B illustrates an interior view of the device. A wrap-around display can be fabricated/constructed by utilizing organic light emitting diodes on a flexible substrate (e.g., DuPont Kapton) with wiring.

With wiring, a small electrical current can be applied to the skin, along with pilocarpine (drug) to induce the skin to sweat for analysis by a wearable diagnostic device A.

Details of a wearable diagnostic device A, wearable diagnostic device B, patch with spiropyran, passive patch and active patch will be described later.

An array of sensors can be fabricated/constructed at the edge of the flexible substrate.

The bioobject(s) 120B can be integrated with a LifeSoC, multichip module electronics to collect reliable signals from the bioobject(s) 120B. Details of LifeSoC are illustrated in FIG. 56C.

FIG. 56C illustrates a LifeSoC in block diagram. LifeSoC has digital signal processing, memory management and power management capabilities, as it is interfacing with various bio/health sensors (e.g., ECG, EEG, stress and oximetry), Bluetooth LE and near field communication. LifeSoC can be fabricated/constructed on a flexible/stretchable substrate.

Details of Life SoC have been described/disclosed in non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

Biomarkers contained in sweat can give indications about the physical state of the body. They include electrolytes (e.g., calcium, chloride, potassium and sodium), metabolites (creatinine, glucose, lactate and uric acid), proteins (interleukins, neuropeptides and tumor necrosis factor) and small molecules (amino acids, cortisol and DHEA).

FIG. 56D illustrates a wearable diagnostic device A on sweat networks on skin.

FIGS. 56E-56G illustrate details of the wearable diagnostic device A.

FIG. 56E illustrates a bottom adhesive film with microfluidic channels to wick sweat from human skin and the microfluidic channels are connected with an ultra absorbent sweat collector/reservoir. The ultra absorbent sweat collector/reservoir is electrically coupled with a flip-chip bonded chip to detect biomarkers in sweat.

Figure 56K:
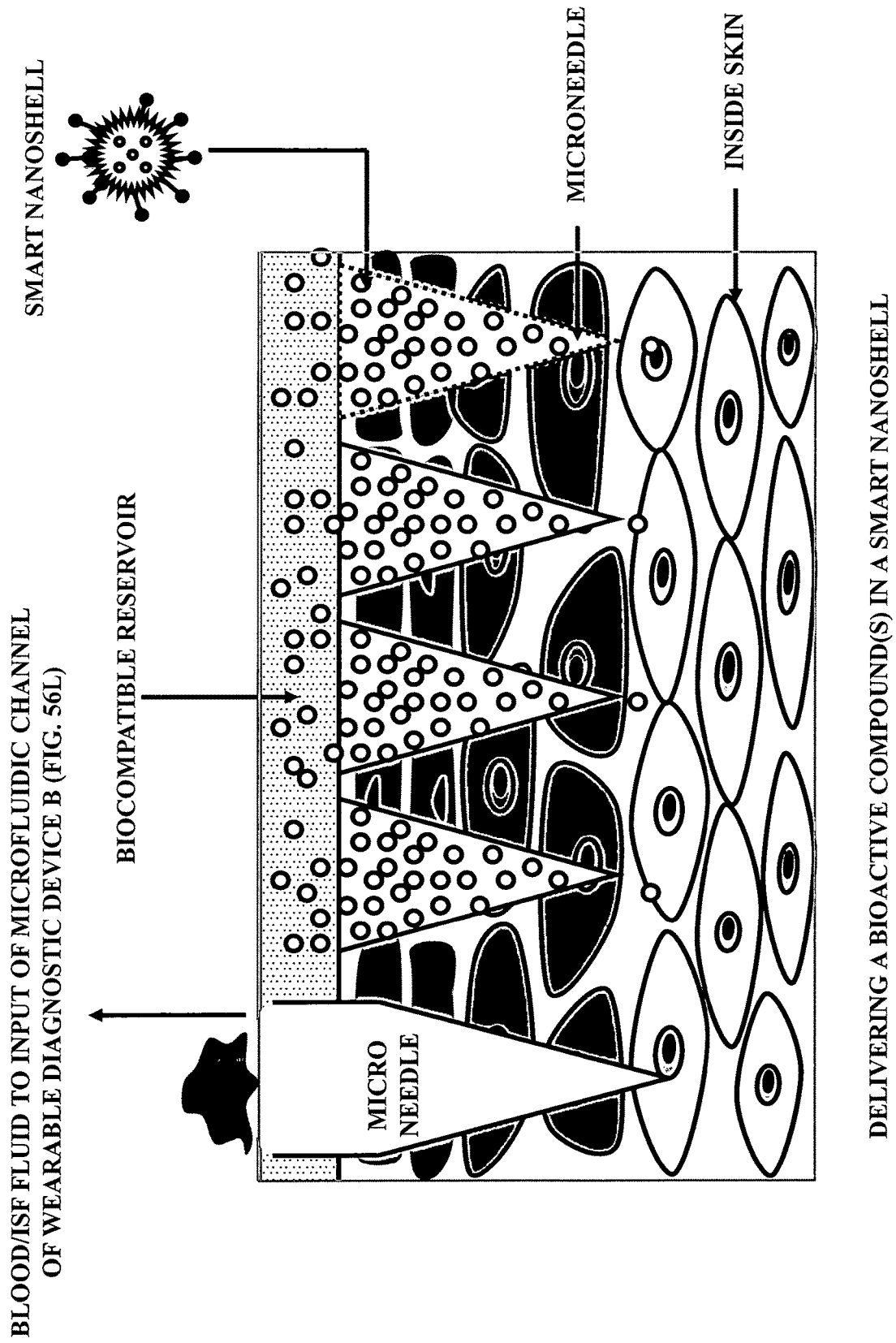
Figure 56L:
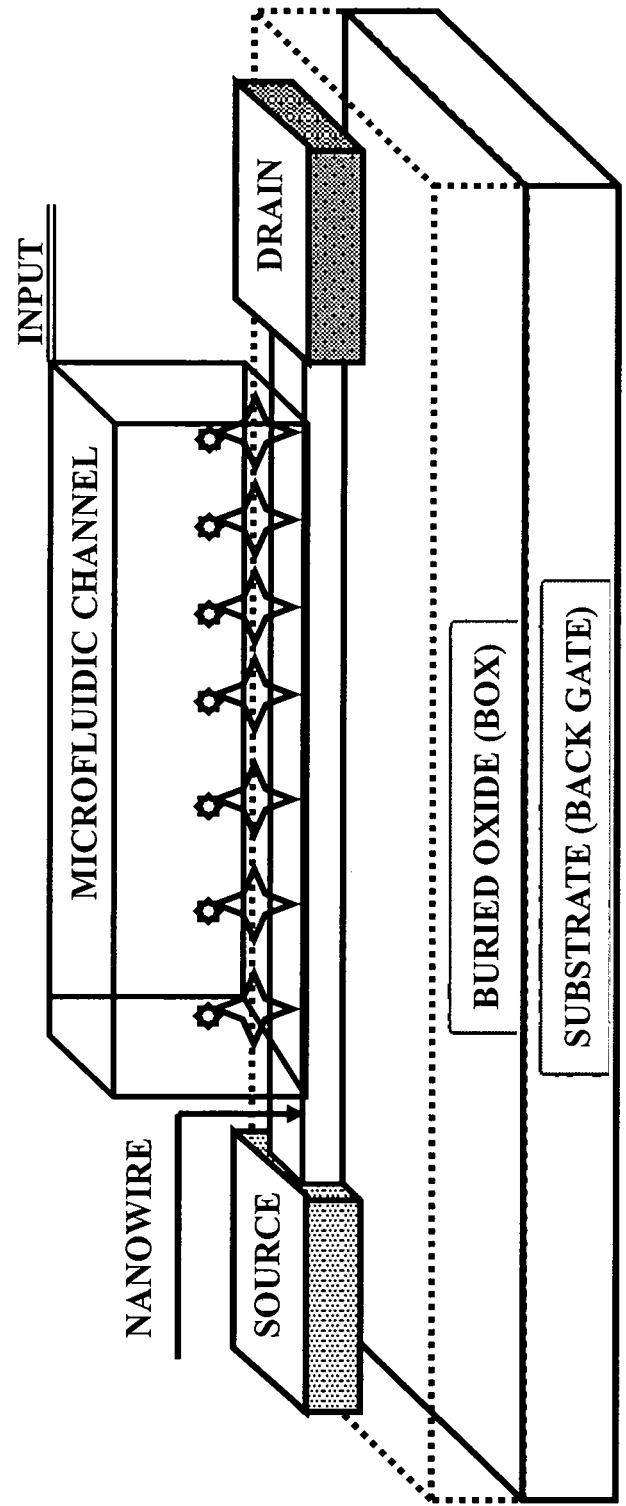

FIG. 56F illustrates the flip-chip bonded chip (on a flexible substrate), which can be as described in FIG. 56L (without the input channel for blood). The flip-chip bonded chip can include many circuits for near real time/real time detection of biomarkers in sweat and an antenna to transmit data.

FIG. 56G illustrates a top protective film, which includes a solar cell on top of a battery and a body patch for providing electrical power.

Details of the body patch have been described/disclosed in non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

The input of the microfluidic channels in FIG. 56E can be also connected to an ultrathin-hydrogels film-embedded with one specific type of biomarker binder (e.g., antibodies/aptamers/designer proteins/molecular beacons). The optical properties of ultrathin-hydrogels film can change, when the specific biomarker binders chemically couple with the biomarkers in sweat. This change can be detected by an optical detector/spectrophotometer.

FIG. 56H illustrates a two-layer patch to measure blood sugar in-situ. The first layer is a porous membrane with spiropyran and it is attached to human skin. The second layer (on top of the first layer) includes hydrogels embedded with glucose sensors (e.g., boronic acid).

If UV light is beamed through spiropyran, the chemical structure of spiropyran is charged (polar) and open structure—enabling more glucose molecules to diffuse through the first layer from skin. If irradiated with visible light, the chemical structure of spiropyran reverts back to normal/closed structure—enabling fewer glucose molecules to diffuse to the first layer from skin. By comparing the optical spectrum taken under UV light against the optical spectrum taken under visible light, glucose in blood can be quantified. By embedding other molecular sensors in the second layer, other biomarkers/analytes (e.g., creatinine and electrolytes) in blood can also be quantified. This method to measure blood sugar in-situ can be integrated with the wearable diagnostic device A.

FIG. 56H illustrates a two-layer patch to measure blood sugar in-situ. The first layer is a porous membrane embedded with spiropyran and the first layer is attached to human skin.

Hydrogels embedded with glucose sensors (e.g., boronic acid) is a second layer. The second layer is attached onto the first layer.

If UV light is beamed through spiropyran, the chemical structure of spiropyran is charged (polar)/open structure—enabling more glucose to diffuse to the first layer from the outer most layer of skin/skin. If visible light is beamed through spiropyran, the chemical structure of spiropyran reverts back to normal/closed structure—enabling less glucose to diffuse to the first layer from the outer most layer of skin/skin. By comparing optical spectra taken under UV and visible light, glucose in blood can be quantified. Additionally, by embedding suitable molecular sensors in the second layer, other analytes (e.g., creatinine and electrolytes) in blood can be quantified.

Alternatively, only the porous membrane spiropyran (the first layer) can be utilized. If UV light is beamed through spiropyran, the chemical structure of spiropyran is charged (polar)/open structure—enabling more glucose to diffuse to the first layer from the outer most layer of skin/skin and glucose can then be quantified by a Raman spectrophotometer. Raman spectra is induced by a laser and propagated through a beam splitter, collimating lens, hyperbolic metal concentrator, an optical filter and focusing lens to the Raman spectrophotometer. The hyperbolic metal concentrator can be utilized to collect scattered photons. Raman measurement can be calibrated with other direct blood sugar measurements. An algorithm can be utilized with the Raman spectrophotometer to correct for any concentration and time lag effects. Thus, a look up table and/or algorithm can enable continuous or quasi-continuous in-situ blood sugar measurement.

Furthermore, the two-layer patch can include nanoshells (e.g., polymeric nanoshells) encapsulating insulin molecules/long acting insulin molecules, wherein the nanoshells can disintegrate upon light activation. Thus, this will enable to deliver insulin molecules/long acting insulin molecules from the two-layer patch.

Additionally, the two-layer patch (including nanoshells encapsulating insulin molecules/long acting insulin molecules) in FIGS. 56A and 56H can be replaced by a separate skin patch (including nanoshells encapsulating insulin molecules/long acting insulin molecules).

FIG. 56I illustrates Raman spectrum under UV light, when more glucose can diffuse to the first layer from skin.

FIG. 56J Raman spectrum under visible light, when few glucose molecules can diffuse to the first layer from skin.

Alternatively, a porous membrane with a biocompatible needle can be utilized to create a microscopic pore at the outermost layer (about 20 microns in depth) of skin for interstitial fluid to cross the outer skin barrier. Glucose in interstitial fluid can be converted into hydrogen peroxide by glucose oxidase. Hydrogen peroxide can chemically react with horseradish peroxidase to generate colored liquid resorufin, which absorbs/emits red light. The optical signature of resorufin is a measure of glucose in human blood and it can be quantified by Raman spectrophotometer/optical coherence tomography/plasmonic interferometer/spectrophotometer/(organic light emitting diode or ultrasensitive detector of the wearable personal health assistant device).

Alternatively, hydrogels (integrated with embedded photonic crystals), a pre-shrink chemical compound (e.g., polyvinyl alcohol) and a glucose binding chemical compound (e.g., boronic acid) with a biocompatible needle can be utilized to create a microscopic pore at the outermost layer (about 20 microns in depth) of skin for interstitial fluid to cross the outer skin barrier. Glucose in interstitial fluid can bind with the glucose binding chemical compound-thus changing arrangement of the photonic crystals and shifting the spectrum of the reflected light from the organic light emitting diode. Such a configuration can be incorporated with the wearable personal health assistant device.

FIG. 56K illustrates an array of biocompatible microneedles (e.g., made from sugar/hyaluronic acid) with built-in nanoscaled (about 10 nm) roughness on the surface of the microneedles to reduce any bacterial infection. These microneedles can enable (a) the transport of blood to an input of the wearable diagnostic device B and (b) also deliver a bioactive compound(s)/a bioactive compound(s) encapsulated within a smart nanoshell in synchronization with in-situ measurements by the wearable diagnostic device B.

The smart nanoshell can be of any shape and build by deoxyribonucleic acid origami method.

The bioactive compound can also mean RNA-i, engineered riboswitch and synthetic notch molecule.

Smart nanoshells can be stored in a biocompatible reservoir (e.g., a microelectromechanical system biocompatible reservoir) and their movement from the biocompatible reservoir can be controlled by a micropump. Smart nanoshells have to meet a suitable external condition(s) and/or couple with a specific receptor(s) to release a bioactive compound.

For example, the smart nanoshell can be made of water-fearing molecules (pointing inward) and water-loving molecules (pointing outward). The smart nanoshell can encapsulate insulin molecules/long acting insulin molecules. The external surface of the smart nanoshell can be coupled with an enzyme to convert glucose into gluconic acid. In the presence of excess glucose, the enzyme (converting glucose into gluconic acid) creates a lack of oxygen and causes water-loving molecules (pointing outward) to collapse—enabling the delivery of insulin/long acting insulin/smart insulin at a suitable external condition.

In another example, a smart nanoshell (fabricated/constructed by deoxyribonucleic acid origami) can be decorated with an aptamer/engineered riboswitch based (excess) glucose sensor. In the presence of excess glucose, the smart nanoshells can collapse—enabling the delivery of insulin/long acting insulin/smart insulin at a suitable external condition.

Smart insulin can be Ins-PBA-F, which can consist of a long-acting insulin derivative that has a chemical moiety with phenylboronic acid added at one end. Under normal conditions, smart insulin can bind with serum proteins (circulating in blood). In the presence of excess glucose, it can bind with phenylboronic acid to release Ins-PBA-F.

In another example, a smart nanoshell (fabricated/constructed by deoxyribonucleic acid based origami) can be decorated with an aptamer/engineered riboswitch to detect cancer cells. In the presence of cancer cells, the smart nanoshell can collapse—enabling the delivery of a synthetic notch molecule/engineered riboswitch to activate a T cell.

In another example, resembling a biological cell, a synthetic cell (e.g., a lipid-based synthetic cell) can sense, when integrated with a synthetic deoxyribonucleic acid template within the natural membrane of a biological tissue (e.g., a cancer tissue) to activate/produce a therapeutic/diagnostic protein—dictated by the integrated synthetic deoxyribonucleic acid template and/or activate a gene, when integrated with a gene enhancer switch molecule (a short segment of deoxyribonucleic acid chemically coupled by a specialized protein (e.g., a transcription factor)).

Furthermore, the synthetic cell can integrate an anticancer bioactive compound and/or a smart molecule, wherein the smart molecule can chemically bind with one or more binding centers on a cell within the biological tissue. A binding center may represent either a disease specific binding center or a disease stage specific binding center.

FIG. 56L illustrates the wearable diagnostic device B, wherein a source electrode and a drain electrode are connected by a nanowire. The nanowire can be fabricated/constructed in two-dimensional materials (e.g., molybdenum disulphide/graphene). The nanowire can be embedded with biomarker binders. The nanowire can be connected with a microfluidic channel, having an input microfluidic to separate serum from blood (propagated from the microneedles). Electrical parameters will change upon chemical coupling of the biomarker binders (on the nanowire) with biomarkers (in serum) and these changes can be quantified.

Details of the smart nanoshells and the wearable diagnostic device B have been described/disclosed in U.S. non-provisional patent application Ser. No. 13/663,376 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Oct. 29, 2012 and in its related U.S. non-provisional patent applications (with all benefit provisional patent applications) are incorporated in its entirety herein with this application.

FIG. 57A illustrates passive delivery of a bioactive compound(s) encapsulated within the smart nanoshell via a porous magnetic membrane patch. Smart nanoshells (encapsulating a bioactive compound(s)) can be stored in a microelectromechanical system reservoir.

FIG. 57B illustrates active (utilizing a micropump-controlled by a control component) delivery of a bioactive compound(s) encapsulated within the smart nanoshell via a membrane patch integrated with microneedles. Smart nanoshells (encapsulating a bioactive compound(s)) can be stored in reservoir 2. Reservoir 2 is connected with reservoir 1 via a microneedle.

FIG. 57C illustrates a smart nanoshell (encapsulating insulin/long acting insulin) decorated with a glucose sensor.

FIG. 57D illustrates an engineered riboswitch glucose sensor.

FIG. 57E illustrates how the smart nanoshell manages excess glucose over time.

FIG. 57F illustrates a molecular arrangement of a riboswitch.

FIG. 57G illustrates a smart nanoshell (encapsulating an engineered riboswitch/synthetic notch molecule). The smart nanoshell is decorated with a ligand(s) to bind with a specific cell receptor (s) to deliver the engineered riboswitch/synthetic notch signaling molecule or a bioactive compound. Instead of the smart nanoshell, a benign plant virus (e.g., tobacco mosaic/cowpea mosaic virus with its infectious components removed) or an artificial virus can be decorated with a ligand(s) to bind with a specific cell receptor (s) to deliver the engineered riboswitch/synthetic notch signaling molecule or a bioactive compound (including siRNA). A plant virus can also degrade under an external (e.g., pH) condition.

For example, the bioactive compound 2-(4-morpholinoanilino)-6-cyclohexylaminopurine or phenanthriplatin can induce death of a cancer cell selectively.

Similarly, the bioactive compound Lomaiviticin A, can induce cell death of a cancer cell selectively, by cleaving a cancer cell's deoxyribonucleic acid structure. Furthermore, a structural/chemical analogue of Lomaiviticin A can also be utilized. The structure of Lomaiviticin A is given below.

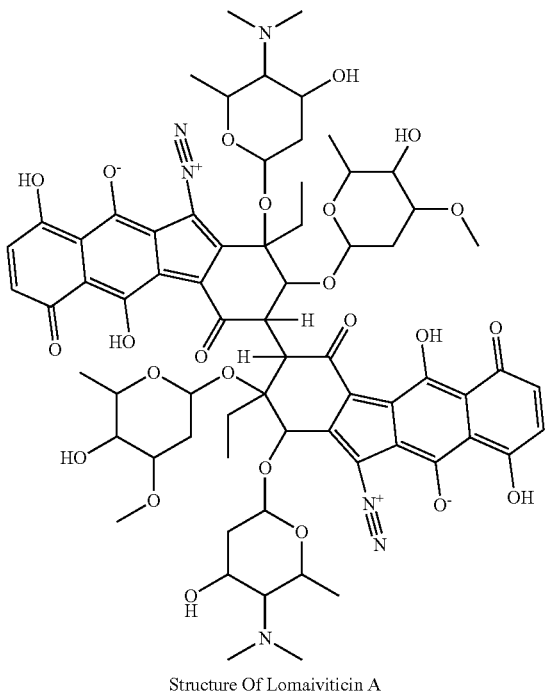 [SMILES: CCC1(OC2CC(O)C(N(C)C)C(C)O2)C2=C([N+]#N)c3c([O-])c4c(c(O)c3=C2C(=O)C(C2C(=O)C3=c5c(O)c6c(c([O-])c5C([N+]#N)=C3C(OC3CC(O)C(N(C)C)C(C)O3)C2(CC)OC2CC(OC)C(O)C(C)O2)=C(O)C=CC6=O)C1OC1CC(OC)C(O)C(C)O1)C(=O)C=CC=4O]

Structure Of Lomaiviticin A

Additionally, the smart nanoshell/benign plant virus can be functionalized to evade the immune system.

Green tea-derived nanocomplex micelles, self-assembled from epigallocatechin-3-O-gallate (EGCG) derivatives can be utilized as a safer smart nanoshell.

Details of the functionalized nanoshell have been described/disclosed in U non-provisional patent application Ser. No. 13/663,376 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Oct. 29, 2012 and in its related U.S. non-provisional patent applications (with all benefit provisional patent applications) are incorporated in its entirety herein with this application.

A glutathione-capped water-soluble biocompatible quantum dot (e.g., including silica-coated nanocomposites) can be utilized as a fluorophore (chemically coupled with the smart nanoshell/benign plant virus) for vivo and bioimaging.

Additionally, selenohydantoins or a structural/chemical analogue of selenohydantoins encapsulated in a smart nanoshell can be utilized as an anticancer bioactive compound. The structure of selenohydantoins is given below.

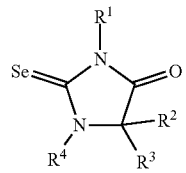

Structure Of Selenohydantoins

The structure of selenohydantoins is given above. Additionally, selenohydantoins or a structural/chemical analogue of selenohydantoins encapsulated in a smart nanoshell can be utilized as an anticancer bioactive compound.

FIG. 57H illustrates implanting/coupling of engineered riboswitch/synthetic notch signaling molecule to a gene of (a specific chromosome) in the nucleus via the nuclear pore.

In the case of the engineered riboswitch, the gene can be turned on and off with a small inducer molecule. Thus, human cells can be programmed/reprogrammed with the engineered riboswitch to manufacture a specific protein only when a person takes a pill (containing the small inducer molecule), otherwise it is neutral or non-programmed.

In the case of the synthetic notch signaling molecule, the genome can be turned on and off. However, a gene can mean either natural or edited gene.

FIG. 57I illustrates an embodiment of Förster/Fluorescence Resonance Energy Transfer. In this case, the biomarker binder has two segments—a segment A and a segment B on a substrate.

The segment A has a donor fluorophore and the segment B has an acceptor fluorophore. The donor fluorophore can be about 2 nm to 10 nm apart from the acceptor fluorophore. The segment A of the biomarker binder (e.g., first molecular beacon/first deoxyribonucleic acid based origami probe coupled with a donor fluorophore) couples (e.g., chemically couples/binds) with a section of the biomarker. Similarly, the segment B of the biomarker binder (e.g., second molecular beacon/second deoxyribonucleic acid based origami probe coupled with a receptor fluorophore) couples (e.g., chemically couples/binds) with another section of the biomarker. Alternatively, the segment B of the biomarker binder can couple with segment A of the biomarker binder and this strategy may work better for the biomarker of small molecular size (e.g., in the case of exosomes/microRNAs).

For example, segment A can be GCT GTT GCT GGG AGC TGT TCT ACT G/3ATTO565N

For example, segment B can be 5ATTO647NN/TA GCT CTG CCC GGT CAT GA

For example, DNA template to which both segment A and segment B to couple can be GGC CCT TGA GTC GTG GTT TCC TGG TCA TGA CCG GGC AGA GCT AAT AGC AGT AGA ACA GCT CCC AGC AAC AGC ATC CTG AGC CCT GAT GTC AGG AGT TTC A Furthermore, segment A can include a metallic (e.g., gold/silver) nanoparticle and segment B can also include a metallic (e.g., gold/silver) nanoparticle.

The donor fluorophore/acceptor fluorophore can consists of inner spherical metal (e.g., silver), followed by spherical dielectric (e.g., silica) spacer and then followed by dye doped dielectric (e.g., silica).

In close proximity between the donor fluorophore and acceptor fluorophore, there is detectable Förster/Fluorescence Resonance Energy Transfer. The emitted fluorescence wavelength from the acceptor fluorophore is distinct from the excitation laser wavelength. The emitted fluorescence wavelength from the acceptor fluorophore can be utilized to identify the presence of the biomarker (e.g., microRNA of a particular cancer cell) at a very early stage of disease progression.

Furthermore, the donor fluorophore and/or acceptor fluorophore can be very long-lived fluorophores (e.g., europium ions)

For example, the segment A of the biomarker binder can be a first half of a molecular beacon. The segment B of the biomarker binder can be a second half of a molecular beacon. The segment A and the segment B can be separated by a spacer molecule. The segment A can bind only onto a certain fragment of a biomarker (e.g., a miRNA). The segment B can bind only onto a certain fragment of the above biomarker.

Additionally, a semiconductor quantum dot (SQD), an upconversion nanoparticle, (UCNP), a graphene quantum dot (GQD) and a suitable material can act as an efficient donor and/or acceptor replacing a fluorescent organic dye molecule. Furthermore, p19 protein-conjugated donor/acceptor may be utilized.

Additionally, a microresonator-barium titanate/polystyrene divinylbenzene (PS-DVB) microsphere filled with a fluorescent protein (e.g., a green fluorescent protein) can be coupled with the donor as an in-situ biological laser (when excited by an external light source (optical pump)).

Furthermore, the microresonator can include or couple with one or more nano optical element/antennas (represented by ∞) to enhance light matter interaction.

A special case of the biomarker binder can be a nanoscaled molecularly imprinted synthetic polymer with a three-dimensional structure to bind only onto a certain fragment of a biomarker. The nanoscaled molecularly imprinted synthetic polymer can be loaded with one or more bioactive compounds.

FIG. 57J is similar to FIG. 57I, except it illustrates an embodiment of plasmonic enhanced Förster/Fluorescence Resonance Energy Transfer between the donor fluorophore and acceptor fluorophore, utilizing a nano optical element/antenna (represented by co) on the substrate. In this case the donor fluorophore and acceptor fluorophore are bounded by the nano optical element/antenna (represented by ∞). The orientation of the donor fluorophore and acceptor fluorophore can be either parallel or perpendicular to the nano optical element/antenna (represented by ∞).

The gap of a nano optical element/antenna (represented by ∞) can be fabricated/constructed with a metamaterial of a special property (e.g., epsilon-near-zero (ENZ) at a particular wavelength range).

For example, a metamaterial with epsilon-near-zero in the visible wavelength range can be realized by 4 pairs of 18 nm Au layer and 81 nm $Al_2O_3$ layer or alternatively, 13 pairs of 20 nm Au layer and 80 nm $SiO_2$ layer.

However, instead of the entire substrate coated with antibodies against a particular type of diseased cells, a relevant section of the substrate (e.g., in the gap of a nano optical element/antenna (represented by ∞)) or the metamaterial of a special property can be coated with antibodies against a particular type of diseased cells to capture the particular type of diseased cells efficiently.

However, instead of the entire substrate coated with antibodies against a particular type of diseased cells, a relevant section of the substrate (e.g., in the gap of a nano optical element/antenna (represented by ∞)) or the metamaterial of a special property can be fabricated with one or more dielectric (e.g., silica/polymer) nanowires, wherein each dielectric nanowire can be coated with antibodies against a particular type of diseased cells to capture the particular type of diseased cells efficiently.

Furthermore, the nano optical element/antenna (represented by ∞) can be caged within a bounded (semi-closed/closed) nanostructure (of dielectric/metal/refractory metal) to reduce the background signal. For example, such a bounded (semi-closed/closed) nanostructure is illustrated in FIGS. 59H-59I.

The nano optical element/antenna (represented by ∞) can be fabricated/constructed of single crystalline/polycrystalline material. The nano optical element/antenna (represented by ∞) can include a fractal geometrical design or optically couple with an index matching liquid. The nano optical element/antenna (represented by ∞) can be fabricated/constructed of a metal/refractory material or a two-dimensional material (e.g., argentine/graphene) or a combination of a metal and a refractory material (e.g., titanium nitride-gold). Furthermore, Langmuir-Blodgett deposited (one/two-dimensional) array of nanoparticles or a nano optical element/antenna (represented by ∞) can be coupled with a (colloidal) photonic crystal(s).

The nano optical element/antenna (represented by ∞) can be fabricated/constructed on a substrate of the biological wafer, wherein the substrate of the biological wafer can include one or more materials.

The substrate can be entirely coated with antibodies against a particular type of diseased cells to capture the particular type of diseased cells. For example, glycoprotein is present on the surfaces of a cancer cell.

The substrate can be selectively coated in the proximity of the nano optical element/antenna (represented by ∞) with antibodies against a particular type of diseased cells to capture the particular type of diseased cells.

For example, one or more materials can be an ultrathin-film (about 50-200 nm in thickness) of an insulator, wherein the ultrathin-film insulator is then deposited on an ultrathin-film (about 50-200 nm in thickness) of a metal, wherein the ultrathin-film metal is then deposited on the substrate of the biological wafer (which can include one or more materials). For example, the one or more materials can be a metamaterial. Additionally, the one or more materials can be a metamaterial of epsilon-near-zero (ENZ) (with respect to the range of the excitation and emission wavelength in Förster/Fluorescence Resonance Energy Transfer).

For example, but not limited to, a metamaterial of epsilon-near-zero is fabricated utilizing a multilayer (about 5) of an ultrathin-film (about 40-150 nm in thickness) of metal-silver and an ultrathin-film (about 35-135 nm in thickness) of insulator-silicon nitride.

For example, but not limited to, a metamaterial of epsilon-near-zero is fabricated utilizing a multilayer (about 5) of an ultrathin-film (about 20-30 nm in thickness) of metal-silver and an ultrathin-film (about 45-75 nm in thickness) of insulator-titanium dioxide.

Furthermore, an ultrathin-film of metal silver can be replaced by graphene.

It should be noted that, the substrate of the biological wafer can be a membrane substrate (e.g., an ultrathin-film insulator on an etched back silicon membrane) to reduce proximity effect of electron beam lithography in order to define a dimension of less than 10 nm.

It should be noted that (a) sub-10 nm gap between the nano optical element/antenna, (b) orthogonal coupling, (c) a substrate of a metamaterial/metamaterial of epsilon-near-zero and (d) a substrate of a high ratio of real-to-imaginary refractive index/permittivity individually or collectively in combination can affect Förster/Fluorescence Resonance Energy Transfer-resulting in stronger fluorescence intensity of the acceptor. Such stronger fluorescence intensity of the acceptor can be detected by an electron-multiplying CCD camera or an equivalent detector.

Details of the nano optical element/antenna, compositions of the nano optical element/antenna, sub-10 nm lithography and substrate of one or more materials have been described/disclosed in U.S. non-provisional patent application Ser. No. 15/731,577 entitled "OPTICAL BIOMODULE FOR DETECTION OF DISEASES AT AN EARLY ONSET, filed on Jul. 3, 2017 and in its related U.S. non-provisional patent applications (with all benefit provisional patent applications) are incorporated in its entirety herein with this application.

FIG. 57K is similar to FIG. 57I, except it illustrates an embodiment of plasmonic enhanced Förster/Fluorescence Resonance Energy Transfer between the donor fluorophore and acceptor fluorophore, utilizing a metal (e.g., silver) nanoparticle between the donor fluorophore and acceptor fluorophore. In the case, the donor fluorophore can be about 100 nm to 200 nm apart from the acceptor fluorophore.

The gap around the metal nanoparticle can be fabricated/constructed with a metamaterial of a special property (e.g., epsilon-near-zero (ENZ) at a particular wavelength range).

For example, a metamaterial with epsilon-near-zero in the visible wavelength range can be realized by 4 pairs of 18 nm Au layer and 81 nm $Al_2O_3$ layer or alternatively, 13 pairs of 20 nm Au layer and 80 nm $SiO_2$ layer.

However, instead of the entire substrate coated with antibodies against a particular type of diseased cells, the metamaterial (of a special property) can be coated with antibodies against a particular type of diseased cells to capture the particular type of diseased cells.

FIG. 57L illustrates an embodiment to measure Förster/Fluorescence Resonance Energy Transfer, utilizing a pulsed vertical cavity surface emitting laser, two beam splitters, a single photon avalanche detector for the donor fluorophore, a single photon avalanche detector for the acceptor fluorophore, a time correlated single photon counting (signal processing) electronic circuitry (TCSPC) and a removable biologic wafer-containing an array of spots (of biomarker binder-biomarker coupling via Förster/Fluorescence Resonance Energy Transfer). The removable biologic wafer can be integrated with a microfluidic device (MFD) to deliver whole blood/plasma/serum.

An application of the device illustrated in FIGS. 57J-57L is discussed here. Triple negative breast cancer (TNBC) is very difficult to treat and accounts for 15% to 20% of all breast cancers in women. A five miRNA signature (miR-92a-3p, miR-342-3p, miR-16, miR-21 and miR-199a-5p) can discriminate triple negative breast cancer from non-triple negative breast cancer. However, the miRNA namely miR-199a-5p evidenced the highest specificity and sensitivity in distinguishing stage of the triple negative breast cancer. A complementary Förster/Fluorescence Resonance Energy Transfer probe to the above gene sequence can positively identify the presence of the miRNA namely miR-199a-5p in a very small quantity in plasma, utilizing the device illustrated in FIGS. 57J-57L.

FIG. 57M illustrates an embodiment of amplified (by Recombinase Polymerase Amplification (RPA) by a heater or Helicase-Dependent Amplification (HDA)) biomarker binder-biomarker coupling integrated with fluorophores. This embodiment has been described/disclosed in U.S. non-provisional patent application Ser. No. 15/731,577 entitled "OPTICAL BIOMODULE FOR DETECTION OF DISEASES AT AN EARLY ONSET, U.S. patent application Ser. No. 15/731,577, filed on Jul. 3, 2017 and in its related U.S. non-provisional patent applications (with all benefit provisional patent applications).

FIG. 57N is similar to 57M illustrates, except it illustrates an embodiment of plasmonic enhanced and amplified (by Recombinase Polymerase Amplification (RPA) by a heater or Helicase-Dependent Amplification) biomarker binder-biomarker coupling integrated with fluorophores and a nano optical element (represented by ∞). This embodiment has been described/disclosed in U.S. non-provisional patent application Ser. No. 15/731,577 entitled "OPTICAL BIOMODULE FOR DETECTION OF DISEASES AT AN EARLY ONSET, U.S. patent application Ser. No. 15/731,577, filed on Jul. 3, 2017 and in its related U.S. non-provisional patent applications (with all benefit provisional patent applications).

FIG. 57O illustrates an embodiment of a wafer scale detection of amplified (by Recombinase Polymerase Amplification) by a heater or Helicase-Dependent Amplification (HDA)) or amplified (by Recombinase Polymerase Amplification by a heater or Helicase-Dependent Amplification) and plasmonic enhanced biomarker binder-biomarker coupling integrated with fluorophores, utilizing an optoelectronic wafer (including an array of vertical cavity surface emitting lasers and detectors, wherein each detector has an optical filter to filter out the incident excitation wavelength of the vertical cavity surface emitting laser). An array of biomarker binders-biomarkers (as described in FIG. 57M or FIG. 57N) are on a removable biologic wafer. The removable biologic wafer can be integrated with a microfluidic device to deliver whole blood/plasma/serum.

FIG. 57P is similar to FIG. 57O, except it illustrates an integration of a complementary metal oxide semiconductor electronic wafer on sapphire substrate for electronic processing. Furthermore, the optoelectronic wafer and complementary metal oxide semiconductor electronic wafer can be bonded.

FIG. 57Q illustrates an asymmetric Mach-Zehnder interferometer (e.g., utilizing silicon nitride as a core waveguide layer), integrating a gratings for vertical coupling from a light source at input, a multi-mode interference (optical) coupler at input, a multi-mode interference (optical) coupler at output and gratings for vertical coupling to a detector at output. The surface (e.g., silicon nitride waveguide layer) of the sensing arm can be treated with ozone plasma and then oxidized with a solution of 10% concentration of $HNO_3$ acid. Carboxyethylsilanetriol, sodium salt (CTES) can be employed as silane agent and the ended carboxylic groups of silane can be activated through the N-(3-dimethylaminopropyl)-N'-ethylcarbodiimide (EDC)/N-Hydroxysuccinimide (NHS) chemistry.

The sensing arm of the asymmetric Mach-Zehnder interferometer can include biomarker binders (for coupling with biomarkers via a microfluidic device, wherein the microfluidic device can deliver whole blood/plasma/serum).

The phase difference $\Delta\Phi$ between two arms $\Delta\Phi=(2\Pi*L/\lambda)*(N_{Sens}-N_{Ref})$. $\lambda$ is the operating wavelength. L is the length of sensing length. $N_{Sen}$ is the refractive index of the sensing arm. $N_{Ref}$ is the refractive index of the reference arm.

There may be false positive reading due to (i) signal ambiguity, (ii) intensity variation and (iii) sensitivity fading. Wavelength modulation can solve problems due to the periodic nature of signal from the asymmetric Mach-Zehnder interferometer. The intensity variation can be monitored by extracting the reference optical signal of the asymmetric Mach-Zehnder interferometer. The biomarker binder-biomarker coupling can be unambiguously determined label free by Fast Fourier Transform (FFT) of the normalized output signal (utilizing raw output signal and reference output signal), for example, inverse tangent of the ratio between a third harmonic and second harmonic.

It should be noted that integrating a first variable attenuator on the sensing arm and/or a second variable attenuator on the reference arm of the asymmetric Mach-Zehnder interferometer can enhance the extinction ratio of the asymmetric Mach-Zehnder interferometer.

It should be noted that one or more ring resonators, optically coupled with the sensing arm of the asymmetric Mach-Zehnder interferometer can enhance sensitivity.

Alternatively, a trench-based asymmetric Mach-Zehnder interferometer can enhance sensitivity.

Furthermore, a slow light one-dimensional/two-dimensional photonic crystal (e.g., air holes of period of about 350 nm, wherein each air hole can be either circular or rectangular in shape. The circular air hole can be about 125 nm in diameter or rectangle of 200 nm by 300 nm in dimension) based Mach-Zehnder interferometer can enhance sensitivity. A two-dimensional photonic crystal is illustrated in FIG. 28F.

The asymmetric Mach-Zehnder interferometer can be arrayed (in one-dimension or two-dimension) on a planar surface to enable a multiplexed device for biological sensing of multiple biomarkers.

Alternatively, one or more whispering gallery mode based resonators (wherein each whispering gallery mode resonators has a quality factor of about $10^8$ can be utilized as a standalone device, instead of the asymmetric Mach-Zehnder interferometer.

Alternatively, a photonic crystal nanolaser (for example as illustrated in FIGS. 28C-28D) can be utilized as a standalone device, instead of the asymmetric Mach-Zehnder interferometer.

Alternatively, a field effect (nanowire) transistor can be utilized as a standalone device, instead of the asymmetric Mach-Zehnder interferometer. This embodiment has been described/disclosed in FIGS. 13C, 13D and 13E of U.S. non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications).

Furthermore, the surface of nanowire of the field effect (nanowire) transistor can be nanostructured (e.g., about 5 to 25 nm surface roughness) to enhance coupling of the biomarker binders-biomarkers.

FIG. 57R is similar to FIG. 57O, except it illustrates an integration of an array of asymmetric Mach-Zehnder interferometers on the removable biologic wafer FIG. 57S is similar to FIG. 57P, except it illustrates an integration of an array of asymmetric Mach-Zehnder interferometers on the removable biologic wafer.

FIG. 57T illustrates an embodiment of a microfluidic based microRNA (about 19-25 bases long) capture system, which includes microchannels, a removable microRNA capture microchamber and a removable miRNA separation+wash microchamber. The removable miRNA capture microchamber includes magnetic nanoparticles/magnetic beads. Each magnetic nanoparticle/magnetic bead can be coupled with p19 protein to tightly bind a microRNA. The removable microRNA separation+wash microchamber includes a magnet to separate magnetic nanoparticles/magnetic beads-thus isolating microRNAs. The microfluidic based microRNA capture system can be integrated with Rolling Circle Amplification (RCA) or Rolling circle extension-actuated loop-mediated isothermal amplification (RCA-LAMP).

The microfluidic based microRNA capture system can be integrated with embodiments described in 57I/57J/57K.

Figure 58A:
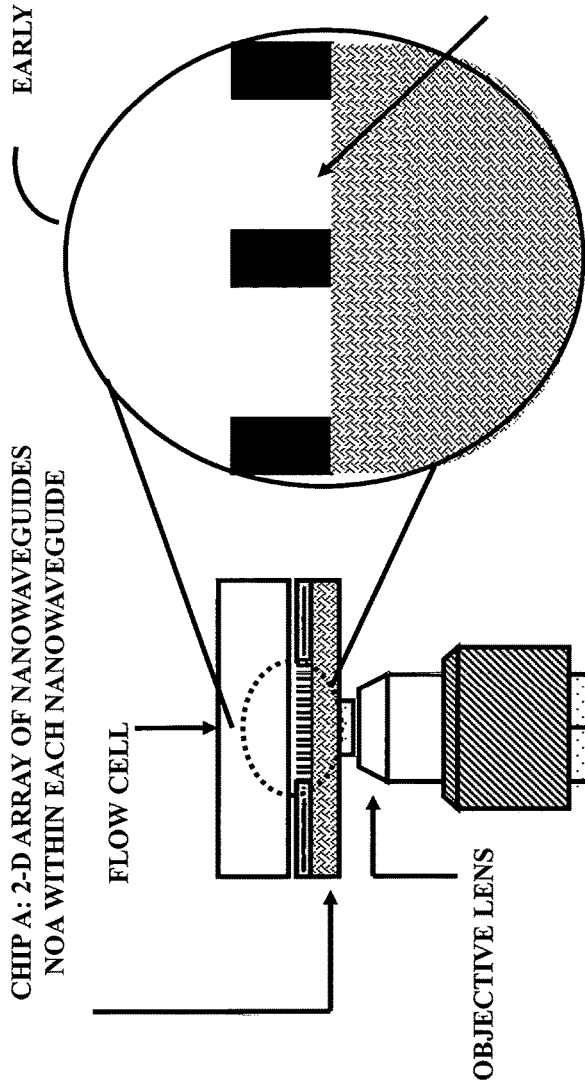
Figure 58A:
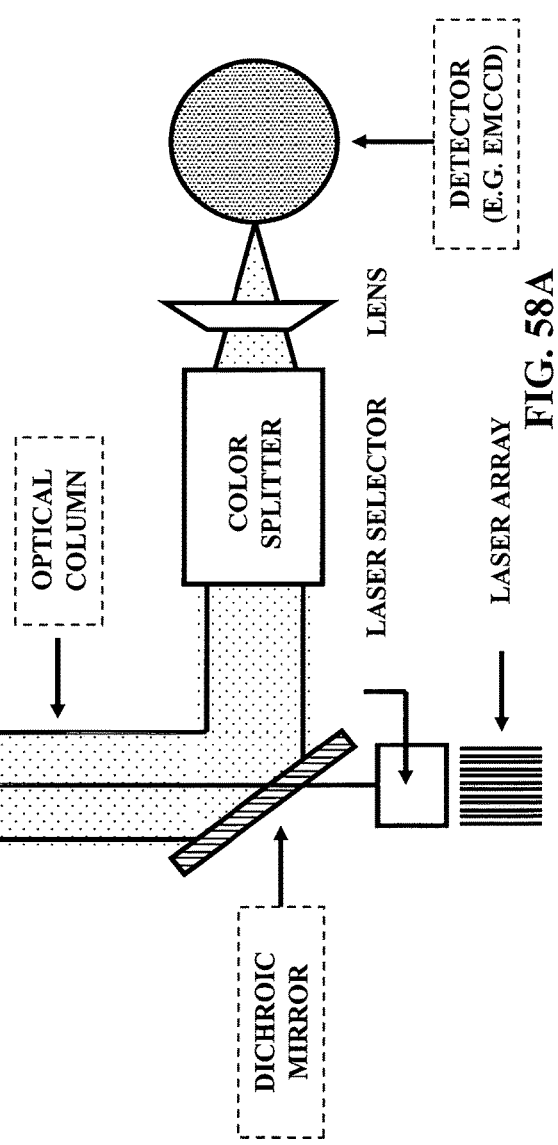

FIG. 58A illustrates an early diagnostic system A, which includes a two-dimensional array of nanowaveguides on a transparent substrate (e.g., glass).

The two-dimensional array of nanowaveguides is within a flow cell. At least one protruded metal/non-metal nano optical antenna (FIGS. 30A-30J) can be fabricated/constructed (e.g., utilizing deoxyribonucleic acid assisted lithography or electron beam lithography) at the bottom of each nanowaveguide. The height of each nanowaveguide can be less than 300 nm. The diameter of each nanowaveguide can be less than 400 nm. The maximum dimension of the protruded metal/non-metal nano optical antenna can be less than 200 nm.

Incident light from only one laser of an array of lasers (e.g., emitting in the visible wavelength range—typically at 470/530/640 nm) via an optical column can excite a fluorophore (fluorescence can be due to chemical coupling/interaction between a biomarker binder and a biomarker, wherein the biomarker is chemically coupled with the fluorophore).

The optical column with an objective lens can be positioned by a precision positioning system from one nanowaveguide to the next, as the center to center distance between nanowaveguides can be larger than the diameter of the nanowaveguide. A dichroic mirror can separate the optical paths of the incident light and fluorescence light. Fluorescence light can be demultiplexed by a color splitter and then focused by a lens onto an ultrasensitive optical detector (e.g., an electron multiplying charged coupled detector/single photon avalanche diode).

Instead of scanning with a single (continuous wave/pulsed/ultrashort pulsed) laser, two lasers can be utilized simultaneously. In the first instant a typical laser is using an appropriate wavelength to excite a material. In the second instant is a key second laser, which is focused so that it produces a donut of light overlapping the focal point of the first laser. This configuration can enable the laser to focus below the Abbey's diffraction limit for high resolution fluorescence.

The nanowaveguide with an integrated protruded metal/non-metal nano optical antenna can allow a single molecule to be isolated for enhanced fluorescence detection at a high concentration. Surface adsorption and appropriate concentration can enable just one molecule in one nanowaveguide. The advantages of the early diagnostic system A are (a) ultimate sensitivity down to the single molecule level, (b) no amplification induced false positive data and (c) small sample volume.

Key fabrication/construction steps of the nanowaveguide with integrated protruded metal/non-metal nano optical antenna on a transparent substrate (e.g., 100 millimeters in diameter and 175 microns in thickness glass) are: (1) deposition and removal of silicon nitride or silicon oxynitride in the selected places, (2) electron beam lithography and lift off of protruded metal (e.g., aluminum/copper/gold/silver) or non-metal nano optical antenna on silicon nitride or silicon oxynitride, (3) electron beam lithography and protection of protruded metal/non-metal nano optical antenna, (4) electron beam lithography of nanowaveguide (utilizing a negative tone process) and lift-off of metal (e.g., aluminum/copper/gold/silver or a combination of aluminum, copper, gold and silver) nanowaveguide, (5) removal of all photoresists, (6) passivation on the walls of nanowaveguide by a biological material (e.g., polyethylene glycol) to increase single molecule occupancy level within the nanowaveguide and (7) dicing of the wafer into chip A.

Furthermore, the nanowaveguide can be fabricated/constructed as a zero-mode waveguide.

Figure 58B:
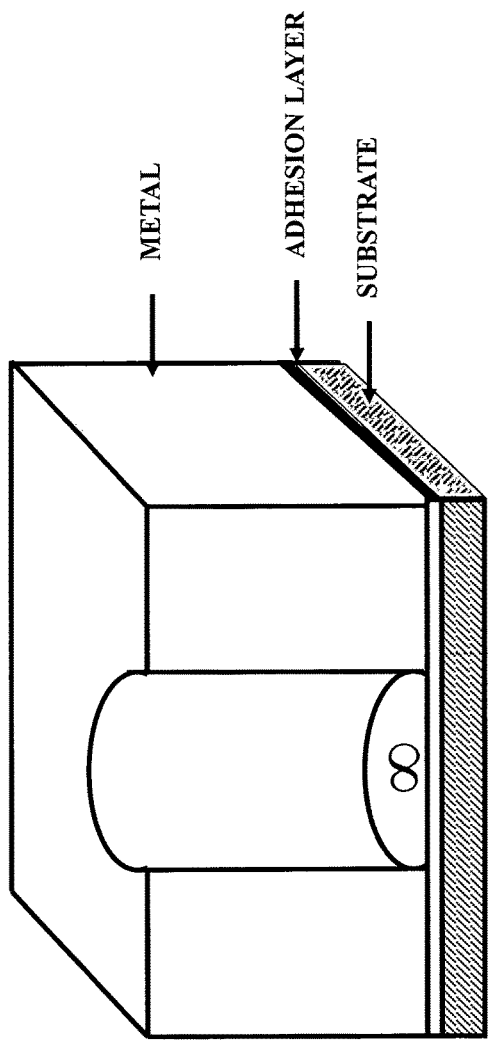

FIG. 58B illustrates a detailed view of the nanowaveguide with an integrated (example) protruded metal/non-metal nano optical antenna. Any protruded metal/non-metal nano optical antennas (designated as ∞) in FIGS. 30A-30J can be utilized.

Deoxyribonucleic acid based origami chemically coupled with a fluorophore can be positioned at a precise location within the gap of protruded metal/non-metal nano optical antennas utilizing electron-beam lithography to etch a sticky binding site that has a complementary shape of origami chemically coupled with a fluorophore.

Figure 58C:
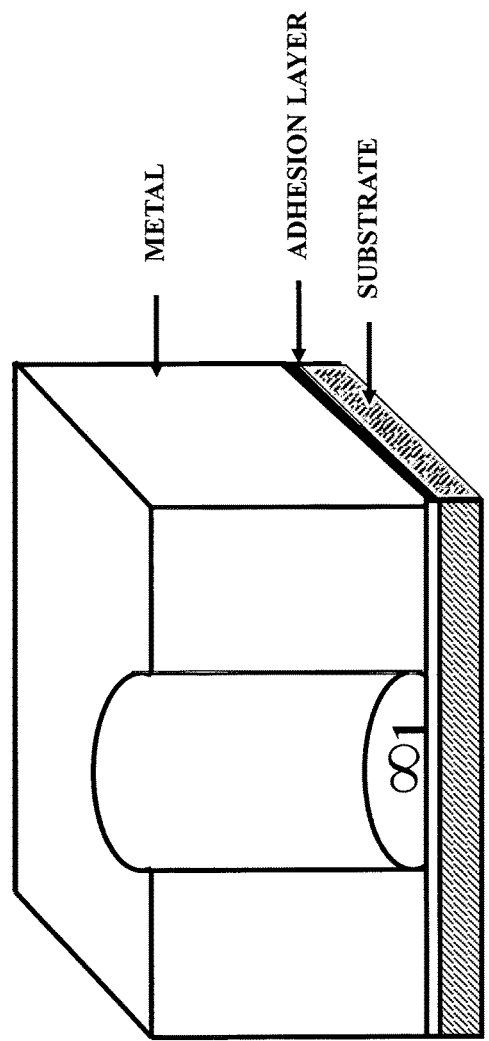

FIG. 58C is similar to 58B, except the protruded metal/non-metal nano optical antenna can be replaced by a hyperbolic metamaterial (designated as ∞). A metamaterial is hyperbolic, when it possesses unique properties leading to the increased output of light.

Figure 58D:
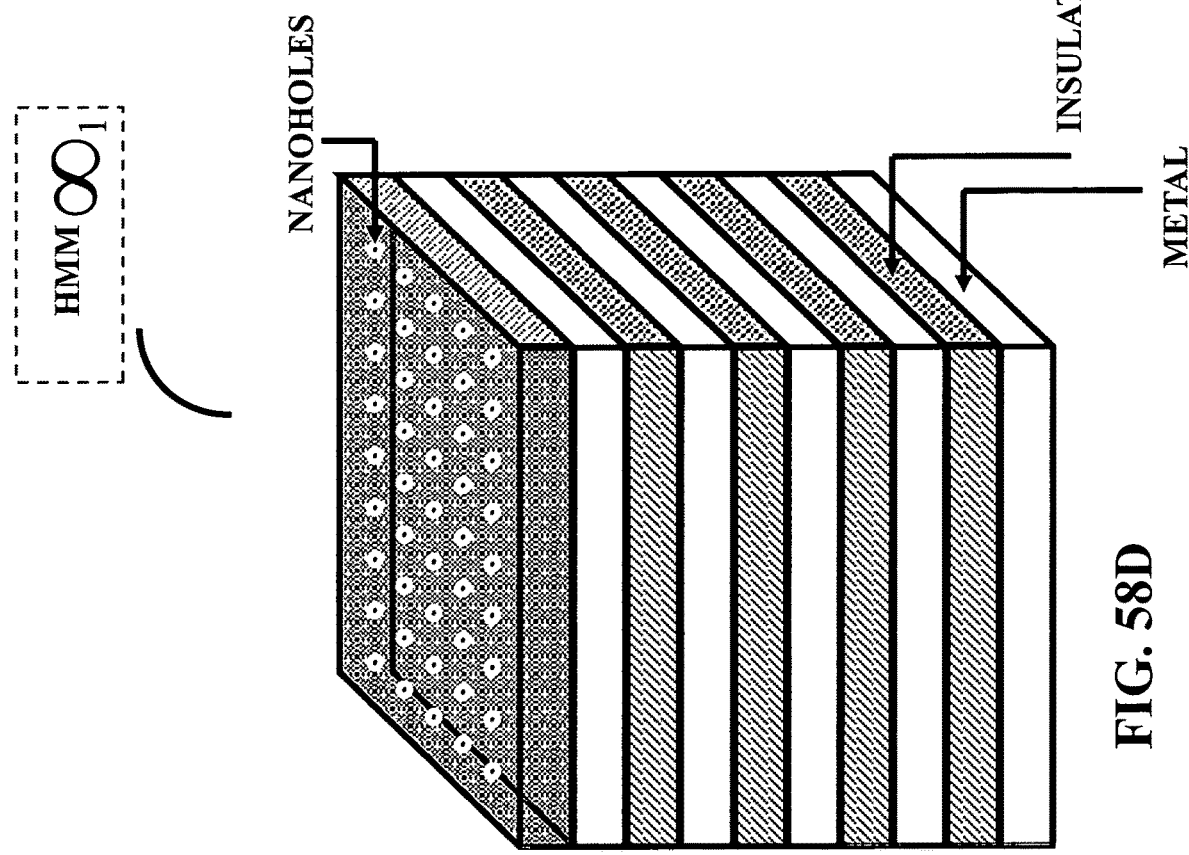

FIG. 58D illustrates a hyperbolic metamaterial of alternating n/2 (e.g., n=8/16/20) ultrathin-film of dielectric (e.g., $Al_2O_3$)/semiconductor and n/2 ultrathin-film of metal (e.g., aluminum/copper/gold/silver) on a transparent substrate. Each ultrathin-film of dielectric/semiconductor is about 30 nm in thickness. Each ultrathin-film of metal is about 15 nm in thickness. The top ultrathin-film metal (which is just below an ultrathin-film spacer layer—the spacer layer is not shown in FIG. 58D) can be fabricated/constructed with nanoholes (of about 100 nm in diameter) for light scattering. Incident light can be confined near the top ultrathin-film metal, causing sharp peaks in the fluorescence/reflection spectrum.

Alternatively, a hyperbolic metamaterial of alternating titanium nitride metal and aluminum scandium nitride insulator, each is about 5 to 20 nm in thickness can be utilized. Alternatively, a hyperbolic metamaterial including only insulators can be also utilized.

Figure 58E:
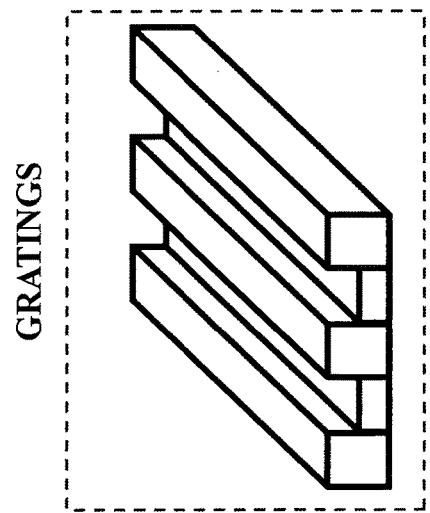

FIG. 58E illustrates two-dimensional gratings (slit width is about 160 nm and pitch is about 500 nm), which can be utilized instead of holes in the top ultrathin-film metal in FIG. 58D.

Additionally, any protruded metal/non-metal nano optical antenna (designated as ∞) can be placed on the hyperbolic metamaterial (designated as ∞). This configuration can enable enhanced fluorescence, when the fluorophore is within or near the gap of the protruded metal (e.g., aluminum/copper/gold/silver) or non-metal nano optical antenna (as illustrated in FIGS. 30B, 30C, 30E, 30F, 30G, 30H, 30I and 30J), wherein the biomarker is chemically coupled with the fluorophore.

In one embodiment, a transparent glass/silicon dioxide ($SiO_2$) substrate can be selectively deposited with silicon nitride (SiNx) or silicon oxynitride (SiONx) except in the gap of the protruded metal/non-metal nano optical antenna (as illustrated in FIGS. 30B, 30C, 30E, 30F, 30G, 30H, 30I and 30J). Then the silicon dioxide gap can be decorated with the linker (A): S-HyNic, which can link with the linker (B): S-4FB. S-4FB can be linked with an antibody/aptamer (an aptamer with less than 50 bases)/molecular beacon/leave-out protein (a leave-out protein less than 200 kilodaltons), wherein the antibody/aptamer/molecular beacon/leave-out protein can contain an amino group. This can enable the positioning of the fluorophore within the gap of the protruded metal/non-metal nano optical antenna.

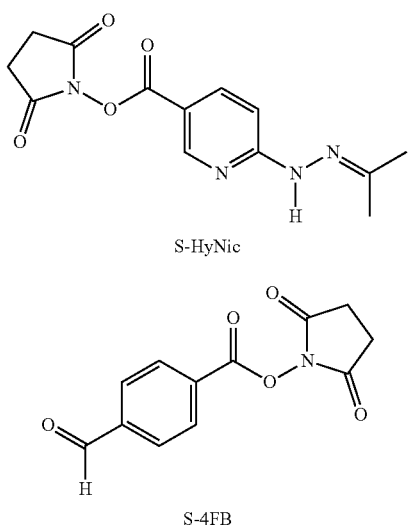

A

S-HyNic

B

S-4FB

Additionally, the antibody/aptamer/molecular beacon/leave-out protein can be chemically coupled with a molecule (e.g., biotin), which can then chemically bind with a biomolecule of interest.

In another embodiment, a transparent glass/silicon dioxide (SiO2) substrate can be selectively deposited with gold in the gap of the protruded metal (e.g., aluminum/copper/gold/silver) nano optical antenna (as generally illustrated as metal/non-metal nano optical antenna in FIGS. 30B, 30C, 30E, 30F, 30G, 30H, 30I and 30J). Dithiobis succinimidyl undecanoate molecules have one end of sulfide which can bind to gold in the gap of the protruded metal nano optical antenna and the other end of Nhydroxysuccinimide (NHS) ester group, which can bind with an amino group of a protein.

Additionally, the amino group of the protein can be chemically coupled with a molecule (e.g., biotin), which can then chemically bind with a biomolecule of interest.

Figure 58F:
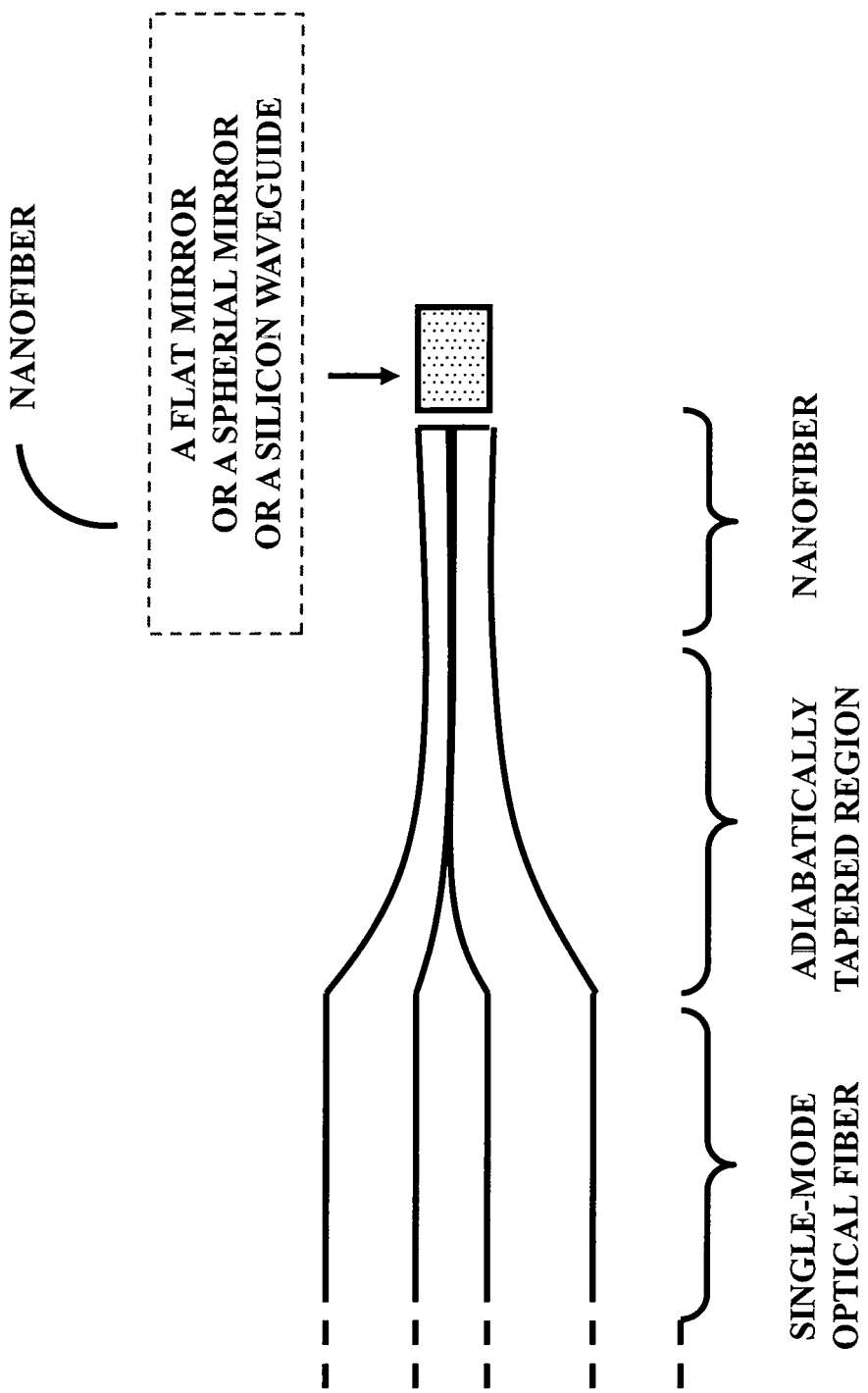

FIG. 58F illustrates a nanofiber. The tip of the nanofiber can be fabricated/constructed with a flat mirror/spherical mirror/silicon waveguide for efficient optical coupling. Instead of bulk optics, an array of nanofibers can be utilized as a conduit for the incident and fluorescence light. The array of nanofibers can be connected to inputs of an N×1 optical switch and the output of the optical switch can be connected to the detector/spectrophotometer. This configuration can enable faster diagnostic analysis.

FIG. 59A illustrates an early diagnostic system B, which includes a two-dimensional array of waveguides/capillaries on a transparent substrate.

FIG. 59A is similar to FIG. 58A, except the diameter of the waveguide/capillary is larger for integrating n (e.g., n=10 to 100) specific protruded metal/non-metal nano optical antennas (FIGS. 30A-30J) at the bottom of each waveguide/capillary.

FIG. 59B illustrates the two-dimensional array of waveguides/capillaries of metal (e.g., aluminum/copper/gold/silver or a combination of aluminum, copper, gold and silver) on an adhesion layer (e.g., 5 nm of chromium) with biomarker binder-biomarker coupling on a protruded metal/non-metal nano optical antenna (represented by a symbol $\Omega_x$).

Figures 59C, 59D:
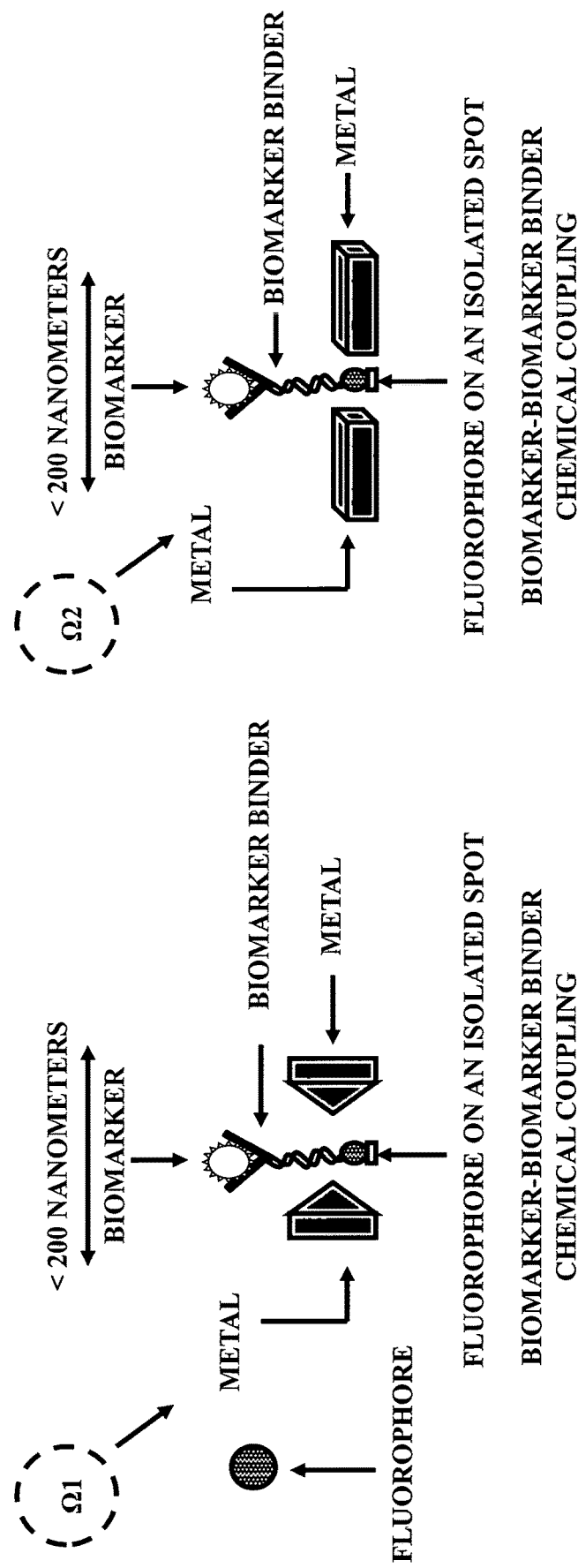
Figure 59F:
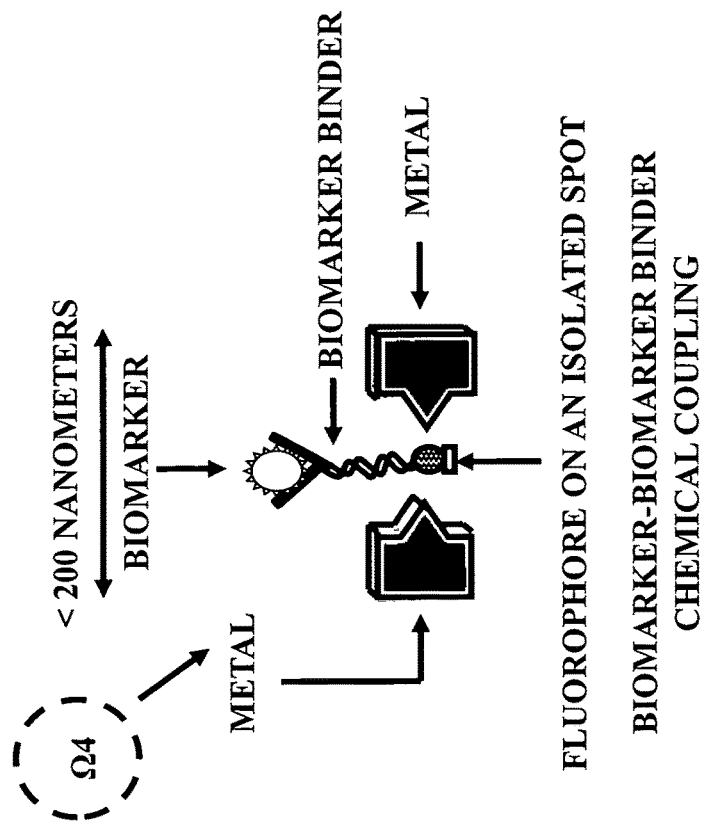
Figure 59E:
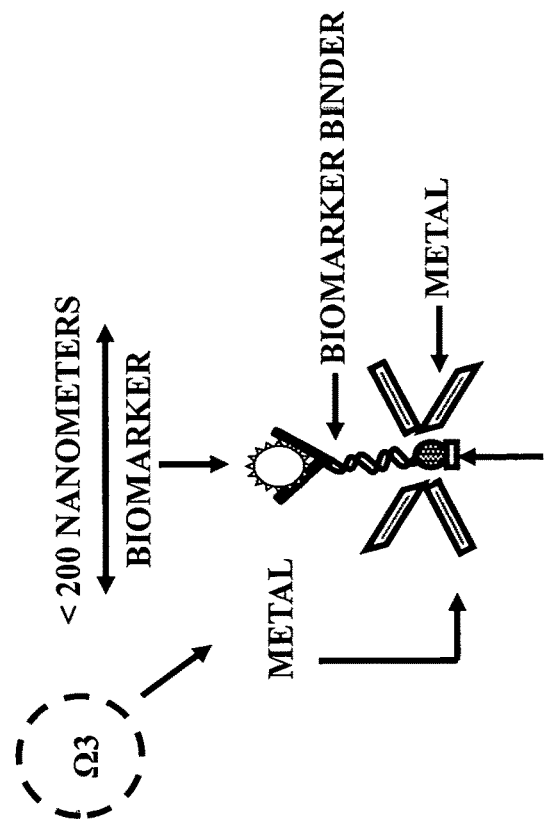

FIG. 59C illustrates biomarker binder-biomarker chemical coupling on the protruded metal/non-metal nano optical antenna (represented by a symbol $\Omega 1$), wherein the protruded metal/non-metal nano optical antenna includes two metal/non-metal triangles, having a gap of less than 50 nm and a maximum dimension of less than 200 nm.

FIGS. 59D-59G are similar to 59C, except the protruded metal/non-metal nano optical antenna includes two rods, v shapes, geometrical shapes and spheres. They are represented by $\Omega 2$, $\Omega 3$, $\Omega 4$, $\Omega 5$ respectively.

The protruded metal/non-metal nano optical antennas $\Omega 1$, $\Omega 2$, $\Omega 3$, $\Omega 4$ and $\Omega 5$ can be enclosed within an open nanoscaled box (FIG. 59H) of maximum dimension less than 400 nm. The enclosed protruded metal/non-metal nano optical antennas $\Omega 1$, $\Omega 2$, $\Omega 3$, $\Omega 4$ and $\Omega 5$ within an open nanoscaled box are represented by $\Omega 6$, $\Omega 7$, $\Omega 8$, $\Omega 9$ and $\Omega 10$ respectively.

The protruded metal/non-metal nano optical antennas $\Omega 1$, $\Omega 2$, $\Omega 3$, $\Omega 4$ and $\Omega 5$ can be enclosed within a closed nanoscaled box (FIG. 59I) of maximum dimension less than 400 nm. The enclosed protruded metal/non-metal nano optical antennas $\Omega 1$, $\Omega 2$, $\Omega 3$, $\Omega 4$ and $\Omega 5$ within a closed nanoscaled box are represented by $\Omega 10$, $\Omega 12$, $\Omega 13$, $\Omega 14$ and $\Omega 15$ respectively.

Figure 59J:
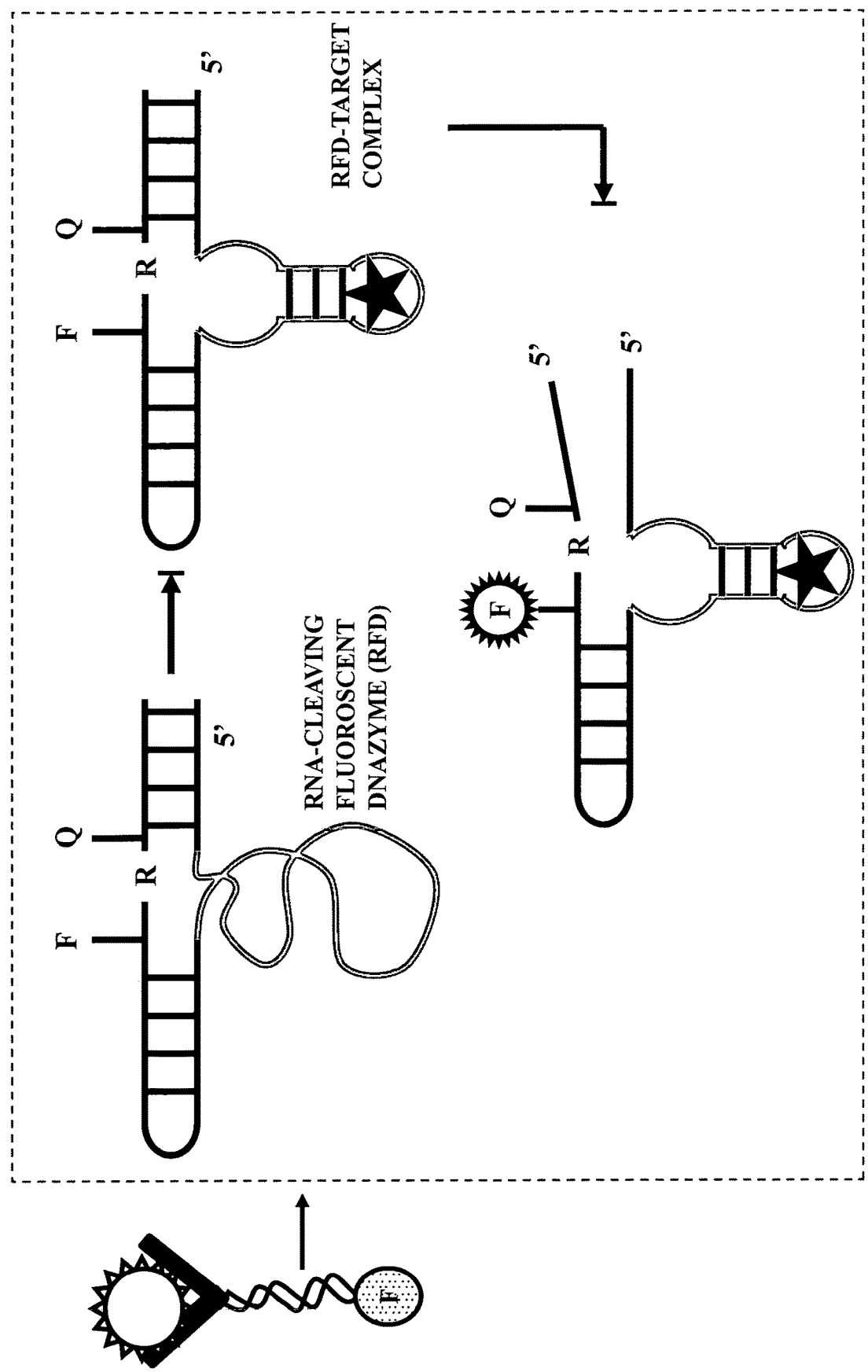

FIG. 59J illustrates a switch-on biomarker binder (e.g., a molecular beacon), which can be utilized instead of an antibody/apatamer to reduce background fluorescence.

Alternatively to the molecular beacon, a fluorescent protein/deoxyribonucleic acid origami based structure with a fluorophore (e.g., quantum dot/polymeric fluorophore) is split into two fragments-A & B. A is attached to a set of nanoparticles (e.g., gold) to bind on a first set of specific biomarkers at a cell surface. B is attached to a set of nanoparticles (e.g., gold) to bind on a second set of specific biomarkers at a cell surface. As two fragments-A & B collide on a specific disease cell (e.g., a cancer cell), they naturally reassemble into the whole fluorescent protein or the integrated deoxyribonucleic acid origami based structure with a fluorophore for detection by a fluorescence spectrophotometer or a Raman spectrophotometer.

As an example, the early diagnostic system A or early diagnostic system B can detect Ciz1 protein or its variants (e.g., b-variant), which are prevalent in the blood of people with early stage lung cancer. Inhibiting Ciz1 protein or its variants by a targeted delivery of a specific small interfering RNA or synthetic notch molecule by the smart nanoshell (decorated with one or more receptor binding ligands) can limit the growth of lung cancer. The smart nanoshell can be coupled with a near-infrared fluorophore (e.g., quantum dot/polymeric fluorophore) for fluorescence detection-enabling visualization of accumulation of smart nanoshells at lung cancer cells.

FIG. 60A illustrates an electro-optical deoxyribonucleic acid sequencing system, wherein deoxyribonucleic acid can be pulled through a nanohole on an angstrom thin membrane (the angstrom thin membrane is mechanically supported by silicon nitride and/or silicon memebrane) electrically. The angstrom thin membrane can be fabricated/constructed in a two-dimensional material. Upon passing through the nanohole, a cutting enzyme can cut nucleotides A, C, G and T of deoxyribonucleic acid in a reaction tube. Then, each nucleotide A, C, G and T can be chemically coupled with a colloidal molecule in the reaction tube. As each nucleotide A, C, G and T chemically (coupled with colloidal molecule) passes through a specific zone of the reaction tube, it is identified by an ultrasensitive Raman spectrophotometer.

At a zone of Raman measurement, a protruded metal/non-metal nano optical antenna can be fabricated/constructed to enhance the Raman signal. The top metal of a protruded metal/non-metal nano optical antenna can be coated with 1.5 nm thick aluminum oxide (utilizing atomic layer deposition) prior to transferring graphene onto aluminum oxide, utilizing poly(methyl methacrylate) (PMMA).

Details of the nanohole based deoxyribonucleic acid sequencing system have been described/disclosed in U.S. non-provisional patent application Ser. No. 13/663,376 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Oct. 29, 2012 and in its related U.S. non-provisional patent applications (with all benefit provisional patent applications) are incorporated in its entirety herein with this application.

FIGS. 60B-60E illustrate chemically coupling of nucleotide A, C, G and T with a colloidal molecule respectively.

FIG. 60F illustrates the Raman shift spectrum of nucleotide A, C, G and T.

FIG. 60G illustrates an electro-optical embodiment of microRNA detection system. FIG. 60G is similar to FIG. 60A, except deoxyribonucleic acid is replaced by microRNA, wherein the microRNA can be coupled with p19 protein. The reaction chamber is replaced by a nanochannel/zero-mode waveguide (ZMG). The nanochannel/zero-mode waveguide includes one or more three-dimensional protruded structures to enhance fluorescence. The optical detection system is fluorescence, not Raman. The electro-optical embodiment of miRNA detection system is based on perturbation of minute current, as the microRNA passes through the nanohole (of about 3 nm diameter) and Förster/Fluorescence Resonance Energy Transfer detection, as illustrated in FIG. 57I/57J/57K.

Exosome contains ribonucleic acids. Cells communicate each other by sending and receiving exosomes. Thus, an exosome can be viewed as cellular Twitter for cell-to-cell biological communication directly by surface expressed ligands or transferring molecules from the originating cells. For example, exosomes can carry material from an originating cancer cell to suppress the immune system and stimulate angiogenesis for the growth of cancer cells. Recipient cells act utilizing ribonucleic acids for protein manufacturing. Thus, exosomes can be utilized as a universal nanoshell to deliver ribonucleic acid (e.g., a specific small interfering ribonucleic acid (siRNA)) for therapeutic purposes.

FIGS. 61A-61C illustrates an exosome diagnostic system for early detection/prediction of a disease.

FIG. 61A illustrates a biochemical chamber to obtain ribonucleic acids/proteins caged within exosomes. The biochemical chamber can be a molded poly(dimethylsiloxane) (PDMS). The biochemical chamber is degassed via vacuum prior to its use. The absorption of gas by poly(dimethylsiloxane) provides the mechanism for actuating and metering the flow of fluid in microfluidic channels and between various parts of the biochemical chamber. The biochemical chamber can take in blood at inlets. The biochemical chamber can use tiny microfluidic channels of about 30 microns in diameter underneath the inlets to separate serum from blood by utilizing laws of microscale physics. The serum moves through the biochemical chamber via a process called degas-driven flow. Alternatively, self-assembled silica microspheres in a (polymeric) microfluidic channel can passively separate serum from human blood Superparamagnetic nanoparticles iron oxide ($Fe_3O_4$) can be synthesized with positive electrical charges to bond onto the membrane surface of exosomes' negative electrical charge due to electrostatic interactions. The biochemical chamber can be integrated with a magnet. Exposure to a magnetic field can separate superparamagnetic nanoparticles iron oxide (once attached with exosomes) from exosomes. Capture of exosomes by superparamagnetic nanoparticles iron oxide is realized in Capture+Wash Microchamber.

Alternatively, a nanosieve/nanomembrane/nanofilter of about 100 nm pore diameter can filter exosomes. For example, a nanosieve/nanomembrane/nanofilter can be graphene based. Nanoholes in graphene (a hexagonal array of carbon atoms) can be fabricated/constructed in a two-stage process. First, a graphene sheet is bombarded with gallium/helium ions, which disrupt the carbon bonds. Second, the graphene sheet is wet etched in an oxidizing solution that reacts strongly with the disrupted carbon bonds, producing a nanohole at each spot, where the gallium/helium ions once bombarded/struck. By controlling how long the graphene sheet is left in the oxidizing solution, the average size of the nanoholes can be controlled.

FIG. 61B illustrates a removable Lysis+Probe Microchamber. A suitable chemical can be added in the removable Lysis+Probe Microchamber to break the membrane surface of exosomes to obtain caged ribonucleic acids and proteins within the exosomes. The removable Lysis+Probe Microchamber which has disease specific biomarker binders (e.g., an aptamer/molecular beacon binder) and can be chemically coupled with a fluorophore (e.g., fluorescent protein/quantum dot fluorophore) to bind with disease specific microRNAs, which were once caged within the exosomes.

The protruded metal/non-metal nano optical antenna can be integrated with the fluorophore to enhance fluorescence. Alternatively, the removable Lysis+Probe Microchamber can be configured with the protruded metal/non-metal nano optical antennas on the floor of the Removable Lysis+Probe Microchamber to enhance fluorescence.

FIG. 61C illustrates another embodiment of the removable Lysis+Probe Microchamber. In this configuration, the disease specific biomarker binders are designer proteins with leave-one-out configuration (each designer protein has an omitted molecular segment to create a binding site to fit a disease specific protein) to bind with disease specific proteins which were once caged within the exosomes. Above miRNAs, mRNAs, proteins and other nanobiological components (e.g., piRNAs) can be analyzed utilizing the early diagnostic system A (FIGS. 58A-58F).

Details of exosome diagnostic system have been described/disclosed in U.S. non-provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and in its related U.S. non-provisional patent applications (with all benefit provisional patent applications) are incorporated in its entirety herein with this application.

FIG. 62A illustrates a three-dimensional micro/nano-printer. A short pulsed laser beam is manipulated by an attenuator and/or a shutter. The laser beam can be divided by a beam splitter. The intensity of the laser beam can be measured by a detector. The laser beam (via an objective) can excite a material (in a material tray). The intensity and spatial movement of the laser beam can be manipulated by a three-axis scanning stage and a controller. The controller is connected/coupled with a cloud computer system and optionally with a (depth/range) precision light detection and ranging subsystem. The three-dimensional printer can remain in locked configuration, unless the cloud computer system generally verifies a desired design against other publicly available designs. A three-dimensional imager scanner can consist of a very large scale integration of coherent interferometers, which can measure the intensity, phase and frequency of the reflected laser light from different points on an object. The three-dimensional micro/nano-printer can be integrated with the three-dimensional image scanner.

A waveguide device (FIG. 29D) can focus the incident laser beam below Abbey's diffraction limit for nanoprinting. Alternatively, a nanohole patterned circular disc (FIG. 29E) can focus the incident laser beam below Abbey's diffraction limit for nanoprinting.

FIG. 62B is similar to 62A, except this configuration utilizes two laser beams for printing, wherein the second laser beam is manipulated by an optical phase plate.

Additionally, two-photon polymerization can be utilized to fabricate/construct microstructures in biocompatible ormocers material. A printed micro/nano component can be attached to live/bioprinted biological materials.

Alternatively, instead of scanning with a single (continuous wave/pulse/ultrashort pulse) laser, two lasers can be utilized simultaneously. The first instant is a typical laser using an appropriate wavelength to excite a material. The second instant is a key second laser, which is focused so that it produces a donut of light overlapping the focal point of the first laser. This configuration can enable the laser to focus below the Abbey's diffraction limit for nanoprinting.

FIG. 63A illustrates the intelligent algorithm 100Y. The intelligent algorithm 100Y includes a digital security protection (DSP) algorithm submodule 100A, a natural language processing algorithm submodule 100B, and an application specific algorithm submodule 100C3 (Human OS). The application specific algorithm submodule 100C3 and a knowledge database 100N4 (Knowledge Database—e.g., Bioinformatics Database) are coupled with a computer vision algorithm submodule 100D, a pattern recognition algorithm submodule 100E, a data mining algorithm submodule 100F, Big Data analysis algorithm submodule 100G, a statistical analysis algorithm submodule 100H, a fuzzy logic (including neuro-fuzzy) algorithm submodule 100I, an artificial neural network/artificial intelligence algorithm submodule 100J, a machine learning (including deep learning/meta-learning and self-learning) algorithm submodule 100K, a predictive analysis algorithm submodule 100L and a prescriptive analysis algorithm submodule 100M.

The application specific algorithm submodule 100C3 (Human OS) and the knowledge database 100N4 (e.g., Bioinformatics Database) can be coupled with a public/consortium/private blockchain.

The connections between various algorithm submodules of the intelligent algorithm 100Y can be similar to synaptic networks to enable deep learning/meta-learning and self-learning of the intelligent algorithm 100Y.

FIG. 63B illustrates a configuration to determine a (Personal) Human Operating System (OS), a healthcare expert system coupled with the Super System on Chip 400A/400B/400C/400D, which includes an intelligent algorithm 100Y. The intelligent algorithm 100Y can be coupled with a learning/quantum learning algorithm. The healthcare expert system connects with (a) a deoxyribonucleic acid sequencing system, (b) an early diagnostic system A/B, (c) an exosome diagnostic system, (d) the intelligent portable internet appliance 160 and (e) healthcare/remote healthcare providers. The intelligent portable internet appliance 160 connects with a point-of-care diagnostic system and a wearable personal health assistant device. The data from the intelligent portable internet appliance 160 is coupled with coupled a public/consortium/private blockchain. Personal Human Operating System can enable predictive disease disposition of the user.

FIG. 63C illustrates another embodiment of a Personal Human Operating System, utilizing a photonic neural learning processor (PNLP), which is coupled with coupled with the Super System on Chip 400A/400B/400C/400D, which includes an intelligent algorithm 100Y.

FIG. 63D illustrates another embodiment of a Personal Human Operating System, over the FIG. 63C, utilizing a photonic neural learning processor, which is further coupled with one or more qubits.

The Josephson Effect is observed in a Josephson junction (e.g., Al/AlO$_x$/Al or Nb/AlO$_x$/Nb), when the flow of a supercurrent between two superconducting electrodes across a non-superconducting gap. The Josephson junction is a nonlinear inductor.

In FIG. 64A a Josephson junction and a capacitor (made of a superconducting material) based qubit is electrically coupled/connected to an in/out coupler (a read out resonator). Such qubits can be connected by a microwave signal line. The Josephson junction can be electro-optically coupled with a photoconductor/atomic scaled switch.

FIG. 64A illustrates an embodiment (identified as M) of electro-optical coupling of a light signal (only activated by weighted electrical/optical signals from neural processing hardware elements) with a qubit based on Josephson junction (JJ).

The photoconductor/atomic scaled switch is coupled with an input excitation laser. The photocurrent in an atomic scaled switch is induced in a photoconductive layer (which is coupled between a metal electrode and a solid-electrolyte electrode) by an input excitation laser. The photocurrent reduces metal ions with positive charges in the solid-electrolyte electrode and this precipitates as metal atoms to form an atomic scaled metal connection between the metal electrode and the solid-electrolyte electrode-operating as an atomic scaled switch, turned on by an input excitation laser and/or an applied electrical activation (e.g., voltage) by an action of weighted electrical signals (from an array of memristors).

The input (excitation) laser is only configured to generate light pulses mimicking a neuron to communicate with many neurons. The input (excitation) laser can be excited only when a network(s) of the first pulsed lasers and second pulsed lasers are activated by an action of weighted electrical signals (from an array of memristors or by converting optical signals of distinct wavelengths from ring resonators/fast tunable ring resonators.

FIG. 64B illustrates a large scale network of Ms.

In FIG. 64C, a nitrogen vacancy based qubit is coupled with an input excitation laser. The input (excitation) laser is only configured to generate light pulses mimicking a neuron to communicate with many neurons. The input (excitation) laser can be excited only when a network(s) of the first pulsed lasers and second pulsed lasers are activated by an action of weighted electrical signals (from an array of memristors or by converting optical signals of distinct wavelengths from ring resonators/fast tunable ring resonators.

FIG. 64C illustrates another embodiment (identified as N) of optical coupling of a light signal (only activated by weighted electrical/optical signals from neural processing hardware elements) with a qubit based on a nitrogen vacancy center in diamond crystal FIG. 64D illustrates a large scale network of Ns.

FIG. 64E illustrates another embodiment of coupling a neural processing element (hardware) with a qubit. In FIG. 64E, a trapped atomic ion (e.g., $^{43}$Ca+, $^{87}$Sr+, $^{137}$Ba+, $^{171}$Yb+) based qubit is coupled with an input excitation laser. Furthermore, complementary metal-oxide-semiconductor devices can be integrated with the atomic ion trap. The input (excitation) laser is only configured to generate light pulses mimicking a neuron to communicate with many neurons. The input (excitation) laser can be excited only when a network(s) of the first pulsed lasers and second pulsed lasers are activated by an action of weighted electrical signals (from an array of memristors or by converting optical signals of distinct wavelengths from ring resonators/fast tunable ring resonators.

FIG. 64E illustrates another embodiment (identified as T) of optical coupling of a light signal (only activated by weighted electrical/optical signals from neural processing hardware elements) with a qubit based on trapped atomic ion.

FIG. 64F illustrates a large scale network of Ts.

For fault-tolerant quantum computation, the surface code (or the concatenated Steane code) in a modular architecture can be utilized.

An ultra-fast N×N Bose-Einstein condensate based optical switch can be realized, utilizing an array of single-mode/multi-mode waveguides on the left-hand side and an array of single-mode/multi-mode waveguides on the right-hand side, wherein the array of single-mode/multi-mode waveguides on the left-hand side and the array of single-mode/multi-mode waveguides on the right-hand side are optically coupled with polariton Bose-Einstein condensate. Short-lived room temperature polariton Bose-Einstein condensate can be created through the interaction of a laser light (bouncing back and forth within multiple dielectric thin-films) and a luminescent polymeric thin-film of about 30 nm in thickness. The luminescent polymeric thin-film is embedded within multiple dielectric thin-films, wherein the multiple dielectric thin-films is then illuminated from the bottom (of the multiple dielectric thin-films, each dielectric thin-film is about 40 nm in thickness) by a vertical surface emitting laser or an in-plane laser integrated with a mirror and a lens.

Details of an ultra-fast N×N Bose-Einstein condensate based optical switch (FIG. 19K) have been described/disclosed in U.S. non-provisional patent application Ser. No. 15/731,577 entitled "OPTICAL BIOMODULE FOR DETECTION OF DISEASES AT AN EARLY ONSET, filed on Jul. 3, 2017 and in its related U.S. non-provisional patent applications (with all benefit provisional patent applications) are incorporated in its entirety herein with this application.

FIG. 64G illustrates integration of above M/N/T with an ultrafast optical switch (e.g., Bose-Einstein condensate switch), input waveguides, output waveguides and photon counting imager. However, a N×N microelectromechanical systems based optical cross-connect switch may replace the Bose-Einstein condensate switch in some applications.

FIG. 65A illustrates integration/coupling of the above coupled qubits M/N/T with the Super System on Chip 400A/400B/400C/400D. This configuration is "Fazila" A+.

FIG. 65B illustrates integration/coupling of the above coupled qubits M/N/T with a photonic neural learning processor. The photonic neural learning processor has been described in previous paragraphs. This configuration is "Fazila" AA+

FIG. 65C illustrates integration/coupling of the above coupled qubits M/N/T with a photonic neural learning processor, wherein the photonic neural learning processor is coupled with the Super System on Chip 400A/400B/400C/400D. This configuration is "Fazila" AAA+.

PREFERRED EMBODIMENTS & SCOPE OF THE INVENTION

As used in the above disclosed specifications, the above disclosed specifications "/" has been used to indicate an "or".

As used in the above disclosed specifications and in the claims, the singular forms "a", "an", and "the" include also the plural forms, unless the context clearly dictates otherwise.

As used in the above disclosed specifications, the term "includes" means "comprises". Also the term "including" means "comprising".

As used in the above disclosed specifications, the term "couples" or "coupled" does not exclude the presence of an intermediate element(s) between the coupled items.

As used in the above disclosed specifications, any weight % in the above disclosed specifications is by way of an approximation only and not by way of any limitation.

Any dimension in the above disclosed specifications is by way of an approximation only and not by way of any limitation.

As used in the above disclosed specifications, unless otherwise specified in the relevant paragraph(s), a nanoscaled dimension shall generally mean a dimension from about 1 nanometer (nm) to about 1000 nanometers.

As used in the above disclosed specifications, the word "unit" is synonymous with the word "media unit" or with the word "media".

As used in the above disclosed specifications, the word cloud based storage unit is synonymous with a cloud based server.

As used in the above disclosed specifications, real-time means near real-time in practice.

Any example in the above disclosed specifications is by way of an example only and not by way of any limitation. Having described and illustrated the principles of the disclosed technology with reference to the illustrated embodiments, it will be recognized that the illustrated embodiments can be modified in any arrangement and detail without departing from such principles. The technologies from any example can be combined in any arrangement with the technologies described in any one or more of the other examples. Alternatives specifically addressed in this application are merely exemplary and do not constitute all possible examples. Claimed invention is disclosed as one of several possibilities or as useful separately or in various combinations. See *Novozymes A/S* v. *DuPont Nutrition Biosciences APS*, 723 F3d 1336,1347.

The best mode requirement "requires an inventor(s) to disclose the best mode contemplated by him/her, as of the time he/she executes the application, of carrying out the invention." " . . . [T]he existence of a best mode is a purely subjective matter depending upon what the inventor(s) actually believed at the time the application was filed." See Bayer AG v. Schein Pharmaceuticals, Inc. The best mode requirement still exists under the America Invents Act (AIA). At the time of the invention, the inventor(s) described preferred best mode embodiments of the present invention. The sole purpose of the best mode requirement is to restrain the inventor(s) from applying for a patent, while at the same time concealing from the public preferred embodiments of their inventions, which they have in fact conceived. The best mode inquiry focuses on the inventor(s)' state of mind at the time he/she filed the patent application, raising a subjective factual question. The specificity of disclosure required to comply with the best mode requirement must be determined by the knowledge of facts within the possession of the inventor(s) at the time of filing the patent application. See *Glaxo, Inc.* v. *Novopharm Ltd.*, 52 F.3d 1043, 1050 (Fed. Cir. 1995). The above disclosed specifications are the preferred best mode embodiments of the present invention. However, they are not intended to be limited only to the preferred best mode embodiments of the present invention.

Embodiment by definition is a manner in which an invention can be made or used or practiced or expressed. "A tangible form or representation of the invention" is an embodiment.

Numerous variations and/or modifications are possible within the scope of the present invention. Accordingly, the disclosed preferred best mode embodiments are to be construed as illustrative only. Those who are skilled in the art can make various variations and/or modifications without departing from the scope and spirit of this invention. It should be apparent that features of one embodiment can be combined with one or more features of another embodiment to form a plurality of embodiments. The inventor(s) of the present invention is not required to describe each and every conceivable and possible future embodiment in the preferred best mode embodiments of the present invention. See *SRI Int'l* v. *Matsushita Elec. Corp. of America*, 775F.2d 1107, 1121, 227 U.S.P.Q. (BNA) 577, 585 (Fed. Cir. 1985) (en-banc).

The scope and spirit of this invention shall be defined by the claims and the equivalents of the claims only. The exclusive use of all variations and/or modifications within the scope of the claims is reserved. The general presumption is that claim terms should be interpreted using their plain and ordinary meaning without improperly importing a limitation from the specification into the claims. See *Continental Circuits LLC* v. *Intel Corp.* (Appeal Number 2018-1076, Fed. Cir. Feb. 8, 2019) and *Oxford Immunotec Ltd.* v. *Oiagen, Inc. et al.*, Action No. 15-cv-13124-NMG. Unless a claim term is specifically defined in the preferred best mode embodiments, then a claim term has an ordinary meaning, as understood by a person with an ordinary skill in the art, at the time of the present invention. Plain claim language will not be narrowed, unless the inventor(s) of the present invention clearly and explicitly disclaims broader claim scope. See *Sumitomo Dainippon Pharma Co.* v. *Emcure Pharm. Ltd.*, Case Nos. 17-1798; -1799; -1800 (Fed. Cir. Apr. 16, 2018) (Stoll, J). As noted long ago: "Specifications teach. Claims claim". See *Rexnord Corp.* v. *Laitram Corp.*, 274 F.3d 1336, 1344 (Fed. Cir. 2001). The rights of claims (and rights of the equivalents of the claims) under the Doctrine of Equivalents-meeting the "Triple Identity Test" (a) performing substantially the same function, (b) in substantially the same way and (c) yielding substantially the same result. See *Crown Packaging Tech., Inc.* v. *Rexam Beverage Can Co.*, 559 F.3d 1308, 1312 (Fed. Cir. 2009)) of the present invention are not narrowed or limited by the selective imports of the specifications (of the preferred embodiments of the present invention) into the claims.

While "absolute precision is unattainable" in patented claims, the definiteness requirement "mandates clarity." See *Nautilus, Inc.* v. *Biosig Instruments, Inc.*, 134 S. Ct. 2120, 2129, 110 USPQ2d 1688, 1693 (2014). Definiteness of claim language must be analyzed NOT in a vacuum, but in light of:

(a) The content of the particular application disclosure,
(b) The teachings of any prior art and
(c) The claim interpretation that would be given by one possessing the ordinary level of skill in the pertinent art at the time the invention was made. (Id.).
See *Orthokinetics, Inc.* v. *Safety Travel Chairs, Inc.*, 806 F.2d 1565, 1 USPQ2d 1081 (Fed. Cir. 1986)

There are number of ways the written description requirement is satisfied. Applicant(s) does not need to describe every claim element exactly, because there is no such requirement (MPEP § 2163). Rather to satisfy the written description requirement, all that is required is "reasonable clarity" (MPEP § 2163.02). An adequate description may be made in any way through express, implicit or even inherent disclosures in the application, including word, structures, figures, diagrams and/or equations (MPEP §§ 2163(I), 2163.02). The set of claims in this invention generally covers a set of sufficient number of embodiments to conform to written description and enablement doctrine. See *Ariad Pharm., Inc.* v. *Eli Lilly &Co.*, 598 F.3d 1336, 1355 (Fed. Cir. 2010), *Regents of the University of California* v. *Eli Lilly & Co.*, 119 F.3d 1559 (Fed. Cir. 1997) & *Amgen Inc.* v. *Chugai Pharmaceutical Co.* 927 F.2d 1200 (Fed. Cir. 1991).

Furthermore, *Amgen Inc.* v. *Chugai Pharmaceutical Co.* exemplifies Federal Circuit's strict enablement requirements. Additionally, the set of claims in this invention is intended to inform the scope of this invention with "reasonable certainty". See *Interval Licensing, LLC* v. *AOL Inc.* (Fed. Cir. Sep. 10, 2014). A key aspect of the enablement requirement is that it only requires that others will not have to perform "undue experimentation" to reproduce it. Enablement is not precluded by the necessity of some experimentation, "[t]he key word is 'undue', not experimentation." Enablement is generally considered to be the most important factor for determining the scope of claim protection allowed. The scope of enablement must be commensurate with the scope of the claims. However, enablement does not require that an inventor disclose every possible embodiment of his invention. The scope of enablement must be commensurate with the scope of the claims. The scope of the claims must be less than or equal to the scope of enablement. See *Promega* v. *Life Technologies* Fed. Cir., December 2014, *Magsil* v. *Hitachi Global Storage* Fed. Cir. August 2012.

The term "means" was not used nor intended nor implied in the disclosed preferred best mode embodiments of the present invention. Thus, the inventor(s) has not limited the scope of the claims as mean plus function.

An apparatus claim with functional language is not an impermissible "hybrid" claim; instead, it is simply an apparatus claim including functional limitations. Additionally, "apparatus claims are not necessarily indefinite for using functional language . . . [f]unctional language may also be employed to limit the claims without using the means-plus-function format." See *National Presto Industries, Inc.* v. *The West Bend Co.*, 76 F. 3d 1185 (Fed. Cir. 1996), *R.A.C.C. Indus.* v. *Stun-Tech, Inc.*, 178 F.3d 1309 (Fed. Cir. 1998) (unpublished), *Microprocessor Enhancement Corp.* v. *Texas Instruments Inc.* & *Williamson* v. *Citrix Online, LLC*, 792 F.3d 1339 (2015).

I claim:

1. A Super System on Chip (SSoC) is coupled electrically, and/or optically, by one or more first optical waveguides, or one or more photodiodes (PDs),
   wherein the Super System on Chip (SSoC) comprises an input, or an output,
   wherein the Super System on Chip (SSoC) further comprises:
   (a) a processor-specific electronic integrated circuit (EIC);
   (b) an array, or a network of memristors for neural processing; and
   (c) a photonic component, or a photonic integrated circuit (PIC),
   wherein the photonic component comprises a second optical waveguide,
   wherein the processor-specific electronic integrated circuit (EIC) in said (a), the array or the network of memristors in said (b), and the photonic component, or the photonic integrated circuit (PIC) in said (c) of the Super System on Chip (SSoC) are interconnected, or coupled in two-dimensions (2-D), or in three-dimensions (3-D) electrically, and/or optically,
   wherein the input, or the output of the Super System on Chip (SSoC) is coupled (i) electrically, and/or (ii) optically, by at least a modulator, or a semiconductor amplifier (SOA),
   wherein the modulator is a Mach-Zehnder modulator, or a ring resonator modulator,
   wherein the modulator comprises a phase transition material, or a phase change material,
   wherein the modulator is activated by a stimulus selected from the group consisting of an electrical signal, an optical signal, and a terahertz signal.

2. The Super System on Chip (SSoC) in claim 1, further comprises a component selected from the group consisting of a microprocessor, an application specific integrated circuits (ASIC), a field programmable gate array (FPGA), and an electrical switch.

3. The Super System on Chip (SSoC) in claim 1, wherein an optical stimulus is provided by an optical waveguide coupler, wherein the optical waveguide coupler comprises at least one hole, or a photonic crystal (PC), wherein the at least one hole, or the photonic crystal (PC) is air-filled, or dielectric-filled.

4. The Super System on Chip (SSoC) in claim 1, wherein the modulator comprising the phase transition material, or the phase change material further comprises a thin-film of diamond.

5. The Super System on Chip (SSoC) in claim 1, is a part of a multichip module (MCM), wherein the multichip module (MCM) comprises one or more third optical waveguides, or one or more photonic wire bond (PWB) waveguides.

6. The Super System on Chip (SSoC) in claim 5, wherein the multichip module (MCM) comprises an array of microchannels for fluid-based cooling, and/or microjets for fluid-based cooling.

7. The Super System on Chip (SSoC) in claim 1 is operable with a first artificial eye, wherein the first artificial eye comprises electrically activated switches.

8. The Super System on Chip (SSoC) in claim 1, is further operable with a second artificial eye, wherein the second artificial eye comprises light activated switches.

9. The Super System on Chip (SSoC) in claim 1, is further operable with a wireless integrated circuit, or a first wireless transceiver, wherein the first wireless transceiver comprises one or more first electronic components.

10. The Super System on Chip (SSoC) in claim 1, comprising the processor-specific electronic integrated circuit (EIC) comprises a topological insulator, or an exciton, wherein the exciton consists of an electron, and a hole.

11. The Super System on Chip (SSoC) in claim 1, comprising the second optical waveguide, wherein the second optical waveguide is a photonic crystal (PC) based optical waveguide.

12. The Super System on Chip (SSoC) in claim 1, further comprises a vertical cavity surface emitting laser (VCSEL), or a photonic crystal based vertical cavity surface emitting laser (PC-VCSEL), or a light emitting diode.

13. The Super System on Chip (SSoC) in claim 1, further comprises a waveguide photodiode, or an optical switch.

14. The Super System on Chip (SSoC) in claim 1, further comprises an all-optical random access memory component.

15. The Super System on Chip (SSoC) in claim 1, is coupled with a photonic neural learning processor (PNLP) for neural processing, wherein the photonic neural learning processor (PNLP) comprises an interferometer, or a laser.

16. The Super System on Chip (SSoC) in claim 15, wherein the photonic neural learning processor (PNLP) is coupled with one or more quantum bits (qubits).

17. Super System on Chip (SSoC) in claim 1, that further comprises an algorithm for predictive memory prefetching, stored in one or more non-transitory storage medias.

18. The Super System on Chip (SSoC) in claim 1, that further comprises an artificial neural network (ANN) algorithm, or a machine learning (ML) algorithm, stored in one or more non-transitory storage medias.

19. The Super System on Chip (SSoC) in claim 1, that further comprises a computer vision algorithm, or an image processing algorithm, stored in one or more non-transitory storage medias.

20. The Super System on Chip (SSoC) in claim 1, is included in a subsystem, wherein the subsystem comprises (a) a second wireless transceiver, or a sensor, wherein the second wireless transceiver comprises one or more second electronic components, and (b) a voice processing module to process a voice command, or an audio command in a natural language, wherein the voice processing module comprises one or more third electronic components.

21. The Super System on Chip (SSoC) in claim 20, is included in the subsystem, wherein the subsystem comprises a set of instructions to process the voice command, or the audio command in the natural language, wherein the said set of instructions is stored in one or more non-transitory storage medias.

22. A Super System on Chip (SSoC) is coupled electrically, and/or optically, by one or more first optical waveguides, or one or more photodiodes (PDs),
   wherein the Super System on Chip (SSoC) comprises an input, or an output,
   wherein the Super System on Chip (SSoC) further comprises:
   (a) a processor-specific electronic integrated circuit (EIC);
   (b) an array, or a network of memristors for neural processing; and
   (c) a photonic component, or a photonic integrated circuit (PIC),
   wherein the photonic component comprises a second optical waveguide,
   wherein the input, or the output of the Super System on Chip (SSoC) is coupled electrically, and/or optically, by at least a modulator, or a semiconductor amplifier (SOA), wherein the modulator is a Mach-Zehnder modulator, or a ring resonator modulator, wherein the modulator is activated by a stimulus selected from the group consisting of an electrical signal, an optical signal, and a terahertz signal.

23. The Super System on Chip (SSoC) in claim 22, further comprises a component selected from the group consisting of a microprocessor, an application specific integrated circuits (ASIC), a field programmable gate array (FPGA), and an electrical switch.

24. The Super System on Chip (SSoC) in claim 22, wherein an optical stimulus is provided by an optical waveguide coupler, wherein the optical waveguide coupler comprises at least one hole, or a photonic crystal (PC), wherein the at least one hole, or the photonic crystal (PC) is air-filled, or dielectric-filled.

25. The Super System on Chip (SSoC) in claim 22, is a part of a multichip module (MCM), wherein the multichip module (MCM) comprises one or more third optical waveguides, or one or more photonic wire bond (PWB) waveguides.

26. The Super System on Chip (SSoC) in claim 25, wherein the multichip module (MCM) comprises an array of microchannels for fluid-based cooling, and/or microjets for fluid-based cooling.

27. The Super System on Chip (SSoC) in claim 22, is operable with a first artificial eye, wherein the first artificial eye comprises electrically activated switches.

28. The Super System on Chip (SSoC) in claim 22, is further operable with a second artificial eye, wherein the second artificial eye comprises light activated switches.

29. The Super System on Chip (SSoC) in claim 22, is further operable with a wireless integrated circuit, or a first wireless transceiver, wherein the first wireless transceiver comprises one or more first electronic components.

30. The Super System on Chip (SSoC) in claim 22, comprising the processor-specific electronic integrated circuit (EIC) comprises a topological insulator, or an exciton, wherein the exciton consists of an electron, and a hole.

31. The Super System on Chip (SSoC) in claim 22, comprising the second optical waveguide, wherein the second optical waveguide is a photonic crystal (PC) based optical waveguide.

32. The Super System on Chip (SSoC) in claim 22, further comprises a vertical cavity surface emitting laser (VCSEL), or a photonic crystal based vertical cavity surface emitting laser (PC-VCSEL), or a light emitting diode.

33. The Super System on Chip (SSoC) in claim 22, further comprises a waveguide photodiode, or an optical switch.

34. The Super System on Chip (SSoC) in claim 22, further comprises an all-optical random access memory component.

35. The Super System on Chip (SSoC) in claim 22, is coupled with a photonic neural learning processor (PNLP) for neural processing, wherein the photonic neural learning processor (PNLP) comprises an interferometer, or a laser.

36. The Super System on Chip (SSoC) in claim 35, wherein the photonic neural learning processor (PNLP) is coupled with one or more quantum bits (qubits).

37. The Super System on Chip (SSoC) in claim 22, that further comprises an algorithm for predictive memory prefetching, stored in one or more non-transitory storage medias.

38. The Super System on Chip (SSoC) in claim 22, that further comprises an artificial neural network (ANN) algorithm, or a machine learning (ML) algorithm, stored in one or more non-transitory storage medias.

39. The Super System on Chip (SSoC) in claim 22, that further comprises a computer vision algorithm, or an image processing algorithm, stored in one or more non-transitory storage medias.

40. The Super System on Chip (SSoC) in claim 22, is included in a subsystem, wherein the subsystem comprises (a) a second wireless transceiver, or a sensor, wherein the second wireless transceiver comprises one or more second electronic components, and (b) a voice processing module to process a voice command, or an audio command in a natural language, wherein the voice processing module comprises one or more third electronic components.

41. Super System on Chip (SSoC) in claim 40, is included in the subsystem, wherein the subsystem comprises a set of instructions to process the voice command, or the audio command in the natural language, wherein the said set of instructions is stored in one or more non-transitory storage medias.

42. A Super System on Chip (SSoC), is coupled electrically, and/or optically, by one or more first optical waveguides, or one or more photodiodes (PDs), wherein the Super System on Chip (SSoC) comprises an input, or an output, wherein the Super System on Chip (SSoC) further comprises:

(a) a processor-specific electronic integrated circuit (EIC);

(b) an array, or a network of memristors for neural processing; and (c) a photonic component, or a photonic integrated circuit (PIC), wherein the photonic component comprises a second optical waveguide, wherein the processor-specific electronic integrated circuit (EIC) in said (a), the array, or the network of memristors in said (b), and the photonic component, or the photonic integrated circuit (PIC) in said (c) of the Super System on Chip (SSoC) are interconnected, or coupled in two-dimensions (2-D), or in three-dimensions (3-D) electrically, and/or optically, wherein the input, or the output of the Super System on Chip (SSoC) is coupled electrically, and/or optically, by at least a modulator, or a semiconductor amplifier (SOA), wherein the modulator is a Mach-Zehnder modulator, or a ring resonator modulator, wherein the modulator is activated by a stimulus selected from the group consisting of an electrical signal, an optical signal, and a terahertz signal.

43. The Super System on Chip (SSoC) in claim 42, further comprises a component selected from the group consisting of a microprocessor, an application specific integrated circuits (ASIC), a field programmable gate array (FPGA), and an electrical switch.

44. The Super System on Chip (SSoC) in claim 42, is a part of a multichip module (MCM), wherein the multichip module (MCM) comprises one or more third optical waveguides, or one or more photonic wire bond (PWB) waveguides.

45. The Super System on Chip (SSoC) in claim 44, wherein the multichip module (MCM) comprises an array of microchannels for fluid-based cooling, and/or microjets for fluid-based cooling.

\* \* \* \* \*